(12) United States Patent
Matasi et al.

(10) Patent No.: US 7,989,464 B2
(45) Date of Patent: *Aug. 2, 2011

(54) MGLUR1 ANTAGONISTS AS THERAPEUTIC AGENTS

(75) Inventors: Julius J. Matasi, Monmouth Junction, NJ (US); Deen Tulshian, Lebanon, NJ (US); Duane A. Burnett, Bernardsville, NJ (US); Wen-Lian Wu, Edison, NJ (US); Peter Korakas, Bound Brook, NJ (US); Lisa S. Silverman, Metuchen, NJ (US); Thavalakulamgara K. Sasikumar, Edison, NJ (US); Li Qiang, Edison, NJ (US); Martin S. Domalski, Verona, NJ (US)

(73) Assignee: Schering Corporation, Kenilworth, NJ (US)

( * ) Notice: Subject to any disclaimer, the term of this patent is extended or adjusted under 35 U.S.C. 154(b) by 109 days.

This patent is subject to a terminal disclaimer.

(21) Appl. No.: 12/356,867

(22) Filed: Jan. 21, 2009

(65) Prior Publication Data
US 2009/0192178 A1 Jul. 30, 2009

Related U.S. Application Data

(60) Division of application No. 11/301,672, filed on Dec. 13, 2005, now Pat. No. 7,598,259, which is a continuation-in-part of application No. 11/152,535, filed on Jun. 14, 2005, now Pat. No. 7,485,648.

(60) Provisional application No. 60/579,920, filed on Jun. 15, 2004.

(51) Int. Cl.
*A01N 43/54* (2006.01)
*A61K 31/505* (2006.01)
*C07D 239/00* (2006.01)
*C07D 471/00* (2006.01)
*C07D 487/00* (2006.01)

(52) U.S. Cl. ....................... 514/267; 544/250
(58) Field of Classification Search .................. 514/267; 544/250
See application file for complete search history.

(56) References Cited

U.S. PATENT DOCUMENTS

| | | | |
|---|---|---|---|
| 6,232,320 B1 | 5/2001 | Stewart et al. | |
| 7,485,648 B2 | 2/2009 | Matasi et al. | |
| 2002/0151544 A1 | 10/2002 | Hayakawa et al. | |
| 2006/0167029 A1 | 7/2006 | Matasi et al. | |
| 2006/0189639 A1 | 8/2006 | Stewart et al. | |
| 2009/0082336 A1 * | 3/2009 | Matasi et al. | 514/217.06 |

FOREIGN PATENT DOCUMENTS

| | | |
|---|---|---|
| WO | WO 01/32632 | 5/2001 |
| WO | WO 02/062803 A1 | 8/2002 |
| WO | WO 2006/002051 A1 | 1/2006 |
| WO | WO 2006/081072 A1 | 8/2006 |

OTHER PUBLICATIONS

Kadushkin, et al., DMF Diethyl Acetyl as a One-carbon Component in the Synthesis of Isomeric Pyridothienopyrimidines, Khimiko-Farmatsevticheskii Zhurnal, 27(3), 40-3 (1993).*
Bhave et al., "Peripheral group I metabotropic glutamate receptors modulate nociception in mice", Nature Neuroscience, vol. 4, pp. 417-423 (2001).
Bousquet et al., "Synthesis and Pharmacological Activity of 3-Substituted Pyrido(3', 2':4,5)Thieno(3,2-d)Pyrimidin-4(3H)-Ones", Institute of Pharmaceutical and Toxicological Chemistry, vol. 39, No. 2, pp. 110-119 (1984).
Chang et al., "Analgesic activity of metabotropic glutamate receptor 1 antagonists on spontaneous post-operative pain in rats", European Journal of Pharmacology, vol. 580, pp. 314-321 (1984).
Dolan et al., "Behavioral evidence supporting a differential role for spinal group I and II metabotropic glutamate receptors in inflammatory hyperalgesia in sheep", Neuropharmacology, (2002) vol. 43, pp. 319-326.
Dolan et al., "Up-regulation of metabotropic glutamate receptor subtypes 3 and 5 in spinal cord in a clinical model of persistent inflammation and hyperalgesia", Pain, vol. 106, pp. 501-512 (2003).
El-Kouhen et al., "Blockade of mGluR1 receptor results in analgesia and disruption of motor and cognitive performances: effects of A-841720, a novel non-competitive mGluR1 receptor antagonist", British Journal of Pharmacology, vol. 149, pp. 761-774 (2006).
Fisher et al., "Hyperalgesia and allodynia induced by intrathecal (RS)-dihydroxyphenylglycine in rats", NeuroReport, vol. 9, pp. 1169-1172 (1998).
Fundytus et al., "Antisense oligonucleotide knockdown of $mGluR_1$ alleviates hyperalgesia and allodynia associated with chronic inflammation", Pharmacology, Biochemistry and Behavior, vol. 73, pp. 401-140 (2002).

(Continued)

*Primary Examiner* — James O Wilson
*Assistant Examiner* — Erich Leeser
(74) *Attorney, Agent, or Firm* — Kenrick L. Vidale; Keith D. MacMillan; John C. Todaro

(57) ABSTRACT

In its many embodiments, the present invention provides tricyclic compounds of formula I (wherein $J^1$-$J^4$, X, and $R^1$-$R^5$ are as defined herein) useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such Alzheimer's disease.

formula I

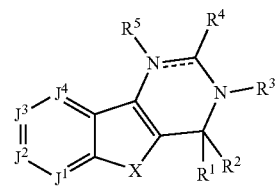

11 Claims, No Drawings

OTHER PUBLICATIONS

Fundytus et al., "In vivo antinociceptive activity of anti-rate mGluR$_1$ and mGluR$_5$ antibodies in rats", NeuroReport, vol. 9, pp. 731-735 (1998).

Fundytus et al., "Knockdown of spinal metabotropic glutamate receptor 1 (mGluR$_1$) alleviates pain and restores opioid efficacy after nerve injury in rats", British Journal of Pharmacology, vol. 132, pp. 354-367 (2001).

Kadushkin et al, "DMF diethyl acetal as a one-carbon component in the synthesis of isomeric pyridothienopyrimidines," Khimiko-Farmatsevticheskii Zhurnal, vol. 27(3), pp. 40-43 (1993) + English Abstract.

Kamble et al, "Synthesis of some new heterocyclic systems bearing (3H)-benzofuropyrimidin-4-one-3-yl moiety as antibacterial agents," Indian Journal of Heterocyclic Chemistry, vol. 9(1), pp. 23-26 (Sep. 1999).

Mahajan et al., "Studies in benzofurans: Part VIII. Synthesis of some 3-N-aryl-, 3-N-alkyl- and 3-amino-3, 4-dihydro-4-oxobenzofuro[3,2-d]pyrimidines", Indian Journal of Chemistry, Section B: Organic Chemistry including Medicinal Chemistry, vol. 19B(5), pp. 402-404 (1980).

Merour, "Specific synthesis of pyrimidines. Concurrent formation of pyrimidines and triazepines," Journal of Heterocyclic Chemistry, vol. 19(6), pp. 1425-1431 (1982) + English Abstract.

Mills and Hulsebosch, "Increased expression of metabotropic glutamate receptor subtype 1 on spinothalamic tract neurons following spinal cord injury in the rat", Neuroscience Letters vol. 319, pp. 59-62 (2002).

More et al., "Comparison of the mGluR1 antagonist A-841720 in rat models of pain and cognition", Behavioral Pharmacology, vol. 18, pp. 273-281 (2007).

Neugebauer et al., "Peripheral metabotropic glutamate receptors: fight the pain where it hurts", Trends in Neurosciences, vol. 24, pp. 550-552 (2001).

Neugebauer et al., "Role of Metabotropic Glutamate Receptor Subtype mGluR1 in Brief Nociception and Central Sensitization of Primate STT Cells", Journal of Neurophysiology, vol. 82, pp. 272-282 (1999).

Russo et al, "New nitrogenous polycyclic systems: Synthesis and pharmacological properties of benzofuro and thienothiadiazolopyrimidine derivatives", Farmaco, Edizione Scientifica, vol. 38(10), pp. 762-764 (1983) + English Abstract.

West et al., Solid State Chemistry and Its Applications, Wiley, New York, 358 (1988).

Young et al., "Antisense Ablation of Type I Metabotropic Glutamate Receptor mGluR$_1$ Inhibits Spinal Nociceptive Transmission", The Journal of Neuroscience, vol. 18, pp. 10180-10188 (1998).

Young et al., "Behavioural and electrophysiological evidence supporting a role for group I metabotropic glutamate receptors in the mediation of nociceptive inputs to the rat spinal cord", vol. 777, pp. 161-169 (1997).

Young et al., "Evidence for a Role of Metabotropic Glutamate Receptors in Sustained Nociceptive Inputs to Rat Dorsal Horn Neurons", Neuropharmacology, vol. 33, pp. 141-144 (1994).

Zheng et al., "Correlation between brain/plasma ratios and efficacy in neuropathic pain models of selective metabotropic glutamate receptor 1 antagonists", Bioorganic & Medicinal Chemistry Letters, vol. 16, pp. 4936-4940 (2006).

Zheng et al., "Structure—Activity Relationship of Triazafluorenone Derivatives as Potent and Selective mGluR1 Antagonists", Journal of Medicinal Chemistry, American Chemical Society, Washington, US, vol. 48, pp. 7374-7388 (2005).

International Search Report for International Application No. PCT/US2005/020972, mailed Oct. 26, 2005 (5 pages).

International Search Report for International Application No. PCT/US2006/046943, mailed Aug. 30, 2007 (5 pages).

* cited by examiner

MGLUR1 ANTAGONISTS AS THERAPEUTIC AGENTS

FIELD OF THE INVENTION

The present invention relates to tricyclic compounds useful as metabotropic glutamate receptor (mGluR) antagonists, particularly as selective metabotropic glutamate receptor 1 antagonists, pharmaceutical compositions containing the compounds, and methods of treatment using the compounds and compositions to treat diseases associated with metabotropic glutamate receptor (e.g., mGluR1) such as, for example, pain, migraine, anxiety, urinary incontinence and neurodegenerative diseases such Alzheimer's disease.

BACKGROUND OF THE INVENTION

Glutamate is an important excitatory neurotransmitter in the mammalian central nervous system. Glutamate synaptic responses in the central nervous system (CNS) are mediated via activation of two families of receptors; ligand-gated cation channels termed ionotropic glutamate receptors, and G-protein-coupled receptors known as metabotropic glutamate receptors (mGluRs). Thus far, eight mGluR subtypes, together with splice variants, have been cloned and characterized in functional studies (Schoepp et al. *Neuropharmacology*, 1999, 38, 1431-1476). The eight mGluRs are grouped into three classes based on structural homology, pharmacology and signal transduction mechanisms.

Group I receptors (mGluR1 and mGluR5) couple through $G_q/_{11}$ proteins to the activation of phospholipase C (PLC) resulting in phosphoinositide (PI) hydrolysis, the release of calcium from intracellular stores. While group II (mGluR2 and mGluR3) and III (mGluR4, mGluR6 mGluR7 and mGluR8) are negatively coupled to adenyl cyclase (AC) through $G_i/G_o$ proteins thereby inhibiting cyclic AMP (cAMP) formation (Francesconi and Duvoisin, 1998).

Glutamate and Pain

Chronic pain is an area of high unmet medical need. Current therapies are not adequate and chronic pain is often refractory to most commonly used analgesics, including opioids. Glutamate plays a major role in nociceptive processing. Glutamate receptors, including mGluRs, are expressed in relevant areas of the brain, spinal cord and periphery that are involved in pain sensation and transmission.

Chronic pain may be due to tissue injury and diseases (inflammatory pain) or of the central and peripheral nervous system (neuropathic pain) and is associated with severe chronic sensory disturbances characterized by spontaneous pain, hyperalgesia (exaggerated responsiveness to painful stimuli) and allodynia (wrong perception of non noxious stimuli as painful). Prevalent symptoms in human patients include cold hyperalgesia, mechanical allodynia and less commonly, heat hyperalgesia.

Chronic pain is a true disease. It is believed to be a result of the plasticity at synapses in nociceptive processing centers, a phenomenon referred to as "central sensitization" which consists of increased excitability of spinal cord dorsal horn neurons. Glutamate receptors have been identified for their key role in central sensitization. Plasticity at synapses involved in nociceptive processing requires activation of ionotropic glutamate receptors NMDA and this plasticity is modulated by mGluRs including mGluR1. NMDA receptor antagonists have been tested in experimental therapies for the prevention and treatment of persistent pain following injury. However there are significant undesirable side effects associated with the use of NMDA antagonists due largely to the critical role of those receptors in normal excitatory synaptic transmission throughout the nervous system. These side effects include psychosis, hyperactivity, fatigue, dizziness, and in the case of higher levels of NMDA antagonists, amnesia and neuronal toxicity. Drugs designed to target mGluRs responsible for persistent alterations in nociception such as antagonists at mGluR1 might have reduced effects on excitatory transmission since their role of modulators of NMDA receptor-dependent plasticity in the dorsal horn, while effectively modifying the abnormal elevation of transmission thought to underlie persistent pain states. Thus mGluR antagonists might perform well clinically in chronic pain states without the side effects inherent to NMDA receptor antagonists.

mGluR1 and Pain

A number of behavioral (Fisher et al. *Neuroreport*, 1998, 20, 1169-1172; Fundytus et al. *Neuroreport*, 1998, 9, 731-735; Bhave et al. *Nature Neurosci.*, 2001, 4, 417-423; Dolan et al. *Neuropharmacology*, 2002, 43, 319-326; Dolan et al. *Pain*, 2003, 106, 501-512) and electrophysiological (Young et al. *Neuropharmacology*, 1994, 33, 141-144; and Young et al. *Brain Res.*, 1997, 777, 161-169) studies have demonstrated a specific role for Group I mGluRs, and in particular mGluR1 receptors, in nociceptive processing in the CNS, including mechanisms of hyperalgesia and inflammation. In the spinal cord, mGluR1 appears to be localized primarily on postsynaptic elements throughout the dorsal and ventral horns. (Neugebauer, *Trends Neurosci.*, 2001, 24, 550-552). The intrinsic activation of spinal mGluR1 in chronic nociception has been demonstrated using antagonists, antibodies and antisense oligonucleotides. Intrathecal administration of an mGluR1 antagonist produced antinociceptive effects in the second phase of formalin-induced nociceptive behavior (Neugebauer, *Trends Neurosci.*, 2001, 24, 550-552). Behavioral studies have also addressed the role of spinal mGluR1 receptors in the spinal injury and ligation models of neuropathic pain. Expression of mGluR1 is increased in rats following spinal cord injury and this may mediate the chronic central pain induced by the injury (Mills and Hulsebosch, *Neurosci. Lett.*, 2002, 319, 59-62). Knockdown of spinal mGluR1 by intrathecal infusion of antisense oligonucleotides attenuated cold hyperalgesia and mechanical allodynia in neuropathic rats (Fundytus et al. *Br. J. Pharmacol.*, 2001, 132, 354-367; and Fundytus et al. *Pharmacol. Biochem. Behav.*, 2002, 73, 401-410). Additionally, spinal administration of anti-mGluR1 IgG antibodies reduced cold hyperalgesia, but not mechanical allodynia, in neuropathic rats (Fundytus et al. *Neuroreport*, 1998, 9, 731-735). The critical role of spinal mGluR1 receptors in pain-related central sensitization is emphasized at the single cell level by electrophysiological in vivo studies in anesthetized animals. Intraspinal administration of an mGluR1 antagonist inhibited the responses of primate spinothalamic tract neurons to brief noxious, but not innocuous, mechanical cutaneous stimuli, as well as central sensitization in the capsaicin pain model (Neugebauer et al. *J. Neurophysiol.*, 1999, 82, 272-282). In rats with knocked down mGluR1 expression, the responses of multireceptive dorsal horn neurons to noxious input evoked by repeated topical applications of the C-fiber irritant mustard oil were significantly reduced compared to control neurons; the responses to innocuous cutaneous stimuli were not significantly different (Young et al. *J. Neurosci.*, 1998, 18, 10180-10188).

SUMMARY OF THE INVENTION

In its many embodiments, the present invention provides a novel class of tricyclic compounds useful as metabotropic glutamate receptor (mGluR) antagonists, particularly as selective mGluR1 antagonists, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the mGluRs, particularly mGluR1, using such compounds or pharmaceutical compositions.

In one aspect, the present application discloses a compound of formula I:

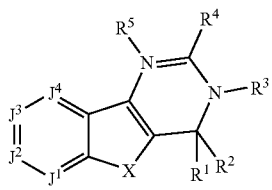

formula I or a pharmaceutically acceptable salt, solvate or ester thereof, wherein:

$J^1$, $J^2$, $J^3$ and $J^4$ are independently N, N→O, or C(R), provided that 0-2 of $J^1$, $J^2$, $J^3$ and $J^4$ are N or N→O;

----- is a single or double bond;

R is selected from the group consisting of H, halo, $-NR^6R^7$, $-OR^6$, $-SR^6$, $-CF_3$, $-OCF_3$, $-OCHF_2$, $-OCH_2F$, $-CN$, $-C(O)R^6$, $-C(O_2)R^6$, $-OC(O)R^6$, $-C(O)NR^6R^7$, $-N(R^6)C(O)R^6$, $-OS(O_2)R^6$, $-S(O_2)R^6$, $-S(O_2)NR^6R^7$, $-N(R^6)S(O_2)R^6$, $-N(R^6)C(O)NR^6R^7$, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein said alkyl, aryl, heteroaryl, aralkyl, heteroaralkyl, cycloalkyl, heterocyclyl, cycloalkylalkyl, and heterocyclylalkyl are optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, $-CF_3$, $-OCF_3$, $-OCHF_2$, $-OCH_2F$, $-CN$, $-NO_2$, $-OR^6$, $-SR^6$, $-NR^6R^7$, $-C(O)R^6$, $-C(O_2)R^6$, $-OCOR^6$, $-C(O)NR^6R^7$, $-N(R^6)C(O)R^6$, $-OS(O_2)R^6$, $-S(O_2)R^6$, $-S(O_2)NR^6R^7$, $-N(R^6)S(O_2)R^6$, or $-N(R^6)C(O)NR^6R^7$, or two adjacent substituents are linked to form a methylenedioxy or ethylenedioxy;

X is O, S, $N(R^8)$, C(O), or $C(R^aR^b)$;

$R^1$ is selected from the group consisting of H, $-OR^6$, $-SR^6$, $-NR^6R^7$, halo, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein said alkyl, aryl, heteroaryl, aralkyl, heteroaralkyl, cycloalkyl, heterocyclyl, cycloalkylalkyl, and heterocyclylalkyl are optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, $-CF_3$, $-OCF_3$, $-OCHF_2$, $-OCH_2F$, $-CN$, $-NO_2$, $-OR^6$, $-SR^6$, $-NR^6R^7$, $-C(O)R^6$, $-C(O_2)R^6$, $-OC(O)R^6$, $-C(O)NR^6R^7$, $-N(R^6)C(O)R^6$, $-OS(O_2)R^6$, $-S(O_2)R^6$, $-S(O_2)NR^6R^7$, $-N(R^6)S(O_2)R^6$, or $-N(R^6)C(O)NR^6R^7$, or two adjacent substituents are linked to form a methylenedioxy or ethylenedioxy;

$R^2$ is selected from the group consisting of H, halo, alkyl, $-N(R^{12})_2$, $-OR^{12}$ and $-SR^{12}$, wherein said alkyl is optionally substituted with one or more substituents independently selected from halo, hydroxy or alkoxy; or $R^1$ and $R^2$ optionally taken together form (=O) or (=S);

$R^3$ is selected from the group consisting of H, $-NR^6R^7$, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein said alkyl, aryl, heteroaryl, aralkyl, heteroaralkyl, cycloalkyl, heterocyclyl, cycloalkylalkyl, and heterocyclylalkyl are optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, $-CF_3$, $-OCF_3$, $-OCHF_2$, $-OCH_2F$, $-CN$, $-NO_2$, $-OR^6$, $-SR^6$, $-NR^6R^7$, $-C(O)R^6$, $-C(O_2)R^6$, $-OC(O)R^6$, $-C(O)NR^6R^7$, $-N(R^6)C(O)R^6$, $-OS(O_2)R^6$, $-S(O_2)R^6$, $-S(O_2)NR^6R^7$, $-N(R^6)S(O_2)R^6$, or $-N(R^6)C(O)NR^6R^7$, or two adjacent substituents are linked to form a methylenedioxy or ethylenedioxy;

$R^4$ is selected from the group consisting of H, $-OR^6$, (=O), (=S), $-SR^6$, $-NR^6R^7$, halo, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein said alkyl, aryl, heteroaryl, aralkyl, heteroaralkyl, cycloalkyl, heterocyclyl, cycloalkylalkyl, and heterocyclylalkyl are optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, $-CF_3$, $-OCF_3$, $-OCHF_2$, $-OCH_2F$, $-CN$, $-NO_2$, $-OR^6$, $-SR^6$, $-NR^6R^7$, $-C(O)R^6$, $-C(O_2)R^6$, $-OC(O)R^6$, $-C(O)NR^6R^7$, $-N(R^6)C(O)R^6$, $-OS(O_2)R^6$, $-S(O_2)R^6$, $-S(O_2)R^6$, $-S(O_2)NR^6R^7$, $-N(R^6)S(O_2)R^6$, or $-N(R^6)C(O)NR^6R^7$, or two adjacent substituents are linked to form a methylenedioxy or ethylenedioxy; or $R^3$ and $R^4$ optionally taken together with intervening atoms form a 5-8 membered heterocyclic ring having 0-3 heteroatoms independently selected from O, N or S in addition to the intervening nitrogen;

$R^5$ is $R^3$ when ----- is a single bond and $R^5$ is absent when ----- is a double bond;

$R^6$ and $R^7$ are independently selected from the group consisting of H, alkyl, alkoxyalkyl, aryloxyalkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein each member of $R^6$ and $R^7$ except H is optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, —$CF_3$, —$OCF_3$, —$OCHF_2$, —$OCH_2F$, —CN, —$NO_2$, —$OR^{10}$, —$SR^{10}$, —$NR^9R^{10}$, —$C(O)R^{10}$, —$C(O_2)R^{10}$, —$OC(O)R^{10}$, —$C(O)NR^9R^{10}$, —$N(R^9)C(O)R^{10}$, —$OS(O_2)R^{10}$, —$S(O_2)R^{10}$, —$S(O_2)NR^9R^{10}$, —$N(R^9)S(O_2)R^{10}$, or —$N(R^9)C(O)NR^9R^{10}$, or two adjacent substituents are linked to form a methylenedioxy or ethylenedioxy; or $R^6$ and $R^7$, when attached to the same nitrogen atom, optionally taken together with the nitrogen atom form a 3-7 membered heterocyclic ring containing 0-3 heteroatoms independently selected from O, N or S in addition to said nitrogen atom;

$R^a$ is selected from the group consisting of H, halo, alkyl, hydroxyalkyl, alkoxyalkyl, and $N(R^{12})_2$;

$R^b$ is selected from the group consisting of H, halo, alkyl, hydroxyalkyl, and alkoxyalkyl;

$R^8$ is selected from the group consisting of H, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein each member of $R^8$ except H is optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, —$CF_3$, —$OCF_3$, —$OCHF_2$, —$OCH_2F$, —CN, —$NO_2$, —$OR^{10}$, —$SR^{10}$, —$NR^{10}R^{10}$, —$C(O)R^{10}$, —$C(O_2)R^{10}$, —$OC(O)R^{10}$, —$C(O)NR^9R^{10}$, —$N(R^9)C(O)R^{10}$, —$OS(O_2)R^{10}$, —$S(O_2)R^{10}$, —$S(O_2)NR^9R^{10}$, —$N(R^9)S(O_2)R^{10}$, or —$N(R^9)C(O)NR^9R^{10}$, or two adjacent substituents are linked to form a methylenedioxy or ethylenedioxy;

$R^9$ is H or alkyl;

$R^{10}$ is selected from H, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), heterocyclylalkyl optionally substituted with one or more (=O) or (=S); wherein each member of $R^{11}$ except H is optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, —$CF_3$, —$OCHF_2$, —$OCH_2F$, —$OCF_3$, —CN, —$NO_2$, —$OR^{12}$, —$SR^{12}$, —$N(R^{12})(R^{12})$, —$C(O)R^{12}$, —$C(O_2)R^{12}$, —$OC(O)R^{12}$, —$C(O)N(R^{12})(R^{12})$, —$N(R^{12})C(O)R^{12}$, —$OS(O_2)R^{12}$, —$S(O_2)R^{12}$, —$S(O_2)N(R^{12})(R^{12})$, —$N(R^{12})S(O_2)R^{12}$, or —$N(R^{12})C(O)N(R^{12})(R^{12})$, or two adjacent substituents are linked to form a methylenedioxy or ethylenedioxy; or $R^9$ and $R^{10}$, when attached to the same nitrogen atom, optionally taken together with the attached nitrogen atom form a 3-7 membered heterocyclic ring containing 0-3 heteroatoms independently selected from O, N or S in addition to the attached nitrogen; and two $R^{12}$s attached to the same nitrogen atom optionally taken together with the attached nitrogen atom form a 3-7 membered heterocyclic ring having 0-3 heteroatoms independently selected from O, N or S in addition to the attached nitrogen;

$R^{11}$ is halo, —$CF_3$, —$OCF_3$, —$OCHF_2$, —$OCH_2F$, —CN, —$NO_2$, —$OR^{12}$, —$SR^{12}$, —$N(R^{12})(R^{12})$, —$C(O)R^{12}$, —$C(O_2)R^{12}$, —$OC(O)R^{12}$, —$C(O)N(R^{12})(R^{12})$, —$N(R^{12})C(O)R^{12}$, —$OS(O_2)R^{12}$, —$S(O_2)R^{12}$, —$S(O_2)N(R^{12})(R^{12})$, —$N(R^{12})S(O_2)R^{12}$, or —$N(R^{12})C(O)N(R^{12})(R^{12})$; and $R^{12}$ is H or alkyl.

The compounds of formula I are useful as selective metabotropic glutamate receptor 1 antagonists and thus are useful in the treatment and prevention of pain (neurotropic or inflammatory), migraine, anxiety, urinary incontinence and neurodegenerative diseases such Alzheimer's disease.

DETAILED DESCRIPTION

In one embodiment, the present invention discloses tricyclic compounds which are represented by structural formula I or a pharmaceutically acceptable salt, solvate or ester thereof, wherein the various moieties are as described above.

In another embodiment, the present invention discloses tricyclic compounds of formula I or a pharmaceutically acceptable salt, solvate or ester thereof, wherein the various moieties are as described above with one of the following provisos 1-11:

proviso 1: when ----- is a double bond; $R^5$ is absent; $R^1$ and $R^2$ taken together are (=O); X is O, S or $NR^{12}$; then $R^3$ is not H;

proviso 2: when ----- is a double bond; $R^5$ is absent; $R^1$ and $R^2$ taken together are (=O); then either (a) $J^1$, $J^2$, $J^3$ and $J^4$ are each C(H);
X is S or O;
$R^3$ is 3-(3-hydroxypiperidin-2-yl)-2-oxo-propyl; and
$R^4$ is not H;
or (b) $J^1$, $J^2$, $J^3$ and $J^4$ are each C(H);
X is NH;
$R^3$ is $C_1$-$C_3$ alkyl or $NH_2$; and
$R^4$ is not H, —$(CH_2)_4$—N-(optionally substituted piperazine) or —S—$(CH_2)_3$—N-(optionally substituted piperazine);
or (c) $J^1$, $J^2$, $J^3$ and $J^4$ are each C(H);
X is NH,
$R^3$ is —$NH_2$, —$(CH_2)_{2-3}$—OH, —$(CH_2)_{2-3}$-halo or —$(CH_2)_{2-3}$—N-(optionally substituted piperazine); and
$R^4$ is not H or $C_1$-$C_3$ alkyl;
or (d)(i) $J^1$ is N, $J^2$ and $J^3$ are each C(H), and $J^4$ is $C(N(CH_3)_2)$;
X is S;
$R^4$ is H; and
$R^3$ is not benzyl, phenyl, p-chlorophenyl, p-methylphenyl, or p-methoxyphenyl;
or (d)(ii) $J^1$ is N, $J^2$ is $C(CH_3)$ or $C(NH_2)$, $J_3$ is C(H), $C(NO_2)$ or $C(C(O)CH_3)$ and $J^4$ is $C(CH_3)$ or C (optionally substituted phenyl);
X is S;
$R^4$ is H or $CH_3$; and
$R^3$ is not benzyl, phenyl, p-chlorophenyl, p-methylphenyl, p-methoxyphenyl, or 2-methyl-4-nitrophenyl;
or (e) $J^1$ is N and $J^2$, $J^3$ and $J^4$ are each $C(R^{13})$, wherein $R^{13}$ is H, $CF_3$, $C_1$-$C_3$ alkyl, —$CONH(C_1$-$C_6$ alkyl), —$CO_2Et$, optionally substituted phenyl or benzyl;
X is O or S;
$R^4$ is H, halo, —$NR^6R^7$, $C_1$-$C_4$ alkyl, or phenyl; and
$R^3$ is not —$NH_2$, —NH(phenyl), or $C_1$-$C_4$ alkyl optionally substituted with halo, OH, pyridyl, —$NR^6R^7$, $CO_2R^2$, $COR^{12}$, —S—$(CH_2)_{2-3}$OH, —SH, or —$S(CH_2)_{2-3}$$CO_2R^{12}$;
or (f) $J^4$ is N and $J^1$, $J^2$ and $J^3$ are each $C(R^{12})$;
X is S;

$R^3$ is $C_1$-$C_4$ alkyl, $NH_2$, or NH-(phenyl); and
$R^4$ is not H, $C_1$-$C_4$ alkyl, or $NH_2$;
or (g) $J^1$ and $J^2$ are each N and $J^3$ and $J^4$ are each C(phenyl) or C(2-furanyl);
  X is S;
  $R^3$ is $NH_2$, optionally substituted phenyl, or $C_1$-$C_4$ alkyl optionally substituted with CN or C(O)-phenyl; and
  $R^4$ is not H, methyl, or —$NR^6R^7$;
or (h) $J^2$ is C(R) and $J^4$ is C(H);
  X is S;
  $R^4$ is H, $C_1$-$C_3$ alkyl, $NH_2$, $N(CH_3)_2$, NH-(phenyl); and $J^1$ and $J^3$ are not both N;
proviso 3: when ---- is a double bond; $R^5$ is absent; $R^1$ and $R^2$ taken together are (=S); $J^1$ is N; $J^2$ is C(H), C($CH_3$) or C(phenyl); $J^3$ is C(H), and $J^4$ is C($CH_3$) or C(N($CH_3$)$_2$); X is S; and $R^4$ is H or $CH_3$; then $R^3$ is not H, $NH_2$, phenyl, halo substituted phenyl, or $C_1$-$C_6$ alkyl optionally substituted with N($C_1$-$C_3$ alkyl)$_2$ or OH;
proviso 4: when ---- is a double bond; $R^5$ is absent; $R^1$ is —$CH_2CO_2Et$ or —$CH_2CN$; $R^2$ is H; $J^1$ and $J^2$ are N and $J^3$ and $J^4$ are C(phenyl); X is S; and $R^3$ is phenyl or p-fluorophenyl; then $R^4$ is not —$NR^6R^7$;
proviso 5: when ---- is a single bond; $R^4$ is (=O); and $R^1$ and $R^2$ taken together are (=O); then
  either (a) X is O, S or N($R^8$); and
    $R^3$ is not alkyl substituted with N-3a,4-dihydrobenzopyrano[3,4-c]pyrrolidine or N-3a,4-dihydrobenzopyrano[3,4-c]piperidine, N-1,2,3,4,4a,5-hexahydropyrazino[2,1-c][1,4]benzoxazine, or N-(2-phenyl)pyrrolidine, wherein said benzo or phenyl is optionally substituted;
  or (b) $J^1$, $J^2$, $J^3$ and $J^4$ are each C($R^{14}$), wherein $R^{14}$ is H, halo, alkoxy, $NO_2$, $NHSO_2$-alkyl, or $NH_2$;
    X is O, S, N(H), N($CH_3$) or N-(optionally substituted benzyl); and
    $R^3$ and $R^5$ are not both H, OH or alkyl;
  or (c) $J^1$, $J^2$, $J^3$ and $J^4$ are each C(H) or C(halo);
    X is S, N($CH_3$) or N(benzyl);
    $R^5$ is H or halo substituted benzyl; and $R^3$ is not —$CH_2CO_2R^{12}$; or $R^5$ is H or —$CH_2CO_2R^{12}$ and $R^3$ is not benzyl or halo substituted benzyl;
  or (d) $J^1$, $J^2$, $J^3$ and $J^4$ are each C(H);
    X is NH, N($CH_3$) or S;
    $R^5$ is H or $CH_3$; and
    $R^3$ is not —$(CH_2)_{2-3}$—N-(optionally substituted piperazine), —$(CH_2)_{2-3}$—N($C_1$-$C_3$ alkyl)$_2$, —$(CH_2)_{2-3}$—N-pyrrolidine, —$(CH_2)_{2-3}$—N-piperidine, or —$(CH_2)_{2-3}$—N-morpholine;
  or (e) $J^1$ is N and $J^2$, $J^3$ and $J^4$ are each C(R);
    X is S;
    $R^5$ is H; and
    $R^3$ is not $NH_2$, optionally substituted phenyl, —$(CH_2)_2NH(CH_2)_2NH_2$, alkyl optionally substituted with halo, hydroxy or amino;
  or (f) $J^1$, $J^2$ and $J^3$ are each CH and $J^4$ is N;
    X is S;
    $R^5$ is H; and
    $R^3$ is not alkyl substituted with N-1,3,3a,4,5,9b-hexahydro-2H-benzo[e]isoindole wherein benzo is optionally substituted;
  or (g) $J^1$ and $J^2$ are each N and $J^3$ and $J^4$ are each C(2-furanyl);
    X is S;
    $R^3$ is phenyl; and
    $R^5$ is not H;
  or (h) $J^1$ and $J^4$ are each N and $J^2$ and $J^3$ are each C(H);

X is S;
$R^3$ and $R^5$ are not both H;
proviso 6: when ---- is a single bond; $R^4$ is (=O); $R^1$ is optionally substituted phenyl; $R^2$ is H; and X is CO; then $R^3$ and $R^5$ are not both H;
proviso 7: when ---- is a single bond; $R^1$ and $R^2$ taken together are (=O); $J^1$ and $J^2$ are each N and $J^3$ and $J^4$ are each C(phenyl); X is S; and $R^4$ is optionally substituted phenyl; then $R^3$ and $R^5$ are not both H;
proviso 8: when ---- is a single bond; $R^4$ is (=S); $R^1$ and $R^2$ taken together are (=O) or (=S); X is S; $R^5$ is H; and (i) $J^1$ and $J^3$ are N or (ii) $J^1$ is N, $J^2$ is C($R^{15}$), $J^3$ is C($R^{16}$) or N, and $J^4$ is C($CH_3$) or C (optionally substituted phenyl), wherein $R^{15}$ is $CH_3$, $NH_2$, phenyl or 2-thienyl and $R^{16}$ is H, —CN, —C(O)$CH_3$ or —$CO_2Et$; then $R^3$ is not H or phenyl;
proviso 9: when $J^1$, $J^2$, $J^3$ and $J^4$ are each C(H); $R^1$ and $R^2$ taken together are (=O); X is NH or S; and $R^4$ is (=S) or —$SR^6$; then $R^3$ is not —$NH_2$;
proviso 10: when $J^1$ is N, $J^3$ is C(H), $J^4$ is C($CH_3$) or C(phenyl) and $J^2$ is C($CH_3$), C (optionally substituted phenyl) or C(2-thienyl); X is S; and $R^4$ is H, (=S) or —$SR^6$; then $R^3$ is not $NH_2$, $C_1$-$C_4$ alkyl, —$CH_2CO_2Et$, or optionally substituted phenyl; and
proviso 11: when $J^1$, $J^2$, $J^3$ and $J^4$ are each C(H); and $R^3$ and $R^4$ form a ring with the intervening atoms; then X is not NH or S.

In one embodiment, X is O, S, or $NR^8$.
In another embodiment, at least one of $J^1$-$J^4$ is N or N→O.
In another embodiment, one of $J^1$-$J^4$ is N or N→O and $R^1$ is selected from the group consisting of H, —$OR^6$, —$SR^6$, halo, alkyl, aryl, heteroaryl, aralkyl, heteroaralkyl, cycloalkyl optionally substituted with one or more (=O) or (=S), heterocyclyl optionally substituted with one or more (=O) or (=S), cycloalkylalkyl optionally substituted with one or more (=O) or (=S), and heterocyclylalkyl optionally substituted with one or more (=O) or (=S); wherein said alkyl, aryl, heteroaryl, aralkyl, heteroaralkyl, cycloalkyl, heterocyclyl, cycloalkylalkyl, and heterocyclylalkyl are optionally substituted with one or more substituents independently selected from halo, alkyl optionally substituted with one or more $R^{11}$, aryl optionally substituted with one or more $R^{11}$, cycloalkyl optionally substituted with one or more $R^{11}$, heteroaryl optionally substituted with one or more $R^{11}$, heterocyclyl optionally substituted with one or more $R^{11}$, —$CF_3$, —$OCF_3$, —$OCHF_2$, —$OCH_2F$, —CN, —$NO_2$, —$OR^6$, —$SR^6$, —$NR^6R^7$, —C(O)$R^6$, —C($O_2$)$R^6$, —$OCOR^6$, —C(O)$NR^6R^7$, —N($R^6$)C(O)$R^6$, —OS($O_2$)$R^6$, —S($O_2$)$R^6$, —S($O_2$)$NR^6R^7$, —N($R^6$)S($O_2$)$R^6$, or —N($R^6$)C(O)$NR^6R^7$, or two adjacent substituents are linked to form a methylenedioxy or ethylenedioxy.

In another embodiment, $R^1$ and $R^2$ are taken together to form (=O) or (=S).

In another embodiment ---- is a double bond and $R^1$ and $R^2$ taken together are (=O) represented by formula Ia. In another embodiment, X is S (formula IIa) or O (formula IIb). In yet another embodiment, X is S (formula IIa).

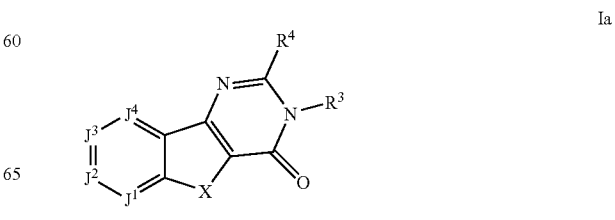

Ia

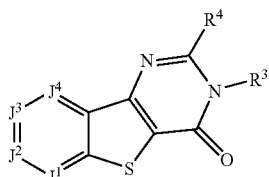
IIa

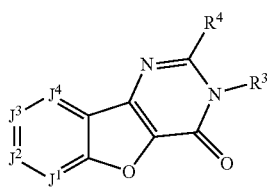
IIb

In another embodiment, $J^1$ is N or N→O and $J^2$, $J^3$ and $J^4$ are each C(R).

In another embodiment, the present compounds are pyrido[3',2':4,5]thieno[3,2-d]pyrimidin-4-ones represented by formula IIIa.

In yet another embodiment, the present compounds are represented by formula IVa, formula Va or formula Vb (in both formulae Va and Vb, $R^{15}$ is a suitable substituent of the phenyl ring as defined herein).

In another embodiment, $J^2$ is N or N→O and $J^1$, $J^3$ and $J^4$ are each C(R).

In another embodiment, the present compounds are pyrido[4',5':4,5]thieno[3,2-d]pyrimidin-4-ones represented by formula IIIb.

In another embodiment, $J^3$ is N or N→O and $J^1$, $J^2$ and $J^4$ are each C(R).

In another embodiment, the present compounds are pyrido[5',4':4,5]thieno[3,2-d]pyrimidin-4-ones represented by formula IIIc.

In another embodiment, $J^4$ is N or N→O and $J^1$, $J^2$ and $J^3$ are each C(R).

In another embodiment, the present compounds are pyrido[2',3':4,5]thieno[3,2-d]pyrimidin-4-ones represented by formula IIId.

In another embodiment, $J^1$ and $J^4$ are each N and $J^2$ and $J^3$ are each C(R).

In another embodiment, the present compounds are pyrazino[3',2':4,5]thieno[3,2-d]pyrimidin-4-ones represented by formula IIIe.

In another embodiment, $J^1$ and $J^2$ are each N and $J^3$ and $J^4$ are each C(R).

In another embodiment, the present compounds are pyridazino[4',3':4,5]thieno[3,2-d]pyrimidin-4-ones represented by formula IIIf.

In another embodiment, $J^1$ and $J^3$ are each N and $J^2$ and $J^4$ are each C(R).

In another embodiment, the present compounds are pyrimido[5',4':4,5]thieno[3,2-d]pyrimidin-4-ones represented by formula IIIg.

In another embodiment, $J^2$ and $J^4$ are each N and $J^1$ and $J^3$ are each C(R).

In another embodiment, the present compounds are pyrimido[4',5':4,5]thieno[3,2-d]pyrimidin-4-ones represented by formula IIIh.

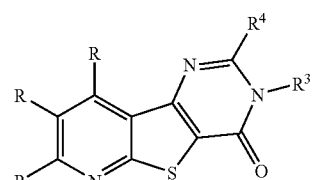
IIIa

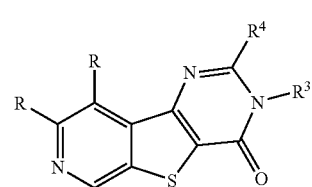
IIIb

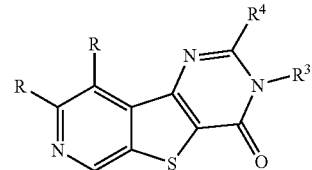
IIIc

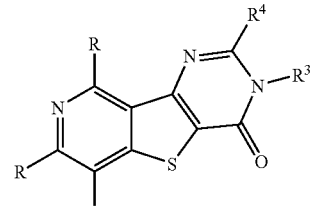
IIId

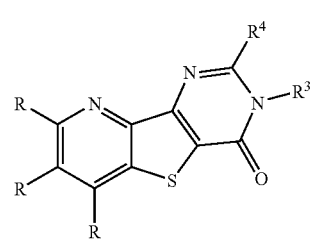
IIIe

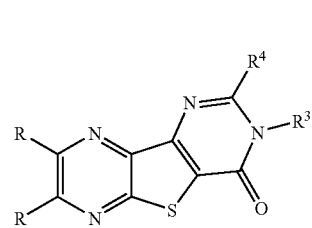
IIIf

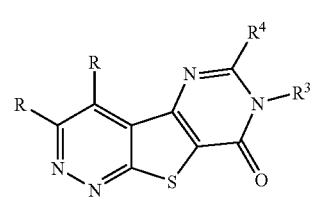
IIIg

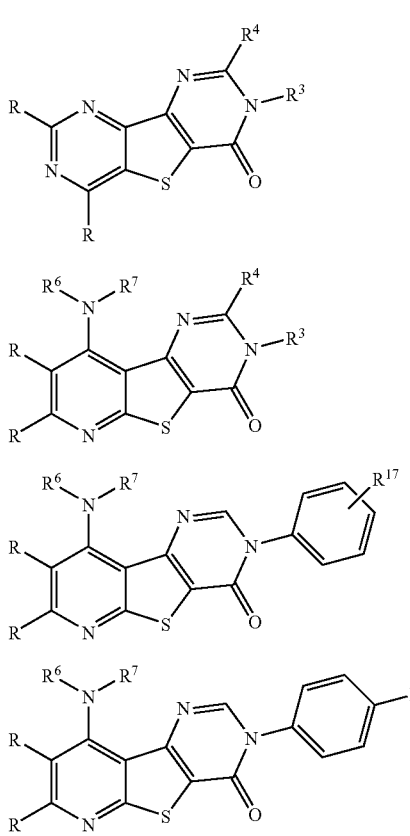

IIIh

IVa

Va

Vb

In yet another embodiment, $J^2$ and $J^3$ are C(H) or C(halo). In another embodiment, $R^4$ is H.

In another embodiment, R is H, halo, alkyl, alkoxy, cycloalkyl, heteroaryl, —$OSO_2R^6$, or —$NR^6R^7$ wherein $R^6$ and $R^7$ optionally taken together with the nitrogen atom form a 4-7 membered heterocyclic ring having 0-1 heteroatoms independently selected from O or N in addition to said nitrogen atom.

In another embodiment, R is H, —N($C_1$-$C_6$ alkyl)$_2$, —NH($C_1$-$C_6$ alkyl), halo, —$C_1$-$C_6$ alkoxy, —$OSO_2CF_3$, —NH—($C_3$-$C_6$ cycloalkyl), —NH-phenyl, N-piperidinyl, N-morpholinyl, $C_1$-$C_6$ alkyl, $C_3$-$C_6$ cycloalkyl, N-pyrrolyl, N-pyrazolyl, N-piperazinyl, or N-pyrrolidinyl optionally substituted with hydroxy or (=O).

In another embodiment, the ($C_1$-$C_6$ alkyl) of said —NH($C_1$-$C_6$ alkyl) is optionally substituted with —OH or —$CF_3$.

In another embodiment, $R^3$ is alkyl, alkoxyalkyl, cycloalkyl, heteroaryl, heteroaralkyl, cycloalkylalkyl, aralkyl, aryl, heterocyclyl or heterocyclylalkyl; wherein each member of $R^3$ is optionally substituted with one or more substituents independently selected from halo, —CN, —$OR^{12}$, alkyl, alkoxy, —$OCF_3$, —$OCHF_2$, amino, alkylamino, dialkylamino, hydroxyalkyl, —$NR^{12}C(O)R^{12}$, —$C(O)N(R^{12})_2$, cyanoalkyl, —$CO_2R^{12}$, —$CF_3$, or two adjacent substituents are linked to form a methylenedioxy or ethylenedioxy; and said heterocyclyl is additionally and optionally substituted by (=O).

In another embodiment, $R^3$ is $C_1$-$C_6$ alkyl, $C_3$-$C_7$ monocyclic cycloalkyl, 9-membered cycloalkylaryl, 9-membered cycloalkenylaryl, 6-membered monocyclic heteroaryl or heterocyclyl, 9- to 10-membered bicyclic heteroaryl or heterocyclyl, $C_6$ cycloalkyl($C_1$-$C_6$)alkyl, ar($C_1$-$C_6$)alkyl, or aryl; wherein said aryl is optionally substituted with one or more substituents independently selected from halo, —CN, —OH, $C_1$-$C_6$ alkyl, $C_1$-$C_6$ alkoxy, —$OCF_3$, —$OCHF_2$, amino, $C_1$-$C_6$ alkylamino, di($C_1$-$C_6$)alkylamino, hydroxy($C_1$-$C_6$) alkyl, or two adjacent substituents of said aryl are linked to form a methylenedioxy or ethylenedioxy. In another embodiment, aryl of $R^3$ is p-substituted.

In yet another embodiment, $R^3$ is cyclobutyl, cyclopentyl, cyclohexyl, cycloheptyl, benzyl, α-phenethyl, pyridyl, n-butyl, indolyl, benzothiazolyl, benzoimidazolyl, benzooxazolyl, cyclohexylmethyl, pyrano, indanyl, indenyl, phenyl, or 3,4-dihydrobenzo[1,4]oxazinyl; wherein said phenyl is optionally substituted with halo, —CN, —OMe, —$OCF_3$, —$OCHF_2$, —$NMe_2$, —OH, —$CH_2OH$, methyl, ethyl or two adjacent substituents of said phenyl are linked to form a methylenedioxy or ethylenedioxy; and said 3,4-dihydrobenzo[1,4]oxazinyl is optionally substituted with (=O). In another embodiment, phenyl of $R^3$ is p-substituted.

A list of representative compounds of the present invention is shown in Table 1 below.

TABLE I

| Cpd | Structure |
|---|---|
| 7A | 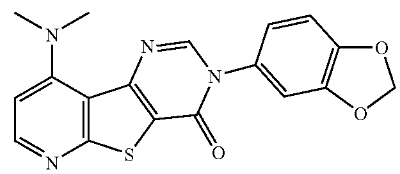 |
| 7B | 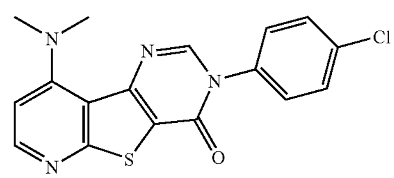 |
| 7C | 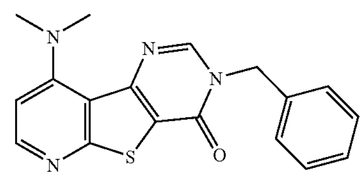 |
| 7D | 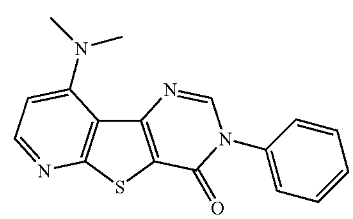 |
| 7E | 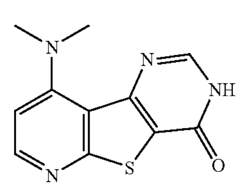 |

TABLE I-continued

| Cpd | Structure |
|---|---|
| 7F | (9-dimethylamino pyrido-thieno-pyrimidinone with 2-chlorophenyl) |
| 7G | (9-dimethylamino pyrido-thieno-pyrimidinone with 4-fluorophenyl) |
| 7H | (9-dimethylamino pyrido-thieno-pyrimidinone with 4-bromophenyl) |
| 7I | (9-dimethylamino pyrido-thieno-pyrimidinone with 4-chlorobenzyl) |
| 7J | (9-dimethylamino pyrido-thieno-pyrimidinone with 1-(ethoxycarbonyl)piperidin-4-yl) |
| 7K | (9-dimethylamino pyrido-thieno-pyrimidinone with 4-cyanophenyl) |
| 7L | (9-dimethylamino pyrido-thieno-pyrimidinone with 3-chlorophenyl) |
| 7M | (9-dimethylamino pyrido-thieno-pyrimidinone with 4-iodophenyl) |
| 7N | (9-dimethylamino pyrido-thieno-pyrimidinone with 2-iodo-4-chlorophenyl) |
| 7O | (9-dimethylamino pyrido-thieno-pyrimidinone with pyridin-3-yl) |
| 7P | (9-dimethylamino pyrido-thieno-pyrimidinone with n-butyl) |
| 7Q | (9-dimethylamino pyrido-thieno-pyrimidinone with cyclohexyl) |
| 7R | (9-dimethylamino pyrido-thieno-pyrimidinone with 3-chlorobenzyl) |

TABLE I-continued

| Cpd | Structure |
|---|---|
| 7S | 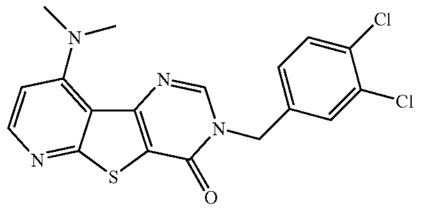 |
| 7T | 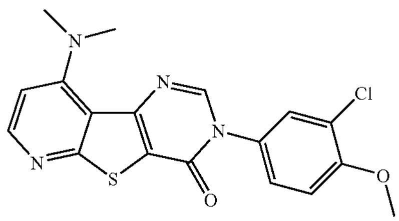 |
| 7U | 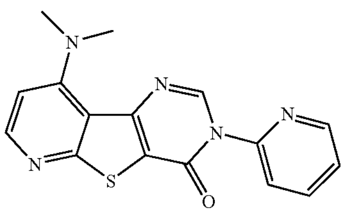 |
| 7V | 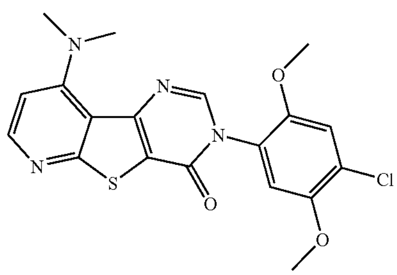 |
| 7W | 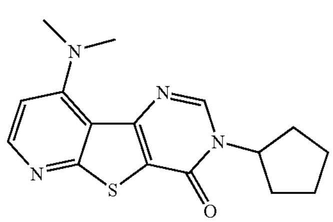 |
| 7X | 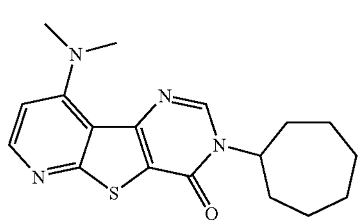 |
| 7Y | 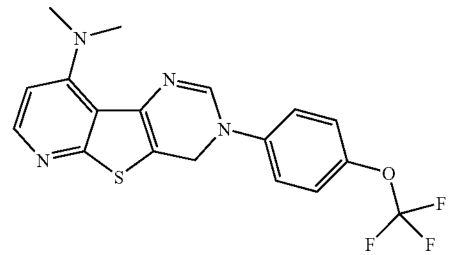 |
| 7Z | 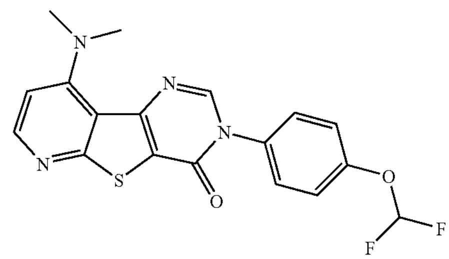 |
| 7AA | 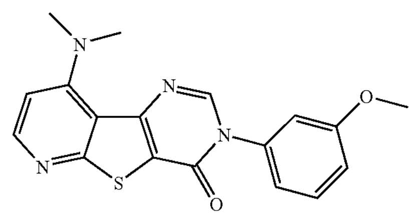 |
| 7AB | 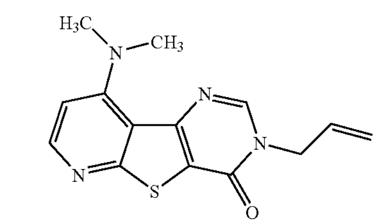 |
| 7AC | 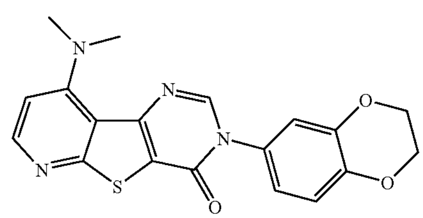 |
| 7AD | 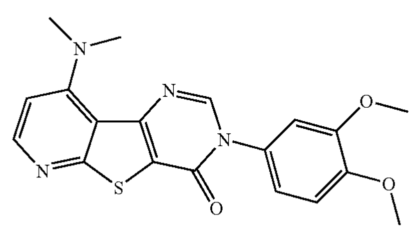 |

TABLE I-continued
| Cpd | Structure |
|---|---|
| 7AE | 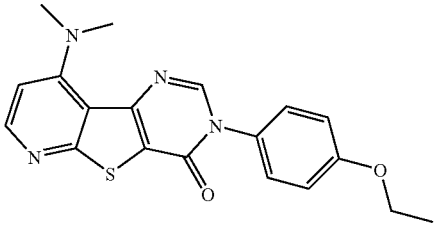 |
| 7AF | 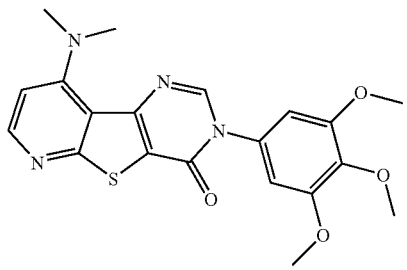 |
| 7AG | 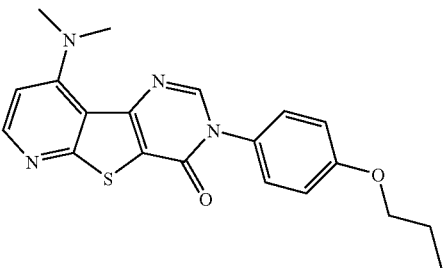 |
| 7AH | 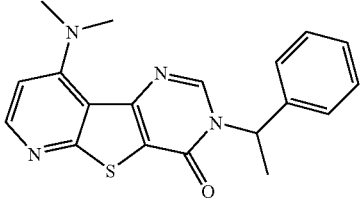 |
| 7AI | 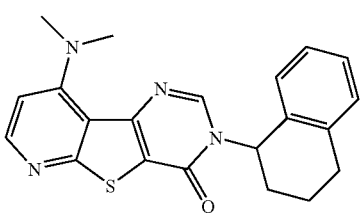 |
| 7AJ | 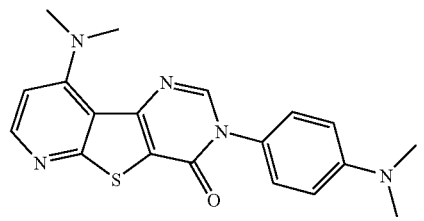 |
| 7AK | 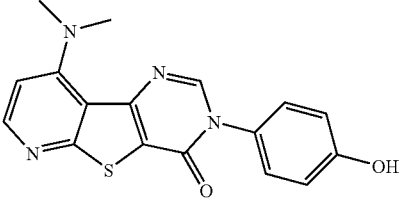 |
| 7AL | 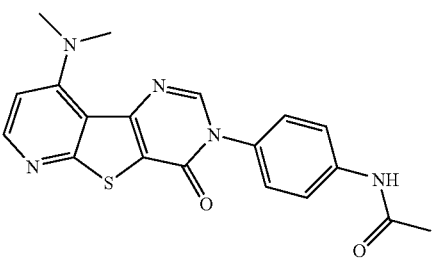 |
| 7AM | 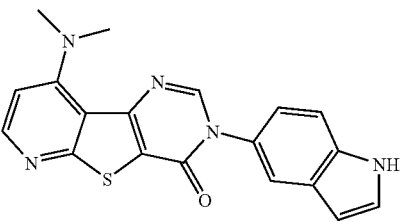 |
| 7AN | 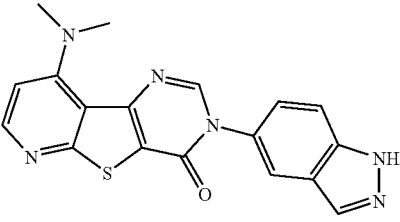 |
| 7AO | 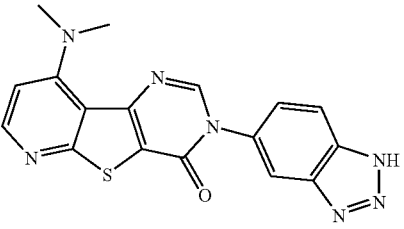 |
| 7AP | 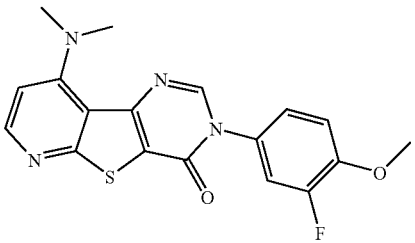 |

TABLE I-continued

| Cpd | Structure |
|---|---|
| 7AQ | (structure) |
| 7AR | (structure) |
| 7AS | (structure) |
| 7AT | (structure) |
| 7AU | (structure) |
| 7AV | (structure) |
| 7AW | (structure) |
| 7AX | (structure) |
| 7AY | (structure) |
| 7AZ | (structure) |
| 7BA | (structure) |
| 7BB | (structure) |

TABLE I-continued

| Cpd | Structure |
|---|---|
| 7BC | |
| 7BD | |
| 7BE | |
| 7BF | |
| 7BG | |
| 7BH | |
| 7BI | |
| 7BJ | |
| 7BK | |
| 7BL | |
| 7BM | |
| 7BN | |
| 7BO | |

TABLE I-continued
| Cpd | Structure |
|---|---|
| 7BP | 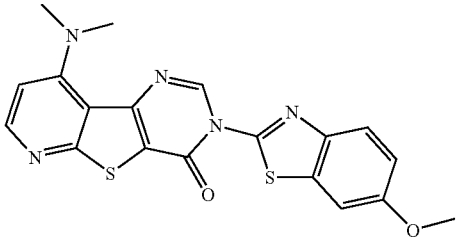 |
| 7BQ | 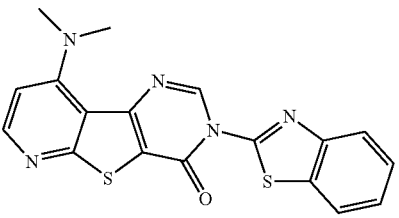 |
| 7BR | 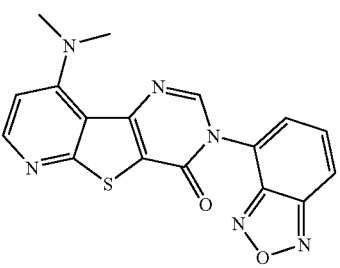 |
| 7BS | 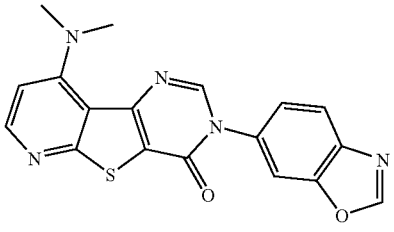 |
| 7BT | 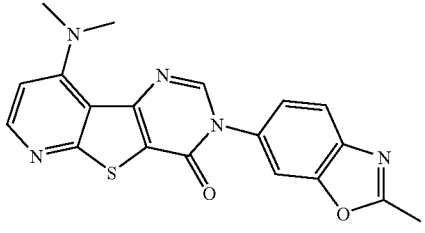 |
| 7BU | 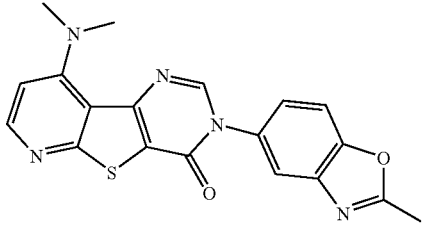 |
| 7BV | 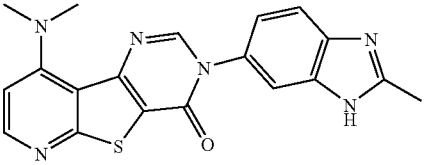 |
| 7BW | 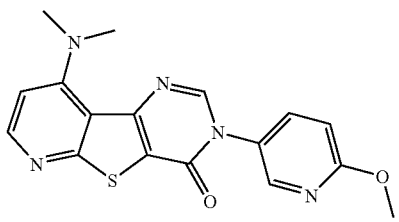 |
| 7BX | 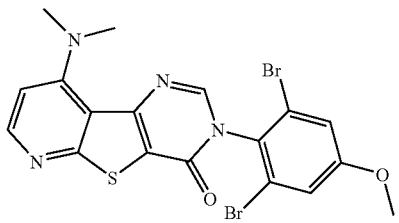 |
| 7BY | 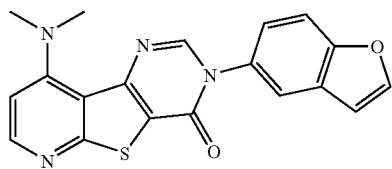 |
| 7BZ | 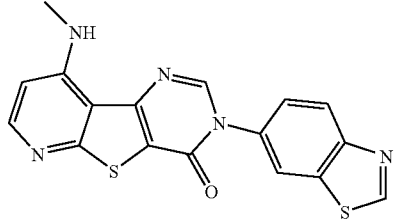 |
| 7CA | 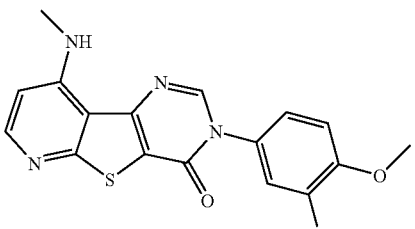 |
| 7CB | 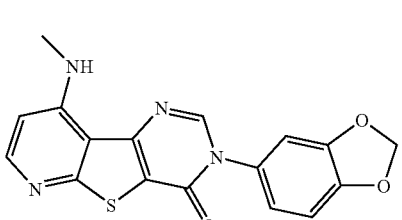 |

TABLE I-continued

| Cpd | Structure |
|---|---|
| 7CC | (structure) |
| 7CD | (structure) |
| 7CE | (structure) |
| 7CF | (structure) |
| 7CG | (structure) |
| 7CH | (structure) |
| 7CI | (structure) |
| 7CJ | (structure) |
| 7CK | (structure) |
| 7CL | (structure) |
| 7CM | (structure) |
| 7CN | (structure) |

TABLE I-continued
| Cpd | Structure |
|---|---|
| 7CO | 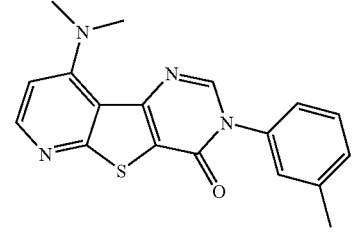 |
| 7CP | 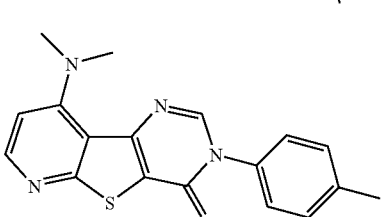 |
| 7CQ | 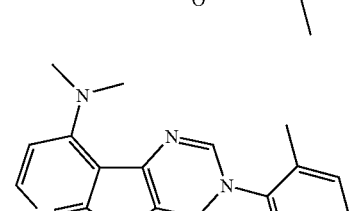 |
| 7CR | 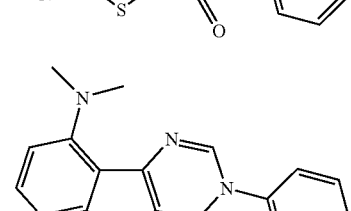 |
| 7CS | 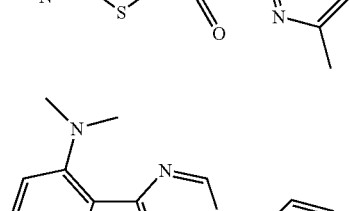 |
| 7CT | 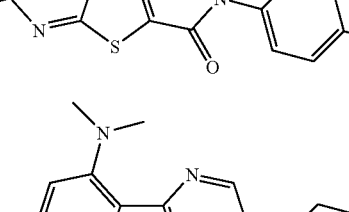 |
| 7CU | 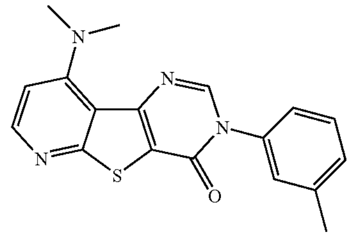 |
| 7CV | 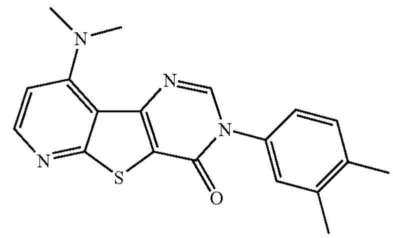 |
| 7CW | 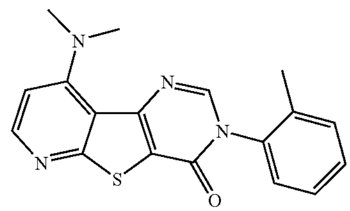 |
| 7CX | 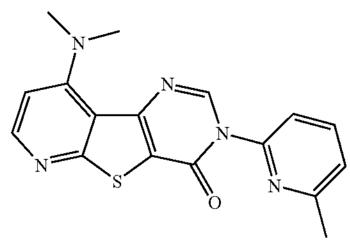 |
| 7CY | 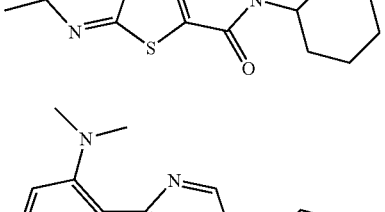 |
| 7CZ | 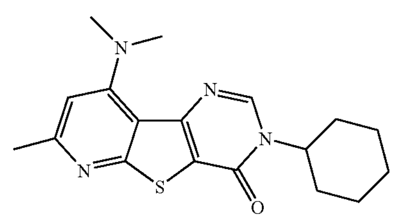 |
| 7DA | 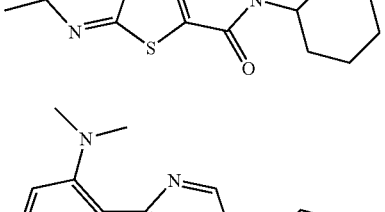 |

TABLE I-continued

| Cpd | Structure |
|---|---|
| 7DB | 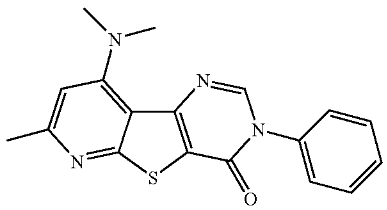 |
| 7DC | 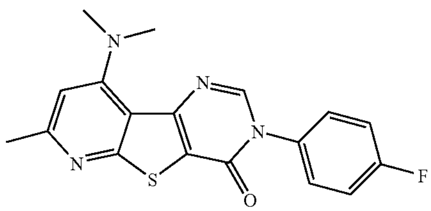 |
| 7DD | 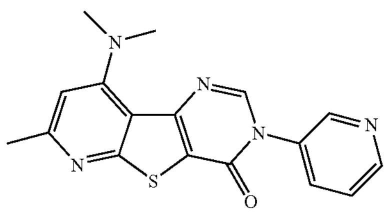 |
| 7DE | 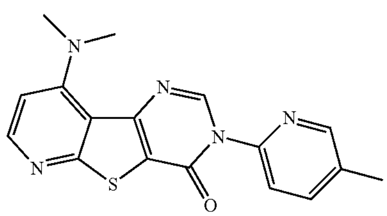 |
| 7DF | 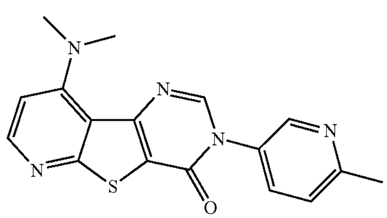 |
| 7DG | 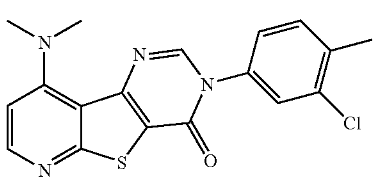 |
| 7DH | 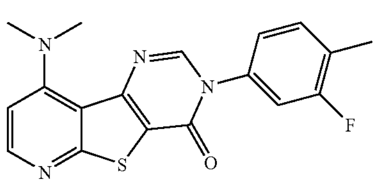 |
| 7DI | 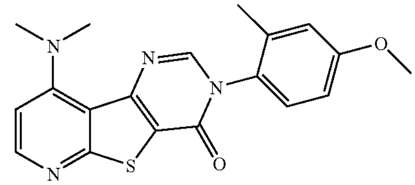 |
| 7DJ | 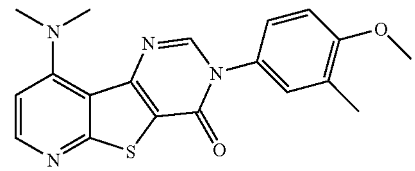 |
| 7DK | 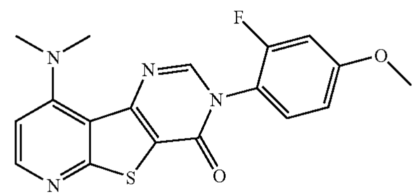 |
| 7DL | 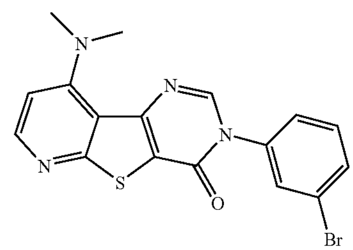 |
| 7DM | 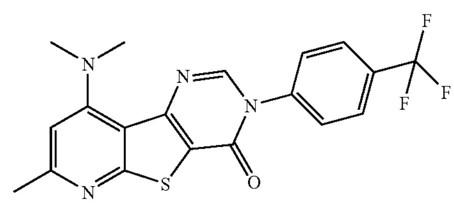 |
| 7DN | 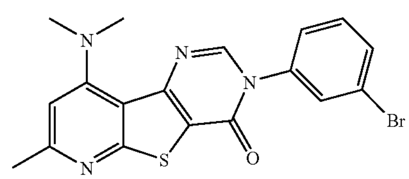 |
| 7DO | 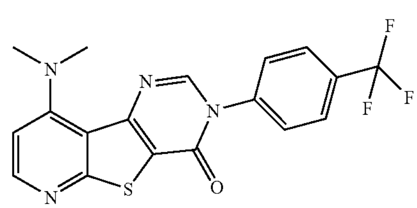 |
| 7DP | 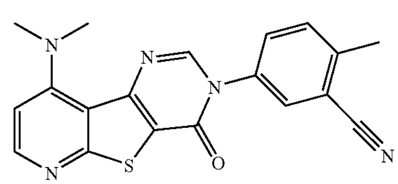 |

TABLE I-continued

| Cpd | Structure |
|-----|-----------|
| 7DQ | 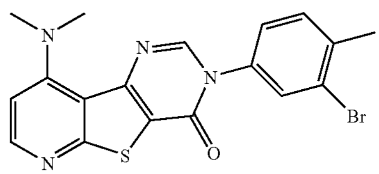 |
| 7DR | 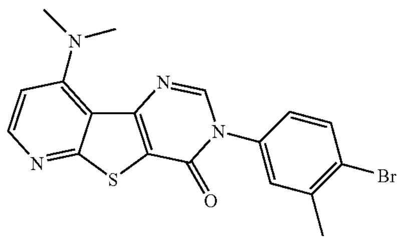 |
| 7DS | 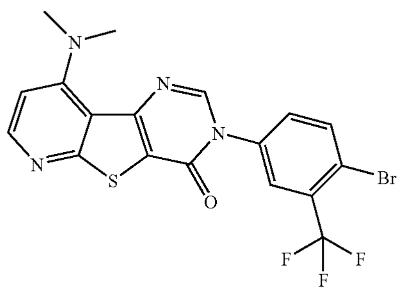 |
| 7DT | 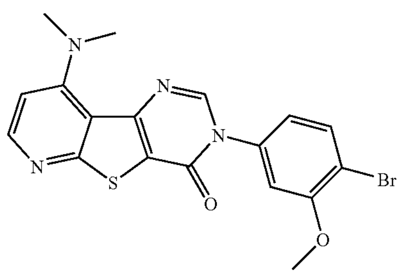 |
| 7DU | 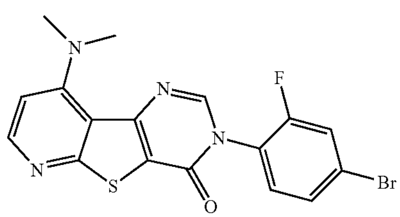 |
| 7DV | 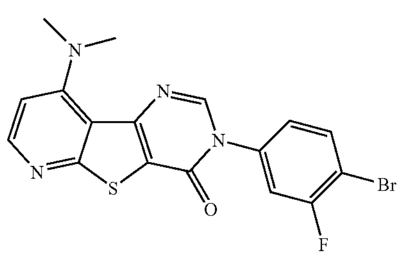 |
| 7DW | |
| 7DX | |
| 7DY | |
| 7DZ | |
| 7EA | |
| 7EB | |

TABLE I-continued

| Cpd | Structure |
|---|---|
| 7EC | 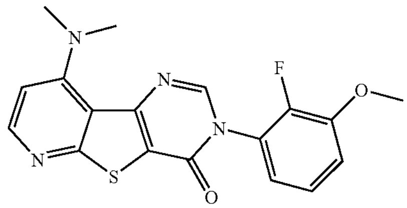 |
| 11 | 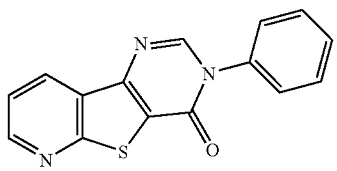 |
| 12A | 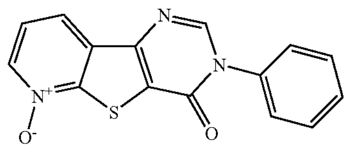 |
| 12B | 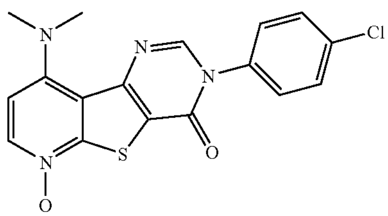 |
| 13 | 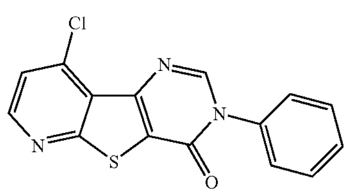 |
| 14 | 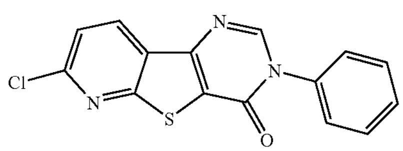 |
| 15A | 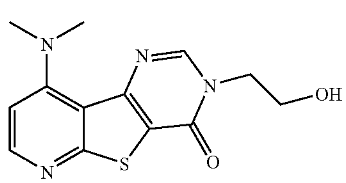 |
| 15B | 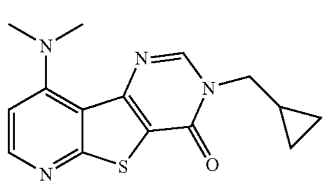 |

TABLE I-continued

| Cpd | Structure |
|---|---|
| 15C | 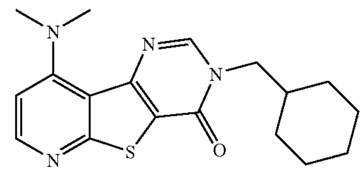 |
| 15D | 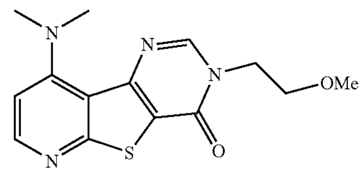 |
| 15E | 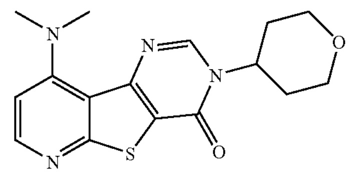 |
| 15F | 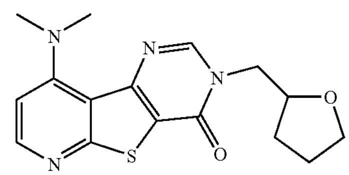 |
| 15G | 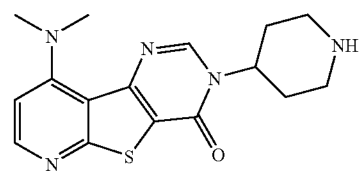 |
| 15H | 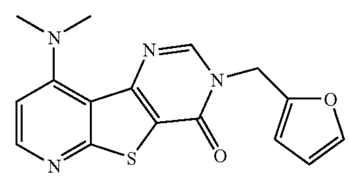 |
| 15I | 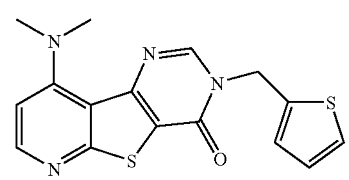 |
| 15J | 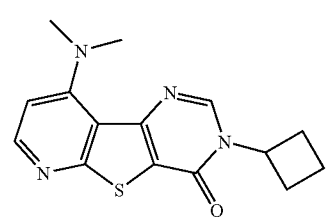 |

TABLE I-continued
| Cpd | Structure |
|---|---|
| 15K | 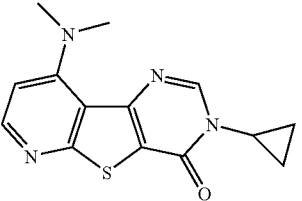 |
| 15N | 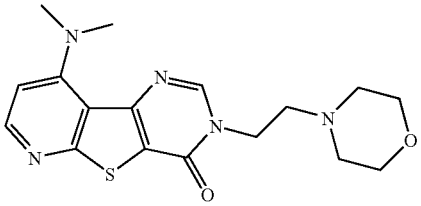 |
| 15O | 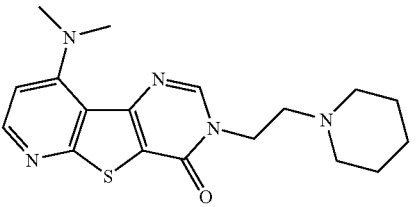 |
| 15P | 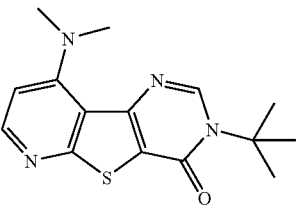 |
| 15Q | 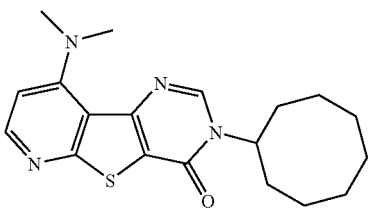 |
| 15R | 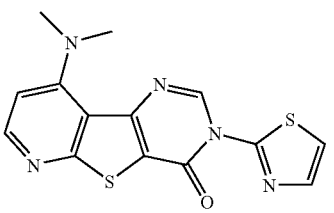 |
| 15S | 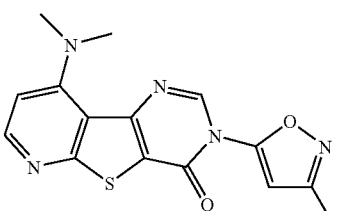 |
| 15T | 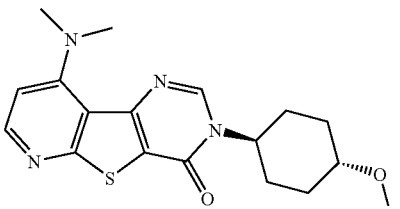 |
| 15U | 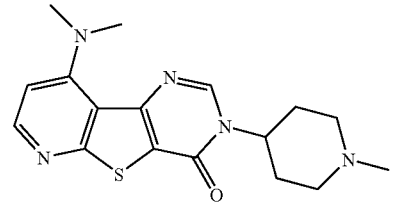 |
| 15V | 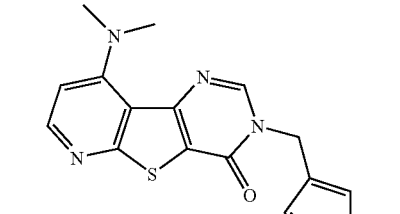 |
| 15W | 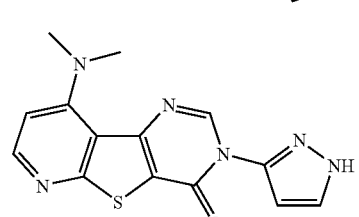 |
| 15X | 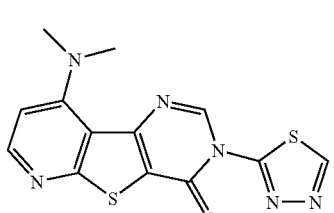 |
| 15Y | 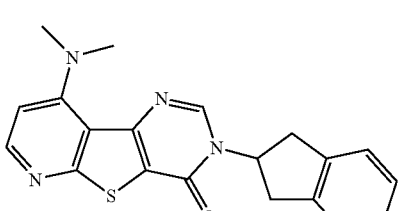 |
| 15Z | 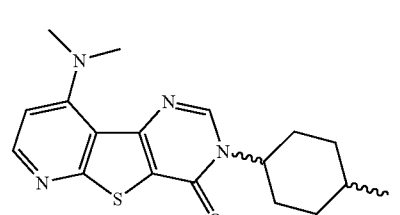 |

TABLE I-continued

| Cpd | Structure |
|---|---|
| 15AA | (structure) |
| 15AB | (structure) |
| 15AC | (structure) |
| 15AD | (structure) |
| 15AE | (structure) |
| 15AF | (structure) |
| 15AG | (structure) |
| 15AH | (structure) |
| 15AI | (structure) |
| 15AJ | (structure) |
| 15AK | (structure) |
| 19 | (structure) |
| 25A | (structure) |
| 25B | (structure) |

TABLE I-continued

| Cpd | Structure |
|---|---|
| 25C | 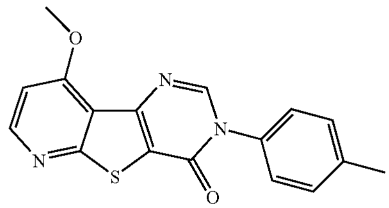 |
| 25D | 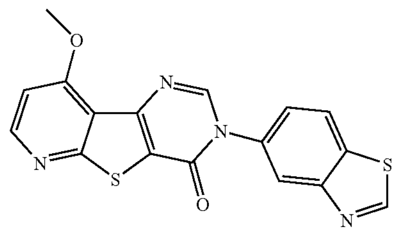 |
| 26A | 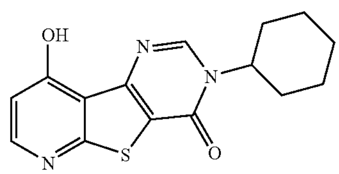 |
| 26C | 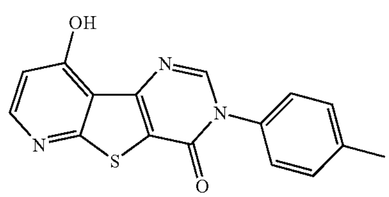 |
| 27A | 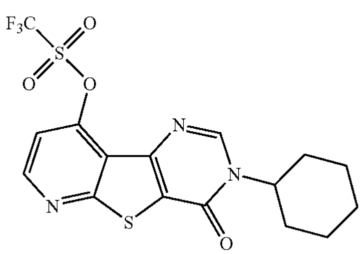 |
| 27B | 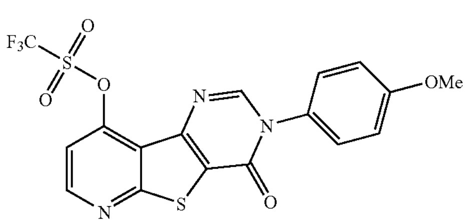 |
| 27C | 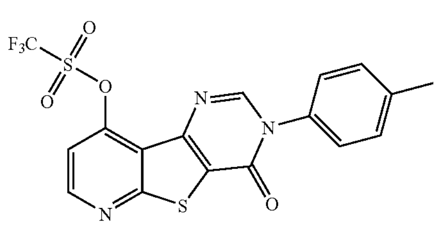 |
| 28A | |
| 28B | |
| 28C | |
| 28D | |
| 28E | |
| 28F | |

TABLE I-continued

| Cpd | Structure |
|---|---|
| 28G | (structure) |
| 28H | (structure) |
| 28I | (structure) |
| 28J | (structure) |
| 28K | (structure) |
| 28L | (structure) |
| 28M | (structure) |
| 28N | (structure) |
| 28O | (structure) |
| 28P | (structure) |
| 28Q | (structure) |
| 28R | (structure) |
| 28S | (structure) |
| 28T | (structure) |

TABLE I-continued

| Cpd | Structure |
|-----|-----------|
| 28U | (piperazinyl-substituted pyrido-thieno-pyrimidinone with N-cyclohexyl) |
| 28V | (azetidinyl-substituted pyrido-thieno-pyrimidinone with N-cyclohexyl) |
| 28W | (cyclobutyl-NH-substituted pyrido-thieno-pyrimidinone with N-cyclohexyl) |
| 28X | (methyl-NH-substituted pyrido-thieno-pyrimidinone with N-cyclohexyl) |
| 28Y | (N-ethyl-N-methylamino-substituted pyrido-thieno-pyrimidinone with N-cyclohexyl) |
| 28Z | (propargyl-NH-substituted pyrido-thieno-pyrimidinone with N-(p-tolyl)) |
| 28AA | (cyanomethyl-NH-substituted pyrido-thieno-pyrimidinone with N-(p-tolyl)) |
| 28AB | (N-propargyl-N-methylamino-substituted pyrido-thieno-pyrimidinone with N-(p-tolyl)) |
| 28AC | (N-allyl-N-methylamino-substituted pyrido-thieno-pyrimidinone with N-(p-tolyl)) |
| 28AD | (2-butynyl-NH-substituted pyrido-thieno-pyrimidinone with N-(p-tolyl)) |
| 28AE | (N-amino-N-methylamino-substituted pyrido-thieno-pyrimidinone with N-(p-tolyl)) |
| 28AF | (4-hydroxypiperidin-1-yl-substituted pyrido-thieno-pyrimidinone with N-cyclohexyl) |

TABLE I-continued

| Cpd | Structure |
|---|---|
| 28AG | (structure) |
| 28AH | (structure) |
| 28AI | (structure) |
| 28AJ | (structure) |
| 28AK | (structure) |
| 28AL | (structure) |
| 28AM | (structure) |
| 28AN | (structure) |
| 28AO | (structure) |
| 28AP | (structure) |
| 28AQ | (structure) |
| 28AR | (structure) |

TABLE I-continued

| Cpd | Structure |
|---|---|
| 28AS | 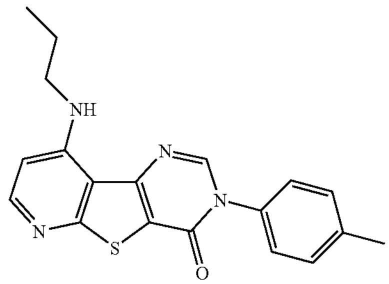 |
| 28AT | 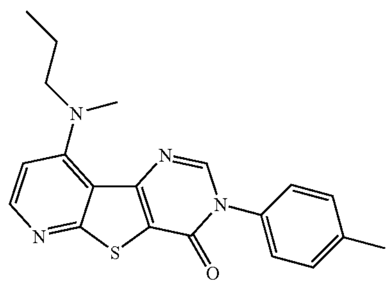 |
| 28AU | 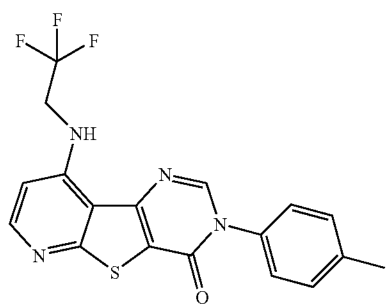 |
| 28AV | 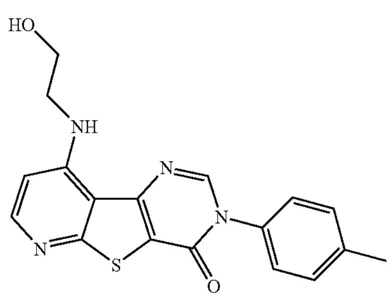 |
| 28AW | 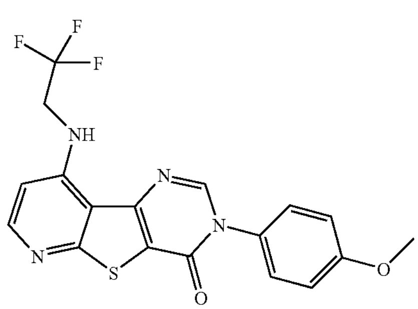 |
| 28AX | |
| 28AY | |
| 28AZ | |
| 28BA | |
| 28BB | |

TABLE I-continued

| Cpd | Structure |
|---|---|
| 28BC | (structure) |
| 29A | (structure) |
| 29B | (structure) |
| 29C | (structure) |
| 29D | (structure) |
| 30A | (structure) |
| 30B | (structure) |
| 30C | (structure) |
| 37A | (structure) |
| 37B | (structure) |
| 37C | (structure) |
| 37D | (structure) |
| 37E | (structure) |
| 37F | (structure) |

TABLE I-continued

| Cpd | Structure |
|-----|-----------|
| 37G | (structure) |
| 37H | (structure) |
| 40 | (structure) |
| 41 | (structure) |
| 42 | (structure) |
| 43 | (structure) |
| 44 | (structure) |
| 45 | (structure) |
| 46 | (structure) |
| 47A | (structure) |
| 47B | (structure) |
| 48 | (structure) |
| 49 | (structure) |
| 50 | (structure) |

TABLE I-continued

| Cpd | Structure |
|---|---|
| 51 | 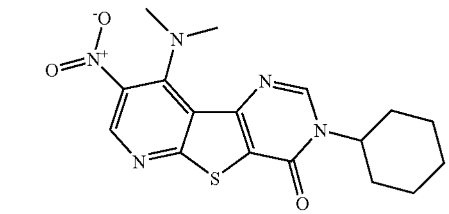 |
| 52 | 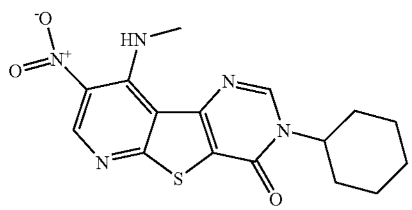 |
| 55 | 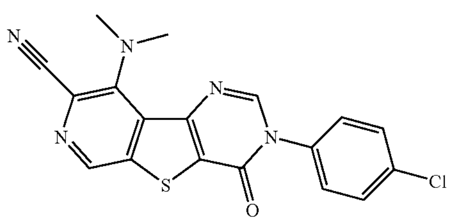 |
| 58 | 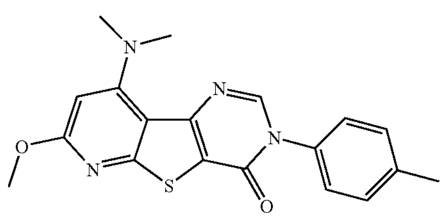 |
| 59A | 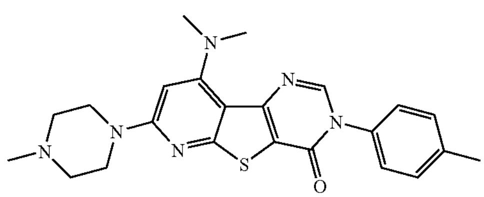 |
| 59B | 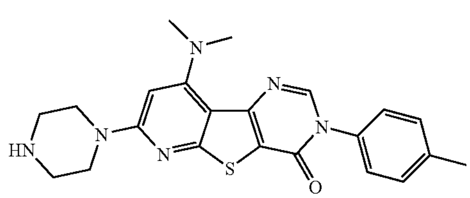 |
| 59C | 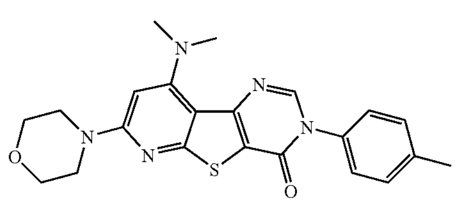 |
| 60A | |
| 60B | |
| 60C | |
| 60D | |
| 60E | |
| 60F | |
| 60G | |

TABLE I-continued

| Cpd | Structure |
| --- | --- |
| 60H | (structure) |
| 60I | (structure) |
| 60J | (structure) |
| 60L | (structure) |
| 61A | (structure) |
| 61B | (structure) |
| 62 | (structure) |
| 63 | (structure) |
| 64 | (structure) |
| 65A | (structure) |
| 65B | (structure) |

TABLE I-continued

| Cpd | Structure |
|---|---|
| 65C | (structure) |
| 65D | (structure) |
| 65E | (structure) |
| 66A | (structure) |
| 66B | (structure) |
| 66C | (structure) |
| 66D | (structure) |
| 66E | (structure) |
| 72A | (structure) |
| 72B | (structure) |
| 72C | (structure) |
| 72D | (structure) |

TABLE I-continued

| Cpd | Structure |
|---|---|
| 72E | (structure) |
| 72F | (structure) |
| 72G | (structure) |
| 72H | (structure) |
| 72I | (structure) |
| 73A | (structure) |
| 73B | (structure) |
| 73C | (structure) |
| 73D | (structure) |
| 73E | (structure) |
| 73F | (structure) |
| 76 | (structure) |

TABLE I-continued

| Cpd | Structure |
|---|---|
| 77 | 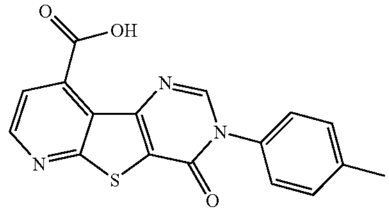 |
| 78 | 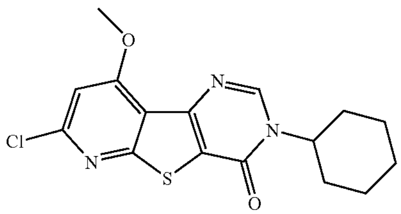 |
| 80 | 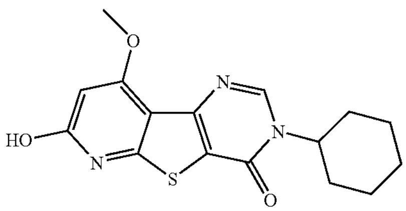 |
| 83 | 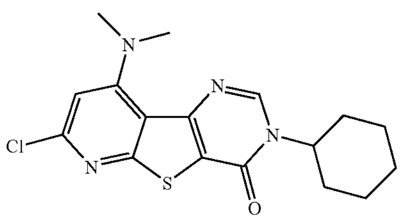 |
| 84 | 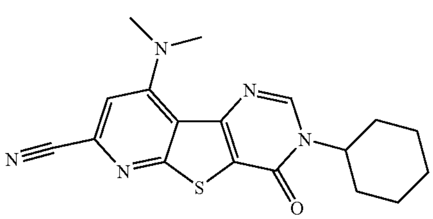 |
| 85 | 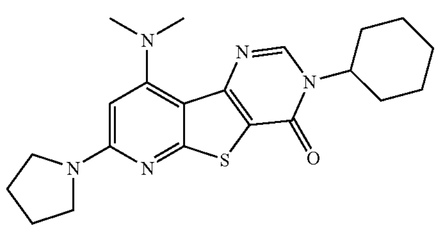 |
| 87A | 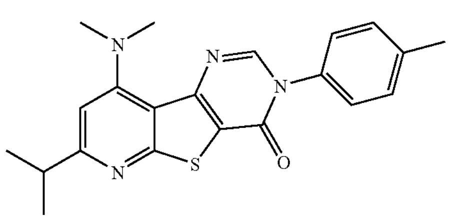 |

TABLE I-continued

| Cpd | Structure |
|---|---|
| 87B | 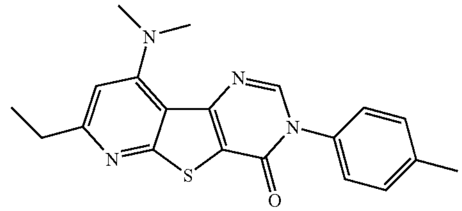 |
| 87C | 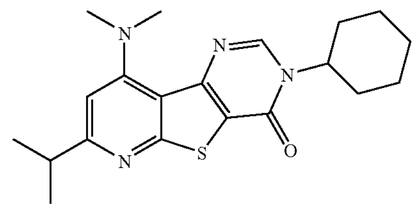 |
| 95A | 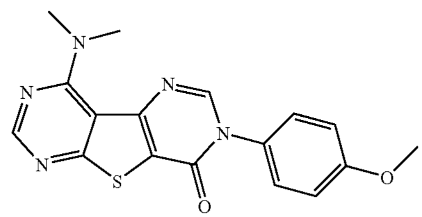 |
| 95B | 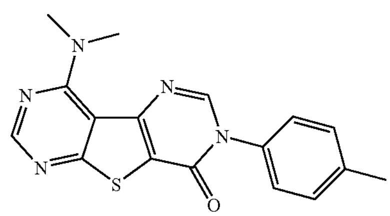 |
| 95C | 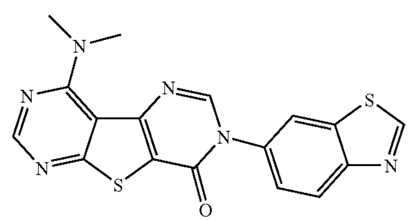 |
| 95D | 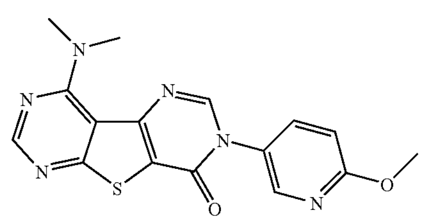 |
| 95E | 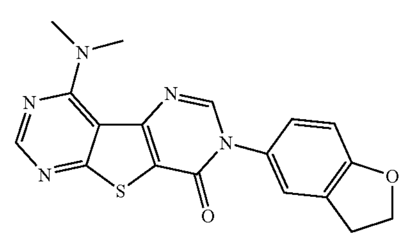 |

TABLE I-continued

| Cpd | Structure |
|---|---|
| 95F | (structure) |
| 95G | (structure) |
| 95H | (structure) |
| 95I | (structure) |
| 95J | (structure) |
| 95K | (structure) |
| 95L | (structure) |
| 95M | (structure) |
| 95N | (structure) |
| 95O | (structure) |
| 95P | (structure) |
| 95Q | (structure) |

TABLE I-continued

| Cpd | Structure |
|---|---|
| 95R | 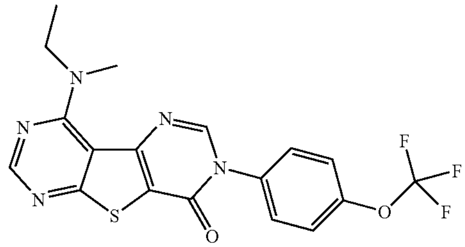 |
| 95S | 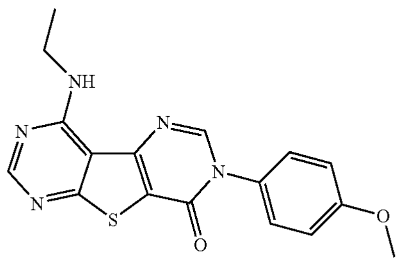 |
| 95T | 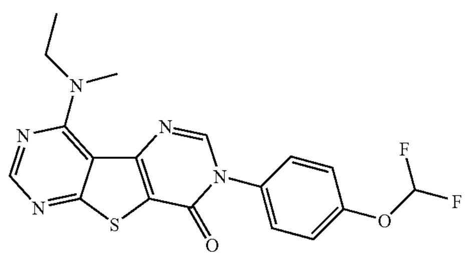 |
| 95U | 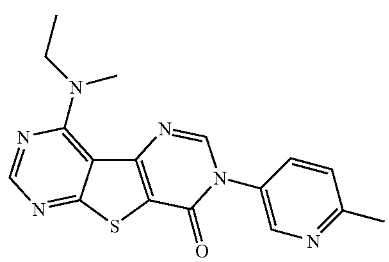 |
| 95V | 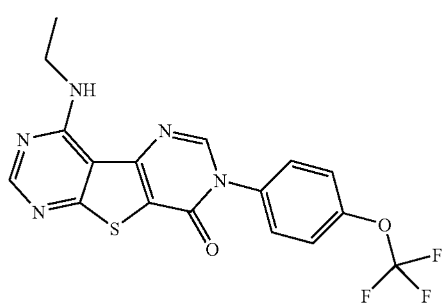 |
| 95W | 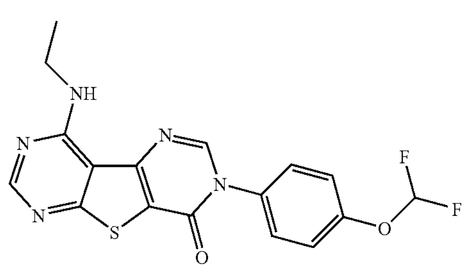 |
| 95X | 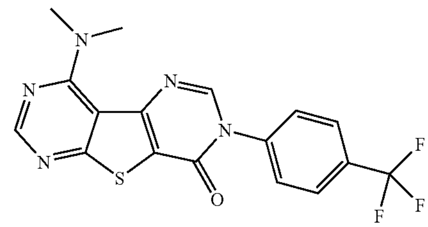 |
| 95Y | 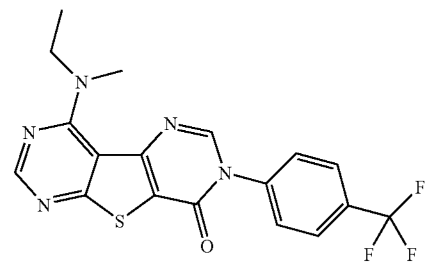 |
| 95Z | 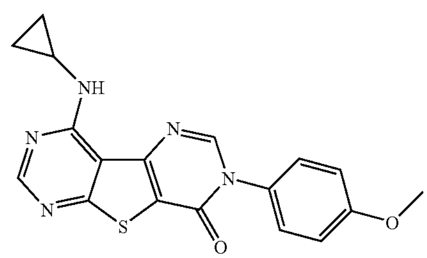 |
| 95AA | 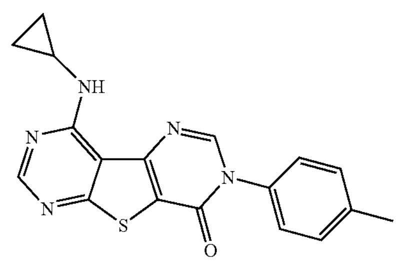 |
| 95AB | 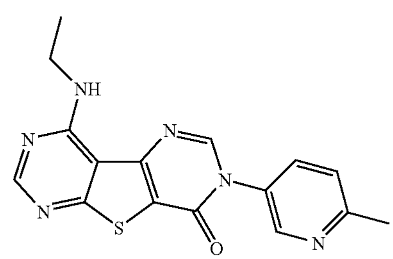 |
| 95AC | 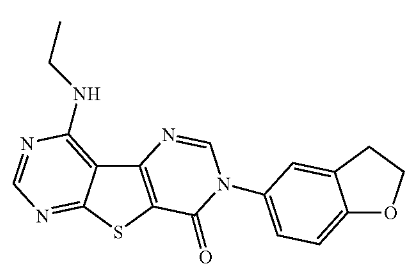 |

TABLE I-continued

| Cpd | Structure |
|---|---|
| 95AD | (structure) |
| 95AE | (structure) |
| 95AF | (structure) |
| 95AG | (structure) |
| 95AH | (structure) |
| 95AI | (structure) |
| 95AJ | (structure) |
| 95AK | (structure) |
| 95AL | (structure) |
| 95AM | (structure) |
| 95AN | (structure) |
| 103A | (structure) |

TABLE I-continued
| Cpd | Structure |
|---|---|
| 103B | 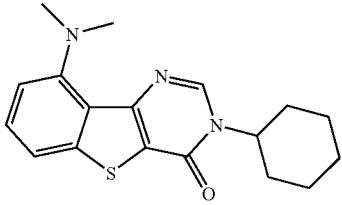 |
| 103C | 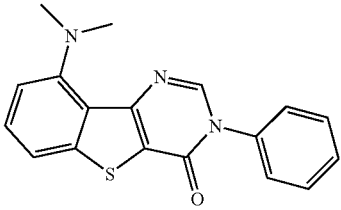 |
| 103D | 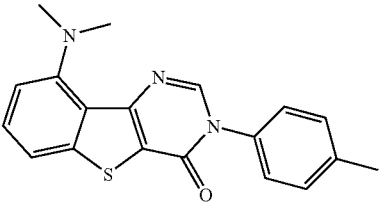 |
| 103E | 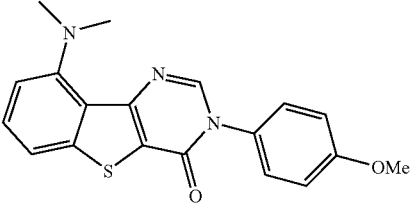 |
| 103F | 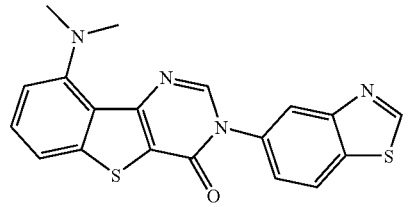 |
| 104 | 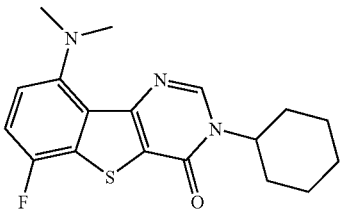 |
| 105 | 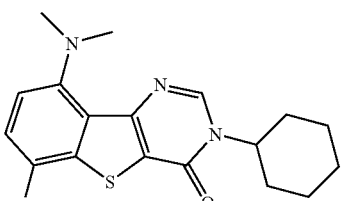 |
| 106 | 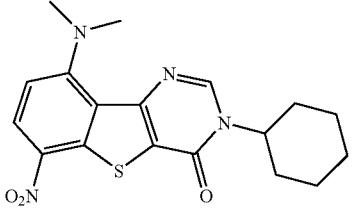 |
| 113A | 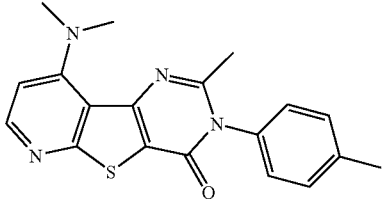 |
| 113B | 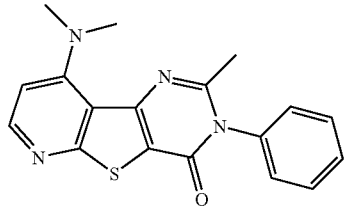 |
| 113C | 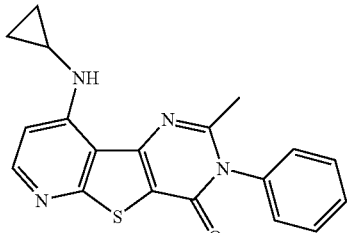 |
| 113D | 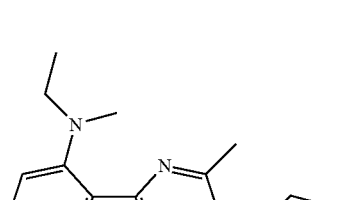 |
| 113E | 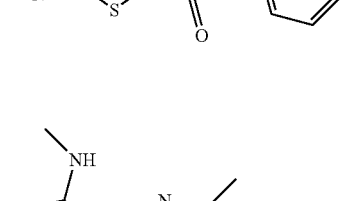 |

TABLE I-continued

| Cpd | Structure |
|---|---|
| 113F | 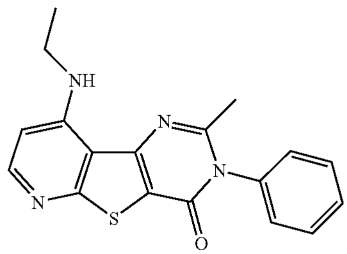 |
| 113G | 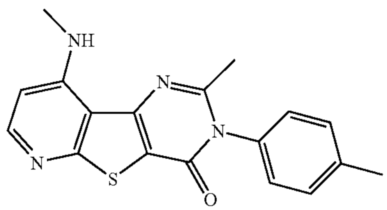 |
| 113H | 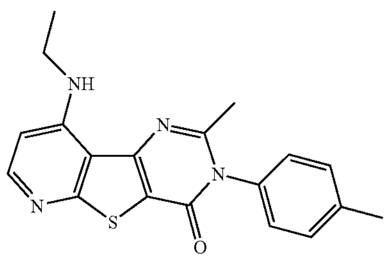 |
| 113I | 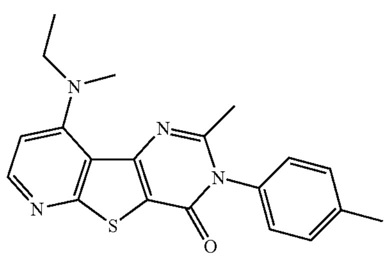 |
| 113J | 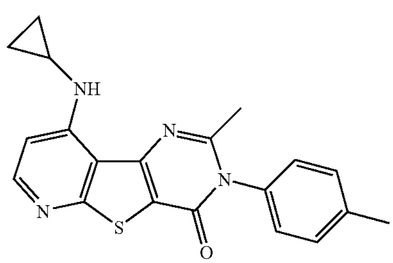 |
| 113K | 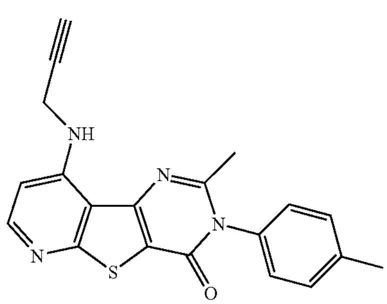 |
| 113L | |
| 113M | |
| 113N | |
| 115 | |
| 116 | |
| 116A | |

TABLE I-continued

| Cpd | Structure |
|---|---|
| 116B | |
| 116C | |
| 116D | |
| 116E | |
| 116F | |
| 116G | |
| 117 | 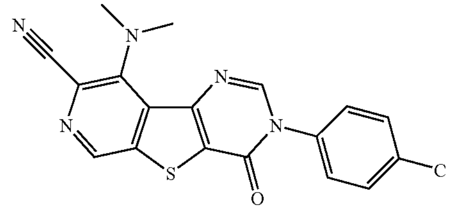 |
| 117A | 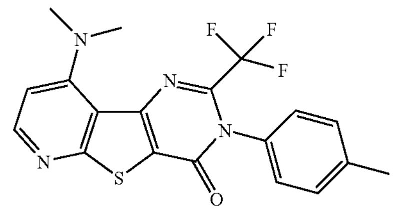 |
| 117B | 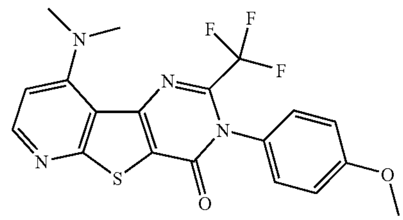 |
| 118 | 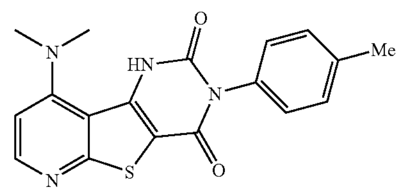 |
| 131A | 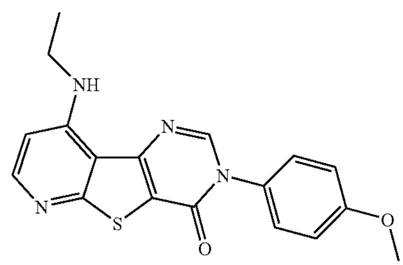 |
| 131B | 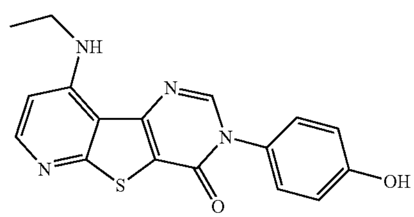 |
| 131C | 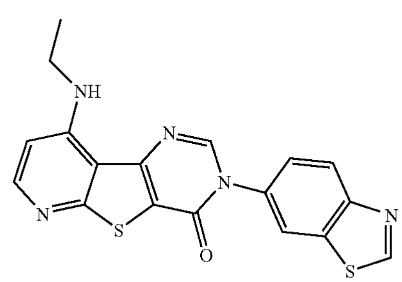 |

TABLE I-continued

| Cpd | Structure |
|---|---|
| 131D | (structure) |
| 131E | (structure) |
| 131F | (structure) |
| 131G | (structure) |
| 134A | (structure) |
| 134B | (structure) |
| 134C | (structure) |
| 134D | (structure) |
| 134E | (structure) |
| 134F | (structure) |
| 134G | (structure) |
| 134H | (structure) |

TABLE I-continued

| Cpd | Structure |
|---|---|
| 134I | |
| 135A | |
| 136 | |
| 137A | |
| 137B | |
| 138 | |
| 144A | 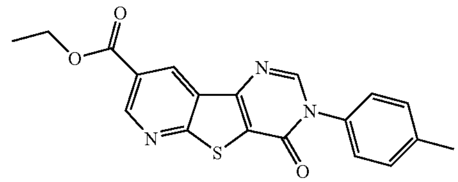 |
| 147A | 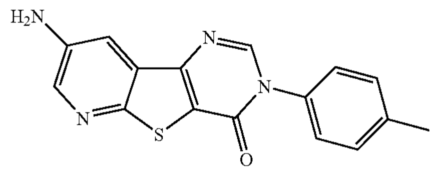 |
| 148 | 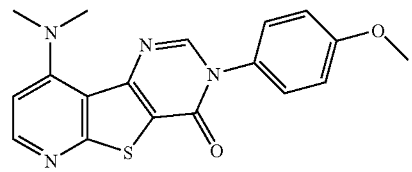 |
| 149 | 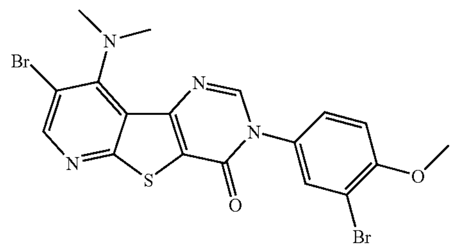 |
| 150 | 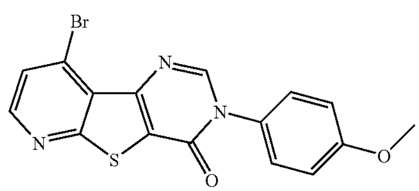 |
| 151 | 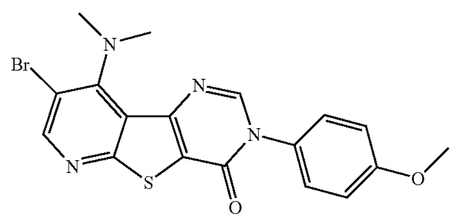 |
| 152 | 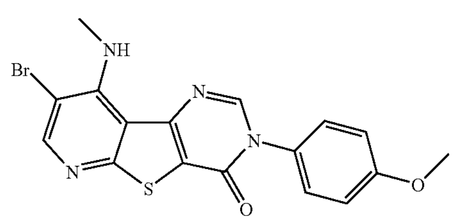 |
| P-1 | 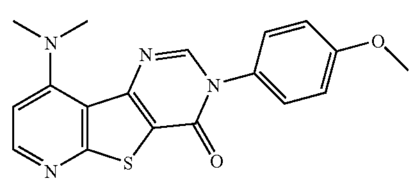 |

TABLE I-continued

| Cpd | Structure |
|---|---|
| P-2 | 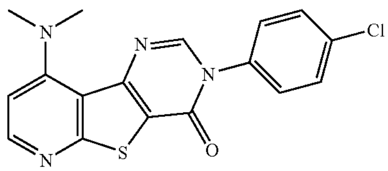 |
| P-3 | 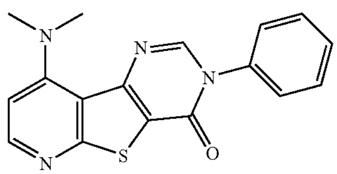 |
| P-4 | 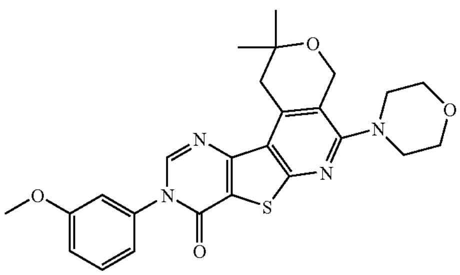 |
| P-5 | 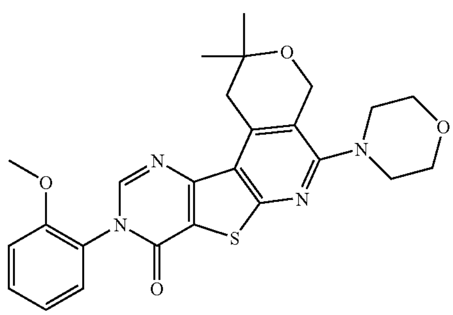 |
| P-6 | 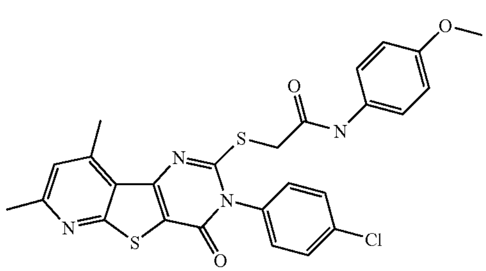 |
| P-7 | 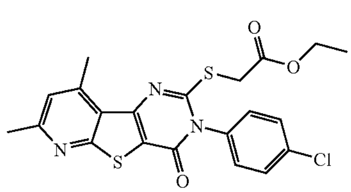 |

TABLE I-continued

| Cpd | Structure |
|---|---|
| P-8 | 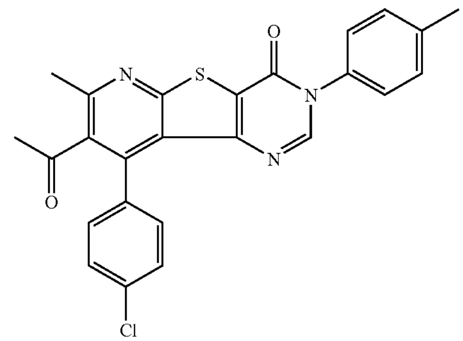 |
| P-9 | 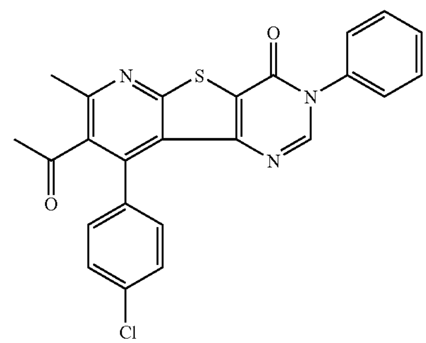 |
| P-10 | 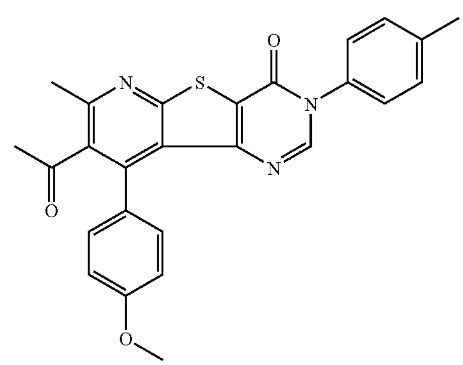 |
| P-11 | 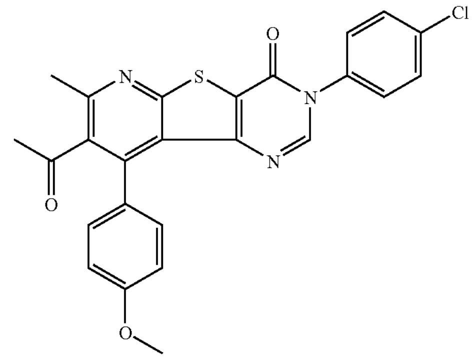 |

TABLE I-continued

| Cpd | Structure |
|---|---|
| P-12 | (structure) |
| P-13 | (structure) |
| P-14 | (structure) |
| P-15 | (structure) | or a pharmaceutically acceptable salt, solvate or ester thereof.

Preferred compounds include 7A, 7B, 7D, 7G, 7H, 7K, 7L, 7Q, 7W, 7X, 7Y, 7Z, 7AA, 7AC, 7AJ, 7AK, 7AM, 7AP, 7AS, 7AV, 7AX, 7AY, 7BF, 7BG, 7BI, 7BJ, 7BL, 7BM, 7BN, 7BO, 7BS, 7BW, 7BY, 7BZ, 7CA, 7CB, 7CC, 7CD, 7CE, 7CF, 7CG, 7CK, 7CM, 7CQ, 7CR, 7CT, 7CU, 7CV, 7CY, 7CZ, 7DB, 7DC, 7DE, 7DF, 7DG, 7DH, 7DI, 7DJ, 7DK, 7DL, 7DO, 7DQ, 7DR, 7DU, 7DV, 7DW, 7DX, 7DZ, 7EA, 15C, 15Q, 15Y, 15Z, 15AA, 15AB, 15AG, 28I, 28P, 28S, 28X, 28Y, 28Z, 28AA, 28AB, 28AC, 28AE, 28AI, 28AK, 28AL, 28AN, 28AO, 28AP, 28AR, 28AS, 28AT, 28AU, 28AV, 28AW, 28AZ, 28BB, 28BC, 37E, 37F, 45, 46, 51, 58, 60A, 60B, 60C, 60D, 60E, 60G, 66A, 66D, 71A, 72A, 72B, 72C, 72G, 72H, 72I, 95A, 95B, 96C, 95D, 95E, 95F, 95G, 95H, 95I, 95K, 95L, 95N, 95O, 95P, 95Q, 95R, 95S, 95T, 95U, 95W, 95X, 95Y, 95Z, 95AA, 95AC, 95AD, 113A, 113B, 113D, 113E, 113F, 113G, 113H, 113I, 113K, 116D, 131A, 131B, 131C, 131D, 131E, 131G, 136, 137A, 137B, 138, 148, 151, and 152, or a pharmaceutically acceptable salt, solvate or ester thereof.

More preferred compounds include 7A, 7B, 7H, 7L, 7Q, 7AC, 7AP, 7AS, 7BI, 7BJ, 7BL, 7BM, 7BS, 7BY, 7CC, 7CE, 7CG, 7CQ, 7CR, 7CT, 7CU, 7CV, 7CY, 7DG, 7DH, 7DK, 7DL, 7DR, 7DU, 7DV, 7DW, 15Q, 15Z, 15AA, 15AG, 28X, 28Y, 28Z, 28AA, 28AE, 28AI, 28AK, 28AL, 37E, 37F, 60A, 60D, 60E, 71A, 72G, 72H, 95A, 95B, 95C, 95E, 95F, 95G, 95H, 95K, 95L, 95P, 95Q, 95S, 95T, 95Z, 95AA, 95AC, 131C, 131D, 131E, 136, 148, and 152, or a pharmaceutically acceptable salt, solvate or ester thereof.

As used above, and throughout the specification, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl). Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "substituted alkenyl" means that the alkenyl group may be substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "substituted alkynyl" means that the alkynyl group may be substituted by one or more substituents which may be the same or different, each substituent being independently selected from the group consisting of alkyl. aryl and cycloalkyl.

"Alkylene" means a difunctional group obtained by removal of a hydrogen atom from an alkyl group that is defined above. Non-limiting examples of alkylene include methylene, ethylene and propylene.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like. "Cycloalkyl" includes "arylcycloalkyl" and "cycloalkylaryl" as defined below.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"cyanoalkyl" means an alkyl as defined above wherein one or more hydrogen atoms on the alkyl is replaced by a cyano group.

"oxo" means (=O) and "thioxo" means (=S).

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

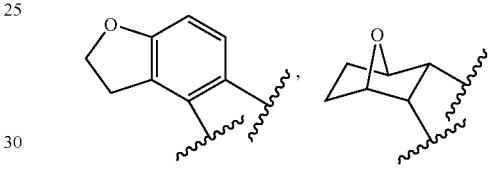

and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. "Cycloalkenyl" includes "arylcycloalkenyl" and "cycloalkenylaryl" as defined below.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like. "Heterocyclyl" includes "heteroarylcycloalkyl" and "cycloalkylheteroaryl" as defined below.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by one or more ring system substituents, wherein "ring system substituent" is as defined above. Non-limiting examples of suitable arylcycloalkenyls include 1,2-dihydronaphthalene, indene, and the like. The bond to the parent moiety is through a non-aromatic carbon atom.

"Cycloalkenylaryl" means a group derived from a fused arylcycloalkenyl as defined herein by removal of hydrogen atom from the aryl portion. Non-limiting examples of suitable cycloalkenylaryls are as described herein for a arylcycloalkenyl, except that the bond to the parent moiety is through an aromatic carbon atom.

"Arylcycloalkyl" means a group derived from a fused aryl and cycloalkyl as defined herein by removal of a hydrogen atom from the cycloalkyl portion. Preferred arylcycloalkyls are those wherein aryl is phenyl and the cycloalkyl consists of about 5 to about 6 ring atoms. The arylcycloalkyl can be optionally substituted by one or more ring system substituents, wherein "ring system substituent" is as defined above. Non-limiting examples of suitable arylcycloalkyls include 1,2,3,4-tetrahydronaphthyl, and the like. The bond to the parent moiety is through a non-aromatic carbon atom.

"Cycloalkylaryl" means a group derived from a fused arylcycloalkyl as defined herein by removal of a hydrogen atom from the aryl portion. Non-limiting examples of suitable cycloalkylaryls are as described herein for an arylcycloalkyl group, except that the bond to the parent moiety is through an aromatic carbon atom.

"Heteroarylcycloalkyl" means a group derived from a fused heteroaryl and cycloalkyl as defined herein by removal of a hydrogen atom from the cycloalkyl portion. Preferred heteroarylcycloalkyls are those wherein the heteroaryl thereof consists of about 5 to about 6 ring atoms and the cycloalkyl consists of about 5 to about 6 ring atoms. The prefix aza, oxa or thia before heteroaryl means that at least a nitrogen, oxygen or sulfur atom is present respectively as a ring atom. The heteroarylcycloalkyl can be optionally substituted by one or more ring system substituents, wherein "ring system substituent" is as defined above. The nitrogen atom of the heteroaryl portion of the heteroarylcycloalkyl can be optionally oxidized to the corresponding N-oxide. Non-limiting examples of suitable heteroarylcycloalkyls include 5,6,7,8-tetrahydroquinolinyl, 5,6,7,8-tetrahydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like. The bond to the parent moiety is through a non-aromatic carbon atom.

"Cycloalkylheteroaryl" means a group derived from a fused beteroarylcycloalkyl as defined herein by removal of a hydrogen atom from the heteroaryl portion. Non-limiting examples of suitable cycloalkylheteroaryls are as described herein for heteroarylcycloalkyl, except that the bond to the parent moiety is through an aromatic carbon atom.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkynyl" means an aryl-alkynyl-group in which the aryl and alkynyl are as previously described. Preferred aralkynyls contain a lower alkynyl group. The bond to the parent moiety is through the alkynyl. Non-limiting examples of suitable aralkynyl groups include phenacetylenyl and naphthylacetylenyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heteroaralkynyl" means an heteroaryl-alkynyl-group in which the heteroaryl and alkynyl are as previously described. Preferred heteroaralkynyls contain a lower alkynyl group. Non-limiting examples of suitable heteroaralkynyl groups include pyrid-3-ylacetylenyl and quinolin-3-ylacetylenyl. The bond to the parent moiety is through the alkynyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Heteroaroyl" means a heteroaryl-C(O)— group in which the heteroaryl group is as previously described. Non-limiting examples of suitable groups include nicotinoyl and pyrrol-2-ylcarbonyl. The bond to the parent moiety is through the carbonyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl groups is as previously described. Non-limiting examples of suitable aralkyloxy groups include benzyloxy and 1- or 2-naphthalenemethoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Arylamino" means an —NH$_2$ or —NH$_3^+$ group in which one or more of the hydrogen atoms on the nitrogen is replaced by an aryl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

Lines drawn into the ring systems, such as, for example:

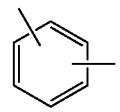

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

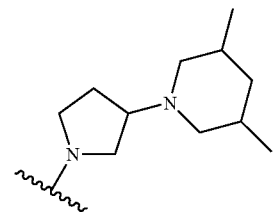

represents

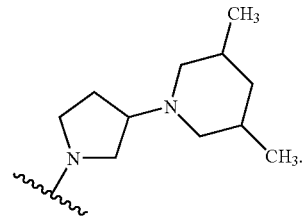

It should also be noted that any carbon or heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of a compound or a composition of the present invention effective in antagonizing mGluRs, in particular mGluR1, and thus producing the desired therapeutic, ameliorative, inhibitory or preventative effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates), undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the present compounds.

Polymorphic forms of the compounds of formula I, and of the salts, solvates and prodrugs of the compounds of formula I, are intended to be included in the present invention.

The compounds according to the invention have pharmacological properties; in particular, the compounds of formula I can be mGluR (metabotropic glutamate receptor) antagonists, more particularly, selective mGluR1 antagonists. Accordingly, the present compounds are useful in the treatment or prevention of conditions that are treatable or preventable by inhibiting mGluR, more particularly, mGluR1 function. Such conditions include a variety of acute and chronic neurological disorders associated with excessive or inappropriate stimulation of excitatory amino acid transmission as well as conditions which lead to glutamate-deficient functions.

Examples of treatable or preventable acute neurological disorders include, but are not limited to, cerebral deficits subsequent to cardiac bypass surgery and grafting, cerebral ischemia, stroke (ischemic or hemorrhagic), spinal cord injuries (due to trauma, infarction/ischemia or inflammation), head trauma, perinatal hypoxia, cardiac arrest and hypoglycemic neuronal damage. Examples of treatable or preventable chronic neurological disorders include, but are not limited to, Alzheimers disease, Huntington's Chorea, amyotrophic lateral sclerosis (ALS), AIDS-induced dementia, inherited ataxias, ocular damage and retinopathy, cognitive disorders, and idiopathic and drug-induced Parkinson's. Other conditions associated with glutamate dysfunctions treatable or preventable by compounds of formula I include, but are not limited to, muscle spasms, convulsions (e.g., epilepsy), spasticity, migraine (including menstrual migraine), psychoses (e.g., schizophrenia and bipolar disorder), urinary incontinence, anxiety and related disorders (e.g. panic attack), emesis, brain edema, tardive dyskinesia, depression, drug tolerance and withdrawal (e.g., opiates, benzodiazepines, nicotine, cocaine, or ethanol), and smoking cessation.

The compounds of formula I are also useful for treating or preventing pain which may be neuropathic (nerve damage) or inflammatory (tissue damage). These compounds are particularly useful for treating or preventing neuropathic pain. Neuropathic pain used herein refers to an abnormal state of pain sensation, in which a reduction of pain threshold and the like are continued, due to functional abnormalities accompanying damage or degeneration of a nerve, plexus or perineural soft tissue, which is caused by wound, compression, infection, cancer, ischemia and the like, or metabolic disorders such as diabetes mellitus and the like. Neuropathic pain includes pain caused by either central or peripheral nerve damage. It also includes the pain caused by either mononeuropathy or polyneuropathy. In some embodiments, the neuropathic pain is induced by diabetes. In other embodiments, the neuropathic pain is induced by compression of nerves.

Examples of neuropathic pain treatable or preventable by the present compounds include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, arthritic pain (e.g., pain due to osteoarthritis or rheumatoid arthritis), bursitis, pain associated with AIDS, visceral pain (e.g., interstitial cystitis and irritable bowel syndrome (IBS)), pain due to spinal trauma and/or degeneration, burn pain, referred pain, enhanced memory of pain and neuronal mechanisms involved in coping with pain. The compounds of the present invention are particularly useful for treating or preventing allodynia and hyperalgesia.

Compounds of formula I are also useful for treating or preventing pain associated with inflammation or an inflammatory disease in a mammal. The pain associated with inflammation or an inflammatory disease treatable or preventable by the present compounds may arise where there is an inflammation of the body tissue which may be a local inflammatory response and/or a systemic inflammation. For example, the present compounds can be used to treat or prevent pain associated with inflammatory diseases including, but not limited to, organ transplant rejection; reoxygenation injury resulting from organ transplantation including transplantation of the heart, lung, liver, or kidney; chronic inflammatory diseases of the joints, including arthritis, rheumatoid arthritis, osteoarthritis and bone diseases associated with increased bone resorption; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory diseases of the gum, including gingivitis and periodontitis; tuberculosis; leprosy; inflammatory diseases of the kidney, including uremic complications, glomerulonephritis and nephrosis; inflammatory diseases of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including diabetic cataract, glaucoma, retinopathy, nephropathy (such as microaluminuria and progressive diabetic nephropathy), polyneuropathy, mononeuropathies, autonomic neuropathy, gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection and necrobiosis lipoidica diabeticorum); immune-complex vasculitis, and systemic lupus erythematosus (SLE); inflammatory diseases of the heart, such as cardiomyopathy, ischemic heart disease hypercholesterolemia, and atherosclerosis; as well as various other diseases that can have significant inflammatory components, including preeclampsia, chronic liver failure, brain and spinal cord trauma, and cancer.

The present compounds can also be used for treating or preventing pain associated with an inflammatory disease that involves a systemic inflammation of the body, such as gram-positive or gram negative shock, hemorrhagic or anaphylactic shock, shock induced by cancer chemotherapy in response to pro-inflammatory cytokines (e.g., shock associated with pro-inflammatory cytokines), and shock induced by a chemotherapeutic agent that is administered as a treatment for cancer.

One aspect of this invention relates to a method of selectively antagonizing mGluR1 in a cell in need thereof, comprising contacting said cell with at least one compound of formula I or a pharmaceutically acceptable salt or solvate thereof.

The term "antagonist of metabatropic glutamate receptor (e.g., mGluR1)" refers to a compound that binds to the metabatropic glutamate receptor (e.g., mGluR1) but fails to elicit a response thereby blocking agonist action, i.e, inhibiting a function of mGluRs (e.g., mGluR1). Accordingly, mGluR (e.g., mGluR1) mediated processes and responses can be inhibited with an antagonist of mGluR (e.g., mGluR1). Preferably, an antagonist selectively antagonizes group I mGluRs. More preferably, an antagonist of the present invention is a selective antagonist of mGluR1. A selective antagonist of mGluR1 is one that antagonizes mGluR1, but antagonizes other mGluRs only weakly or substantially not at all, or at least antagonizes other mGluRs with an $IC_{50}$ at least 10 or even 100 or 1000 times greater than the $IC_{50}$ at which it antagonizes mGluR1. Most preferred antagonists are those which can selectively antagonize mGluR1 at low concentrations, for example, those that cause a level of antagonism of 50% or greater at a concentration of 100 nM or less.

Another aspect of this invention relates to a method of treating or preventing a disease or condition associated with mGluR1 in a mammal (e.g., human) in need thereof comprising administering a therapeutically effective amount of at least one compound of formula I or a pharmaceutically acceptable salt or solvate thereof to said mammal.

A preferred dosage is about 0.001 to 500 mg/kg of body weight/day of the compound of formula III. An especially preferred dosage is about 0.01 to 25 mg/kg of body weight/day of a compound of formula I or a pharmaceutically acceptable salt or solvate thereof.

The compounds of this invention may also be useful in combination (administered together or sequentially) with one or more additional therapeutic agents for the treatment of the above disorders or conditions. Such additional therapeutic agents may be a pain management agent, including non-opioid analgesics such as acetylsalicylic acid, choline magnesium trisalicylate, acetaminophen, ibuprofen, fenoprofen, diflusinal, and naproxen; and opioid analgesics, such as morphine, hydromorphone, methadone, levorphanol, fentanyl, oxycodone, and oxymorphone. Other such therapeutic agents may be a non-steroid anti-inflammatory agent, an antimigraine agent, a Cox-II inhibitor, an antiemetic, a β-adrenergic blocker, an anticonvulsant, an antidepressant, a $Ca^{2+}$-channel blocker, an anticancer agent, an agent for treating or preventing UI, an agent for treating Alzheimer's disease, an agent for treating or preventing IBD, an agent for treating or preventing IBS, an agent for treating Parkinson's disease and parkinsonism, an agent for treating anxiety, an agent for treating epilepsy, an agent for treating a stroke, an agent for treating psychosis, an agent for treating Huntington's chorea, an agent for treating ALS, an agent for treating vomiting, an agent for treating dyskinesia, or an agent for treating depression, and mixtures thereof.

If formulated as a fixed dose, such combination products employ the compounds of this invention within the dosage range described herein and the other pharmaceutically active agent or treatment within its dosage range. Compounds of formula I may also be administered sequentially with known therapeutic agents when a combination formulation is inappropriate. The invention is not limited in the sequence of administration; compounds of formula I may be administered either prior to or after administration of the known therapeutic agent. Such techniques are within the skills of persons skilled in the art as well as attending physicians.

Accordingly, in one aspect, this invention includes combinations comprising an amount of at least one compound of formula I or a pharmaceutically acceptable salt or solvate thereof, and an amount of one or more additional therapeutic agents listed above wherein the amounts of the compounds/treatments result in desired therapeutic effect.

The pharmacological properties of the compounds of this invention may be confirmed by a number of pharmacological assays. The selective antagonistic activity of the present compounds towards the metabotropic glutamate receptor 1 (mGluR1) may be assayed by methods known in the art, for example, by using the methods as described in the examples.

The actions of the compounds of formula I for the treatment or prevention of pain may be assessed by various animal models, for example, by the following tests:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection, the mouse is immediately put back into the Plexiglas observation chamber (30×20×20 cm) and the nociceptive response of the animal to formalin injection is observed for a period of 60 min. The duration of licking and flinching of the injected paw is recorded and quantified every 5 min for the total observation period. The recording of the early phase (first phase) starts immediately and lasts for 5 min. The late phase (second phase) starts about 10-15 min after formalin injection.

L5 and L6 spinal nerve ligation of the sciatic nerve (neuropathic pain model): The peripheral neuropathy is produced by ligating the L5 and L6 spinal nerves of the right sciatic nerve, according to the method previously described by Kim and Chung (1992) except for small changes. Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In POST-TREATMENT protocol, rats are tested 3 hours after carrageenan treatment to establish the presence of hyperalgesia and then at different times after drug administration. In PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioural test): Behavioral tests are conducted by observer blinded to the treatment during the light cycle to avoid circadian rhythm fluctuation. Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioural test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 sec. The instrument cut-off is fixed at 21 sec to prevent tissue damage.

Weight bearing (behavioural test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents. Each carrier, adjuvant or vehicle must be acceptable in the sense of being compatible with the other ingredients of the composition and not injurious to the mammal in need of treatment.

Accordingly, this invention also relates to pharmaceutical compositions comprising at least one compound of formula I, or a pharmaceutically acceptable salt, solvate or ester thereof and at least one pharmaceutically acceptable carrier, adjuvant or vehicle.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts, solvates or esters thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of formula I or a pharmaceutically acceptable salt, solvate, or ester thereof and at least one pharmaceutically acceptable carrier, adjuvant or vehicle.

Yet another aspect of this invention is a kit comprising an amount of at least one compound of formula I or a pharmaceutically acceptable salt, solvate or ester thereof and an amount of at least one additional therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

EXAMPLES

In general, the compounds of this invention may be prepared from known or readily prepared starting materials, following methods known to one skilled in the art and those illustrated below. All stereoisomers and tautomeric forms of the compounds are contemplated.

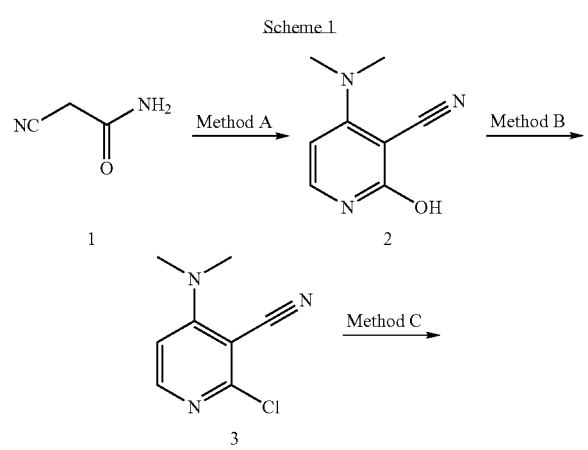

Scheme 1

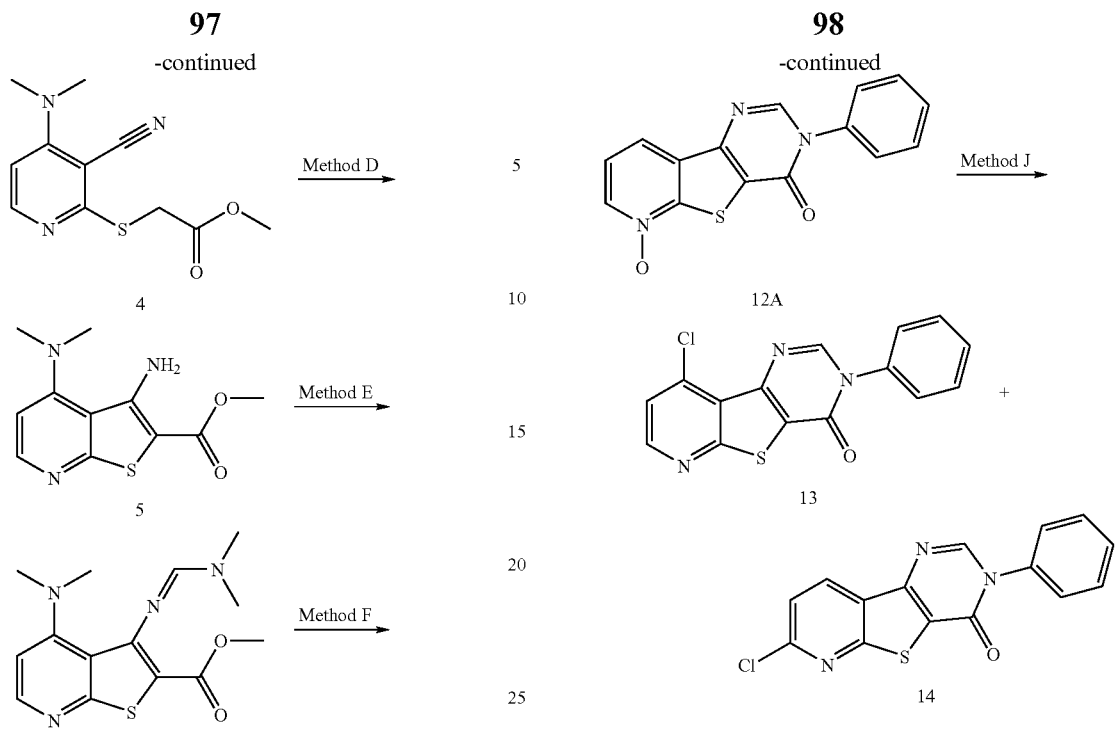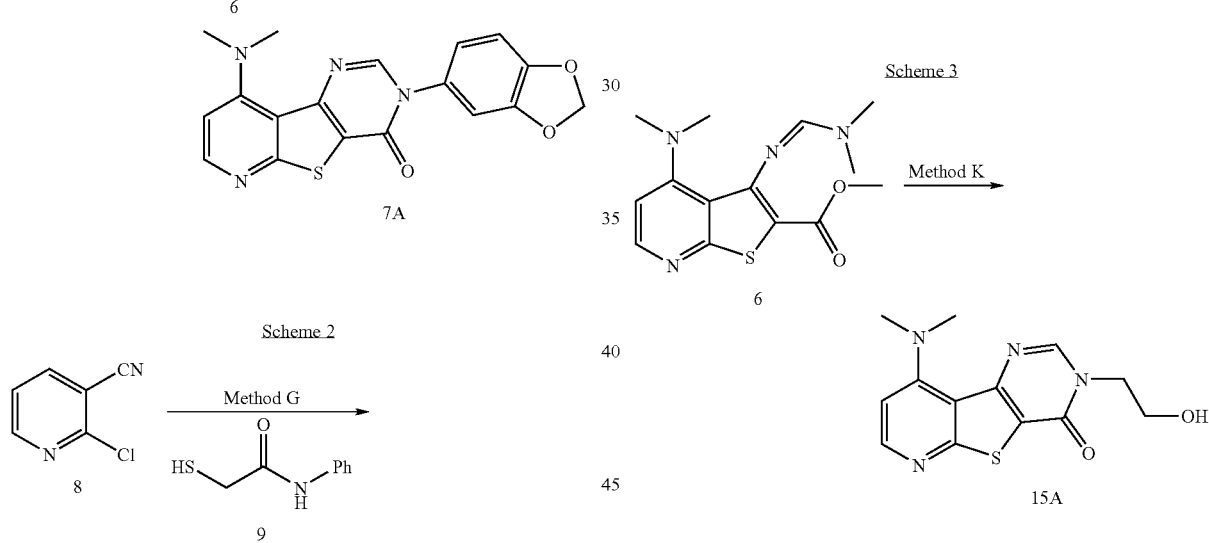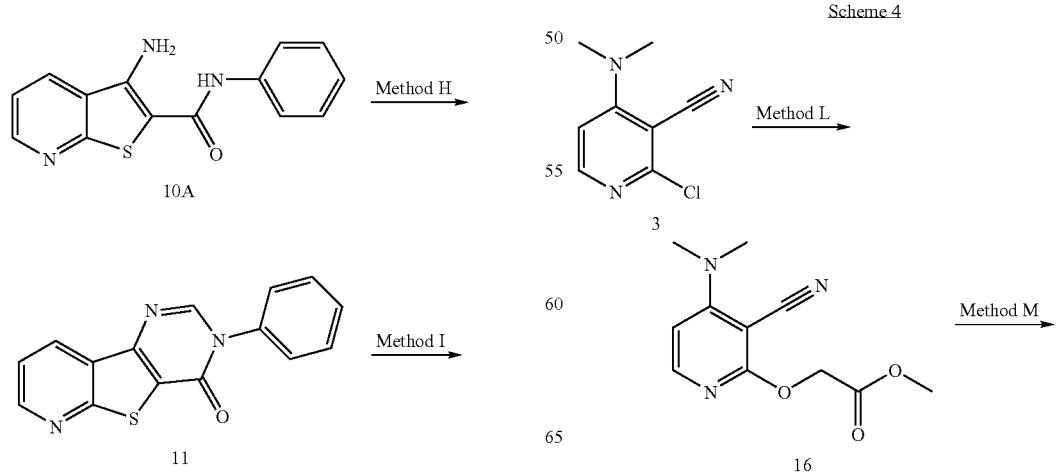

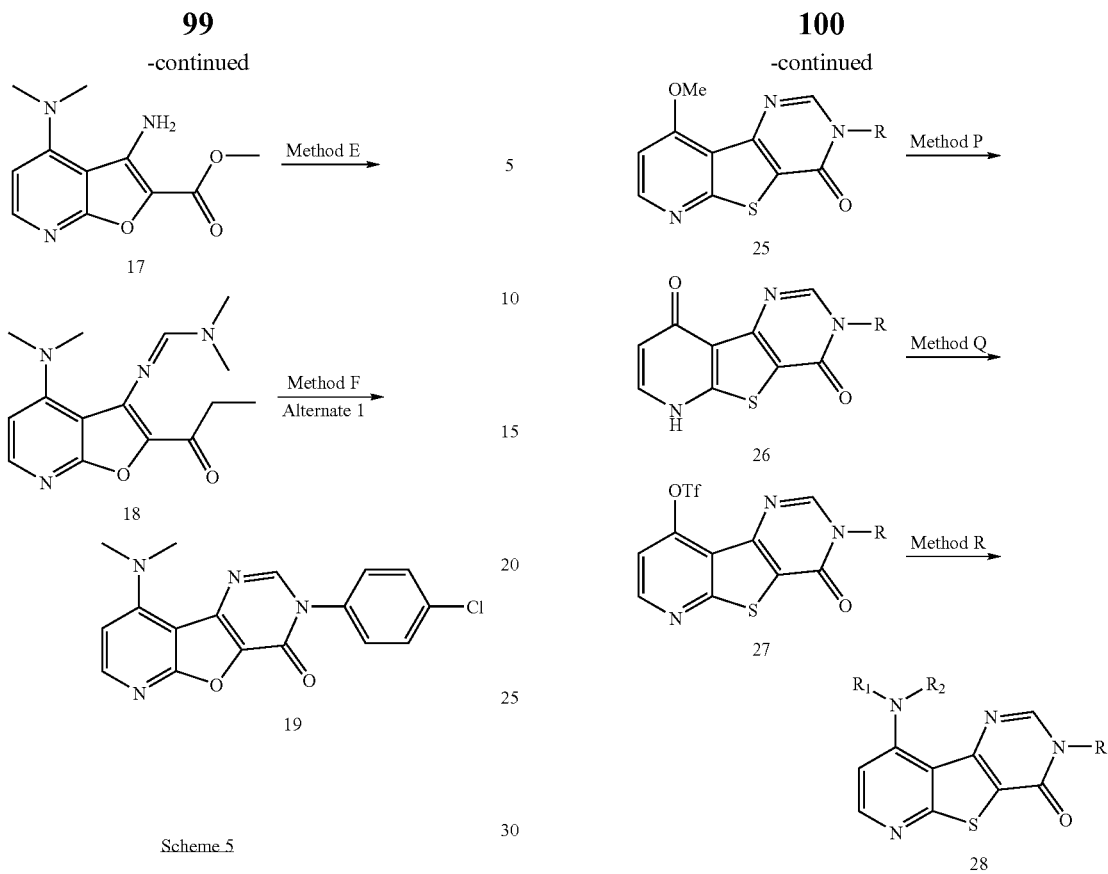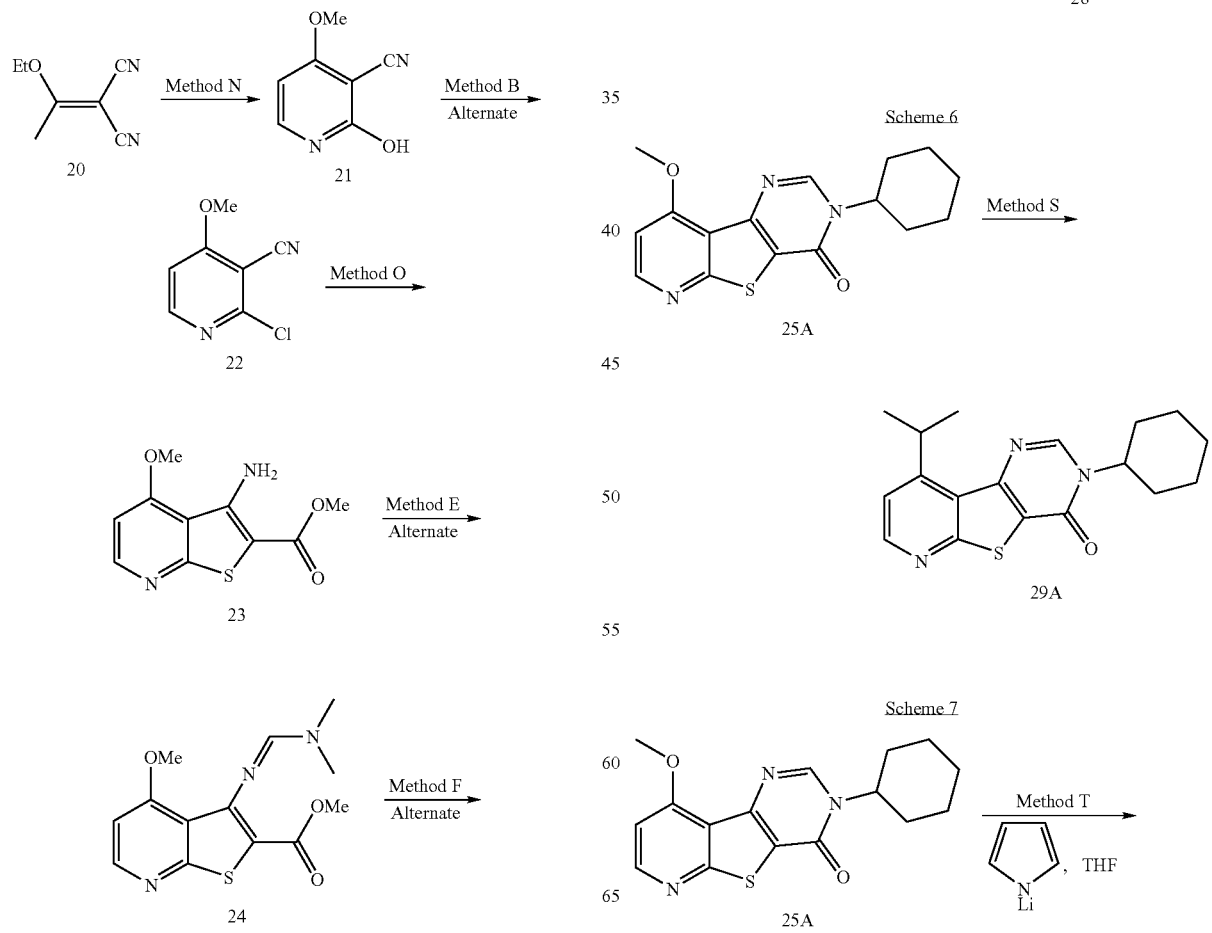

101
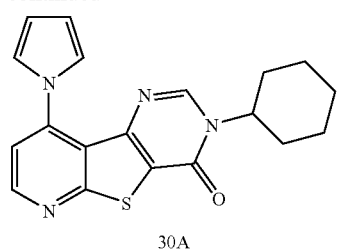
30A
Scheme 8
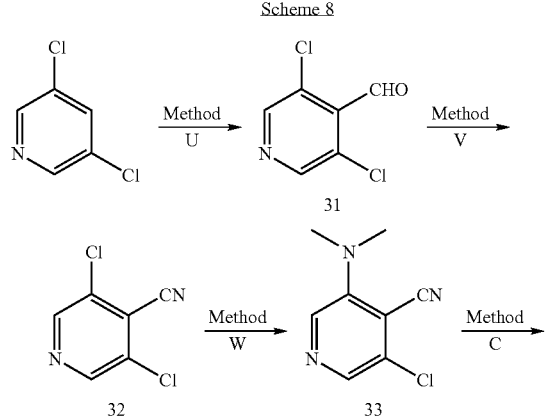
Scheme 9
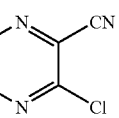
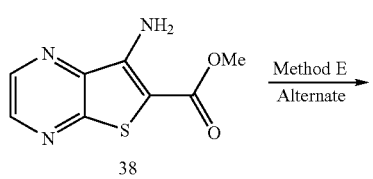
38
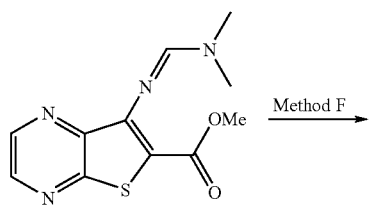
39
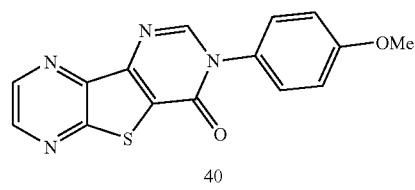
40
Scheme 10
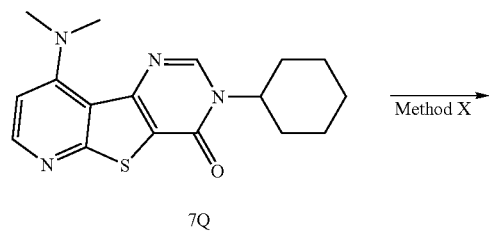
7Q
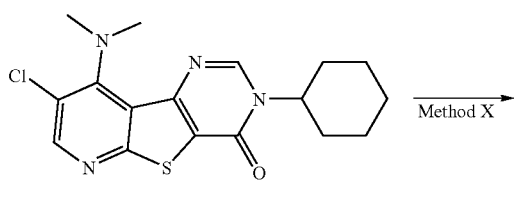
41
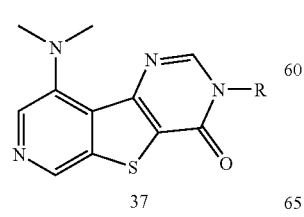
37
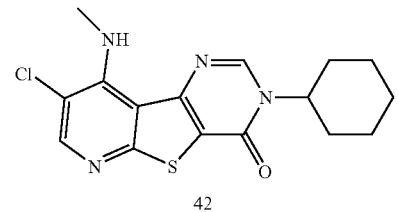
42

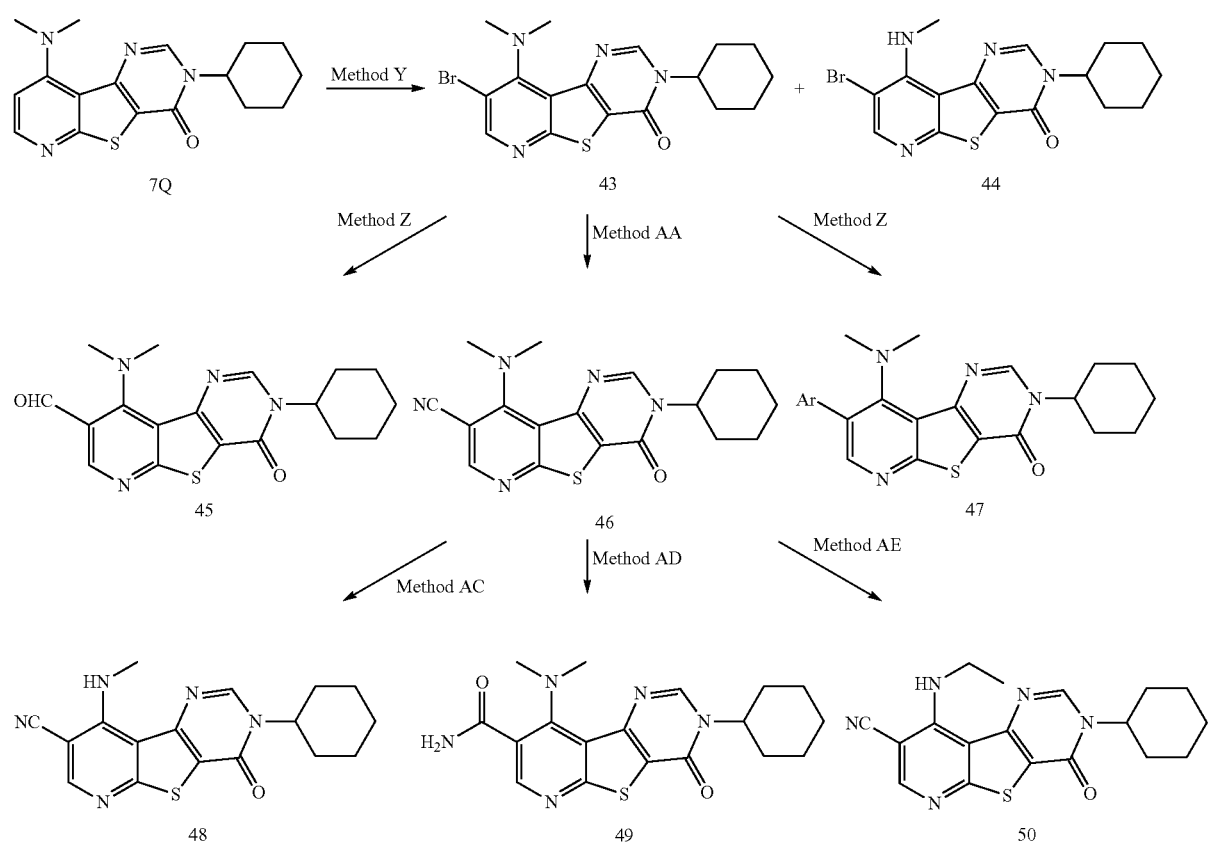
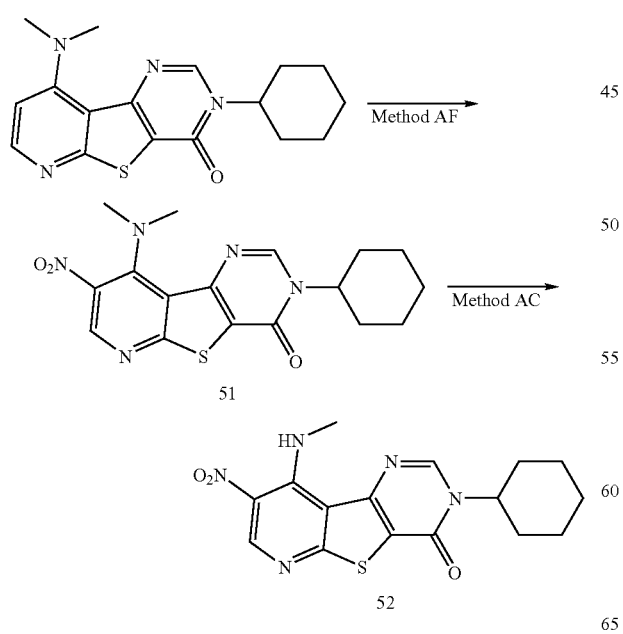
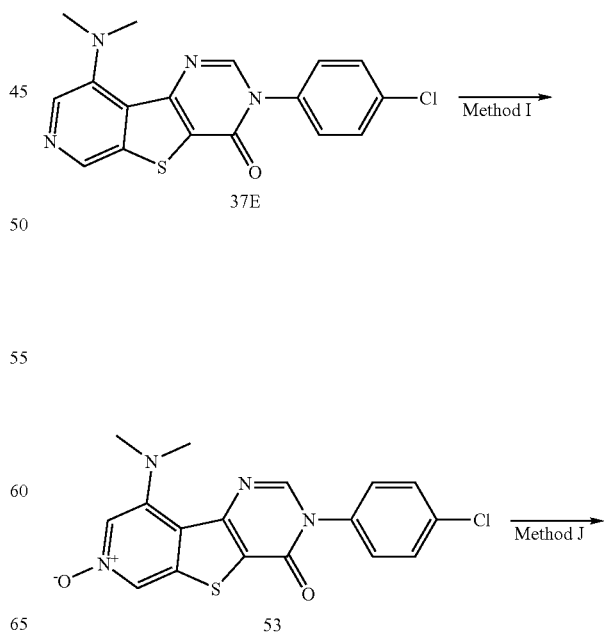

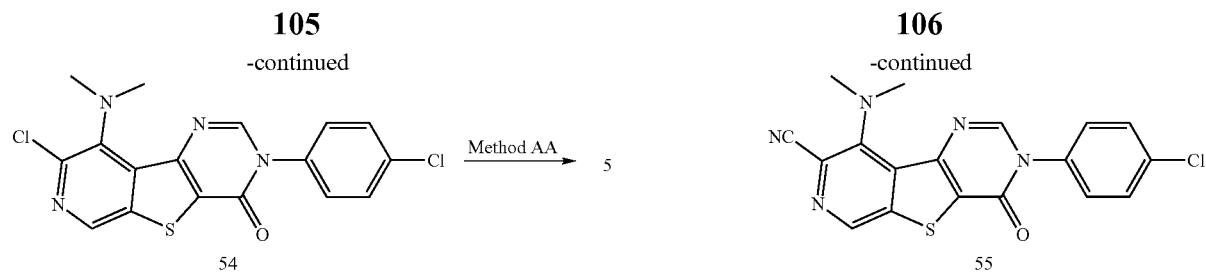
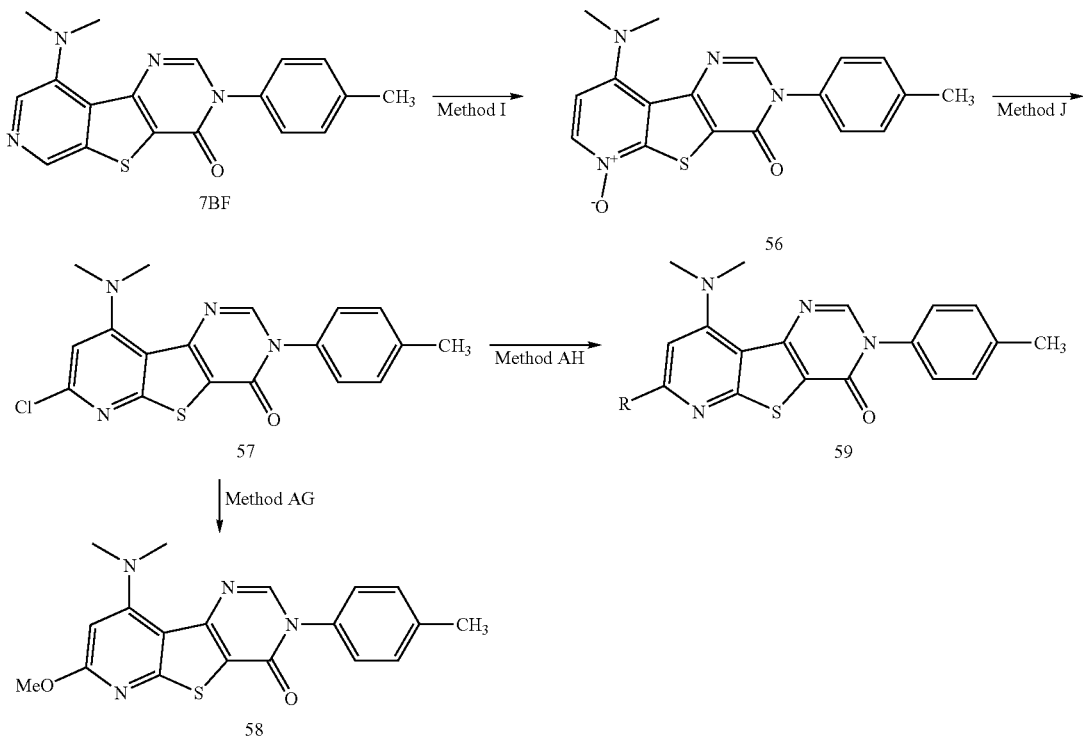
Scheme 14
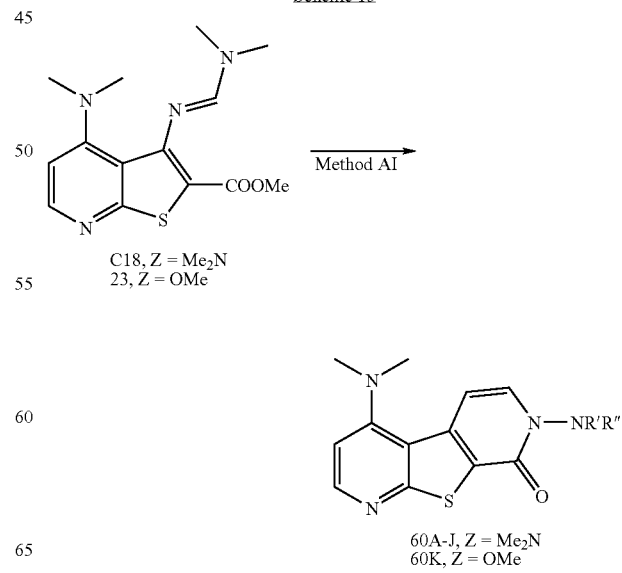
Scheme 15

Scheme 16
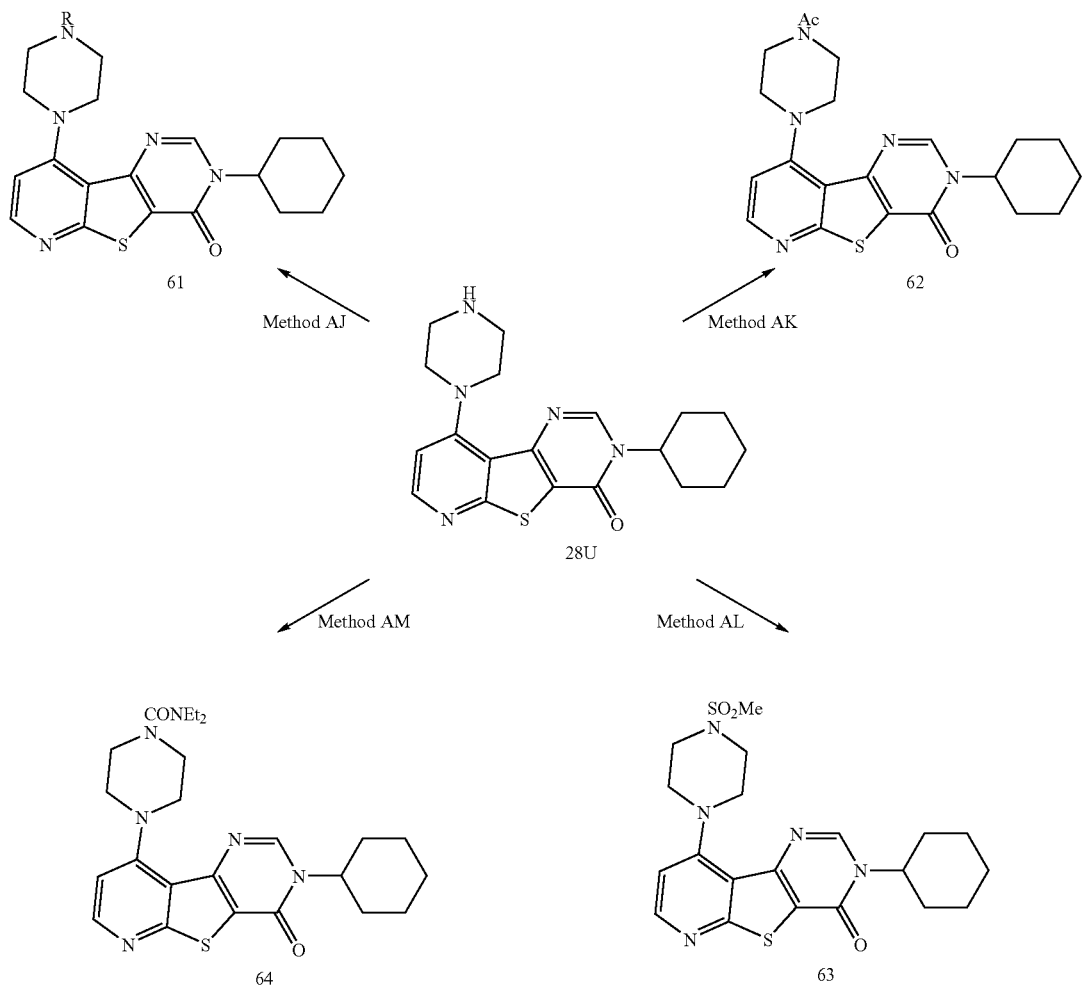
Scheme 17
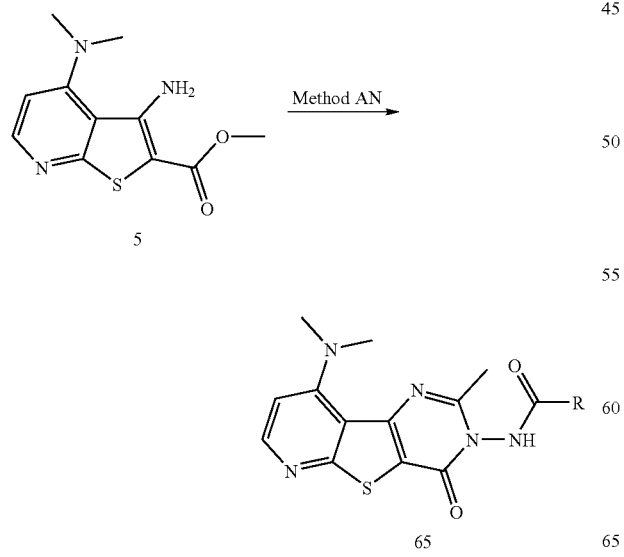
Scheme 18
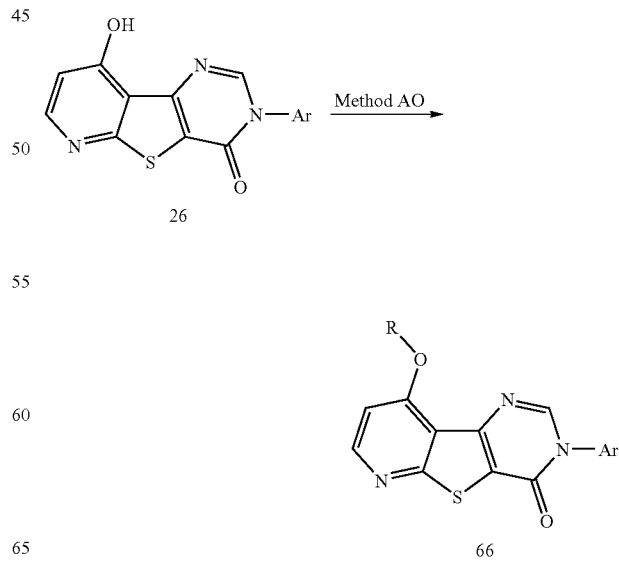

Scheme 19
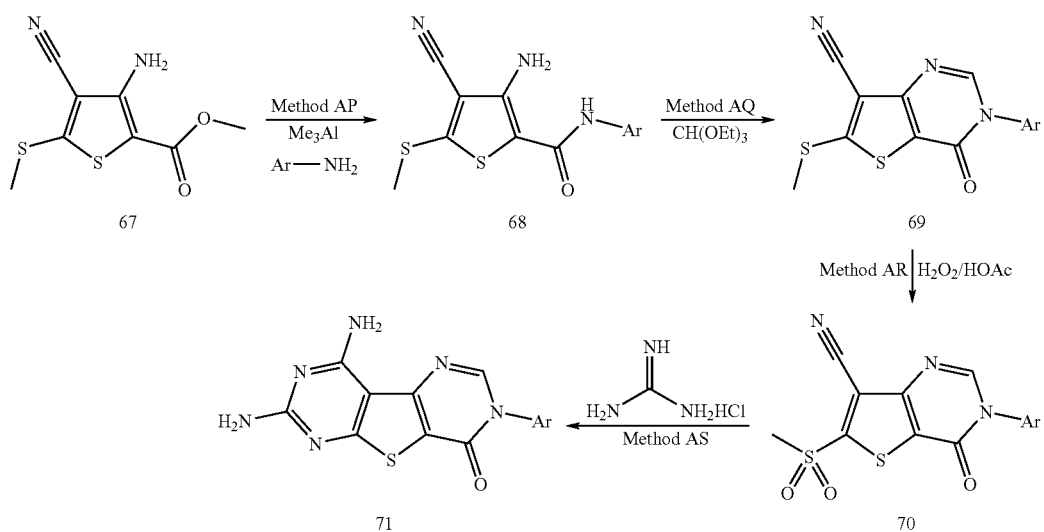
Scheme 20
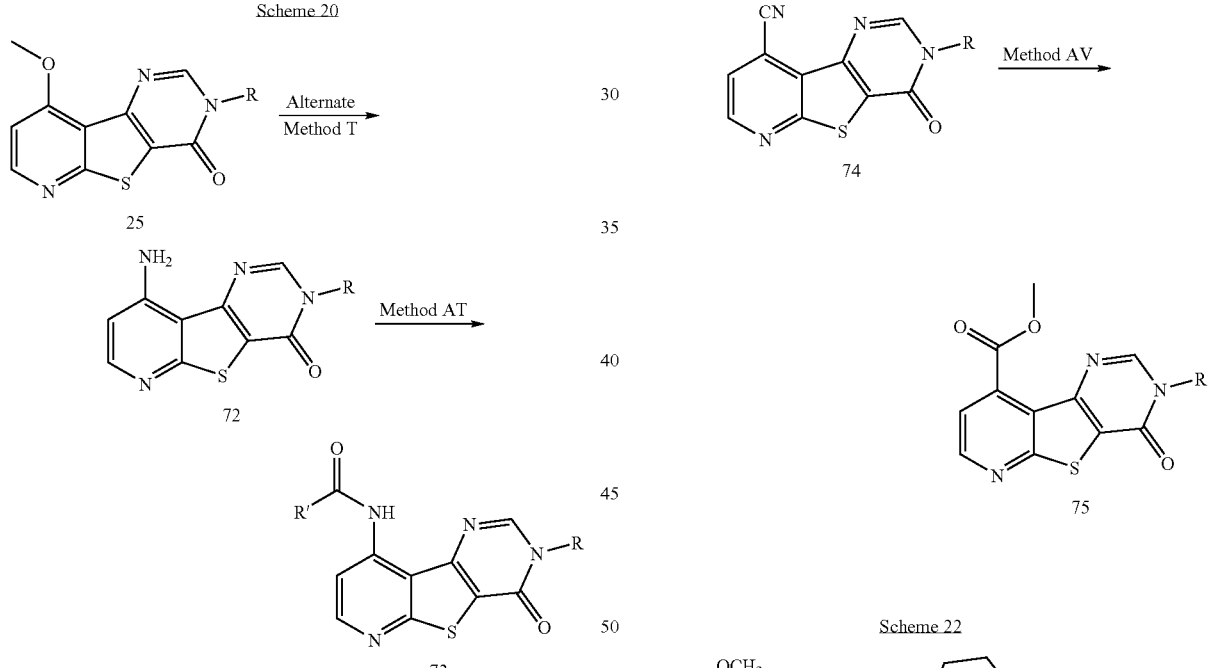
Scheme 21
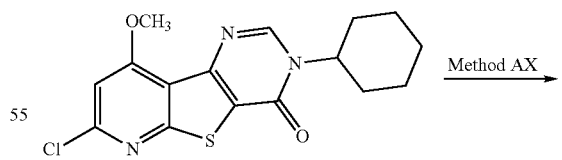
Scheme 22
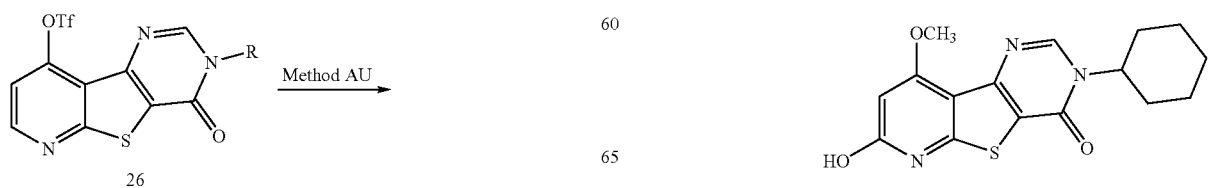

Scheme 23
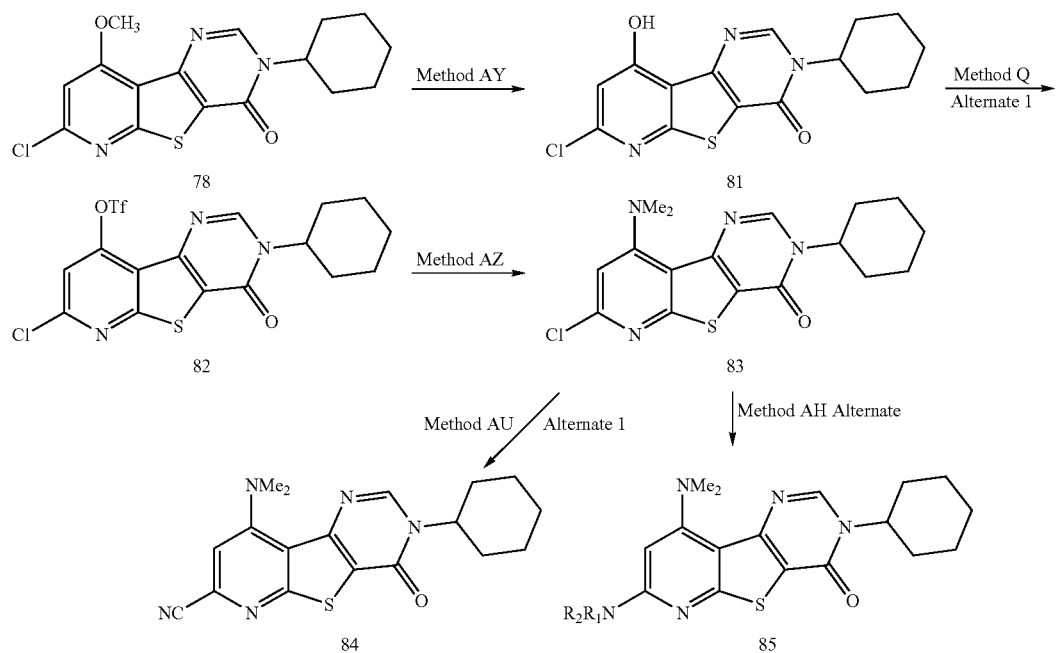
Scheme 24
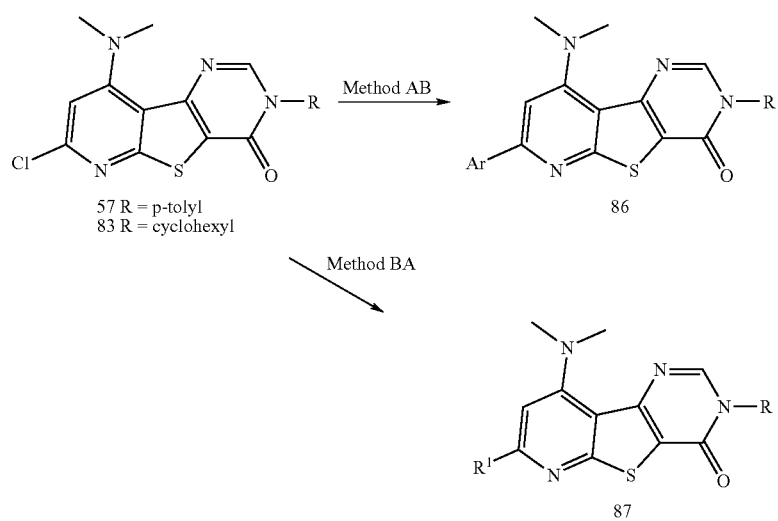
Scheme 25
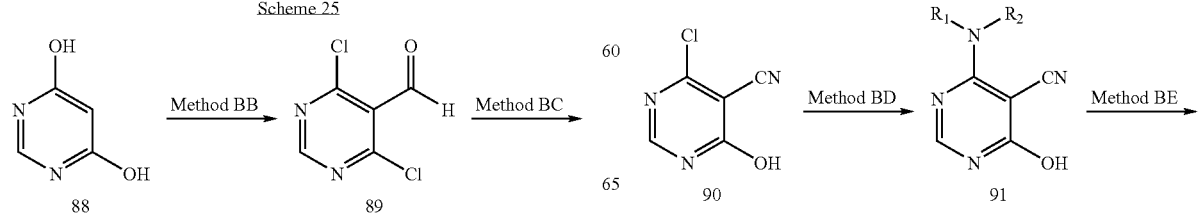

113
-continued
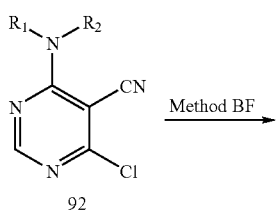
92
Method BF →
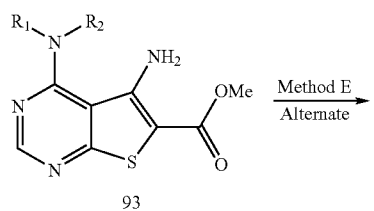
93
Method E
Alternate →
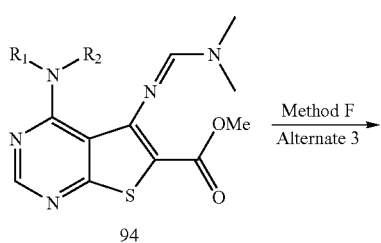
94
Method F
Alternate 3 →
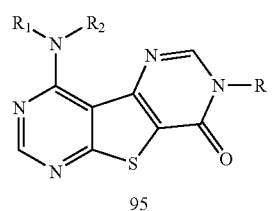
95
Scheme 26
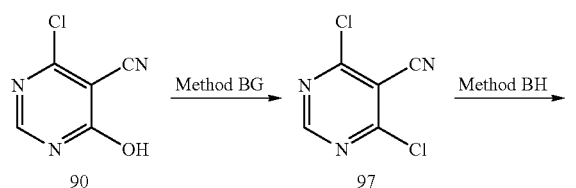
90    Method BG →    97    Method BH →
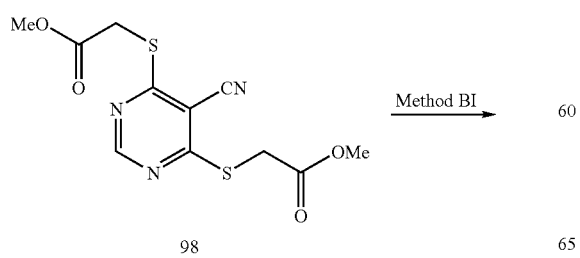
98    Method BI →
114
-continued
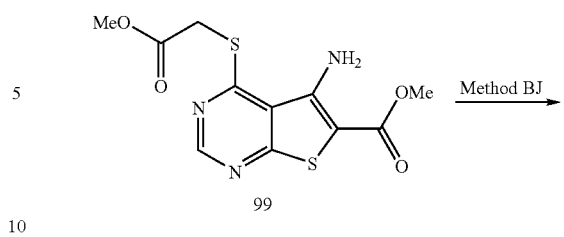
99    Method BJ →
93G
Scheme 27
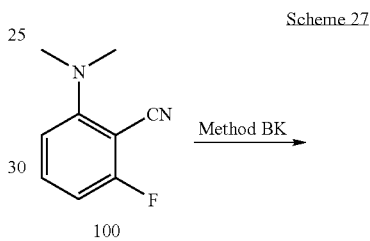
100    Method BK →
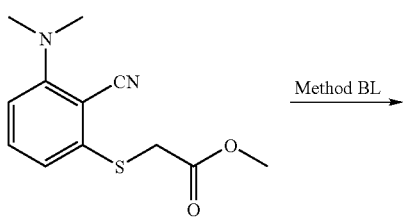
101    Method BL →
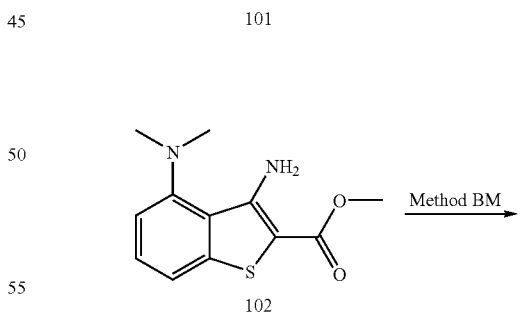
102    Method BM →
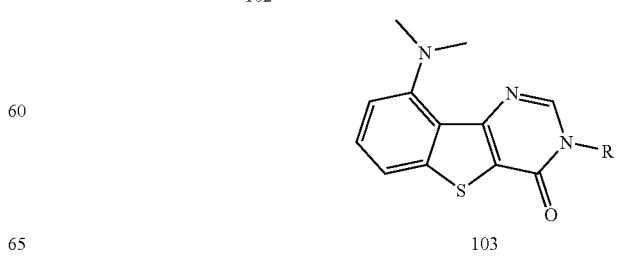
103

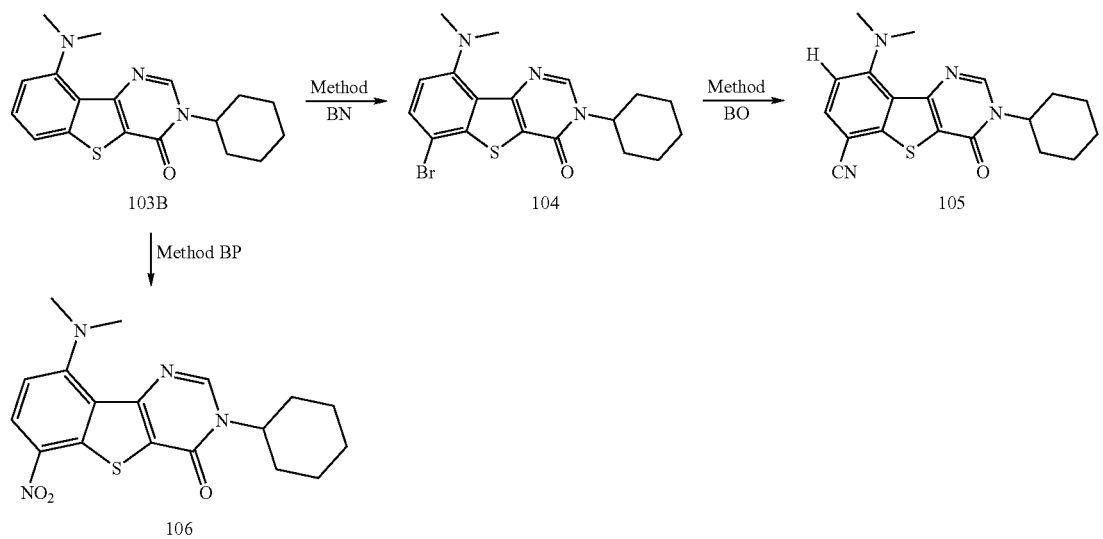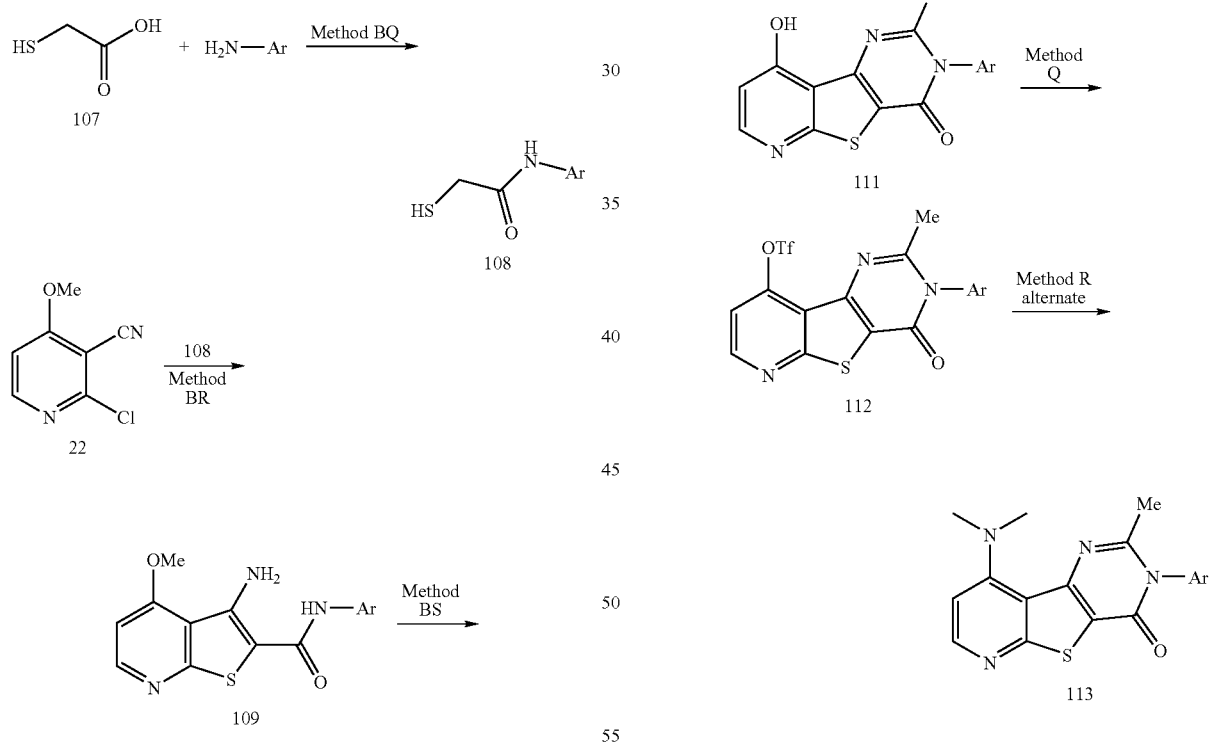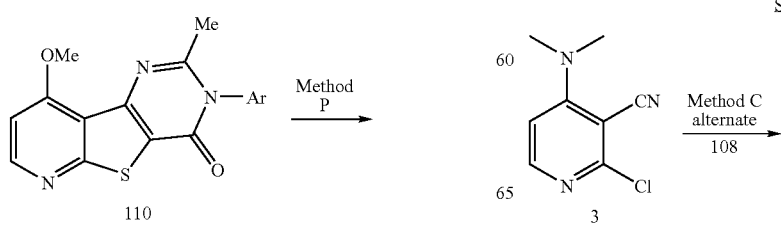

117
-continued
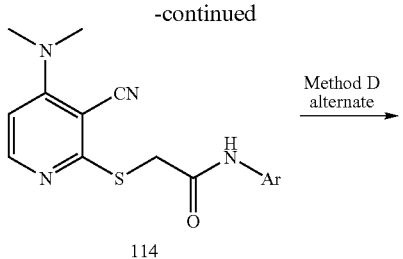
114
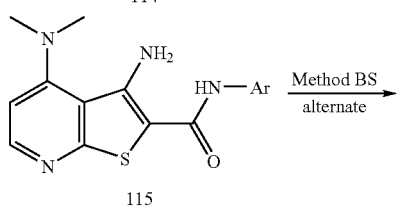
115
Scheme 31
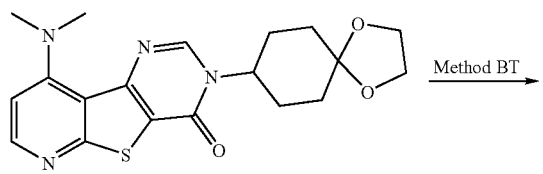
15AH
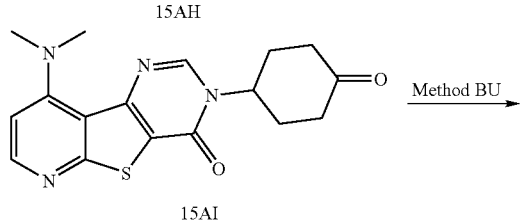
15AI
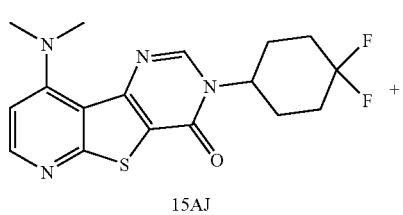
15AJ
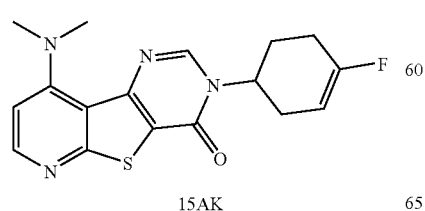
15AK
118
Scheme 32
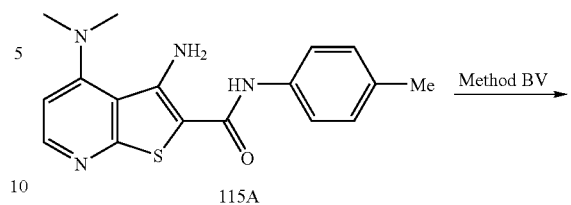
115A
118
Scheme 33
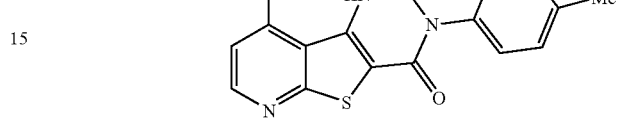
from Method A
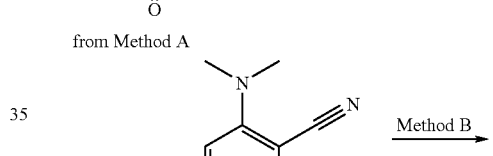
119
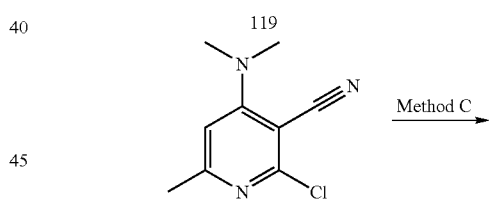
120
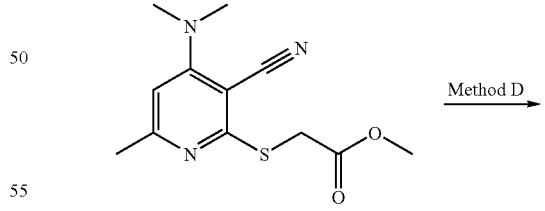
121
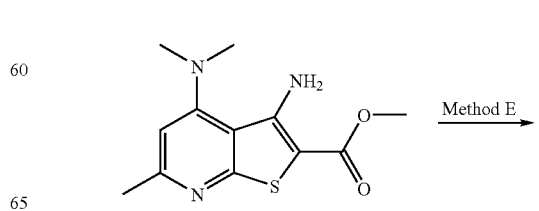
122

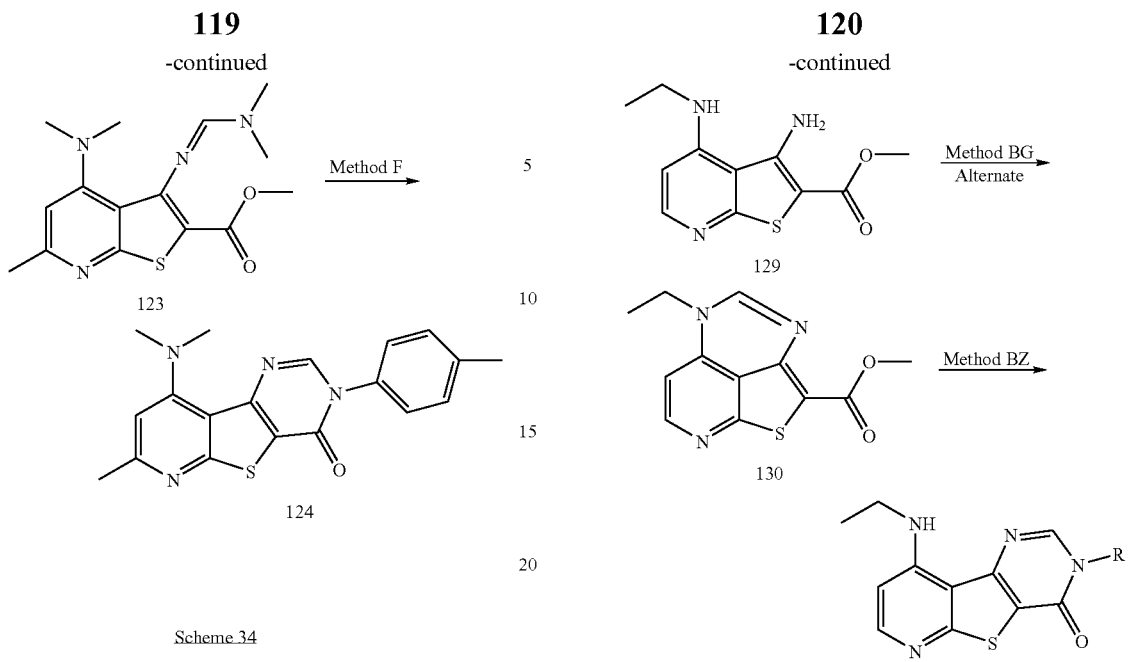
Scheme 34
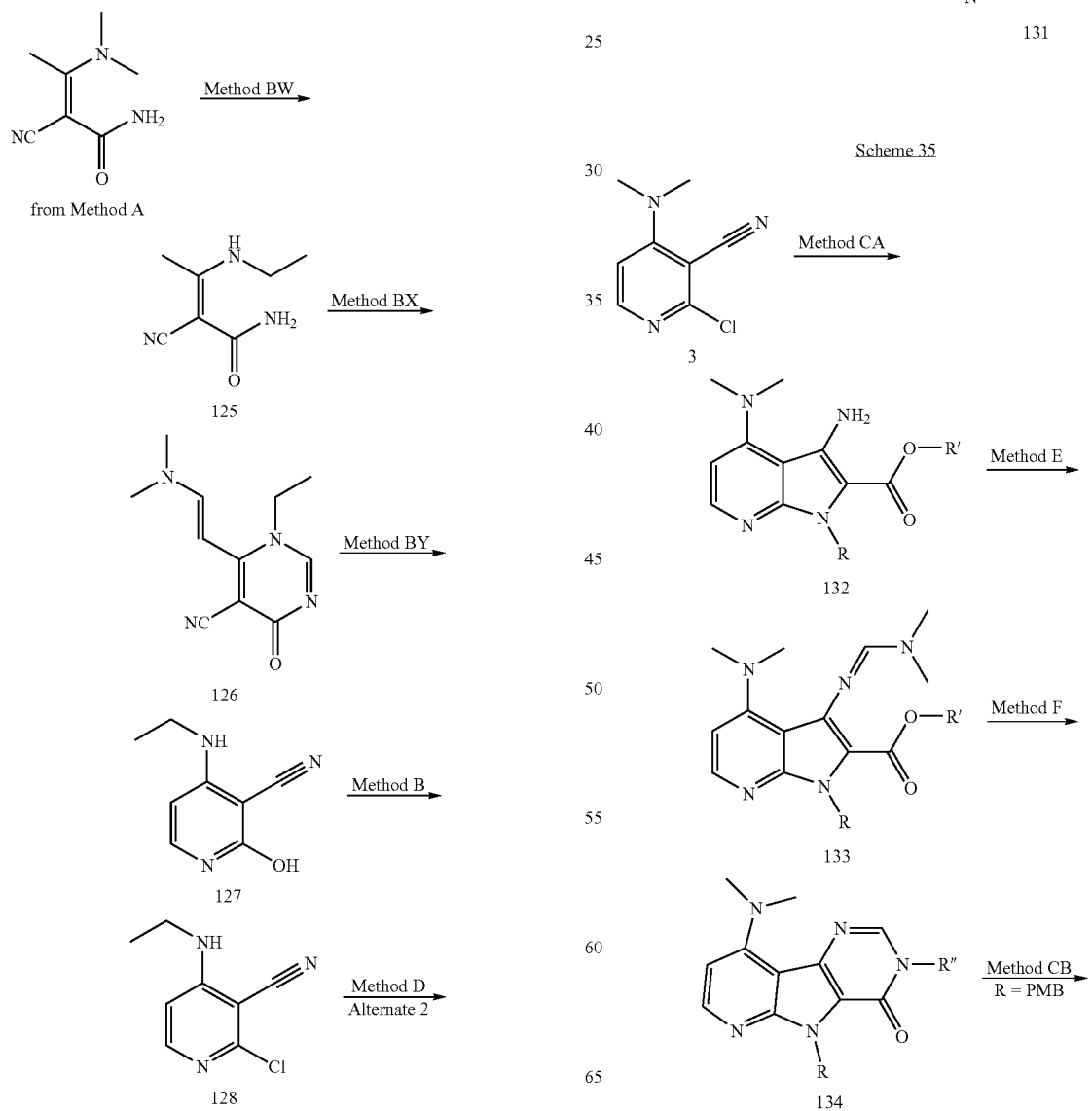
Scheme 35

121
-continued
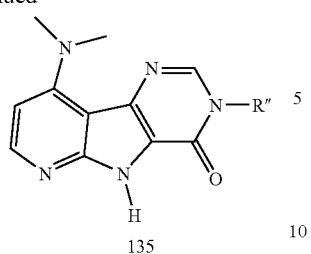
135
122
-continued
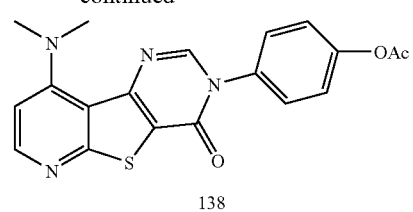
138
Scheme 36
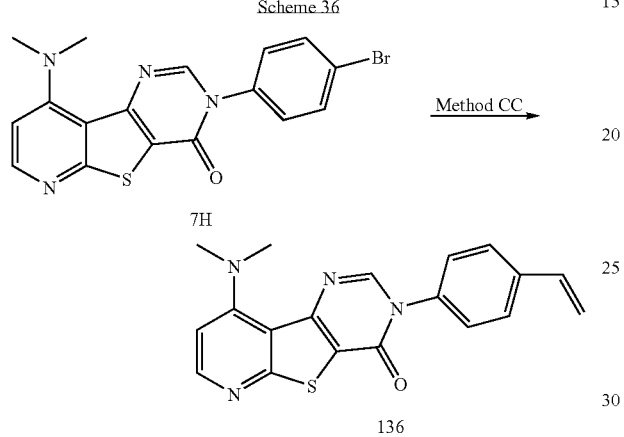
Scheme 37
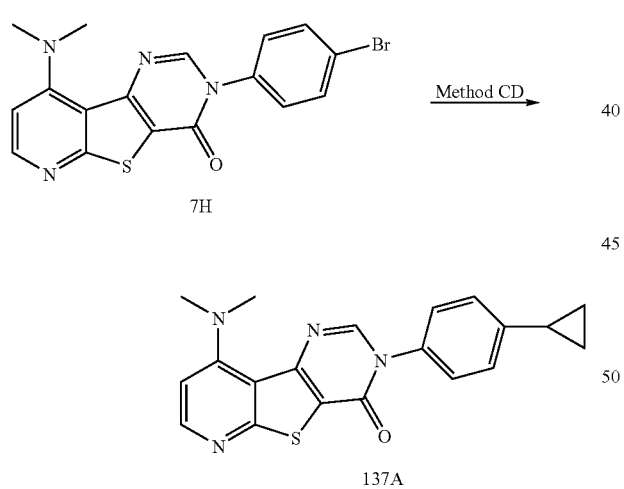
Scheme 38
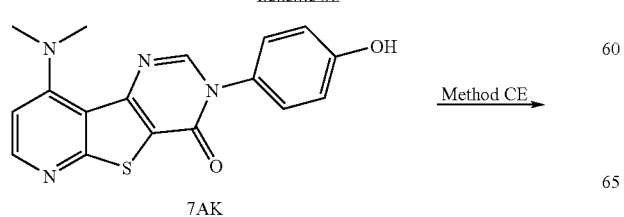
Scheme 39
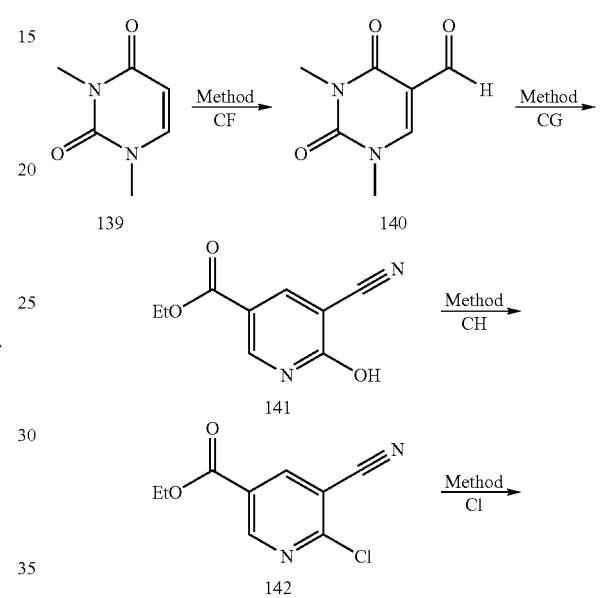

123
-continued

147

Scheme 40

148 → Method Y Alternate →

149 +

150

151 +

152

Scheme 41

+ N₂H₄·2HCl  Method CN →

124
-continued

153 → Method CO →

154 → Method CP →

155 → Method AA →

156 → Method CQ →

157 → Method B →

158 → Method C →

159 → Method D →

160 → Method BM →

125
-continued
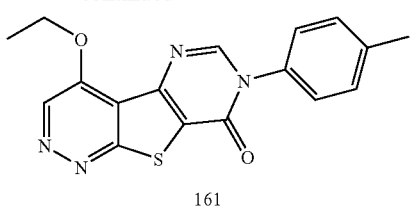
161
126
-continued
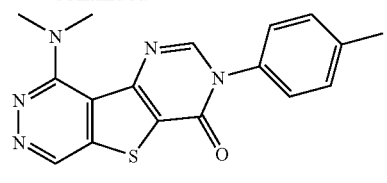
167
Scheme 42
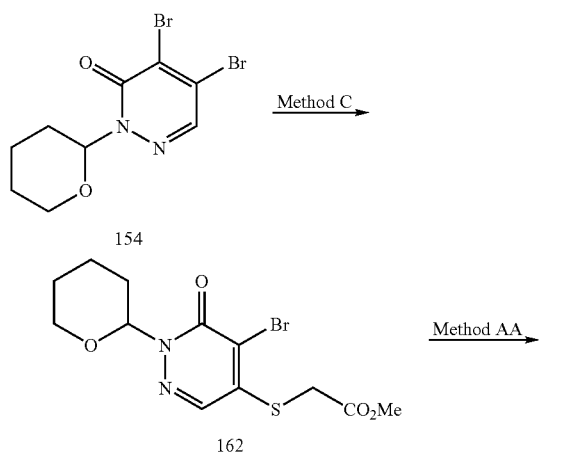
154
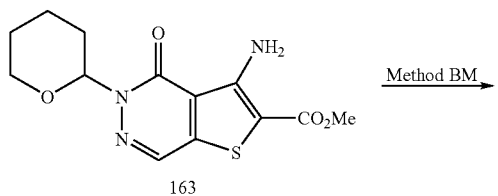
162
Method C→
Method AA→
Scheme 43
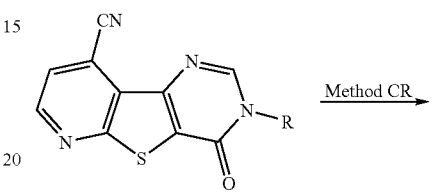
74
Method CR→
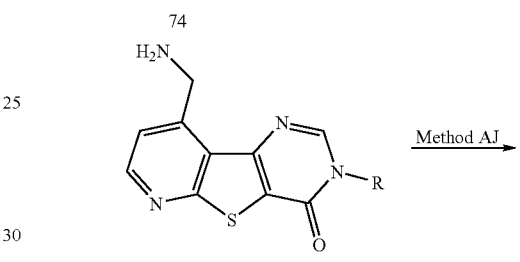
168
Method AJ→
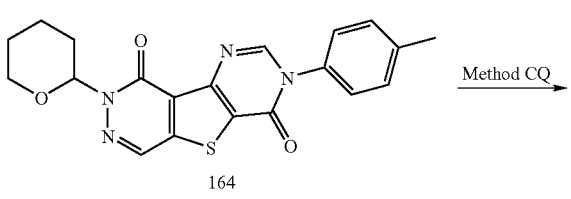
163
Method BM→
169
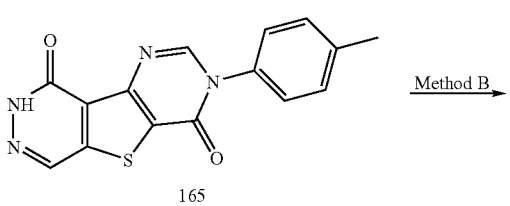
164
Method CQ→
Scheme 44
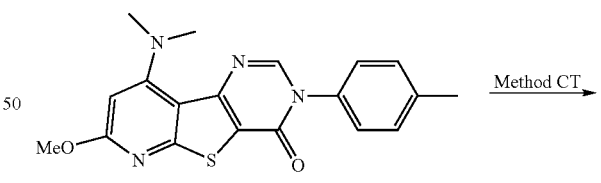
58
Method CT→
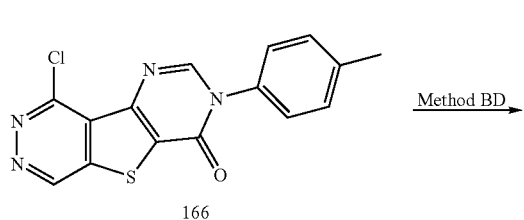
165
Method B→
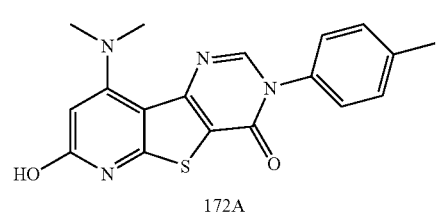
172A
+
166
Method BD→

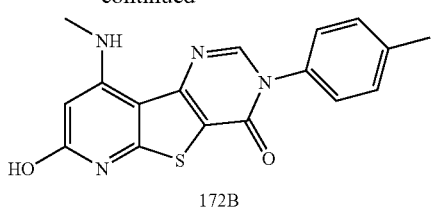
172B
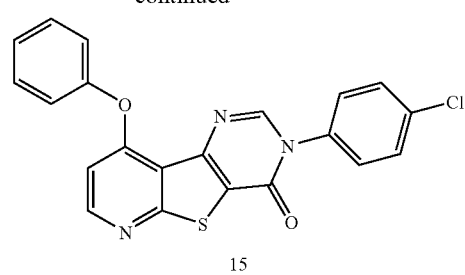
Scheme 45
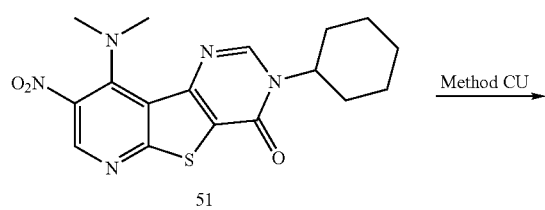 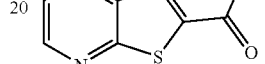 Method CU
51
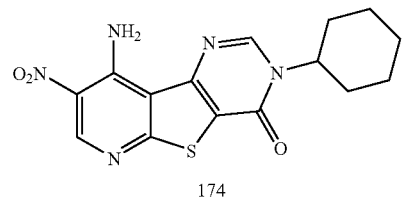
174
Scheme 46
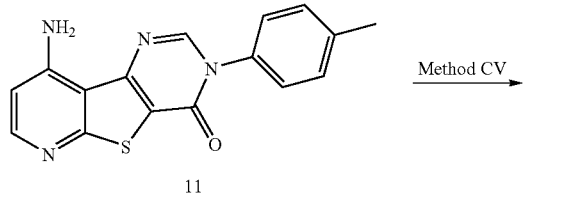 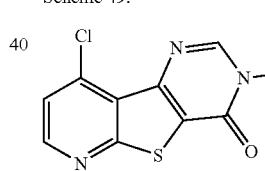 Method CV
11
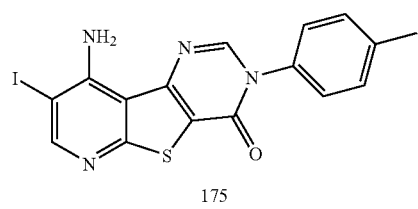
175
Scheme 47
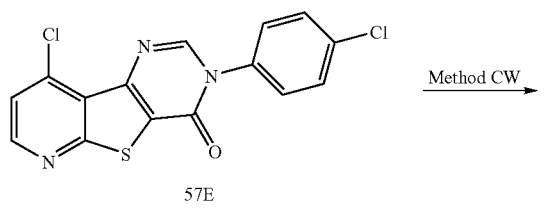 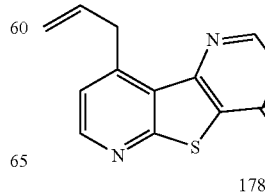 Method CW
57E
Scheme 48:
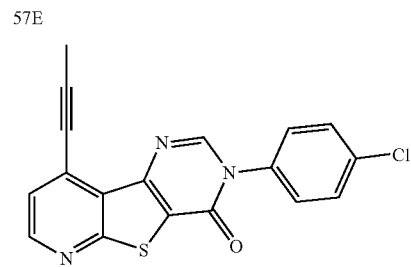 Method CX
57E
177
Scheme 49:
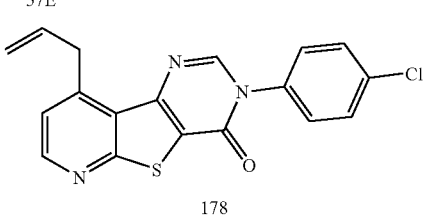 Method CY
57E
178
Scheme 49:
178 Method CZ

129
-continued
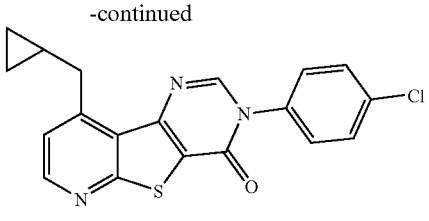
179
Scheme 50:
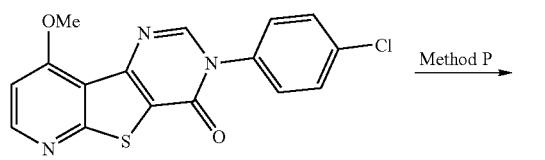
180
Method P →
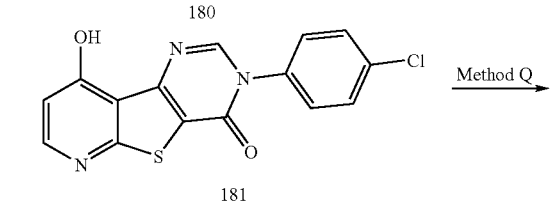
181
Method Q →
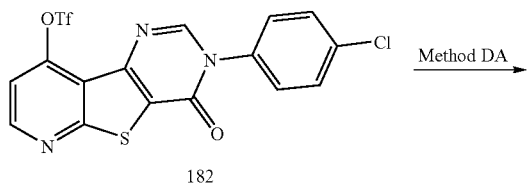
182
Method DA →
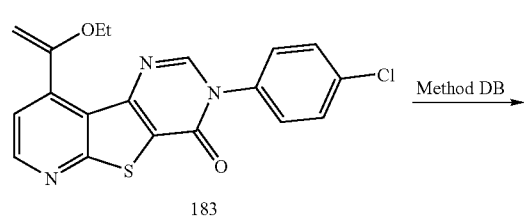
183
Method DB →
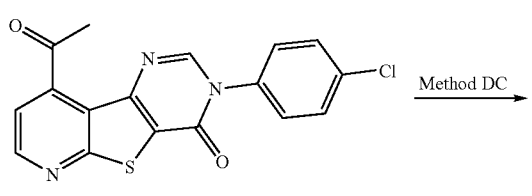
184
Method DC →
| Method DD
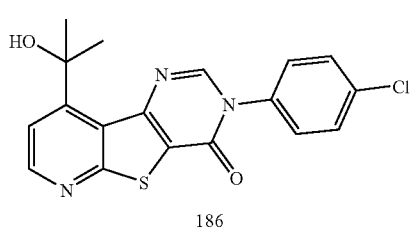
186
130
-continued
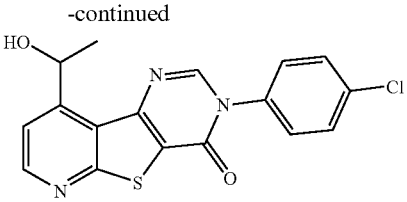
185
Scheme 51:
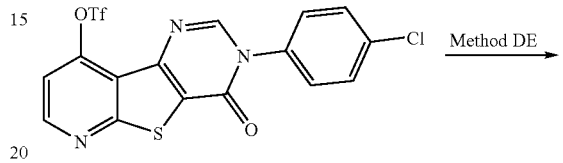
182
Method DE →
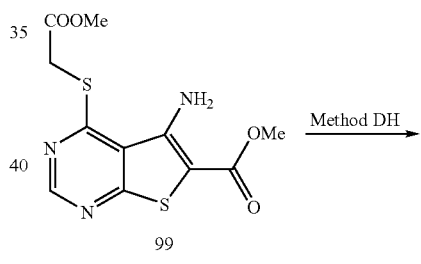
187
Scheme 52:
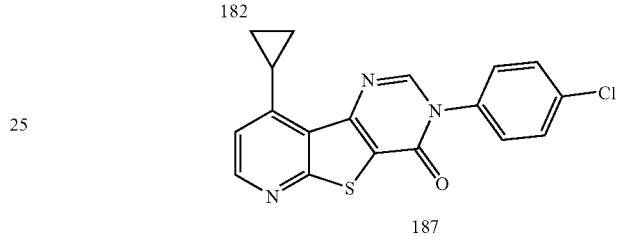
99
Method DH →
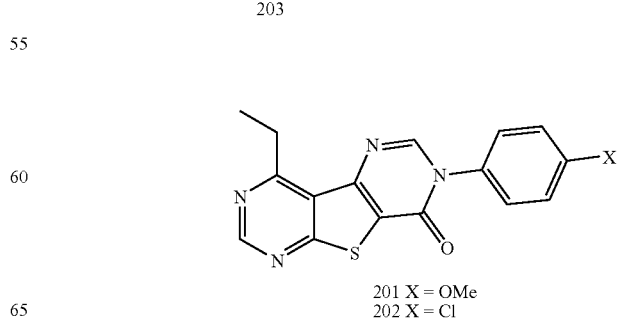
203
Method E / Method F
201 X = OMe
202 X = Cl

Scheme 53:

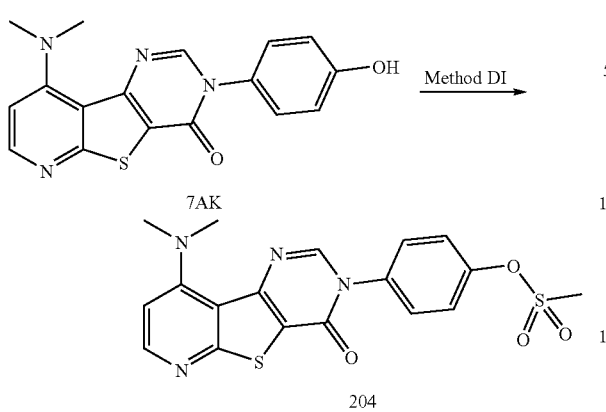

Scheme 54:

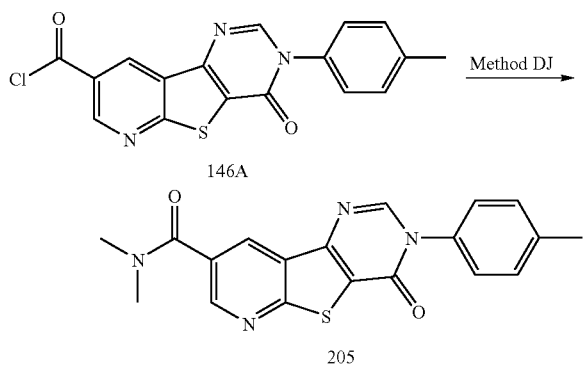

Scheme 55:

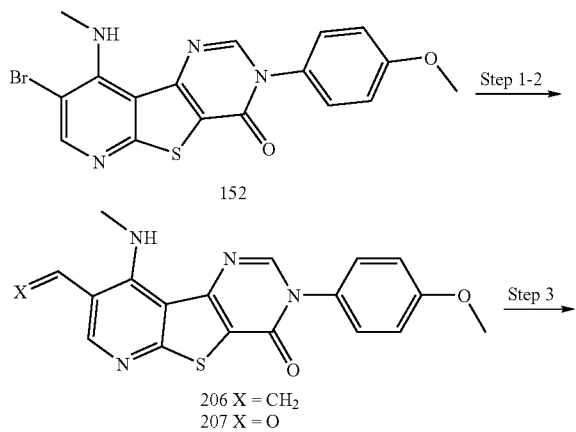

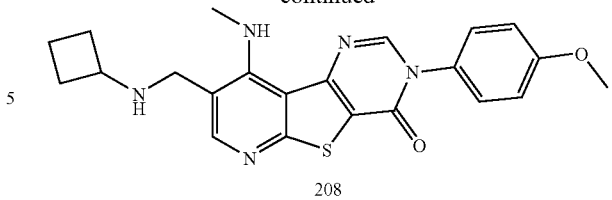

Experimental Procedures

Method A: (ref: H. Zipse and L.-H. Wang, *Liebigs Ann.* 1996, 1501-1509).

A mixture of cyanoacetamide (8.4 g, 0.1 mol) and dimethylacetamide dimethylacetal (14.6 mL, 0.1 mol) was heated under reflux in dry ethanol (150 mL) for 2.5 h under a nitrogen atmosphere. The resulting white crystals of 2-cyano-3-(dimethylamino)-2-butenamide (10.0 g, 0.068 mol) were filtered, washed with ethanol and dried under vacuum. To this, was added N,N-dimethyl-formamide dimethylacetal (8.1 g, 0.068 mol) and the mixture heated under reflux in dry toluene (100 mL) for 1 h before evaporating the solvent under reduced pressure. The residue was heated neat at 150° C. for 30 min, cooled, washed twice with acetone and dried under vacuum to give compound 2. $^1$H NMR (DMSO-d$_6$) δ 7.22 (d, 1H), 5.86 (d, 1H), 3.13 (s, 6H); Mass Spectrum (M$^{+1}$): m/z calcd. for C$_8$H$_{10}$N$_3$O$^+$=164.1, found m/z=164.2.

Alternatively, the intermediate 2-cyano-3-(dimethylamino)-2-butenamide (2.5 g, 0.0163 mol) (intermediate from above) and dimethylacetamide dimethyl acetal (2.2 ml, 0.0163 mol) was heated under reflux in dry toluene (25 ml) for 2.5 h under a nitrogen atmosphere before evaporating the solvent under reduced pressure. The residue was then heated neat at 150° C. for 30 minutes, cooled and washed twice with acetone and dried under vacuum to give compound 119. $^1$H NMR (DMSO-d$_6$) δ 11.12 (br. s, 1H), 5.74 (s, 1H), 3.10 (s, 6H), 2.14 (s, 3H).

Method B: (ref.: M. Yu. Yakovlev, O. B. Romanova, S. I. Grizik, A. V. Kadushkin, and V. G. Granik, *Khimiko-Farmatsevticheskii Zhurnal*, 1997, 31 (11), 44-47).

To compound 2 (9.34 g, 0.057 mol) was added phosphorous oxychloride (95 mL, 1.02 mol) and to the mixture was added triethylamine (4 mL, 0.029 mol) dropwise. The resultant mixture was heated at reflux for a period of 3 h, cooled to room temperature and quenched with ice-water. The mixture was then basified using 40% sodium hydroxide solution and the resulting precipitate filtered, washed with water until neutral and dried in a vacuum oven to give chloropyridine compound 3. $^1$H NMR (CDCl$_3$): δ 7.95 (d, 1H), 6.48 (d, 1H), 3.20 (s, 6H).

The following compounds 120, 128, 158 and 166 were prepared analogously from 119, 127, 157 and 165, respectively.

| Cpd | Structure | Formula | MW | m/z Found (M + 1)$^+$ |
|---|---|---|---|---|
| 120 | 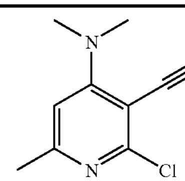 | C$_9$H$_{10}$ClN$_3$ | 195.6 | 196.0 |

-continued

| Cpd | Structure | Formula | MW | m/z Found (M + 1)⁺ |
|---|---|---|---|---|
| 128 | 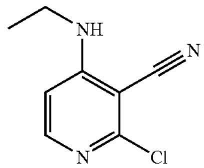 | C₈H₈ClN₃ | 181.6 | 182.1 |
| 158 | 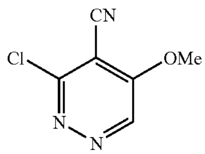 | C₆H₄ClN₃O | 169.6 | 170.1 |
| 166 | 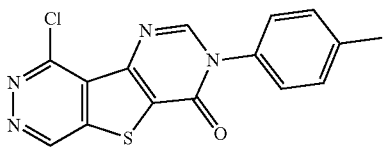 | C₁₅H₉ClN₄OS | 328.8 | 329.1 |

Method C: (ref.: M. Yu. Yakovlev, O. B. Romanova, S. I. Grizik, A. V. Kadushkin, and V. G. Granik, *Khimiko-Farmatsevticheskii Zhurmal*, 1997, 31 (11), 44-47).

A solution of compound 3 (6.02 g, 0.033 mol), methyl thioglycolate (7.05 g, 0.066 mol) and potassium carbonate (6.88 g, 0.050 mol) in DMF (50 mL) was stirred for a period of 5 h at room temperature under a nitrogen atmosphere. Water (200 mL) was added, and the resulting precipitate filtered and dried in a vacuum oven to give ester 4. ¹H NMR (CDCl₃): δ 7.97 (d, 1H), 6.28 (d, 1H), 3.93 (s, 2H), 3.70 (s, 3H), 3.18 (s, 6H).

The following compounds were prepared analogously:

| Cpd | Structure | Formula | m/z calcd (M + 1)⁺ | m/z Found (M + 1)⁺ |
|---|---|---|---|---|
| 34 | 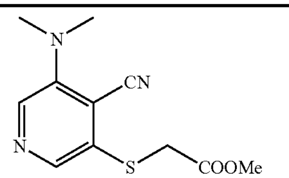 | C₁₁H₁₄N₃O₂S⁺ | 252.1 | 252.1 |
| 121 | 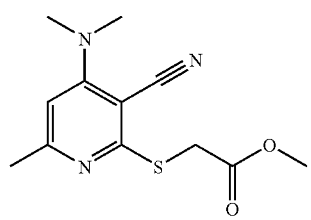 | ¹H NMR (CDCl₃) δ 6.13 (s, 1 H), 3.89 (s, 2 H), 3.69 (s, 3 H), 3.14 (s, 6 H), 2.29 (s, 3 H). | | |
| 159 | 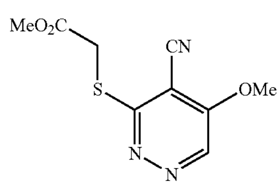 | C₉H₁₀N₃O₃S⁺ | 240.04 | 240.09 |
| 162 | 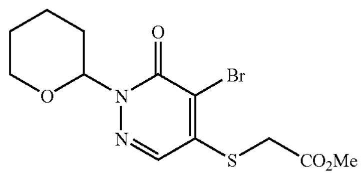 | ¹H NMR (CDCl₃) δ 7.69 (s, 1 H), 5.99 (dd, 1 H), 4.05 (d, 1 H), 3.73-3.68 (m, 6 H), 2.10-1.98 (m, 2 H), 1.66-1.50 (m, 4 H). | | |

Method D

A solution of compound 4 (8.33 g, 0.033 mol) and sodium methoxide (3.77 g, 0.070 mol) in methanol was heated at reflux for 3 h under a nitrogen atmosphere. The reaction was cooled to room temperature, water was added and the product isolated by extraction with dichloromethane (150 mL). The organic layer was dried over anhydrous sodium sulfate, filtered and evaporated under reduced pressure to give the desired product 5. $^1$H NMR (CDCl$_3$): δ 8.41 (d, 1H), 6.81 (d, 1H), 6.70 (br.s, 2H), 3.82 (s, 3H), 2.81 (s, 6H). Mass Spectrum (M$^{+1}$): m/z calcd. for C$_{11}$H$_{14}$N$_3$O$_2$S$^+$=252.1, found m/z=252.1.

The following compounds were prepared analogously:

| Cpd | Structure | Formula | m/z calcd (M + 1)$^+$ | m/z Found (M + 1)$^+$ |
|---|---|---|---|---|
| 35 | 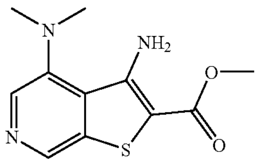 | C$_{11}$H$_{14}$N$_3$O$_2$S$^+$ | 252.1 | 252.1 |
| 122 | 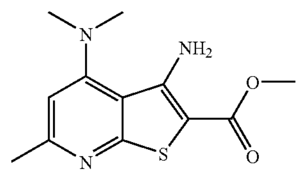 | $^1$H NMR (CDCl$_3$) δ 6.67 (br. s, 3 H), 3.82 (s, 3 H), 2.79 (s, 6 H), 2.55 (s, 3 H). | | |
| 160 | 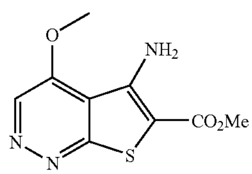 | C$_9$H$_{10}$N$_3$O$_3$S$^+$ | 240.04 | 240.09 |

Method E: (ref.: N. P. Solov'eva, A. V. Kadushkin, and V. G. Granik, *Khimiko-Farmatsevticheskii Zhurmal*, 1993, 27 (3), 40-43).

To bicyclic ester 5 (7.24 g, 0.029 mol) was added N,N-dimethylformamide dimethylacetal (7.7 mL, 0.058 mol) and mixture heated in toluene under reflux for a period of 5-24 h under a nitrogen atmosphere. The solvent was evaporated under reduced pressure to give amidine product 6 by proton NMR and mass spectrum. $^1$H NMR (CDCl$_3$): δ 8.24 (d, 1H), 7.35 (s, 1H), 6.54 (d, 1H), 3.76 (s, 3H), 3.11 (s, 3H), 3.01 (s, 3H), 2.92 (s, 6H).

The following compounds were prepared analogously:

| Cpd | Structure | Formula | m/z calcd (M + 1)$^+$ | m/z Found (M + 1)$^+$ |
|---|---|---|---|---|
| 36 | 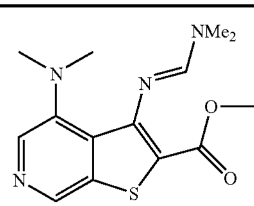 | C$_{14}$H$_{19}$N$_4$O$_2$S$^+$ | 307.1 | 307.1 |
| 123 | 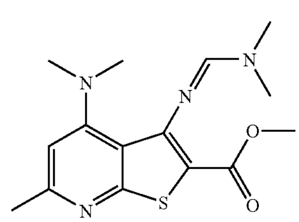 | C$_{15}$H$_{21}$N$_4$O$_2$S$^+$ | 321.1 | 321.1 |

-continued

| Cpd | Structure | Formula | m/z calcd (M + 1)+ | m/z Found (M + 1)+ |
|---|---|---|---|---|
| 133A | 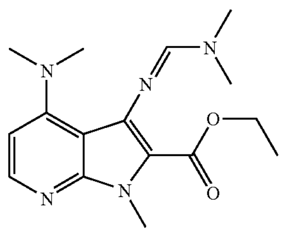 | C$_{16}$H$_{24}$N$_5$O$_2$$^+$ | 318.2 | 318.2 |
| 133B | 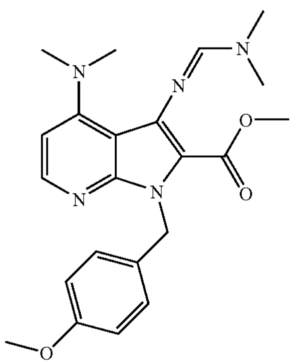 | C$_{22}$H$_{27}$N$_5$O$_3$ | 409.5 | 410.2 |

Method F: (ref: N. P. Solov'eva, A. V. Kadushkin, and V. G. Granik, *Khimiko-Farmatsevticheskii Zhurmal*, 1993, 27 (3), 40-43).

Amidine 6 (0.22 g, 0.7 mmol) and 3,4-(methylenedioxy) aniline (0.20 g, 1.4 mmol) was heated in 10% acetic acid in toluene or 100% acetic acid at 80-100° C. for a period of 30 minutes to 24 h. The reaction was cooled to room temperature, ice-water was added. The mixture was made basic with saturated sodium bicarbonate or concentrated ammonium hydroxide solutions, and the resultant solid filtered. The solid was dissolved in dichloromethane, dried with sodium sulfate, filtered, and concentrate under reduced pressure. Trituration of the residue with diethyl ether, ethyl acetate, or hexane/ethyl acetate affords the desired compound 7A. $^1$H NMR (CDCl$_3$): δ 8.40 (d, 1H), 8.22 (s, 1H), 6.91 (d, 2H), 6.82 (dd, 1H), 6.76 (d, 1H), 6.04 (s, 2H), 3.11 (s, 6H). Mass spectrum (M+1)$^+$: m/z calcd. for C$_{18}$H$_{15}$N$_4$O$_3$S$^+$=367.1, found m/z=367.2.

Alternatively, the basic aqueous mixture was extracted with dichloromethane, dried with sodium sulfate, filtered, and concentrated under reduced pressure. The residue was purified via preparative TLC or column chromatography on silica gel with dichloromethane/ethyl acetate to afford the desired compound.

The following compounds were prepared analogously.

| Cpd | Structure | Formula | MW | m/z Found (M + 1)+ |
|---|---|---|---|---|
| 7A | 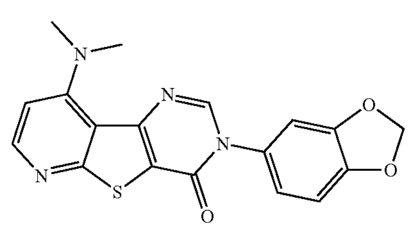 | C$_{18}$H$_{14}$N$_4$O$_3$S | 366.4 | 367.2 |
| 7B | 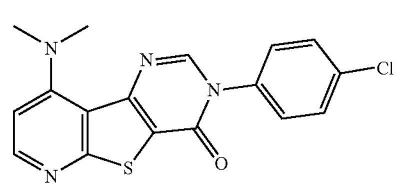 | C$_{17}$H$_{13}$ClN$_4$OS | 356.8 | 357.1 |

-continued

| Cpd | Structure | Formula | MW | m/z Found (M + 1)+ |
|---|---|---|---|---|
| 7C | 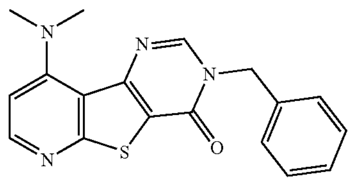 | C₁₈H₁₆N₄OS | 336.4 | 337.1 |
| 7D | 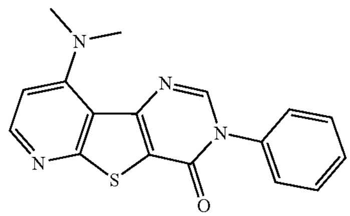 | C₁₇H₁₄N₄OS | 322.4 | 323.1 |
| 7E | 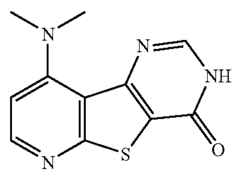 | C₁₁H₁₀N₄OS | 246.3 | |
| 7F | 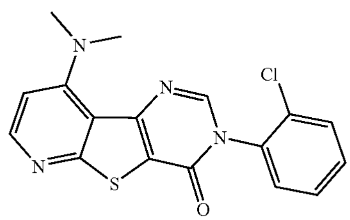 | C₁₇H₁₃ClN₄OS | 356.8 | 357.1 |
| 7G | 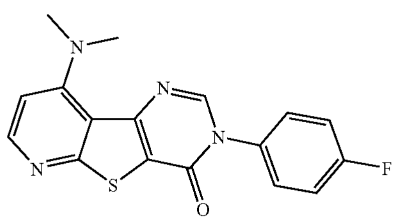 | C₁₇H₁₃FN₄OS | 340.4 | 341.1 |
| 7H | 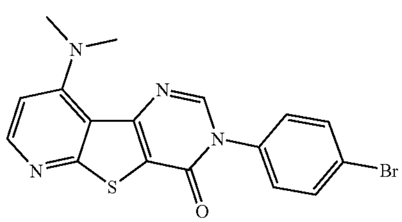 | C₁₇H₁₃BrN₄OS | 401.3 | 403.1 |
| 7I | 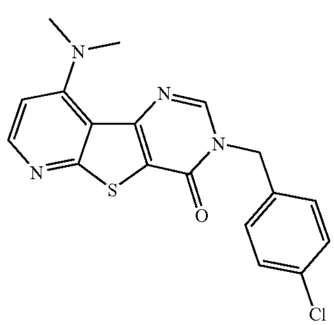 | C₁₈H₁₅ClN₄OS | 370.9 | 371.2 |

-continued

| Cpd | Structure | Formula | MW | m/z Found (M + 1)+ |
|---|---|---|---|---|
| 7J | 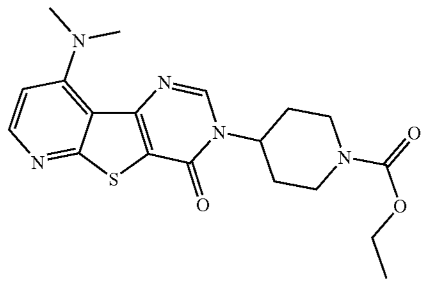 | $C_{19}H_{23}N_5O_3S$ | 401.5 | 402.1 |
| 7K | 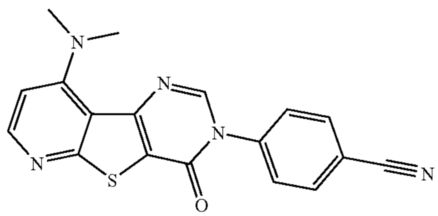 | $C_{18}H_{13}N_5OS$ | 347.4 | 348.1 |
| 7L | 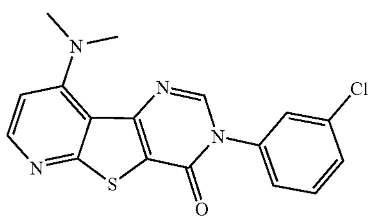 | $C_{17}H_{13}ClN_4OS$ | 356.8 | 357.2 |
| 7M | 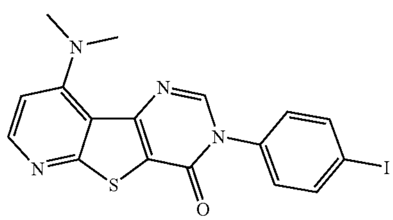 | $C_{17}H_{13}IN_4OS$ | 448.3 | 449.1 |
| 7N | 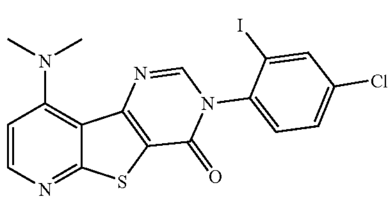 | $C_{17}H_{12}ClIN_4OS$ | 482.7 | 483.1 |
| 7O | 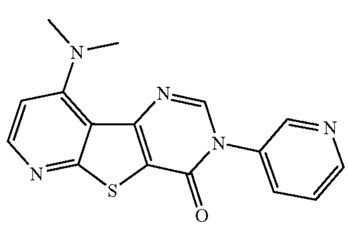 | $C_{16}H_{13}N_5OS$ | 323.4 | 324.1 |

-continued

| Cpd | Structure | Formula | MW | m/z Found (M + 1)+ |
|---|---|---|---|---|
| 7P | 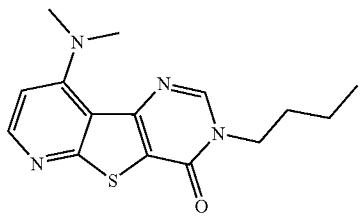 | C15H18N4OS | 302.4 | 303.1 |
| 7Q | 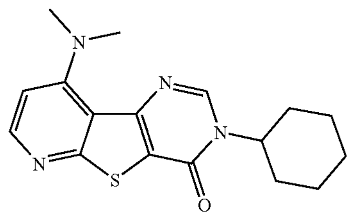 | C17H20N4OS | 328.4 | 329.1 |
| 7R | 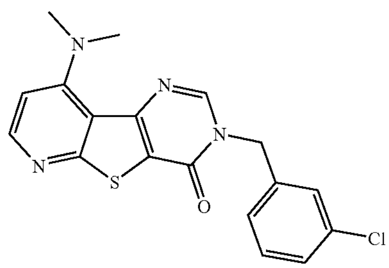 | C18H15ClN4OS | 370.9 | 371.1 |
| 7S | 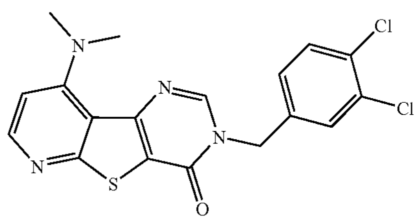 | C18H14Cl2N4OS | 405.3 | 405.1 |
| 7T | 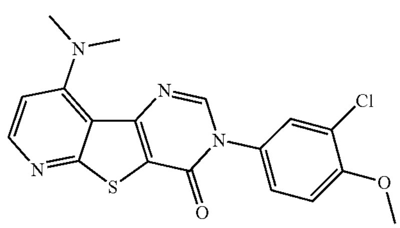 | C18H15ClN4O2S | 386.9 | 387.2 |
| 7U | 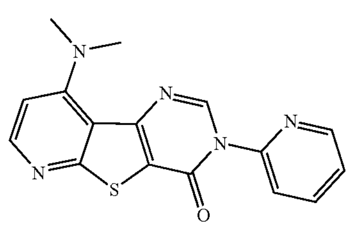 | C16H13N5OS | 323.4 | 324.1 |

-continued

| Cpd | Structure | Formula | MW | m/z Found (M + 1)+ |
|---|---|---|---|---|
| 7V | 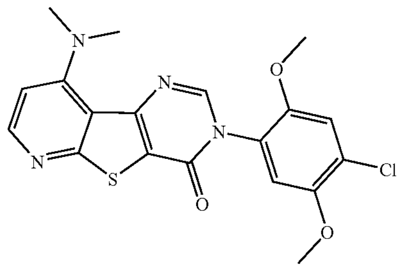 | $C_{19}H_{17}ClN_4O_3S$ | 416.9 | 417.1 |
| 7W | 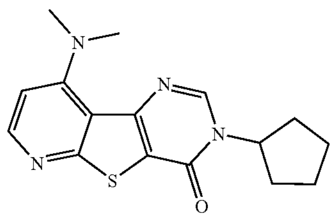 | $C_{16}H_{18}N_4OS$ | 314.4 | 315.1 |
| 7X | 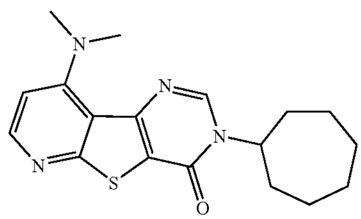 | $C_{18}H_{22}N_4OS$ | 342.5 | 343.1 |
| 7Y | 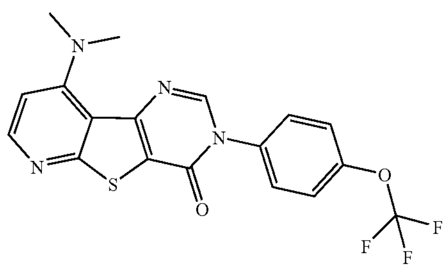 | $C_{18}H_{13}F_3N_4O_2S$ | 406.4 | 407.1 |
| 7Z | 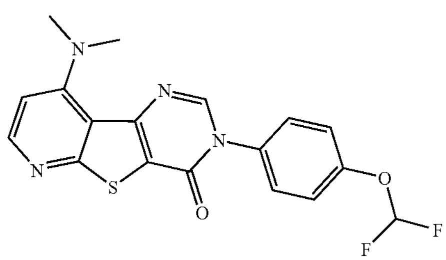 | $C_{18}H_{14}F_2N_4O_2S$ | 388.4 | 389.1 |
| 7AA | 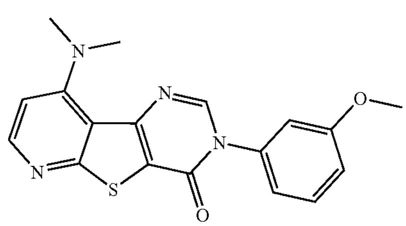 | $C_{18}H_{16}N_4O_2S$ | 352.4 | 353.1 |

-continued

| Cpd | Structure | Formula | MW | m/z Found (M + 1)⁺ |
|---|---|---|---|---|
| 7AB | 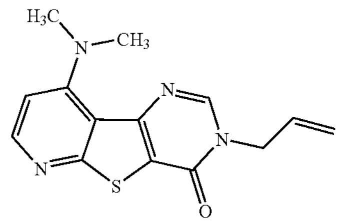 | $C_{14}H_{14}N_4OS$ | 286.4 | 287.2 |
| 7AC | 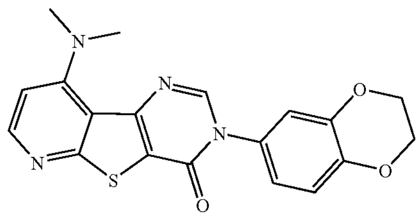 | $C_{19}H_{16}N_4O_3S$ | 380.4 | 381.2 |
| 7AD | 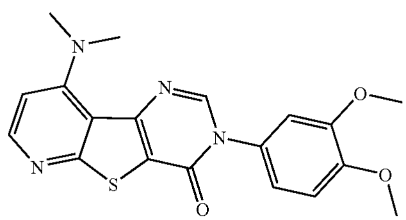 | $C_{19}H_{18}N_4O_3S$ | 382.4 | 383.2 |
| 7AE | 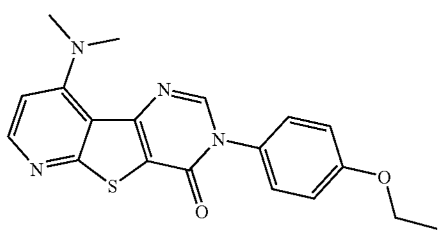 | $C_{19}H_{18}N_4O_2S$ | 366.4 | 367.1 |
| 7AF | 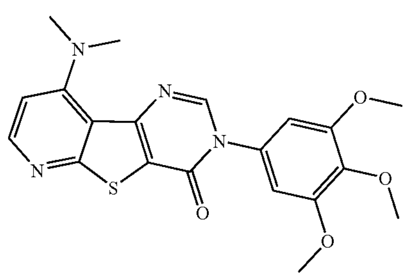 | $C_{20}H_{20}N_4O_4S$ | 412.5 | 413.1 |
| 7AG | 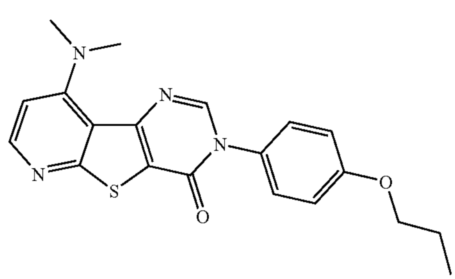 | $C_{20}H_{20}N_4O_2S$ | 380.5 | 381.1 |

-continued
| Cpd | Structure | Formula | MW | m/z Found (M + 1)+ |
|---|---|---|---|---|
| 7AH | 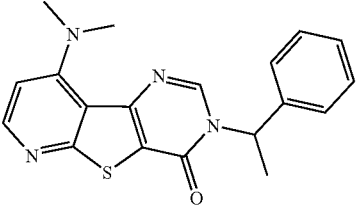 | C19H18N4OS | 350.4 | 351.1 |
| 7AI | 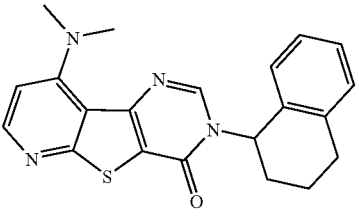 | C21H20N4OS | 376.5 | 377.1 |
| 7AJ | 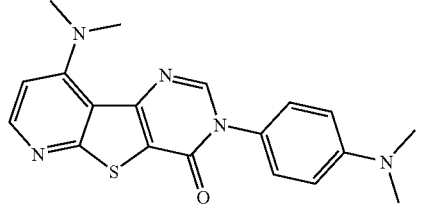 | C19H19N5OS | 365.5 | 366.1 |
| 7AK | 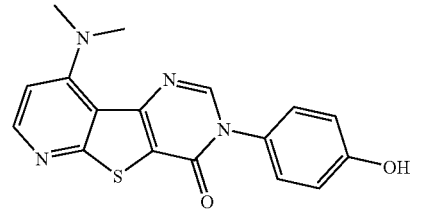 | C17H14N4O2S | 338.4 | 339.1 |
| 7AL | 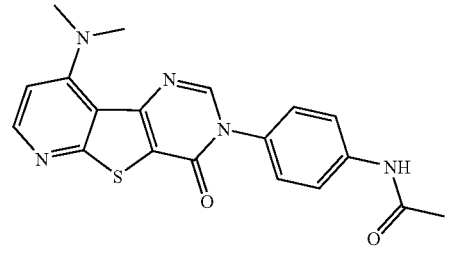 | C19H17N5O2S | 379.4 | 380.1 |
| 7AM | 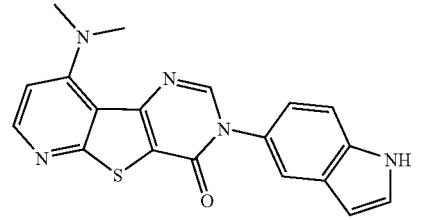 | C19H15N5OS | 361.4 | 362.1 |

-continued

| Cpd | Structure | Formula | MW | m/z Found (M + 1)+ |
|---|---|---|---|---|
| 7AN | 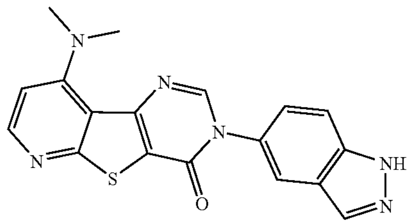 | $C_{18}H_{14}N_6OS$ | 362.4 | 363.1 |
| 7AO | 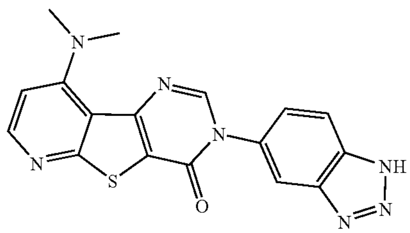 | $C_{17}H_{13}N_7OS$ | 363.4 | 363.1 (M+) |
| 7AP | 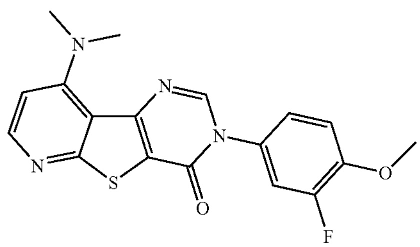 | $C_{18}H_{15}FN_4O_2S$ | 370.4 | 371.1 |
| 7AQ | 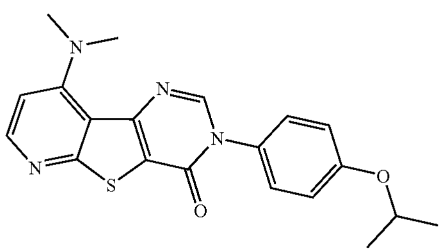 | $C_{20}H_{20}N_4O_2S$ | 380.5 | 381.1 |
| 7AR | 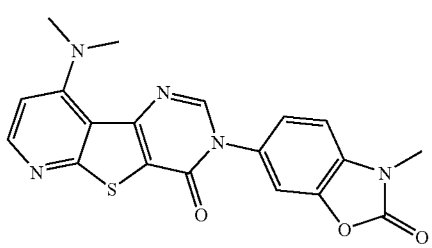 | $C_{19}H_{15}N_5O_3S$ | 393.4 | 394.1 |
| 7AS | 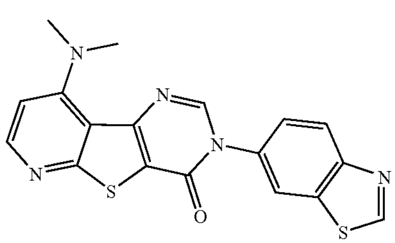 | $C_{18}H_{13}N_5OS_2$ | 379.5 | 380.1 |

-continued

| Cpd | Structure | Formula | MW | m/z Found (M + 1)+ |
|---|---|---|---|---|
| 7AT | 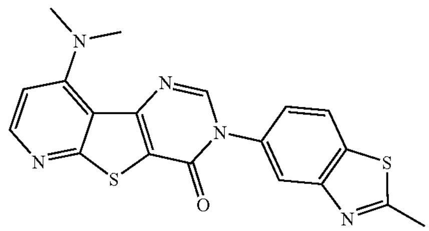 | $C_{19}H_{15}N_5OS_2$ | 393.5 | 394.1 |
| 7AU | 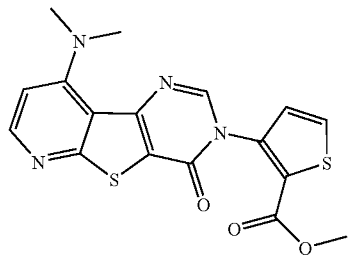 | $C_{17}H_{14}N_4O_3S_2$ | 386.4 | 387.1 |
| 7AV | 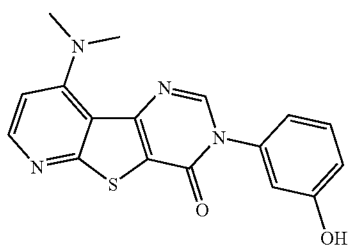 | $C_{17}H_{14}N_4O_2S$ | 338.4 | 339.2 |
| 7AW | 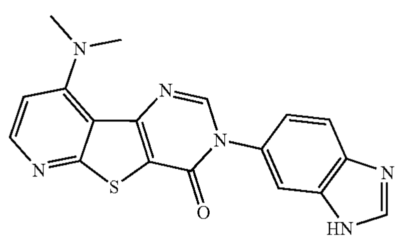 | $C_{18}H_{14}N_6OS$ | 362.4 | 363.1 |
| 7AX | 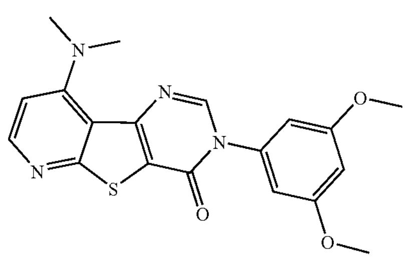 | $C_{19}H_{18}N_4O_3S$ | 382.4 | 383.1 |
| 7AY | 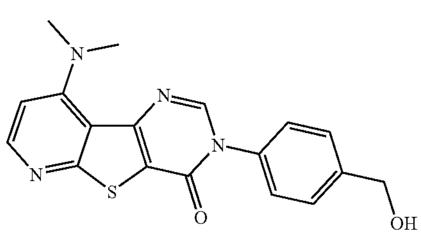 | $C_{18}H_{16}N_4O_2S$ | 352.4 | 353.2 |

-continued

| Cpd | Structure | Formula | MW | m/z Found (M + 1)+ |
|---|---|---|---|---|
| 7AZ | 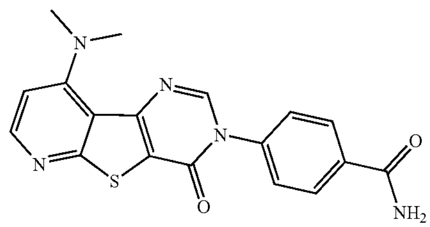 | $C_{18}H_{15}N_5O_2S$ | 365.4 | 366.2 |
| 7BA | 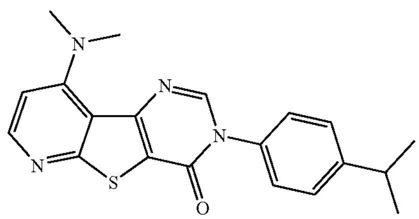 | $C_{20}H_{20}N_4OS$ | 364.5 | 365.2 |
| 7BB | 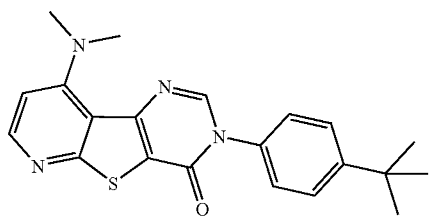 | $C_{21}H_{22}N_4OS$ | 378.5 | 379.2 |
| 7BC | 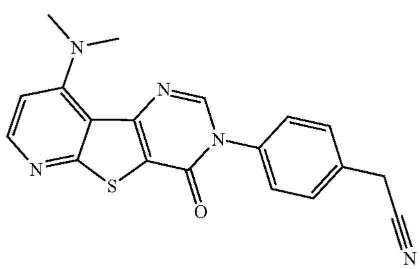 | $C_{19}H_{15}N_5OS$ | 361.4 | 362.2 |
| 7BD | 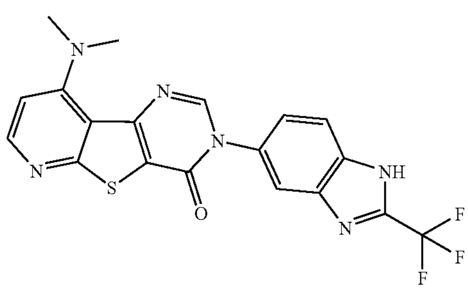 | $C_{19}H_{13}F_3N_6OS$ | 430.4 | 431.2 |
| 7BE | 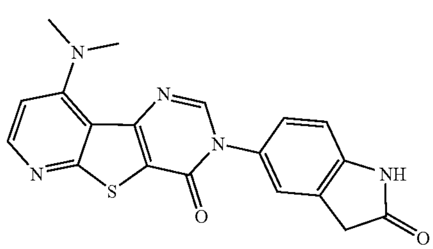 | $C_{19}H_{15}N_5O_2S$ | 377.4 | 378.2 |

-continued

| Cpd | Structure | Formula | MW | m/z Found (M + 1)+ |
|---|---|---|---|---|
| 7BF | 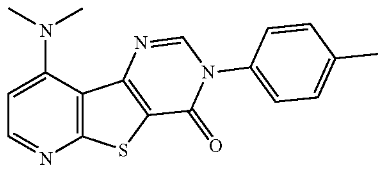 | $C_{18}H_{16}N_4OS$ | 336.4 | 337.1 |
| 7BG | 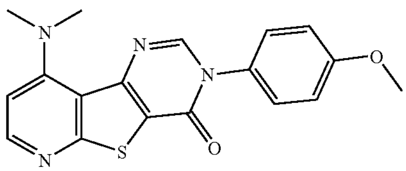 | $C_{18}H_{16}N_4O_2S$ | 352.4 | 353.1 |
| 7BH | 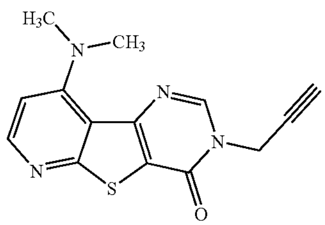 | $C_{14}H_{12}N_4OS$ | 284.3 | 285.1 |
| 7BI | 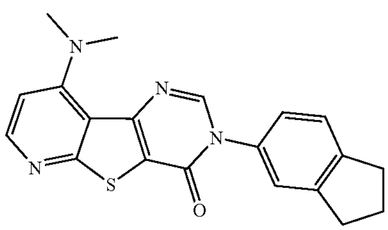 | $C_{20}H_{18}N_4OS$ | 362.4 | 363.1 |
| 7BJ | 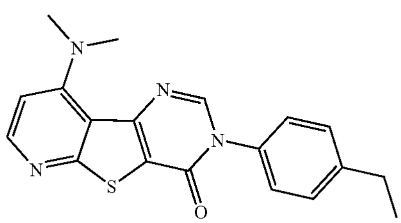 | $C_{19}H_{18}N_4OS$ | 350.4 | 351.1 |
| 7BK | 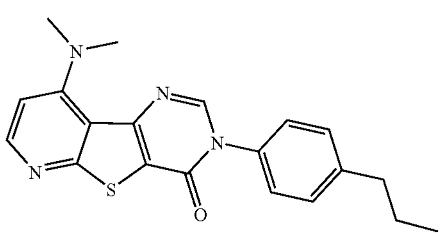 | $C_{20}H_{20}N_4OS$ | 364.5 | 365.1 |
| 7BL | 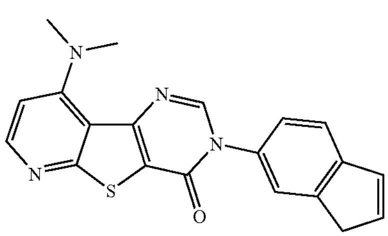 | $C_{20}H_{16}N_4OS$ | 360.4 | 361.1 |

-continued
| Cpd | Structure | Formula | MW | m/z Found (M + 1)+ |
|---|---|---|---|---|
| 7BM | 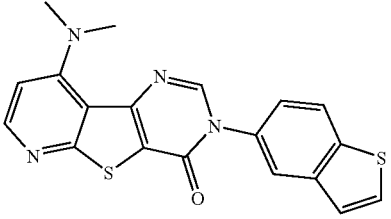 | $C_{19}H_{14}N_4OS_2$ | 378.5 | 379.2 |
| 7BN | 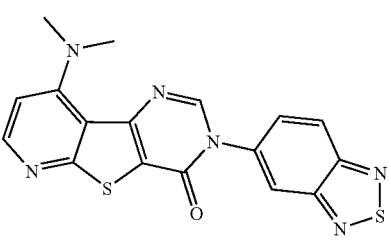 | $C_{17}H_{12}N_6OS_2$ | 380.4 | 381.2 |
| 7BO | 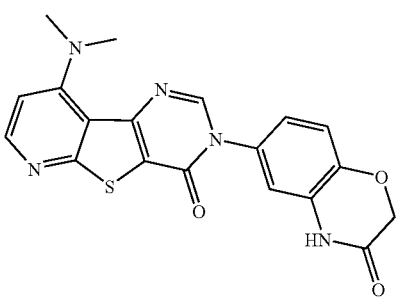 | $C_{19}H_{15}N_5O_3S$ | 393.4 | 394.2 |
| 7BP | 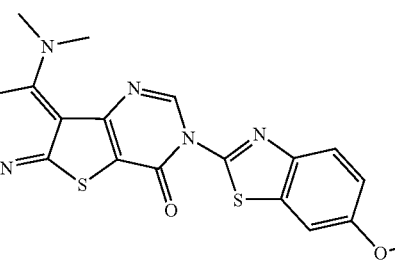 | $C_{19}H_{15}N_5O_2S_2$ | 409.5 | 410.2 |
| 7BQ | 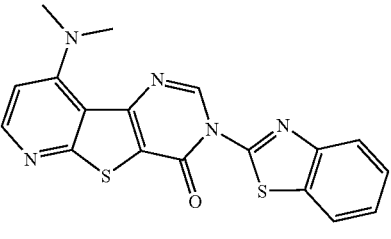 | $C_{18}H_{13}N_5OS_2$ | 379.5 | 380.2 |
| 7BR | 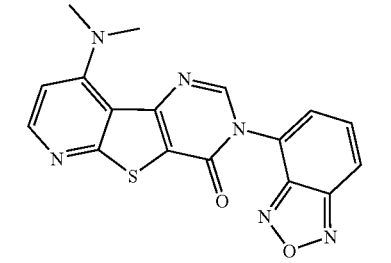 | $C_{17}H_{12}N_6O_2S$ | 364.4 | 365.1 |

-continued

| Cpd | Structure | Formula | MW | m/z Found (M + 1)+ |
|---|---|---|---|---|
| 7BS | 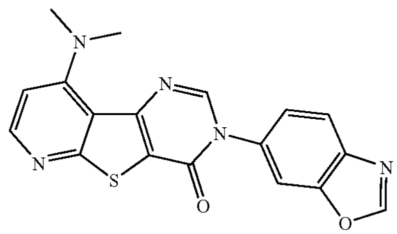 | $C_{18}H_{13}N_5O_2S$ | 363.4 | 364.2 |
| 7BT | 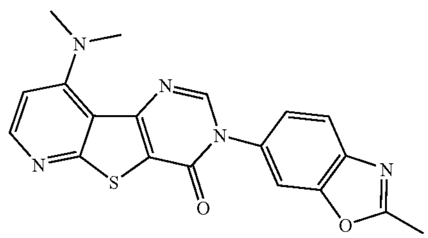 | $C_{19}H_{15}N_5O_2S$ | 377.4 | 378.2 |
| 7BU | 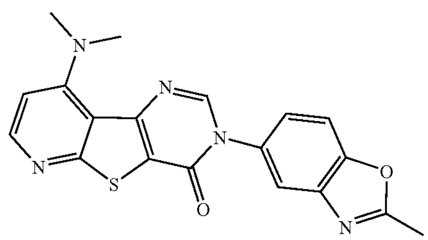 | $C_{19}H_{15}N_5O_2S$ | 377.4 | 378.2 |
| 7BV | 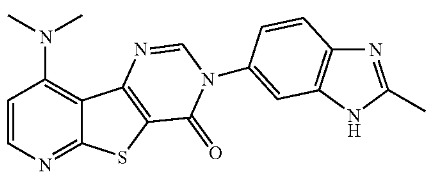 | $C_{19}H_{16}N_6OS$ | 376.4 | 377.2 |
| 7BW | 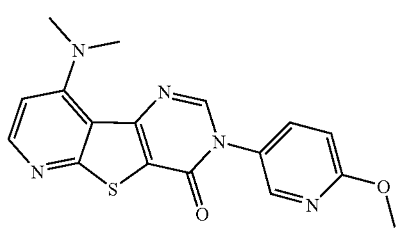 | $C_{17}H_{15}N_5O_2S$ | 353.4 | 354.2 |
| 7BX | 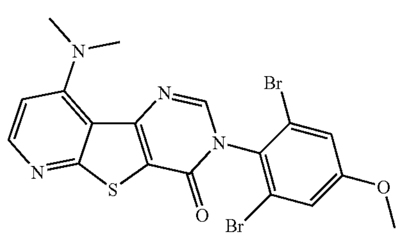 | $C_{18}H_{14}Br_2N_4O_2S$ | 510.2 | 511.1 |
| 7BY | 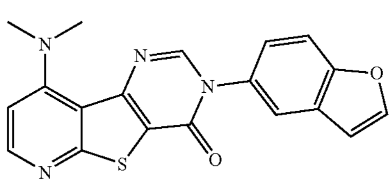 | $C_{19}H_{14}N_4O_2S$ | 362.4 | 363.1 |

-continued

| Cpd | Structure | Formula | MW | m/z Found (M + 1)+ |
|---|---|---|---|---|
| 7BZ | 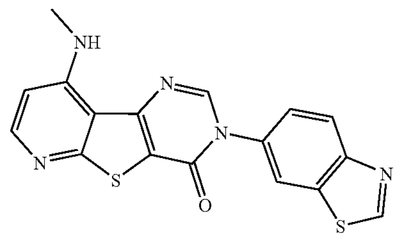 | C17H11N5OS2 | 365.4 | 366.1 |
| 7CA | 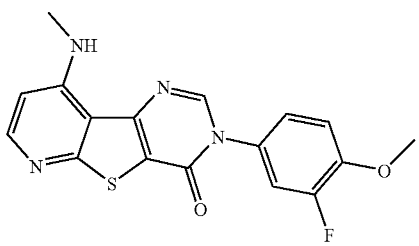 | C17H13FN4O2S | 356.4 | 357.2 |
| 7CB | 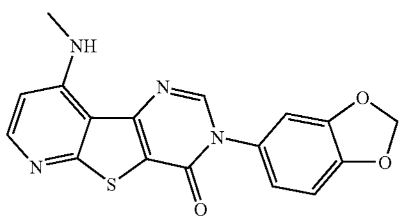 | C17H12N4O3S | 352.4 | 353.2 |
| 7CC | 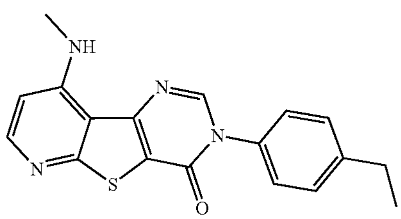 | C18H16N4OS | 336.4 | 337.1 |
| 7CD | 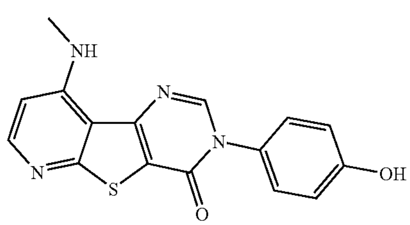 | C16H12N4O2S | 324.4 | 325.2 |
| 7CE | 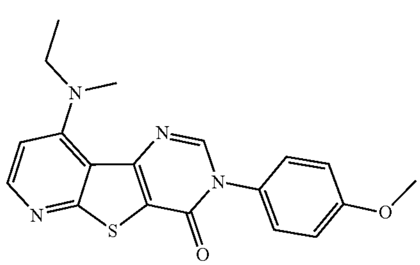 | C19H18N4O2S | 366.4 | 367.1 |

-continued

| Cpd | Structure | Formula | MW | m/z Found (M + 1)+ |
|---|---|---|---|---|
| 7CF | 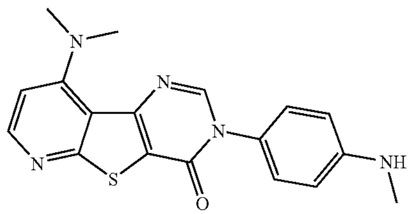 | C₁₈H₁₇N₅OS | 351.4 | 352.2 |
| 7CG | 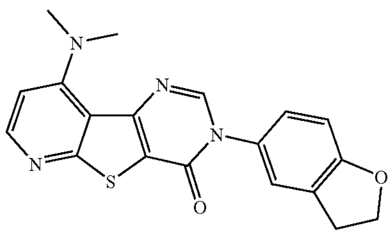 | C₁₉H₁₆N₄O₂S | 364.4 | 365.1 |
| 7CH | 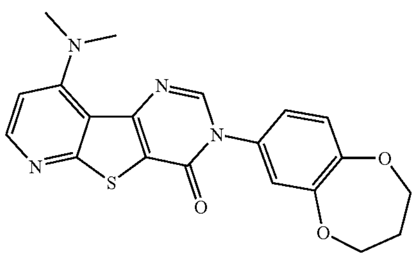 | C₂₀H₁₈N₄O₃S | 394.4 | 395.1 |
| 7CI | 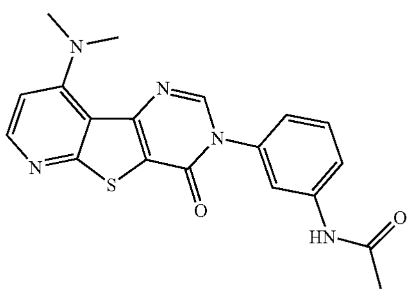 | C₁₉H₁₇N₅O₂S | 379.4 | 380.1 |
| 7CJ | 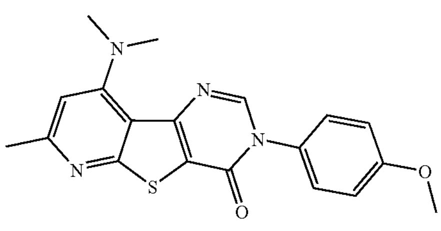 | C₁₉H₁₈N₄O₂S | 366.4 | 367.1 |
| 7CK | 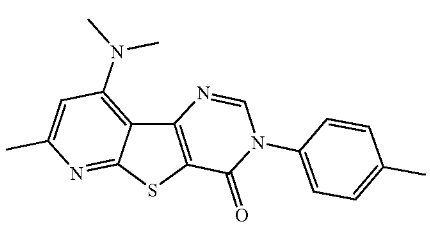 | C₁₉H₁₈N₄OS | 350.4 | 351.1 |

-continued

| Cpd | Structure | Formula | MW | m/z Found (M + 1)+ |
|---|---|---|---|---|
| 7CL | 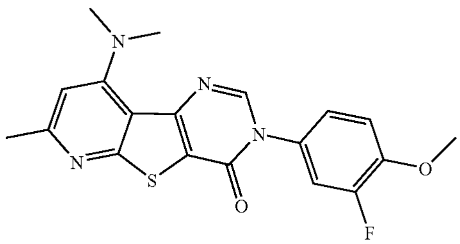 | $C_{19}H_{17}FN_4O_2S$ | 384.4 | 385.1 |
| 7CM | 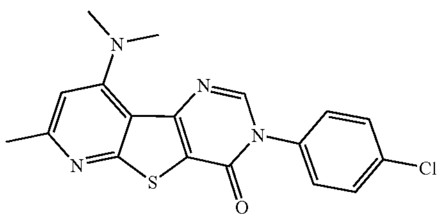 | $C_{18}H_{15}ClN_4OS$ | 370.9 | 371.1 |
| 7CN | 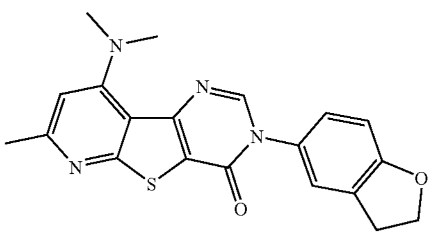 | $C_{20}H_{18}N_4O_2S$ | 378.4 | 379.1 |
| 7CO | 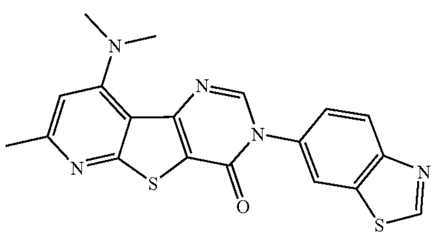 | $C_{19}H_{15}N_5OS_2$ | 393.5 | 394.1 |
| 7CP | 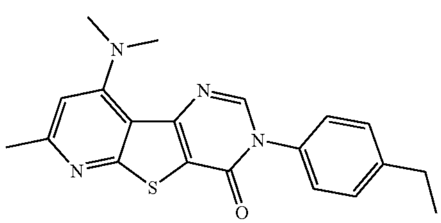 | $C_{20}H_{20}N_4OS$ | 364.5 | 365.1 |
| 7CQ | 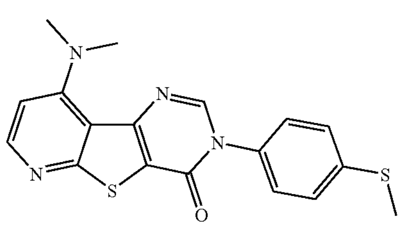 | $C_{18}H_{16}N_4OS_2$ | 368.5 | 369.1 |

-continued

| Cpd | Structure | Formula | MW | m/z Found (M + 1)+ |
|---|---|---|---|---|
| 7CR | 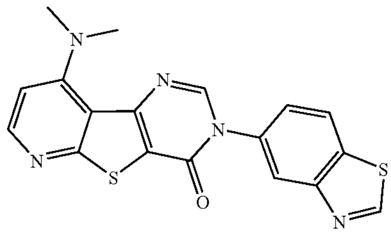 | $C_{18}H_{13}N_5OS_2$ | 379.5 | 380.1 |
| 7CS | 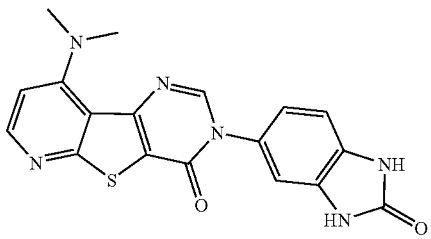 | $C_{18}H_{14}N_6O_2S$ | 378.4 | 379.1 |
| 7CT | 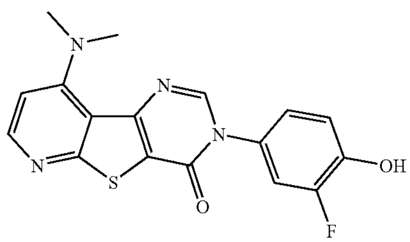 | $C_{17}H_{13}FN_4O_2S$ | 356.4 | 357.1 |
| 7CU | 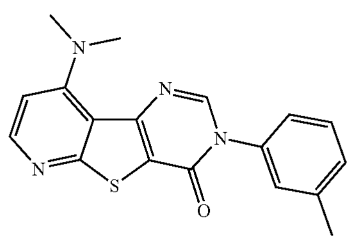 | $C_{18}H_{16}N_4OS$ | 336.4 | 337.1 |
| 7CV | 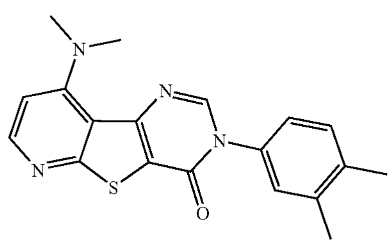 | $C_{19}H_{18}N_4OS$ | 350.4 | 351.1 |
| 7CW | 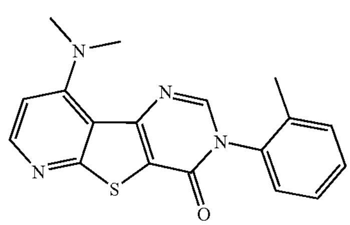 | $C_{18}H_{16}N_4OS$ | 336.4 | 337.1 |

-continued

| Cpd | Structure | Formula | MW | m/z Found (M + 1)+ |
|---|---|---|---|---|
| 7CX | 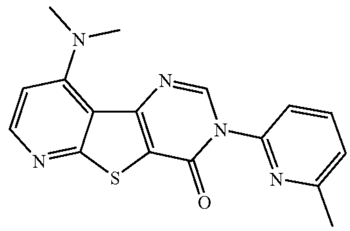 | $C_{17}H_{15}N_5OS$ | 337.4 | 338.1 |
| 7CY | 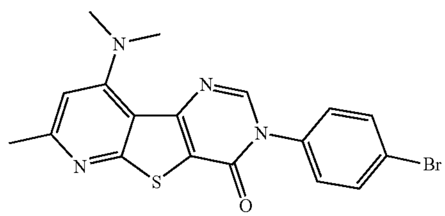 | $C_{18}H_{15}BrN_4OS$ | 415.3 | 417.1 415.1 |
| 7CZ | 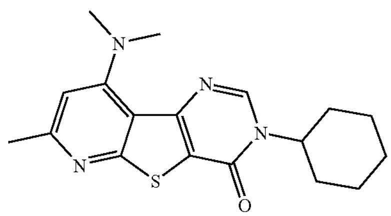 | $C_{18}H_{22}N_4OS$ | 342.5 | 343.2 |
| 7DA | 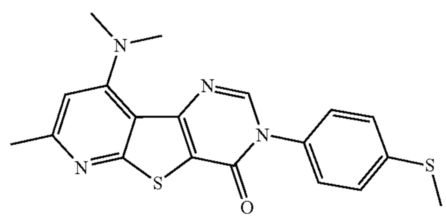 | $C_{19}H_{18}N_4OS_2$ | 382.5 | 383.2 |
| 7DB | 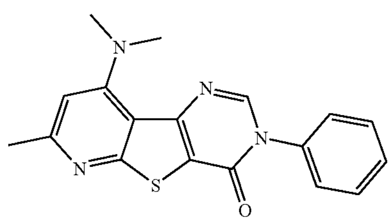 | $C_{18}H_{16}N_4OS$ | 336.4 | 337.1 |
| 7DC | 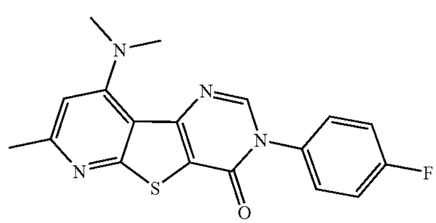 | $C_{18}H_{15}FN_4OS$ | 354.4 | 355.2 |
| 7DD | 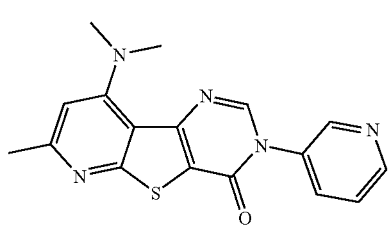 | $C_{17}H_{15}N_5OS$ | 337.4 | 338.2 |

-continued

| Cpd | Structure | Formula | MW | m/z Found (M + 1)+ |
|---|---|---|---|---|
| 7DE | 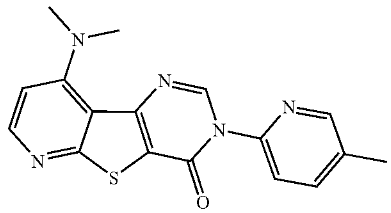 | C17H15N5OS | 337.4 | 338.1 |
| 7DF | 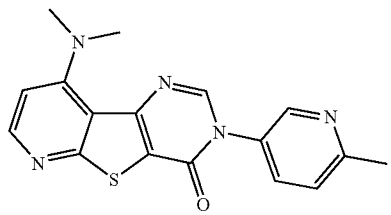 | C17H15N5OS | 337.4 | 338.1 |
| 7DG | 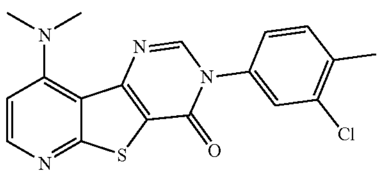 | C18H15ClN4OS | 370.9 | 371.1 |
| 7DH | 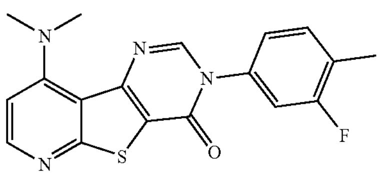 | C18H15FN4OS | 354.4 | 355.1 |
| 7DI | 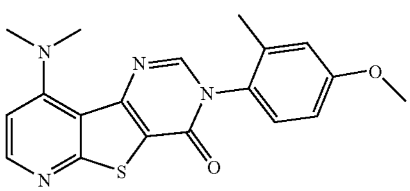 | C19H18N4O2S | 366.4 | 367.1 |
| 7DJ | 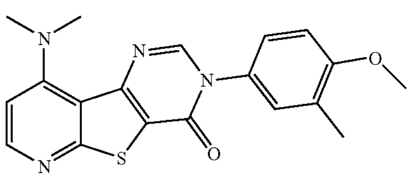 | C19H18N4O2S | 366.4 | 367.1 |
| 7DK | 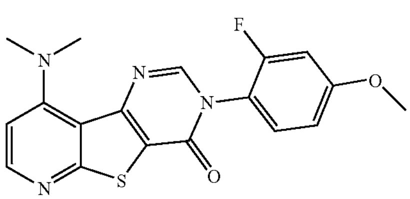 | C18H15FN4O2S | 370.4 | 371.1 |

-continued

| Cpd | Structure | Formula | MW | m/z Found (M + 1)+ |
|---|---|---|---|---|
| 7DL | 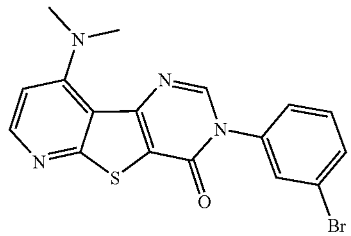 | C17H13BrN4OS | 401.3 | 403.1 |
| 7DM | 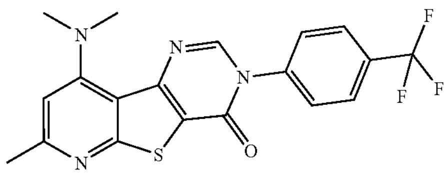 | C19H15F3N4OS | 404.4 | 405.2 |
| 7DN | 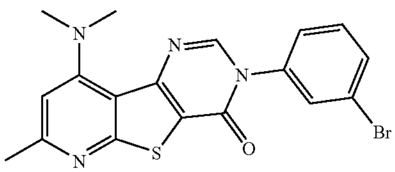 | C18H15BrN4OS | 415.3 | 415.1<br>417.1 |
| 7DO | 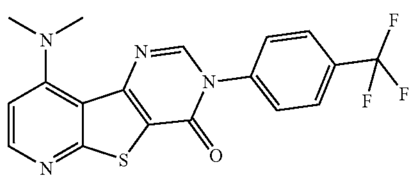 | C18H13F3N4OS | 390.4 | 391.2 |
| 7DP | 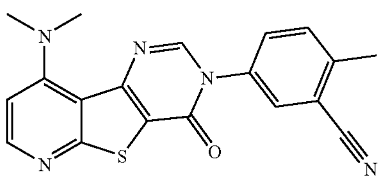 | C19H15N5OS | 361.4 | 462.1 |
| 7DQ | 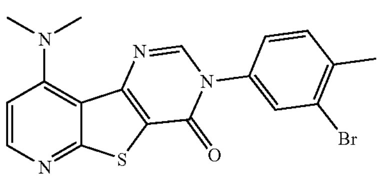 | C18H15BrN4OS | 415.3 | 417.1<br>415.1 |
| 7DR | 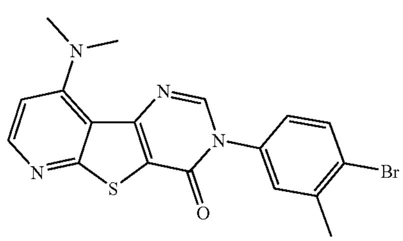 | C18H15BrN4OS | 415.3 | 417.1<br>415.1 |

-continued

| Cpd | Structure | Formula | MW | m/z Found (M + 1)+ |
|---|---|---|---|---|
| 7DS | 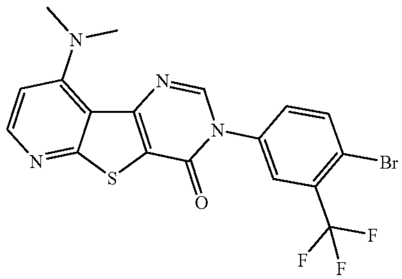 | $C_{18}H_{12}BrF_3N_4OS$ | 469.3 | 471.1 |
| 7DT | 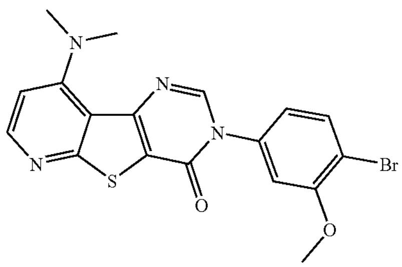 | $C_{18}H_{15}BrN_4O_2S$ | 431.3 | 433.1 |
| 7DU | 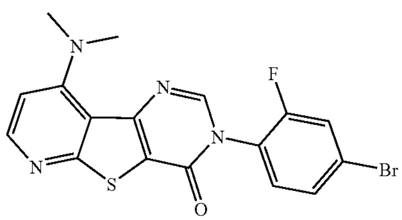 | $C_{17}H_{12}BrFN_4OS$ | 419.3 | 421.1<br>419.1 |
| 7DV | 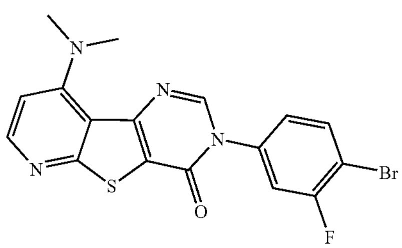 | $C_{17}H_{12}BrFN_4OS$ | 419.3 | 421.1<br>419.1 |
| 7DW | 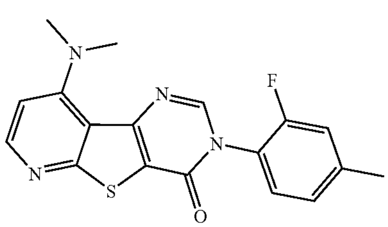 | $C_{18}H_{15}FN_4OS$ | 354.4 | 355.1 |
| 7DX | 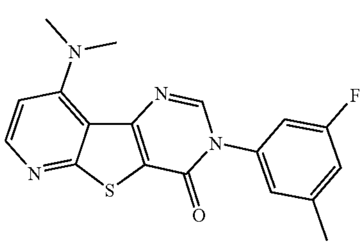 | $C_{18}H_{15}FN_4OS$ | 354.4 | 355.1 |

-continued

| Cpd | Structure | Formula | MW | m/z Found (M + 1)+ |
|---|---|---|---|---|
| 7DY | 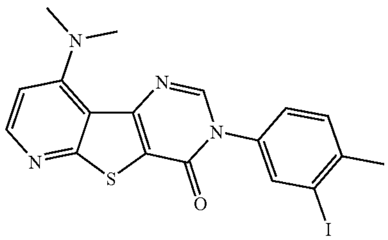 | $C_{18}H_{15}IN_4OS$ | 462.3 | 463.1 |
| 7DZ | 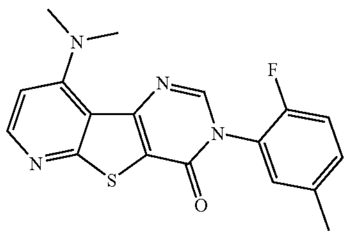 | $C_{18}H_{15}FN_4OS$ | 354.4 | 355.2 |
| 7EA | 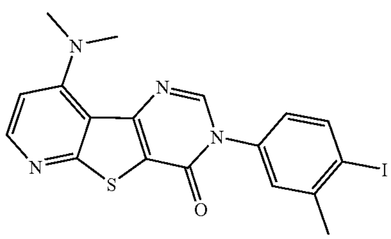 | $C_{18}H_{15}IN_4OS$ | 462.3 | 463.3 |
| 7EB | 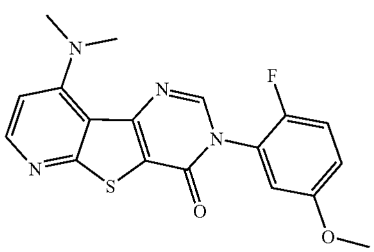 | $C_{18}H_{15}FN_4O_2S$ | 370.4 | 371.2 |
| 7EC | 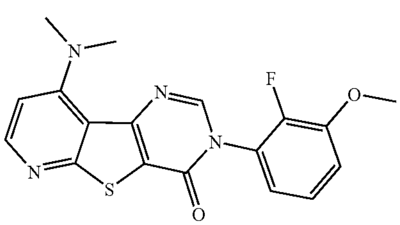 | $C_{18}H_{15}FN_4O_2S$ | 370.4 | 371.2 |
| 37A | 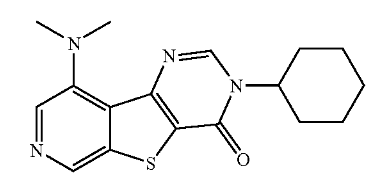 | $C_{17}H_{20}N_4OS$ | 328.1 | 329.1 |
| 37B | 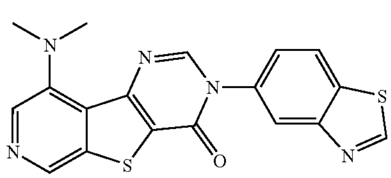 | $C_{18}H_{13}N_5OS_2$ | 379.1 | 380.2 |

-continued
| Cpd | Structure | Formula | MW | m/z Found (M + 1)+ |
|---|---|---|---|---|
| 37C | 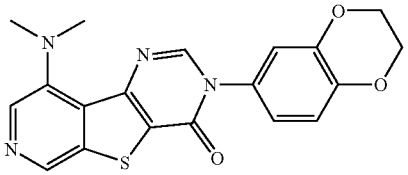 | $C_{19}H_{16}N_4O_3S$ | 380.1 | 381.2 |
| 37D | 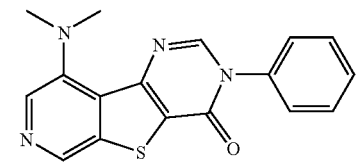 | $C_{17}H_{14}N_4OS$ | 322.1 | 323.1 |
| 37E | 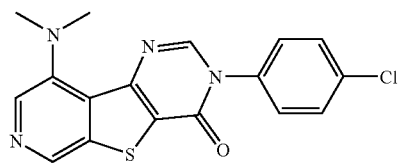 | $C_{17}H_{13}ClN_4OS$ | 356.1 | 357.2 |
| 37F | 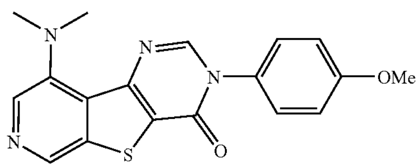 | $C_{18}H_{16}N_4O_2S$ | 352.1 | 353.2 |
| 37G | 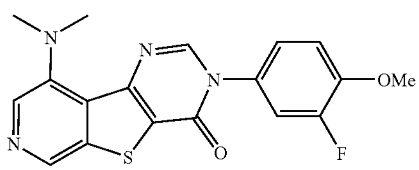 | $C_{18}H_{15}FN_4O_2S$ | 370.4 | 371.2 |
| 37H | 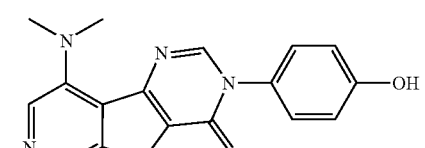 | $C_{17}H_{14}N_4O_2S$ | 338.4 | 339.2 |
| 40 | 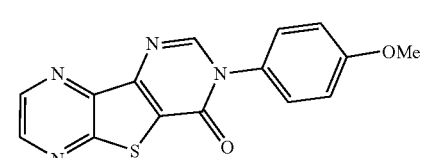 | $C_{15}H_{10}N_4O_2S$ | 310.1 | 311.0 |
| 134A | 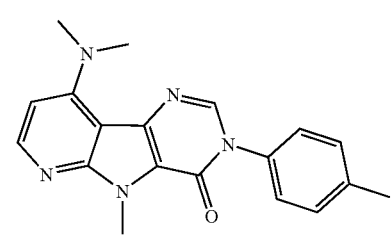 | $C_{19}H_{19}N_5O$ | 333.4 | 334.1 |

-continued

| Cpd | Structure | Formula | MW | m/z Found (M + 1)+ |
|---|---|---|---|---|
| 134B | 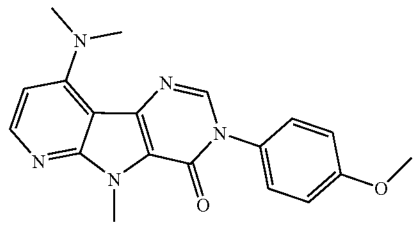 | $C_{19}H_{19}N_5O_2$ | 349.4 | 350.1 |
| 134C | 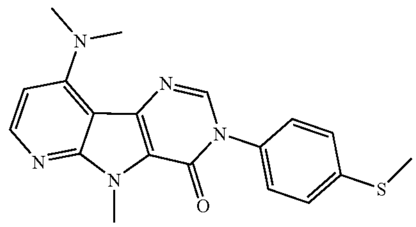 | $C_{19}H_{19}N_5OS$ | 365.5 | 366.1 |
| 134D | 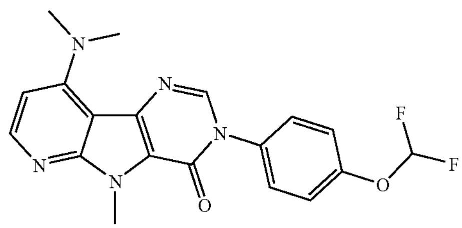 | $C_{19}H_{17}F_2N_5O_2$ | 385.4 | 386.1 |
| 134E | 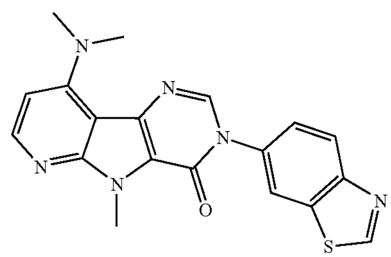 | $C_{19}H_{16}N_6OS$ | 376.4 | 377.1 |
| 134F | 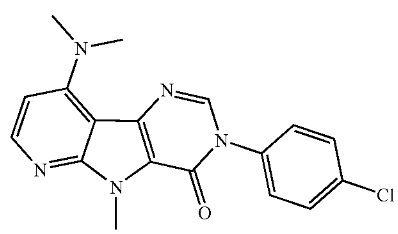 | $C_{18}H_{16}ClN_5O$ | 353.8 | 354.1 |
| 134G | 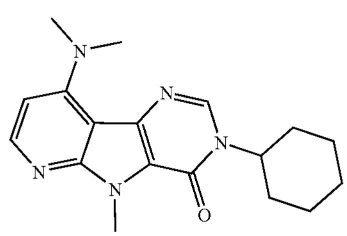 | $C_{18}H_{23}N_5O$ | 325.4 | 326.1 |

-continued

| Cpd | Structure | Formula | MW | m/z Found (M + 1)+ |
|---|---|---|---|---|
| 134H | 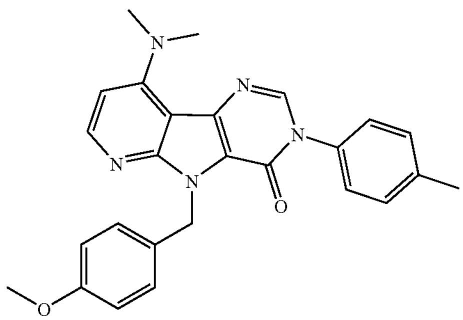 | $C_{26}H_{25}N_5O_2$ | 439.5 | 440.1 |
| 134I | 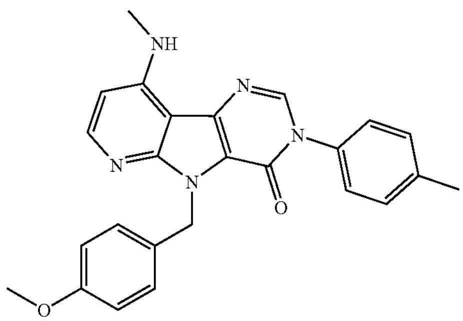 | $C_{25}H_{23}N_5O_2$ | 425.5 | 426.1 |

Method G:

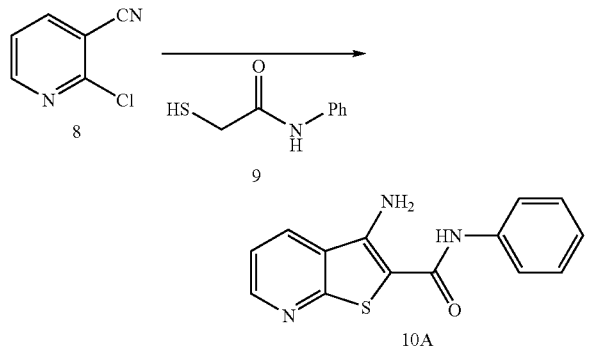

(refs.: (a) A. D. Dunn, R. Norrie, *J. Heterocyclic Chem.* 1987, 24, 85; (b) J. A. Van Allan, *J. Amer. Chem. Soc.* 1947, 69, 2914.)

To 5.00 g (36.1 mmol) of 2-chloro-3-pyridine carbonitrile (8) in 75 mL of DMF was added 6.04 g of thiol 9 (36.1 mmol) followed by the addition of 1.95 g of sodium methoxide (36.1 mmol). The reaction mixture was allowed to stir at room temperature for 1 hour and subsequently poured onto $H_2O$ (300 mL). The resulting suspension was filtered and the yellow solids recrystallized from absolute ethanol to yield 5.30 g of 10A as a yellow solid. $^1$H NMR (DMSO-$d_6$) δ 9.44 (s, 1H), 8.66 (dd, 1H), 8.49 (dd, 1H), 7.69 (d, 1H), 7.67 (d, 1H), 7.46 (dd, 1H), 7.38 (bs, 2H), 7.30 (dd, 2H), 7.06 (t, 1H). MS m/z calcd. for $C_{14}H_{12}N_3OS^+$=270.1; found m/z=270.1.

The following compounds were prepared analogously.

| Cpd | Structure | Formula | MW | m/z Found (M + 1)+ |
|---|---|---|---|---|
| 10B | 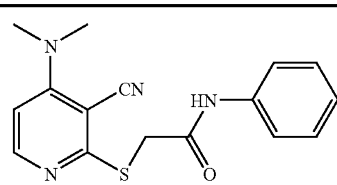 | $C_{16}H_{16}N_4OS$ | 312.4 | 313.1 |
| 10C | 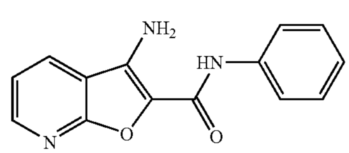 | $C_{14}H_{11}N_3O_2$ | 253.3 | 254.1 |

| Cpd | Structure | Formula | MW | m/z Found (M + 1)+ |
|---|---|---|---|---|
| 10D | (cyclohexyl-NH, NH2, thienopyridine, C(=O)NH-phenyl) | C20H22N4OS | 366.5 | 367.2 |

Method H:

To compound 10A (5.00 g, 18.5 mmol) was added trimethylorthoformate (116 mL). The resulting mixture was heated to reflux and stirred overnight. The reaction was then cooled and the solvents removed in vacuo. The crude solid was purified via silica gel chromatography eluting with 5% acetone/dichloro-methane to give 2.52 g of tricycle 11 as a yellow solid. $^1$H NMR (CDCl$_3$) δ 8.82 (dd, 1H), 8.59 (dd, 1H), 8.29 (s, 1H), 7.62-7.50 (m, 4H), 7.47 (d, 2H). MS m/z calcd. for C$_{15}$H10N$_3$OS$^+$=280.1; found m/z=280.1.

Method I:

To a stirred solution of compound 11 (1.42 g, 5.07 mmol) in dichloro-methane (34 mL) was added MCPBA (70%) (1.88 g, 7.61 mmol) at 0° C. The reaction mixture was stirred at 0° C. and allowed to warm to room temperature overnight. The mixture was washed with NaHCO$_3$ (sat. aq.) (50 mL). The organic layer was separated, dried over MgSO$_4$ and the solvents removed in vacuo. The crude off-white solid was purified via silica chromatography eluting with 10% methanol/dichloromethane to afford 902 mg of pure 12A as a white solid. $^1$H NMR (DMSO-d$_6$) δ 8.71 (d, 1H), 8.71 (s, 1H), 8.26 (d, 1H), 7.89-7.86 (m, 1H), 7.72 (dd, 1H), 7.61-7.50 (m, 4H). MS m/z calcd for C$_{14}$H$_{12}$N$_3$O$_2$S$^+$=296.1; found m/z=296.1.

The following compound was prepared analogously.

| Cpd | Structure | Formula | MW | m/z Found (M + 1)+ |
|---|---|---|---|---|
| 12B | (N-oxide pyridine fused thienopyrimidinone, 4-Cl-phenyl) | C17H13ClN4O2S | 372.8 | 373.1 |
| 53 | (isomeric N-oxide pyridine fused thienopyrimidinone, 4-Cl-phenyl) | C17H13ClN4O2S | 372.8 | 373.1 |
| 56 | (N-oxide pyridine fused thienopyrimidinone, 4-CH3-phenyl) | C18H16N4O2S | 352.4 | ... |

Method J:

To compound 12 (902 mg, 3.04 mmol) was added POCl$_3$ (30 mL). The reaction mixture was stirred at reflux for 4 h. The solvents were then removed in vacuo, the residue taken up in dichloromethane (50 mL) and washed with 20% NaOH (50 mL). The organic layer was separated, dried over MgSO$_4$ and concentrated in vacuo. The resulting residue was chromatographed on silica gel eluting with 5% acetone/dichloromethane to provide a white solid product containing a mixture of 2 and 4 chlorinated pyridines (13, 14). $^1$H NMR (CDCl$_3$) (13) δ 8.51 (d, 1H), 8.29 (s, 1H), 7.62-7.51 (m, 4H), 7.48-7.43 (m, 2H). MS m/z calcd. for C$_{15}$H$_9$ClN$_3$OS$^+$=314.0; found m/z=314.1. $^1$H NMR (CDCl$_3$) (14) & 8.67 (bs, 1H), 8.36 (s, 1H), 7.64-7.50 (m, 4H), 7.50-7.43 (m, 2H). MS m/z calcd. for C$_{15}$H$_9$ClN$_3$OS$^+$=314.0; found m/z=314.1.

The following analogs can be prepared similarly:

| Cpd | Structure | Formula | MW | m/z Found (M + 1)+ |
|---|---|---|---|---|
| 54 | 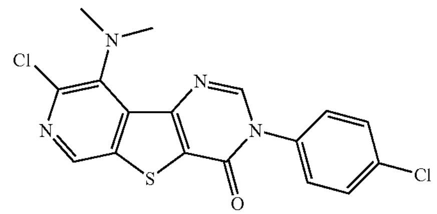 | $C_{17}H_{12}Cl_2N_4OS$ | 391.3 | 391.1 |
| 57 | 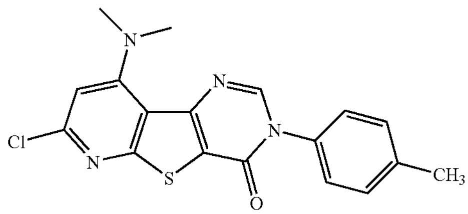 | $C_{18}H_{15}ClN_4OS$ | 370.9 | 371.2 |
| 78 | 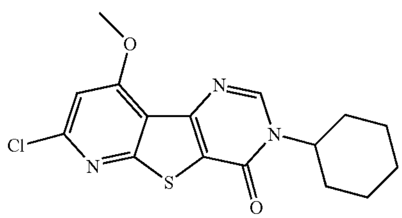 | $C_{16}H_{16}ClN_3O_2S$ | 349.8 | 350.1 |

Method K:

Compound 6 (0.150 g, 0.49 mmol) and ethanolamine (0.120 g, 1.96 mmol) in 10% acetic acid in toluene or 100% acetic acid (~0.20 M) were combined and irradiated in a 300 W power microwave oven at 160° C. for 10 minutes. The mixture was concentrated in vacuo, diluted with ice-water, basified with concentrated NH$_4$OH (aq.). The resultant solid was collected by filtration. The solid was then dissolved in dichloromethane, dried with MgSO$_4$, filtered and concentrated in vacuo. The residue was triturate d with Et$_2$O. The resulting solid was collected by filtration, washed with Et$_2$O, and dried to afford the compound 15A as a solid. $^1$H NMR (CDCl$_3$): δ 8.37 (d, 1H), 8.23 (s, 1H), 6.74 (d, 1H), 4.23 (t, 2H), 4.00 (q, 2H), 3.09 (s, 6H), 2.29 (t, 1H). MS m/z calcd. for $C_{13}H_{15}N_4O_2S^+$=291.1; found m/z=291.1.

Alternatively, the basic aqueous mixture was extracted with dichloro-methane, dried with MgSO$_4$, filtered, and concentrated in vacuo. Purification via preparative TLC or column chromatography on silica gel with dichloromethane/ethyl acetate (1:1) or methanol/dichloromethane (1:10) afforded the desired compound.

The following compounds were prepared analogously:

| Cpd | Structure | Formula | MW | m/z Found (M + 1)+ |
|---|---|---|---|---|
| 15B | 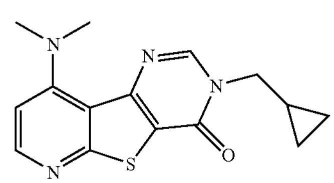 | $C_{15}H_{16}N_4OS$ | 300.4 | 301.2 |
| 15C | 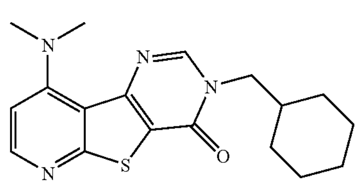 | $C_{18}H_{22}N_4OS$ | 342.5 | 343.1 |

-continued

| Cpd | Structure | Formula | MW | m/z Found (M + 1)+ |
|---|---|---|---|---|
| 15D | 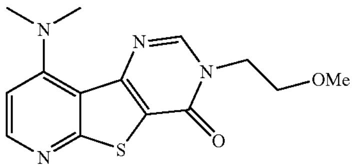 | C14H16N4O2S | 304.4 | 305.0 |
| 15E | 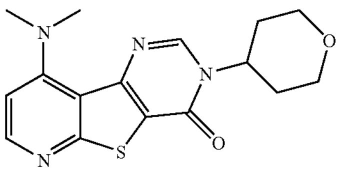 | C16H18N4O2S | 330.4 | 331.2 |
| 15F | 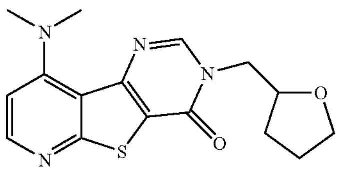 | C16H18N4O2S | 330.4 | 331.1 |
| 15G | 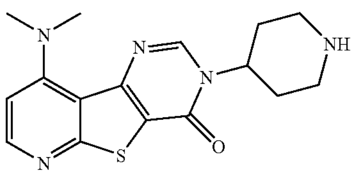 | C16H19N5OS | 329.4 | 330.1 |
| 15H | 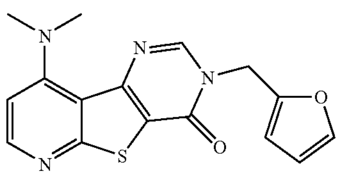 | C16H14N4O2S | 326.4 | 327.1 |
| 15I | 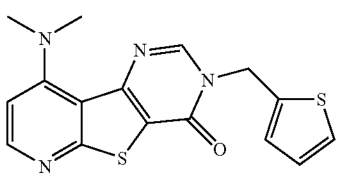 | C16H14N4OS2 | 342.4 | 343.1 |
| 15J | 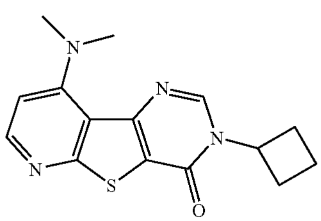 | C15H16N4OS | 300.4 | 301.1 |
| 15K | 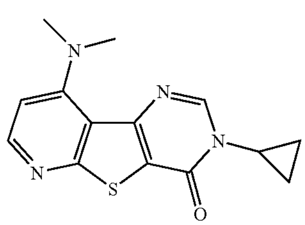 | C14H14N4OS | 286.4 | 287.0 |

-continued

| Cpd | Structure | Formula | MW | m/z Found (M + 1)+ |
|---|---|---|---|---|
| 15L | 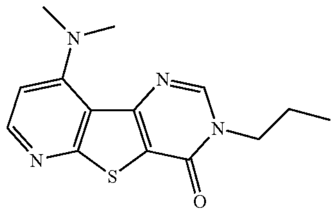 | $C_{14}H_{16}N_4OS$ | 288.4 | 289.0 |
| 15M | 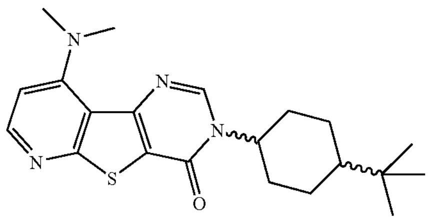 | $C_{21}H_{28}N_4OS$ | 384.5 | 385.2 |
| 15N | 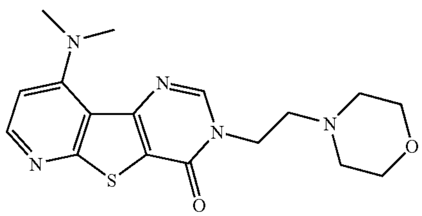 | $C_{17}H_{21}N_5O_2S$ | 359.5 | 360.1 |
| 15O | 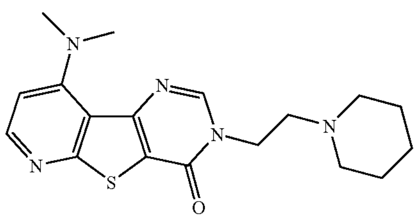 | $C_{18}H_{23}N_5OS$ | 357.5 | 358.1 |
| 15P | 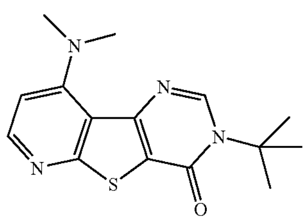 | $C_{15}H_{18}N_4OS$ | 302.4 | 303.2 |
| 15Q | 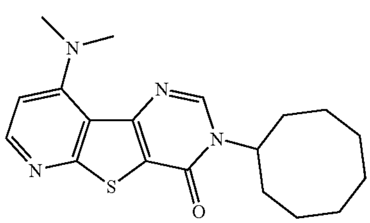 | $C_{19}H_{24}N_4OS$ | 356.5 | 357.1 |
| 15R | 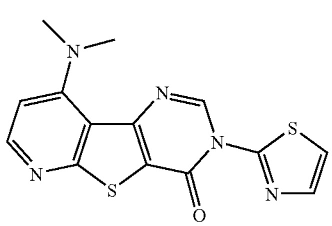 | $C_{14}H_{11}N_5OS_2$ | 329.4 | 330.1 |

-continued

| Cpd | Structure | Formula | MW | m/z Found (M + 1)+ |
|---|---|---|---|---|
| 15S | 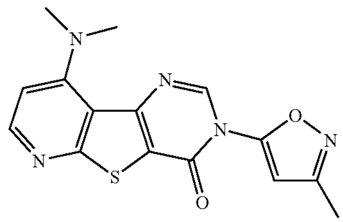 | $C_{15}H_{13}N_5O_2S$ | 327.4 | 328.1 |
| 15T | 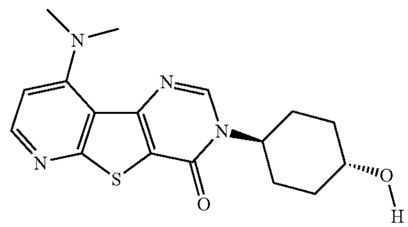 | $C_{17}H_{20}N_4O_2S$ | 344.4 | 345.1 |
| 15U | 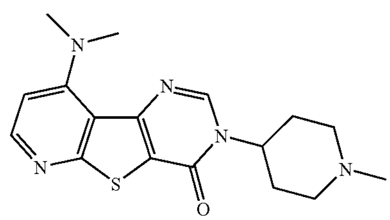 | $C_{17}H_{21}N_5OS$ | 343.4 | 344.1 |
| 15V | 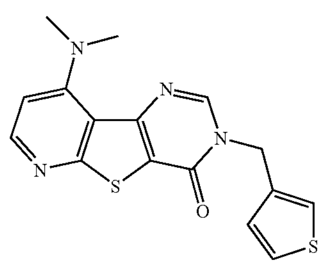 | $C_{16}H_{14}N_4OS_2$ | 342.4 | 343.1 |
| 15W | 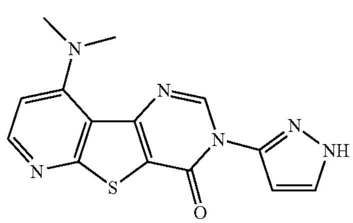 | $C_{14}H_{12}N_6OS$ | 312.3 | 313.2 |
| 15X | 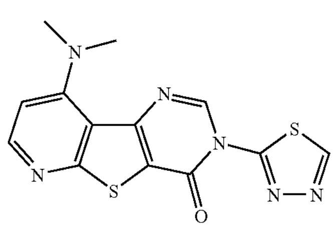 | $C_{13}H_{10}N_6OS_2$ | 330.4 | 331.2 |

-continued

| Cpd | Structure | Formula | MW | m/z Found (M + 1)+ |
|---|---|---|---|---|
| 15Y | 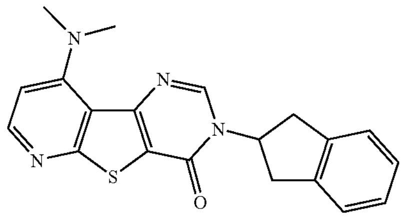 | C20H18N4OS | 362.4 | 363.1 |
| 15Z | 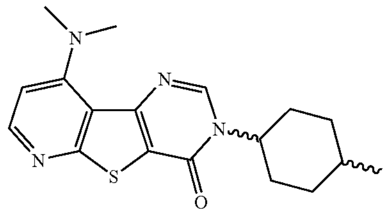 | C18H22N4OS | 342.5 | 343.1 |
| 15AA | 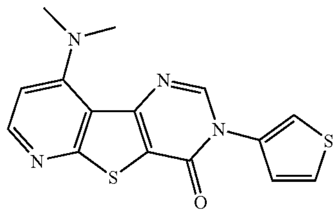 | C15H12N4OS2 | 328.4 | 329.2 |
| 15AB | 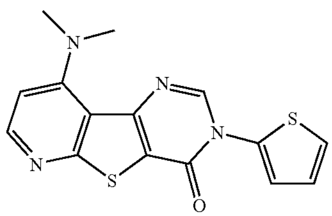 | C15H12N4OS2 | 328.4 | 329.1 |
| 15AC | 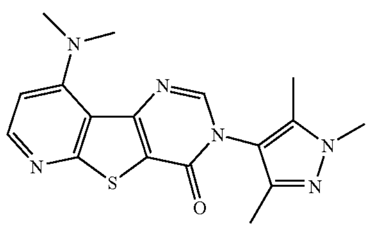 | C17H18N6OS | 354.4 | 355.2 |
| 15AD | 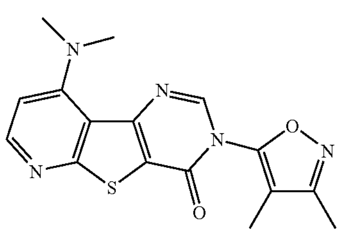 | C16H15N5O2S | 341.4 | 342.2 |
| 15AE | 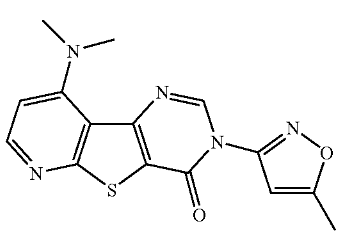 | C15H13N5O2S | 327.4 | 328.2 |

| Cpd | Structure | Formula | MW | m/z Found (M + 1)+ |
|---|---|---|---|---|
| 15AF | 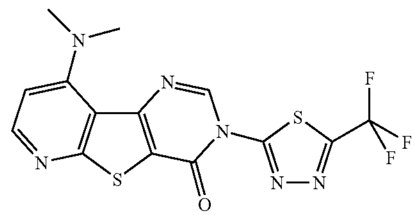 | $C_{14}H_9F_3N_6OS_2$ | 398.4 | 399.1 |
| 15AG | 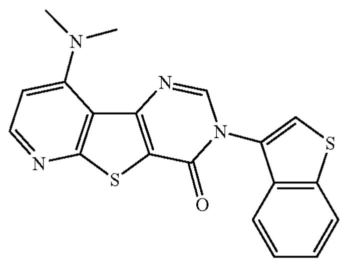 | $C_{19}H_{14}N_4OS_2$ | 378.5 | 379.1 |
| 15AH | 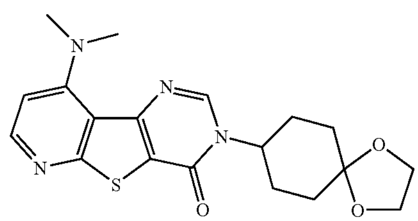 | $C_{19}H_{22}N_4O_3S$ | 386.5 | 387.2 |

Method L:

Compound 3 (1.0 g, 5.5 mmol), methyl glyocate (2.47 g, 0.028 mol) and sodium hydride (1.10 g, 0.028 mol of 60% in mineral oil) in ethylene glycol dimethyl ether (20 mL) were heated at 60° C. for 4 h under a nitrogen atmosphere. The reaction was cooled to room temperature and added ice-water, extracted by dichloromethane, dried using sodium sulfate, filtered and evaporated under reduced pressure to give the desired ester 16. $^1$H NMR (CDCl$_3$): & 7.71 (d, 1H), 6.21 (d, 1H), 4.87 (s, 2H), 3.70 (s, 3H), 3.20 (s, 6H). MS m/z calcd. for $C_{11}H_{14}N_3O_3{}^+$=236.1; found m/z=236.1.

Method M:

A solution of 16 (1.00 g, 0.004 mol) and sodium methoxide (2.30 g, 0.043 mol) in methanol was heated under reflux for 3 h under a nitrogen atmosphere. The reaction was cooled to room temperature, partitioned between water and dichloromethane (150 mL). The dichloromethane layer was dried using anhydrous sodium sulfate, filtered and evaporated under reduced pressure to give the desired bicyclic ester 17. $^1$H NMR (CDCl$_3$): δ 8.17 (d, 1H), 6.56 (d, 1H), 5.21 (br.s, 2H), 3.89 (s, 3H), 2.94 (s, 6H).

Method E: (Alternate)

To compound 17 (0.04 g, 0.20 mmol) was added N,N-dimethylformamide dimethyl acetal (0.20 g, 1.7 mmol) and the mixture was heated in toluene (10 mL) under reflux for a period of 1½ h under a nitrogen atmosphere. The solvent was then evaporated under reduced pressure to give product 18 which was used without purification. MS m/z calcd. for $C_{14}H_{19}N_4O_3{}^+$=291.1; found m/z=291.1.

Method F: (Alternate 1)

Compound 18 (0.049 g, 0.2 mmol) and 4-chloroaniline (0.033 g, 2.6 mmol) were heated in acetic acid (3 mL) at 80° C. for a period of 5 h. The reaction was cooled to room temperature, ice-water was added and the mixture was basified using concentrated ammonium hydroxide solution. The mixture was then extracted by dichloromethane, dried using sodium sulfate, filtered and evaporated under reduced pressure. Purification using preparative TLC on silica gel using dichloromethane/ethyl acetate (9:1) led to product 19. $^1$H NMR (CDCl$_3$): δ 8.17 (d, 1H), 8.08 (s, 1H), 7.50 (d, 2H), 7.36 (d, 2H), 6.49 (d, 1H), 3.37 (s, 6H). MS m/z calcd. for $C_{17}H_{14}ClN_4O_2{}^+$=341.1; found m/z=341.1.

Method N:

Refs.: (a) S. Yano, T. Ohno, K. Ogawa, *Heterocycles* 1993, 36, 145. (b) M. Mittelbach, G. Kastner, H. Junek, *Arch. Pharm.* 1985, 318, 481.

(1-Ethoxyethylidene)malononitrile (20) (40.0 g, 294 mmol) and N,N-dimethylformamide dimethyl acetal (63.0 ml, 470 mmol) were reacted according to Mittelbach and Yano's procedures to give 23.5 g of 21 as a yellow-orange solid. $^1$H NMR (DMSO-d$_6$) δ 12.12 (bs, 1H), 7.77 (d, 1H), 6.33 (d, 1H), 3.95 (s, 3H).

Method B: (Alternate)

To compound 21 (23.5 g, 157 mmol) was added POCl$_3$ (300 mL) and Et$_3$N (15 mL). The reaction mixture was stirred at reflux for 2 h and the solvents removed in vacuo. The resulting brown solid was quenched dropwise with water and basified with 40% aq. NaOH. The aqueous suspension was extracted with three 100 mL portions of dichloromethane, dried over MgSO$_4$ and concentrated in vacuo to provide 23.9 g of compound 22 as a brown solid. $^1$H NMR (CDCl$_3$) δ 8.42 (d, 1H), 6.89 (d, 1H), 4.03 (s, 3H).

Method O:

To a solution of compound 22 (10.0 g, 59.2 mmol) in 200 mL of DMF was added methylthioglycolate (7.15 mL, 65.0 mmol) and sodium methoxide (3.60 g, 65.0 mmol). The reaction was allowed to stir at room temperature for 2 h and poured onto 500 mL of water. The solid was filtered off and recrystallized from ethanol to give 10.0 g of compound 23 as a yellow solid. $^1$H NMR (CDCl$_3$) δ 8.37 (d, 1H), 6.64 (d, 1H), 4.02 (s, 2H), 3.97 (s, 3H), 3.74 (s, 3H).

Method E: (alternate 2) (ref.: N. P. Solov'eva, A. V. Kadushkin, and V. G. Granik, *Khimiko-Farmatsevticheskii Zhurmal*, 1993, 27 (3), 40-43).

A solution of compound 23 (10.0 g, 42.0 mmol), and N,N-dimethyl-formamide dimethyl acetal (25.0 mL, 187 mmol) in abs. ethanol (36 mL) was allowed to stir at reflux for 3 h. The solvent was removed in vacuo and the resulting solid was recrystallized from ethanol to give 7.50 g of compound 24 as a yellow solid. $^1$H NMR (CDCl$_3$) δ 8.46 (d, 1H), 7.55 (s, 1H), 6.65 (d, 1H), 3.94 (s, 3H), 3.82 (s, 3H), 3.10 (bd, 6H).

Method F: (Alternate 2)

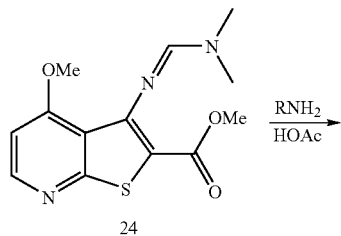

(ref.: N. P. Solov'eva, A. V. Kadushkin, and V. G. Granik, *Khimiko-Farmatsevticheskii Zhurmal*, 1993, 27 (3), 40-43).

To a mixture of compound 24 (3.00 g, 10.2 mmol) in glacial acetic acid (11 mL) was added cyclohexylamine (2.40 mL, 20.5 mmol). The reaction was allowed to stir at 80° C. overnight. The reaction mixture was then poured onto water (100 mL), basified with conc. NH$_4$OH and extracted with 3-25 mL portions of dichloromethane. The organic layer was separated, dried over MgSO$_4$ and concentrated in vacuo. The crude solid was then purified via silica gel chromatography eluting with 10% acetone/dichloromethane to give 2.07 g of compound 25A as a white solid. $^1$H NMR (CDCl$_3$) δ 8.62 (d, 1H), 8.34 (s, 1H), 6.91 (d, 1H), 4.90 (tt, 1H), 4.16 (s, 3H), 2.06 (d, 2H), 1.96 (d, 2H), 1.81 (d, 1H), 1.69-1.47 (m, 5H), 1.34-1.21 (m, 1H). C$_{16}$H$_{18}$N$_3$O$_2$S$^+$=316.1; found m/z=316.1.

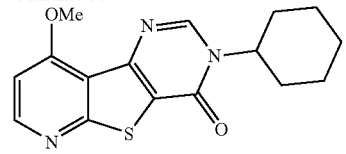

The following compound were prepared analogously:

| Cpd | Structure | Formula | MW | m/z Found (M + 1)$^+$ |
|---|---|---|---|---|
| 25A | 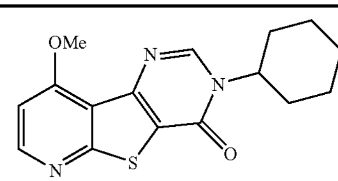 | C$_{16}$H$_{17}$N$_3$O$_2$S | 315.4 | 316.1 |
| 25B | 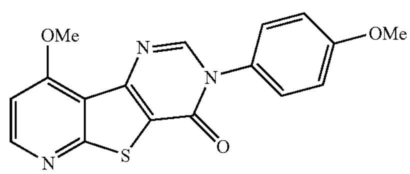 | C$_{17}$H$_{13}$N$_3$O$_3$S | 399.4 | 340.1 |
| 25C | 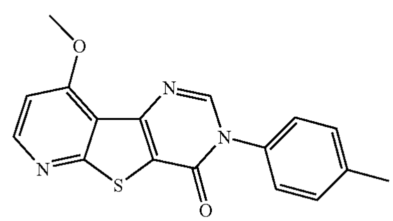 | C$_{17}$H$_{13}$N$_3$O$_2$S | 323.4 | 324.1 |
| 25D | 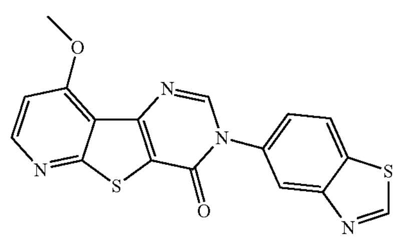 | C$_{17}$H$_{10}$N$_4$O$_2$S$_2$ | 366.4 | 367.1 |

Method P:

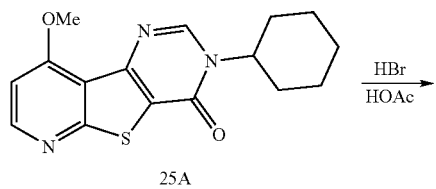

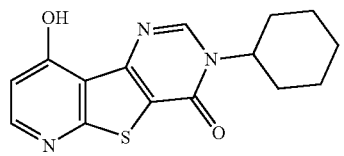

Method Q:

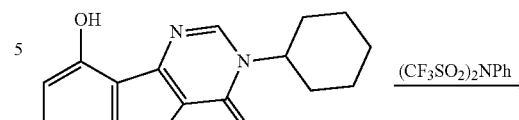

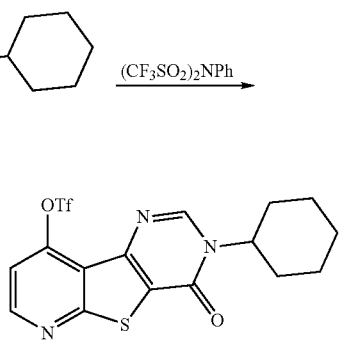

(ref.: C. L. Cywin, Z. Chen, J. Emeigh, R. W. Fleck, M. Hao, E. Hickey, W. Liu, D. R. Marshall, T. Morwick, P. Nemoto, R. J. Sorcek, S. Sun, J. Wu, PCT Int. Appl. WO 03/103661 (2003)).

To compound 25A (2.07 g, 6.55 mmol) was added 33% HBr in acetic acid (26.0 mL). The reaction mixture was stirred at 100° C. in a sealed tube for 2 h, cooled to room temperature, filtered and washed with water. The resulting white solid was dried in vacuo overnight to give 1.90 g of 26A as a white solid. $^1$H NMR (CD$_3$OD) δ 8.70 (s, 1H), 8.69 (d, 1H), 7.22 (d, 1H), 4.80 (tt, 1H), 2.08-1.75 (m, 7H), 1.62-1.49 (m, 2H), 1.43-1.30 (m, 1H). MS m/z calcd. for $C_{15}H_{16}N_3O_2S^+$=302.1; found m/z=302.1.

The following compounds were prepared analogously:

(ref.: C. L. Cywin, Z. Chen, J. Emeigh, R. W. Fleck, M. Hao, E. Hickey, W. Liu, D. R. Marshall, T. Morwick, P. Nemoto, R. J. Sorcek, S. Sun, J. Wu, PCT Int. Appl. WO 03/103661 (2003)).

To a solution of compound 26A (1.90 g, 6.30 mmol) in 1,4-dioxane (17 mL) was added N,N-diisopropylethylamine (1.91 mL, 10.9 mmol) and N-phenyltrifluoromethane sulfonimide (3.79 g, 10.6 mmol). The reaction was allowed to stir at room temperature overnight and diluted with ethyl acetate (50 mL). The mixture was then washed with 50 mL of water, 50 mL of saturated aqueous NH$_4$Cl, and 50 mL of saturated aqueous NaHCO$_3$. The organic layer was separated, dried over MgSO$_4$, and concentrated in vacuo. The resulting crude

| Cpd | Structure | Formula | MW | m/z Found (M + 1)$^+$ |
|---|---|---|---|---|
| 26A | 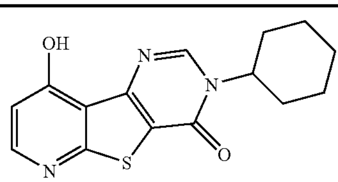 | $C_{15}H_{15}N_3O_2S$ | 301.4 | 302.1 |
| 26C | 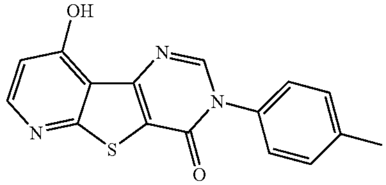 | $C_{16}H_{11}N_3O_2S$ | 309.3 | 310.0 |
| 111 | | $C_{16}H_{11}N_3O_2S$ | 309.3 | 310.0 | off-white solid was purified via silica gel chromatography eluting with 5% acetone/dichloromethane to yield 1.20 g of compound 27A as a white solid. $^1$H NMR (CDCl$_3$) δ 8.84 (d, 1H), 8.35 (s, 1H), 7.35 (d, 1H), 4.89 (tt, 1H), 2.09 (d, 2H), 1.98 (d, 2H), 1.82 (d, 1H), 1.71-1.68 (m, 2H), 1.62-1.47 (m, 2H), 1.34-1.21 (m, 1H). MS m/z calcd. for $C_{16}H_{15}F_3N_3O_4S_2^+$=434.1; found m/z=434.1.

The following compounds were prepared analogously:

| Cpd | Structure | Formula | MW | m/z Found (M + 1)$^+$ |
|---|---|---|---|---|
| 27A | 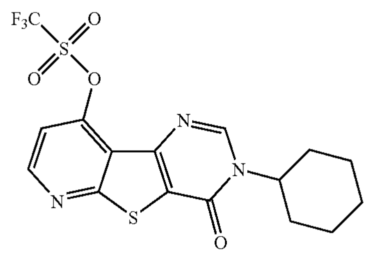 | C$_{16}$H$_{14}$F$_3$N$_3$O$_4$S$_2$ | 433.4 | 434.1 |
| 27B | 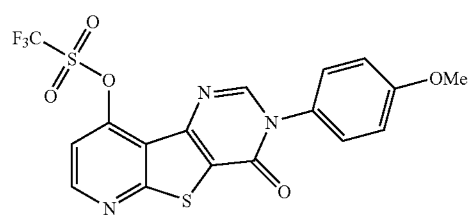 | C$_{17}$H$_{10}$F$_3$N$_3$O$_5$S$_2$ | 457.4 | 457.9 |
| 27C | 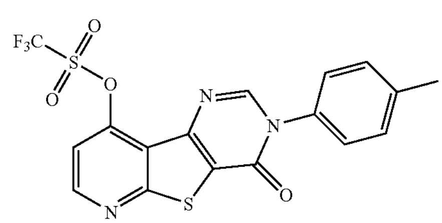 | C$_{17}$H$_{10}$F$_3$N$_3$O$_4$S$_2$ | 441.4 | 441.8 |
| 112A | 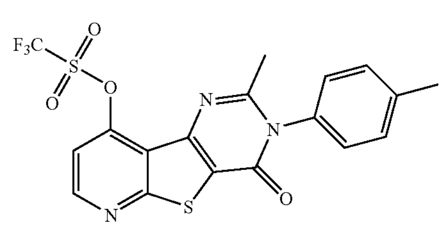 | C$_{18}$H$_{12}$F$_3$N$_3$O$_4$S$_2$ | 455.4 | 456.0 |
| 112B | 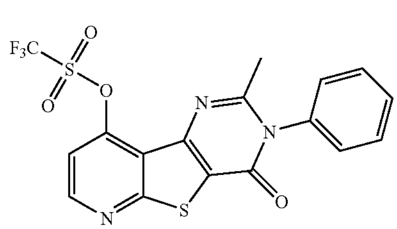 | C$_{17}$H$_{10}$F$_3$N$_3$O$_4$S$_2$ | 441.4 | 441.9 |

Method R:

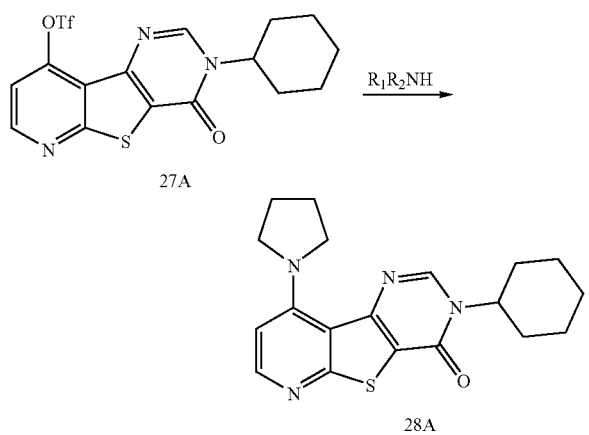

(ref: C. L. Cywin, Z. Chen, J. Emeigh, R. W. Fleck, M. Hao, E. Hickey, W. Liu, D. R. Marshall, T. Morwick, P. Nemoto, R. J. Sorcek, S. Sun, J. Wu, PCT int. Appl. WO 03/103661 (2003)).

To a solution of compound 27A (100 mg, 0.231 mmol) in 3 mL of THF was added pyrrolidine (95 δ l, 1.15 mmol). The reaction mixture was allowed to stir at 60° C. for 1 h. Upon completion (as indicated by TLC) the reaction was diluted with 20 mL of ethyl acetate and washed with four 25 mL portions of water. The organic layer was separated, dried over $MgSO_4$, and concentrated in vacuo. The resulting crude white solid was applied to a 2000 micron silica gel prep plate that was developed twice in 10% acetone/dichloromethane. The band was eluted with 50% acetone/dichloromethane to yield 26 mg of product 28A as a white solid. $^1$H NMR ($CDCl_3$) δ 8.26 (d, 1H), 8.19 (s, 1H), 6.58 (d, 1H), 4.89 (tt, 1H), 3.73 (t, 4H), 2.13-1.99 (m, 6H), 1.95 (d, 2H), 1.81 (d, 1H), 1.73-1.46 (m, 4H), 1.33-1.19 (m, 1H). MS m/z calcd. for $C_{19}H_{23}N_4OS^+$ m/z=355.2; found m/z=355.1.

Analogously, To a solution of compound 27C (300 mg, 0.680 mmol) in 9 mL of THF was added ethanolamine (90 δ l, 1.36 mmol). The reaction mixture was allowed to stir at reflux for 3 h. Upon completion (as indicated by TLC) the solvents were removed in vacuo. The resulting residue was purified via silica gel chromatography eluting with 10% methanol/dichloromethane to yield 180 mg of product 28AV as a white solid. $^1$H NMR ($CDCl_3$) δ 8.11 (bs, 1H), 8.10 (s, 1H), 7.95 (bt, 1H), 7.24 (d, 2H), 7.22 (d, 2H), 6.39 (d, 1H), 3.95 (t, 2H), 3.52 (q, 2H), 2.39 (s, 3H). MS m/z calcd. for $C_{18}H_{16}N_4O_2S^+$ m/z=353.1; found m/z=353.2.

The following additional compounds were prepared analogously:

| Cpd | Structure | Formula | MW | m/z Found (M + 1)+ |
|---|---|---|---|---|
| 28A | 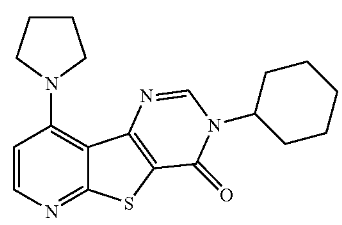 | $C_{19}H_{22}N_4OS$ | 354.5 | 355.1 |
| 28B | 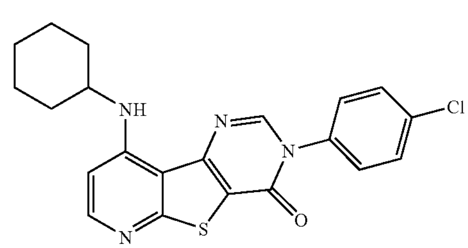 | $C_{21}H_{19}ClN_4OS$ | 410.9 | 411.1 |
| 28C | 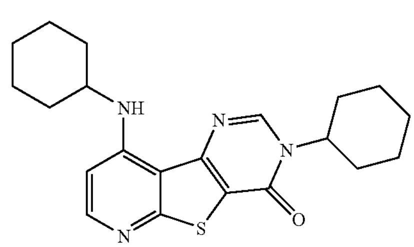 | $C_{21}H_{26}N_4OS$ | 382.5 | 383.1 |

-continued

| Cpd | Structure | Formula | MW | m/z Found (M + 1)+ |
|---|---|---|---|---|
| 28D | 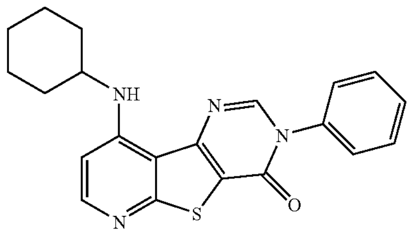 | $C_{21}H_{20}N_4OS$ | 376.5 | 377.1 |
| 28E | 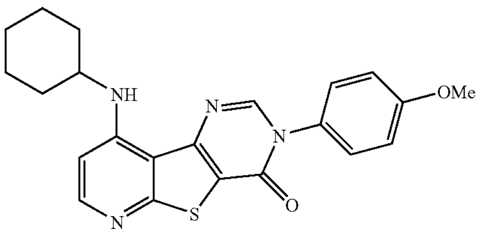 | $C_{22}H_{22}N_4O_2S$ | 406.5 | 407.1 |
| 28F | 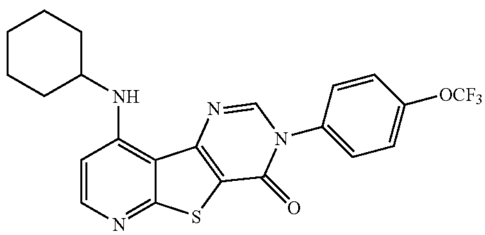 | $C_{22}H_{19}F_3N_4O_2S$ | 460.5 | 461.3 |
| 28G | 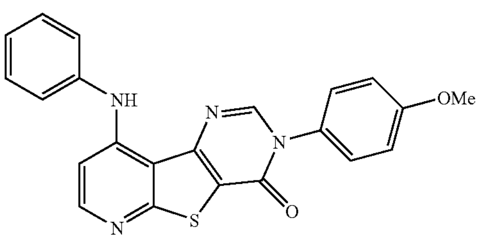 | $C_{22}H_{16}N_4O_2S$ | 400.5 | 401.1 |
| 28H | 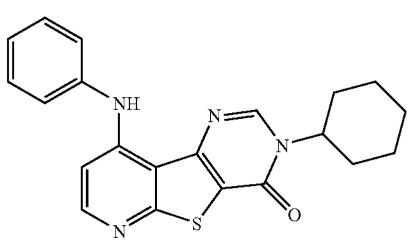 | $C_{21}H_{20}N_4OS$ | 376.5 | 377.1 |
| 28I | 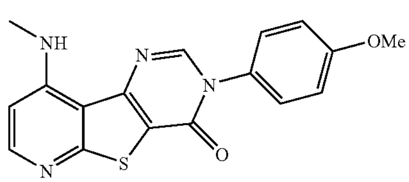 | $C_{17}H_{14}N_4O_2S$ | 338.4 | 339.1 |
| 28J | 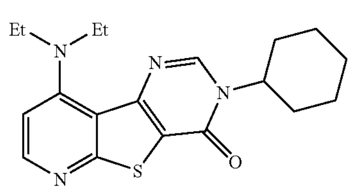 | $C_{19}H_{24}N_4OS$ | 356.5 | 356.1 |

| Cpd | Structure | Formula | MW | m/z Found (M + 1)+ |
|---|---|---|---|---|
| 28K | 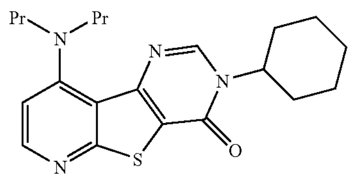 | C21H28N4OS | 384.5 | 385.1 |
| 28L | 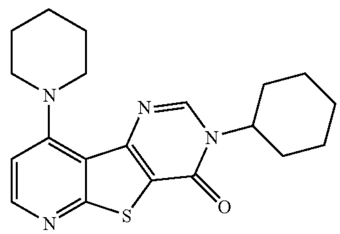 | C20H24N4OS | 368.5 | 369.1 |
| 28M | 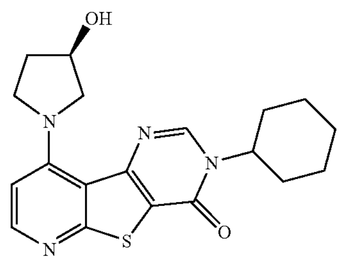 | C19H22N4O2S | 370.5 | 371.1 |
| 28N | 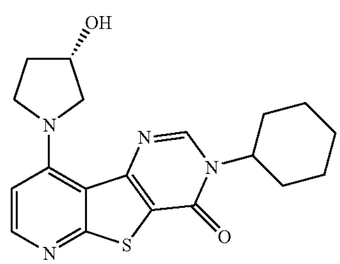 | C19H22N4O2S | 370.5 | 371.1 |
| 28O | 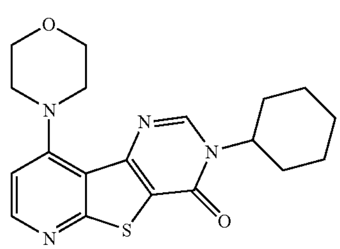 | C19H22N4O2S | 370.5 | 371.1 |
| 28P | 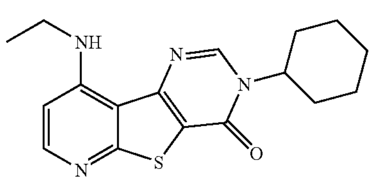 | C17H20N4OS | 328.4 | 329.1 |
| 28Q | 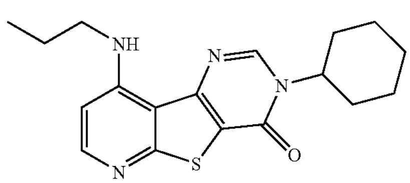 | C18H22N4OS | 342.5 | 343.1 |

| Cpd | Structure | Formula | MW | m/z Found (M + 1)+ |
|---|---|---|---|---|
| 28R | 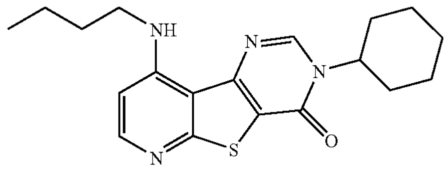 | C19H24N4OS | 356.5 | 357.1 |
| 28S | 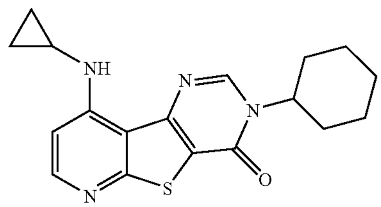 | C18H20N4OS | 340.4 | 341.1 |
| 28T | 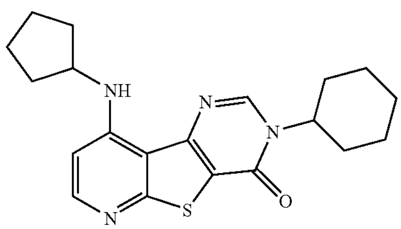 | C20H24N4OS | 368.5 | 369.1 |
| 28U | 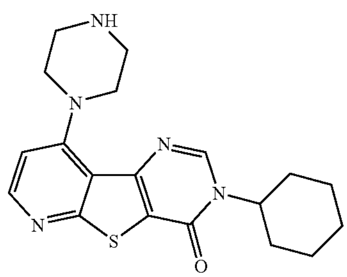 | C19H23N5OS | 369.5 | 370.1 |
| 28V | 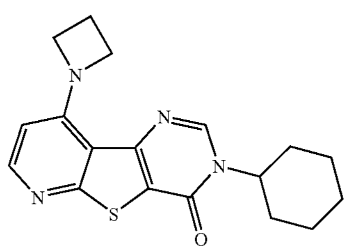 | C18H20N4OS | 340.4 | 341.1 |
| 28W | 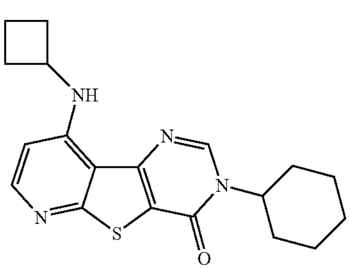 | C19H22N4OS | 354.5 | 355.1 |

-continued

| Cpd | Structure | Formula | MW | m/z Found (M + 1)+ |
|---|---|---|---|---|
| 28X | 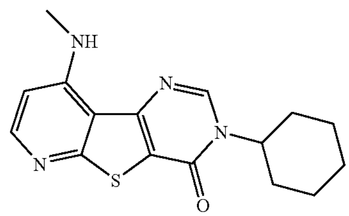 | $C_{16}H_{18}N_4OS$ | 314.4 | 315.2 |
| 28Y | 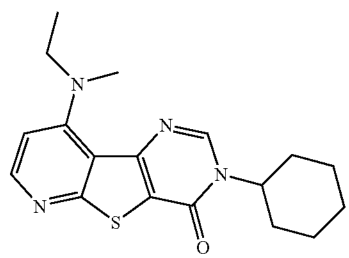 | $C_{18}H_{22}N_4OS$ | 342.5 | 353.1 |
| 28Z | 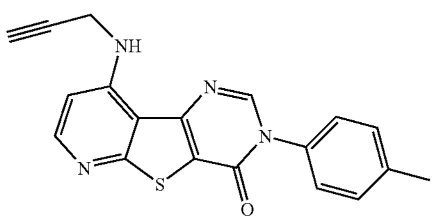 | $C_{19}H_{14}N_4OS$ | 346.4 | 347.1 |
| 28AA | 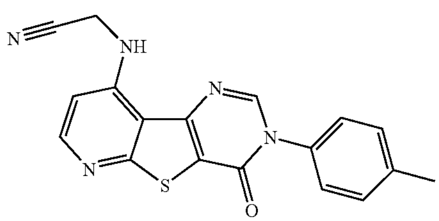 | $C_{18}H_{13}N_5OS$ | 347.4 | 348.1 |
| 28AB | 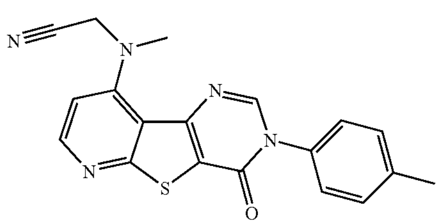 | $C_{20}H_{16}N_4OS$ | 360.4 | 361.1 |
| 28AC | 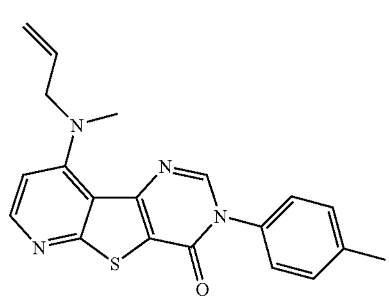 | $C_{20}H_{18}N_4OS$ | 362.4 | 363.1 |

-continued

| Cpd | Structure | Formula | MW | m/z Found (M + 1)+ |
|---|---|---|---|---|
| 28AD | 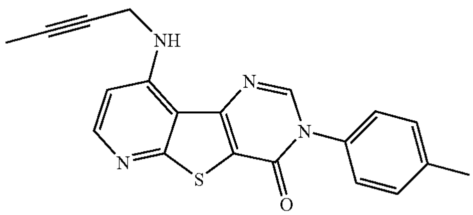 | $C_{20}H_{16}N_4OS$ | 360.4 | 361.1 |
| 28AE | 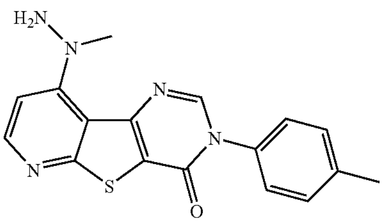 | $C_{17}H_{15}N_5OS$ | 337.4 | 338.1 |
| 28AF | 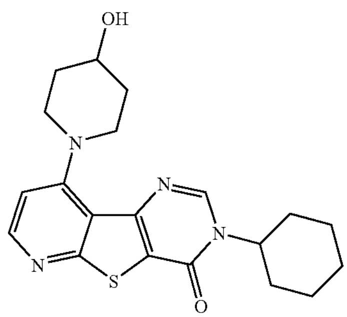 | $C_{20}H_{24}N_4O_2S$ | 384.5 | 385.1 |
| 28AG | 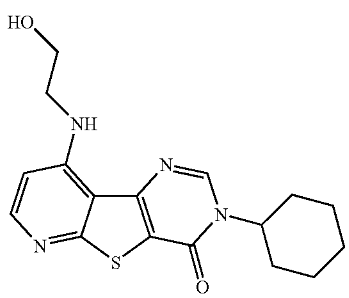 | $C_{17}H_{20}N_4O_2S$ | 344.4 | 345.1 |
| 28AH | 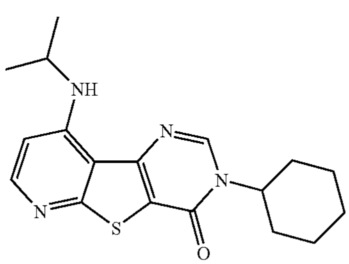 | $C_{18}H_{22}N_4OS$ | 342.5 | 343.1 |
| 28AI | 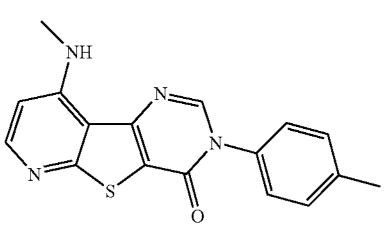 | $C_{17}H_{14}N_4OS$ | 322.4 | 323.1 |

-continued
| Cpd | Structure | Formula | MW | m/z Found (M + 1)+ |
|---|---|---|---|---|
| 28AJ | 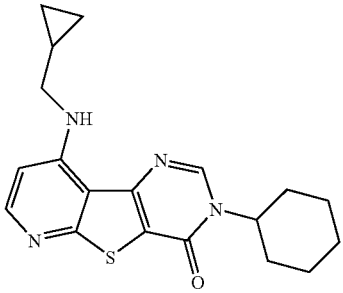 | $C_{19}H_{22}N_4OS$ | 354.5 | 355.1 |
| 28AK | 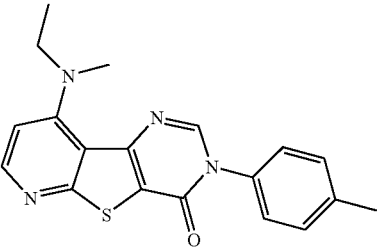 | $C_{19}H_{18}N_4OS$ | 350.4 | 351.1 |
| 28AL | 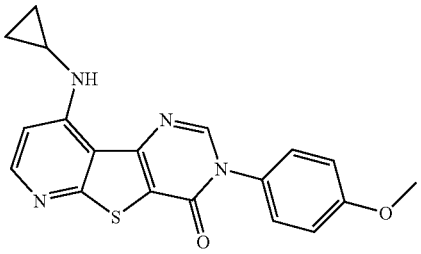 | $C_{19}H_{16}N_4O_2S$ | 364.4 | 365.2 |
| 28AM | 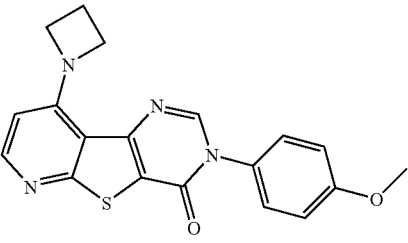 | $C_{19}H_{16}N_4O_2S$ | 364.4 | 365.2 |
| 28AN | 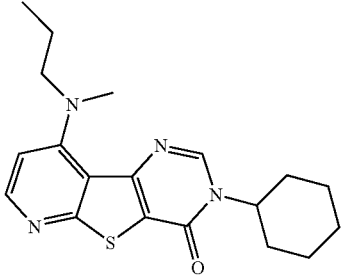 | $C_{19}H_{24}N_4OS$ | 356.5 | 357.1 |

-continued

| Cpd | Structure | Formula | MW | m/z Found (M + 1)+ |
|---|---|---|---|---|
| 28AO | 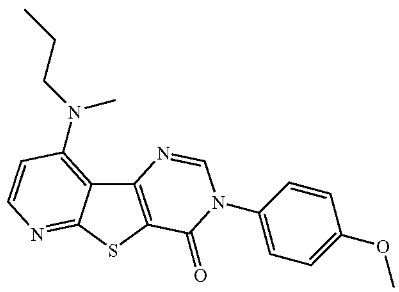 | C20H20N4O2S | 380.5 | 381.1 |
| 28AP | 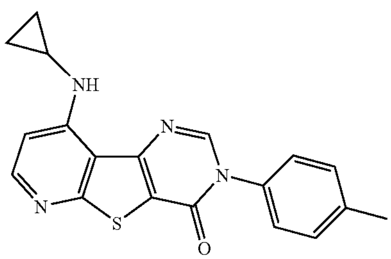 | C19H16N4OS | 348.4 | 349.1 |
| 28AQ | 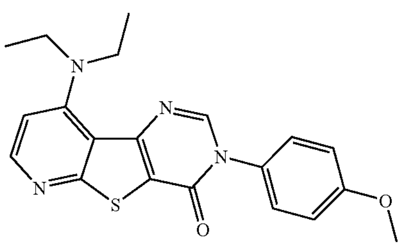 | C20H20N4O2S | 380.5 | 381.1 |
| 28AR | 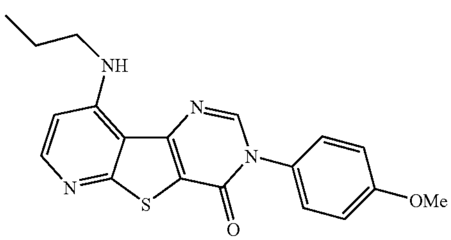 | C19H18N4O2S | 366.4 | 367.1 |
| 28AS | 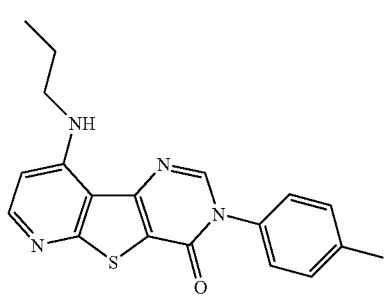 | C19H18N4OS | 350.4 | 351.2 |

-continued

| Cpd | Structure | Formula | MW | m/z Found (M + 1)+ |
|---|---|---|---|---|
| 28AT | 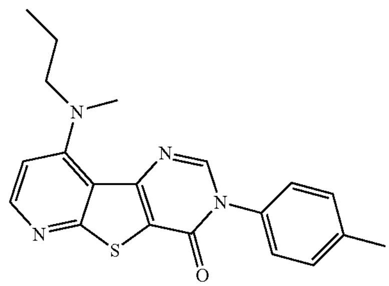 | $C_{20}H_{20}N_4OS$ | 364.5 | 365.2 |
| 28AU | 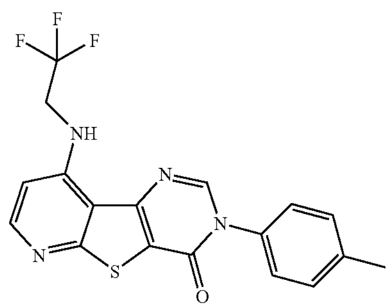 | $C_{18}H_{13}F_3N_4OS$ | 390.4 | 391.2 |
| 28AV | 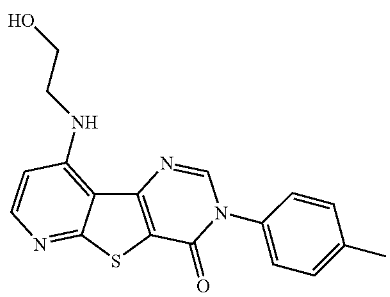 | $C_{18}H_{16}N_4O_2S$ | 352.4 | 353.2 |
| 28AW | 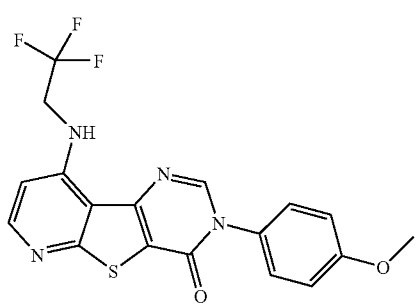 | $C_{18}H_{13}F_3N_4O_2S$ | 406.4 | 407.2 |
| 28AX | 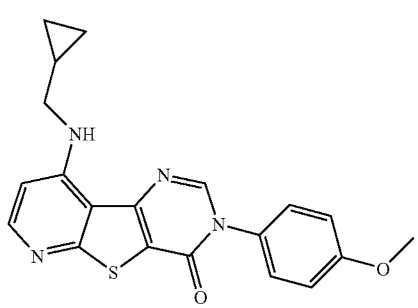 | $C_{20}H_{18}N_4O_2S$ | 378.4 | 379.2 |

-continued

| Cpd | Structure | Formula | MW | m/z Found (M + 1)+ |
|---|---|---|---|---|
| 28AY | 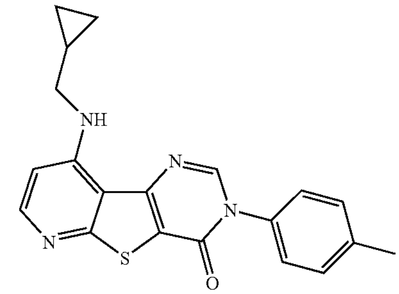 | $C_{20}H_{18}N_4OS$ | 362.4 | 363.2 |
| 28AZ | 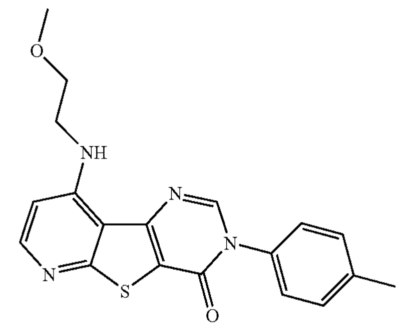 | $C_{19}H_{18}N_4O_2S$ | 366.4 | 367.1 |
| 28BA | 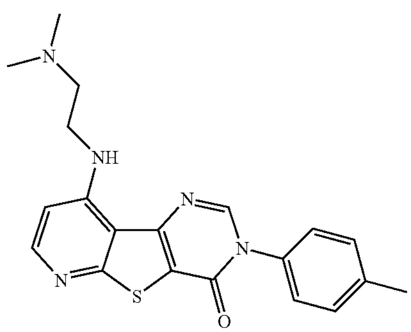 | $C_{20}H_{21}N_5OS$ | 379.5 | 380.1 |
| 28BB | 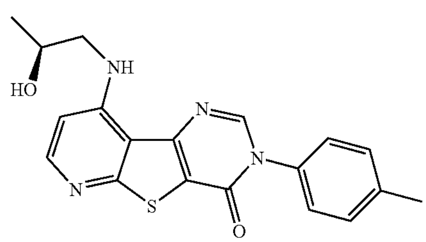 | $C_{19}H_{18}N_4O_2S$ | 366.4 | 367.2 |
| 28BC | 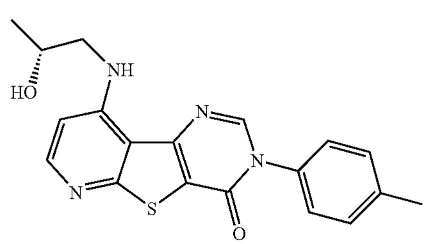 | $C_{19}H_{18}N_4O_2S$ | 366.4 | 367.2 |

Method R (Alternate):

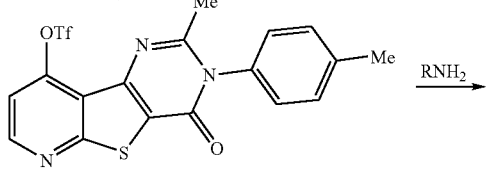

To a solution of compound 112A (50 mg, 0.11 mmol) in 1.4 mL of THF was added 2 M dimethyl amine in THF (0.55 mL, 1.1 mmol). The reaction mixture was stirred and refluxed for 1½ h. Upon completion (as indicated by TLC) the reaction mixture was concentrated in vacuo. The resultant yellow oil was purified via preparative silica gel TLC with 11% acetone/methylene chloride to afford 36 mg of compound 113A as a white foam. $^1$H NMR (CDCl$_3$): δ 8.37 (d, 1H), 7.33 (d, 2H), 7.12 (d, 2H), 6.72 (d, 1H), 3.14 (s, 6H), 2.41 (s, 3H), 2.30 (s, 3H). MS m/z calcd. for $C_{19}H_{19}N_4OS^+$=351.1; found m/z=351.1.

The following compounds were prepared analogously:

| Cpd | Structure | Formula | MW | m/z Found (M + 1)$^+$ |
|---|---|---|---|---|
| 113A | 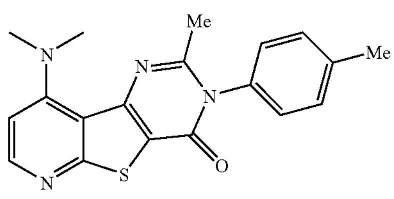 | $C_{19}H_{18}N_4OS$ | 350.4 | 351.1 |
| 113B | 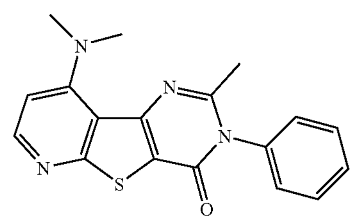 | $C_{18}H_{16}N_4OS$ | 336.4 | 337.1 |
| 113C | 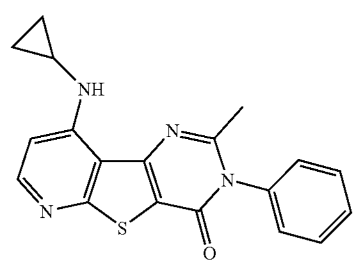 | $C_{19}H_{16}N_4OS$ | 348.4 | 349.1 |
| 113D | 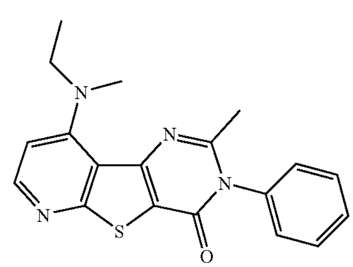 | $C_{19}H_{18}N_4OS$ | 350.4 | 351.1 |

-continued

| Cpd | Structure | Formula | MW | m/z Found (M + 1)+ |
|---|---|---|---|---|
| 113E | 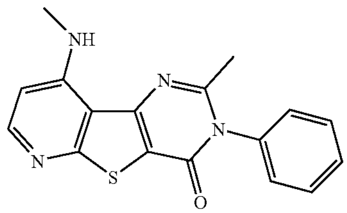 | $C_{17}H_{14}N_4OS$ | 322.4 | 323.1 |
| 113F | 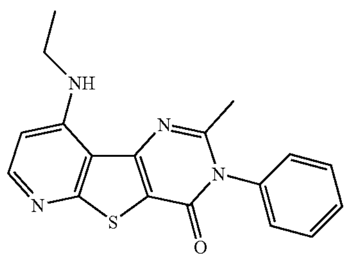 | $C_{18}H_{16}N_4OS$ | 336.4 | 337.1 |
| 113G | 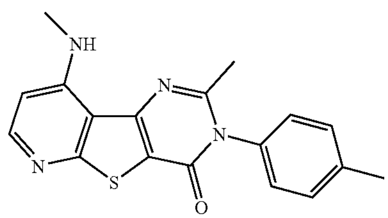 | $C_{18}H_{16}N_4OS$ | 336.4 | 337.1 |
| 113H | 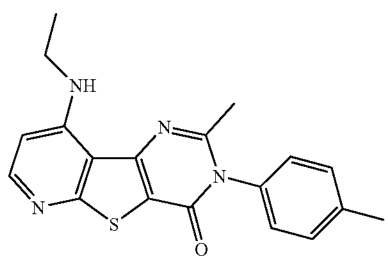 | $C_{19}H_{18}N_4OS$ | 350.4 | 351.1 |
| 113I | 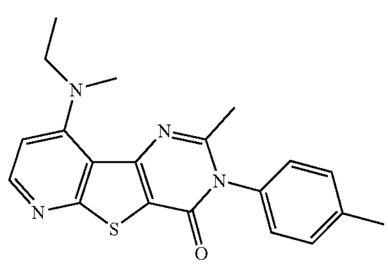 | $C_{20}H_{20}N_4OS$ | 364.5 | 365.1 |
| 113J | 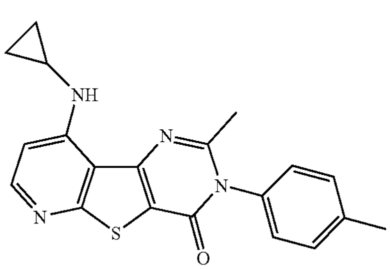 | $C_{20}H_{18}N_4OS$ | 362.4 | 363.1 |

-continued

| Cpd | Structure | Formula | MW | m/z Found (M + 1)+ |
|---|---|---|---|---|
| 113K | 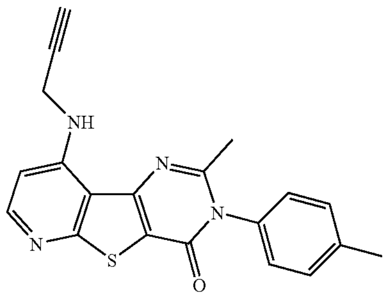 | C20H16N4OS | 360.4 | 361.1 |
| 113L | 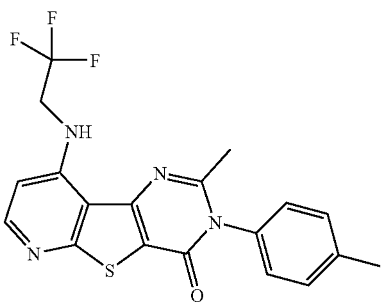 | C19H15F3N4OS | 404.4 | 405.2 |
| 113M | 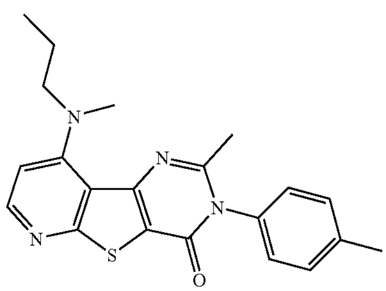 | C21H22N4OS | 378.5 | 379.2 |
| 113N | 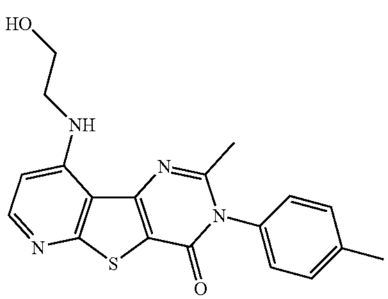 | C19H18N4O2S | 366.4 | 367.2 |

Method S:

To a suspension of 0.063 g (0.2 mmol) of compound 25A in 4 mL of toluene was added 0.2 mL (0.4 mmol) of isopropylmagnesium bromide at room temperature. After being stirred for 2 h, it was quenched with 30 mL of water, and extracted with two 30 mL portions of dichloromethane. The combined organic extracts were washed with 15 mL of brine and concentrated. The residue was purified by preparative TLC eluting with 5% methanol in dichloromethane to give 0.019 g of compound 29A. MS m/z calcd. for $C_{19}H_{22}N_3OS^+$ m/z=328.1; found m/z=328.1.

The following compounds were prepared analogously:

| Cpd | Structure | Formula | MW | m/z Found (M + 1)+ |
|---|---|---|---|---|
| 29B | 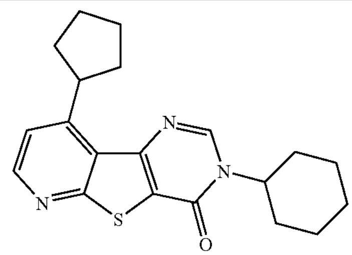 | $C_{20}H_{23}N_3OS$ | 353.5 | 354.1 |
| 29C | 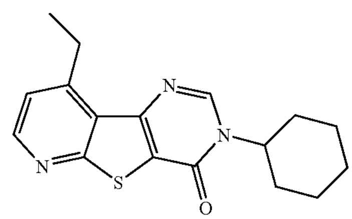 | $C_{17}H_{19}N_3OS$ | 313.4 | 314.2 |
| 29D | 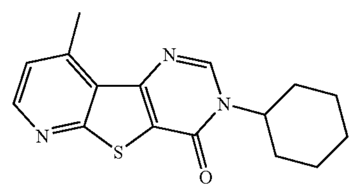 | $C_{16}H_{17}N_3OS$ | 299.4 | 300.1 |

Method T:

To a solution of 0.04 g (0.6 mmol) of pyrrole in 3 mL of THF was added 0.38 mL (0.6 mmol) of n-BuLi at 0° C. After being stirred for 15 min., 0.063 g of compound 25A (0.2 mmol) was added as a solid. The mixture was stirred at room temperature for 2 h and at reflux for 18 h, then cooled to room temperature. It was quenched with 0.2 mL of water, and concentrated. The residue was purified by preparative TLC eluting with 4% methanol in dichloromethane containing 0.2% NH$_4$OH to give 0.038 g of compound 30A. MS m/z calcd. for $C_{19}H_{19}N_4OS^+$ m/z=351.1; found m/z=351.1.

The following compound were prepared analogously:

| Cpd | Structure | Formula | MW | m/z Found (M + 1)+ |
|---|---|---|---|---|
| 30B | 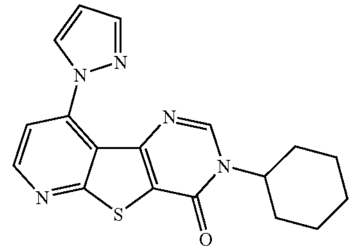 | $C_{18}H_{17}N_5OS$ | 351.4 | 352.1 |

| Cpd | Structure | Formula | MW | m/z Found (M + 1)+ |
|---|---|---|---|---|
| 30C | 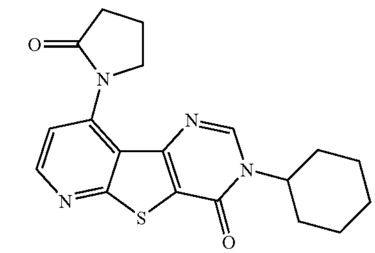 | $C_{19}H_{20}N_4O_2S$ | 368.5 | 369.2 |

Method U:

To a solution of 5.21 g (37.2 mmol) of diisopropylamine in 10 mL of THF was added 23.1 mL (37 mmol) of n-BuLi in hexanes at 0° C. After 30 min, it was diluted with 30 mL of THF and cooled to −78° C. To this solution was added a solution of 5.00 g (33.8 mmol) of 3,5-dichloropyridine in 60 mL of THF. After 1 h, a solution of 3.14 mL (50.7 mmol) of N,N-dimethyl formate in 15 mL of THF was added dropwise over 30 min. The reaction was stirred at −78° C. for 2 hrs and poured into 400 mL of sodium bicarbonate. The mixture was stirred vigorously and portioned with 600-700 mL of ethyl acetate. The combined organic extracts were washed with two 100 mL portions of sodium bicarbonate, 100 mL of brine and dried over. magnesium sulfate. It was filtered and the filtrate was concentrated. The residue was chromatographed over $SiO_2$ eluting with 10% ethyl acetate in hexanes to give 4.81 g (81%) of product 31. $^1H$ NMR ($CDCl_3$) δ 0.42 (s, 1H), 8.61 (s, 2H).

Method V:

A mixture of 4.71 g (26.8 mmol) of the aldehyde 31, 20 mL of formic acid, 2.42 g (34.8 mmol) of hydroxylamine hydrochloride and 2-3 drops of conc. sulfuric acid was heated at reflux for 4 hrs. The reaction was cooled to room temperature and the formic acid was evaporated under vacuum. The residue was partitioned between 80 mL of ether and 40 mL of water. The organic layer was washed with two 50 mL portions of saturated sodium bicarbonate and 40 mL of brine. It was dried over anhydrous sodium sulfate and filtered. The filtrate was concentrated to give 4.48 g (96%) of compound 32. $^1H$ NMR ($CDCl_3$) δ 8.70 (s, 2H).

Method W:

A sealed tube containing 6-8 mL of dimethylamine and 4.18 g (24.2 mmol) of compound 32 was warmed from −78° C. to room temperature over 1 h and then heated at 50° C. for an additional 1 h. The reaction mixture was cooled to 0° C. and partitioned between 20 mL of water and 50 mL of ethyl acetate. The organic layer was washed with 10 mL of water, 20 mL of brine, and dried over sodium sulfate. It was filtered and the filtrate was concentrated to give 4.37 g (98%) of compound 33. MS calcd for $C_8H_9ClN_3$=182.1; found=182.1.

Method X:

To a solution of 0.13 g (0.40 mmol) of compound 7Q in 5 mL of acetonitrile was added 0.10 g (0.8 mmol) of N-Chlorosuccinimide (NCS). The mixture was stirred at reflux for 18 h and concentrated. The residue was purified by chromatography eluting with 1 to 3% methanol in methylene chloride plus 1% ammonium hydroxide to give 0.11 g of compound 41. Calcd MS for $C_{17}H_{20}ClN_4OS$=363.1; found m/z=363.1.

Compound 42 was prepared analogously. MS calcd for $C_{16}H_{18}ClN_4OS$=349.1; found m/z=349.2.

| Cpd | Structure | Formula | MW | m/z Found (M + 1)+ |
|---|---|---|---|---|
| 41 | 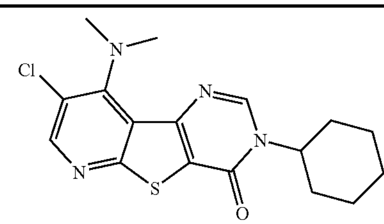 | $C_{17}H_{19}ClN_4OS$ | 362.9 | 363.1 |
| 42 | 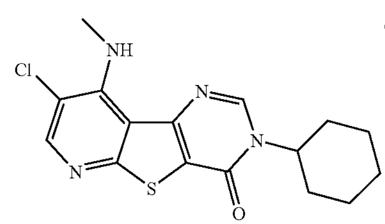 | $C_{16}H_{17}ClN_4OS$ | 348.8 | 349.2 |

Method Y:

To a solution of 0.16 g (0.5 mmol) of compound 7Q in 4 mL of THF was added 0.086 g (0.3 mmol) of 1,3-dibromohydantoin. The mixture was stirred at room temperature for 30 min, quenched with 20 mL of saturated sodium bicarbonate. It was extracted with two 30 mL portions of methylene chloride. The combined organic extracts were washed with 10 mL of brine, then concentrated. The residue was purified by preparative TLC eluting with 3% methanol in methylene chloride to give 0.060 g of compound 43 and 0.022 g of compound 44. Compound 43, MS calcd for $C_{76}H_{20}B_rN_4OS$=409.1; found m/z=409.2. Compound 44, MS calcd for $C_{16}H_{18}B_rN_4OS$=395.1; found m/z=395.2.

Method AA:

A mixture of 0.285 g (0.7 mmol) of compound 43, 0.082 g (0.7 mmol) of zinc cyanide and 0.025 g (0.021 mmol) of $Pd(PPh_3)_4$ in 5 mL of DMF was heated at 120° C. using microwave irradiation (PersonalChemistry) for 5 min., and concentrated. The residue was purified by chromatography eluting with 1 to 4% methanol in methylene chloride plus 1% ammonium hydroxide to give 0.225 g of compound 46. MS calcd for $C_{18}H_{20}N_5OS$=354.1; found m/z=354.2.

Compounds 55, 156 and 163 could be prepared analogously from compounds 54, 155 and 162 respectively:

| Cpd | Structure | Formula | MW | m/z Found (M + 1)+ |
|---|---|---|---|---|
| 46 | 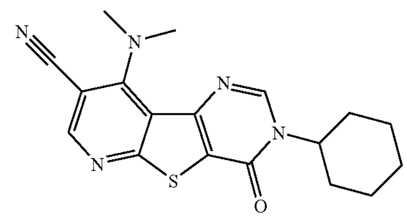 | $C_{18}H_{19}N_5OS$ | 353.4 | 354.2 |
| 55 | 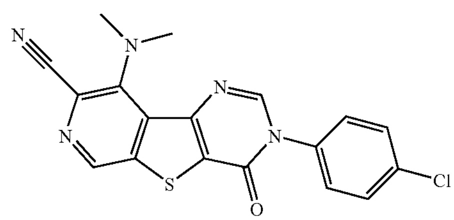 | $C_{18}H_{12}ClN_5OS$ | 381.8 | 382.1 |
| 156 | 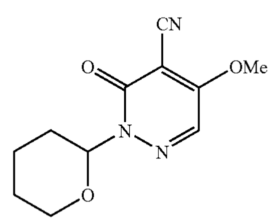 | $C_{11}H_{13}N_3O_3$ | 235.2 | 236.2 |
| 163 | 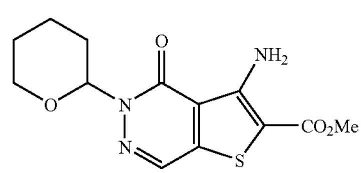 | $C_{13}H_{15}N_3O_4S$ | 309.3 | 310.1 |

Method Z:

To a stirred solution of 0.10 g (0.25 mmol) of compound 43 in 4 mL of ether was added 0.25 mL (0.4 mmol) of n-BuLi at −78° C. After 1 h, a solution of 0.1 mL of DMF in 1 mL of ether was introduced. The mixture was stirred for 3 h and quenched with 30 mL of water. It was extracted with two 30 mL portions of ethyl acetate. The combined organic extracts were washed 20 mL of brine, and concentrated. The residue was purified by preparative TLC eluting with 7% methanol in methylene chloride to give 0.03 g of compound 45. MS calcd for $C_{18}H_{21}N_4O_2S$=357.1; found m/z=357.2.

Method AB:

A mixture of 0.04 g (0.1 mmol) of compound 43, 0.02 g (0.135 mmol) of 3-cyanophenylboronic acid, 0.015 g (cat.) of $Pd(PPh_3)_4$ in 4 mL of toluene-methanol (1:1) and 0.2 mL of 2N sodium carbonate in a sealed tube was heated at 120° C. for 5 min. using microwave irradiation (Personalchemistry). It was diluted with 25 mL of methanol and filtered. The filtrate was concentrated; the residue was purified by preparative TLC eluting with 5% methanol in methylene chloride to give 0.036 g of compound 47A. MS calcd for $C_{24}H_{24}N_5OS$=430.2; found m/z=430.2. Compound 47B was prepared analogously.

| Cpd | Structure | Formula | MW | m/z Found (M + 1)+ |
|---|---|---|---|---|
| 47A | 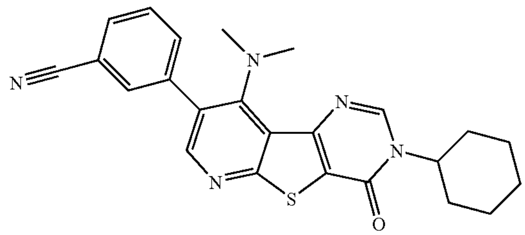 | C24H23N5OS | 429.5 | 430.2 |
| 47B | 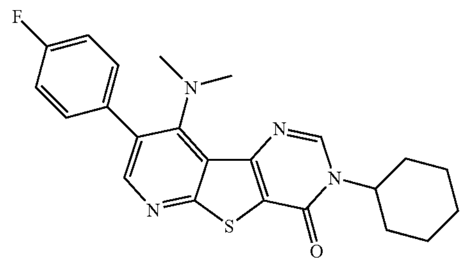 | C23H24FN4OS | 422.5 | 423.2 |

The following compounds were prepared analogously from compounds 57 or 83.

| Cpd | Structure | Formula | MW | m/z Found (M + 1)+ |
|---|---|---|---|---|
| 86A | 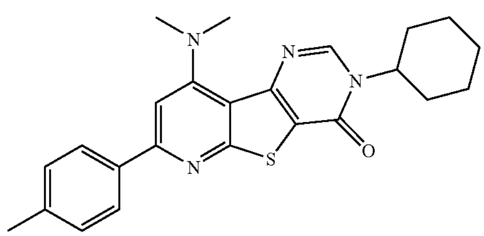 | C24H26N4OS | 418.6 | 419.2 |
| 86B | 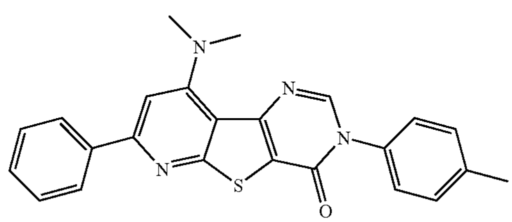 | C24H20N4OS | 412.5 | 413.1 |
| 86C | 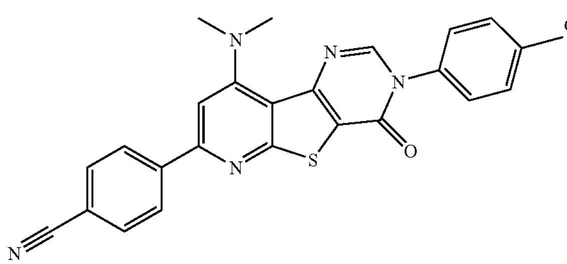 | C25H19N5OS | 437.5 | 438.1 |

| Cpd | Structure | Formula | MW | m/z Found (M + 1)+ |
|---|---|---|---|---|
| 86D | 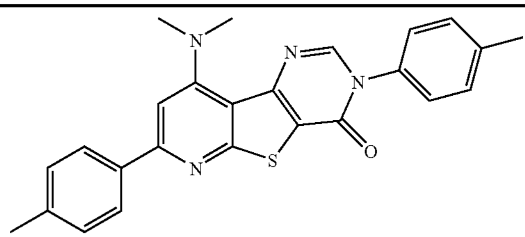 | C25H22N4OS | 426.5 | 427.1 |
| 86E | 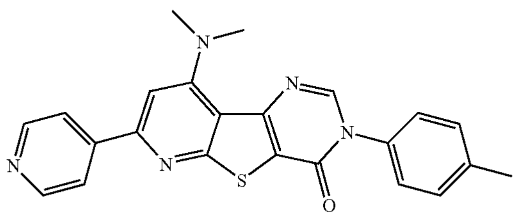 | C23H19N5OS | 413.5 | 414.2 |

Method AC:

To a solution of 0.042 g (0.12 mmol) of Compound 46 in 4 mL of acetonitrile was added a solution of 0.023 g (0.13 mmol) of N-bromosuccinimide (NBS). The mixture was stirred at the same temperature for 3 h, and concentrated. The residue was purified by preparative TLC eluting with 4% methanol in methylene chloride to give 0.03 g of compound 48. MS calcd for $C_{17}H_{18}N_5OS$=340.1; found m/z=340.1.

Compound 52 was prepared from compound 51 analogously. MS calcd for $C_{16}H_{18}N_5O_3S$=360.1; found m/z=360.1.

methylene chloride to give 0.021 g of compound 49. MS calcd for $C_{18}H_{22}N_5O_2S$=372.2; found m/z=372.2.

Method AE:

A solution of 0.039 g (0.11 mmol) of compound 46 and 0.5 mL (1 mmol) of ethylamine (2.0M THF solution) in 2 mL of acetonitrile in a sealed tube was heated at 80° C. for 18 h and 120° C. for 16 h, and concentrated. The residue was purified by preparative TLC eluting with 4% methanol in methylene chloride to give 0.030 g of compound 50. MS calcd for $C_{18}H_{20}N_5OS$=354.1; found m/z=354.2.

| Cpd | Structure | Formula | MW | m/z Found (M + 1)+ |
|---|---|---|---|---|
| 48 | 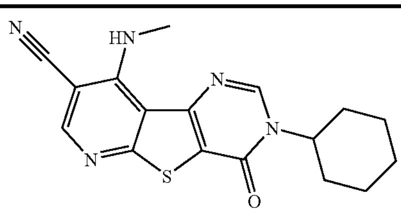 | C17H17N5OS | 339.4 | 340.1 |
| 52 | 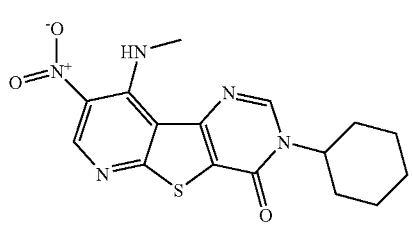 | C16H17N4O3S | 422.5 | 423.2 |

Method AD:

A solution of 0.036 g (0.1 mmol) of compound 46 in 1.5 mL of concentrated sulfuric acid was stirred at 60° C. for 18 h, and poured into 40 mL of water. It was basified with sodium bicarbonate, and extracted with two 40 mL portions of methylene chloride. The combined organic extracts were washed with 20 mL of brine, and concentrated. The residue was purified by preparative TLC eluting with 7% methanol in Method AF:

To a solution of 0.066 g (0.2 mmol) of compound 7Q in 2 mL of concentrated sulfuric acid was added 0.2 mL of concentrated nitric acid at 0° C. The mixture was stirred at room temperature for 1 h, and poured into 20 mL of ice-water. It was basified with sodium carbonate, and extracted with two 30 mL portions of methylene chloride. The combined organic extracts were washed with 20 mL of brine, and concentrated. The residue was purified by preparative TLC eluting with 4% methanol in methylene chloride to give 0.021 g of compound 51. MS calcd for $C_{17}H_{20}N_5O_3S$=374.1; found m/z=374.1.

Method AG:

A mixture of 0.075 g (0.2 mmol) of compound 57, 0.11 g (2 mmol) of sodium methoxide in 3 mL of methanol in a sealed tube was heated at 80° C. for 50 h and cooled to room temperature. It was quenched with 30 mL of 95% methanol and concentrated. The residue was purified by preparative TLC eluting with 4% methanol in methylene chloride to give 0.05 g of compound 58. MS calcd for $C_{19}H_{19}N_4O_2S$=367.1; found m/z=367.1.

Method AH:

A mixture of 0.022 g (0.06 mmol) of compound 57, 0.02 g (0.2 mmol) of 1-methylpiperazine in 3 mL of ethanol in a sealed tube was heated at 120° C. for 90 h and cooled to room temperature. It was concentrated; the residue was purified by preparative TLC eluting with 10% methanol in methylene chloride plus 1% ammonium hydroxide to give 0.027 g of compound 59A. Calcd MS for $C_{23}H_{27}N_6OS$=435.2; found m/z=435.1.

Compounds 59B and 59C can be prepared analogously. Compounds 79 can be prepared analogously starting with chloropyridine 78.

| Cpd | Structure | Formula | MW | m/z Found (M + 1)+ |
|---|---|---|---|---|
| 59A | 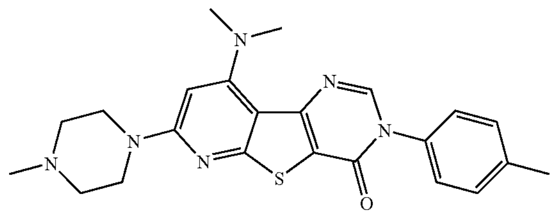 | $C_{23}H_{26}N_6OS$ | 434.6 | 435.1 |
| 59B | 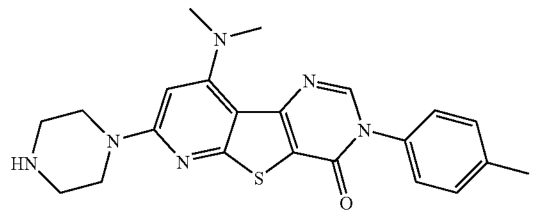 | $C_{22}H_{24}N_6OS$ | 420.5 | 421.1 |
| 59C | 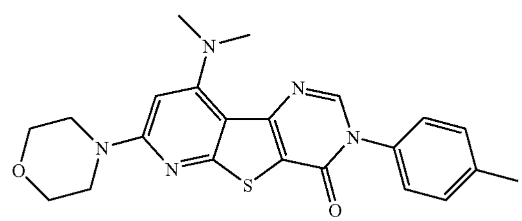 | $C_{22}H_{23}N_5O_2S$ | 421.5 | 422.1 |
| 79A | 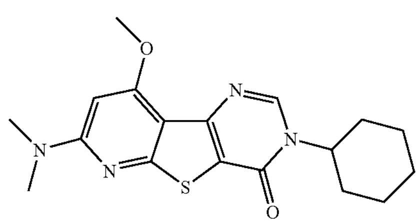 | $C_{18}H_{22}N_4O_2S$ | 358.5 | 359.1 |

Method AI:

A mixture of 0.092 g (0.3 mmol) of compound C18, 0.04 g (0.2 mmol) of 1-aminopiperidine and 0.1 mL of acetic acid in 5 mL of toluene was heated at reflux for 2 h and cooled to room temperature. It was concentrated; the residue was purified by preparative TLC eluting with 5% methanol in methylene chloride plus 1% ammonium hydroxide to give 0.083 g of compound 60A. MS calcd for $C_{16}H_{20}N_5OS$=330.1; found m/z=330.1.

The following compounds can be prepared analogously from the appropriate starting materials:
| Cpd | Structure | Formula | MW | m/z Found (M + 1)+ |
|---|---|---|---|---|
| 60A | 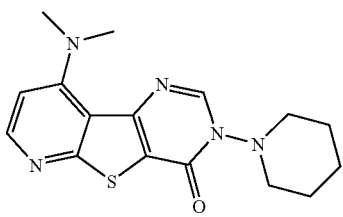 | C16H19N5OS | 329.4 | 330.1 |
| 60B | 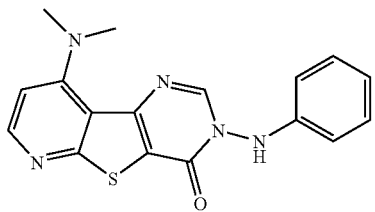 | C17H15N5OS | 337.4 | 338.1 |
| 60C | 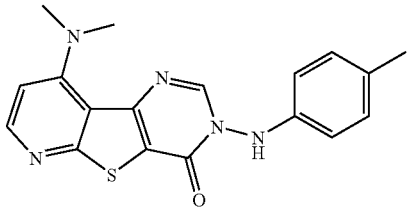 | C18H17N5OS | 351.4 | 352.1 |
| 60D | 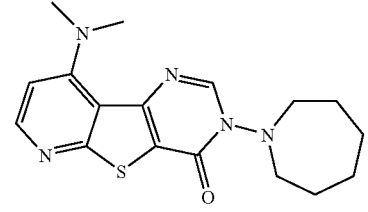 | C17H21N5OS | 343.4 | 344.2 |
| 60E | 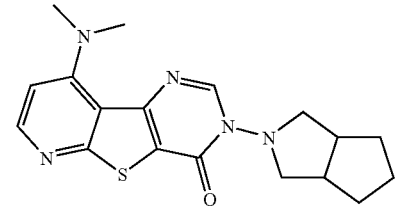 | C18H21N5OS | 355.5 | 356.1 |
| 60F | 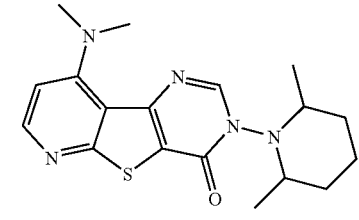 | C18H23N5OS | 357.5 | 358.1 |

-continued

| Cpd | Structure | Formula | MW | m/z Found (M + 1)+ |
|---|---|---|---|---|
| 60G | 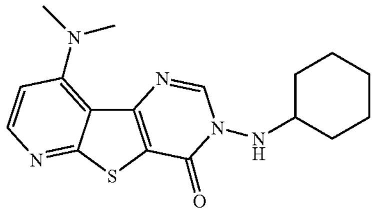 | C17H21N5OS | 343.4 | 344.1 |
| 60H | 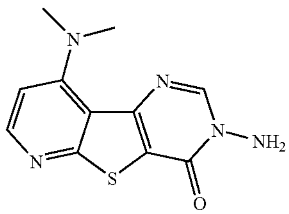 | C11H11N5OS | 261.3 | 262.1 |
| 60I | 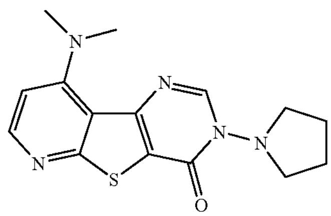 | C15H17N5OS | 315.4 | 316.1 |
| 60J | 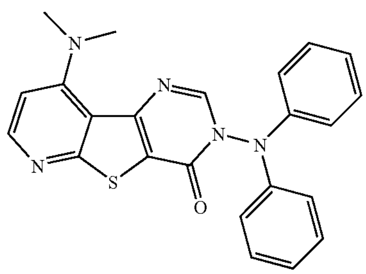 | C23H19N5OS | 413.5 | 414.1 |
| 60L | 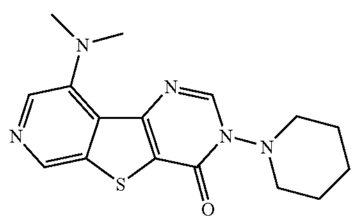 | C16H19N5OS | 329.4 | 330.1 |

The following compound can be prepared from compound 23 analogously.

| Cpd | Structure | Formula | MW | m/z Found (M + 1)+ |
|---|---|---|---|---|
| 60K | 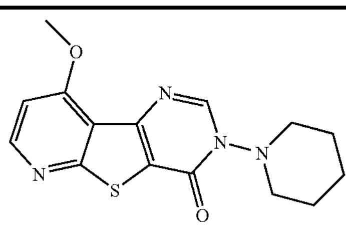 | C15H17N4O2S | 337.4 | 338.1 |

Method AJ:

A mixture of 0.037 g (0.1 mmol) of compound 28U, 0.1 mL of 37% formaldehyde and 0.05 g (0.23 mmol) of sodium triacetoxyborohydride in 2.5 mL of methylene chloride was stirred at room temperature for 18 h. It was purified by chromatography eluting with 1 to 7% methanol in methylene chloride plus 1% ammonium hydroxide to give 0.039 g of compound 61A. Calcd MS for $C_{20}H_{26}N_5OS=384.2$; found m/z=384.1.

Compound 61B could be prepared analogously:

Method AN:

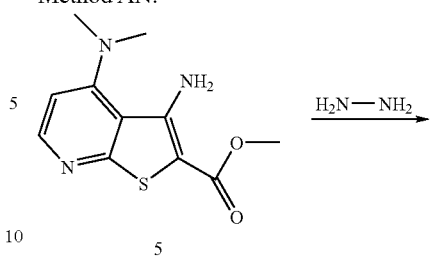

| Cpd | Structure | Formula | MW | m/z Found (M + 1)+ |
|---|---|---|---|---|
| 61A | 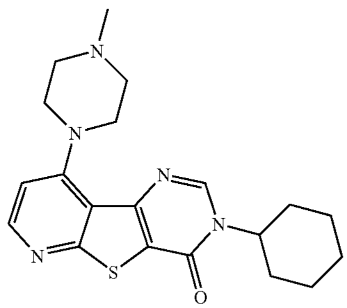 | $C_{20}H_{25}N_5OS$ | 383.5 | 384.1 |
| 61B | 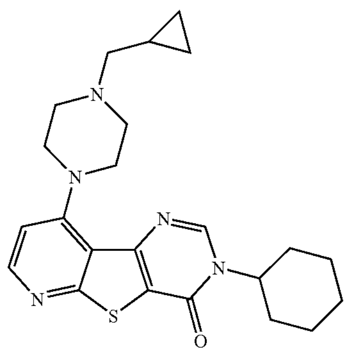 | $C_{23}H_{29}N_5O2S$ | 423.6 | 424.1 |

Method AK:

A mixture of 0.037 g (0.1 mmol) of compound 28U, 0.02 g (0.2 mmol) of acetic anhydride and 0.05 g (0.5 mmol) of triethylamine in 2 mL of methylene chloride was stirred at room temperature for 70 h. It was purified by chromatography eluting with 1 to 7% methanol in methylene chloride plus 1% ammonium hydroxide to give 0.037 g of compound 62. MS calcd for $C_{21}H_{26}N_5O_2S=412.2$; found m/z=412.2.

Method AL:

A mixture of 0.037 g (0.1 mmol) of compound 28U, 0.028 g (0.2 mmol) of methanesulfonyl chloride and 0.05 g (0.5 mmol) of triethylamine in 2 mL of methylene chloride was stirred at room temperature for 70 h. It was purified by chromatography eluting with 1 to 6% methanol in methylene chloride plus 1% ammonium hydroxide to give 0.036 g of compound 63. Calcd MS for $C_{20}H_{26}N_5O_3S_2=448.2$; found m/z=448.2.

Method AM:

A mixture of 0.037 g (0.1 mmol) of compound 28U, 0.027 g (0.2 mmol) of N,N-diethylaminocarbonyl chloride and 0.05 g (0.5 mmol) of triethylamine in 2 mL of methylene chloride was stirred at room temperature for 70 h. It was purified by chromatography eluting with 1 to 6% methanol in methylene chloride plus 1% ammonium hydroxide to give 0.036 g of compound 64. MS calcd for $C_{24}H_{33}N_6O_2S=469.2$; found m/z=469.3.

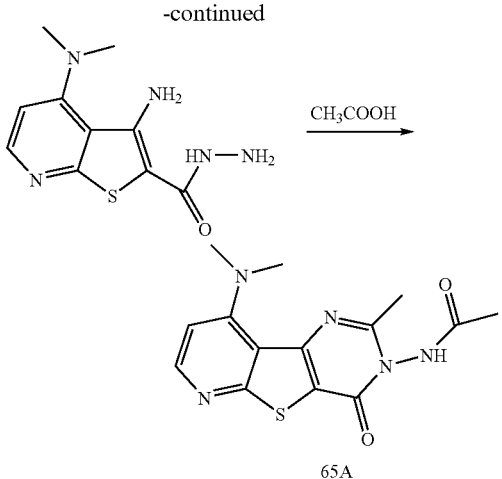

To a solution of 5 (0.2 g, 0.796 mmol) in ethanol (2 mL) was added hydrazine hydrate (0.5 mL, excess) and the mixture was heated at 100° C. in a sealed tube for 16 hours. The reaction mixture was cooled to room temperature and the precipitated hydrazide was isolated by filtration. The product was washed several times with pentane to intermediate hydrazide. $^1$H NMR (CDCl$_3$): δ 8.45 (d, 1H), 6.88 (d, 1H), 6.87 (s, 2H), 6.8 (s, 1H), 4.03 (s, 1H), 2.87 (s, 6H). MS calcd for C$_{10}$H$_{14}$N$_5$OS$^+$ m/z=252.09, found m/z=252.1

The hydrazide (0.1 g, 0.398 mmol) was dissolved in glacial acetic acid (10 mL) and heated at 100° C. for 48 h. The solvent was removed in vacuo and the product was isolated by column chromatography using 0-5% methanol in dichloromethane as eluent to afford compound 65A. $^1$H NMR (CDCl$_3$): δ 8.83 (s, 1H), 8.35 (d, 1H), 6.74 (d, 1H), 3.18 (s, 6H), 2.64 (s, 3H), 2.30 (s, 3H). MS calcd for C$_{14}$H16N$_5$O$_2$S$^+$=318.1, found m/z=318.1

The following compounds could be prepared analogously:

Method AO:

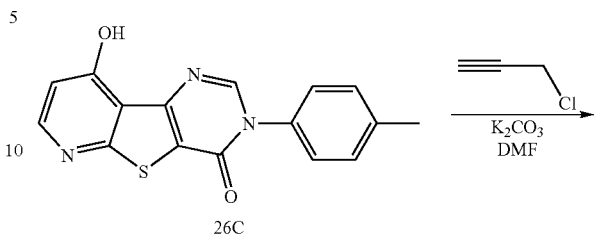

26C

| Cpd | Structure | Formula | MW | m/z Found (M + 1)$^+$ |
|---|---|---|---|---|
| 65A | 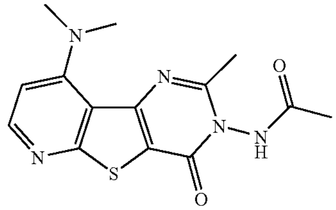 | C$_{14}$H$_{15}$N$_5$O$_2$S | 317.4 | 318.1 |
| 65B | 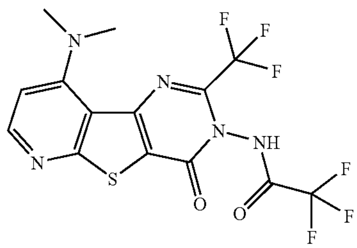 | C$_{14}$H$_9$F$_6$N$_5$O$_2$S | 425.3 | 426.1 |
| 65C | 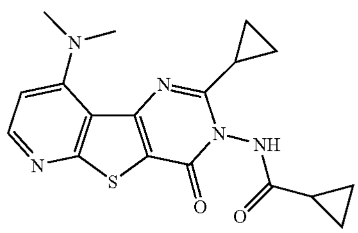 | C$_{18}$H$_{19}$N$_5$O$_2$S | 369.4 | 370.1 |
| 65D | 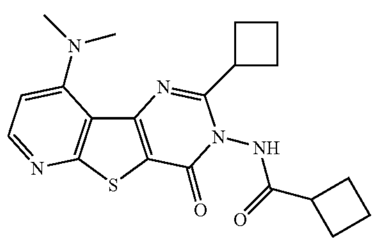 | C$_{20}$H$_{23}$N$_5$O$_2$S | 397.5 | 398.1 |
| 65E | 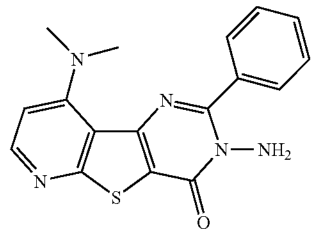 | C$_{17}$H$_{15}$N$_5$OS | 337.4 | 338.1 |

-continued

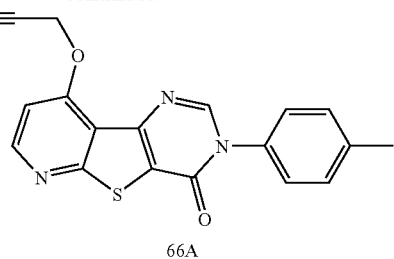
66A

Hydroxy pyridine 26C (0.05 g, 0.16 mmol) was dissolved in DMF (2 mL) and treated with $K_2CO_3$ (0.05 g, 0.36 mmol) followed by propargyl chloride (0.05 g, 0.67 mmol) and the reaction mixture was stirred at room temperature overnight. Water was added and the mixture was extracted with dichloromethane. The organic layer was dried and concentrated in vacuo. The product was isolated by silica gel chromatography eluting with 0-10% methanol in dichloromethane to give compound 66A. $^1$H NMR (CDCl$_3$): δ 8.68 (d, 1H), 8.34 (s, 1H), 7.33 (m, 4H), 7.11 (d, 1H), 5.10 (s, 2H), 2.65 (s, 1H), 2.45 (s, 3H). MS calcd. for $C_{19}H_{14}N_3O_2S^+$=348.1, found m/z=348.1

The following compounds could be prepared analogously:

| Cpd | Structure | Formula | MW | m/z Found $(M + 1)^+$ |
|---|---|---|---|---|
| 66A | 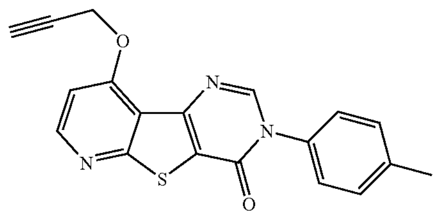 | $C_{19}H_{13}N_3O_2S$ | 347.4 | 348.1 |
| 66B | 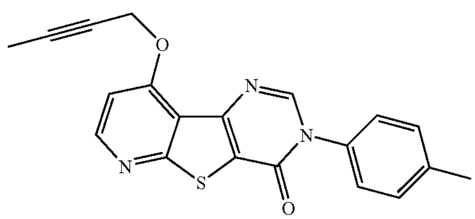 | $C_{20}H_{15}N_3O_2S$ | 361.4 | 362.1 |
| 66C | 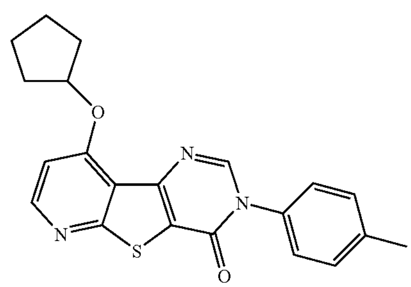 | $C_{21}H_{19}N_3O_2S$ | 377.5 | 378.2 |
| 66D | 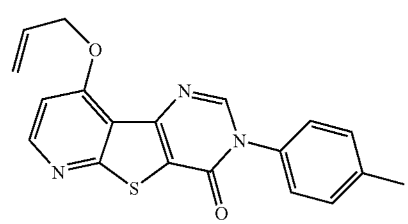 | $C_{19}H_{15}N_3O_2S$ | 349.4 | 350.2 |
| 66E | 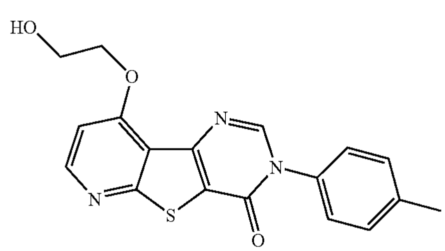 | $C_{18}H_{15}N_3O_3S$ | 353.4 | 354.1 |

Method AP:

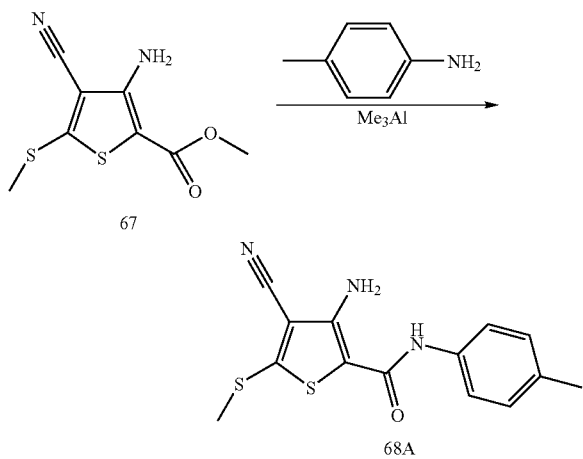

Method AR:

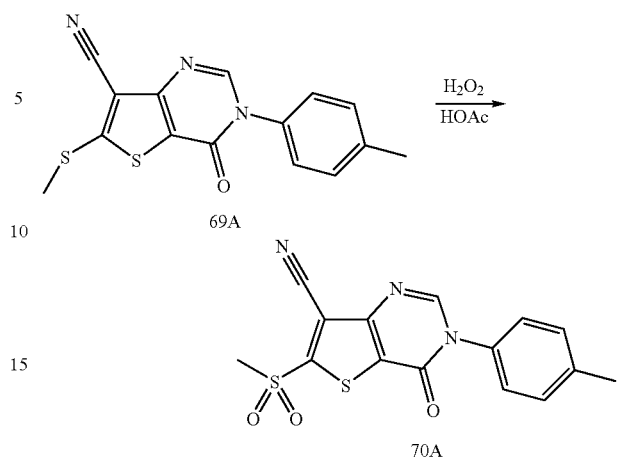

Compound 69A (2.5 g, 7.98 mmol) was dissolved in glacial acetic acid (50 mL) and treated with 10 mL 30% hydrogen peroxide. The reaction mixture was heated at 100° C. for 2 h. The reaction mixture was cooled to 0° C. and the precipitated sulfone 70A was washed several times with water and ether.

$^1$H NMR (CDCl$_3$): δ 8.70 (s, 1H), 7.42 (m, 4H), 3.66 (s, 3H), 2.40 (s, 3H). MS calcd. for $C_{15}H_{12}N_3O_3S_2{}^+$=346.03, found m/z=346.1

Method AS:

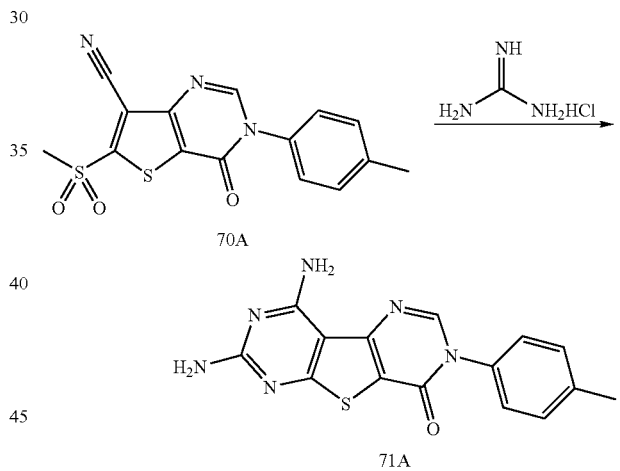

To a solution of p-toluidine (2.5 g, 0.0233 mol) in toluene (50 mL) was added trimethyl aluminum (2 M in THF, 12 mL) at 0° C. and the reaction was stirred for 10 minutes. Compound 67 (5 g, 0.0219 mol) was introduced to the above solution and the contents were heated at 120° C. for 16 h. The reaction mixture was cooled to room temperature and quenched by the addition of water (5 mL) and extracted several times with dichloromethane and ethyl acetate. The combined extracts were washed with Rochelle salt, dried and the solvents were removed in vacuo. The residue 68A was used for the next step without further purification.

$^1$H NMR (CDCl$_3$): δ 7.32 (d, 2H), 7.11 (d, 2H), 6.82 (s, 1H), 6.00 (s, 2H), 2.63 (s, 3H), 2.30 (s, 3H). MS calcd. for $C_{14}H_{14}N_3OS_2{}^+$=304.06, found m/z=304.1

Method AQ:

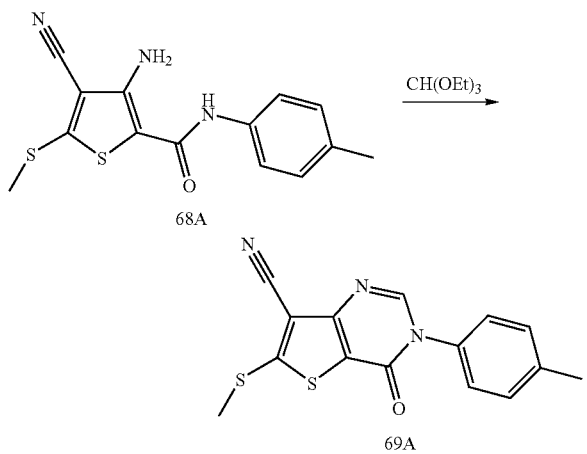

Solid 68A was suspended in triethyl orthoformate (50 mL) and treated with acetic anhydride (10 mL). The contents were heated at 100° C. for 7 hours. The solvent was removed in vacuo and the product was isolated by column chromatography using 0-5% MeOH/dichloromethane as eluent to give compound 69A. $^1$H NMR (CDCl$_3$): δ 8.52 (s, 1H), 7.40 (m, 4H), 2.87 (s, 3H), 2.39 (s, 3H). MS calcd. for $C_{15}H_{12}N_3OS_2{}^+$=314.04, found m/z=314.2

A solution of compound 70A (0.05 g, 0.1449 mmol) and guanidine hydrochloride (0.02 g, 0.2 mmol) in DMF was heated at 100° C. for 16 h. The solvent was removed in vacuo and the product was isolated by reverse phase HPLC using CH$_3$CN/H$_2$O as eluent to give compound 71A. $^1$H NMR (CDCl$_3$): δ 8.43 (s, 1H), 7.62 (s, 1H), 7.34 (d, 2H), 7.29 (d, 2H), 6.9 (s, 1H), 6.76 (s, 1H), 2.33 (s, 3H). MS calcd. for $C_{15}H_{13}N_6OS^+$=325.09, found m/z=325.1

Alternate Method T:

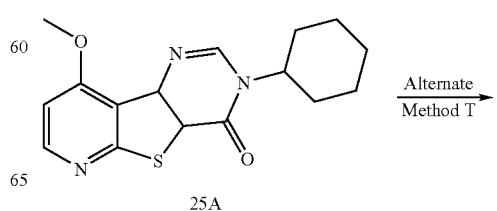

-continued

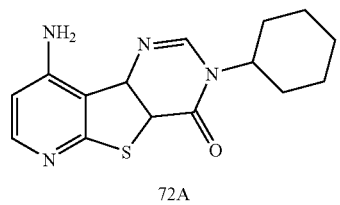

72A

To compound 25A (0.60 g, 0.0019 mol) was added ammonium acetate (5 g) and the contents were heated in a sealed tube at 150° C. for 16 hours. The reaction mixture was cooled to room temperature and water was added (50 mL). The precipitated solid was collected by filtration and dried over vacuum. The crude solid was purified by silica gel column chromatography using 5% methanol in dichloromethane as eluent to afford compound 72A. $^1$H NMR (CD$_3$OD) δ 8.56 (s, 1H), 8.11 (d, 1H), 6.64 (d, 1H), 3.31-3.29 (m, 3H), 1.99-1.36 (m, 10H). MS m/z calcd. for C$_{15}$H$_{16}$N$_4$OS$^+$=301.4; found m/z=301.2.

The following compounds could be prepared analogously:

| Cpd | Structure | Formula | MW | m/z Found (M + 1)$^+$ |
|---|---|---|---|---|
| 72A | 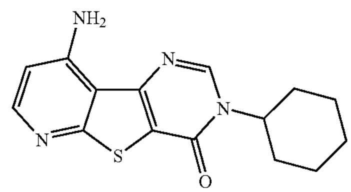 | C$_{15}$H$_{15}$N$_4$OS | 300.4 | 301.2 |
| 72B | 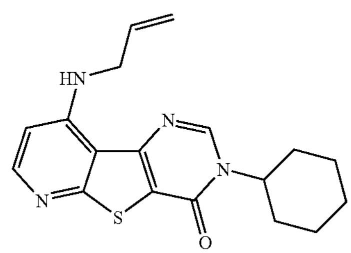 | C$_{18}$H$_{20}$N$_4$OS | 340.4 | 341.2 |
| 72C | 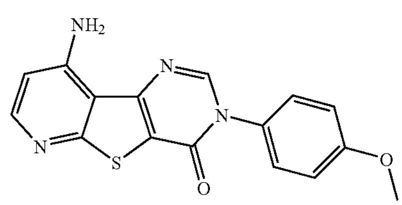 | C$_{16}$H$_{12}$N$_4$O$_2$S | 324.4 | 325.2 |
| 72D | 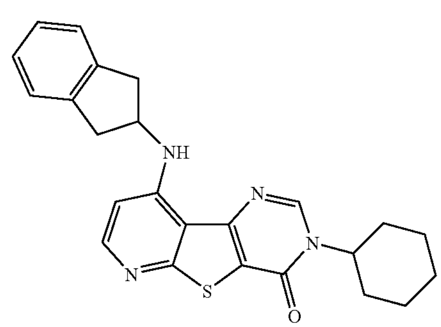 | C$_{24}$H$_{24}$N$_4$OS | 416.5 | 417.1 |

-continued
| Cpd | Structure | Formula | MW | m/z Found (M + 1)+ |
|---|---|---|---|---|
| 72E | 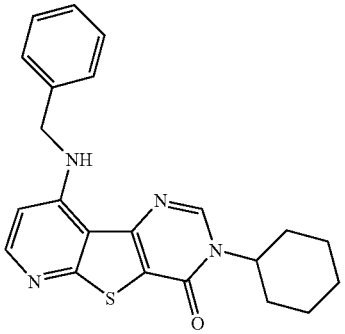 | C22H22N4OS | 390.5 | 391.1 |
| 72F | 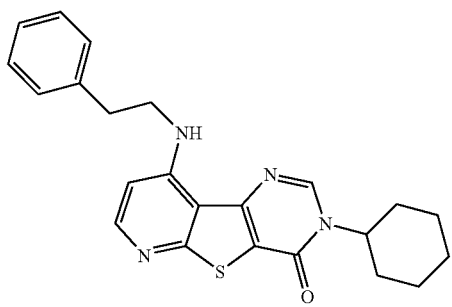 | C23H24N4OS | 404.5 | 405.1 |
| 72G | 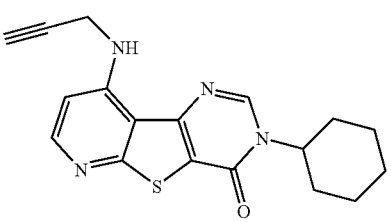 | C18H18N4OS | 338.4 | 339.1 |
| 72H | 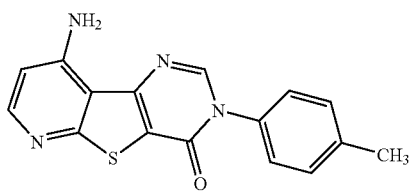 | C16H12N4OS | 308.4 | 309.0 |
| 72I | 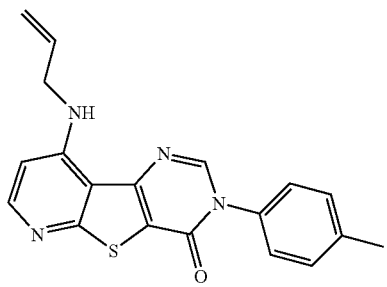 | C19H16N4OS | 348.4 | 349.1 |

Method AT:

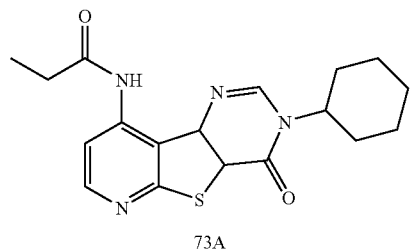

Compound 72A (0.010 g, 0.033 mmol) in dichloroethane (1 mL) was treated with triethylamine (0.025 mL, 0.018 mmol) and propionyl chloride (0.040 mL, 0.46 mmol) and allowed to stir at room temperature for 3 hours. The solvent was evaporated in vacuo and the resulting residue was purified by preparative TLC eluting with 5% methanol/94.5% dichloromethane/0.5% ammonia hydroxide to give compound 73A. $^1$H NMR (CDCl$_3$) δ 8.61 (d, 1H), 8.51 (d, 1H), 8.30 (s, 1H), 2.62-2.11 (q, 2H), 2.11-2.09 (d, 2H), 2.00-1.95 (d, 2H), 1.80-1.82 (d, 1H), 1.55-1.68 (m, 5H), 1.36-1.32 (t, 3H). MS m/z calcd. for $C_{18}H_{20}N_4O_2S^+$=357.4; found m/z=357.1.

The following compounds were prepared analogously:

| Cpd | Structure | Formula | MW | m/z Found (M + 1)$^+$ |
|---|---|---|---|---|
| 73A | 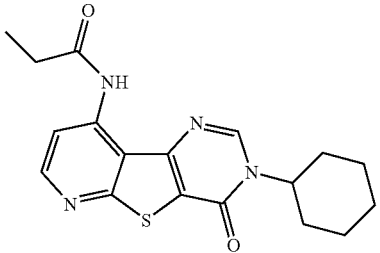 | $C_{18}H_{20}N_4O_2S$ | 356.4 | 357.1 |
| 73B | 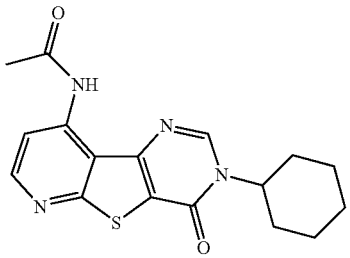 | $C_{17}H_{18}N_4O_2S$ | 342.4 | 343.2 |
| 73C | 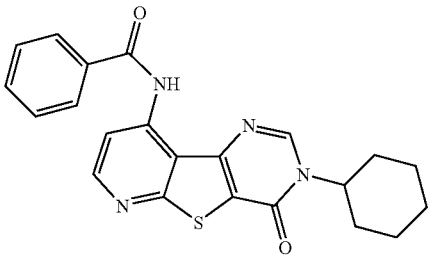 | $C_{22}H_{20}N_4O_2S$ | 404.5 | 405.1 |

| Cpd | Structure | Formula | MW | m/z Found (M + 1)+ |
|---|---|---|---|---|
| 73D | 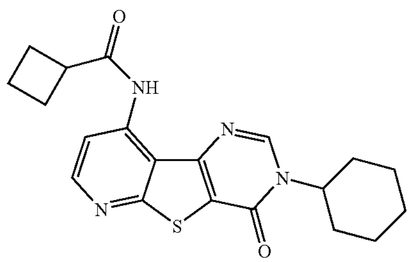 | C20H22N4O2S | 382.5 | 383.1 |
| 73E | 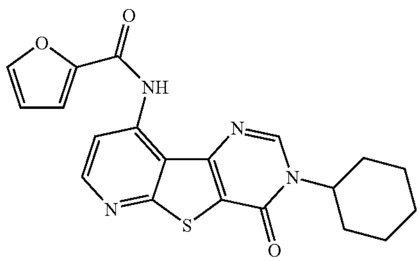 | C20H18N4O3S | 394.4 | 395.1 |
| 73F | 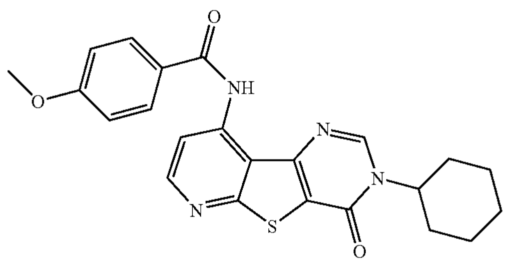 | C23H22N4O3S | 434.5 | 435.1 |
| 73G | 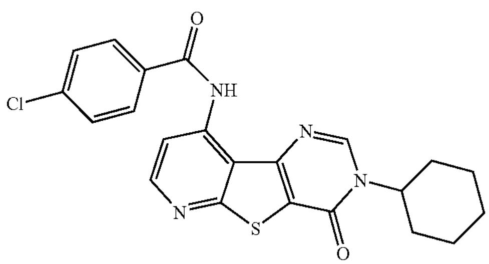 | C22H19ClN4O2S | 438.9 | 439.1 |

Method AU:

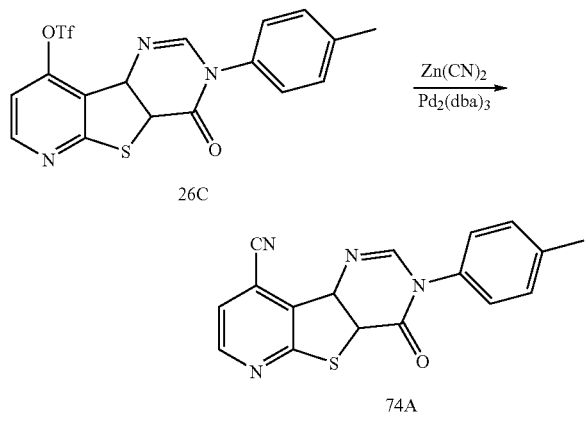

Compound 26C (0.020 g, 0.045 mmol) in DMF (1 mL) was treated with zinc cyanide (0.005 g, 0.043 mmol), dppf (0.005 g, 0.009 mmol), water (5 μL) followed by tris(dibenzylideneacetone)dipalladium(0) (0.004 g, 0.0044 mmol) under nitrogen atmosphere and the contents were heated in a sealed tube at 130° C. for 3 hours. The reaction mixture was passed through a short pad of celite and all the solvent was evaporated under reduced pressure. The residue was redissolved in dichloromethane (10 mL) and washed with water (10 mL). The organic layer was dried with sodium sulfate and evaporated under reduced pressure. The resulting residue was purified by preparative TLC eluting with dichloromethane to give compound 74A. $^1$H NMR (CDCl$_3$) δ 8.94 (d, 1H), 8.40 (s, 1H), 7.80 (d, 1H), 7.38-7.26 (m, 4H), 2.47 (s, 3H). MS m/z calcd. for C$_{17}$H$_{10}$N$_4$OS$^+$=319.4; found m/z 319.1.

Method AV:

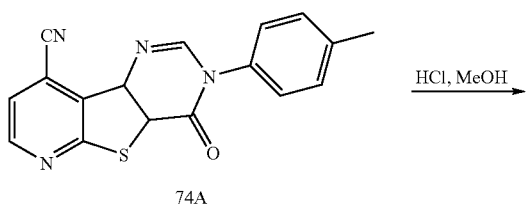

Compound 74A (0.025 g, 0.079 mmol) was suspended in methanol (10 mL) and HCl gas was bubbled for 5 minutes at 0° C. The reaction mixture was allowed to stir at room temperature for 20 minutes and then heated under reflux for 10 minutes. The reaction mixture was cooled and the solvent was removed in vacuo. The residue was redissolved in dichloromethane (20 mL) and washed with sodium bicarbonate solution (10 mL). The organic layer was dried with sodium sulfate and evaporated under reduced pressure. The resulting residue was purified by preparative TLC eluting with 2% methanol/97.5% dichloromethane/0.5% ammonia hydroxide to give compound 75A. $^1$H NMR (CDCl$_3$) δ 8.82 (s, 1H), 8.20 (s, 1H), 7.47 (d, 1H), 7.33-7.26 (m, 4H), 4.02 (s, 3H), 2.41 (s, 3H). MS m/z calcd. for $C_{18}H_{13}N_3O_3S^+$=352.4; found m/z=352.1.

Method AW:

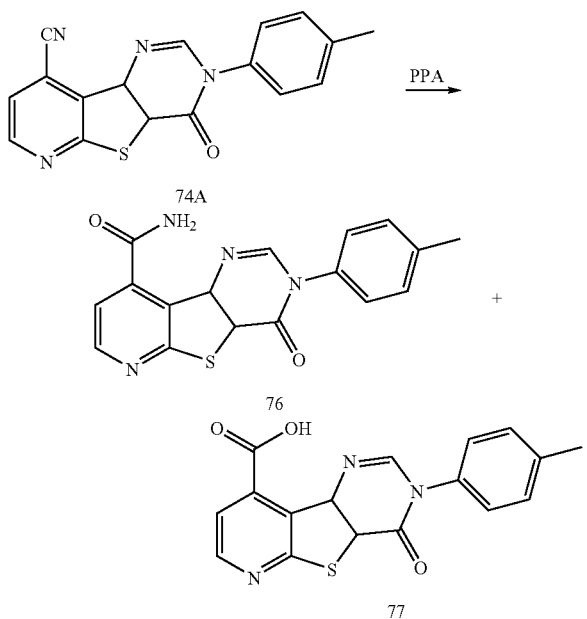

To compound 74A (0.038 g, 0.11 mmol) was added PPA (0.25 mL) and heated at 130° C. for 3 hours. The reaction mixture was cooled to room temperature and diluted with water (30 mL). The white precipitate was collected by filtration and dried under vacuum. The solid was dissolved in 1 mL of 60% DMSO/30% MeCN/10% formic acid and purified by BHK alpha C-18 column ramping from 95% water/5% MeCN/ 0.1% formic acid to 5% water/95% MeCN/0.1% formic acid over 12 minutes at flow rate of 20 mL/min to give compounds 76 and 77. Compound 76 $^1$H NMR (DMSO) δ 8.88-8.85 (m, 1H), 8.60 (d, 1H), 7.65-7.62 (m, 1H), 7.47-7.37 (m, 4H), 2.48 (s, 3H). MS m/z calcd. for $C_{17}H_{12}N_4O_2S^+$=337.4; found m/z=337.1. Compound 77 $^1$H NMR (DMSO) δ 8.88-8.85 (m, 1H), 8.60 (d, 1H), 7.66-7.62 (m, 1H), 7.47-7.37 (m, 4H), 2.48 (s, 3H). MS m/z calcd. for $C_{17}H_{11}N_3O_3S^+$=338.4; found m/z=338.1.

Method AX:

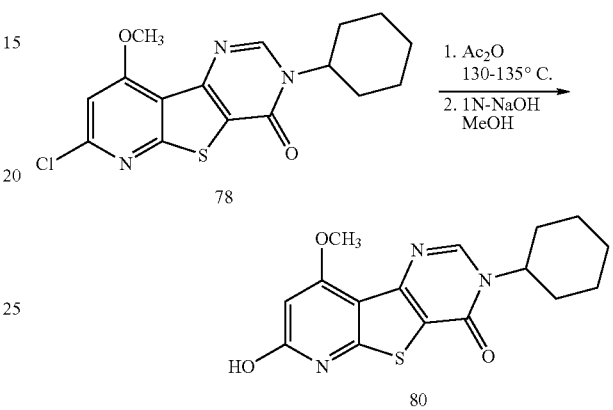

A stirring mixture of the compound 78 (0.400 g, 1.21 mmol) in acetic anhydride (5.00 mL) was heated at 130 to 135° C. for 3 hrs. The reaction was monitored by quenching a sample with saturated sodium bicarbonate and extracting with ethyl acetate. The ethyl acetate was analyzed by tlc (5% acetone/dichloromethane). Upon completion, the reaction was added in portions to a stirring ice cold saturated sodium bicarbonate solution (200 mL). The aqueous phase was partitioned with dichloromethane (150 mL). The organic extract was washed with saturated sodium bicarbonate (100 mL) and brine (50 mL). The dichloromethane was dried over anhydrous sodium sulfate and evaporated to a solid (0.440 g). This material was purified by flash column chromatography on silica gel (20 g) eluting with a solvent gradient 1% acetone/ dichloromethane to 5% acetone/dichloromethane yielded the resulting acetoxy analog as a solid (0.174 g, 40%). A stirring suspension of the acetate (0.100 g, 0.268 mmol) in MeOH (15 mL) at room temperature was treated with 1N-NaOH (1 mL) to give a solution. The solution was continued to be stirred for 20 min and was analyzed by tlc (5% acetone/dichloromethane). 1N—HCl (1 mL) was added dropwise to yield a precipitate. This was followed by the addition of saturated sodium bicarbonate until weakly basic (pH 8). The material was collected by vacuum filtration and was washed with water (1-2 mLi). The hydroxyl product was dried under vacuum to give compound 80 as a solid (0.075 g, 85%). MS m/z calcd. for $C_{16}H_{18}N_3O_3S^+$=332.1; found m/z=332.1.

Method AY:

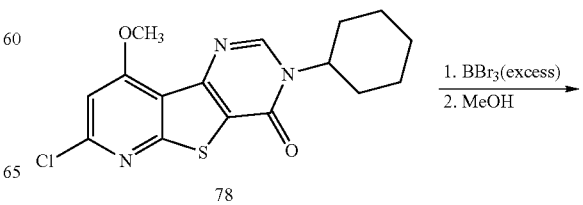

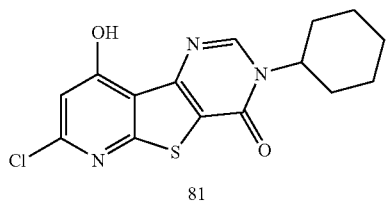

81

A solution of the methoxy compound 78 (0.101 g, 0.286 mmol) in dichloromethane (10 mL) at room temperature was treated with the dropwise addition of 1M boron tribromide in dichloromethane (1.15 mL, 1.15 mmol). The reaction was stirred at room temperature for 20 hrs. It was cooled to 0° C. and methanol (1 mL) was added dropwise. The solution was then stirred at room temperature for 20 min and then heated to reflux for 1 hr. The reaction was cooled and was concentrated under vacuum. The solid was stirred with water (3 mL) and made basic with saturated sodium bicarbonate. The solid was stirred and collected by filtration. This material was washed with water and dried under vacuum to give the hydroxyl product 81 as a powder (0.082 g, 85%). MS m/z calcd. for $C_{15}H_{15}ClN_3O_2S^+$=336.0 $(M+1)^+$; found m/z=336.0.

Method Q (Alternate 1):

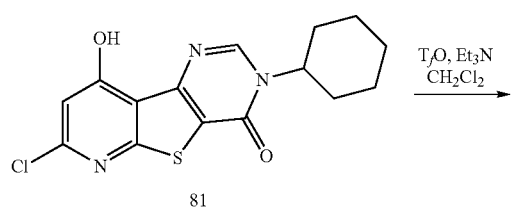

81

A stirring mixture of the hydroxyl compound 81 (0.050 g, 0.149 mmol) and triethylamine (0.030 g, 0.298 mmol) in dichloromethane (1.50 mL) was treated with the dropwise addition of triflic anhydride (0.084 g, 0.298 mmol) at room temperature. The reaction was stirred at room temperature for 4 hrs. The reaction was diluted with dichloromethane (5 mL) and was washed with saturated sodium bicarbonate (3 mL). The layers were separated and the water was washed with dichloromethane (5 mL). The combined dichloromethane extracts were dried over anhydrous sodium sulfate, filtered and evaporated to a semi-solid (0.097 g). This material was purified by flash column on silica gel (5 g) eluting with 100% dichloromethane to give the triflate 82 as a solid (0.059 g, 84%). MS m/z calcd. for $C_{16}H_{14}ClF_3N_3O_4S_2^+$=468.0 $(M+1)^+$; found m/z=467.9.

Method AZ:

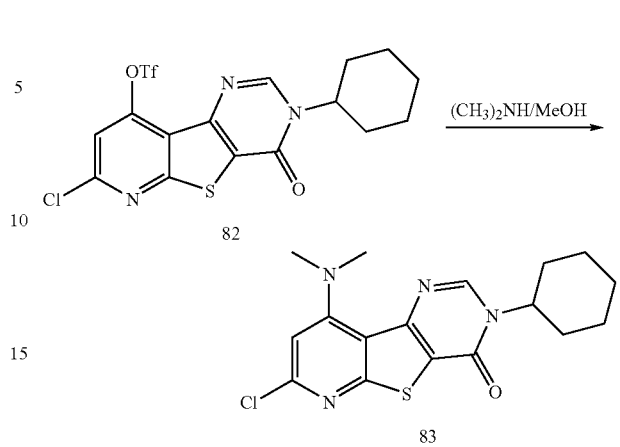

The 2M-dimethylamine/MeOH (0.555 mL, 1.11 mmol) was added to a stirring mixture of the triflate 82 (0.400 g, 0.855 mmol) in methanol (6 mL) at room temperature. The suspension was continued to be stirred at room temperature for 3 hrs. The methanol was evaporated under vacuum and the solid residue was partitioned between dichloromethane (70 mL) and saturated sodium bicarbonate (15 mL). The organic phase was washed with water (15 mL) and brine (15 mL). The dichloromethane solution was dried over anhydrous sodium sulfate and evaporated to a solid, which was purified by flash column chromatography on silica gel (10 g) eluting with a solvent gradient from 100% dichloromethane to 2% acetone/dichloromethane yielded the dimethylamino product 83 as a solid (0.200 g, 65%). MS calcd for $C_{17}H_{20}ClN_4OS^+$ m/z=363.1, found m/z=363.1.

Method AA (Alternate 1):

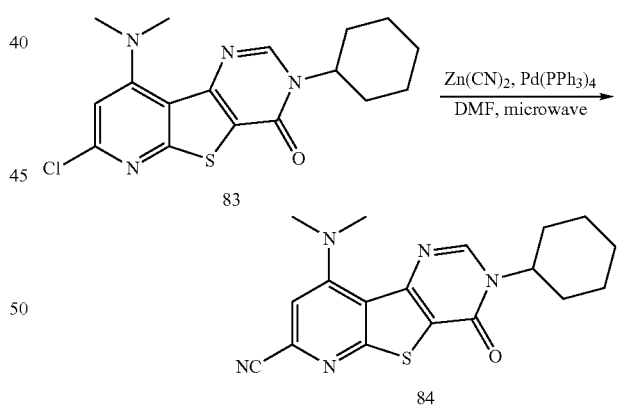

The chloro compound 83 (0.010 g, 0.028 mmol), zinc cyanide (0.0033 g, 0.028 mmol) and tetrakis(triphenylphosphine)palladium (0) (0.005 g, 0.0043 mmol) in DMF (1.50 mL) were subjected to microwave conditions at 180° C. for 10 min. The DMF was evaporated under vacuum. The solid residue obtained was washed several times with dichloromethane. The combined washings were evaporated to a solid (0.018 g). This crude product was purified by flash column chromatography on silica gel (1 g) eluting with 1% acetone/dichloromethane gave the cyano product 84 as a solid (0.009 g, 90%). MS calcd for $C_{18}H_{20}N_5OS^+$ m/z=354.1, found m/z=354.1.

Method AH (Alternate 1):

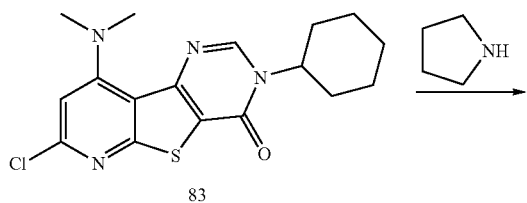

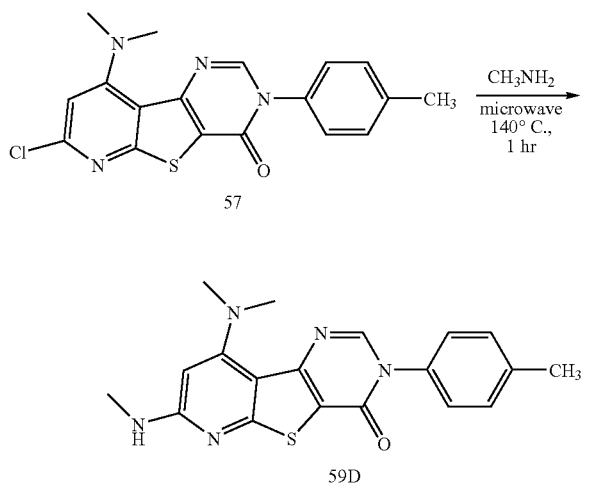

A stirring mixture of the chloro compound 83 (0.010 g, 0.028 mmol) and pyrrolidine (0.100 g, 1.41 mmol) in methanol (0.80 mL) was heated in an oil bath at 100° C. for 1.50 hrs. The reaction was cooled and concentrated under vacuum to give an oily residue (0.013 g). This material was purified by flash column chromatography on silica gel (1 g) eluting with a solvent gradient from 1% acetone/dichloromethane to 4% acetone/dichloromethane to give the pyrrolidinyl product 85 (0.009 g, 81%). MS calcd for $C_{21}H_{28}N_5OS^+$ m/z=398.2, found m/z=398.2.

Method AH (Alternate 2):

A stirring mixture of the chloro compound 57 (0.020 g, 0.054 mmol) in MeOH (1 mL)/2M methylamine in methanol (2.50 mL) was subjected to microwave conditions at 140° C. for 1 hr. The solvent was evaporated under vacuum. The residue was purified by flash column chromatography on silica gel (2 g) eluting with a solvent gradient from 100% dichloromethane to 8% acetone/dichloromethane to give the methylamino product 59D as a solid (0.014 g, 70%). MS calcd for $C_{19}H_{20}N_5OS^+$ m/z=366.1, found m/z=366.2.

Method AH (Alternate 3):

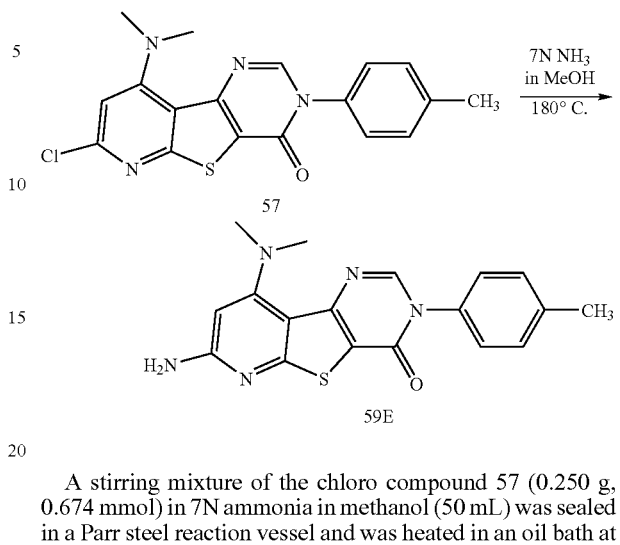

A stirring mixture of the chloro compound 57 (0.250 g, 0.674 mmol) in 7N ammonia in methanol (50 mL) was sealed in a Parr steel reaction vessel and was heated in an oil bath at 180-185° C. for 20 hrs. The reaction was cooled to room temperature concentrated under vacuum to a solid (0.269 g). The solid was purified by flash column chromatography on silica gel (25 g) eluting with a solvent gradient from 100% dichloromethane to 2% methanol in dichloromethane to give 59E as a solid (0.101 g, 43%). MS calcd for $C_{18}H_{18}N_5OS^+$ m/z=352.1, found m/z=352.1.

Method BA:

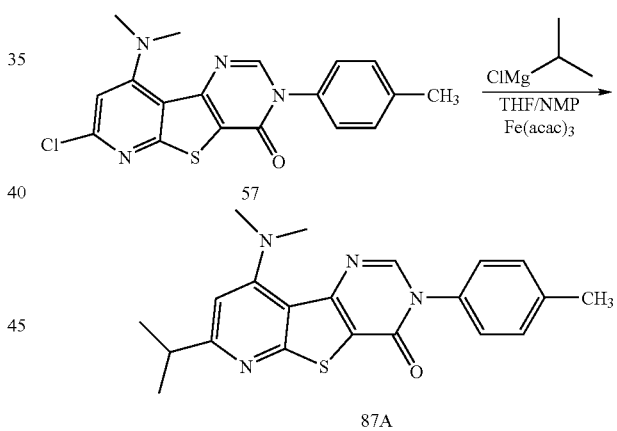

The chloro compound 57 (0.015 g, 0.040 mmol) was dissolved in THF (2 mL) containing NMP (0.20 mL) at room temperature. The iron (III) acetylacetonate (1.4 mg, 0.004 mmol) was added. An orange-red solution was obtained. The 2M isopropyl magnesium chloride in THF (0.034 mL, 0.068 mmol) was added dropwise. The reaction was stirred at room temperature for 40 min. The reaction was quenched with saturated sodium bicarbonate (1-2 mL) and was diluted with water (3-4 mL). It was extracted with ethyl acetate (15 mL). The ethyl acetate extracts were washed with brine (10 mL), dried over anhydrous sodium sulfate and evaporated to an oil. The crude material was purified by flash column chromatography on silica gel (10 g) eluting with a solvent gradient from 100% dichloromethane to 3% acetone in dichloromethane to give the isopropyl derivative 87A as a solid (0.003 g, 20%). The following compounds could be prepared analogously starting with 57 or with 83:

| Cpd | Structure | Formula | MW | m/z Found (M + 1)+ |
|---|---|---|---|---|
| 87A | 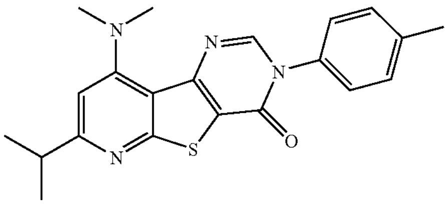 | C21H22N4OS | 378.5 | 379.1 |
| 87B | 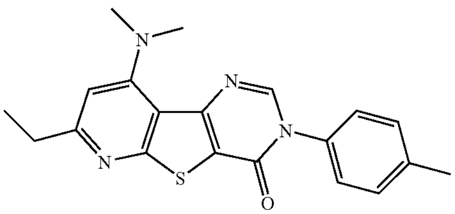 | C20H20N4OS | 364.5 | 365.1 |
| 87C | 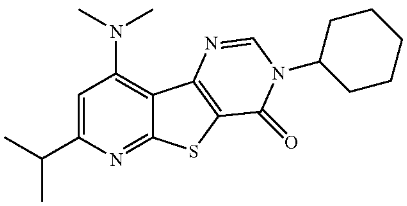 | C20H26N4OS | 370.5 | 371.2 |

Method BB:

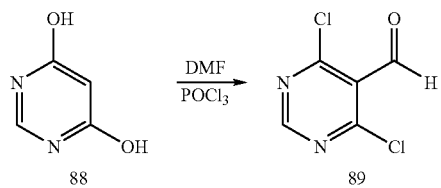

(Ref: A. Gomtsyan, S. Didomenico, C-H. Lee, M. A. Matulenko, K. Kim, E. A. Kowaluk, C. T. Wismer, J. Mikusa, H. Yu, K. Kohlhass, M. F. Jarvis, S. S. Bhagwat; *J. Med. Chem.*, 2002, 45, 3639-3648).

A mixture of DMF (32 mL) and POCl$_3$ (100 mL) at 0° C. was stirred for 1 h, treated with 4,6-dihydroxypyrimidine (25.0 g, 223 mmol), and stirred for 0.5 h at room temperature. The heterogeneous mixture was then heated to refluxed and stirred for 3 h. The reaction was cooled to room temperature and the resulting viscous, black liquid was poured onto ice water and extracted with diethyl ether (6×100 mL). The organic phase was subsequently washed with NaHCO$_3$, and water, dried over MgSO$_4$, and concentrated to give 89 as a yellow solid (20.0 g, 57% yield). $^1$H NMR (CDCl$_3$) δ 10.41 (s, 1H), 8.85 (s, 1H).

Method BC:

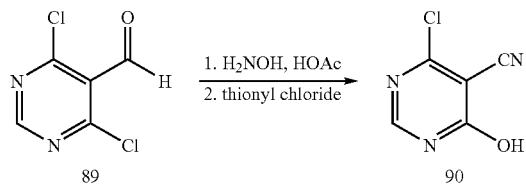

Step 1: (ref: A. A. Santilli, D. H. Kim, and S. V. Wanser; *J. Heterocyclic Chem.*, 1971, 8, 445-453) Aldehyde 89 (29.0 g, 164 mmoles) and hydroxylamine hydrochloride were dissolved in AcOH (0.83 M, 198 mL) by heating to reflux. The reaction was allowed to stir at reflux for 0.5 h and then cooled to room temperature. The solvents were removed in vacuo. The resulting yellow solids were taken up in H$_2$O and the product filtered off. The solid product was then dried under vacuum overnight to provide the oxime as a yellow solid which was dried under vacuum and used crude in the next step.

Step 2: (ref: A. A. Santilli, D. H. Kim, and S. V. Wanser; *J. Heterocyclic Chem.*, 1971, 8, 445-453) A solution of the above oxime (5.00 g, 26.0 mmol) in thionyl chloride (104 mL) was allowed to stir at reflux for 3 h. The reaction was cooled to room temperature and the solvents removed in vacuo. The resulting yellow-brown solid was dried under vacuum overnight to yield 90 (3.90 g, 96% yield). $^{13}$C NMR (DMSO-d$_6$) δ 164.7, 159.5, 152.3, 117.4, 102.2.

Method BD:

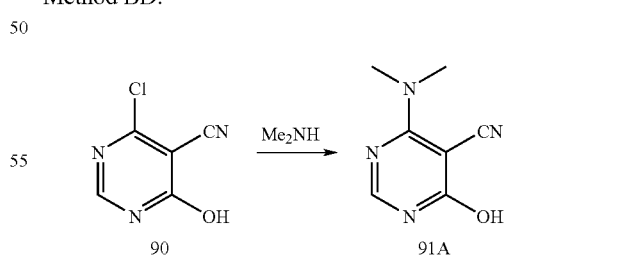

To a solution of compound 90 (3.00 g, 19.2 mmoles) in THF (65 mL) was added dimethyl amine (2.0 M in THF, 11.5 mL). The reaction mixture was stirred at reflux for 3 h and subsequently cooled to room temperature. The solvents were then removed in vacuo to provide 91A as a yellow-brown solid (3.0 g, 95% yield). Mass Spectrum (M$^{+1}$): m/z calcd. for C$_7$H$_8$N$_4$O$^+$=165.1, found m/z=165.2.

The following compounds were prepared analogously:

| Cpd | Structure | Formula | MW | m/z Found (M + 1)+ |
|---|---|---|---|---|
| 91A | 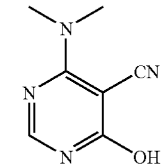 | $C_7H_7N_4O$ | 164.2 | 165.2 |
| 91B | 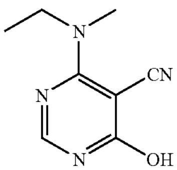 | $C_8H_{10}N_4O$ | 178.2 | 179.2 |
| 91C | 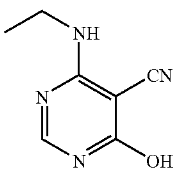 | $C_7H_8N_4O$ | 164.2 | 165.2 |
| 91D | 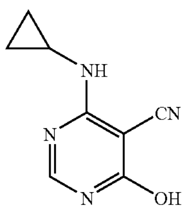 | $C_8H_8N_4O$ | 176.2 | 177.2 |
| 91E | 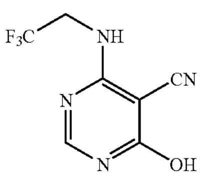 | $C_7H_5F_3N_4O$ | 218.1 | 219.1 |
| 91F | 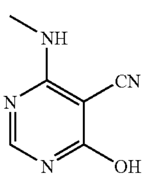 | $C_6H_6N_4O$ | 150.1 | 151.1 |

Method BE:

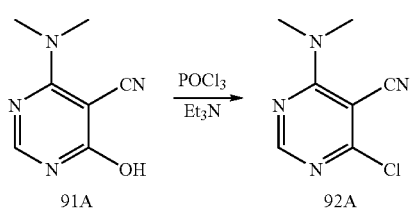

To compound 91A (3.00 g, 18.2 mmoles) was added POCl₃ (35.2 mL) and Et₃N (2.0 mL). The reaction mixture was stirred at reflux for 3 h and the solvents removed in vacuo. The resulting brown solid was quenched dropwise with water and basified with 40% aq. NaOH. The aqueous suspension was extracted with dichloromethane (100 ml×3), dried over MgSO₄ and concentrated in vacuo to provide 2.50 g of 92A as a brown solid. Mass Spectrum (M⁺¹): m/z calcd. for $C_7H_7N_4Cl^+$=183.1, found m/z=183.1.

The following compounds were prepared analogously:

| Cpd | Structure | Formula | MW | m/z Found (M + 1)+ |
|---|---|---|---|---|
| 92A | 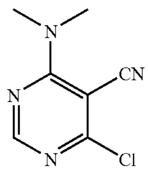 | $C_7H_6N_4Cl$ | 182.6 | 183.1 |
| 92B | 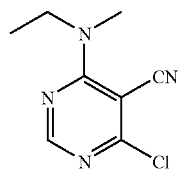 | $C_8H_9ClN_4$ | 196.6 | 197.2 |
| 92C | 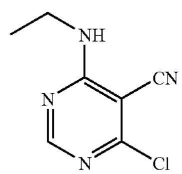 | $C_7H_7ClN_4$ | 182.6 | 182.1 |
| 92D | 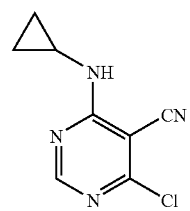 | $C_8H_7ClN_4$ | 194.6 | 195.1 |
| 92E | 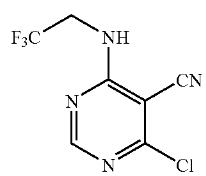 | $C_7H_4ClF_3N_4$ | 236.6 | 237.0 |
| 92F | 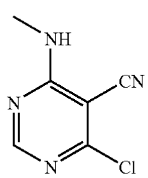 | $C_6H_5ClN_4$ | 168.6 | 169.1 |

Method BF:

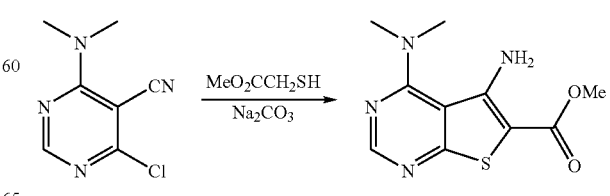

To a solution of 92A (2.50 g, 13.7 mmoles) in ethanol (70 mL) was added methylthioglycolate (1.65 mL, 15.0 mmoles) and sodium carbonate (2.20 g, 20.5 mmoles). The reaction was allowed to stir at reflux for 3 h and cooled to room temperature. The solvents were removed in vacuo. The resulting solids were taken up in H$_2$O and filtered to yield 93A as a yellow solid (3.10 g, 90% yield). $^1$H NMR (CDCl$_3$) δ 8.56 (s, 1H), 6.23 (bs, 2H), 3.83 (s, 3H), 3.03 (s, 6H).

The following compounds were prepared analogously:

| Cpd | Structure | Formula | MW | m/z Found (M + 1)$^+$ |
|---|---|---|---|---|
| 93A | 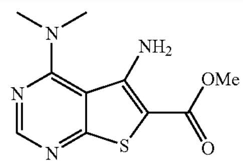 | C$_{10}$H$_{12}$N$_4$O$_2$S | 252.3 | 253.1 |
| 93B | 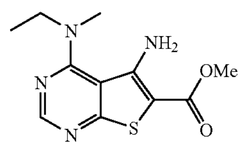 | C$_{11}$H$_{14}$N$_4$O$_2$S | 266.3 | 267.2 |
| 93C | 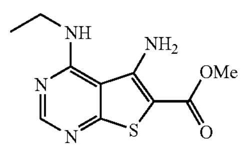 | C$_{10}$H$_{12}$N$_4$O$_2$S | 252.3 | 253.2 |
| 93D | 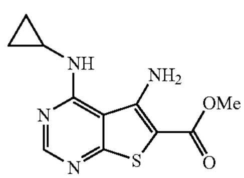 | C$_{11}$H$_{12}$N$_4$O$_2$S | 264.3 | 265.2 |
| 93E | 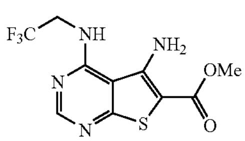 | C$_{10}$H$_9$F$_3$N$_4$OS | 306.3 | 307.1 |
| 93F | | C$_9$H$_{10}$N$_4$O$_2$S | 238.3 | 239.1 |

Method BG:

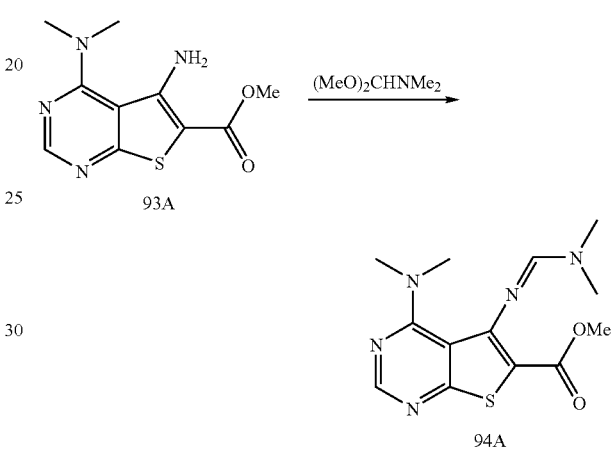

A solution of 93A (3.10 g, 12.3 mmoles), and N,N-dimethylformamide dimethyl acetal (8.21 mL, 61.3 mmoles) in abs. EtOH (13 ml) was allowed to stir at reflux for 3 h. The solvents were removed in vacuo and the resulting solids triturated with boiling ethanol to give 94A as a yellow solid (2.0 g, 53% yield). $^1$H NMR (CDCl$_3$) δ 8.38 (s, 1H), 7.35 (s, 1H), 3.74 (s, 3H), 3.17 (s, 6H), 3.10 (s, 3H), 3.02 (s, 3H).

The following compounds were prepared analogously from compounds 93:

| Cpd | Structure | Formula | MW | m/z Found (M + 1)$^+$ |
|---|---|---|---|---|
| 94A | 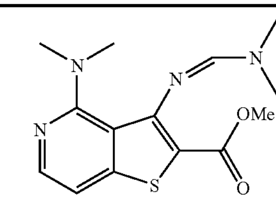 | C13H17N5O2S | 307.4 | 308.1 |
| 94B | 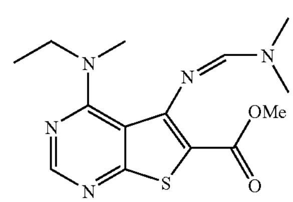 | C$_{14}$H$_{19}$N$_5$O$_2$S | 321.4 | 322.2 |

-continued

| Cpd | Structure | Formula | MW | m/z Found (M + 1)+ |
|---|---|---|---|---|
| 96A | 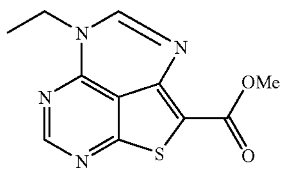 | $C_{11}H_{10}N_4O_2S$ | 262.3 | 263.1 |
| 96B | 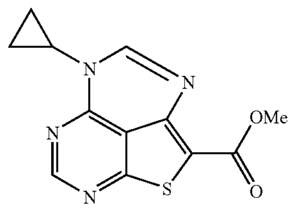 | $C_{12}H_{10}N_4O_2S$ | 274.3 | 275.1 |
| 94C | 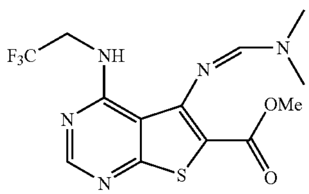 | $C_{13}H_{14}F_3N_5O_2S$ | 361.3 | 362.0 |
| 96C | 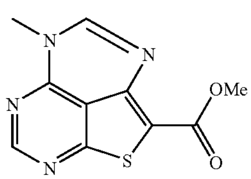 | $C_{10}H_8N_4O_2S$ | 248.3 | 249.1 |
| 96D | 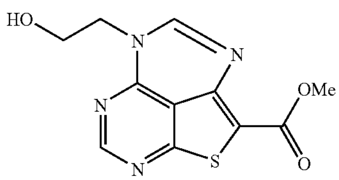 | $C_{11}H_{10}N_4O_3S$ | 278.3 | 279.1 |

Method F (Alternate 3):

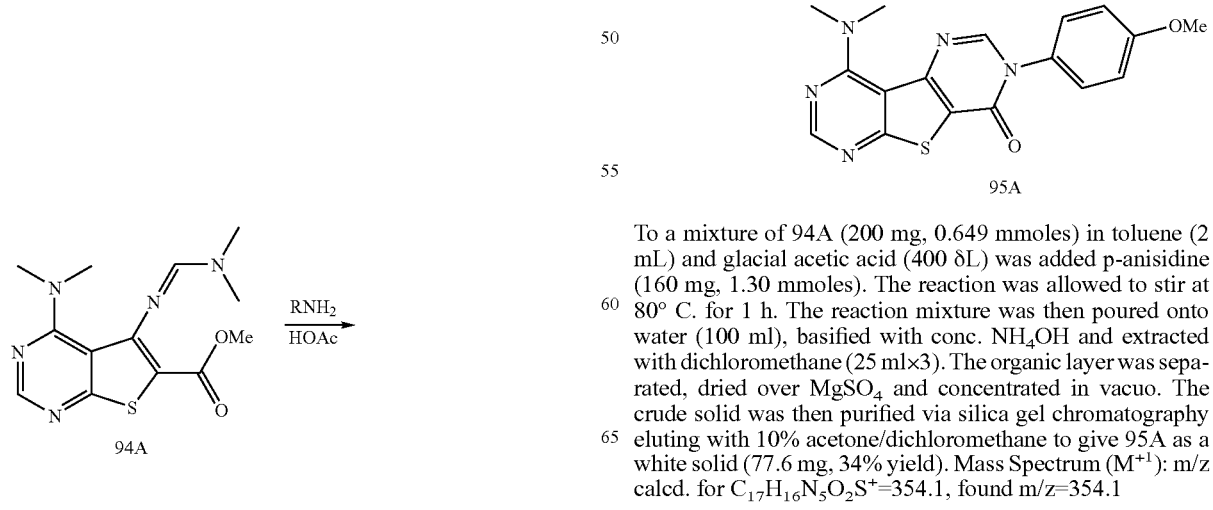

To a mixture of 94A (200 mg, 0.649 mmoles) in toluene (2 mL) and glacial acetic acid (400 δL) was added p-anisidine (160 mg, 1.30 mmoles). The reaction was allowed to stir at 80° C. for 1 h. The reaction mixture was then poured onto water (100 ml), basified with conc. NH$_4$OH and extracted with dichloromethane (25 ml×3). The organic layer was separated, dried over MgSO$_4$ and concentrated in vacuo. The crude solid was then purified via silica gel chromatography eluting with 10% acetone/dichloromethane to give 95A as a white solid (77.6 mg, 34% yield). Mass Spectrum (M$^{+1}$): m/z calcd. for $C_{17}H_{16}N_5O_2S^+$=354.1, found m/z=354.1

The following compounds could be prepared analogously from either 94 or 96

| Cpd | Structure | Formula | MW | m/z Found (M + 1)+ |
|---|---|---|---|---|
| 95A | 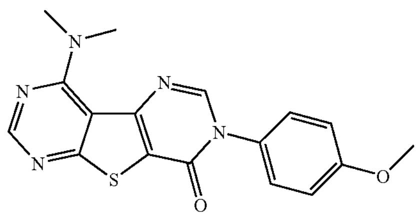 | C₁₇H₁₅N₅O₂S | 353.4 | 354.1 |
| 95B | 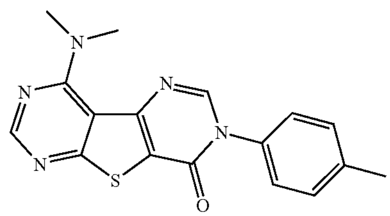 | C₁₇H₁₅N₅OS | 337.4 | 338.1 |
| 95C | 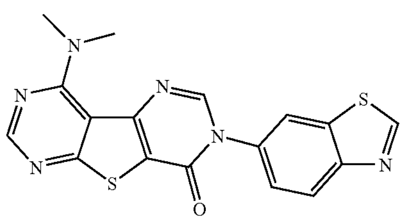 | C₁₇H₁₂N₆OS₂ | 380.4 | 381.1 |
| 95D | 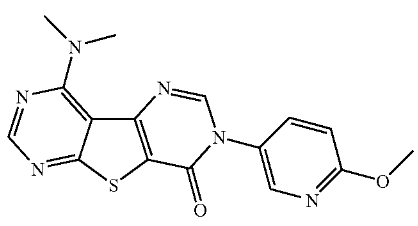 | C₁₆H₁₄N₆O₂S | 354.4 | 355.2 |
| 95E | 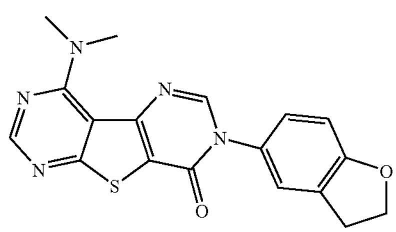 | C₁₈H₁₅N₅O₂S | 365.4 | 366.2 |
| 95F | 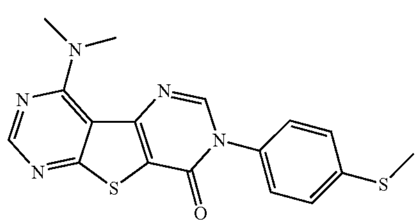 | C₁₇H₁₅N₅OS₂ | 369.5 | 370.1 |

| Cpd | Structure | Formula | MW | m/z Found (M + 1)+ |
|---|---|---|---|---|
| 95G | 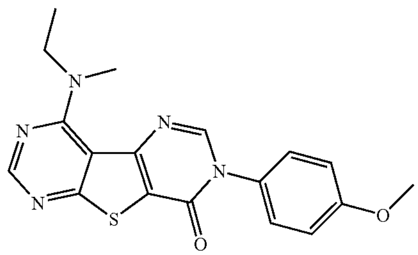 | C18H17N5O2S | 367.4 | 368.1 |
| 95H | 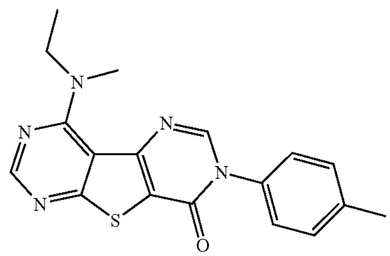 | C18H17N5OS | 351.4 | 352.1 |
| 95I | 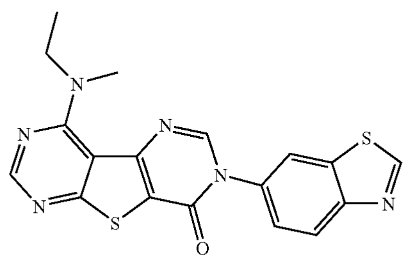 | C18H14N6OS2 | 394.5 | 395.1 |
| 95J | 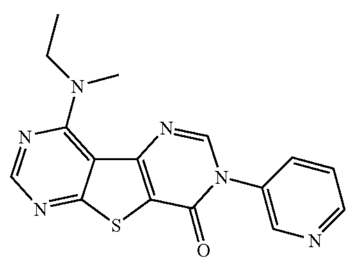 | C15H12N6OS | 324.4 | 325.1 |
| 95K | 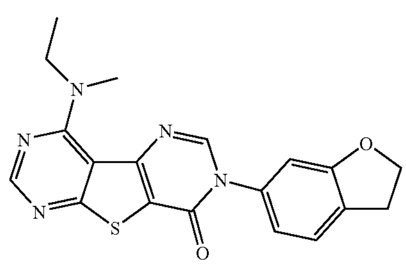 | C19H17N5O2S | 379.4 | 380.1 |
| 95L | 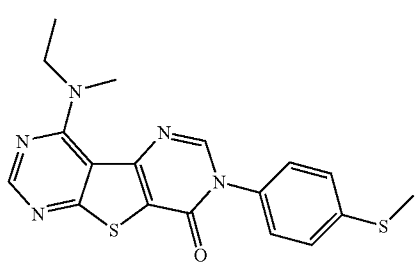 | C18H17N5OS2 | 383.5 | 384.1 |

-continued

| Cpd | Structure | Formula | MW | m/z Found (M + 1)+ |
|---|---|---|---|---|
| 95M | 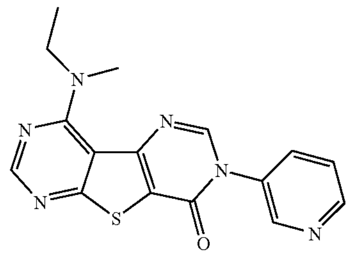 | C₁₆H₁₄N₆OS | 338.4 | 339.1 |
| 95N | 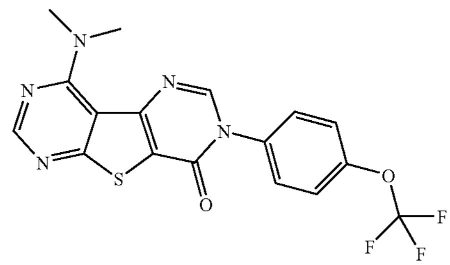 | C₁₇H₁₂F₃N₅O₂S | 407.4 | 408.1 |
| 95O | 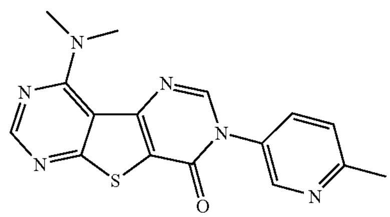 | C₁₆H₁₄N₆OS | 338.4 | 339.1 |
| 95P | 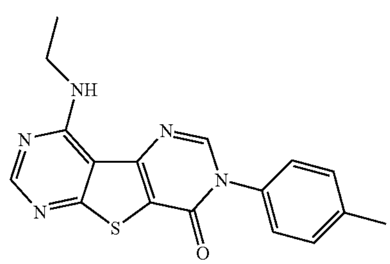 | C₁₇H₁₅N₅OS | 337.4 | 338.1 |
| 95Q | 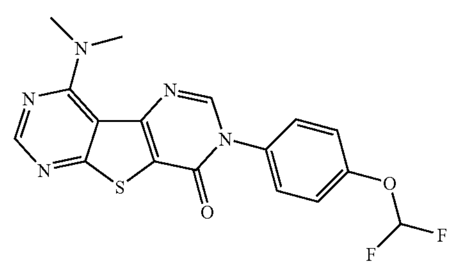 | C₁₇H₁₃F₂N₅O₂S | 389.4 | 390.2 |
| 95R | 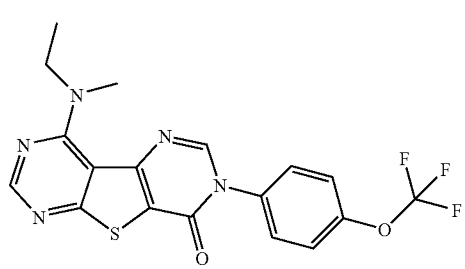 | C₁₈H₁₄F₃N₅O₂S | 421.4 | 422.2 |

-continued

| Cpd | Structure | Formula | MW | m/z Found (M + 1)+ |
|---|---|---|---|---|
| 95S | 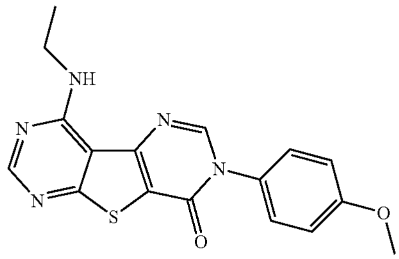 | C17H15N5O2S | 353.4 | 354.2 |
| 95T | 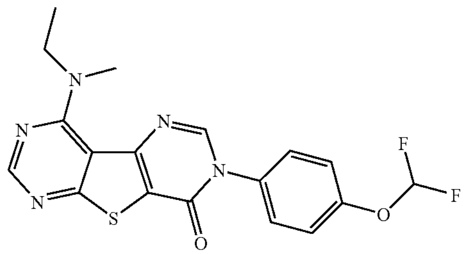 | C18H15F2N5O2S | 403.4 | 404.1 |
| 95U | 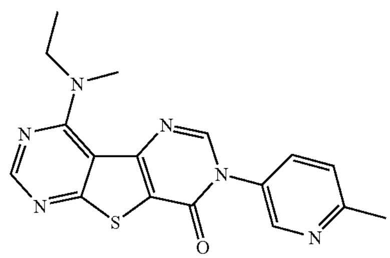 | C17H16N6OS | 352.4 | 353.1 |
| 95V | 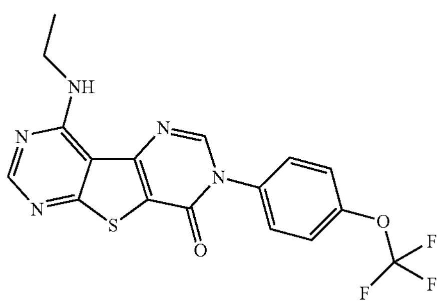 | C17H12F3N5O2S | 407.4 | 408.2 |
| 95W | 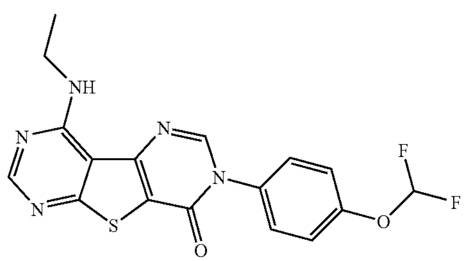 | C17H13F2N5O2S | 389.4 | 390.1 |
| 95X | 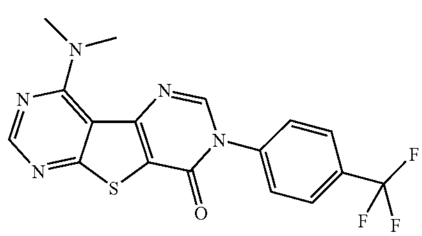 | C17H12F3N5OS | 391.4 | 392.2 |

| Cpd | Structure | Formula | MW | m/z Found (M + 1)+ |
|---|---|---|---|---|
| 95Y | 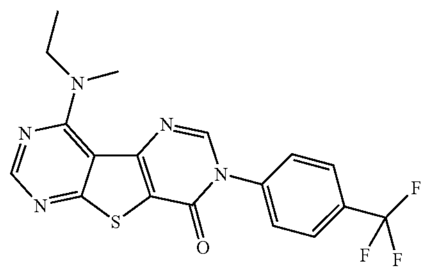 | C₁₈H₁₄F₃N₅OS | 405.4 | 406.2 |
| 95Z | 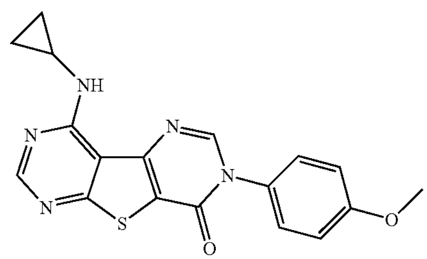 | C₁₈H₁₅N₅O₂S | 365.4 | 366.1 |
| 95AA | 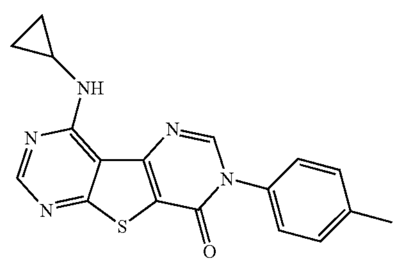 | C₁₈H₁₅N₅OS | 349.4 | 350.1 |
| 95AB | 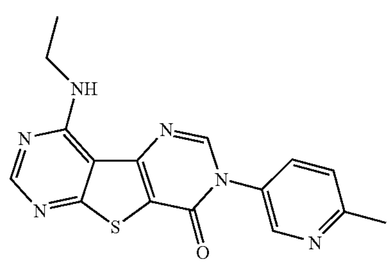 | C₁₆H₁₄N₆OS | 338.4 | 339.1 |
| 95AC | 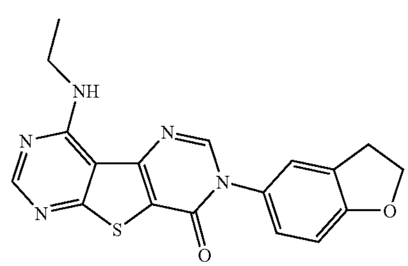 | C₁₈H₁₅N₅O₂S | 365.4 | 366.1 |
| 95AD | 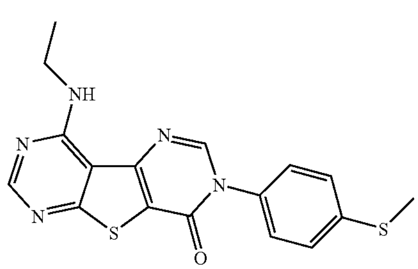 | C₁₇H₁₅N₅OS₂ | 369.5 | 370.1 |

-continued

| Cpd | Structure | Formula | MW | m/z Found (M + 1)+ |
|---|---|---|---|---|
| 95AE | 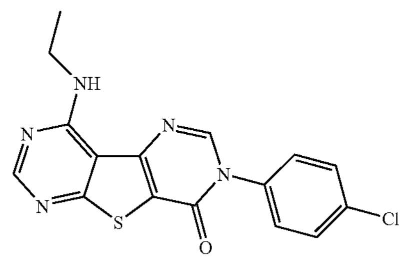 | $C_{16}H_{12}ClN_5OS$ | 357.8 | 358.2 |
| 95AF | 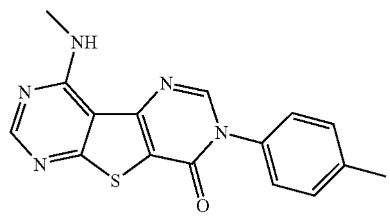 | $C_{16}H_{13}N_5OS$ | 323.4 | 324.2 |
| 95AG | 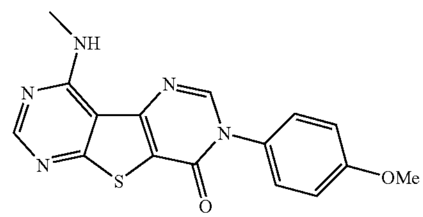 | $C_{16}H_{13}N_5O_2S$ | 339.4 | 340.1 |
| 95AH | 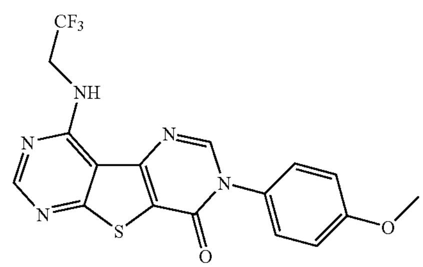 | $C_{17}H_{12}F_3N_5O_2S$ | 407.4 | 408.2 |
| 95AI | 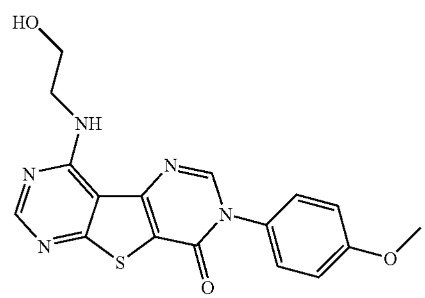 | $C_{17}H_{15}N_5O_3S$ | 369.4 | 370.2 |
| 95AJ | 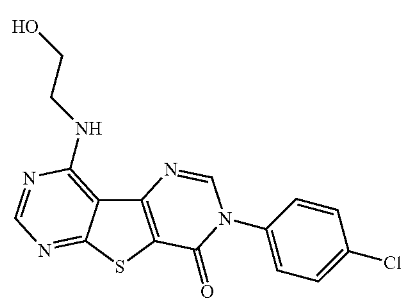 | $C_{16}H_{12}ClN_5O_2S$ | 373.8 | 374.2 |

| Cpd | Structure | Formula | MW | m/z Found (M + 1)+ |
|---|---|---|---|---|
| 95AK | 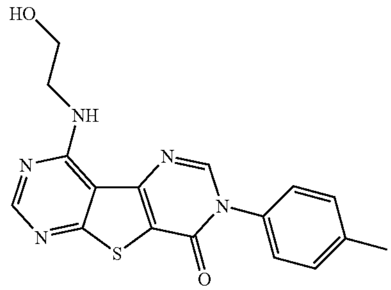 | $C_{17}H_{15}N_5O_2S$ | 353.4 | 354.2 |
| 95AL | 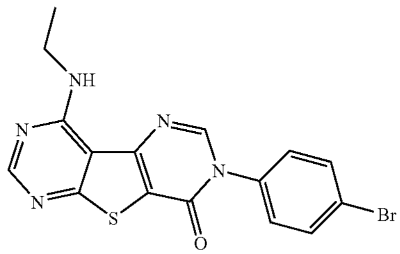 | $C_{16}H_{12}BrN_5OS$ | 402.3 | 402.2 |
| 95AM | 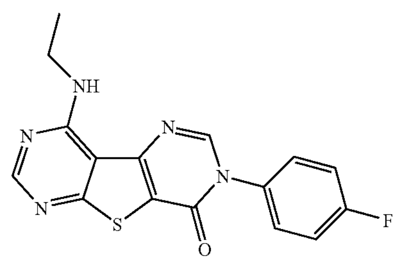 | $C_{16}H_{12}FN_5OS$ | 341.4 | 342.1 |
| 95AN | 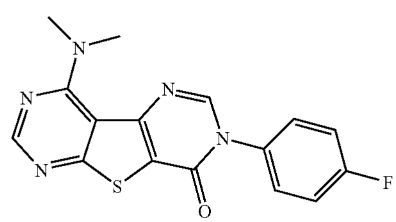 | $C_{16}H_{12}FN_5OS$ | 341.4 | 342.1 |

Method BG:

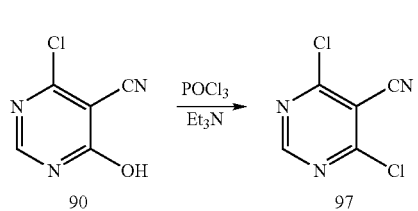

To compound 90 (2.50 g, 16.0 mmoles) was added POCl$_3$ (31 mL) and Et$_3$N (2.0 mL). The reaction mixture was stirred at reflux for 3 h and the solvents removed in vacuo The resulting brown solid was quenched dropwise with water and basified with 40% aq. NaOH. The aqueous suspension was extracted with dichloromethane (100 ml×3), dried over MgSO$_4$ and concentrated in vacuo to provide 2.64 g of 97 as a brown solid. Mass Spectrum (M$^{+1}$): m/z calcd. for C$_7$H$_7$N$_4$Cl$^+$=183.1, found m/z=183.1.

Method BH:

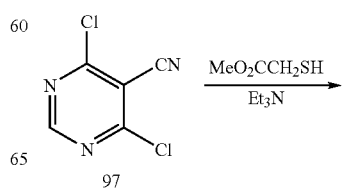

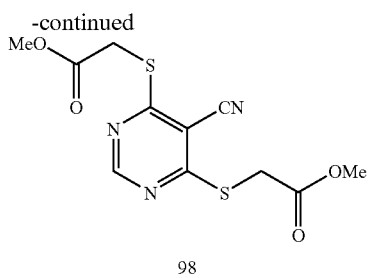

Ref: J. Clark, M. S. Shahhet, D. Korakas, G. Varvounis; *J. Heterocyclic Chem.,* 1993, 30, 1065-1072

To compound 97 (100 mg, 0.58 mmols) and methyl thioglycolate (127 □L, 1.16 mmols) in THF (2.5 mL) was added Et$_3$N (162 δ L, 1.16 mmols). The reaction immediately formed yellow precipitate and was allowed to stir for 10 min. at room temperature. The solvents were subsequently removed in vacuo and the resulting yellow solid taken up in a minimum amount of H$_2$O. The aqueous suspension was stirred for 5 min. and room temperature and filtered to yield 150 mg of 98 as a yellow solid. Mass Spectrum (M$^{+1}$): m/z calcd. for C$_{11}$H$_{11}$N$_3$O$_4$S$_2^+$=314.0, found m/z=314.0.

Method BI:

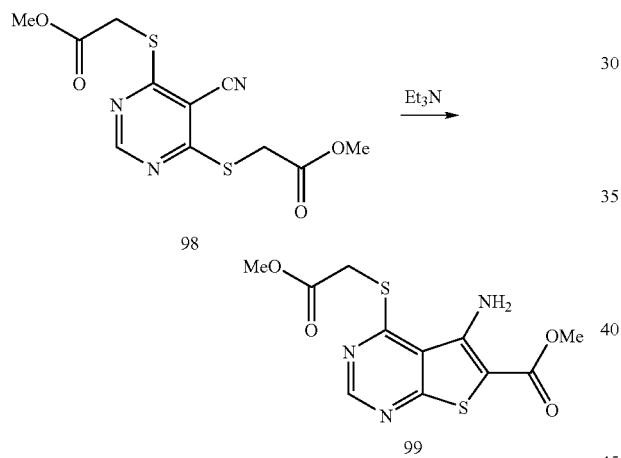

Ref: J. Clark, M. S. Shahhet, D. Korakas, G. Varvounis; *J. Heterocyclic Chem.,* 1993, 30, 1065-1072

To compound 98 (156 mg, 0.50 mmols) in toluene (3.1 mL) was added Et$_3$N (80 μL, 0.55 mmols). The reaction was stirred at reflux for 4 hours. The mixture was subsequently cooled to room temperature and the solvents removed in vacuo to provide 150 mg of 99 as a yellow solid. $^1$H NMR (CDCl$_3$) δ 8.71 (s, 1H), 6.43 (bs, 2H), 4.17 (s, 2H), 3.84 (s, 3H), 3.74 (s, 3H).

Method BJ:

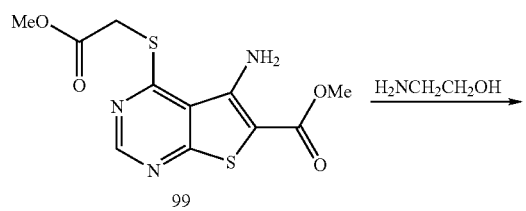

To compound 99 (1.34 g, 4.27 mmols) in methanol (14.5 mL) was added ethanol amine (7.0 mL, 113 mmols). The reaction was stirred at reflux for 0.5 h. The mixture was cooled to room temperature and the solvents removed in vacuo. The resulting residue was taken up in 1:1 dichloromethane:water (50 mL). The aqueous layer was extracted with dichloromethane (3×25 mL). The organic layers were combined, dried with MgSO$_4$, and the solvents removed in vacuo to yield 1.0 g of 93G as a yellow solid. Mass Spectrum (M$^{+1}$): m/z calcd. for C$_{10}$H$_{12}$N$_4$O$_3$S$^+$=269.1, found m/z=269.1

Method BK:

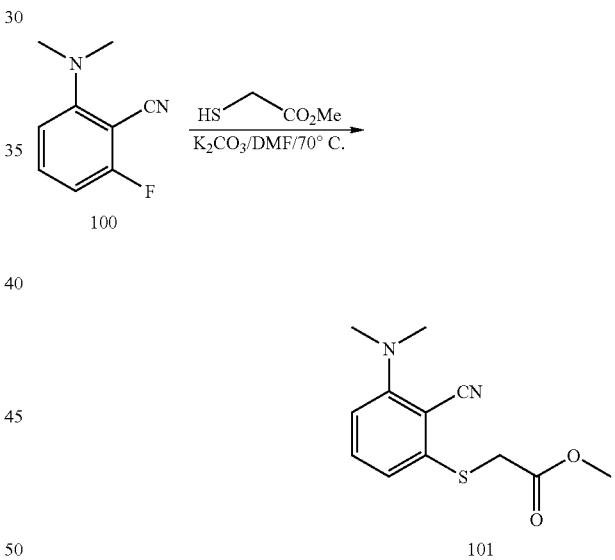

To compound 100 (9.5 g, 0.0578 mol) in DMF (100 mL) was added K$_2$CO$_3$ (10 g, 0.0723 mol) at room temperature. Methylthioglycolate (5.5 mL, 0.0615 mol) was added to the above solution and heated at 70° C. for 48 hours. The reaction mixture was poured into 500 mL ice water and extracted with ethyl acetate. The solvent was removed in vacuo to give 101 which was used for the next step without further purification. $^1$H NMR (CDCl$_3$): δ 7.32 (t, 1H), 6.94 (d, 1H), 6.78 (d, 1H), 3.72 (s, 3H), 3.71 (s, 2H), 3.01 (s, 6H). Mass Spectrum (M+1): m/z calcd. for C$_{12}$H$_{14}$N$_2$O$_2$S$^+$=251.1, found m/z=251.0.

Method BL:

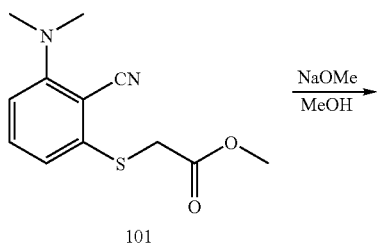

101

The above oil 101 was dissolved in methanol (200 mL) and treated with a 25% solution of sodium methoxide in methanol (50 mL) and the contents were heated at 80° C. for 1 hour. The solvent was removed in vacuo and the precipitate was washed several times with water to afford compound 102 as white solid. $^1$H NMR (CDCl$_3$): δ 7.34 (d, 1H), 7.28 (t, 1H), 6.99 (d, 1H), 3.78 (s, 3H), 2.68 (s, 6H). Mass Spectrum (M$^{+1}$): m/z calcd. for C$_{12}$H$_{14}$N$_2$O$_2$S$^+$=251.08, found m/z=251.0.

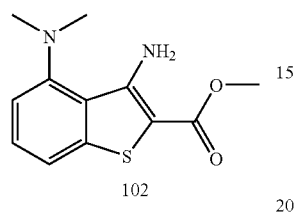

102

Method BM:

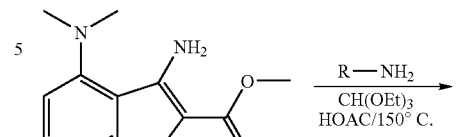

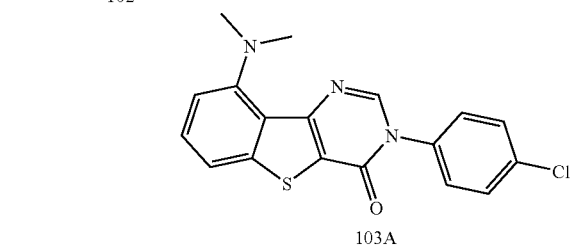

103A

Compound 102 (0.1 g, 0.399 mmol) was dissolved in 1 mL triethyl orthoformate and treated with acetic acid (0.1 mL) and 4-chloroaniline (0.15 g, 1.17 mmol). The contents were heated in a sealed tube at 150° C. for 16 h. The solvent was removed in vacuo and the product was isolated by preparative TLC using 5% methanol in dichloromethane to afford compound 103A as off white solid. $^1$H NMR (CDCl$_3$): δ 7.30 (s, 1H), 7.50 (m, 6H), 7.05 (d, 1H), 3.01 (s, 6H). Mass Spectrum (M$^{+1}$): m/z calcd. for C$_{18}$H$_{15}$ClN$_3$OS$^+$=356.1, found m/z=356.2.

The following compounds were prepared analogously:

| Cpd | Structure | Formula | MW | m/z Found (M + 1)$^+$ |
|---|---|---|---|---|
| 103A | 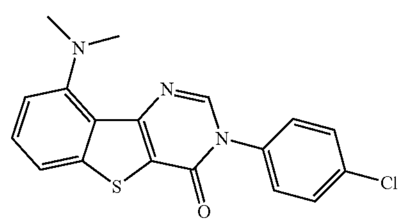 | C$_{18}$H$_{14}$ClN$_3$OS | 355.8 | 356.2 |
| 103B | 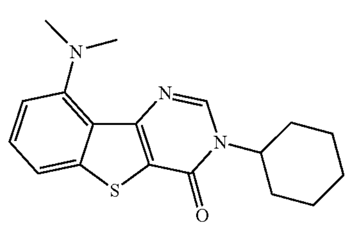 | C$_{18}$H$_{21}$N$_3$OS | 327.4 | 328.2 |
| 103C | 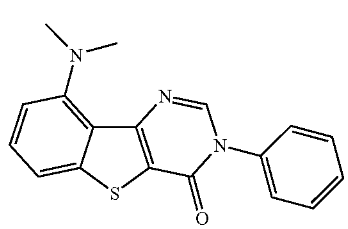 | C$_{18}$H$_{15}$N$_3$OS | 321.4 | 322.2 |

-continued

| Cpd | Structure | Formula | MW | m/z Found (M + 1)+ |
|---|---|---|---|---|
| 103D | 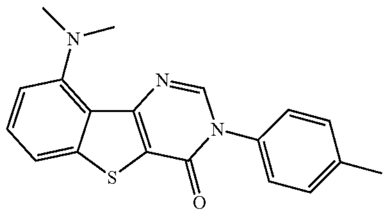 | $C_{19}H_{17}N_3OS$ | 335.4 | 336.2 |
| 103E | 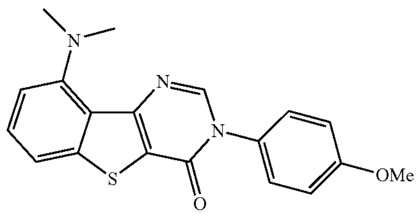 | $C_{19}H_{17}N_3O_2S$ | 351.4 | 352.2 |
| 103F | 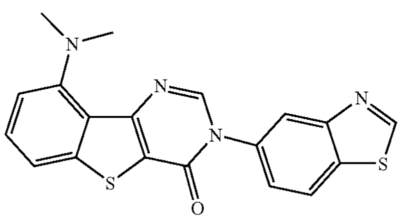 | $C_{19}H_{14}N_4OS_2$ | 378.5 | 379.2 |

Method BN:

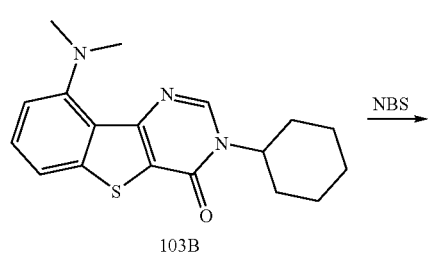

Method BO:

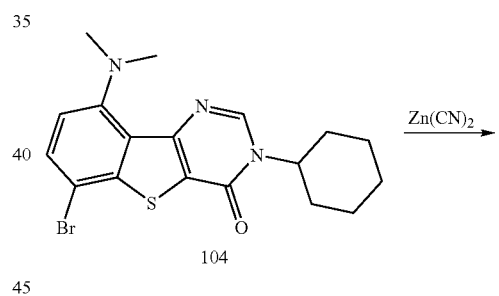

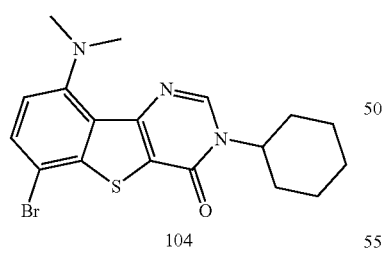

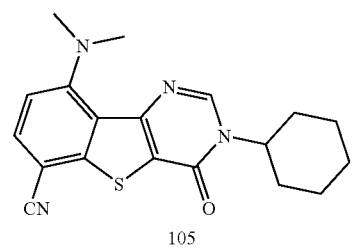

Compound 103B (0.05 g, 0.152 mmol) was dissolved in acetonitrile (2 mL) and treated with NBS (0.03 g, 0.168 mmol) and the reaction mixture was stirred at room temperature for 1 hour. The solvent was removed in vacuo and the product was isolated by preparative TLC using 4% methanol in dichloromethane to give compound 104 as an off-white solid. $^1$H NMR (CDCl$_3$): δ 8.36 (s, 1H), 7.55 (d, 1H), 6.91 (d, 1H), 4.92 (m, 1H), 2.99 (s, 6H), 2.09-1.25 (m, 10H). Mass Spectrum (M$^{+1}$): m/z calcd. for $C_{18}H_{21}BrN_3OS^+$=406.1, found m/z=406.2.

Compound 104 (0.023 g, 0.0567 mmol) was dissolved in DMF (2 mL) and treated with Zn(CN)$_2$ (0.01 g, 0.0851 mmol) followed by Pd(PPh$_3$)$_4$ (0.01 g, 0.0086 mmol). The contents were heated at 180° C. in a microwave oven for 10 minutes. The solvent was removed in vacuo and the product was isolated by preparative TLC to get compound 105. $^1$H NMR (CDCl$_3$): δ 8.33 (s, 1H), 7.72 (d, 1H), 6.97 (d, 1H), 4.91 (m, 1H), 3.10 (s, 6H), 2.09-1.25 (m, 10H). Mass Spectrum (M$^{+1}$): m/z calcd. for $C_{19}H_{21}N_4OS^+$=353.1, found m/z=353.2.

Method BP:

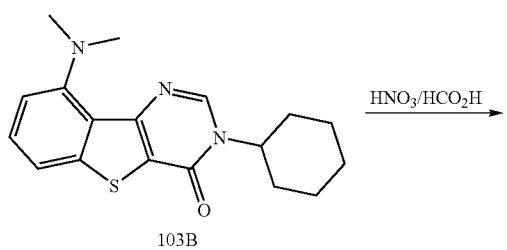

a 110 mL of benzene (acidified with several drops of conc. HCl). Next, the solid was quickly transferred to a flask containing 250 mL of water (acidified to pH=3 with conc. HCl). The flask was sealed with a glass stopper and stored at RT for 1 week. The resultant white crystals were collected via vacuum filtration, washed with water (acidified to pH=3 with conc. HCl), and dried to afford 13.56 g of 108A which was stored in a dark glass bottle sealed under $N_2$. $^1$H NMR (CDCl$_3$) δ 8.40 (bs, 1H), 7.38 (d, 2H), 7.10 (d, 2H), 3.35 (d, 2H), 2.28 (s, 3H), 1.97 (t, 1H). MS m/z calcd. for $C_9H_{12}NOS^+$=182.0; found m/z=182.0.

The following compound was prepared analogously.

| Cpd | Structure | Formula | MW | m/z Found (M + 1)$^+$ |
|---|---|---|---|---|
| 108B | 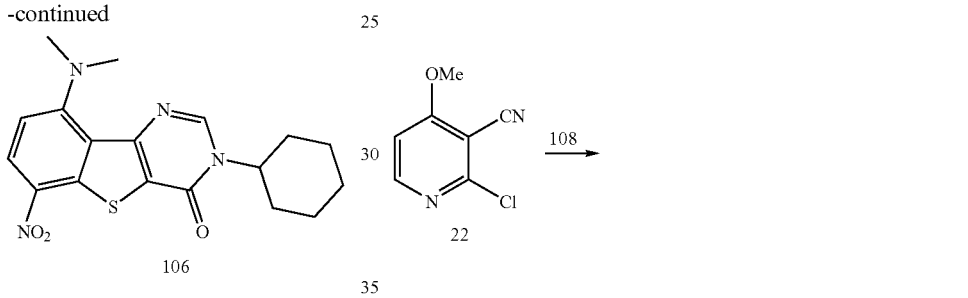 | $C_9H_{11}NO_2S$ | 197.3 | 198.2 |

-continued

[Structure 106 with NMe$_2$, NO$_2$, cyclohexyl, thienopyrimidinone]

Compound 103B (0.2 g, 0.61 mmol) was dissolved in formic acid (3 mL) and treated with conc. HNO$_3$ (0.05 mL, 1.25 eq) at 0° C. Stirred at 0° C. for 30 minutes and warmed to room temperature. The reaction mixture was stirred at rt for 2 hours. The solvent was removed in vacuo and the product was isolated by preparative TLC using 50% ethyl acetate-hexane as eluent to afford compound 106. 1H NMR (CDCl$_3$): δ 8.45 (d, 1H), 8.31 (s, 1H), 6.97 (d, 1H), 4.91 (m, 1H), 3.18 (s, 6H), 2.10-1.26 (m, 10H). Mass Spectrum (M+1): m/z calcd. for $C_{18}H_{21}N_4O_3S^+$=373.1, found m/z=373.1.

Method BQ:

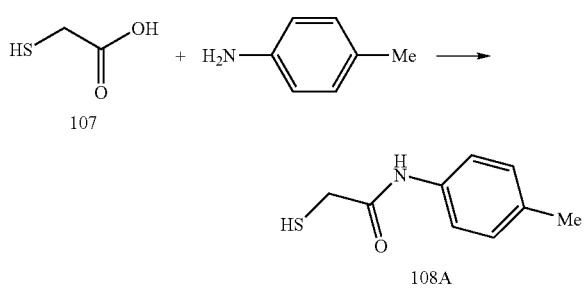

Thioglycolic acid (20 g, 217 mmol) and p-toluidine (23.26 g, 217 mmol) and benzene (110 mL) were combined in a one neck round bottom flask fitted with a Dean Stark apparatus, a reflux condenser, and a N$_2$ inlet line. The mixture was stirred and heated under reflux for 7 h and then cooled to RT and stored under N$_2$ for 48 h. The resultant solid was quickly collected via vacuum filtration and immediately washed with Method BR:

[Structure 22: 4-methoxy-3-cyano-2-chloropyridine] → 108

[Structure 109A: OMe, NH$_2$, thieno[2,3-b]pyridine carboxamide with N-(4-methylphenyl)]

Compound 22 (1.0 g, 5.92 mmol), compound 108A (1.18 g, 6.51 mmol), potassium carbonate (1.23 g, 8.89 mmol), and DMF (23 mL) were combined, stirred under N$_2$, and heated at ~80° C. for 2 h. The reaction mixture was poured into ice water and stirred vigorously. The resultant solid was collected via vacuum filtration, washed with water, and dried under vacuum to afford 1.75 g of a pale pink solid which was combined with sodium methoxide (0.408 g, 7.55 mmol) and methanol (87 mL), stirred under N$_2$, refluxed for 2 h, and then stirred overnight at RT. The mixture was concentrated in vacuo and mixed vigorously with ice water. The resultant solid was collected via vacuum filtration, washed with water, and dried in a vacuum oven at 40° C. to afford 1.59 g of compound 109A as a pale yellow solid. $^1$H NMR (CDCl$_3$): δ 8.45 (d, 1H), 7.39 (d, 2H), 7.12 (d, 2H), 6.99 (s, 1H), 6.82 (bs, H), 6.67 (d, 1H), 4.01 (s, 3H), 2.29 (s, 3H). Mass Spectrum (M$^{+1}$): m/z calcd. for $C_{16}H_{16}N_3O_2S^+$=314.1, found m/z=314.1.

The following compounds were prepared analogously.

| Cpd | Structure | Formula | MW | m/z Found (M + 1)+ |
|---|---|---|---|---|
| 109B | OMe, NH2, thieno[2,3-b]pyridine-2-carboxamide N-(4-methoxyphenyl) | C16H15N3O3S | 329.4 | 330.1 |
| 109C | OMe, NH2, thieno[2,3-b]pyridine-2-carboxamide N-phenyl | C15H13N3O2S | 299.4 | 300.0 |

Method BS:

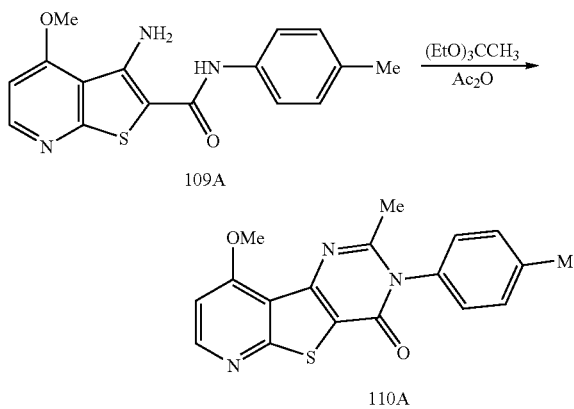

Compound 109A (1.0 g, 3.20 mmol), triethyl orthoacetate (11.2 mL), and acetic anhydride (5.60 mL) were combined, stirred, and irradiated in a 300 W power microwave oven at 180° C. for 20 minutes. The mixture was concentrated in vacuo, diluted with ice water, basified with concentrated NH4OH (aq.), and stirred vigorously overnight. The resultant solid was collected by filtration, washed with water, and dried to afford 1.05 g of compound 110A as a light tan solid. $^1$H NMR (CDCl$_3$): δ 8.58 (d, 1H), 7.33 (d, 2H), 7.11 (d, 2H), 6.86 (d, 1H), 4.11 (s, 3H), 2.41 (s, 3H), 2.33 (s, 3H). MS m/z calcd. for $C_{18}H_{16}N_3O_2S^+$=338.1; found m/z=338.1.

The following compounds were prepared analogously.

| Cpd | Structure | Formula | MW | m/z Found (M + 1)+ |
|---|---|---|---|---|
| 110B | OMe, Me, 4-methoxyphenyl derivative | C18H15N3O3S | 353.4 | 354.2 |
| 110C | OMe, Me, phenyl derivative | C17H13N3O2S | 323.4 | 324.1 |
| 116A | NMe2, Et, 4-methylphenyl derivative | C20H20N4OS | 364.5 | 365.2 |

| Cpd | Structure | Formula | MW | m/z Found (M + 1)+ |
|---|---|---|---|---|
| 116B | 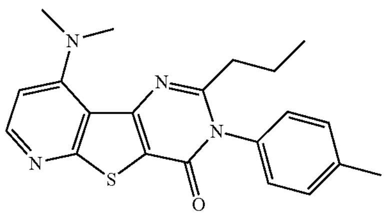 | C21H22N4OS | 378.5 | 379.1 |
| 116C | 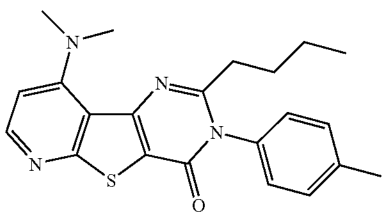 | C22H24N4OS | 392.5 | 393.1 |
| 116D | 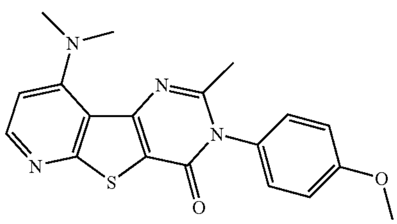 | C19H18N4O2S | 366.4 | 367.1 |
| 116E | 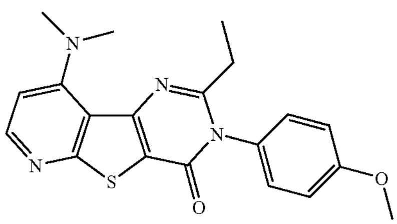 | C20H20N4O2S | 380.5 | 381.1 |
| 116F | 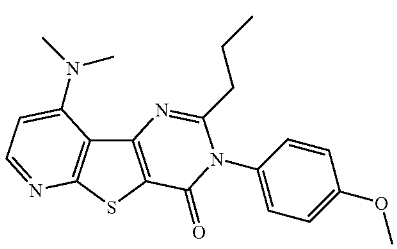 | C21H22N4O2S | 394.5 | 395.1 |
| 116G | 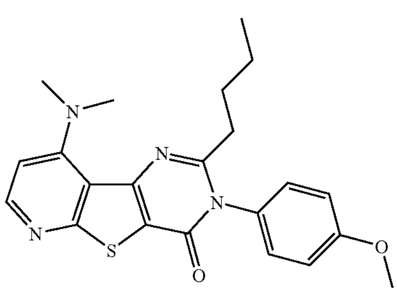 | C22H24N4O2S | 408.5 | 409.2 |

Method BS (Alternate):

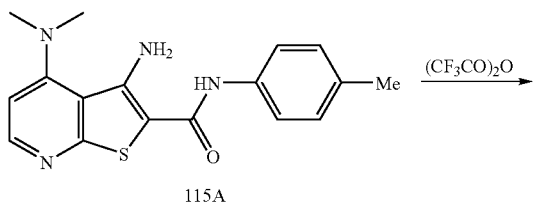

Method C (Alternate):

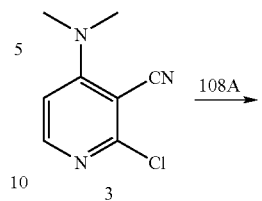

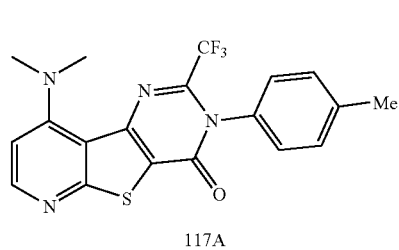

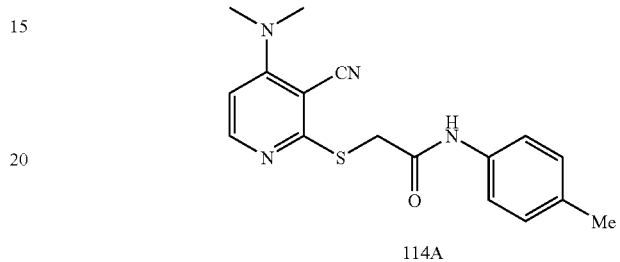

Compound 115A (50 mg, 0.15 mmol), trifluoroacetic anhydride (0.25 mL), and toluene (1 mL) were combined, stirred, and irradiated in a 300 W power microwave oven at 150° C. for 15 minutes. The mixture was concentrated in vacuo, diluted with ice water, basified with concentrated NH$_4$OH (aq.), and stirred vigorously overnight. The resultant solid was collected by filtration, washed with water, and dried in a vacuum oven at 40° C. to afford 30 mg of compound 117A as a pale yellow solid. $^1$H NMR (CDCl$_3$): δ 8.38 (d, 1H), 7.31 (d, 2H), 7.16 (d, 2H), 6.73 (d, 1H), 3.17 (s, 6H), 2.42 (s, 3H). MS m/z calcd. for C$_{19}$H$_{16}$F$_3$N$_4$OS$^+$=405.1; found m/z=405.1. The following compounds were prepared by this method:

Compound 3 (1.5 g, 8.26 mmol), compound 108A (1.65 g, 9.09 mmol), potassium carbonate (1.71 g, 12.4 mmol), and DMF (20 mL) were combined, stirred under N$_2$, and heated for 3 h at 65° C. The reaction mixture was poured into ice water and stirred vigorously. The resultant solid was collected via vacuum filtration, washed with water, and dried in a vacuum oven at 40° C. to afford 2.62 g of compound 114A as a light yellow solid. $^1$H NMR (CDCl$_3$): δ 9.65 (bs, 1H), 8.09 (d, 1H), 7.29 (d, 2H), 7.04 (d, 2H), 6.39 (d, 1H), 3.86 (s, 2H), 3.23 (s, 6H), 2.24 (s, 3H). MS m/z calcd. for C$_{17}$H$_{19}$N$_4$OS$^+$=327.1; found m/z=327.1.

| Cpd | Structure | Formula | MW | m/z Found (M + 1)$^+$ |
|---|---|---|---|---|
| 117A | ![structure] | C$_{19}$H$_{15}$F$_3$N$_4$OS | 404.4 | 405.1 |
| 117B | ![structure] | C$_{19}$H$_{15}$F$_3$N$_4$O$_2$S | 420.4 | 421.2 |

The following compound was prepared analogously.

| Cpd | Structure | Formula | MW | m/z Found (M + 1)+ |
|---|---|---|---|---|
| 114A | 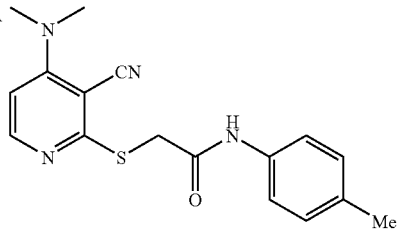 | C₁₇H₁₈N₄OS | 326.4 | 327.1 |
| 114B | 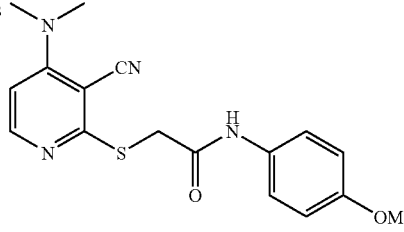 | C₁₇H₁₈N₄O₂S | 342.4 | 343.1 |

Method D (Alternate):

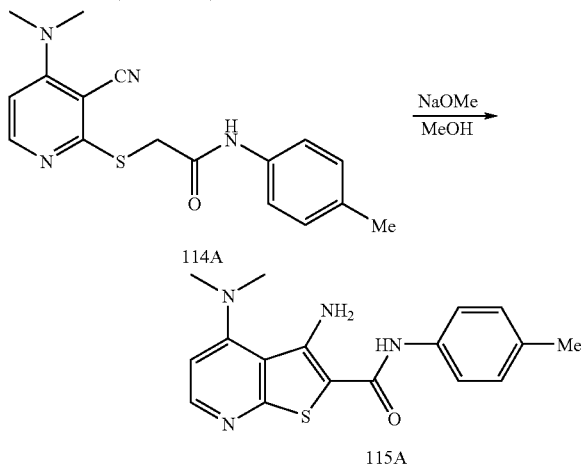

Compound 114A (2.62 g, 8.03 mmol), sodium methoxide (0.59 g, 10.8 mmol), and methanol (125 mL) were combined, stirred under N₂, heated under reflux for 2½ h, and then stirred overnight at RT. The mixture was concentrated in vacuo and mixed vigorously with ice water. The resultant solid was collected via vacuum filtration, washed with water, and dried in a vacuum oven at 40° C. to afford 2.53 g of compound 115A as a pale yellow solid. ¹H NMR (CDCl₃): δ 8.42 (dd, 1H), 7.40 (d, 2H), 7.12 (d, 2H), 7.02 (s, 1H), 6.96 (bs, 2H), 6.86 (d, 1H), 2.84 (s, 6H), 2.30 (s, 3H). MS m/z calcd. for C₁₇H₁₉N₄OS⁺=327.1; found m/z=327.1.

The following compound was prepared analogously.

| Cpd | Structure | Formula | MW | m/z Found (M + 1)+ |
|---|---|---|---|---|
| 115A | 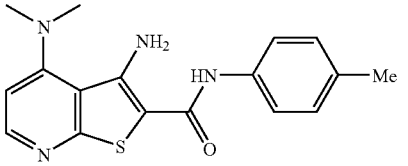 | C₁₇H₁₈N₄OS | 326.4 | 327.1 |
| 115B | 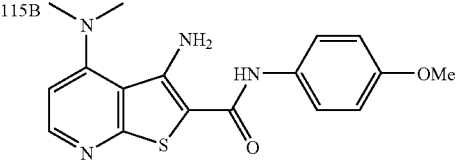 | C₁₇H₁₈N₄O₂S | 342.4 | 343.1 |

Method BT:

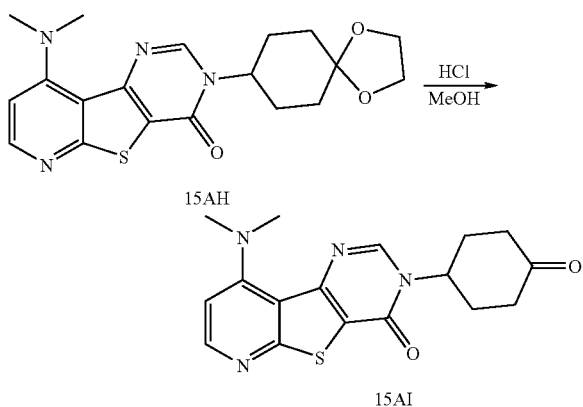

To compound 15AH (780 mg, 2.02 mmol) in methanol (35 mL) was added 6 N HCl$_{(aq)}$ (7 mL) at RT. The reaction mixture was stirred under N$_2$ and heated at 90° C. for 18 h after which time the reaction was ~50% complete (as indicated by TLC). Consequently, refluxing at 110° C. was continued for another 6 h after which time the reaction was ~90% complete (as indicated by TLC). Additional 6 N HCl$_{(aq)}$ (1.5 mL) was added to the reaction mixture and refluxing at 110° C. was continued for another 15 h. After cooling to RT, water (3 mL) was added to the reaction mixture and the MeOH was removed in vacuo at ≦25° C. The residue was partitioned between dichloromethane and saturated NaHCO$_3$. The organic layer was removed and the aqueous layer was re-extracted with dichloromethane. The organics were combined, washed with saturated NaCl, dried over MgSO$_4$, filtered, and concentrated in vacuo to afford 656 mg of compound 15AI as an off white solid. $^1$H NMR (CDCl$_3$): δ 8.38 (d, 1H), 8.21 (s, 1H), 6.75 (d, 1H), 5.37 (m, 1H), 3.09 (s, 6H), 2.69-2.13 (m, 8H). MS m/z calcd. for C$_{17}$H$_{19}$N$_4$O$_2$S$^+$=343.1; found m/z=343.1.

Method BU

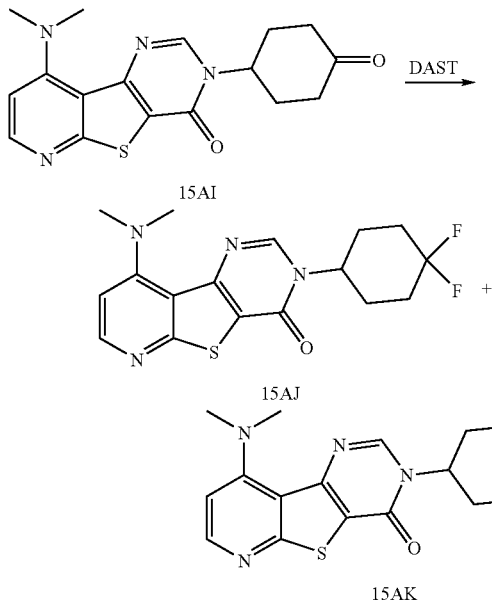

Compound 15AI (70 mg, 0.21 mmol), DAST (0.08 mL, 0.62 mmol), and dichloroethane (1.5 mL) were combined, stirred, and irradiated in a 300 W power microwave oven at 100° C. (high absorption) for 10 minutes. The reaction mixture was partitioned between dichloromethane and 1N NaOH. The organic layer was removed and the aqueous layer was re-extracted with dichloromethane. The organics were combined, washed with saturated NaCl, dried over MgSO$_4$, filtered, and concentrated in vacuo to afford a tan residue which was purified via preparative silica gel TLC with 5% methanol/dichloromethane to afford 35 mg of a ~1:1 mixture of compounds a16 and a17, along with other minor impurities, as a pale yellow foam. Crystallization from ethyl acetate/hexane afforded 25 mg of an analytically pure, 1:1 mixture of compounds 15AJ and 15AK as a pale yellow solid. 15AJ $^1$H NMR (CDCl$_3$): δ 8.39 (d, 1H), 8.24 (s, 1H), 6.75 (d, 1H), 5.15 (m, 1H), 3.09 (s, 6H), 2.35-1.95 (m, 8H). MS m/z calcd. for C$_{17}$H$_{19}$F$_2$N$_4$OS$^+$=365.1; found m/z=365.1.

15AK $^1$H NMR (CDCl$_3$): δ 8.38 (d, 1H), 8.23 (s, 1H), 6.74 (d, 1H), 5.28 (m, 1H), 5.06 (m, 1H), 3.09 (s, 6H), 2.65-2.20 (m, 6H). MS m/z calcd. for C$_{17}$H$_{18}$FN$_4$OS$^+$=345.1; found m/z=345.1.

Method BV:

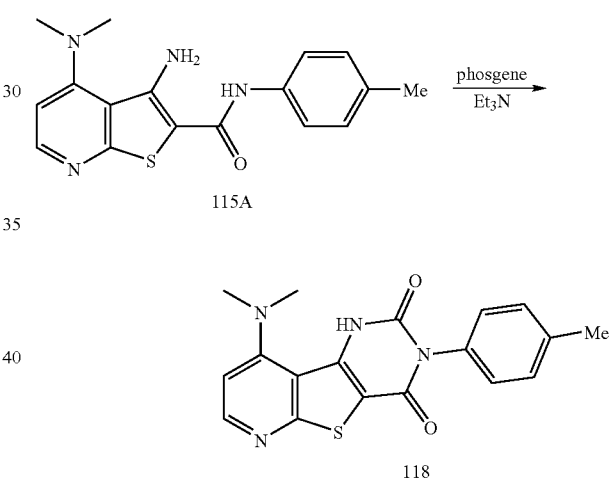

Ref.: M. D. Meyer, I. Drizin, R. J. Altenbach, et. al., *J. Med. Chem.* 2000, 43, 1586-1603.

To a mixture of compound 115A (100 mg, 0.31 mmol) and Et$_3$N (69 mg, 0.68 mmol) in dichloromethane (2.5 mL), cooled to −78° C. under N$_2$, was added 1.9 M phosgene in toluene (0.16 mL, 0.31 mmol). The mixture was stirred at −78° C. for 2 h and then at RT for 48 h. After concentrating the reaction mixture in vacuo, the residue was suspended in THF (2 mL), treated with 1M KOtBu in THF (0.37 mL), and stirred under N$_2$ at RT for 4 days. Insoluble material was removed from the reaction mixture via filtration and washed with dichloromethane. The filtrate was concentrated in vacuo and purified via preparative silica gel TLC with 40% ethyl acetate/dichloromethane to afford 22 mg of compound 118 as a yellow-orange solid. This solid was repurified via preparative silica gel TLC with 40% ethyl acetate/dichloromethane to afford 3.3 mg of compound 118 as a yellow solid. $^1$H NMR (CDCl$_3$): δ 9.28 (bs, 1H), 8.57 (d, 1H), 7.30 (d, 2H), 7.17 (d, 2H), 7.01 (d, 1H), 2.88 (s, 6H), 2.38 (s, 3H). MS m/z calcd. for C$_{18}$H$_{17}$N$_4$O$_2$S$^+$=353.1; found m/z=353.1.

Method BW:

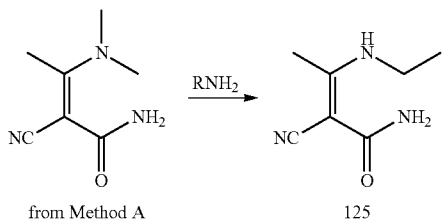

from Method A      125

(Ref: *Chemistry of Heterocyclic Compounds*, 39 (3), 2003, 328-334)

A mixture of 2-cyano-3-(dimethylamino)-2-butenamide (5 g, 0.0327 mol) (intermediate from method A) and ethylamine (49 ml of 2.0 M solution in THF) in ethanol (40 ml) was stirred at room temperature for a period of 22 h. The precipitate was filtered to give the product 125 as white crystals. $^1$H NMR (DMSO-d$_6$): δ 6.63 (br. s, 2H), 3.31 (q, 2H), 2.15 (s, 3H), 1.11 (t, 3H).

Methods BX and BY:

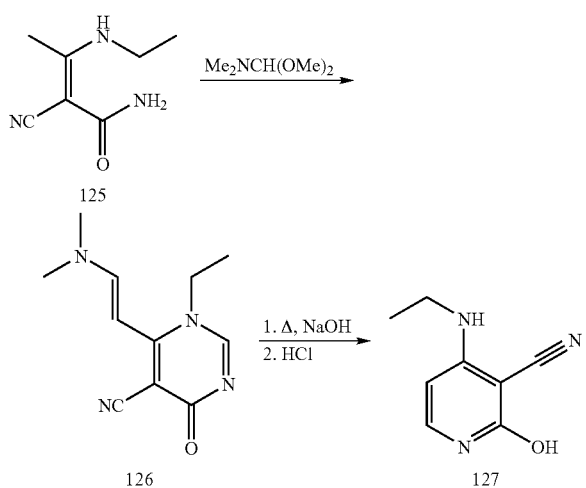

Compound 125 (5.0 g, 0.0327) and N,N-dimethylformamide dimethyl acetal (26.1 ml) in ethanol (33 ml) were heated at reflux under a nitrogen atmosphere for 30 minutes. The reaction mixture was concentrated under reduced pressure to give compound 126. Compound 126 (7.12 g, 0.0327 mol) was heated under reflux with 5% sodium hydroxide solution (130 ml) for 1 h, cooled to room temperature and then acidified with dilute hydrochloric acid to pH 6-7 and the product 127 was isolated by filtration. After drying in a vacuum oven, 127 was used without further purification. $^1$H NMR (DMSO-d$_6$) δ 11.04 (br. s, 1H), 7.31 (br. s, 2H), 5.86 (m, 1H), 3.26 (m, 2H), 1.08 (t, 3H).

Method D (Alternate 2):

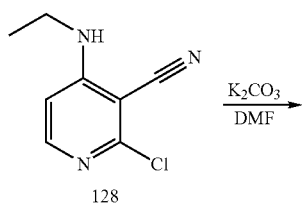

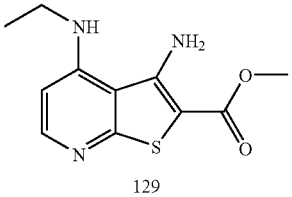

Compound 128 (1.42 g, 0.0079 mol), thiol (1.41 ml, 0.0157 mol) and potassium carbonate (1.63 g, 0.0118 mol) in DMF (20 ml) were stirred at room temperature. Water was then added and the resulting precipitate filtered. The precipitate was then dried in a vacuum oven to provide product 129 which was used in subsequent reactions without purification. $^1$H NMR (CDCl$_3$) δ 8.09 (d, 1H), 6.80 (br. s, 3H), 6.44 (d, 1H), 3.74 (s, 3H), 3.25 (q, 2H), 1.20 (t, 3H).

Method BG (Alternate 1):

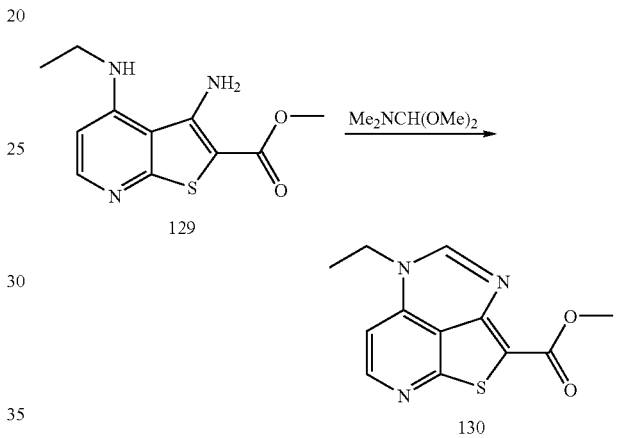

Compound 129 (1.44 g, 0.0057 mol) and N,N-dimethylformamide dimethyl acetal (1.53 ml, 0.0114 mol) in toluene (15 ml) were heated at reflux for 2 h. The reaction was cooled to room temperature and product 130 which precipitated was collected by filtration. $^1$H NMR (CDCl$_3$): δ 8.36 (d, 1H), 7.58 (s, 1H), 6.32 (d, 1H), 3.88 (s, 3H), 3.75 (q, 2H), 1.37 (t, 3H). MS m/z calcd. for $C_{12}H_{12}N_3O_2S^+$=262.1; found m/z=262.1 ($M^{+1}$).

Method BZ:

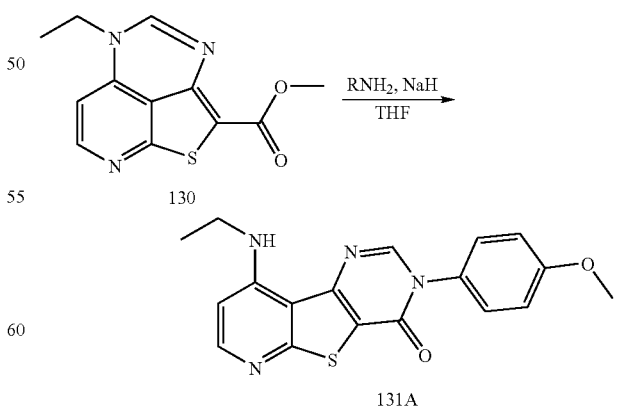

A mixture of p-anisidine (0.26 g, 0.0021 mol) and sodium hydride (0.132 g, 0.0033 mol of 60% slurry in mineral oil) in THF (10 ml) were stirred at room temperature for 30 minutes before adding compound 130 (0.145 g, 0.00055 mol). The resultant mixture was heated at reflux for 3 h, cooled to room temperature and ice-water was added. The precipitate was collected by filtration, dissolved in dichloromethane, dried (Na$_2$SO$_4$) and evaporated to give the desired product 131A.

$^1$H NMR (CDCl$_3$): δ 8.27 (d, 1H), 8.16 (s, 1H), 7.60 (br. s, 1H), 7.31 (d, 2H), 7.02 (d, 2H), 6.42 (d, 1H), 3.84 (s, 3H), 3.37 (q, 2H), 1.36 (t, 3H). MS m/z calcd. for C$_{18}$H$_{17}$N$_4$O$_2$S$^+$=353.1; found m/z=353.1 (M$^{+1}$).

The following compounds were prepared analogously:

| Cpd | Structure | Formula | MW | m/z Found (M + 1)$^+$ |
|---|---|---|---|---|
| 131A | 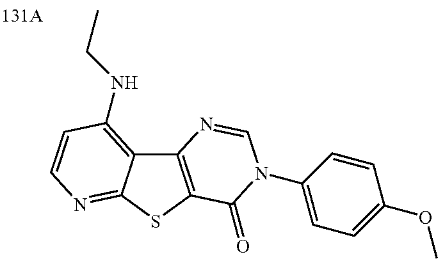 | C$_{18}$H$_{16}$N$_4$O$_2$S | 352.4 | 353.1 |
| 131B | 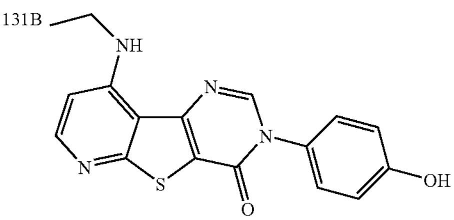 | C$_{17}$H$_{14}$N$_4$O$_2$S | 338.4 | 339.1 |
| 131C | 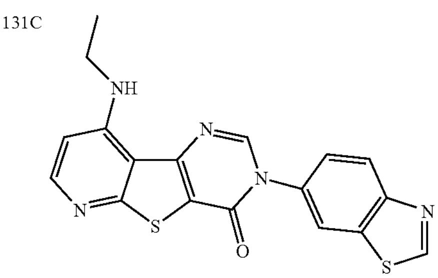 | C$_{18}$H$_{13}$N$_5$OS$_2$ | 379.5 | 380.1 |
| 131D | 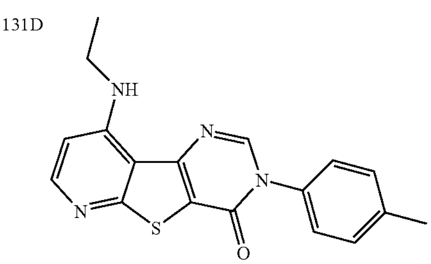 | C$_{18}$H$_{16}$N$_4$OS | 336.4 | 337.1 |
| 131E | 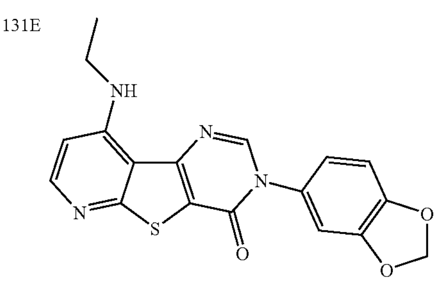 | C$_{18}$H$_{14}$N$_4$O$_3$S | 366.4 | 367.1 |

| Cpd | Structure | Formula | MW | m/z Found (M + 1)+ |
|---|---|---|---|---|
| 131F | 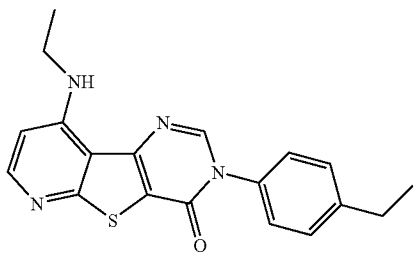 | $C_{19}H_{18}N_4OS$ | 350.4 | 351.1 |
| 131G | 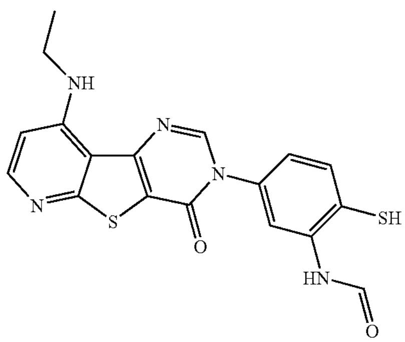 | $C_{18}H_{15}N_5O_2S_2$ | 397.5 | 397.1 |

Method CA:

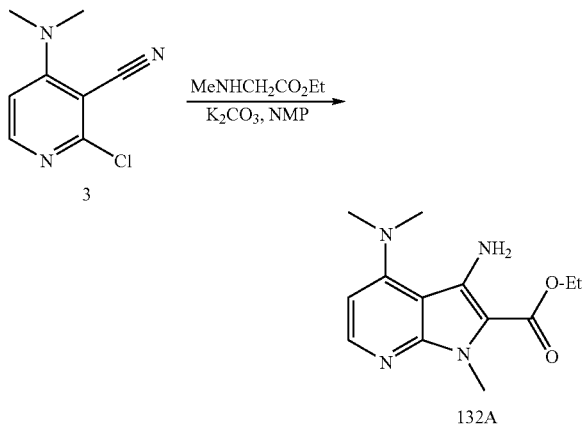

Compound 3 (4.89 g, 0.0269 mol), N-methylglycine ethyl ester (8.25 g, 0.0537 mol) and potassium carbonate (11.14 g, 0.0806 mol) in NMP (50 mL) were heated at 135° C. overnight under a nitrogen atmosphere. The reaction was cooled to room temperature and ice-water was added. It was extracted by ethyl acetate (100 mL×3) combined fractions washed with water and dried using sodium sulfate, filtered and evaporated under reduced pressure. Purification by column chromatography on silica gel using dichloromethane/ ethyl acetate (9:1 to 4:1) led to product 132A. $^1$H NMR (CDCl$_3$): δ 8.17 (d, 1H), 6.36 (d, 1H), 5.28 (br. s, 2H), 4.35 (q, 2H), 3.91 (s, 3H), 2.87 (s, 6H), 1.37 (t, 3H). MS m/z calcd. for $C_{13}H_{19}N_4O_2{}^+$=263.2; found m/z=263.3 (M$^{+1}$).

The following compounds were prepared analogously:

| Cpd | Structure | Formula | MW | m/z Found (M + 1)+ |
|---|---|---|---|---|
| 132A | 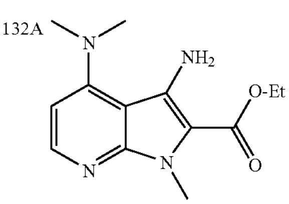 | $C_{13}H_{18}N_4O_2$ | 262.3 | 263.3 |

| Cpd | Structure | Formula | MW | m/z Found (M + 1)+ |
|---|---|---|---|---|
| 132B | 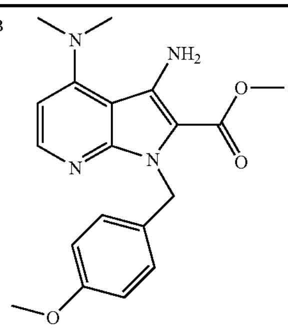 | | | ¹H NMR (CDCl₃): δ 8.20 (d, 1 H), 7.02 (d, 2 H), 6.69 (d, 2 H), 6.40 (d, 1 H), 5.65 (s, 2 H), 5.30 (br. s, 2 H), 3.79 (s, 3 H), 3.68 (s, 3 H), 2.87 (s, 6 H) |

Method CB:

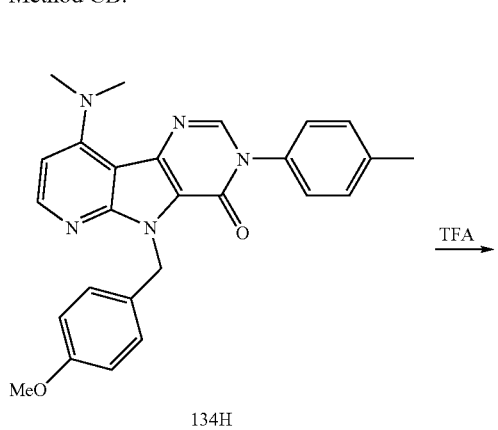

A solution of compound 134H (0.017 g, 0.00004 mol) in trifluoroacetic acid (1.5 ml) was stirred in a microwave oven at 120° C. for 2 h. After the evaporation of the solvent, the residue was transferred to a preparative TLC and eluted using dichlormethane/ethyl acetate (4:1) to give the product 135A. ¹H NMR (CDCl₃): δ 8.33 (br. s, 1H), 8.03 (s, 1H), 7.31 (m, 4H), 6.40 (d, 1H), (s, 6H), 2.41 (s, 3H). MS m/z calcd. for $C_{18}H_{18}N_5O^+$=320.2; found m/z=320.2 (M⁺¹).

Method CC:

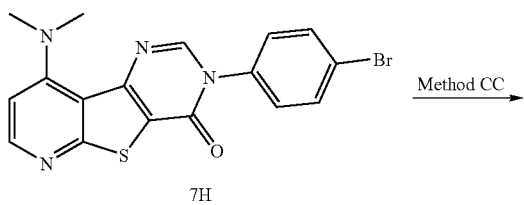

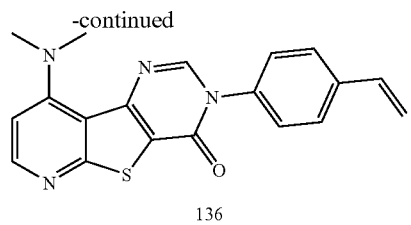

A mixture of compound 7H (0.12 g, 0.3 mmol), vinyltributyltin (0.099 g, 0.31 mmol) and tetrakis(triphenylphosphine)palladium (0.017 g, 0.015 mmol) in toluene (10 mL) was heated at reflux under a nitrogen atmosphere for 16 h. The reaction mixture was cooled to room temperature and transferred to a prep TLC and eluted using dichloromethane/ethyl acetate (9:1) several times to give the product 136. ¹H NMR (CDCl₃): δ 8.40 (d, 1H), 8.25 (s, 1H), 7.55 (d, 2H), 7.39 (d, 2H), 6.76 (d, 1H), 6.74 (dd, 1H), 5.81 (d, 1H), 5.34 (d, 1H), 3.12 (s, 6H). MS m/z calcd. for $C_{19}H_{17}N_4OS^+$=349.1; found m/z=349.1 (M⁺¹).

Method CD:

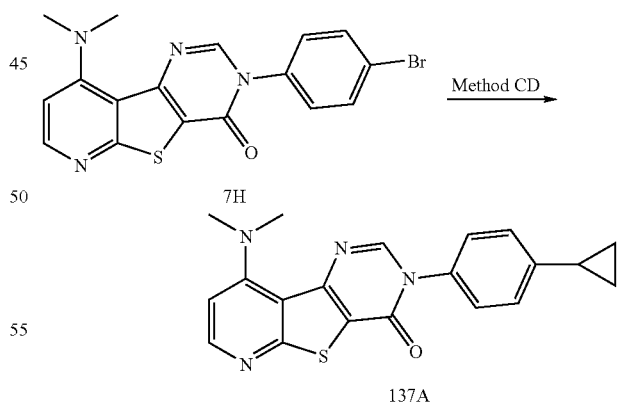

(Ref: *Tetrahedron Lett.* 43, 2002, 6987-6990)

To a suspension of bromide 7H (0.40 g, 0.99 mmol), cyclopropyl boronic acid (0.11 g, 1.3 mmol), potassium phosphate (0.74 g, 0.0035 mol), and tricyclohexylphosphine (0.028 g, 0.99 mmol) in toluene (5 mL) and water (200 □L) under a nitrogen atmosphere was added palladium acetate (0.011 g, 0.05 mmol). The mixture was heated at 100° C. for 3 h and then cooled to room temperature. The reaction was transferred to a prep TLC and eluted using dichloromethane/ethyl acetate (9:1) to give the product 137A. $^1$H NMR (CDCl$_3$): δ 8.39 (d, 1H), 8.23 (s, 1H), 7.29 (d, 2H), 7.19 (d, 2H), 6.76 (d, 1H), 3.13 (s, 6H), 1.94 (m, 1H), 1.02 (m, 2H), 0.73 (m, 2H). MS m/z calcd. for C$_{20}$H$_{19}$N$_4$OS$^+$=363.1; found m/z=363.1 (M$^{+1}$).

The following compound was prepared analogously:

| Cpd | Structure | Formula | MW | m/z Found (M + 1)$^+$ |
|---|---|---|---|---|
| 137B | 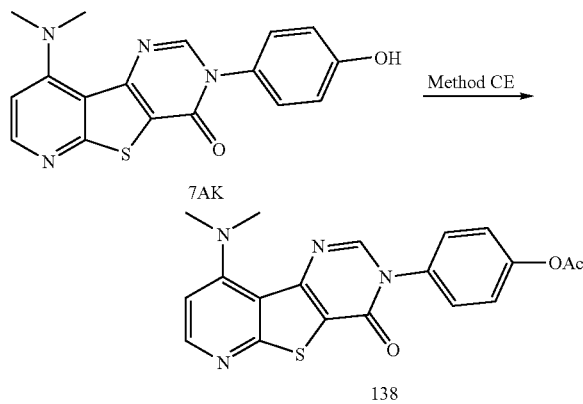 | C$_{20}$H$_{18}$N$_4$OS | 362.4 | 363.1 |

Method CE:

[Structure of 7AK with Method CE arrow to structure 138]

Compound 7AK (0.056 g, 0.17 mmol) was heated at reflux in acetic anhydride (3 mL) for 15 minutes. The reaction was cooled to room temperature and transferred to a preparative TLC. Elution using dichloromethane/ethyl acetate (9:1) led to product 138. $^1$H NMR (CDCl$_3$): δ 8.40 (d, 1H), 8.25 (s, 1H), 7.45 (d, 2H), 7.26 (d, 2H), 6.77 (d, 1H), 3.13 (s, 6H), 2.31 (s, 3H). MS m/z calcd. for C$_{19}$H$_{17}$N$_4$O$_3$S$^+$=381.1; found m/z=381.1 (M$^{+1}$).

Method CF:

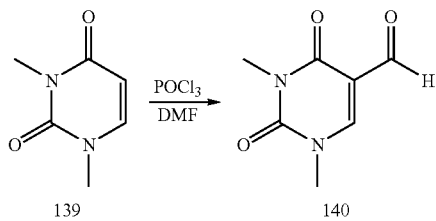

(Ref: *Tetrahedron* 59, 2003, 341-352)
To a solution of compound 139 (10.54 g, 0.0752 mol) in dry DMF (60 mL) at 0° C., was added phosphorous oxychloride (14 ml, 0.150 mol) and mixture heated at 90° C. for 1 h. The solvent was evaporated under reduced pressure and ice-water was added. Product 140 was obtained by extracting the aqueous solution several times using dichloromethane, dried (Na$_2$SO$_4$) and concentration. $^1$H NMR (CDCl$_3$): δ 9.99 (s, 1H), 8.02 (s, 1H), 3.49 (s, 3H), 3.45 (s, 3H).

Method CG:

[Structure 140 with NaOEt/CNCH$_2$CONH$_2$ arrow to structure 141]

(Ref: J. Org. Chem. 1981, 46, 3949-3953)
To a solution of NaOEt in ethanol, prepared by slowly adding sodium (4.78 g) to dry ethanol (600 mL), was added aldehyde 140 (10.59 g, 0.063 mol) and cyanoacetamide (17.50 g, 0.208 mol). The mixture was then heated at reflux for a period of 2 h before evaporating solvent under reduced pressure. Water was then added to the residue and acidified by slow addition of conc. HCl until crystals started forming. This mixture was cooled in ice and filtered to give product 141. $^1$H NMR (DMSO-d$_6$): δ 8.41 (d, 1H), 8.27 (d, 1H), 4.19 (q, 2H), 1.22 (t, 3H).

Method CH:

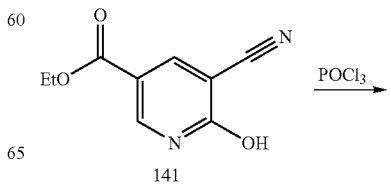

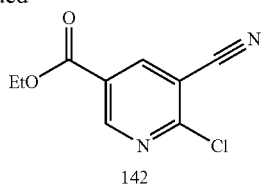

142

(Ref: *Pharmaceutical Chemistry Journal* 31 (11), 1997, 615-618)

A solution of 141 (6.75 g, 0.0352 mol) in phosphorous oxychloride (40 mL) was heated at reflux for 1 h, and excess solvent was evaporated under reduced pressure. Water was then added and the pH adjusted to pH~7.5 using a 1N sodium hydroxide solution. The resulting precipitate 142 was collected, washed with water and dried under vacuum. $^1$H NMR (CDCl$_3$): δ 9.11 (d, 1H), 8.54 (d, 1H), 4.22 (q, 2H), 1.39 (t, 3H).

Method CI:

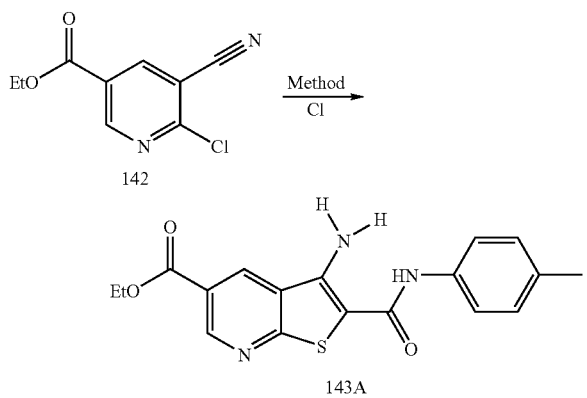

A mixture of 2-chloro-3-pyridine carbonitrile derivative 142 (1.97 g, 0.0094 mol), thiol derivative 108A (1.95 g, 0.0108 mol) and potassium carbonate (1.94 g, 0.014 mol) in DMF (30 mL) was stirred at 60° C. for 2 h. The reaction was cooled to room temperature before adding ice-water. The precipitate 143 was collected by filtration, washed with water and dried in a vacuum oven. $^1$H NMR (CDCl$_3$): δ 9.22 (d, 1H), 8.55 (d, 1H), 7.41 (d, 2H), 7.14 (d, 2H), 7.13 (s, 1H), 6.24 (s, 2H), 4.43 (q, 2H), 2.30 (s, 3H), 1.41 (t, 3H). MS m/z calcd. for C$_{18}$H$_{18}$N$_3$O$_3$S$^+$=356.1; found m/z=356.1 (M$^{+1}$).

Method CJ:

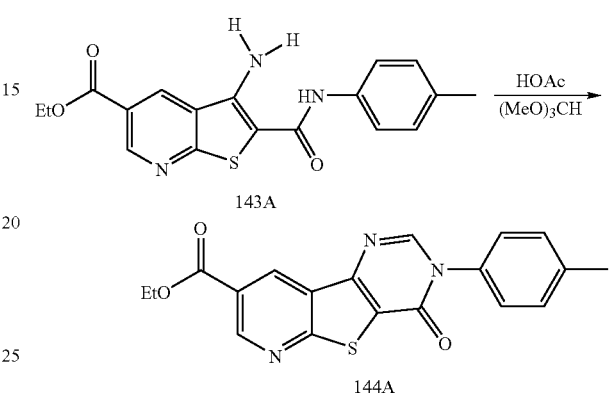

A mixture of compound 143A (3.06 g, 0.0086 mol) and triethylorthoformate (7.2 ml, 0.0431 mol) in 1% solution of acetic acid in toluene (30 mL) was heated at reflux overnight. The reaction was cooled to room temperature, diluted with ether and the solid precipitate was filtered. The solid was washed with more ether and dried under vacuum to give the desired product 144A. $^1$H NMR (CDCl$_3$): δ 9.37 (d, 1H), 9.15 (d, 1H), 8.27 (s, 1H), 7.26-7.34 (m, 4H), 4.45 (q, 2H), 2.42 (s, 3H), 1.43 (t, 3H). MS m/z calcd. for C$_{19}$H$_{16}$N$_3$O$_3$S$^+$=366.1; found m/z=366.1 (M$^{+1}$).

The following compounds were also prepared using Method CJ:

| Cpd | Structure | Formula | MW | m/z Found (M + 1)$^+$ |
|---|---|---|---|---|
| 144B | ethyl ester structure with methoxyphenyl | C19H15N3O4S | 381.4 | 382.2 |
| 144C | ethyl ester structure with CF3 and methylpyridyl | C20H14F3N3O3S | 433.4 | 434.2 |

Method CK:

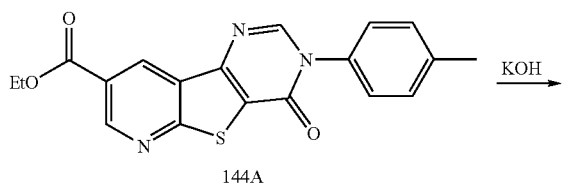

Compound 144A (1.02 g, 0.00279 mol) and potassium hydroxide (0.25 g, 0.0062 mol) were heated in refluxing ethanol for 1 h. Evaporated the solvent under vacuum and then quenched with water. The resulting solution was acidified with conc. HCl and the precipitate was filtered, washed with water and dried in a vacuum oven to give the desired acid 145A. $^1$H NMR (CDCl$_3$): δ 9.24 (d, 1H), 8.91 (d, 1H), 8.63 (s, 1H), 7.42 (d, 2H), 7.34 (d, 2H), 2.35 (s, 3H). MS m/z calcd. for $C_{17}H_{12}N_3O_3S^+$=338.1; found m/z=338.0 (M$^{+1}$).

Method CL:

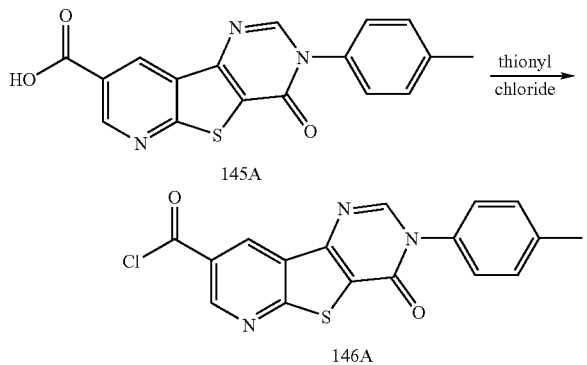

Compound 145A (0.656 g, 0.00195 mol) was heated under reflux in thionyl chloride (10 mL) for a period of 2 h. The solvent was evaporated under reduced pressure and the residue was used in subsequent reactions without purification. $^1$H NMR (CDCl$_3$): δ 9.34 (d, 1H), 9.22 (d, 1H), 8.27 (s, 1H), 7.33 (d, 2H), 7.28 (d, 2H), 2.40 (s, 3H). MS m/z calcd. for $C_{17}H_{11}ClN_3O_2S^+$=356.0; found m/z=356.0 (M$^{+1}$).

Method CM:

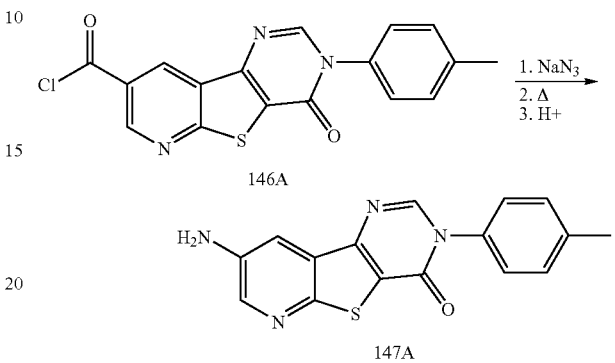

Compound 146A (0.692 g, 0.00195 mol) and sodium azide (0.127 g, 0.00195 mol) were heated in a mixture of toluene and DMF (1:1) at 90° C. under a nitrogen atmosphere for 2 h. The solvent was then evaporated under reduced pressure leaving a solid residue. To this was added 8N hydrochloric acid (15 ml) and the mixture heated at reflux for 1 h. The reaction was cooled to room temperature and filtered. The filtrate was basified using concentrated ammonium hydroxide and extracted with dichloromethane. The organic layer was dried (Na$_2$SO$_4$) and evaporated in vacuo. Purification by preparative TLC using dichloromethane/acetone (9:1) led to product 147A.

$^1$H NMR (DMSO-d$_6$): δ 8.47 (s, 1H), 8.23 (d, 1H), 7.61 (d, 1H), 7.39 (d, 2H), 7.32 (d, 2H), 5.72 (s, 2H), 2.34 (s, 3H). MS m/z calcd. for $C_{16}H_{13}N_4OS^+$=309.1; found m/z=309.1 (M$^+$).

Method Y (Alternate):

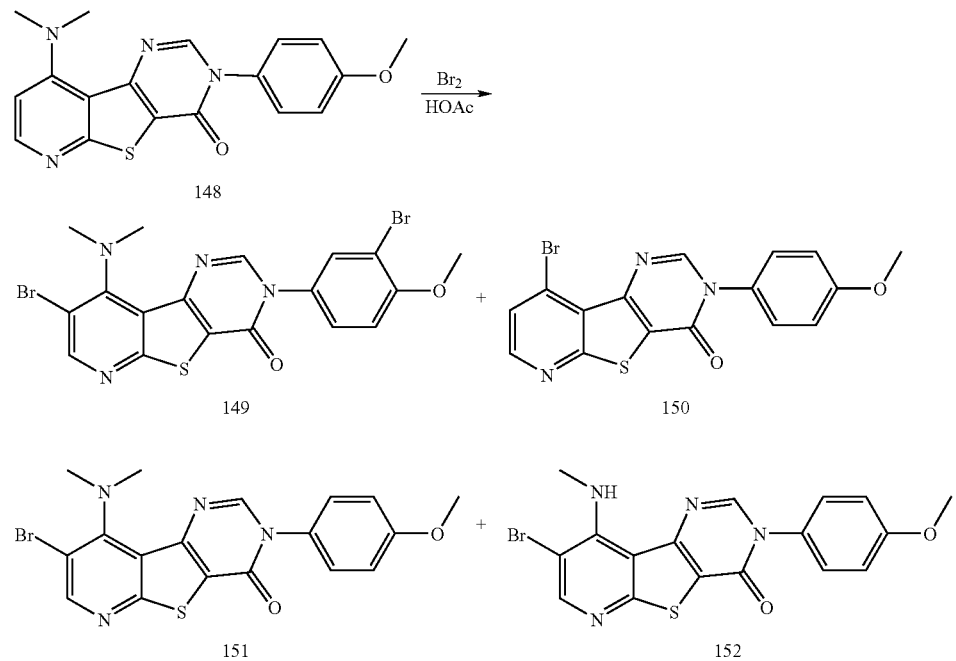

To a solution of compound 148 (4.70 g, 0.0134 mol) in acetic acid (60 mL) was added bromine (1.4 mL, 0.0267 mol) and the mixture heated at reflux overnight. The solvent was then evaporated under reduced pressure leaving a solid residue to which was added water. This mixture was basified using concentrated ammonium hydroxide and extracted with dichloromethane, dried ($Na_2SO_4$), filtered and evaporated under reduced pressure. Purification by column chromatography on silica gel followed by preparative TLC led to the isolation of compounds 149-152. Compound 149: $^1$H NMR ($CDCl_3$): δ 8.60 (s, 1H), 8.19 (s, 1H), 7.62 (d, 1H), 7.37 (dd, 1H), 7.02 (d, 1H), 3.94 (s, 3H), 3.20 (s, 6H). Compound 150: $^1$H NMR ($CDCl_3$): δ 8.51 (d, 1H), 8.31 (s, 1H), 7.69 (d, 1H), 7.33 (d, 2H), 7.03 (d, 2H), 3.85 (s, 3H). Compound 151: $^1$H NMR ($CDCl_3$): δ 8.60 (s, 1H), 8.22 (s, 1H), 7.33 (d, 2H), 7.02 (d, 2H), 3.84 (s, 3H), 3.21 (s, 6H). MS m/z calcd. for $C_{18}H_{16}BrN_4O_2S^+$=433.0; found m/z=433.1 ($M^{+1}$). Compound 41: $^1$H NMR (DMSO-$d_6$): δ 8.58 (s, 1H), 8.38 (s, 1H), 8.30 (m, 1H), 7.44 (d, 2H), 7.06 (d, 2H), 3.78 (s, 3H), 3.38 (d, 3H). MS m/z calcd. for $C_{17}H_{14}BrN_4O_2S^+$=419.0; found m/z=419.1 ($M^{+1}$).

Method CN:

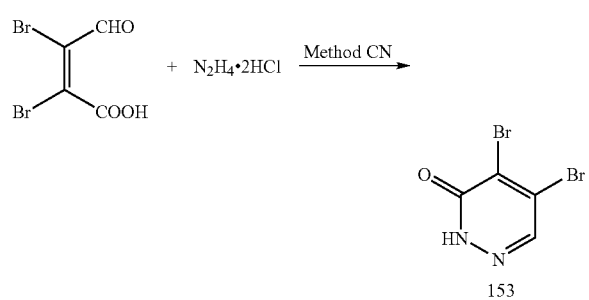

The mixture of mucobromic acid (5.0 g, 0.019 mol), hydrazine dihydrochloride (2.13 g, 0.020 mol) and sodium acetate (3.97 g, 0.048 mol) in water (30 mL) was heated to 100° C. for 16 hours. The reaction mixture was cooled to room temperature. The precipitated solid was collected by filtration and dried over vacuum to afford the crude solid 153 (2.58 g). $^1$H NMR ($CD_3OD$) δ 8.02 (s, 1H). MS m/z calcd. for $C_4H_3Br_2N_2O^+$=254.88; found m/z=254.96.

Method CO:

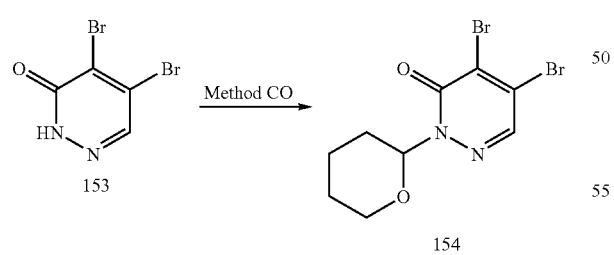

The mixture of 153 (2.58 g, 0.01 mol), dihydropyran (1.4 mL, 0.015 mol), p-toluenesulfonic acid monohydrate (0.19 g, 0.001 mol) and 30 mL THF was heated to reflux for 24 hours. Additional dihydropyran (2.8 mL, 0.030 mol) was added at 16 hours. The reaction mixture was allowed to cool to room temperature and concentrated in-vacuo to an oily residue. The residue was taken up in ethyl acetate (100 mL) and washed with sodium bicarbonate solution (50 mL). The organic layer was washed with Brine (50 mL) and dried with sodium sulfate. The solvent was removed in-vacuo to give an oily residue. The residue was purified by flash chromatography eluting with 0-40% ethyl acetate/hexane to afford 154 (2.96 g). MS m/z calcd. for $C_9H_{11}Br_2N_2O^+$=339.0; found m/z=338.93.

Method CP:

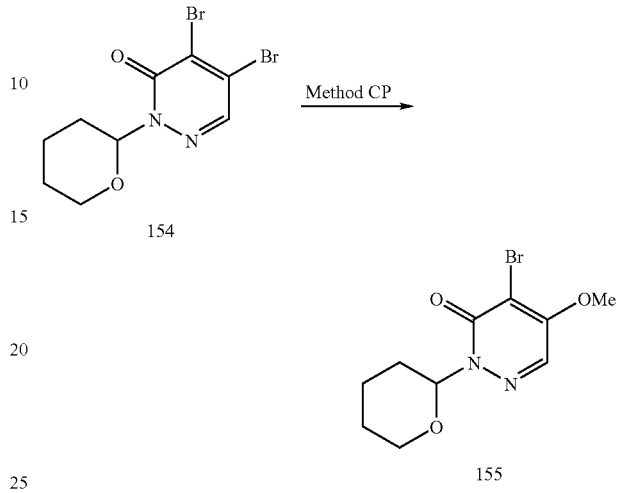

Compound 154 (1.5 g, 0.0044 mol) was dissolved in 10 mL methanol and cooled to OC. To this solution was added 25% sodium methoxide in methanol (1.02 mL, 0.0044 mol). The reaction mixture was allowed to stir for additional 2 hours at room temperature. The solvent was evaporated to give a residue. This residue was taken up in ethyl acetate (100 mL) washed with water (50 mL) and then brine (50 mL). The organic layer was dried with sodium sulfate and evaporated to afford the crude 155. $^1$H NMR ($CDCl_3$) δ 7.75 (s, 1H), 6.04 (dd, 1H), 4.05 (d, 1H), 4.00 (s, 3H), 3.69 (t, 1H), 2.15-1.98 (m, 2H), 1.69-1.65 (m, 4H).

Method CQ:

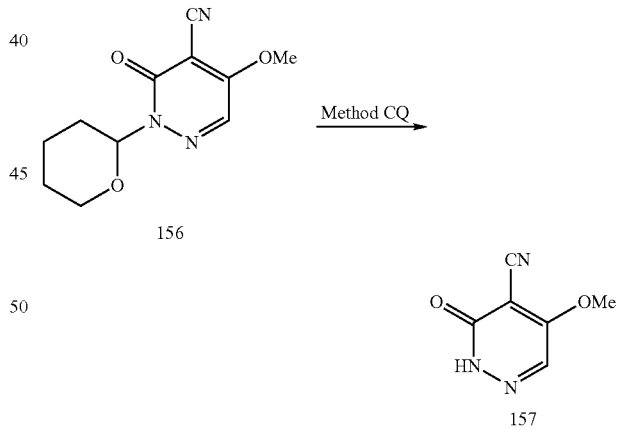

Compound 156 (0.58 g, 0.0025 mol) and 4 mL methanol was added 6N HCl (8 mL) and heated to reflux for 1 hour. The reaction mixture was allowed to cool to room temperature. The solvent was evaporated in-vacuo. The residue was taken up in ethyl acetate (50 mL), then washed with saturated sodium bicarbonate (25 mL). The aqueous layer was extracted with ethyl acetate (2×50 mL). The combined organic layer was washed with brine, dried with sodium sulfate and evaporated in-vacuo. The residue was purified by flash column eluting with 0-6% methanol/methylene chloride with 0.5% ammonia hydroxide to afford 157. $^1$H NMR ($CD_3OD$) δ 8.13 (s, 1H), 4.16 (s, 3H). MS m/z calcd. for $C_6H_6N_3O_2^+$=152.12; found m/z=152.10.

The following compound was also prepared using Method CQ:

| Cpd | Structure | Formula | MW | m/z Found (M + 1)+ |
|---|---|---|---|---|
| 165 | 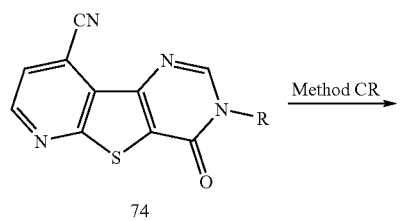 | C15H10N4O2S | 310.3 | 311.1 |

Method CR:

![Method CR scheme showing compound 74 converted via Method CR]

To a solution of 74 (0.1 g, 0.314 mmol) in con HCl (1 mL) was added anhydrous tin chloride (0.1 g, 0.527 mmol) and heated at 70° C. for one hour. The excess HCl was removed in vacuo and redissolved in DCM. The product was isolated by preparative reverse phase HPLC using acetonitrile/water as the eluent to get compound 168. $^1$H NMR (CDCl$_3$): 8.8 (d, 1H), 8.67 (s, 1H), 8.60 (m, 1H), 7.7 (d, 1H), 7.39 (m, 3H), 4.8 (s, 2H), 2.35 (s, 3H). Mass Spectrum (M$^+$+1) m/z calcd. for C$_{17}$H$_{15}$N$_4$OS$^+$=323.10, found m/z=323.2

Method CS:

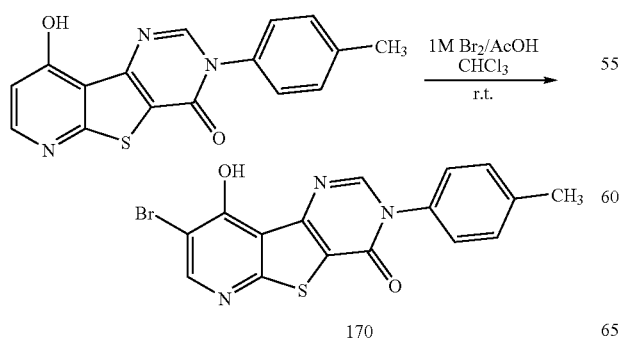

The 1M Br$_2$/AcOH (17.80 mls, 17.80 mmol) was added dropwise to a stirring suspension of phenol (5.00 g, 16.20 mmol) in glacial AcOH (500 mls) at room temperature. The reaction was continued to be stirred at room temperature for 6 hrs. The AcOH was evaporated under vacuum. The solid was taken up with CH$_2$Cl$_2$ (2×100 mls) and evaporated each time. The product 170 was fully dried to a powder (7.07 g, 97%) (obtained as the acetic acid salt). MS (M+1)$^+$ m/z calcd for C$_{16}$H$_{11}$BrN$_3$O$_2$S$^+$=389.2, observed m/z=389.9

Method CT:

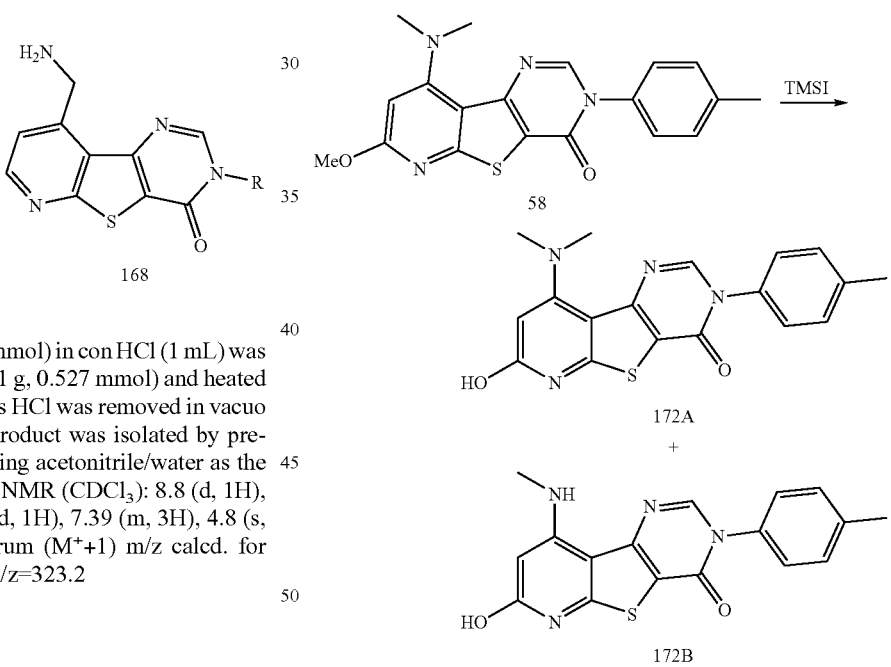

To a solution of 0.013 g (0.040 mmol) of compound 58 in 5 mL of 1,2-dichloroethane was added 0.3 mL (excess) of iodotrimethylsilane. The mixture was stirred at 60° C. for 5 h and cooled to room temperature. It was quenched with 5 mL of methanol and concentrated. The residue was purified by preparative TLC eluting with 7% methanol in methylene chloride to give 0.002 g of compound 172A. Calcd MS for C$_{17}$H$_{15}$N$_4$O$_2$S=353.1; found m/z=353.2. And 0.002 g of Compound 172B. Calcd MS for C$_{16}$H$_{18}$ClN$_4$OS=339.1; found m/z=339.2

Method CU:

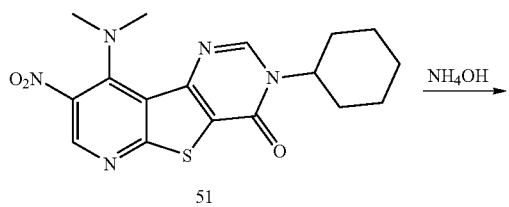

A solution of 0.11 g (0.3 mmol) of compound 51 and 0.5 mL of 28% aqueous ammonium hydroxide in 5 mL of MeCN in a sealed tube was stirred at 100° C. for 3 h, and cooled to room temperature. It was liluted with 4 mL of methanol and filtered to give 0.074 g of compound. Compound 174, Calcd MS for $C_{15}H_{16}N_5O_3S$=346; found m/z=346.1

Method CV:

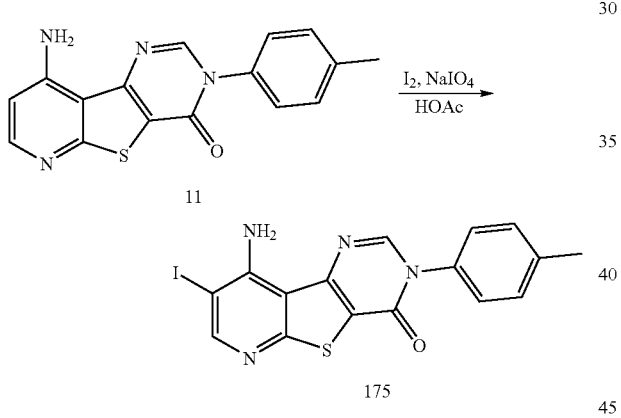

To a suspension of 0.031 g (0.12 mmol) of compound 11 in 5 mL of acetic acid were added a solution of 0.026 g (0.1 mmol) of iodine and 0.022 g (0.1 mmol) of sodium periodate. The mixture was stirred at the same temperature for 2 days, and concentrated. The residue was purified by chromatography eluting with 1% to 3% methanol in methylene chloride to give 0.021 g of compound 175. Calcd MS for $C_{16}H_{12}IN_4OS$=435.0; found m/z=435.1

Method CW:

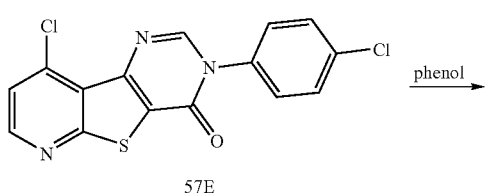

-continued

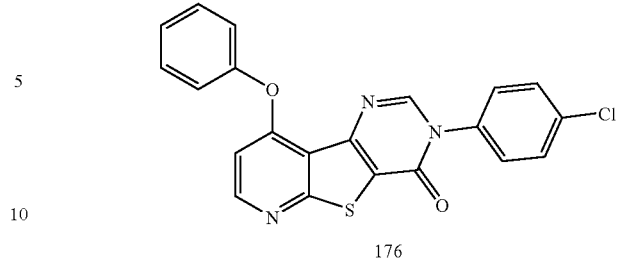

A mixture of 0.63 g (0.18 mmol) of compound 57E and 2 g of phenol was stirred at 120° C. for 18 h and 140° C. for 4 h. It was concentrated; the residue was purified by preparative TLC eluting with 3% methanol in methylene chloride to give 0.028 g of compound 176. Calcd MS for $C_{21}H_{13}ClN_3O_2S$=372.2; found m/z=406.2

Method CX:

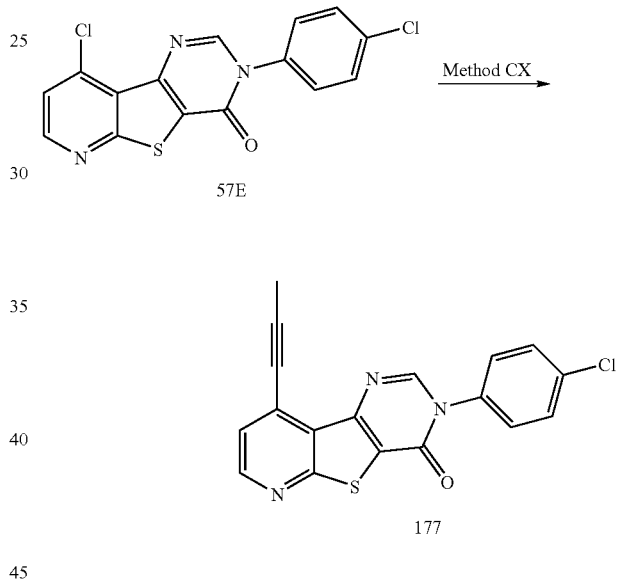

A mixture of 0.050 g (0.14 mmol) of compound 57E, 0.07 g (0.22 mmol) of 1-propargyltributyltin, and 0.06 g (0.49 mmol) of diisopropylethylamine, and 0.02 g of Pd(PPh₃)₄ in 3 mL of toluene and 2 mL of trifluoromethylbenzene in a sealed tube was heated at 180° C. for 40 min (in microwave, personalChemistry). It was concentrated, the residue was purified by preparative TLC eluting with 4% methanol in methylene chloride to give 0.034 g of compound 177. Calcd MS for $C_{18}H_{11}ClN_3OS$=352.0; found m/z=352.2

Method CY:

A mixture of 0.24 g (0.7 mmol) of compound 57E, 0.37 g (1.1 mmol) of allyltributyltin, and 0.27 g (2.1 mmol) of diisopropylethylamine, and 0.06 g of Pd(PPh₃)₄ in 3 mL of toluene and 2 mL of trifluoromethylbenzene in a sealed tube was heated at 180° C. for 40 min (in microwave, personalChemistry). It was concentrated, the residue was purified by chromatography eluting with 4% methanol in methylene chloride to give 0.034 g of compound 178A. Calcd MS for $C_{18}H_{13}ClN_3OS$=354.1; found m/z=354.2.

The following compounds were prepared using method CY:

| Cpd | Structure | Formula | MW | m/z Found (M + 1)+ |
|---|---|---|---|---|
| 178A | 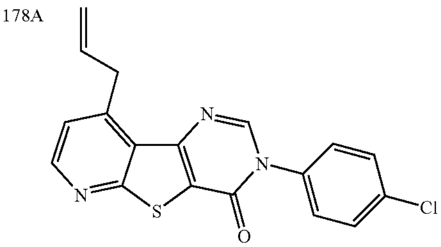 | C18H12ClN3OS | 353.8 | 354.2 |
| 178B | 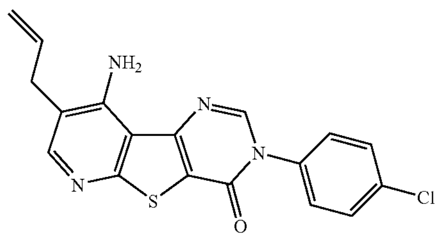 | C18H13ClN4OS | 368.8 | 369.2 |

Method CZ:

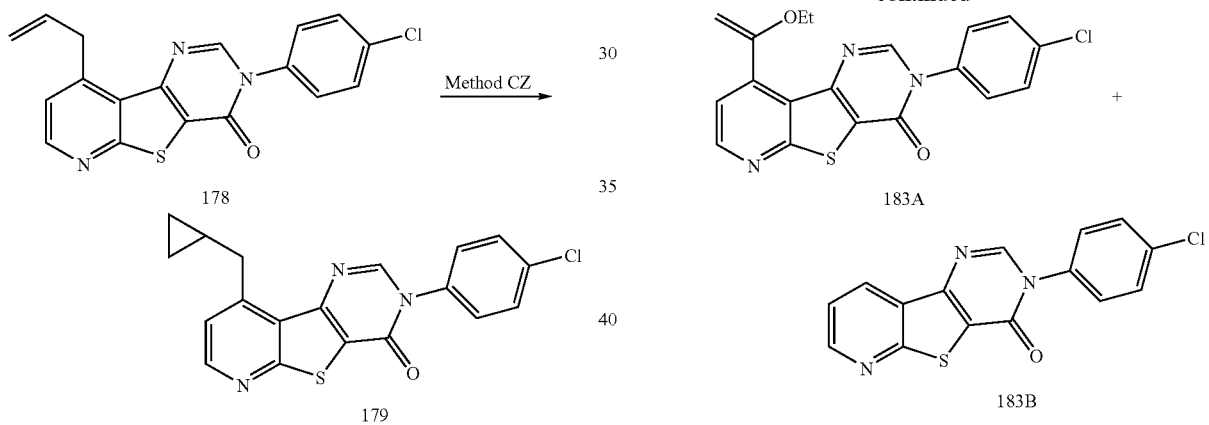

To a solution of 0.1 mL (1.36 mmol) of chloroiodomethane in 3 mL of 1,2-dichloroethane was added 1 mL (1.0 mmol) of diethylzinc in ether. After 5 min, a solution of 0.03 g (0.1 mmol) of compound 178 in 2 mL of dichloroethane was added. the mixture was stirred at room temperature for 30 min, and quenched with 1 mL of methanol. It was concentrated, the residue was purified by preparative TLC eluting with 4% methanol in methylene chloride to give 0.04 g of compound 179. Calcd MS for $C_{19}H_{15}ClN_3OS$=368.1; found m/z=368.2.

Method DA:

A mixture of 0.28 g (0.6 mmol) of compound 182, 0.33 g (1.1 mmol) of ethoxyvinyltributyltin, and 0.23 g (1.8 mmol) of diisopropylethylamine, and 0.04 g of Pd(PPh₃)₄ in 4 mL of toluene and 1 mL of trifluoromethylbenzene in a sealed tube was heated at 140° C. for 1 min (in microwave, personalChemistry). It was concentrated, the residue was purified by chromatography eluting with 1% to 4% methanol in methylene chloride plus 1% ammonium hydroxide to give 0.106 g of compound 183A. Calcd MS for $C_{19}H_{15}ClN_3O_2S$=384.1; found m/z=384.2. and 0.047 g of compound 183B Calcd MS for $C_{15}H_9ClN_3OS$=314.1; found m/z=314.2.

Method DB:

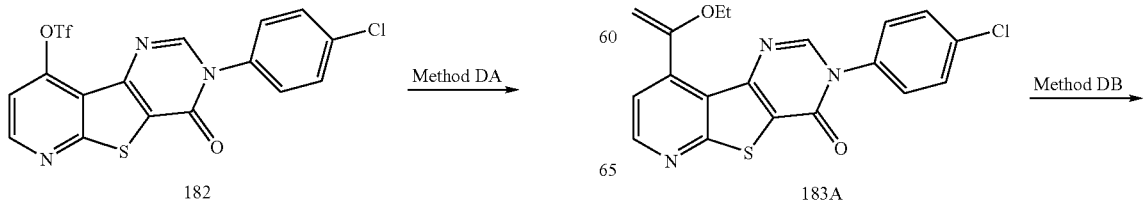

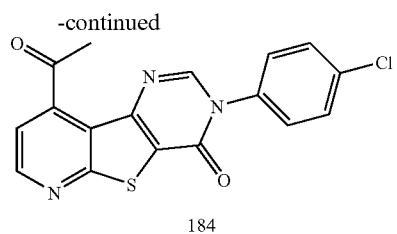

184

A mixture of 0.1 g (0.26 mmol) of compound 183A 1 mL of conc. HCl in 8 mL of THF was stirred at reflux for 18 h and concentrated. The residue was purified by preparative TLC eluting with 5% methanol in methylene chloride to give 0.073 g of compound 184. Calcd MS for $C_{17}H_{11}ClN_3O_2S=356.0$; found m/z=356.2.

Method DC:

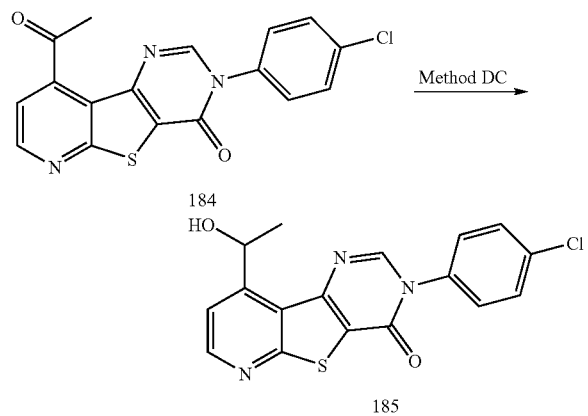

184

185

To a suspension of 0.015 g (0.04 mmol) of compound 184 in 15 mL of methanol was added 0.004 g (0.1 mmol) of sodium borohydride slowly. The reaction was monitored by TLC and quenched with 1 drop of 37% aqueous HCHO. It was concentrated; the residue was purified by preparative TLC eluting with 6% methanol in methylene chloride to give 0.011 g of compound 185. Calcd MS for $C_{17}H_{13}ClN_3O_2S=358.0$; found m/z=358.2

Method DD:

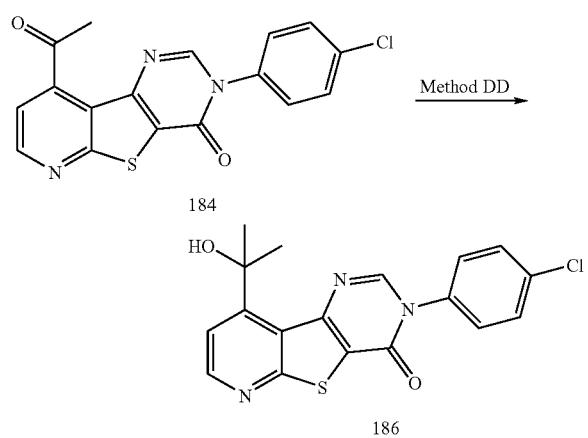

184

186

To a suspension of 0.03 g (0.08 mmol) of compound 184 in 3 mL of THF was added 0.4 mL (0.12 mmol) of methylmagnesiumbromide in ether at −78° C. The reaction was stirred for 20 min and quenched with 1 mL of methanol It was concentrated; the residue was purified by preparative TLC eluting with 5% methanol in methylene chloride to give 0.027 g of compound 186. Calcd MS for $C_{18}H_{15}ClN_3O_2S=372.0$; found m/z=372.2.

Method DE:

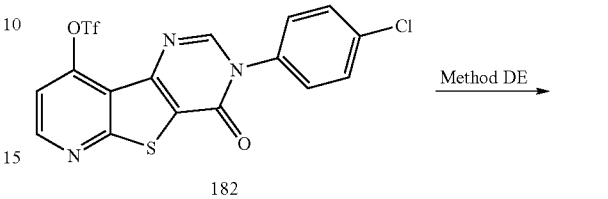

182

187

A mixture of 0.046 g (0.1 mmol) of compound 182, 0.1 g (0.12 mmol) of cyclopropylboronic acid, 0.036 g (0.4 mmol) of potassium fluoride dehydrate, 0.1 g (0.1 mmol) of sodium bromide and 0.1 g of $Pd(PPh_3)_4$ in 3 mL of toluene in a sealed tube was stirred at 100° C. for 3 h. It was diluted with 10 mL of methylene chloride and filtered. The filtrate was concentrated; the residue was purified by preparative TLC eluting with 5% methanol in methylene chloride to give 0.029 g of compound 187. Calcd MS for $C_{18}H_{13}ClN_3OS=354.1$; found m/z=354.2.

Method DF:

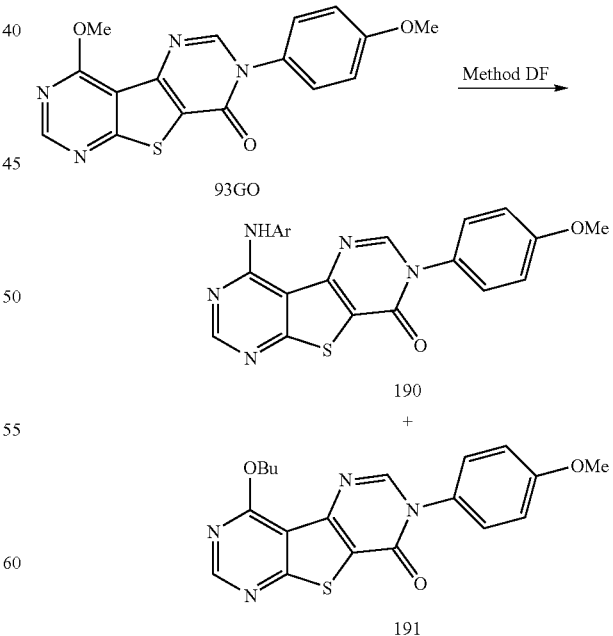

93GO

190

+

191

To a stirred solution of 0.044 g (0.4 mmol) of 4-fluoroaniline in 5 mL of THF was added 0.25 mL (0.4 mmol) of n-BuLi in hexanes at 0° C. After 20 min, 0.068 g (0.2 mmol) of compound 93GO was added. The mixture was stirred at reflux for 4 h, and concentrated. The residue was purified preparative TLC eluting with 5% methanol in methylene chloride to give 0.01 g of compound 190A. Calcd MS for $C_{21}H_{15}FN_5O_2S$=420.1; found m/z=420.2 and 0.004 g of compound 191: Calcd MS for $C_{19}H_{19}N_4O_3S$=383.1; found m/z=383.2

The following compounds were prepared using Method DF:

| Cpd | Structure | Formula | MW | m/z Found (M + 1)+ |
|---|---|---|---|---|
| 190A | 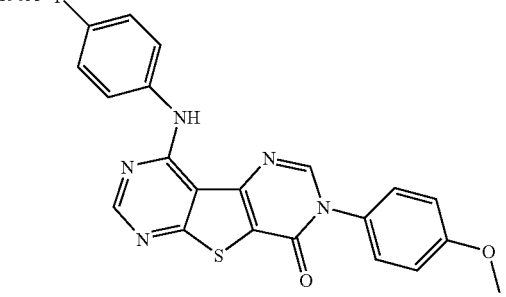 | C21H14FN5O2S | 419.4 | 420.2 |
| 190B | 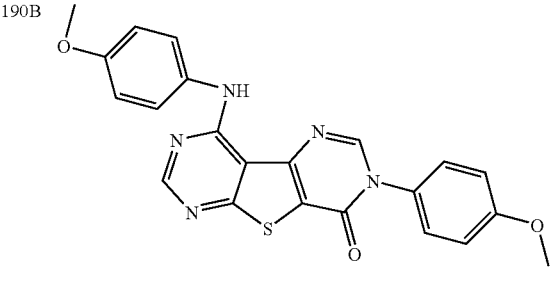 | C22H17N5O3S | 431.5 | 432.2 |
| 190C | 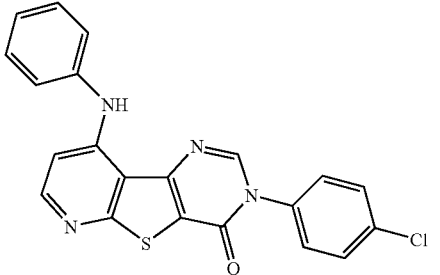 | C21H13ClN4OS | 404.9 | 405.2 |
| 190D | 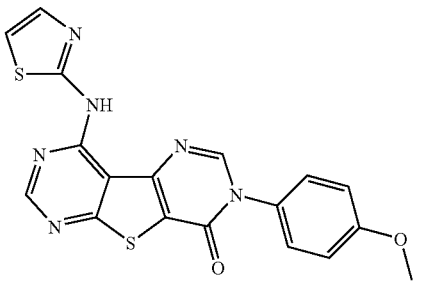 | C18H12N6O2S2 | 408.5 | 408.2 |

-continued

| Cpd | Structure | Formula | MW | m/z Found (M + 1)+ |
|---|---|---|---|---|
| 190E | 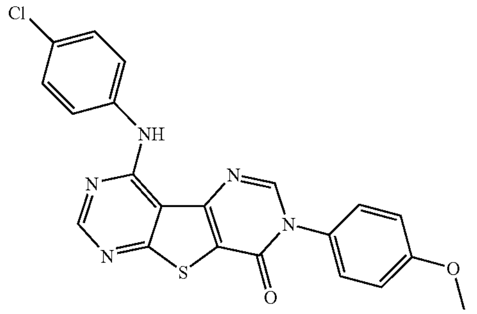 | C21H14ClN5O2S | 435.9 | 436.2 |
| 190F | 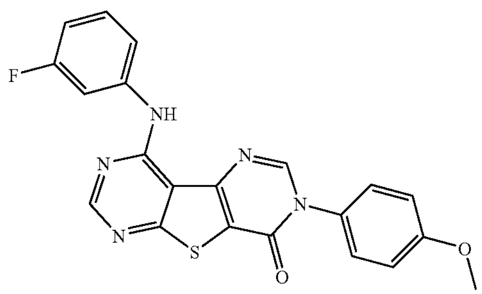 | C21H14FN5O2S | 419.4 | 420.2 |
| 190G | 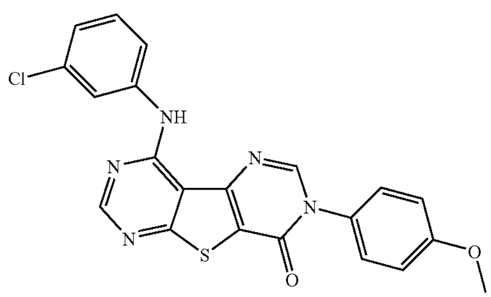 | C21H14ClN5O2S | 435.9 | 436.2 |
| 190H | 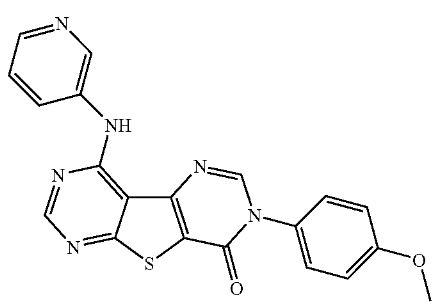 | C20H14N6O2S | 402.4 | 403.2 |
| 190I | 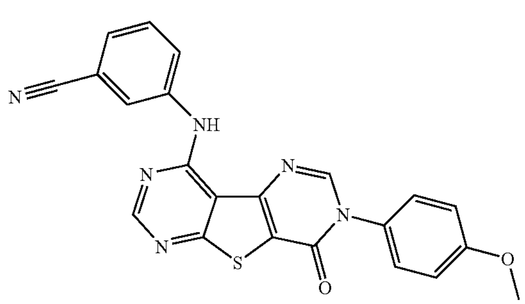 | C22H14N6O2S | 426.5 | 427.2 |

-continued
| Cpd | Structure | Formula | MW | m/z Found (M + 1)+ |
|---|---|---|---|---|
| 190J | 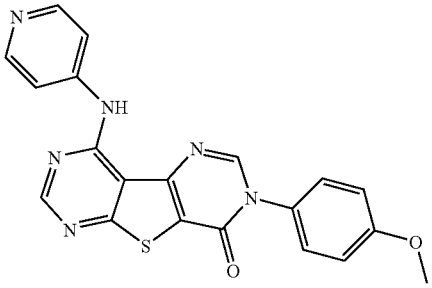 | C20H14N6O2S | 402.4 | 403.2 |
| 190K | 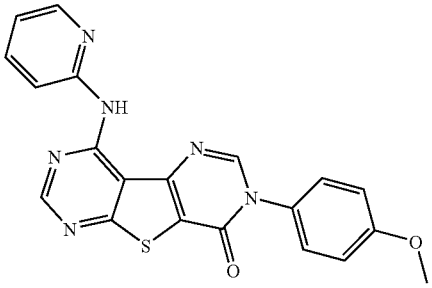 | C20H14N6O2S | 402.4 | 403.2 |
| 190L | 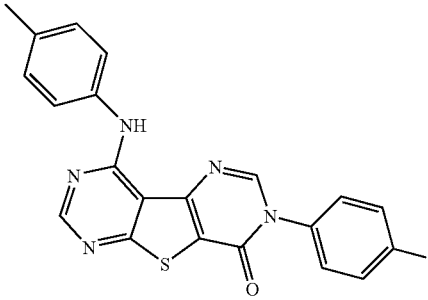 | C22H17N5O2S | 415.5 | 416.2 |
| 190M | 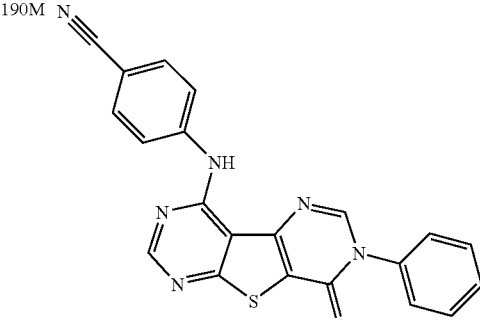 | C22H14N6O2S | 426.5 | 427.2 |
| 190N | 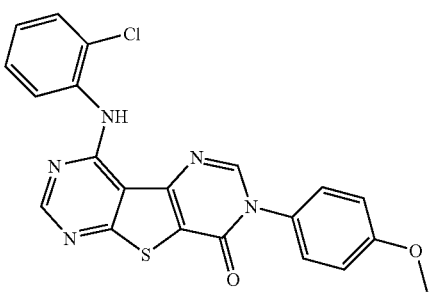 | C21H14ClN5O2S | 435.9 | 436.2 |

| Cpd | Structure | Formula | MW | m/z Found (M + 1)+ |
|---|---|---|---|---|
| 191 | 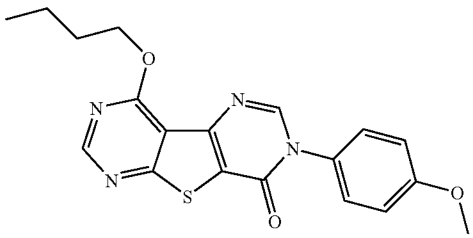 | C19H18N4O3S | 382.4 | 383.2 |

Method DG:

Method DH:

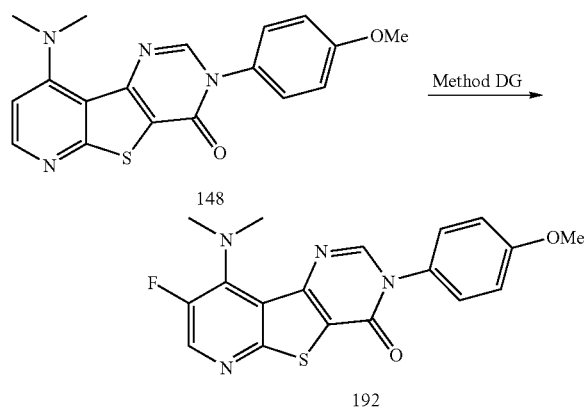

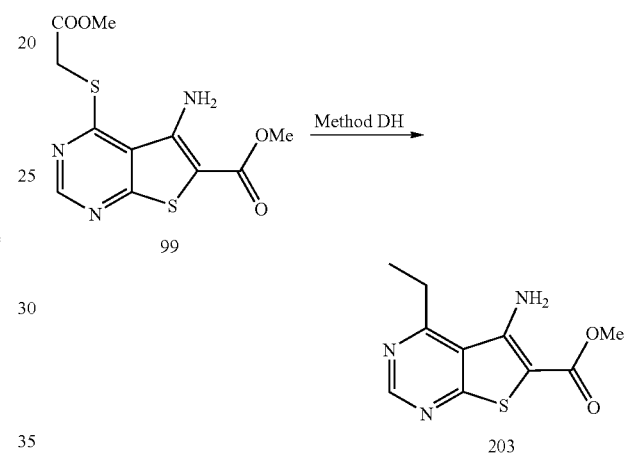

To a stirred solution of 0.018 g (0.05 mmol) of compound 148 in 4 mL of MeCN was added 0.036 g (0.1 mmol) of Selectfluor. The mixture was stirred at room temperature for 2 h and concentrated. The residue was purified preparative TLC eluting with 5% methanol in methylene chloride to give 0.002 g of compound 192. Calcd MS for $C_{18}H_{15}FN_4O_2S$=371.1; found m/z=371.2

The following compounds were prepared using Method DG:

To a stirred suspension of 2.0 g (6.38 mmol) of compound 99 and 0.1 g of Pd(PPh$_3$)$_4$ in 40 mL of THF was added 20 mL (20 mmol) of diethylzinc in hexanes at room temperature. The mixture was stirred at reflux for 1.5 h, cooled to room temperature, and quenched with 15 mL of saturated sodium bicarbonate. It was diluted with 300 mL of methylene chlo-

| Cpd | Structure | Formula | MW | m/z Found (M + 1)+ |
|---|---|---|---|---|
| 192 | 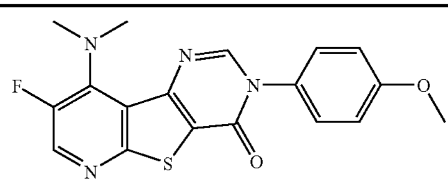 | C18H15FN4O2S | 370.4 | 371.2 |
| 193 | | C16H11ClN4OS | 342.8 | 343.2 | ride, filtered through a pad of celite. The filtrate was concentrated; the residue was purified by chromatography eluting with 1% to 5% methanol in methylene chloride plus 1% ammonium hydroxide to give 0.7 g of compound 203. Calcd MS for $C_{10}H_{12}N_3O_2S$=238.1; found m/z=238.1.

Method DI:

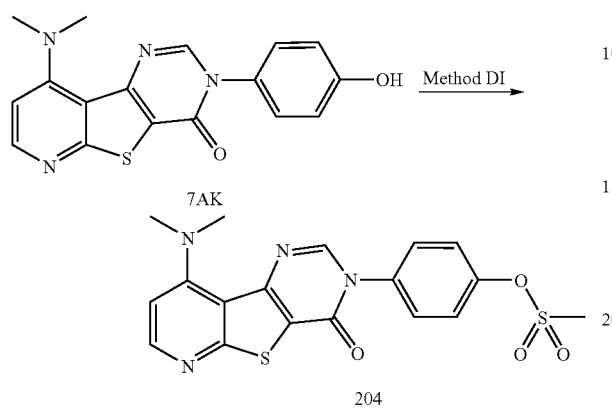

To a solution of compound 7AK (0.143 g, 0.0004 mol) and diisopropylethylamine (0.11 mL, 0.0007 mol) in CH2Cl2 (5 mL) was added methylsulfonyl chloride (0.05 mL, 0.0006 mol) dropwise at RT. After 1 h, the mixture was transferred to a preparative TLC and Eluted using 10% acetone in dichloromethane to product. $^1$H NMR (CDCl$_3$): δ 8.46 (br.s, 1H), 8.29 (s, 1H), 7.50 (m, 2H), 7.30 (m, 2H), 6.83 (br.s, 1H), 3.12 (s, 6H). Mass spectrum (M$^{+1}$): 417.2

Method DJ:

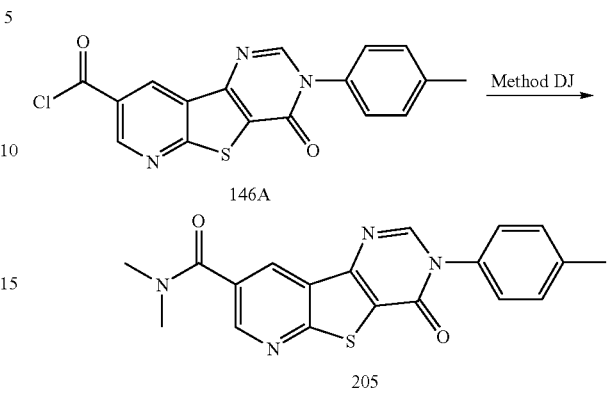

To a solution of acyl chloride 146A in dichloromethane (10 mL) at RT under nitrogen atmosphere, was added dimethylamine (2 mL, 40% solution in water). After 30 min., water was added and the mixture extracted with $CH_2Cl_2$, dried ($Na_2SO_4$), filtered and evaporated under vacuum. Solid residue was then tritrated in ether and filtered to give product 205A. $^1$H NMR (CDCl$_3$): δ 8.86 (s, 1H), 8.61 (s, 1H), 8.24 (s, 1H), 7.34 (d, 2H), 7.31 (d, 2H), 3.16 (s, 3H), 3.07 (s, 3H), 2.42 (s, 3H). Mass spectrum (M$^{+1}$): 365.1

The following compounds were prepared using Method DJ:

| Cpd | Structure | Formula | MW | m/z Found (M + 1)$^+$ |
|---|---|---|---|---|
| 205A | 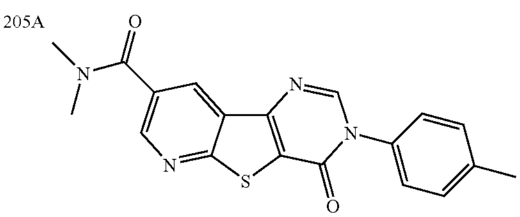 | C19H16N4O2S | 364.4 | 365.1 |
| 205B | 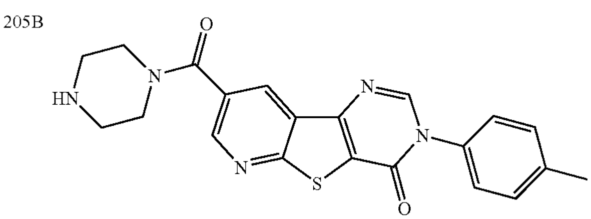 | C21H19N5O2S | 405.5 | 406.2 |
| 205C | 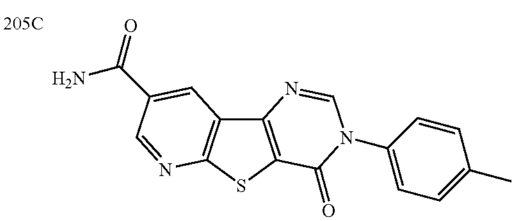 | C17H12N4O2S | 336.4 | 337.1 |

Method DK:

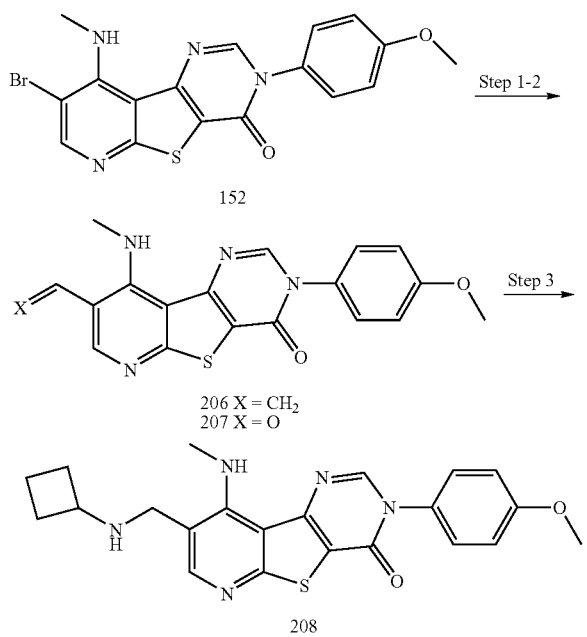

Step 1: A mixture of compound 152 (1.83 g, 0.0044 mol), vinyltributyltin (1.52 g, 0.0048 mol) and tetrakis(triphenylphosphine)palladium (0.25 g, 0.00022 mol) in toluene (50 ml) was heated at reflux under a nitrogen atmosphere for 1 h. This was then cooled to room temperature, evaporated the solvent and purified by column eluted using dichloromethane/ethyl acetate to give the product 206. Mass spectrum $(M^{+1})$: m/z=365.07

Step 2: To a suspension compound 206 (0.23 g, 0.6 mmol) in THF/water (2:1), was added $OSO_4$ (0.4 mL, 4% wt in water). After 5 min., $NaIO_4$ (0.14 g, 0.0006 mol) was added and mixture stirred at RT overnight. Added 10% $Na_2SO_3$ solution and extracted by dichloromethane (100 mL×2) dried $(Na_2SO_4)$, filtered and evaporated to give product 207. Mass spectrum $(M^{+1})$: m/z=366.99.

Step 3: A mixture of compound 207 (0.2 g, 0.00055 mol), cyclobutylamine (0.1 mL) and $Na(OAc)_3BH$ (0.19 g, 0.87 mmol) in dichloromethane (20 ml) was stirred at RT under a nitrogen atmosphere for 24 h. Added a NaOH solution (1M) and extracted with dichloromethane (100 mL×3), dried $(Na_2SO_4)$, filtered and evaporated under vacuum. Purification prep TLC using 4% methanol in dichloromethane followed tritration in ether to give the product 208 after filtration. $^1H$ NMR (DMSO-$d_6$): δ 8.59 (s, 1H), 8.29 (m, 1H), 8.08 (s, 1H), 7.48 (d, 2H), 7.10 (d, 2H), 4.08 (m, 1H), 3.82 (s, 3H), 3.41 (d, 3H), 3.20 (m, 1H), 3.14 (d, 2H), 2.08 (m, 2H), 1.45-1.75 (m, 4H). Mass spectrum $(M^{+1})$: m/z=422.2.

The following compounds were prepared using Method F (Alternate 1):

| Cpd | Structure | Formula | MW | m/z Found $(M + 1)^+$ |
|---|---|---|---|---|
| 180 | 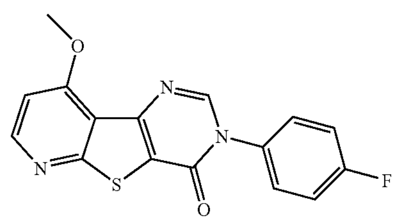 | C16H10FN3O2S | 327.3 | 328.2 |
| 28FR | 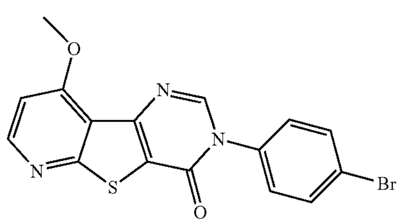 | C16H10BrN3O2S | 388.2 | 388.2 |
| 28FS | 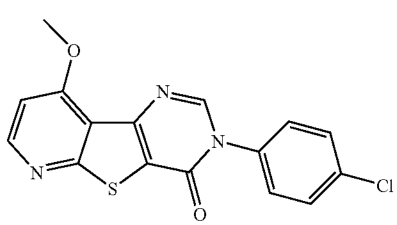 | C16H10ClN3O2S | 343.8 | 344.2 |

-continued
| Cpd | Structure | Formula | MW | m/z Found (M + 1)+ |
|---|---|---|---|---|
| 28FT | 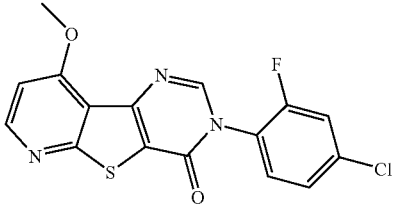 | C16H9ClFN3O2S | 361.8 | 362.2 |
| 28FU | 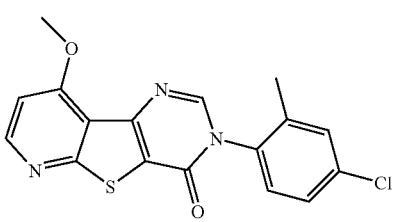 | C17H12ClN3O2S | 357.8 | 358.2 |
| 28FV | 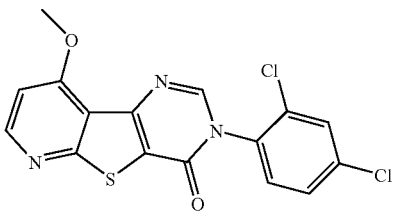 | C16H9Cl2N3O2S | 378.2 | 378.2 |
| 28FW | 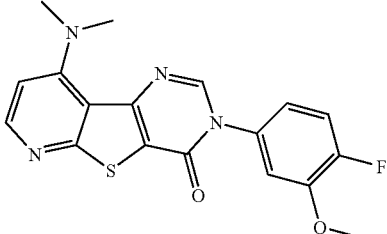 | C18H15FN4O2S | 370.4 | 371.1 |
| 28FX | 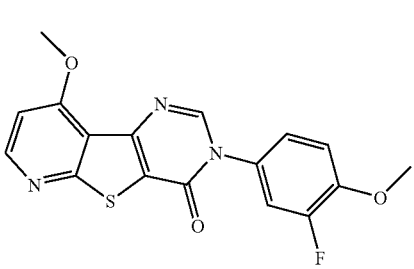 | C17H12FN3O3S | 357.4 | 358.2 |
| 28FY | 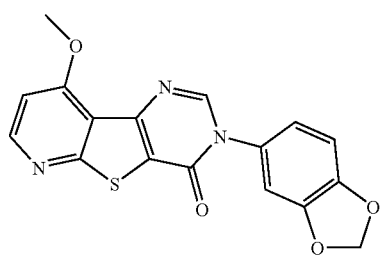 | C17H11N3O4S | 353.4 | 354.2 |

-continued

| Cpd | Structure | Formula | MW | m/z Found (M + 1)+ |
|---|---|---|---|---|
| 28FZ | 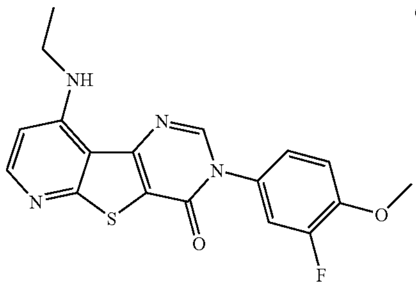 | C18H15FN4O2S | 370.4 | 371.2 |

The following compounds were prepared using Method F (Alternate 2):

| Cpd | Structure | Formula | MW | m/z Found (M + 1)+ |
|---|---|---|---|---|
| 25E | 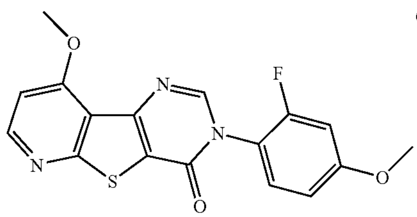 | C17H12FN3O3S | 357.4 | 358.2 |
| 25F | 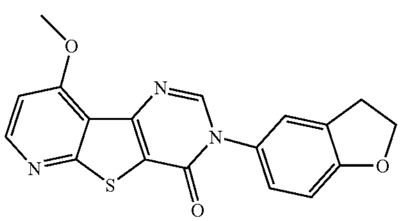 | C18H13N3O3S | 351.4 | 352.2 |
| 25G | 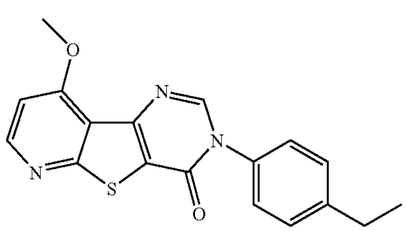 | C18H15N3O2S | 337.4 | 338.2 |

The following compounds were prepared using Method F (Alternate 3):

| Cpd | Structure | Formula | MW | m/z Found (M + 1)+ |
|---|---|---|---|---|
| 95DA | 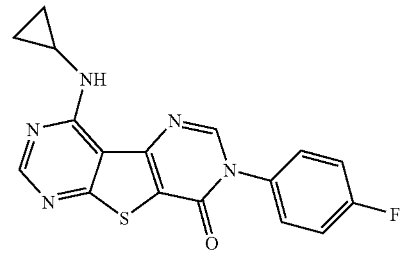 | C17H12FN5OS | 353.4 | 354.2 |
| 95DB | 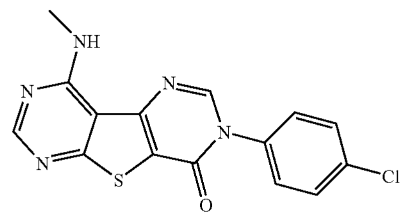 | C15H10ClN5OS | 343.8 | 344.2 |
| 95DC | 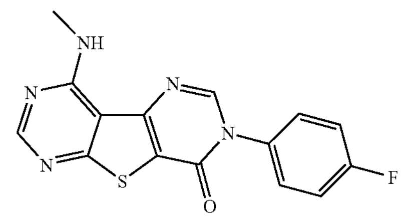 | C15H10FN5OS | 327.3 | 328.2 |
| 95DD | 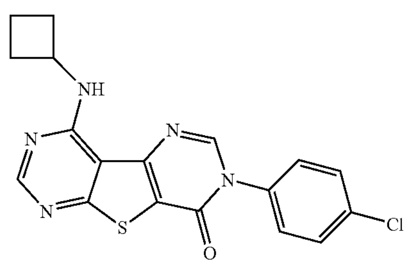 | C18H14ClN5OS | 383.9 | 384.2 |
| 95DE | 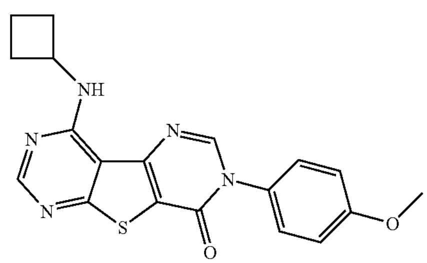 | C19H17N5O2S | 379.4 | 380.2 |
| 95DF | 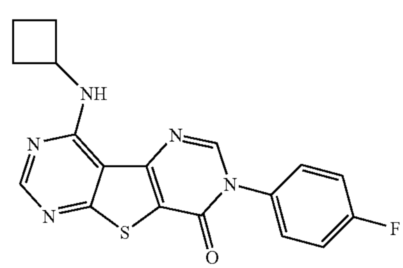 | C18H14FN5OS | 367.4 | 368.2 |

-continued

| Cpd | Structure | Formula | MW | m/z Found (M + 1)+ |
|---|---|---|---|---|
| 95DG | 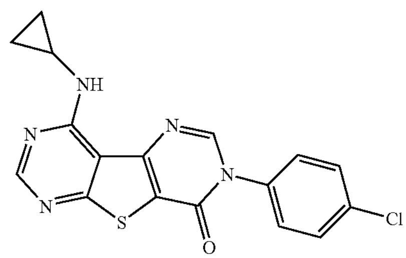 | C17H12ClN5OS | 369.8 | 370.1 |
| 95DH | 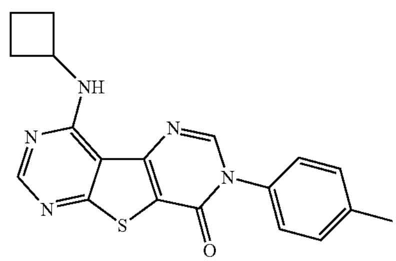 | C19H17N5OS | 363.4 | 364.2 |
| 95DI | 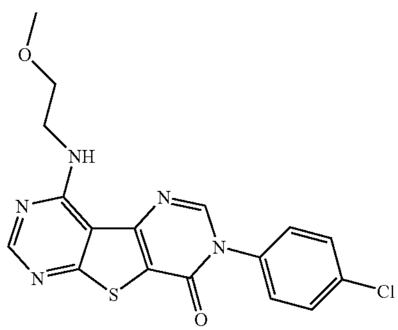 | C17H14ClN5O2S | 387.8 | 388.2 |
| 95DJ | 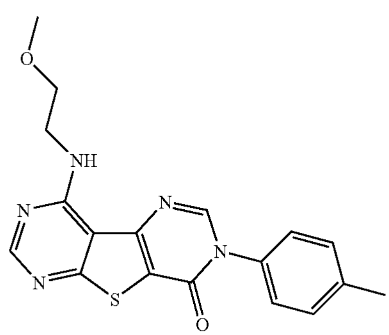 | C18H17N5O2S | 367.4 | 368.1 |
| 95DK | 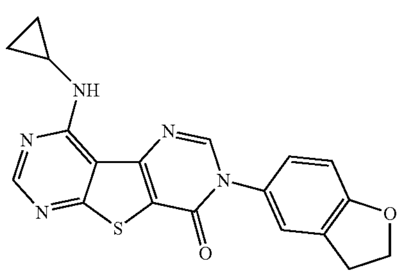 | C19H15N5O2S | 377.4 | 378.1 |

-continued

| Cpd | Structure | Formula | MW | m/z Found (M + 1)+ |
|---|---|---|---|---|
| 95DL | 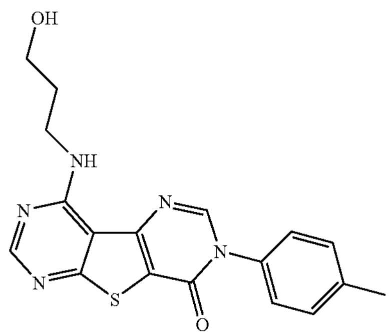 | C18H17N5O2S | 367.4 | 368.2 |
| 95DM | 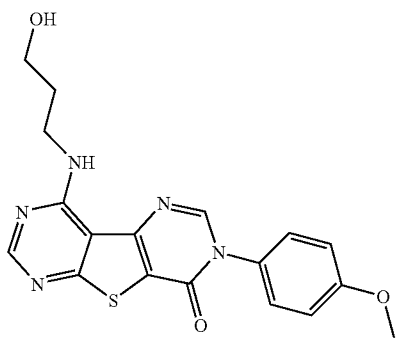 | C18H17N5O3S | 383.4 | 384.2 |
| 95DN | 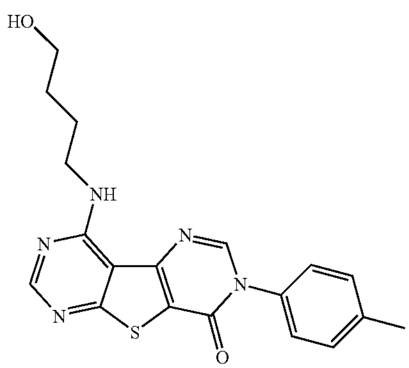 | C19H19N5O2S | 381.5 | 382.2 |
| 95DO | 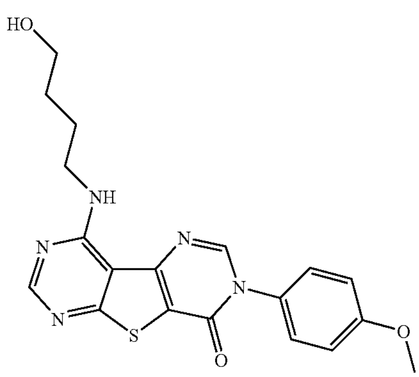 | C19H19N5O3S | 397.5 | 398.2 |

-continued

| Cpd | Structure | Formula | MW | m/z Found (M + 1)+ |
|---|---|---|---|---|
| 95DP | 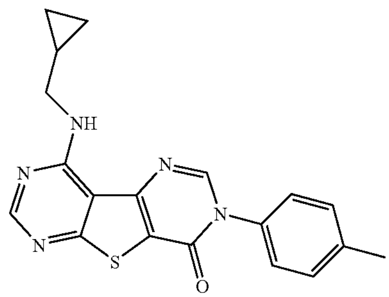 | C19H17N5OS | 363.4 | 364.2 |
| 95DQ | 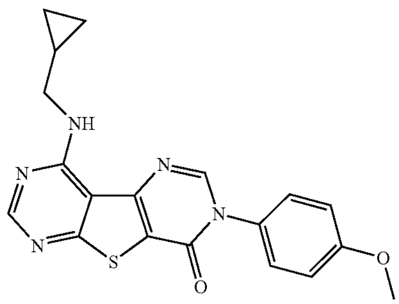 | C19H17N5O2S | 379.4 | 380.2 |
| 95DR | 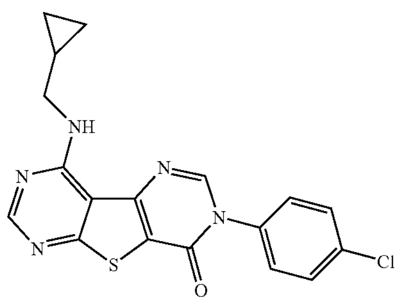 | C18H14ClN5OS | 389.9 | 384.2 |
| 95DS | 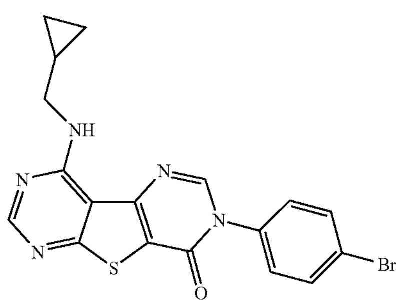 | C18H14BrN5OS | 428.3 | 430.2 |
| 95DT | 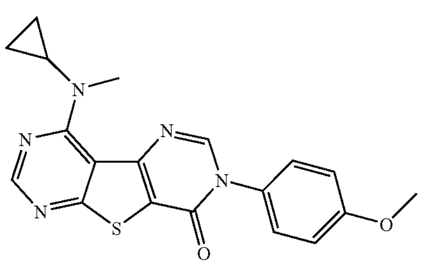 | C19H17N5O2S | 379.4 | 380.2 |

-continued

| Cpd | Structure | Formula | MW | m/z Found (M + 1)+ |
|---|---|---|---|---|
| 95DU | 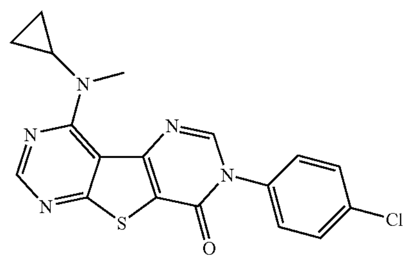 | C18H14ClN5OS | 383.9 | 384.2 |
| 95DV | 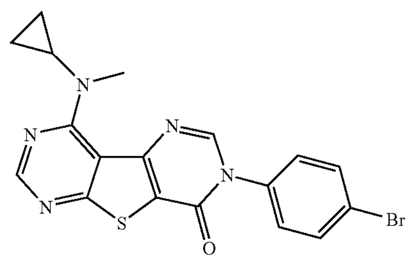 | C18H14BrN5OS | 428.3 | 430.2 |
| 95DW | 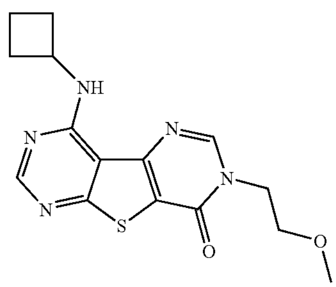 | C15H17N5O2S | 331.4 | 332.2 |
| 95DX | 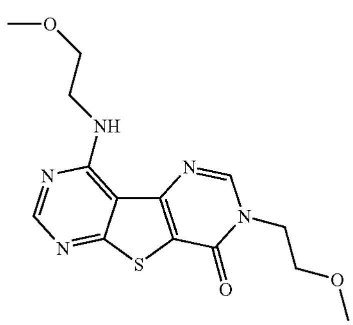 | C14H17N5O3S | 335.4 | 336.2 |
| 95DY | 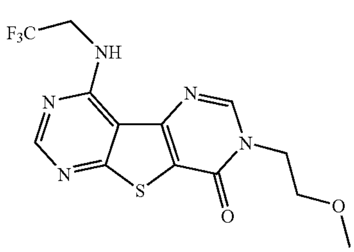 | C13H12F3N5O2S | 359.3 | 360.2 |

| Cpd | Structure | Formula | MW | m/z Found (M + 1)+ |
|---|---|---|---|---|
| 95DZ | 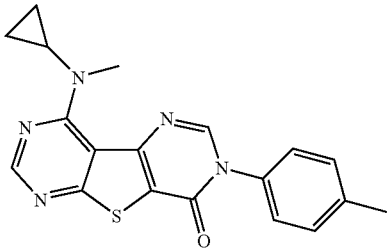 | C19H17N5OS | 363.4 | 364.2 |
| 95EA | 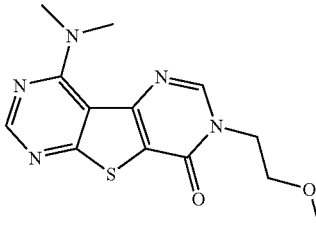 | C13H15N5O2S | 305.4 | 306.2 |
| 95EB | 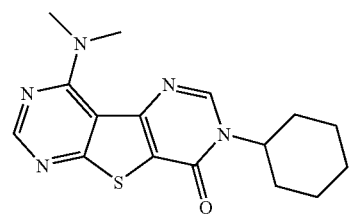 | C16H19N5OS | 329.4 | 330.2 |
| 95EC | 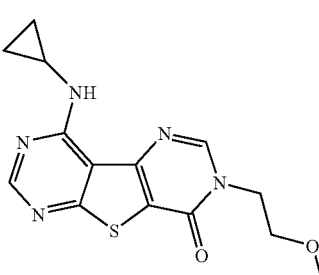 | C14H15N5O2S | 317.4 | 318.2 |
| 95ED | 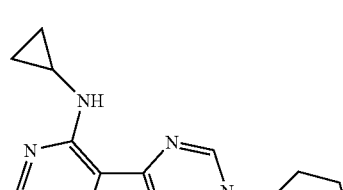 | C17H19N5OS | 341.4 | 342.2 |
| 95EE | 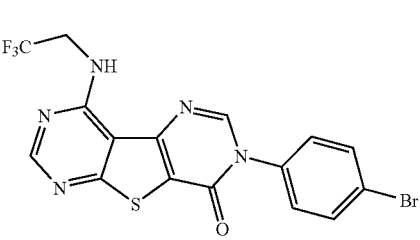 | C16H9BrF3N5OS | 456.2 | 456.3 |

-continued

| Cpd | Structure | Formula | MW | m/z Found (M + 1)+ |
|---|---|---|---|---|
| 95EF | 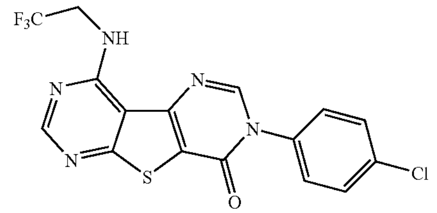 | C16H9ClF3N5OS | 411.8 | 412.2 |
| 95EG | 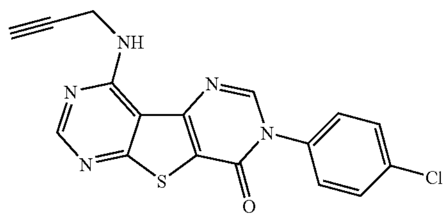 | C17H10ClN5OS | 367.8 | 368.2 |
| 95EH | 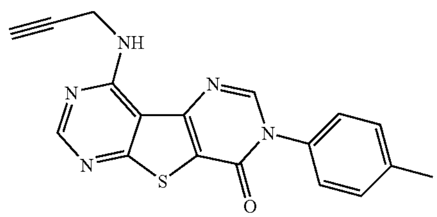 | C18H13N5OS | 347.4 | 348.2 |
| 95EI | 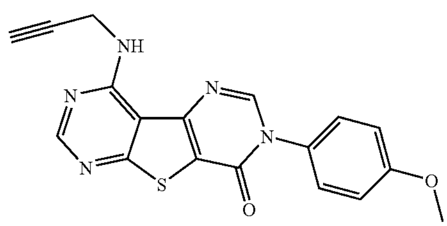 | C18H13N5O2S | 363.4 | 364.2 |
| 95EJ | 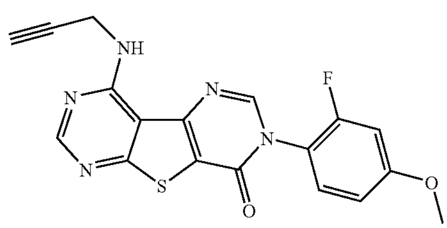 | C18H12FN5O2S | 381.4 | 382.2 |
| 95EK | 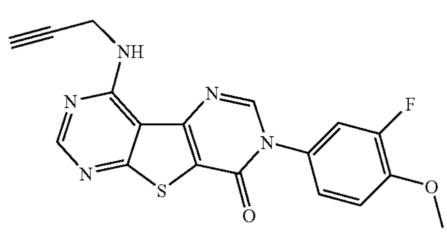 | C18H12FN5O2S | 381.4 | 382.2 |
| 95EL | 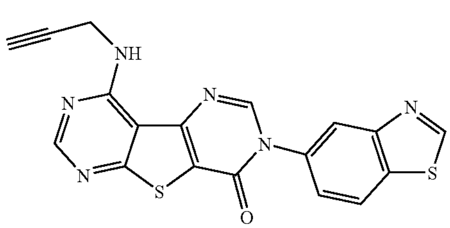 | C18H10N6OS2 | 390.4 | 391.2 |

-continued

| Cpd | Structure | Formula | MW | m/z Found (M + 1)+ |
|---|---|---|---|---|
| 95EM | 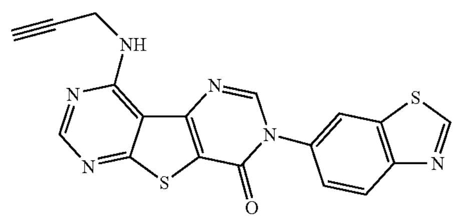 | C18H10N6OS2 | 390.4 | 391.2 |
| 95EN | 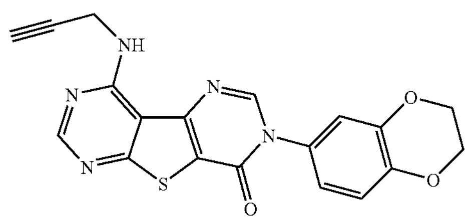 | C19H13N5O3S | 391.4 | 392.2 |
| 95EO | 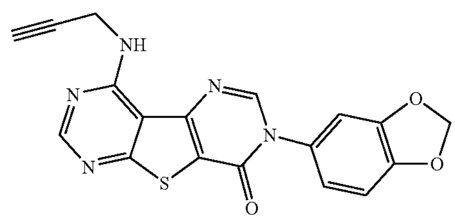 | C18H11N5O3S | 377.4 | 378.2 |
| 95EP | 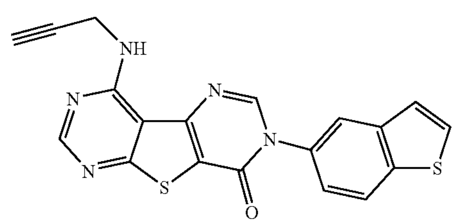 | C19H11N5OS2 | 389.4 | 390.2 |
| 95EQ | 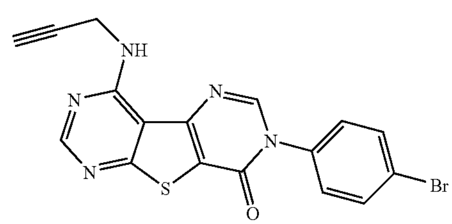 | C17H10BrN5OS | 412.3 | 412.2 |
| 95ER | 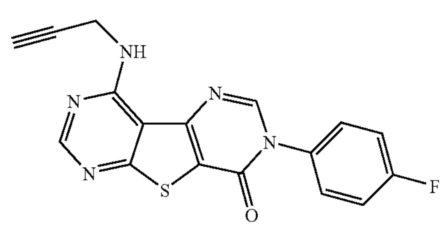 | C17H10FN5OS | 351.4 | 352.2 |
| 95ES | 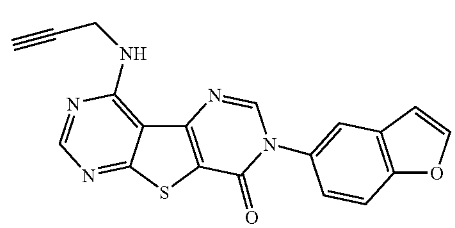 | C19H11N5O2S | 373.4 | 374.2 |

-continued

| Cpd | Structure | Formula | MW | m/z Found (M + 1)+ |
|---|---|---|---|---|
| 95ET | 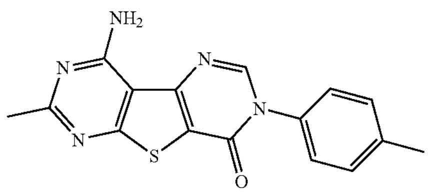 | C16H13N5OS | 323.4 | 324.2 |
| 95EU | 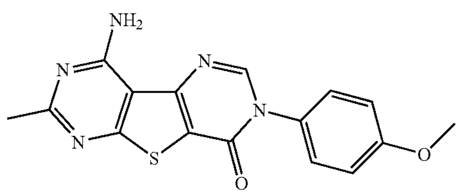 | C16H13N5O2S | 339.4 | 340.1 |
| 95EV | 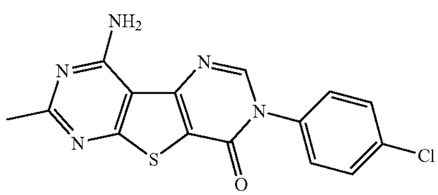 | C15H10ClN5OS | 343.8 | 344.0 |
| 95EW | 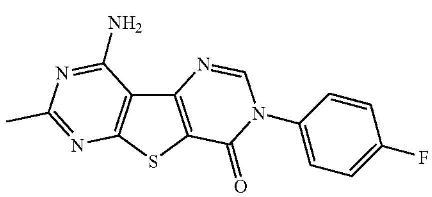 | C15H10FN5OS | 327.3 | 328.1 |
| 95EX | 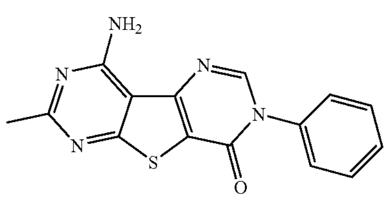 | C15H11N5OS | 309.3 | 310.2 |
| 95EY | 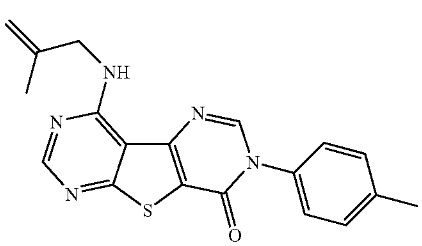 | C19H17N5OS | 363.4 | 364.2 |
| 95EZ | 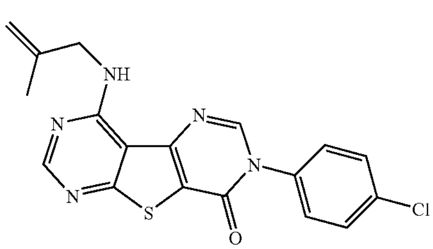 | C18H14ClN5OS | 383.9 | 384.2 |

-continued

| Cpd | Structure | Formula | MW | m/z Found (M + 1)+ |
|---|---|---|---|---|
| 95FA | 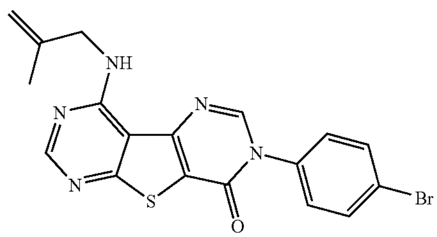 | C18H14BrN5OS | 428.3 | 430.2 |
| 95FB | 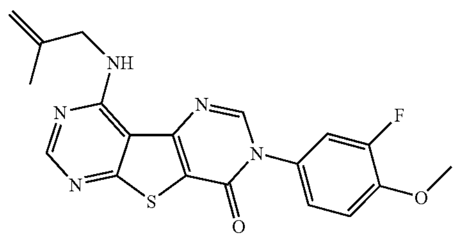 | C19H16FN5O2S | 397.4 | 398.2 |
| 95FC | 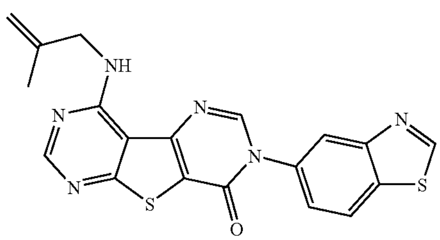 | C19H14N6OS2 | 406.5 | 407.2 |
| 95FD | 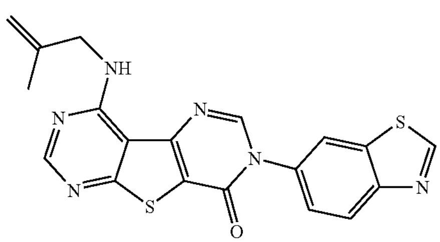 | C19H14N6OS2 | 406.5 | 407.2 |
| 95FE | 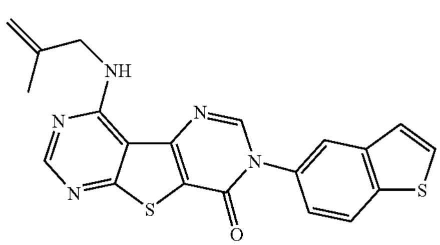 | C20H15N5OS2 | 405.5 | 406.2 |
| 95FF | 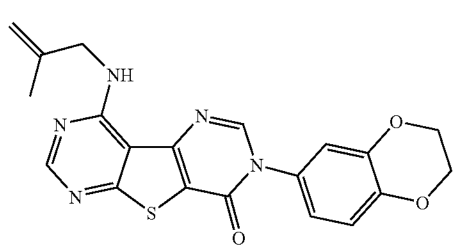 | C20H17N5O3S | 407.4 | 408.2 |

| Cpd | Structure | Formula | MW | m/z Found (M + 1)+ |
|---|---|---|---|---|
| 95FG | 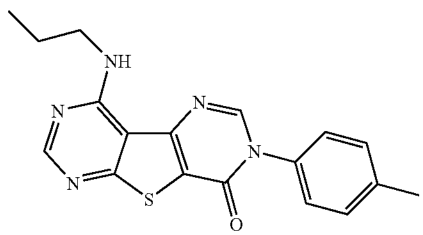 | C18H17N5OS | 351.4 | 352.2 |
| 95FH | 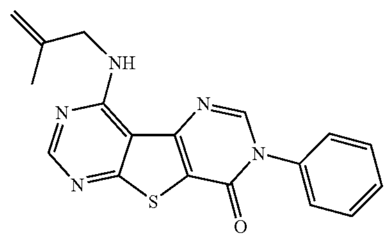 | C18H15N5OS | 349.4 | 350.2 |
| 95FI | 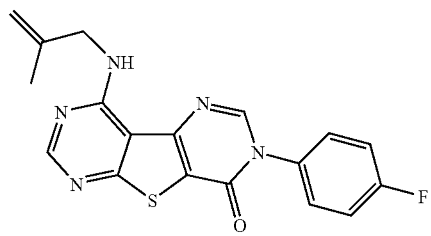 | C18H14FN5OS | 367.4 | 368.0 |
| 95FJ | 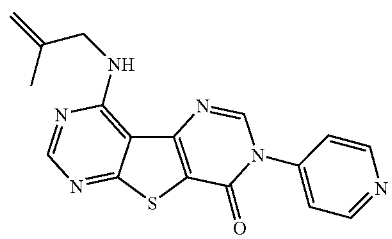 | C17H14N6OS | 350.4 | 351.2 |
| 95FK | 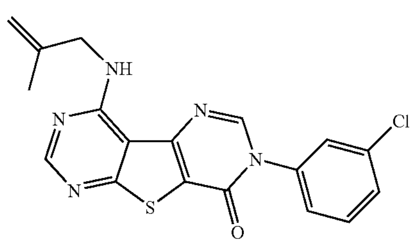 | C18H14ClN5OS | 383.9 | 384.2 |
| 95FL | 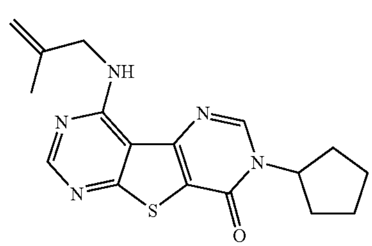 | C17H19N5OS | 341.4 | 342.2 |

-continued

| Cpd | Structure | Formula | MW | m/z Found (M + 1)+ |
|---|---|---|---|---|
| 95FP | 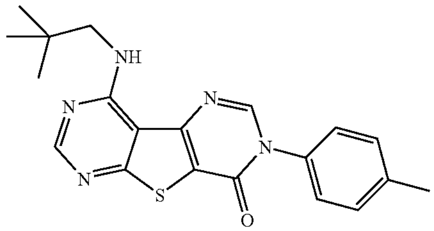 | C20H21N5OS | 379.5 | 380.2 |
| 95FQ | 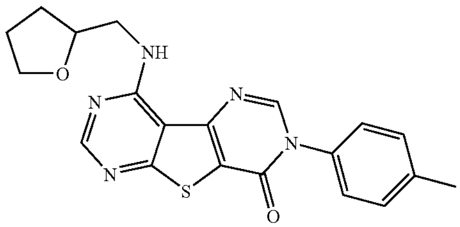 | C20H19N5O2S | 393.5 | 394.2 |
| 95FR | 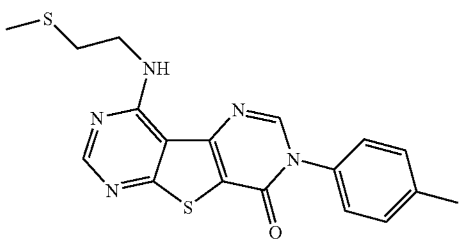 | C18H17N5OS2 | 383.5 | 384.2 |
| 95FS | 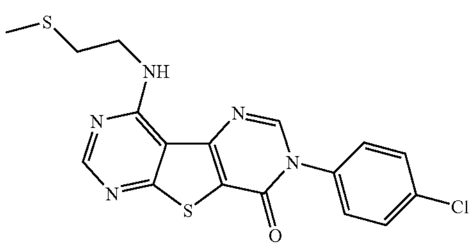 | C17H14ClN5OS2 | 403.9 | 404.2 |
| 95FT | 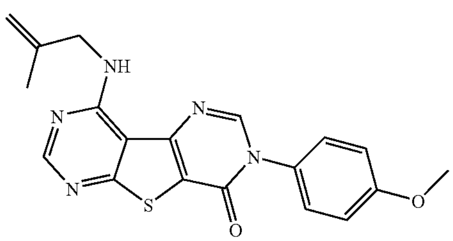 | C19H17N5O2S | 379.4 | 380.2 |
| 95FW | 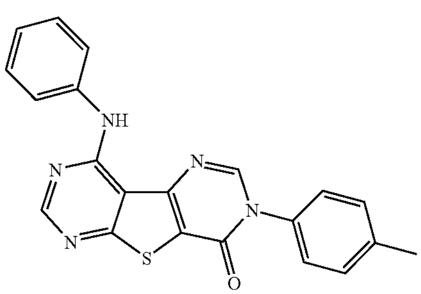 | C21H15N5OS | 385.4 | 386.2 |

-continued

| Cpd | Structure | Formula | MW | m/z Found (M + 1)+ |
|---|---|---|---|---|
| 95FX | 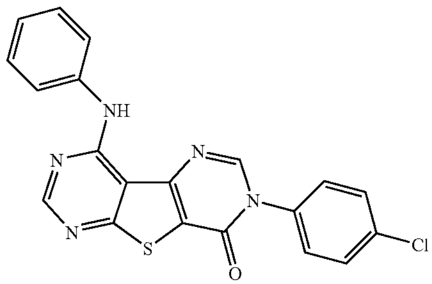 | C20H12ClN5OS | 405.9 | 406.2 |
| 95FY | 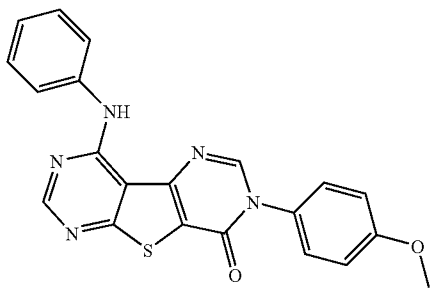 | C21H15N5O2S | 401.4 | 402.2 |
| 95FZ | 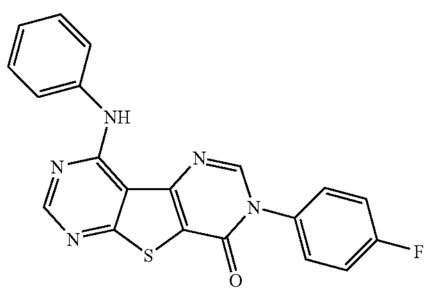 | C20H12FN5OS | 389.4 | 390.2 |
| 95GA | 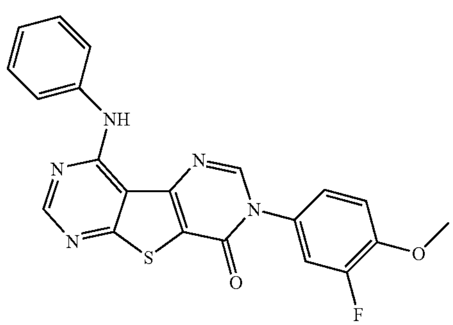 | C21H14FN5O2S | 419.4 | 420.2 |
| 95GB | 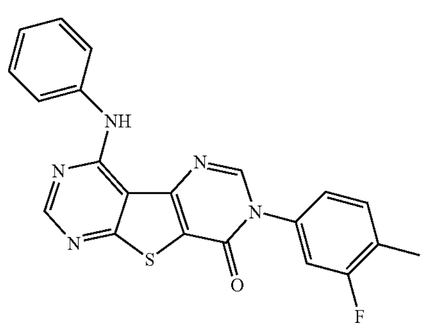 | C21H14FN5OS | 403.4 | 404.2 |

-continued

| Cpd | Structure | Formula | MW | m/z Found (M + 1)+ |
|---|---|---|---|---|
| 95GC | 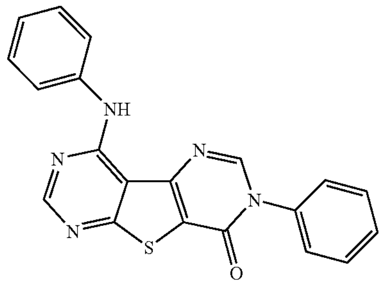 | C20H13N5OS | 371.4 | 372.2 |
| 95GD | 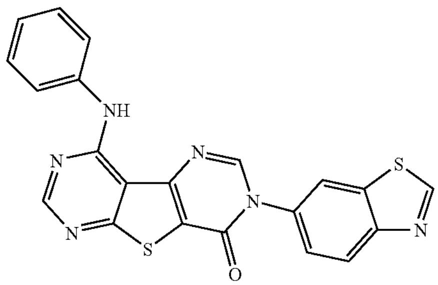 | C21H12N6OS2 | 428.5 | 429.2 |
| 95GE | 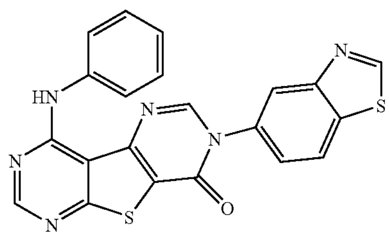 | C21H12N6OS2 | 428.5 | 429.2 |
| 95GF | 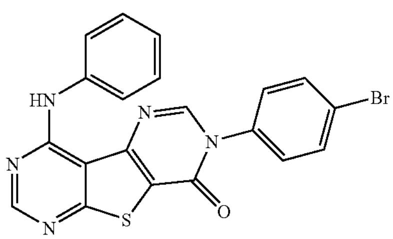 | C20H12BrN5OS | 450.3 | 452.2 |
| 95GG | 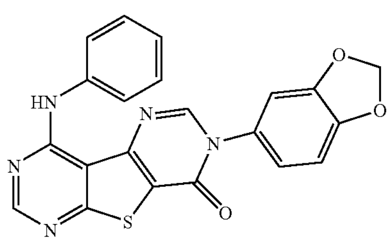 | C21H13N5O3S | 415.4 | 416.2 |
| 95GH | 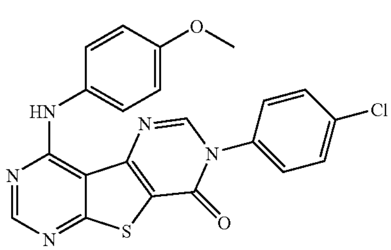 | C21H14ClN5O2S | 435.9 | 436.2 |

-continued

| Cpd | Structure | Formula | MW | m/z Found (M + 1)+ |
|---|---|---|---|---|
| 95GI | 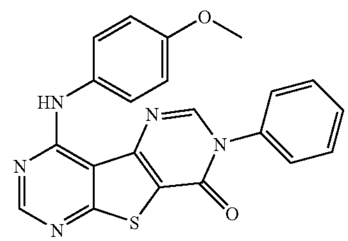 | C21H15N5O2S | 401.4 | 402.2 |
| 95GJ | 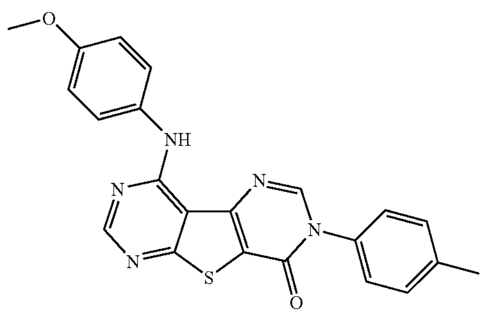 | C22H17N5O2S | 415.5 | 416.2 |
| 95GK | 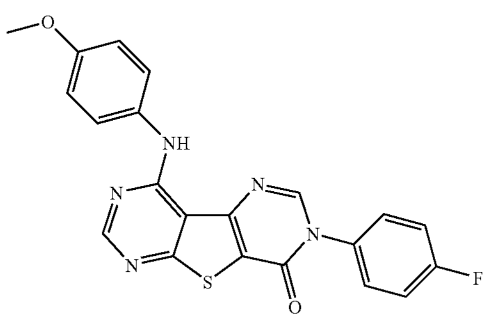 | C21H14FN5O2S | 419.4 | 420.2 |
| 95GL | 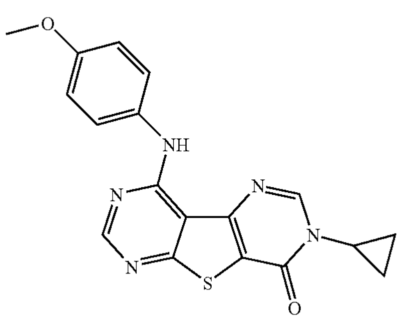 | C18H15N5O2S | 365.4 | 366.2 |
| 95GM | 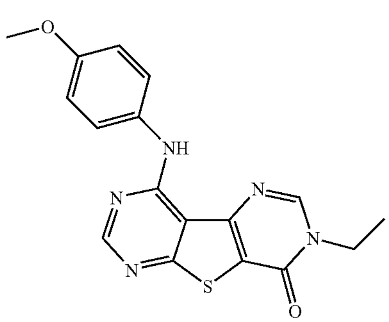 | C17H15N5O2S | 353.4 | 354.2 |

-continued
| Cpd | Structure | Formula | MW | m/z Found (M + 1)+ |
|---|---|---|---|---|
| 95GN | 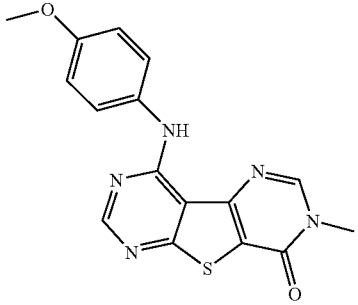 | C16H13N5O2S | 339.4 | 340.2 |
| 95GO | 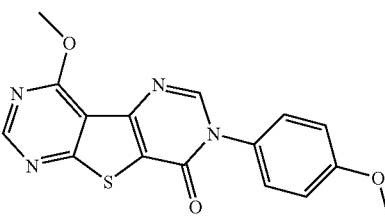 | C16H12N4O3S | 340.4 | 341.2 |
| 95GP | 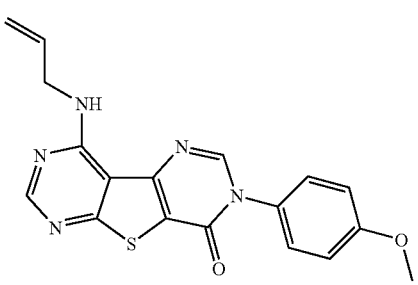 | C18H15N5O2S | 365.4 | 366.2 |
| 95GQ | 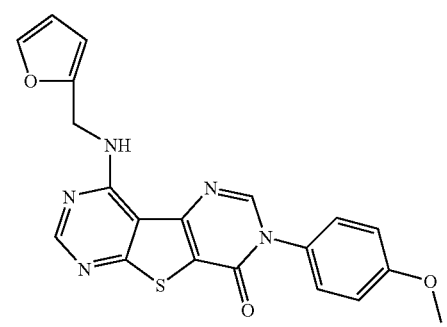 | C20H15N5O3S | 405.4 | 406.2 |
| 201 | 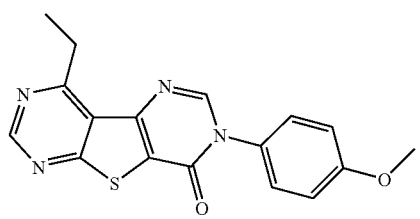 | C17H14N4O2S | 338.4 | 339.2 |

| Cpd | Structure | Formula | MW | m/z Found (M + 1)+ |
|---|---|---|---|---|
| 202 | 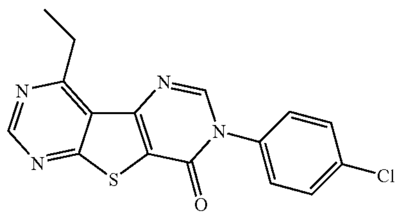 | C16H11ClN4OS | 342.8 | 343.2 |

Method H (Alternate 1):

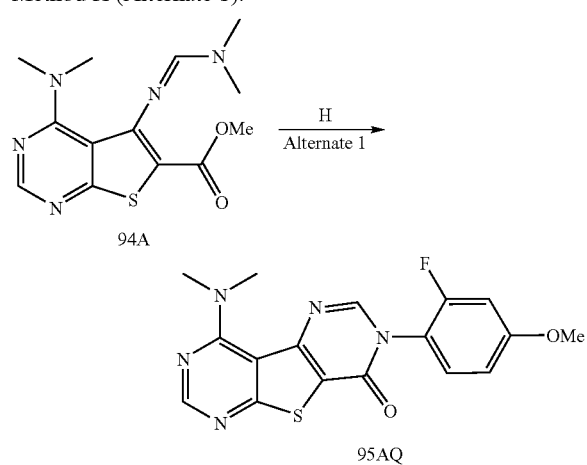

Ref: *Synthetic Communications* 23 (3), 1993, 335-341.

To a mixture of 94A (2.50 g, 8.12 mmoles) in toluene (36 mL) and glacial acetic acid (9.0 mL) was added 2-fluoro-4-methoxyaniline (160 mg, 1.30 mmoles) freshly prepared from the corresponding carboxylic acid. The reaction was allowed to stir at reflux for 2 h. The reaction mixture was then poured onto water (360 ml), basified with conc. NH$_4$OH and filtered. The crude solid was then purified via silica gel chromatography eluting with 10% acetone/CH$_2$Cl$_2$ to give 95AQ as an off-white solid (381 mg, 13% yield). $^1$H NMR (CDCl$_3$): δ 8.58 (s, 1H), 8.5 (s, 1H), 7.36-7.31 (m, 1H), 6.89-6.82 (m, 2H), 3.88 (s, 3H), 3.49 (s, 6H), MS m/z calcd. for C$_{17}$H$_{15}$FN$_5$O$_2$S$^+$=372.1; found m/z=372.2 (M$^{+1}$)

The following compounds were prepared using Method J:

| Cpd | Structure | Formula | MW | m/z Found (M + 1)+ |
|---|---|---|---|---|
| 171 | 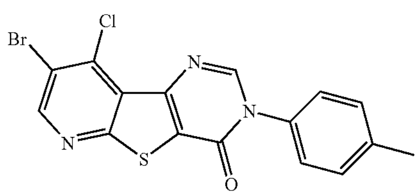 | C16H9BrClN3OS | 406.7 | 408.2 |
| 57B | 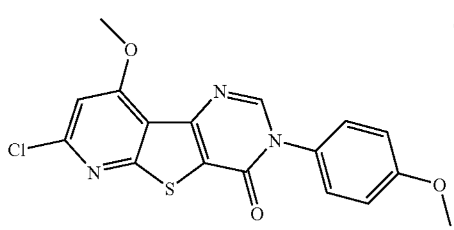 | C17H12ClN3O3S | 373.8 | 374.2 |
| 195 | 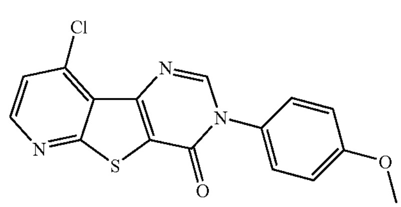 | C16H10ClN3O2S | 343.8 | 344.2 |

The following compounds were prepared using Method K:

| Cpd | Structure | Formula | MW | m/z Found (M + 1)+ |
|---|---|---|---|---|
| 95AO | 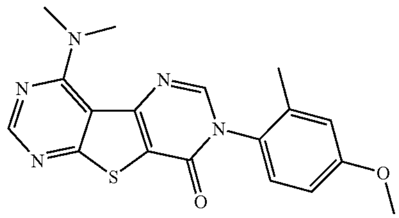 | $C_{18}H_{17}N_5O_2S$ | 367.4 | 368.2 |
| 95AP | 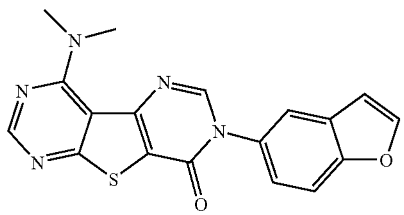 | $C_{18}H_{13}NF_5O_2S$ | 363.4 | 364.2 |
| 95AQ | 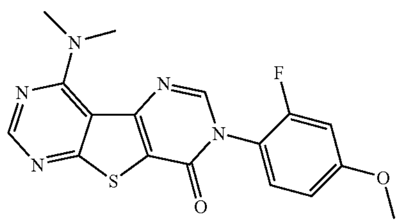 | $C_{17}H_{14}FN_5O_2S$ | 371.4 | 372.2 |
| 95AR | 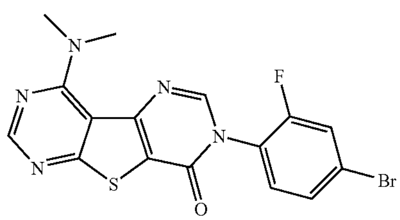 | C16H11BrFN5OS | 420.3 | 420.2 |
| 95AS | 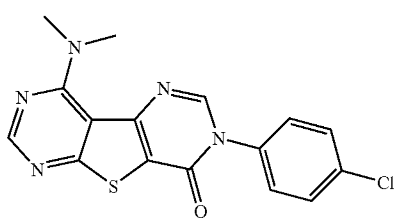 | C16H12ClN5OS | 357.8 | 358.2 |
| 95AT | 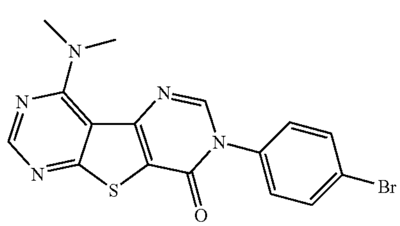 | C16H12BrN5OS | 402.3 | 404.2 |

-continued

| Cpd | Structure | Formula | MW | m/z Found (M + 1)+ |
|---|---|---|---|---|
| 95AU | 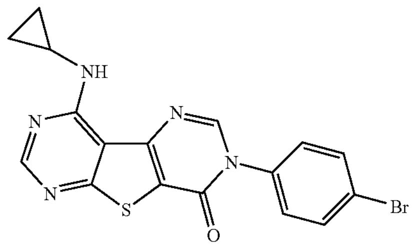 | C17H12BrN5OS | 414.3 | 416.2 |
| 95AV | 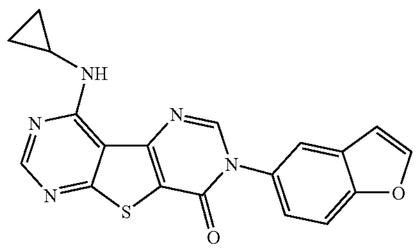 | C19H13N5O2S | 375.4 | 376.2 |
| 95AW | 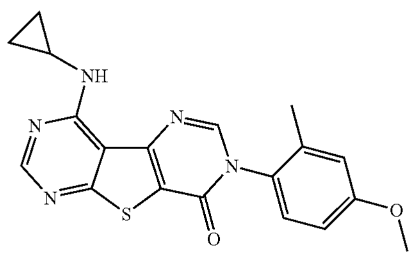 | C19H17N5O2S | 379.4 | 380.2 |
| 95AX | 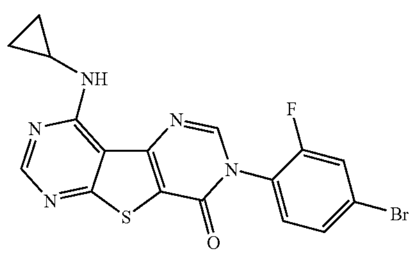 | C17H11BrFN5OS | 432.3 | 434.2 |
| 95AY | 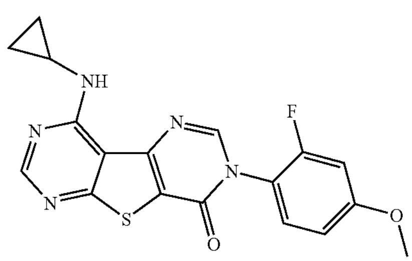 | C18H14FN5O2S | 383.4 | 384.2 |
| 95AZ | 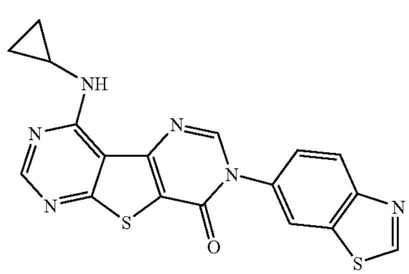 | C18H12N6OS2 | 392.5 | 393.1 |

| Cpd | Structure | Formula | MW | m/z Found (M + 1)+ |
|---|---|---|---|---|
| 95BA | 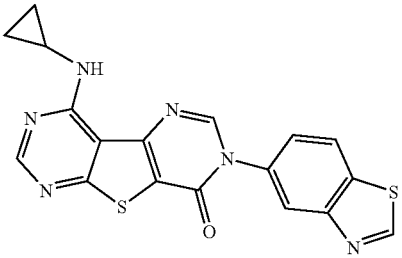 | C18H12N6OS2 | 392.5 | 393.1 |
| 95BB | 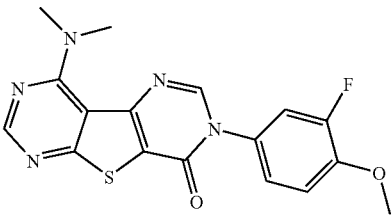 | C17H14FN5O2S | 371.4 | 372.2 |
| 95BC | 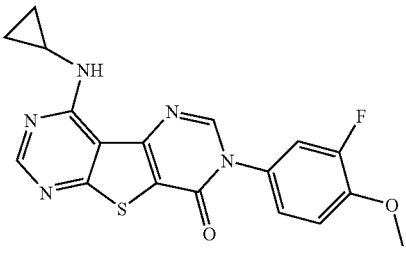 | C18H14FN5O2S | 383.4 | 384.2 |
| 95BD | 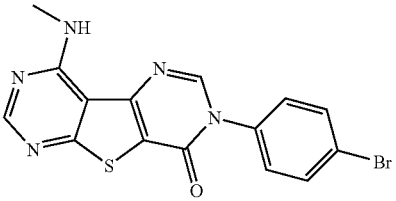 | C15H10BrN5OS | 388.2 | 388.1 |
| 95BE | 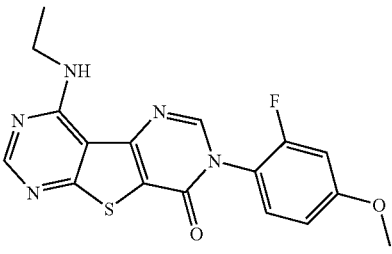 | C17H14FN5O2S | 371.4 | 372.2 |
| 95BF | 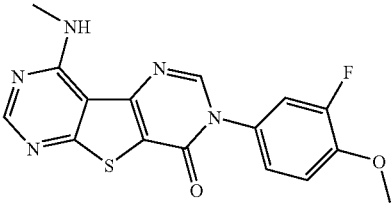 | C16H12FN5O2S | 357.4 | 358.2 |

| Cpd | Structure | Formula | MW | m/z Found (M + 1)+ |
|---|---|---|---|---|
| 95BG | 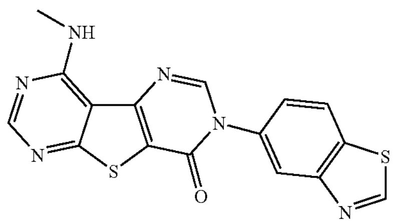 | C16H10N6O2S | 366.4 | 367.2 |
| 95BH | 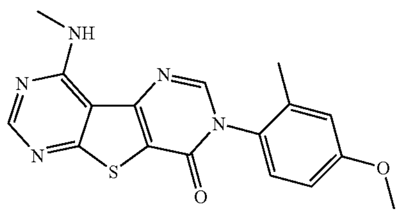 | C17H15N5O2S | 353.4 | 354.2 |
| 95BI | 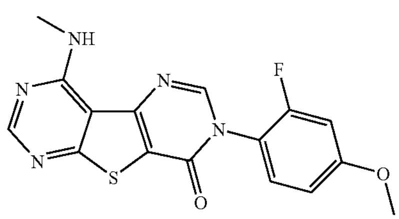 | C16H12FN5O2S | 357.4 | 358.2 |
| 95BJ | 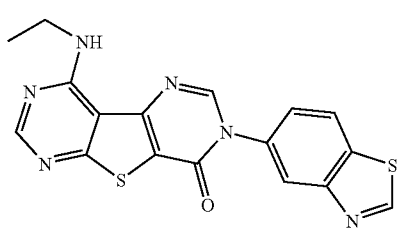 | C17H12N6O2S | 380.4 | 381.2 |
| 95BK | 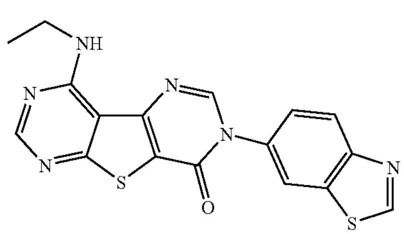 | C17H12N6O2S | 380.4 | 381.2 |

| Cpd | Structure | Formula | MW | m/z Found (M + 1)+ |
|---|---|---|---|---|
| 95BL | 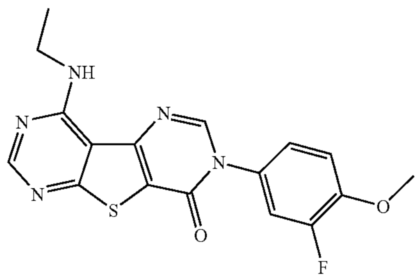 | C17H14FN5O2S | 371.4 | 372.2 |
| 95BM | 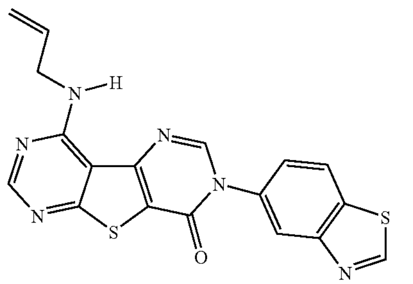 | C18H12N6O2S | 392.5 | 393.2 |
| 95BN | 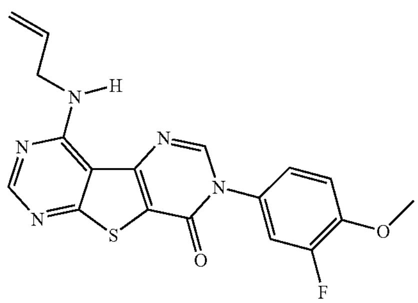 | C18H14FN5O2S | 383.4 | 384.2 |
| 95BO | 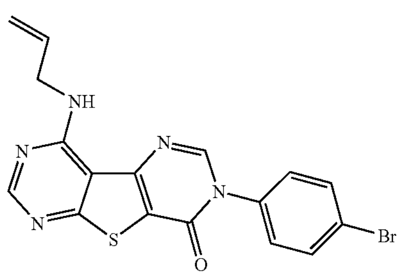 | C17H12BrN5OS | 414.3 | 416.2 |
| 95BP | 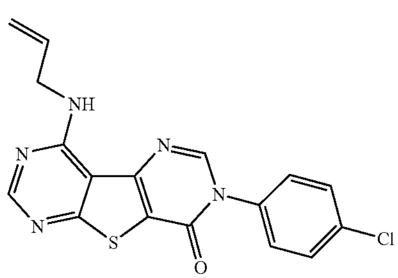 | C17H12ClN5OS | 369.8 | 370.2 |

The following compounds were prepared using Method R:
| Cpd | Structure | Formula | MW | m/z Found (M + 1)+ |
|---|---|---|---|---|
| 28BD | 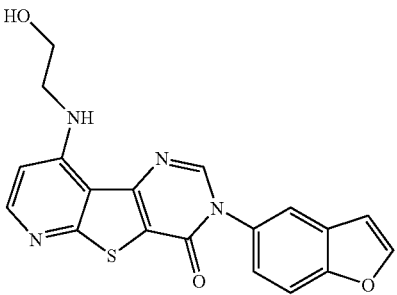 | C19H14N4O3S | 378.4 | 379.2 |
| 28BE | 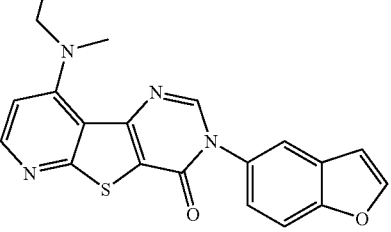 | C20H16N4O3S | 392.4 | 393.2 |
| 28BF | 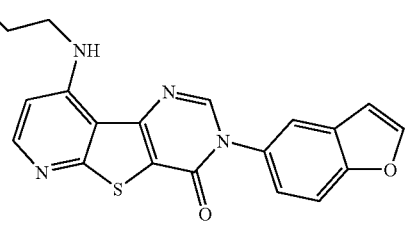 | C20H16N4O3S | 392.4 | 393.2 |
| 28BG | 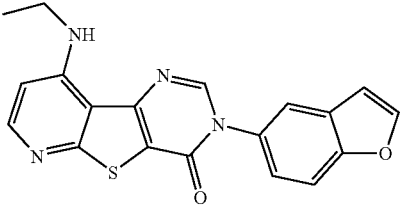 | C19H14N4O2S | 362.4 | 363.2 |
| 28BH | 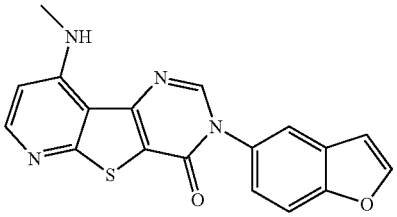 | C18H12N4O2S | 348.4 | 349.2 |

| Cpd | Structure | Formula | MW | m/z Found (M + 1)+ |
|---|---|---|---|---|
| 28BI | 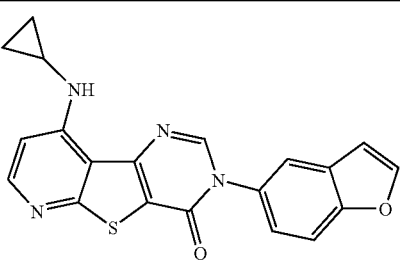 | C20H14N4O2S | 374.4 | 375.2 |
| 28BJ | 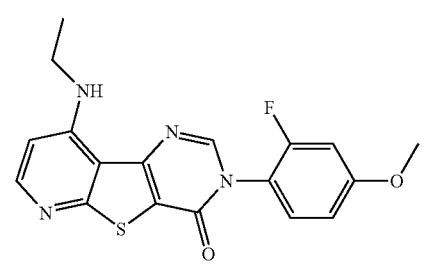 | C18H15FN4O2S | 370.4 | 371.2 |
| 28BK | 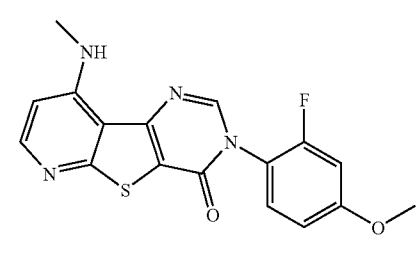 | C17H13FN4O2S | 356.4 | 357.2 |
| 28BL | 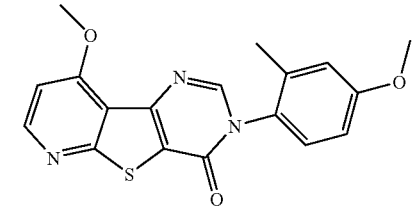 | C18H15N3O3S | 353.4 | 354.2 |
| 28BM | 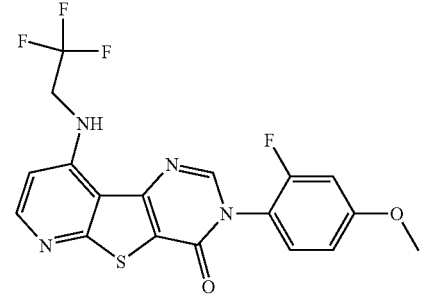 | C18H12F4N4O2S | 424.4 | 425.2 |
| 28BN | 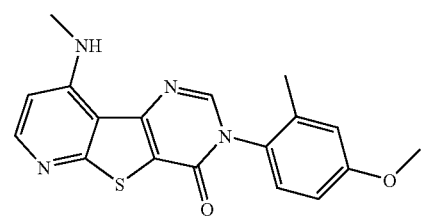 | C18H16N4O2S | 352.4 | 353.2 |

-continued

| Cpd | Structure | Formula | MW | m/z Found (M + 1)+ |
|---|---|---|---|---|
| 28BO | 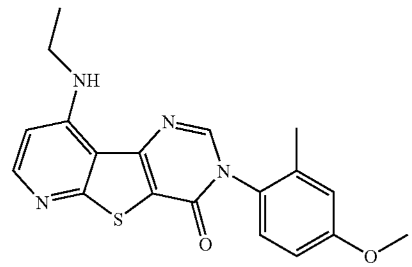 | C19H18N4O2S | 366.4 | 367.2 |
| 28BP | 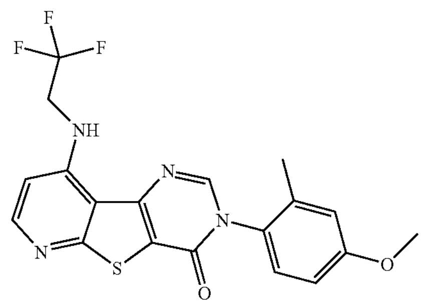 | C19H15F3N4O2S | 420.4 | 421.2 |
| 28BQ | 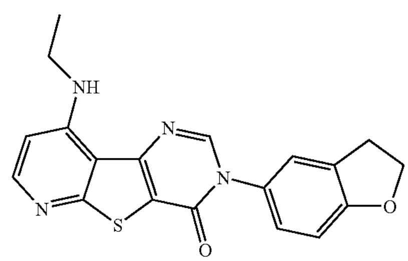 | C19H16N4O2S | 364.4 | 365.2 |
| 28BR | 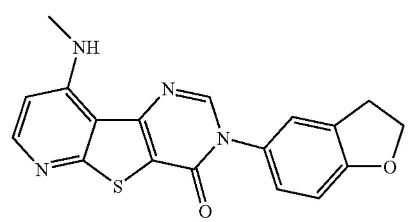 | C18H14N4O2S | 350.4 | 351.2 |
| 28BS | 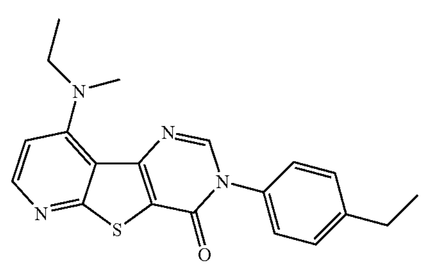 | C20H20N4OS | 364.5 | 365.2 |

-continued

| Cpd | Structure | Formula | MW | m/z Found (M + 1)+ |
|---|---|---|---|---|
| 28BT | 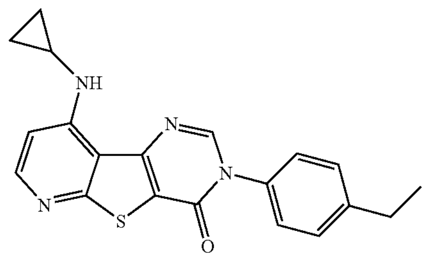 | C20H18N4OS | 362.4 | 363.2 |
| 28BU | 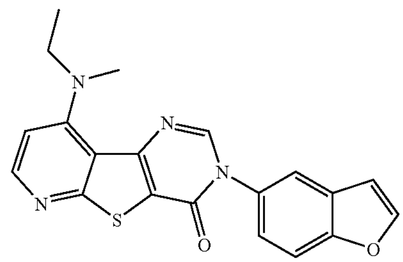 | C20H16N4O2S | 376.4 | 377.2 |
| 28BV | 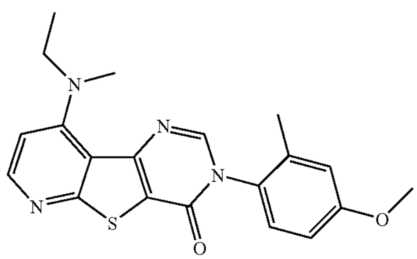 | C20H20N4O2S | 380.5 | 381.2 |
| 28BW | 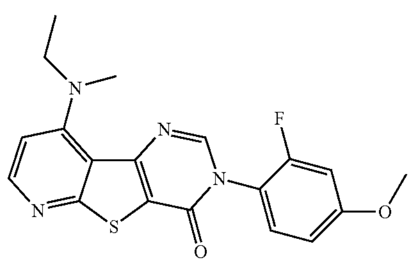 | C19H17FN4OS2 | 384.4 | 385.2 |
| 28BX | 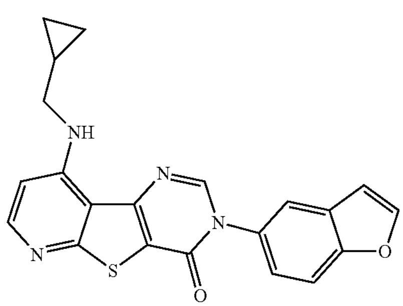 | C21H16N4O2S | 388.4 | 389.2 |

-continued

| Cpd | Structure | Formula | MW | m/z Found (M + 1)+ |
|---|---|---|---|---|
| 28BY | 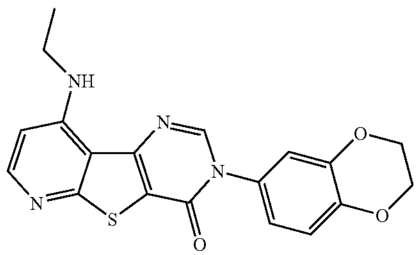 | C19H16N4O3S | 380.4 | 381.2 |
| 28BZ | 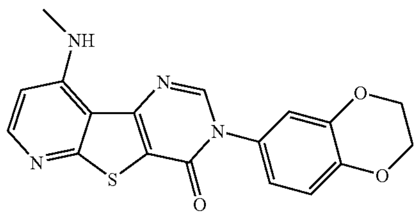 | C18H14N4O3S | 366.4 | 366.2 |
| 28CA | 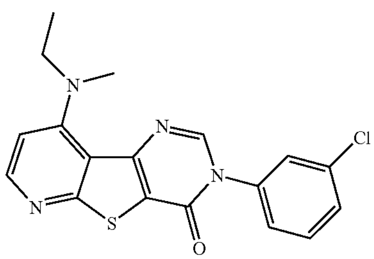 | C18H15ClN4OS | 370.9 | 371.2 |
| 28CB | 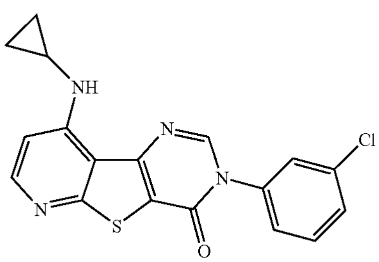 | C18H13ClN4OS | 368.8 | 369.2 |
| 28CC | 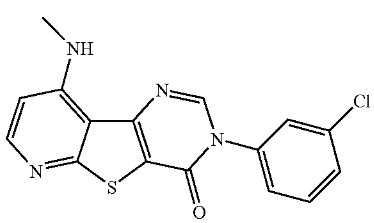 | C16H11ClN4OS | 342.8 | 343.2 |
| 28CD | 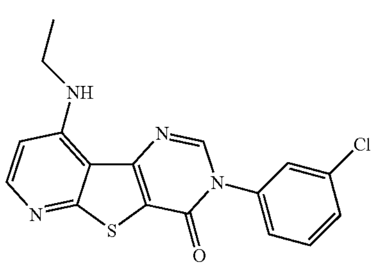 | C17H13ClN4OS | 356.8 | 357.2 |

-continued

| Cpd | Structure | Formula | MW | m/z Found (M + 1)+ |
|---|---|---|---|---|
| 28CE | 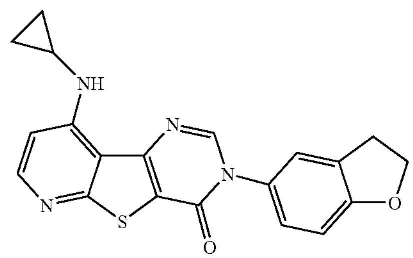 | C20H16N4O2S | 376.4 | 377.2 |
| 28CF | 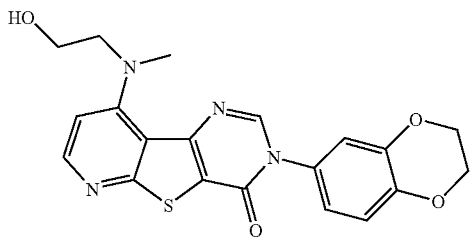 | C20H18N4O4S | 410.4 | 411.2 |
| 28CG | 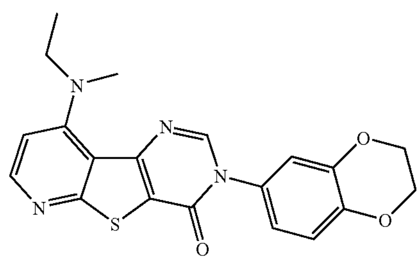 | C20H18N4O3S | 394.4 | 395.2 |
| 28CH | 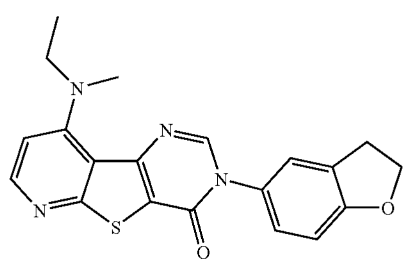 | C20H18N4O2S | 378.4 | 379.2 |
| 28CI | 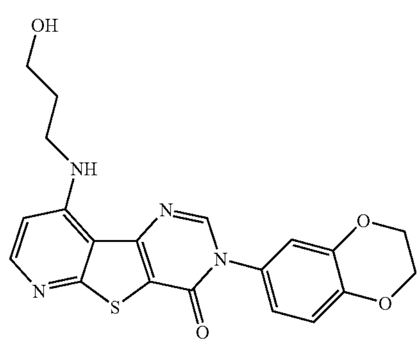 | C20H18N4O4S | 410.4 | 411.2 |

-continued

| Cpd | Structure | Formula | MW | m/z Found (M + 1)+ |
|---|---|---|---|---|
| 28CJ | 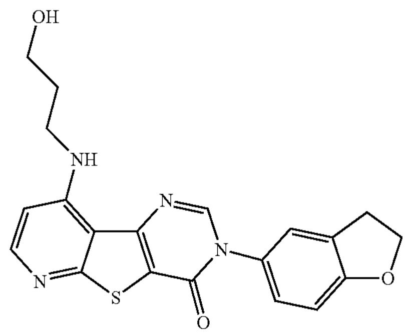 | C20H18N4O3S | 394.4 | 395.2 |
| 28CK | 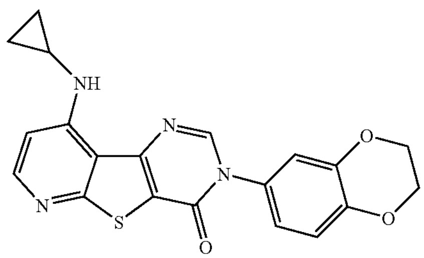 | C20H16N4O3S | 392.4 | 393.2 |
| 28CL | 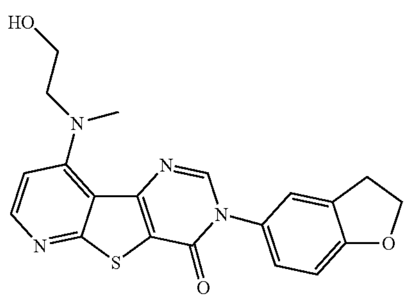 | C20H18N4O3S | 394.4 | 395.2 |
| 28CM | 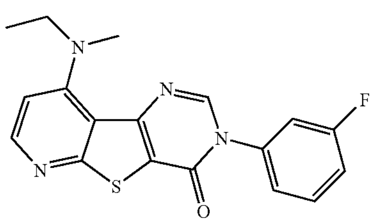 | C18H15FN4OS | 354.4 | 355.2 |
| 28CN | 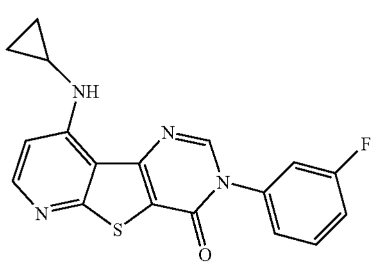 | C18H13FN4OS | 352.4 | 353.2 |

-continued

| Cpd | Structure | Formula | MW | m/z Found (M + 1)+ |
|---|---|---|---|---|
| 28CO | 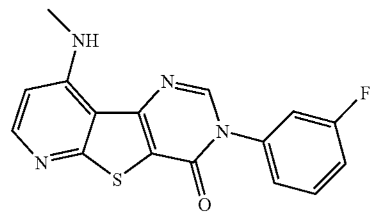 | C16H11FN4OS | 326.3 | 327.2 |
| 28CP | 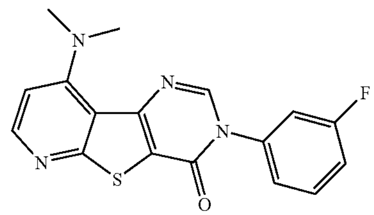 | C17H13FN4OS | 340.4 | 341.2 |
| 28CQ | 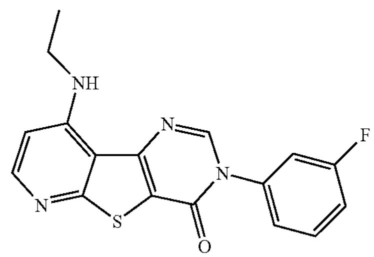 | C17H13FN4OS | 340.4 | 341.2 |
| 28CR | 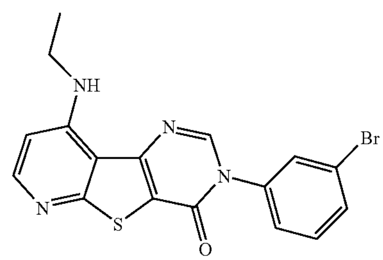 | C17H13BrN4OS | 401.3 | 403.2 |
| 28CS | 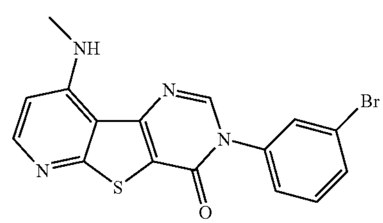 | C16H11BrN4OS | 387.3 | 387.2 |
| 28CT | 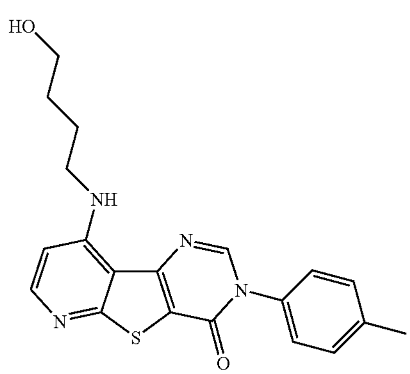 | C20H20N4O2S | 380.5 | 381.2 |

-continued

| Cpd | Structure | Formula | MW | m/z Found (M + 1)+ |
|---|---|---|---|---|
| 28CU | 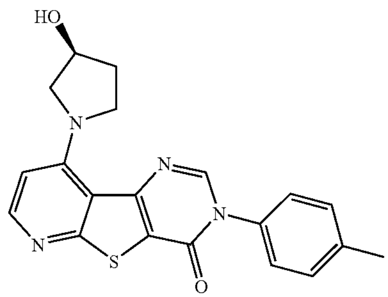 | C20H18N4O2S | 378.4 | 379.2 |
| 28CV | 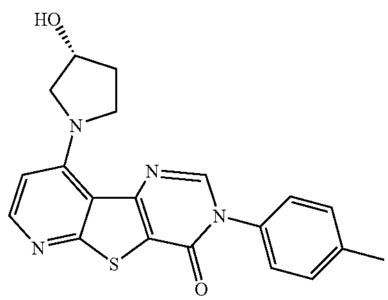 | C20H18N4O2S | 378.4 | 379.2 |
| 28CW | 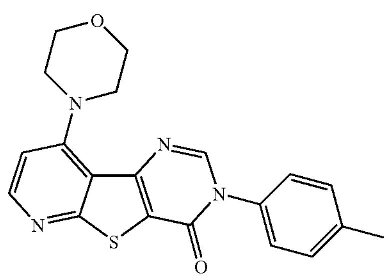 | C20H18N4O2S | 378.4 | 379.2 |
| 28CX | 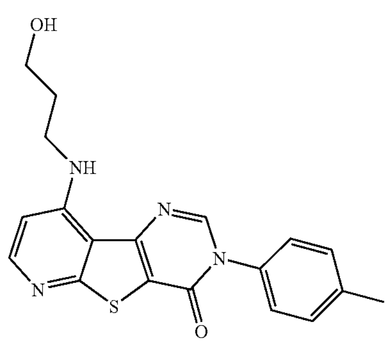 | C19H18N4O2S | 366.4 | 367.1 |
| 28CY | 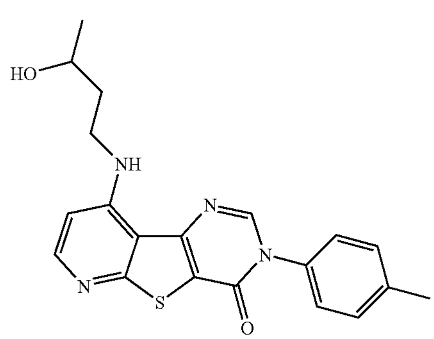 | C20H20N4O2S | 380.5 | 381.1 |

-continued
| Cpd | Structure | Formula | MW | m/z Found (M + 1)+ |
|---|---|---|---|---|
| 28CZ | 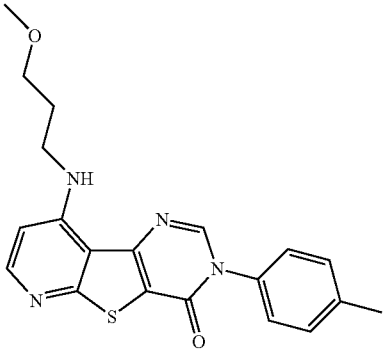 | C20H20N4O2S | 380.5 | 381.1 |
| 28DA | 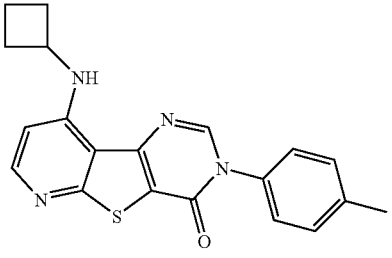 | C20H18N4OS | 362.4 | 363.2 |
| 28DB | 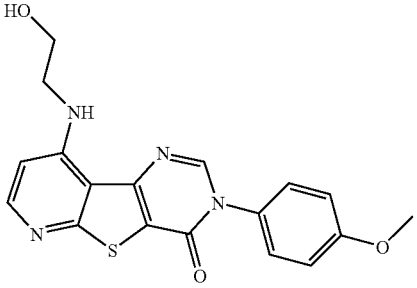 | C18H16N4O3S | 368.4 | 369.2 |
| 28DC | 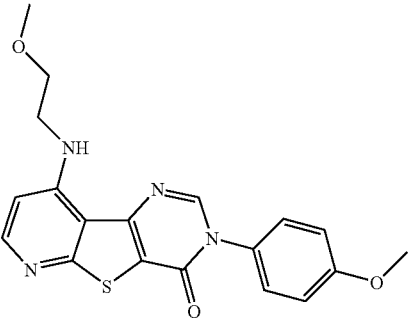 | C19H18N4O3S | 382.4 | 383.1 |
| 28DD | 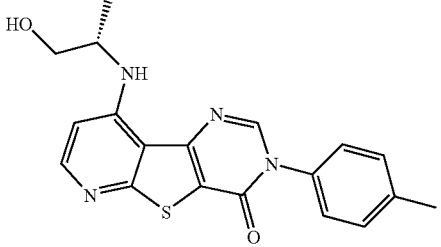 | C19H18N4O2S | 366.4 | 367.2 |

-continued

| Cpd | Structure | Formula | MW | m/z Found (M + 1)+ |
|---|---|---|---|---|
| 28DE | 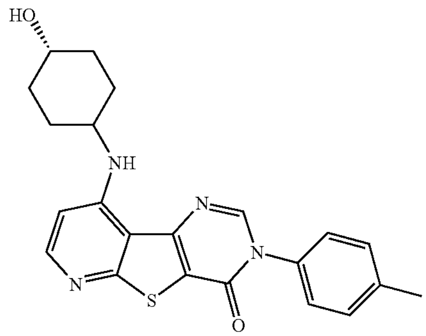 | C22H22N4O2S | 406.5 | 407.2 |
| 28DF | 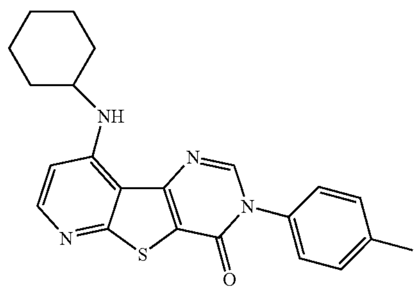 | C22H22N4OS | 390.5 | 391.2 |
| 28DG | 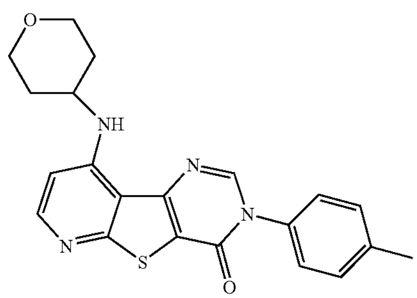 | C21H20N4O2S | 392.5 | 393.2 |
| 28DH | 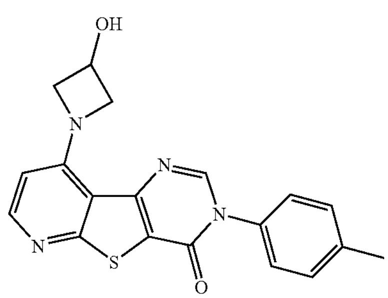 | 364.4 | 365.2 | 364.4 |
| 28DI | 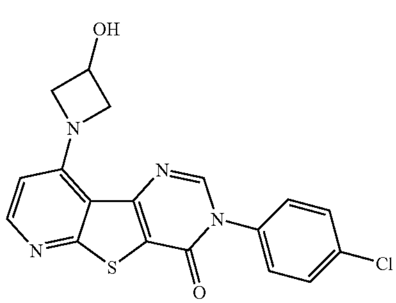 | 384.8 | 385.2 | 384.8 |

-continued

| Cpd | Structure | Formula | MW | m/z Found (M + 1)+ |
|---|---|---|---|---|
| 28DJ | 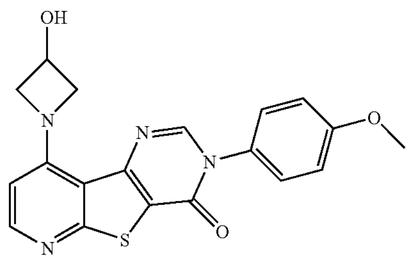 | | 380.4 | 381.2 380.4 |
| 28DK | 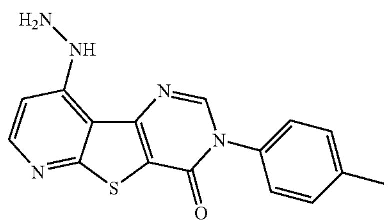 | C16H13N5OS | 323.4 | 324.1 |
| 28DL | 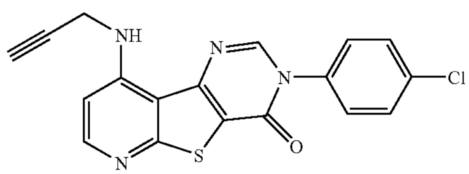 | C18H11ClN4OS | 366.8 | 367.1 |
| 28DM | 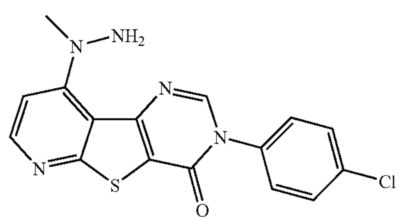 | C16H12ClN5OS | 357.8 | 358.1 |
| 28DN | 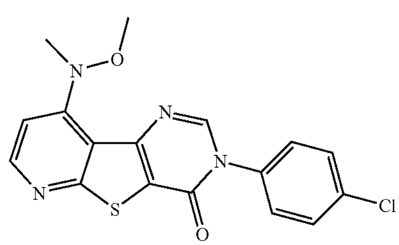 | C17H13ClN4O2S | 372.8 | 373.2 |
| 28DO | 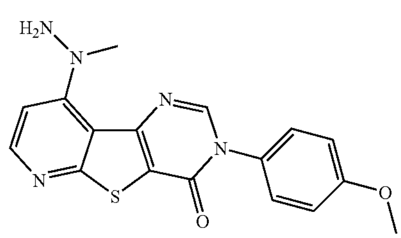 | C17H15N5O2S | 353.4 | 354.2 |

-continued

| Cpd | Structure | Formula | MW | m/z Found (M + 1)+ |
|---|---|---|---|---|
| 28DP | 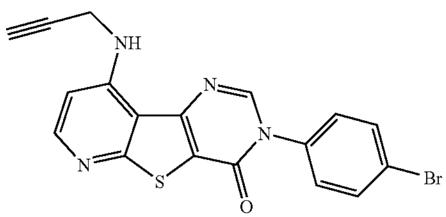 | C18H11BrN4OS | 411.3 | 411.2 |
| 28DQ | 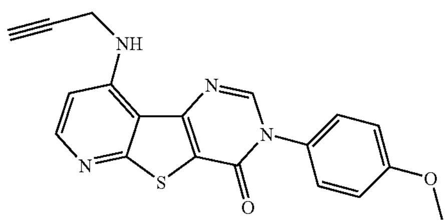 | C19H14N4O2S | 362.4 | 363.2 |
| 28DR | 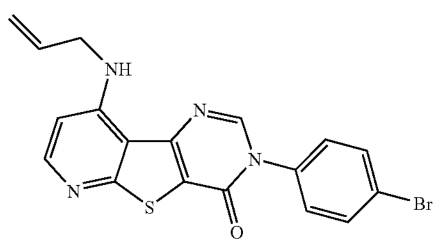 | C18H13BrN4OS | 413.3 | 414.2 |
| 28DS | 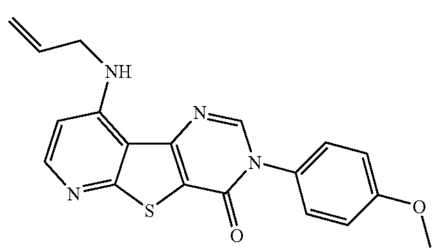 | C19H16N4O2S | 364.4 | 365.2 |
| 28DT | 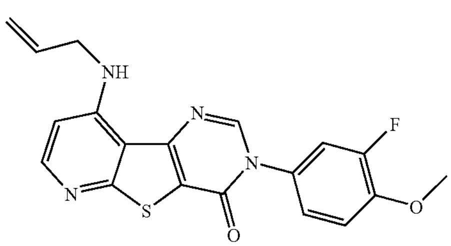 | C19H15FN4O2S | 382.4 | 383.2 |
| 28DU | 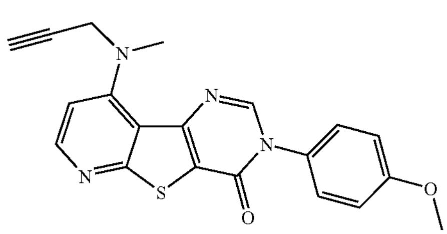 | C20H16N4O2S | 376.4 | 377.2 |

-continued
| Cpd | Structure | Formula | MW | m/z Found (M + 1)+ |
|---|---|---|---|---|
| 28DV | 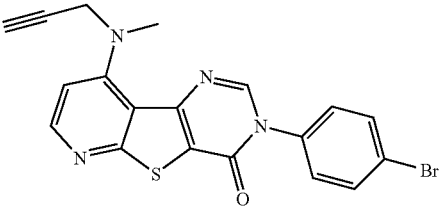 | C19H13BrN4OS | 425.3 | 425.2 |
| 28DW | 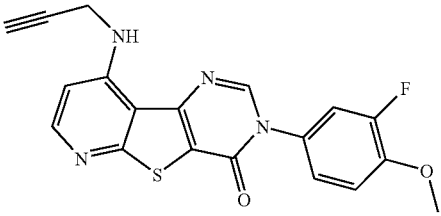 | C19H13FN4O2S | 380.4 | 381.2 |
| 28DX | 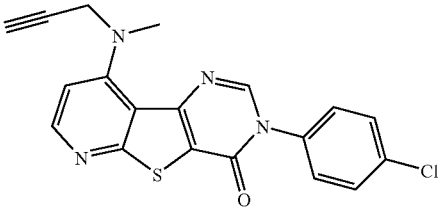 | C19H13ClN4OS | 380.9 | 381.2 |
| 28DY | 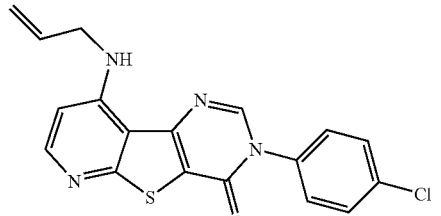 | C18H13ClN4OS | 368.8 | 369.2 |
| 28DZ | 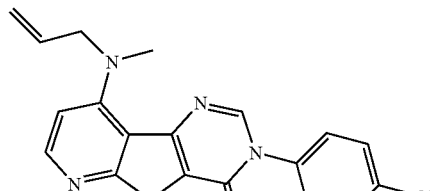 | C19H15ClN4OS | 382.9 | 383.2 |
| 28EA | 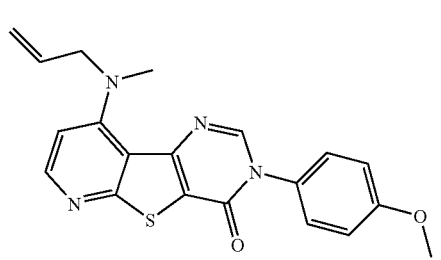 | C20H18N4O2S | 378.4 | 379.2 |

-continued

| Cpd | Structure | Formula | MW | m/z Found (M + 1)+ |
|---|---|---|---|---|
| 28EB | 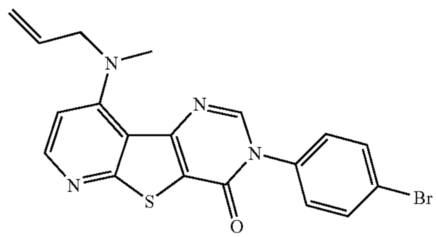 | C19H15BrN4OS | 427.3 | 427.2 |
| 28EC | 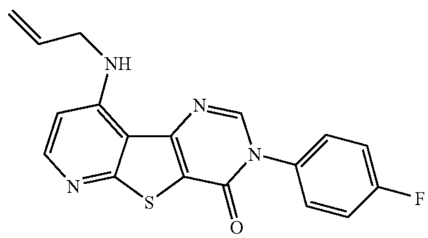 | C18H13FN4OS | 352.4 | 353.2 |
| 28ED | 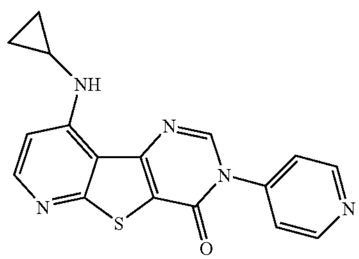 | C17H13N5OS | 335.4 | 336.2 |
| 28EE | 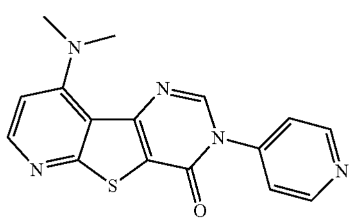 | C16H13N5OS | 323.4 | 324.2 |
| 28EF | 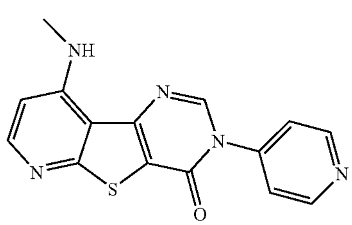 | C15H11N5OS | 309.3 | 310.2 |
| 28EG | 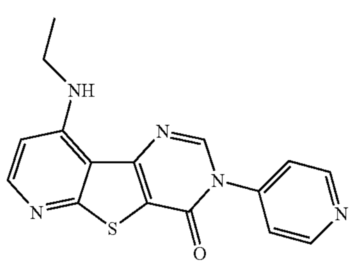 | C16H13N5OS | 323.4 | 324.2 |

| Cpd | Structure | Formula | MW | m/z Found (M + 1)+ |
|---|---|---|---|---|
| 28EO | 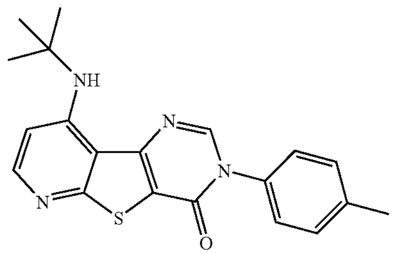 | C20H20N4OS | 364.5 | 365.2 |
| 28EP | 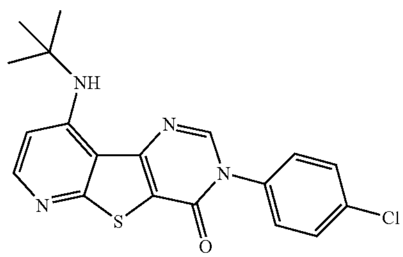 | C19H17ClN4OS | 384.9 | 385.2 |
| 28EQ | 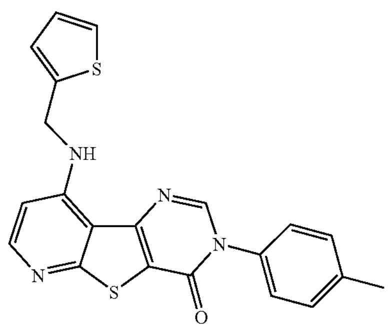 | C21H16N4OS2 | 404.5 | 405.2 |
| 28ER | 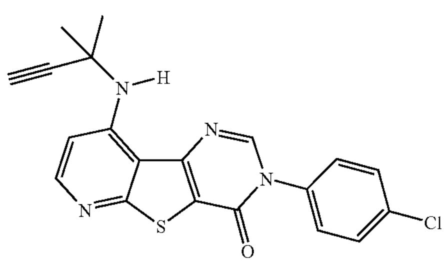 | C20H15ClN4OS | 394.9 | 395.2 |
| 28ES | 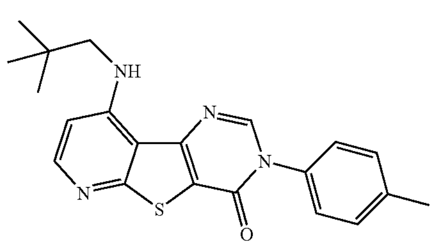 | C21H22N4OS | 378.5 | 379.2 |

-continued

| Cpd | Structure | Formula | MW | m/z Found (M + 1)+ |
|---|---|---|---|---|
| 28ET | 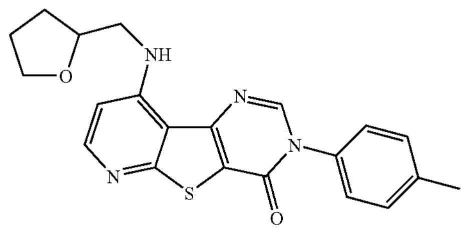 | C21H20N4O2S | 392.5 | 393.2 |
| 28EU | 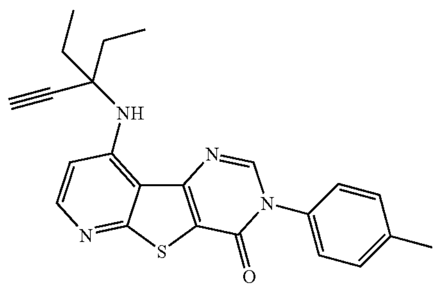 | C23H22N4OS | 402.5 | 403.2 |
| 28EV | 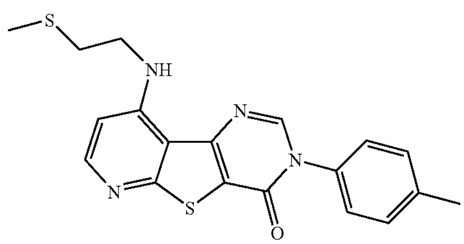 | C19H18N4OS2 | 382.5 | 383.2 |
| 28EW | 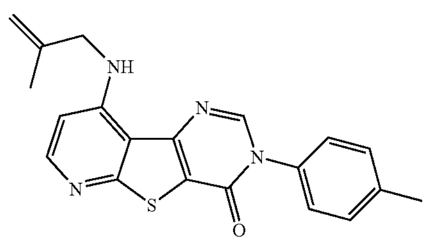 | C20H18N4OS | 362.4 | 363.2 |
| 28EX | 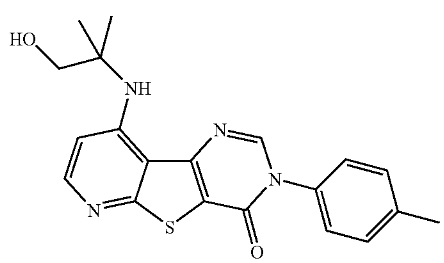 | C20H20N4O2S | 380.5 | 381.2 |
| 28EY | 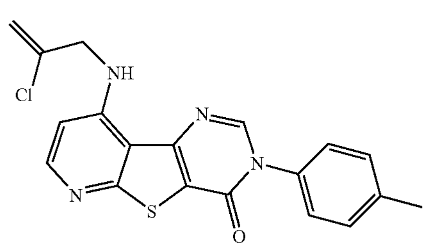 | C19H15ClN4OS | 382.9 | 383.2 |

-continued

| Cpd | Structure | Formula | MW | m/z Found (M + 1)+ |
|---|---|---|---|---|
| 28EZ | 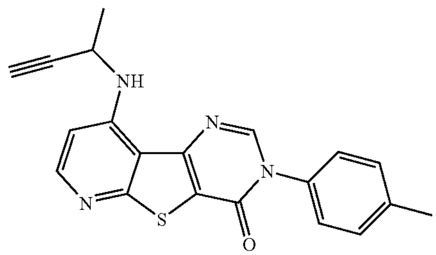 | C20H16N4OS | 360.4 | 361.2 |
| 28FA | 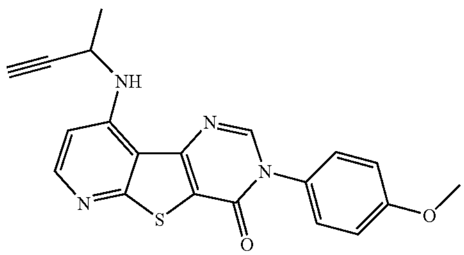 | C20H16N4O2S | 376.4 | 377.2 |
| 28FB | 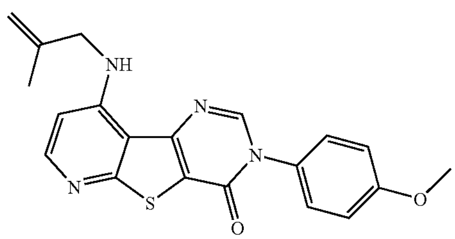 | C20H18N4O2S | 378.4 | 379.2 |
| 28FC | 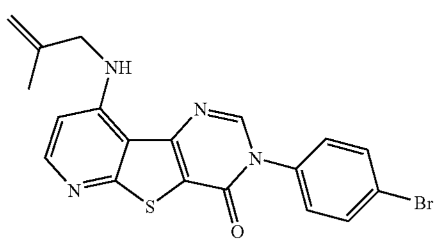 | C19H15BrN4OS | 427.3 | 429.0 |
| 28FD | 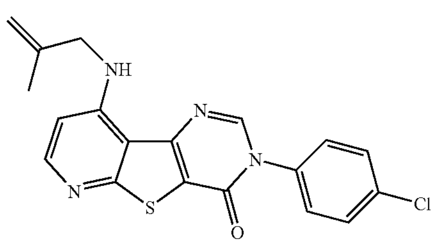 | C19H15ClN4OS | 382.9 | 384.0 |
| 28FE | 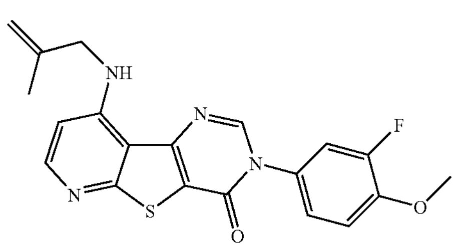 | C20H17FN4O2S | 396.4 | 397.2 |

-continued

| Cpd | Structure | Formula | MW | m/z Found (M + 1)+ |
|---|---|---|---|---|
| 28FF | 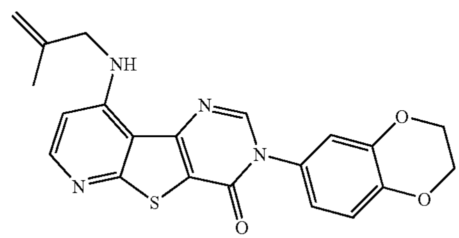 | C21H18N4O3S | 406.5 | 407.2 |
| 28FG | 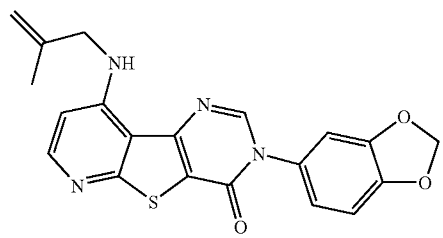 | C20H16N4O3S | 392.4 | 393.2 |
| 28FH | 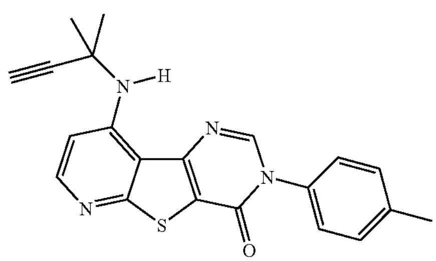 | C21H18N4OS | 374.5 | 375.2 |
| 28FI | 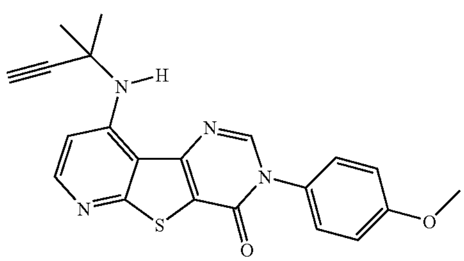 | C21H18N4O2S | 390.5 | 391.2 |
| 28FP | 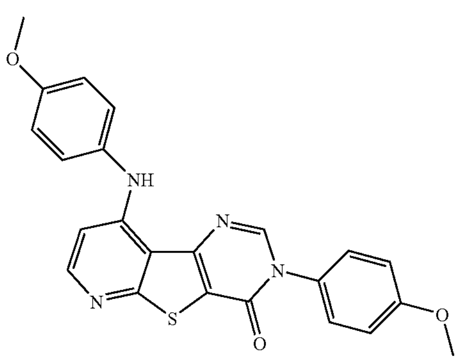 | C23H18N4O3S | 430.5 | 431.2 |

-continued

| Cpd | Structure | Formula | MW | m/z Found (M + 1)+ |
|---|---|---|---|---|
| 95FV | 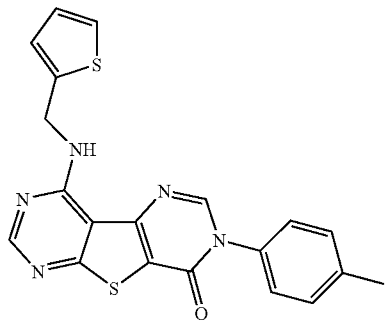 | C20H15N5OS2 | 405.5 | 406.2 |
| 28GA | 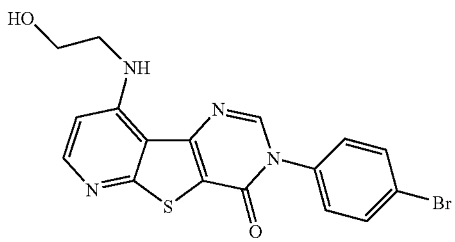 | C17H13BrN4O2S | 417.3 | 419.1 |
| 28GB | 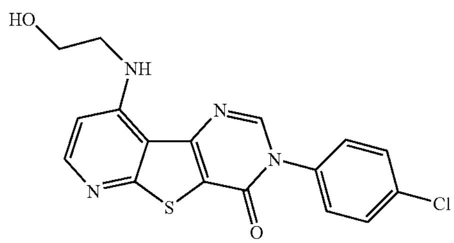 | C17H13ClN4O2S | 372.8 | 373.2 |
| 28GC | 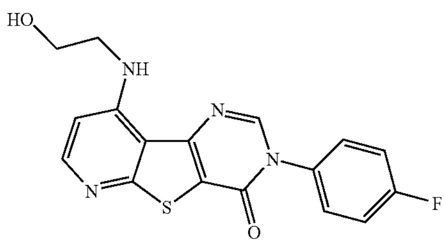 | C17H13FN4O2S | 356.4 | 357.1 |
| 28GD | 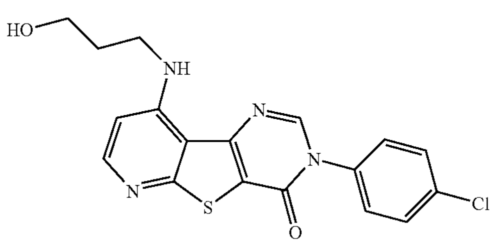 | C18H15ClN4O2S | 386.9 | 387.2 |
| 28GE | 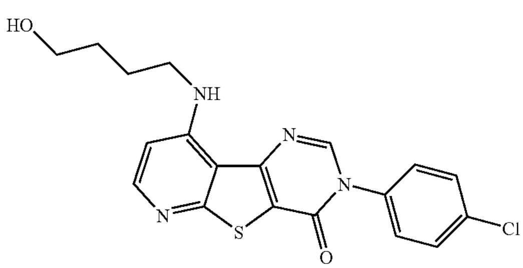 | C19H17ClN4O2S | 400.9 | 401.2 |

-continued

| Cpd | Structure | Formula | MW | m/z Found (M + 1)+ |
|---|---|---|---|---|
| 28GF | 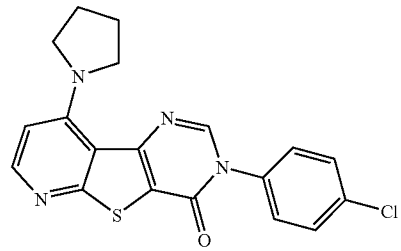 | C19H15ClN4OS | 382.9 | 383.2 |
| 28GG | 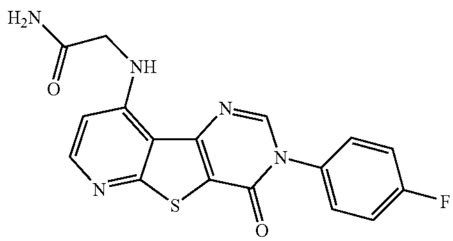 | C17H12FN5O2S | 369.4 | 370.2 |
| 28GH | 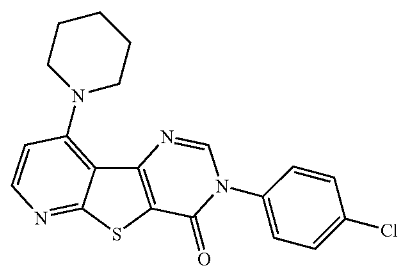 | C20H17ClN4OS | 396.9 | 397.1 |
| 28GI | 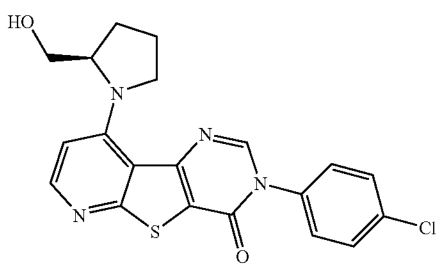 | C20H17ClN4O2S | 412.9 | 413.2 |
| 28GJ | 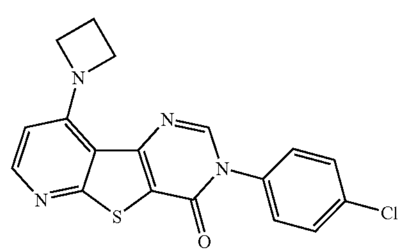 | C18H13ClN4OS | 368.8 | 369.1 |
| 28GK | 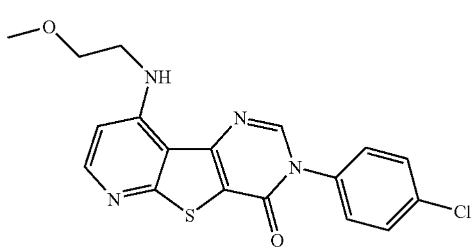 | C18H15ClN4O2S | 386.9 | 387.1 |

-continued

| Cpd | Structure | Formula | MW | m/z Found (M + 1)+ |
|---|---|---|---|---|
| 28GL | 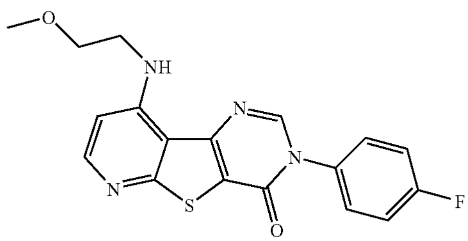 | C18H15FN4O2S | 370.4 | 371.1 |
| 28GM | 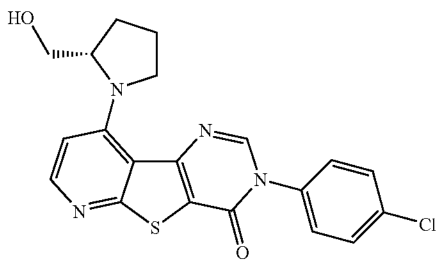 | C20H17ClN4O2S | 412.9 | 413.2 |
| 28GN | 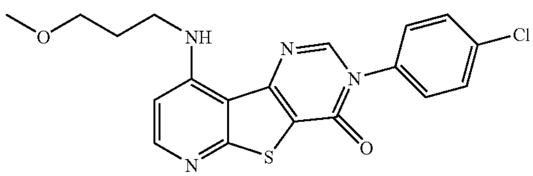 | C19H17ClN4O2S | 400.9 | 401.2 |
| 28GO | 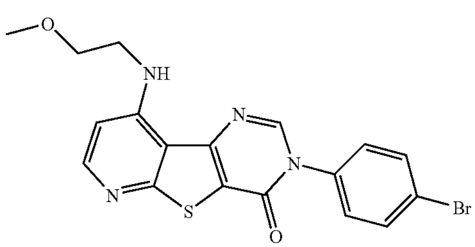 | C18H15BrN4O2S | 431.3 | 433.2 |
| 28GP | 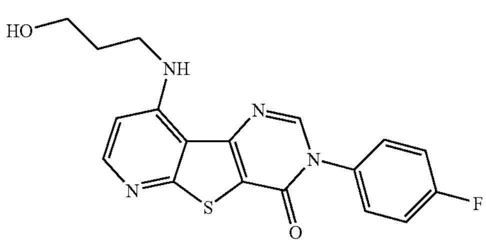 | C18H15FN4O2S | 370.4 | 371.2 |
| 28GQ | 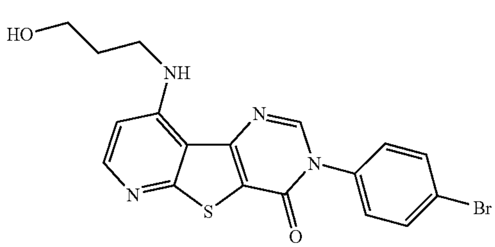 | C18H15BrN4O2S | 431.3 | 433.2 |

| Cpd | Structure | Formula | MW | m/z Found (M + 1)+ |
|---|---|---|---|---|
| 28GR | 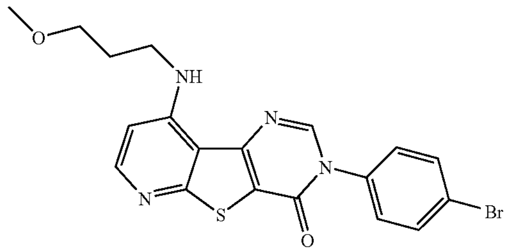 | C19H17BrN4O2S | 445.3 | 447.2 |
| 28GS | 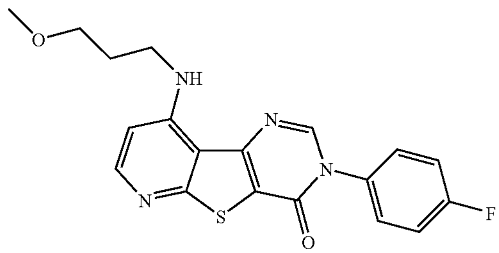 | C19H17FN4O2S | 384.4 | 385.2 |
| 28GT | 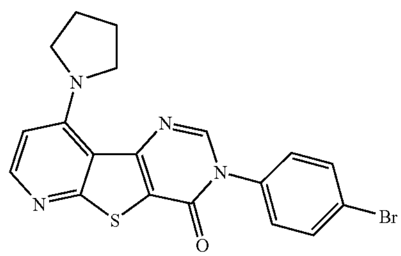 | C19H15BrN4OS | 427.3 | 430.2 |
| 28GU | 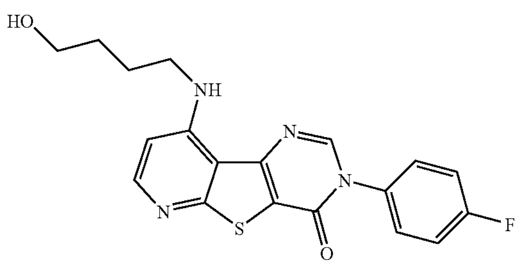 | C19H17FN4O2S | 384.4 | 385.2 |
| 28GV | 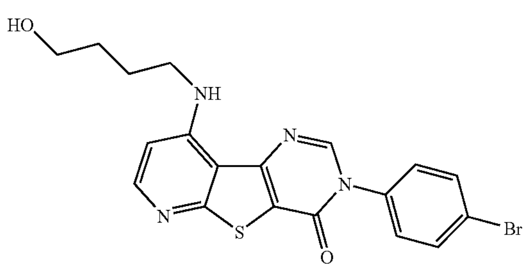 | C19H17BrN4O2S | 445.3 | 447.2 |
| 28GW | 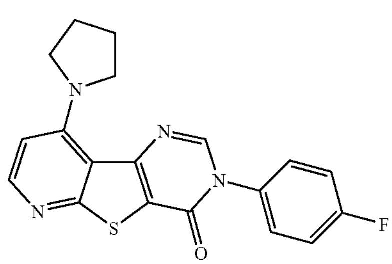 | C19H15FN4OS | 366.4 | 367.2 |

| Cpd | Structure | Formula | MW | m/z Found (M + 1)+ |
|---|---|---|---|---|
| 28GX | 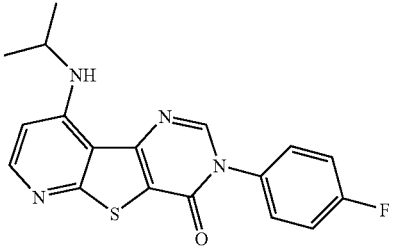 | C18H15FN4OS | 354.4 | 355.2 |
| 28GY | 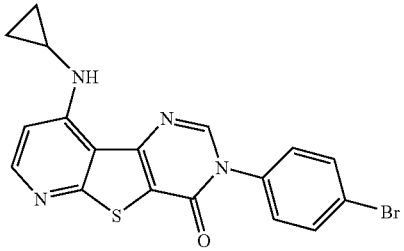 | C18H13BrN4OS | 413.3 | 415.2 |
| 28GZ | 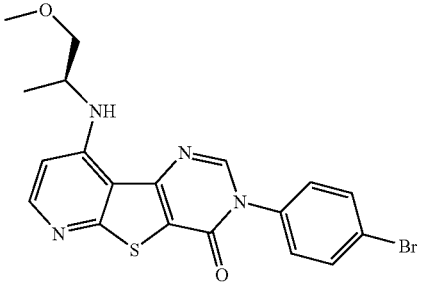 | C19H17BrN4O2S | 445.3 | 447.2 |
| 28HA | 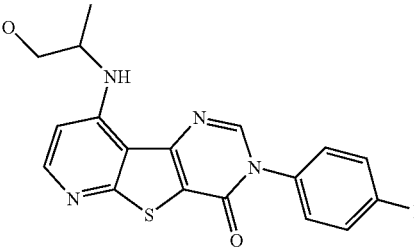 | C19H17BrN4O2S | 445.3 | 447.2 |
| 28HB | 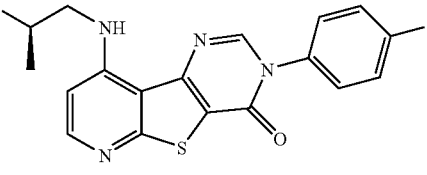 | C18H15BrN4O2S | 431.3 | 431.2 |
| 28HC | 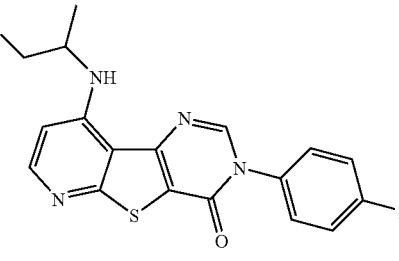 | C18H15BrN4O2S | 431.3 | 431.2 |

-continued

| Cpd | Structure | Formula | MW | m/z Found (M + 1)+ |
|---|---|---|---|---|
| 28HD | 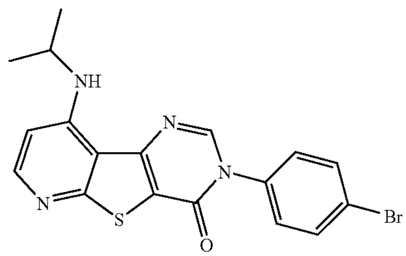 | C18H15BrN4OS | 415.3 | 417.2 |
| 28HE | 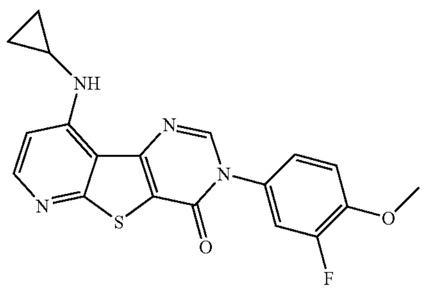 | C19H15FN4O2S | 382.4 | 383.2 |
| 28HF | 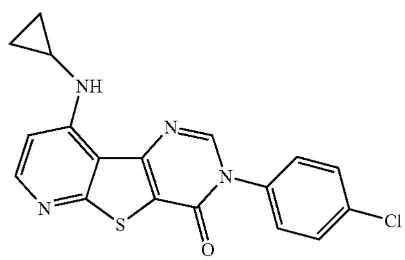 | C18H13ClN4OS | 368.8 | 369.2 |
| 28HG | 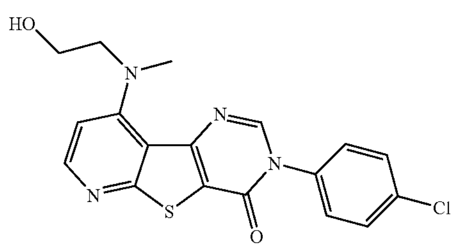 | C18H15ClN4O2S | 386.9 | 387.1 |
| 28HH | 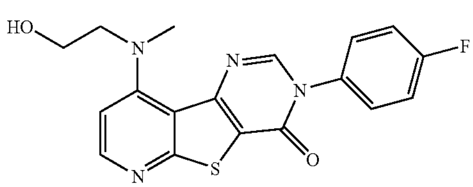 | C18H15FN4O2S | 370.4 | 371.1 |
| 28HI | 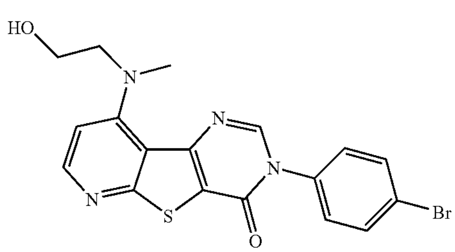 | C18H15BrN4O2S | 431.3 | 433.1 |

-continued

| Cpd | Structure | Formula | MW | m/z Found (M + 1)+ |
|---|---|---|---|---|
| 28HJ | 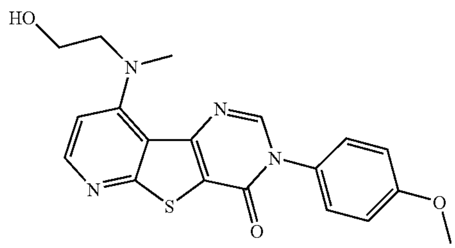 | C19H18N4O3S | 382.4 | 383.2 |
| 28HK | 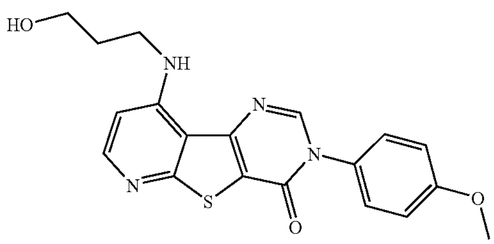 | C19H18N4O3S | 382.4 | 383.2 |
| 28HL | 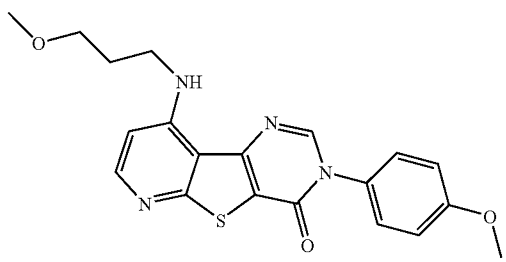 | C20H20N4O3S | 396.5 | 397.1 |
| 28HM | 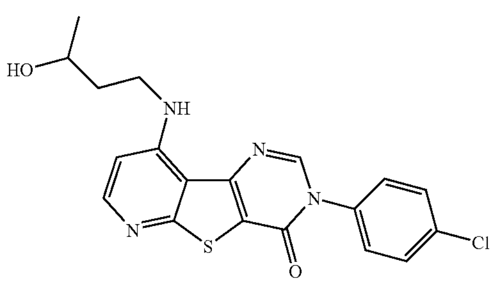 | C19H17ClN4O2S | 400.9 | 401.1 |
| 28HN | 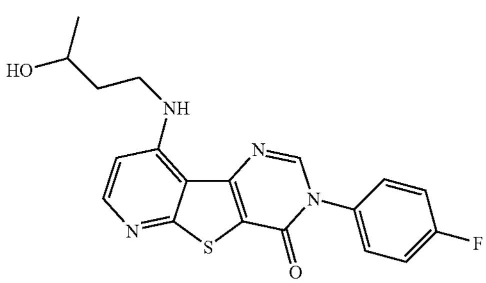 | C19H17FN4O2S | 384.4 | 385.1 |

-continued

| Cpd | Structure | Formula | MW | m/z Found (M + 1)+ |
|---|---|---|---|---|
| 28HO | 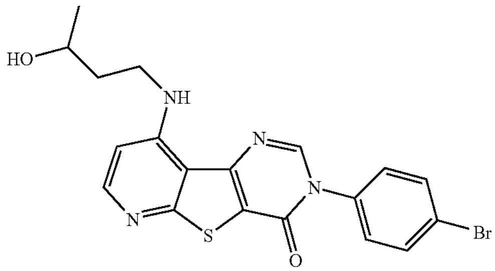 | C19H17BrN4O2S | 445.3 | 447.1 |
| 28HP | 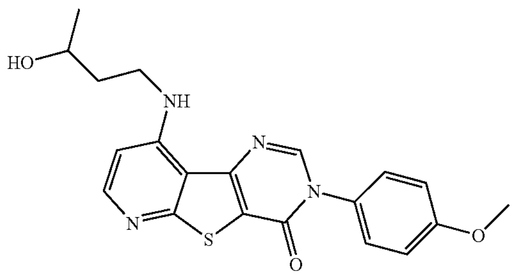 | C20H20N4O3S | 396.5 | 397.1 |
| 28HQ | 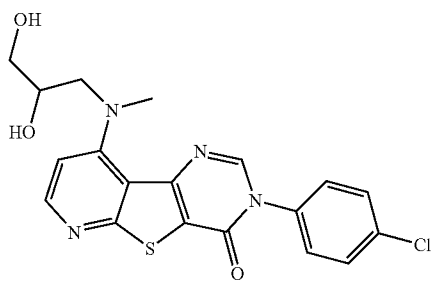 | C19H17ClN4O3S | 416.9 | 417.2 |
| 28HR | 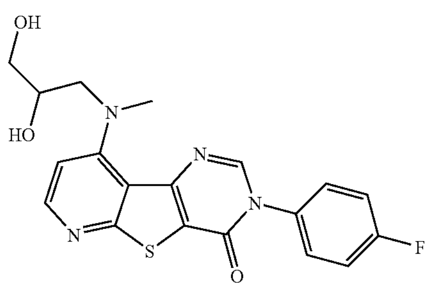 | C19H17FN4O3S | 400.4 | 401.2 |
| 28HS | 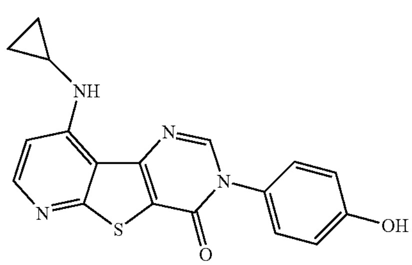 | C18H14N4O2S | 350.4 | 351.2 |

-continued

| Cpd | Structure | Formula | MW | m/z Found (M + 1)+ |
|---|---|---|---|---|
| 28HT | 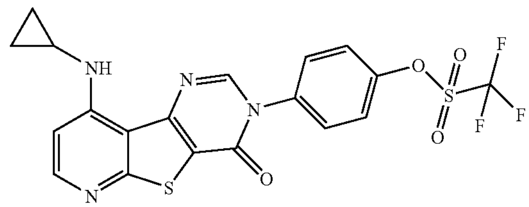 | C19H13F3N4O4S2 | 482.5 | 483.3 |
| 28HU | 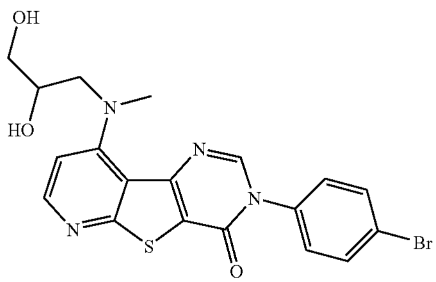 | C19H17BrN4O3S | 461.3 | 463.3 |
| 28HV | 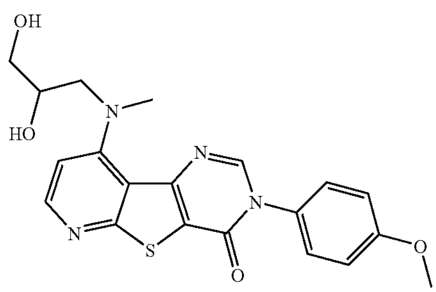 | C20H20N4O4S | 412.5 | 413.2 |
| 28HW | 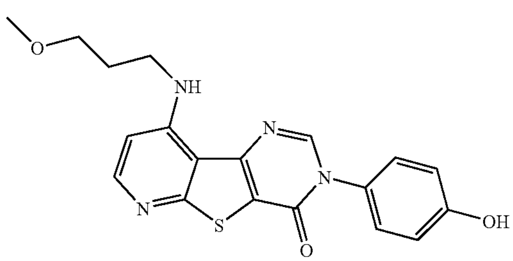 | C19H18N4O3S | 382.4 | 383.2 |
| 28HX | 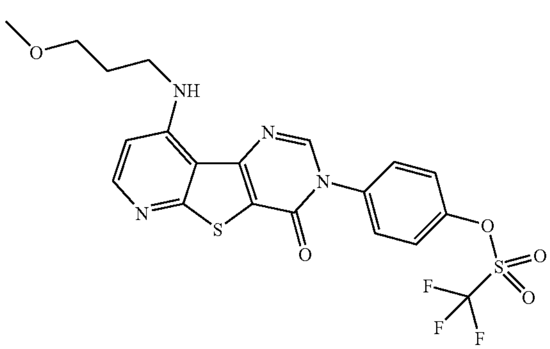 | C20H17F3N4O5S2 | 514.5 | 515.3 |

-continued

| Cpd | Structure | Formula | MW | m/z Found (M + 1)+ |
|---|---|---|---|---|
| 28HY | 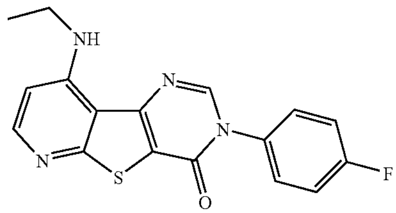 | C17H13FN4OS | 340.4 | 341.2 |
| 28HZ | 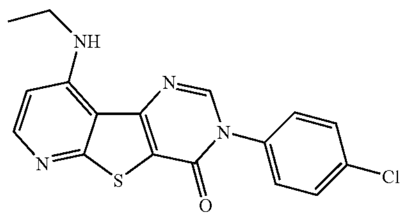 | C17H13ClN4OS | 356.8 | 357.2 |
| 28IA | 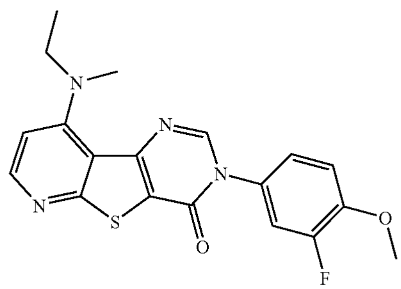 | C19H17FN4O2S | 384.4 | 385.2 |
| 28IB | 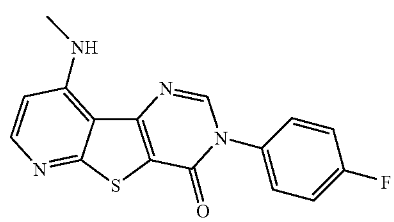 | C16H11FN4OS | 326.3 | 327.2 |
| 28IC | 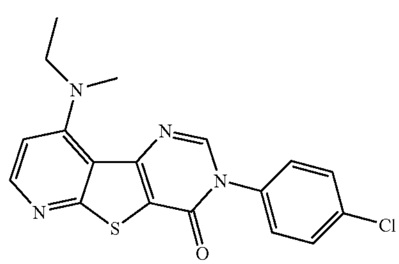 | C18H15ClN4OS | 370.9 | 371.2 |
| 28ID | 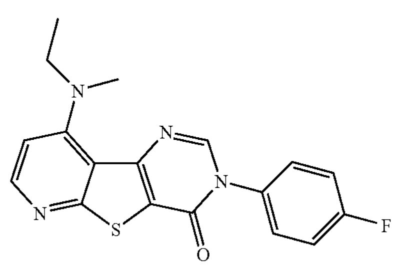 | C18H15FN4OS | 354.4 | 355.2 |

-continued

| Cpd | Structure | Formula | MW | m/z Found (M + 1)+ |
|---|---|---|---|---|
| 28IE | 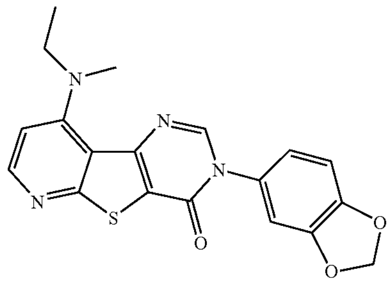 | C19H16N4O3S | 380.4 | 381.2 |

The following compounds were prepared using Method T:

| Cpd | Structure | Formula | MW | m/z Found (M + 1)+ |
|---|---|---|---|---|
| 28FK | 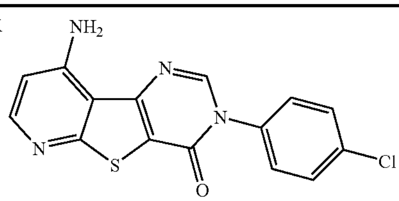 | C15H9ClN4OS | 328.8 | 329.2 |
| 95FU | 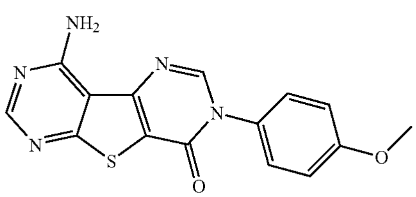 | C15H11N5O2S | 325.3 | 326.1 |

The following compounds were prepared using Method X:

| Cpd | Structure | Formula | MW | m/z Found (M + 1)+ |
|---|---|---|---|---|
| 197 | 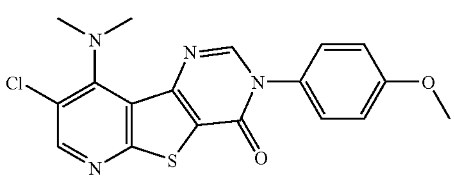 | C18H15ClN4O2S | 386.9 | 387.2 |
| 198 | 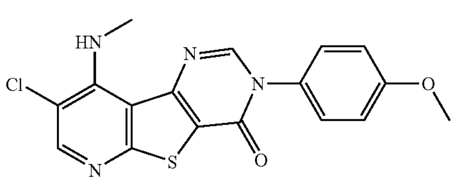 | C17H13ClN4O2S | 372.8 | 373.2 |

| Cpd | Structure | Formula | MW | m/z Found (M + 1)+ |
|---|---|---|---|---|
| 199 | 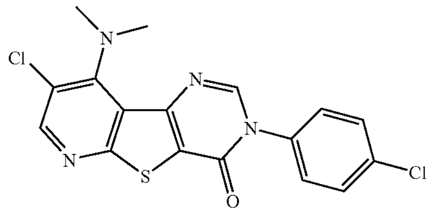 | C17H12Cl2N4OS | 391.3 | 391.2 |
| 200 | 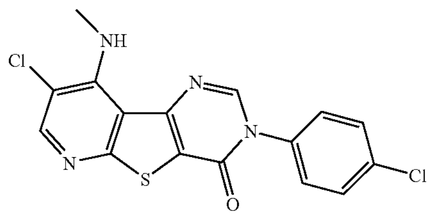 | C16H10Cl2N4OS | 377.2 | 377.2 |

Method X (Alternate 1):
The following compound was prepared using Method X substituting NBS for NCS:

| Cpd | Structure | Formula | MW | m/z Found (M + 1)+ |
|---|---|---|---|---|
| 188 | 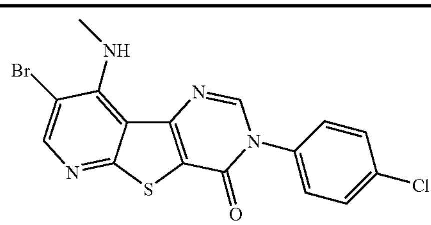 | C16H10BrClN4OS | 421.7 | 423.2 |

The following compound was prepared using Method Y:

| Cpd | Structure | Formula | MW | m/z Found (M + 1)+ |
|---|---|---|---|---|
| 173A | 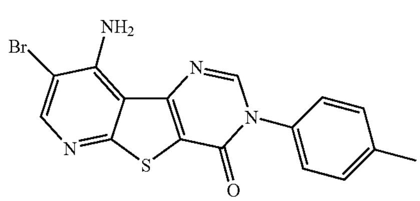 | C16H11BrN4OS | 387.3 | 387.1 |

-continued

| Cpd | Structure | Formula | MW | m/z Found (M + 1)+ |
|---|---|---|---|---|
| 173B | 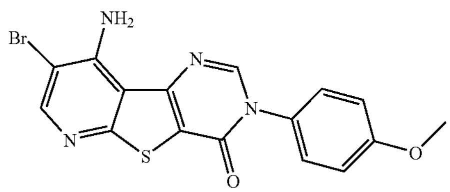 | C16H11BrN4O2S | 403.3 | 405.2 |
| 196 | 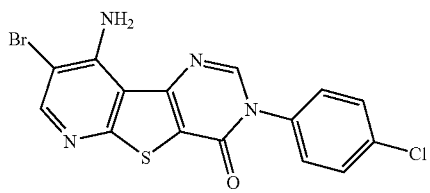 | C15H8BrClN4OS | 407.7 | 409.2 |

The following compounds were prepared using Method AA:

| Cpd | Structure | Formula | MW | m/z Found (M + 1)+ |
|---|---|---|---|---|
| 189 | 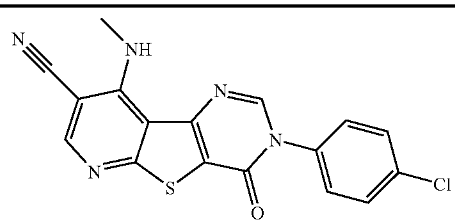 | C17H10ClN5OS | 367.8 | 368.2 |
| 194 | 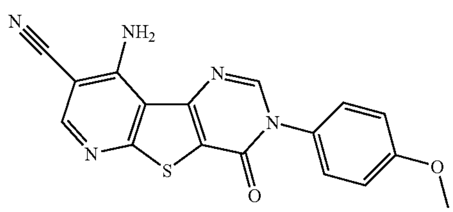 | C17H11N5O2S | 349.4 | 350.2 |

Method AH (Alternate 3, additional example):

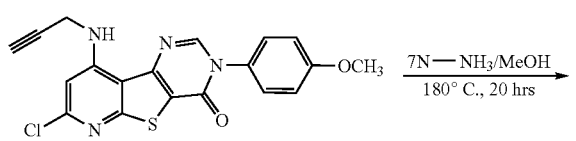

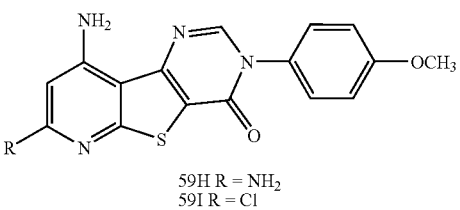

59H R = $NH_2$
59I R = Cl

A stirring mixture of n-propargyl amine tricyclic (0.035 g, 0.088 mmol) in 7N—$NH_3$/methanol (40 mls) was sealed in a Parr steel reaction vessel and was heated in an oil bath at 180-185° C. for 20 hrs. The reaction was cooled to room temperature and was analyzed by tlc (20% acetone/$CH_2Cl_2$). The solvent was concentrated under vacuum to give a solid (0.056 g). The crude product was purified by reverse-phase HPLC (C18 column). Elution with solvent gradient 5% $CH_3CN/H_2O$/0.1% formic acid to 95% $CH_3CN/H_2O$/0.1% formic acid gave 59H (0.005 g) and 59I (0.011 g). Product 59H: MS (M+1)+ m/z calcd for $C_{16}H_{14}N_5O_2S^+$=340.1, observed m/z=340.2 Product 59I: MS (M+1)+ m/z calcd for $C_{16}H_{12}ClN_4O_2S^+$=359.0, observed m/z=359.2

The following compounds were prepared using Method AH:

| Cpd | Structure | Formula | MW | m/z Found (M + 1)+ |
|---|---|---|---|---|
| 28FM | 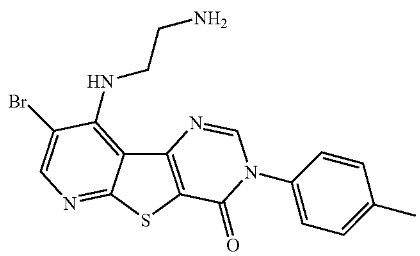 | C18H16BrN5OS | 430.3 | 432.2 |
| 28FN | 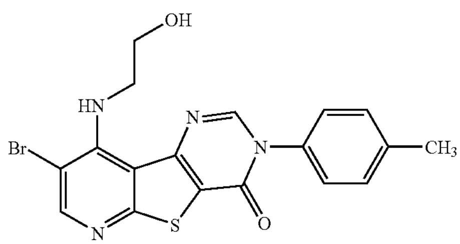 | C18H15BrN4O2S | 431.3 | 433.2 |
| 28FO | 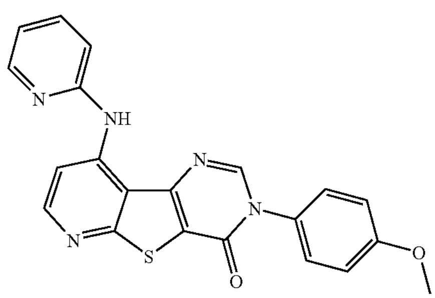 | C21H15N5O2S | 401.4 | 402.2 |
| 59F | 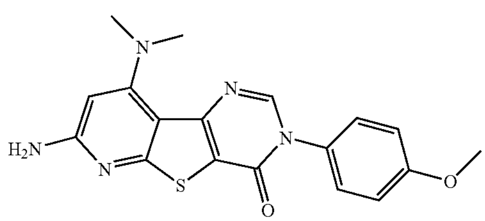 | C18H17N5O2S | 367.4 | 368.2 |
| 59G | 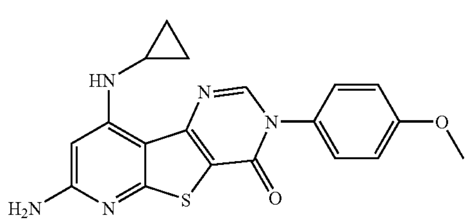 | C19H17N5O2S | 379.4 | 380.2 |

The following compounds were prepared using Method AJ:

| Cpd | Structure | Formula | MW | m/z Found (M + 1)+ |
|---|---|---|---|---|
| 169A | 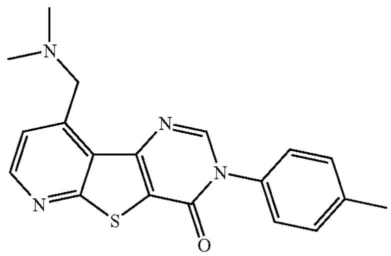 | C19H18N4OS | 350.4 | 351.2 |
| 169B | 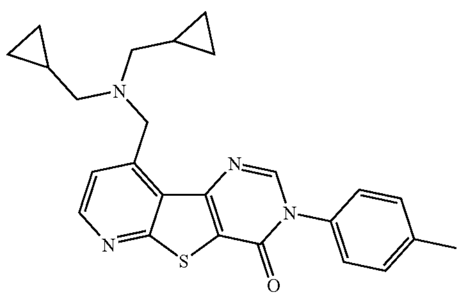 | C25H26N4OS | 430.6 | 431.2 |

The following compounds were prepared using Method AL*:

| Cpd | Structure | Formula | MW | m/z Found (M + 1)+ |
|---|---|---|---|---|
| 73J | 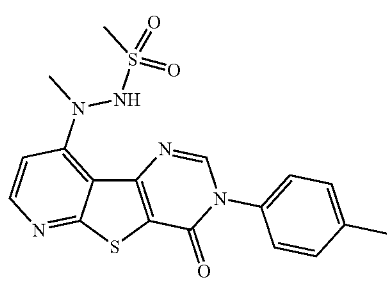 | C18H17N5O3S2 | 415.5 | 416.2 |
| 28FL | 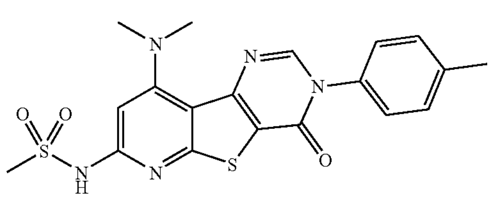 | C19H19N5O3S2 | 429.5 | 430.2 |

*including a MeOH, NaOMe hydrolysis of a bis-sulfonylated product for compound 28FL (Method AL-Alternate-1)

The following compounds were prepared using Method AO:

| Cpd | Structure | Formula | MW | m/z Found (M + 1)+ |
|---|---|---|---|---|
| 66F | 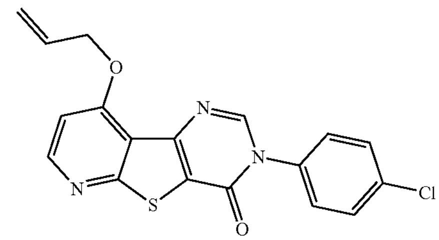 | C18H12ClN3O2S | 369.8 | 370.2 |
| 66G | 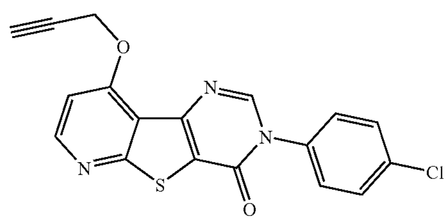 | C18H10ClN3O2S | 367.8 | 368.2 |
| 66H | 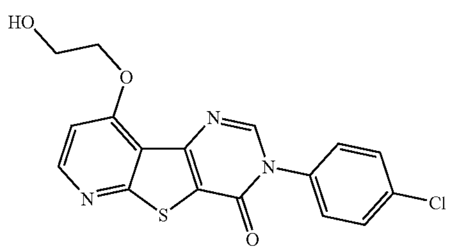 | C17H12ClN3O3S | 373.8 | 374.2 |
| 66I | 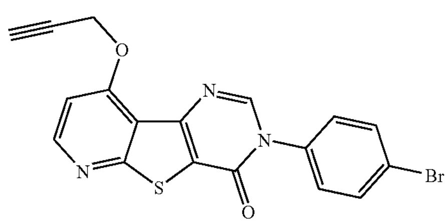 | C18H10BrN3O2S | 412.3 | 414.0 |
| 66J | 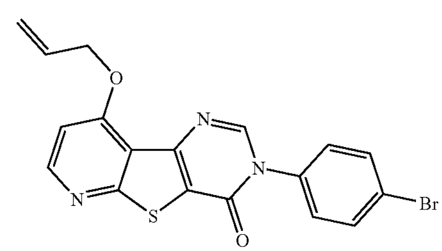 | C18H12BrN3O2S | 414.3 | 416.0 |
| 66K | 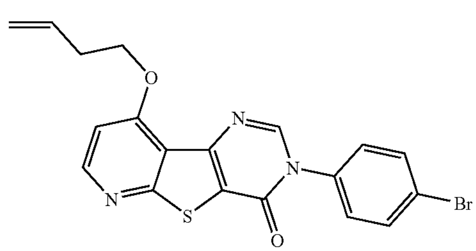 | C19H14BrN3O2S | 428.3 | 430.0 |

-continued

| Cpd | Structure | Formula | MW | m/z Found (M + 1)+ |
|---|---|---|---|---|
| 66L | 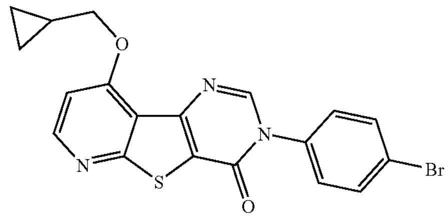 | C19H14BrN3O2S | 428.3 | 430.0 |
| 66M | 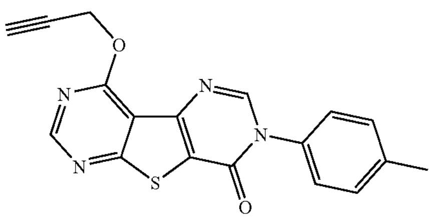 | C18H12N4O2S | 348.4 | 349.2 |

The following compounds were prepared using Method AS:

| Cpd | Structure | Formula | MW | m/z Found (M + 1)+ |
|---|---|---|---|---|
| 71B | 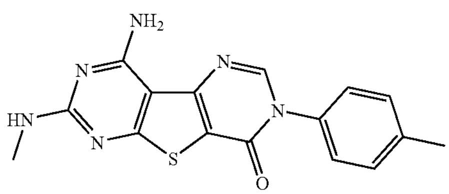 | C16H14N6OS | 338.4 | 339.2 |
| 71C | 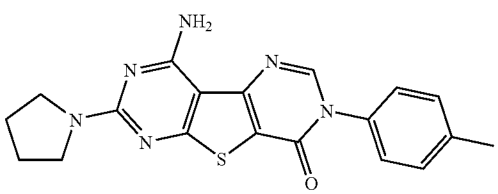 | C19H18N6OS | 378.5 | 379.2 |
| 71D | 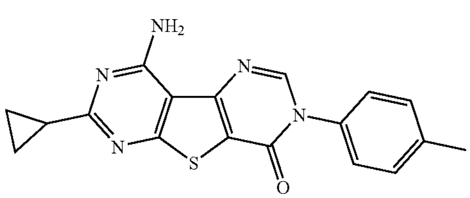 | C18H15N5OS | 349.4 | 350.1 |
| 71E | 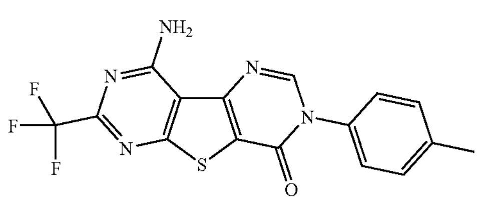 | C16H10F3N5OS | 377.3 | 378.2 |

-continued
| Cpd | Structure | Formula | MW | m/z Found (M + 1)+ |
|---|---|---|---|---|
| 71F | 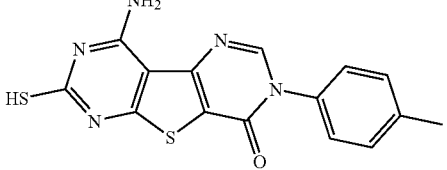 | C15H11N5OS2 | 341.4 | 342.1 |
The following compounds were prepared using Method AT:
| Cpd | Structure | Formula | MW | m/z Found (M + 1)+ |
|---|---|---|---|---|
| 73H | 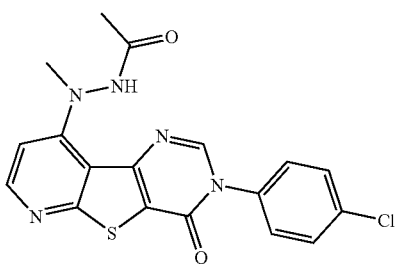 | C18H14ClN5O2S | 399.9 | 400.2 |
| 73I | 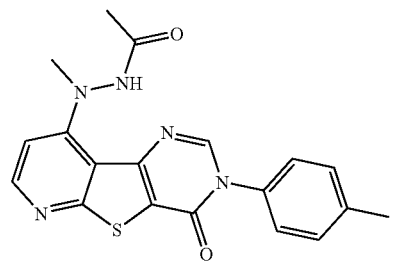 | C19H17N5O2S | 379.4 | 380.2 |
The following compound were prepared using Method AZ:
| Cpd | Structure | Formula | MW | m/z Found (M + 1)+ |
|---|---|---|---|---|
| 57C | 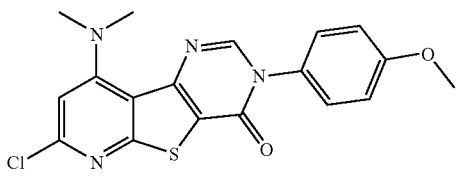 | C18H15ClN4O2S | 386.9 | 387.2 |
| 57D | 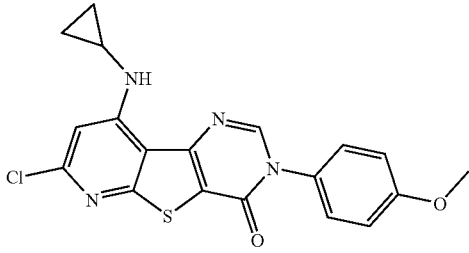 | C19H15ClN4O2S | 398.9 | 399.2 |

The following compounds were prepared using Method BA:

| Cpd | Structure | Formula | MW | m/z Found (M + 1)+ |
|---|---|---|---|---|
| 29F | 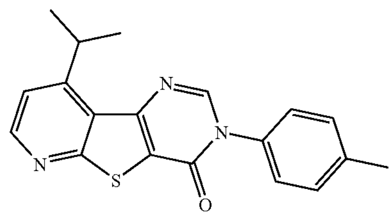 | C19H17N3OS | 335.4 | 336.1 |
| 29G | 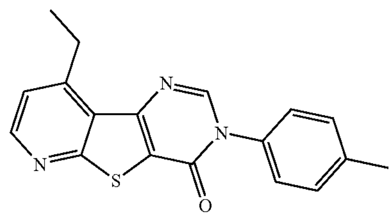 | C18H15N3OS | 321.4 | 322.2 |
| 29H | 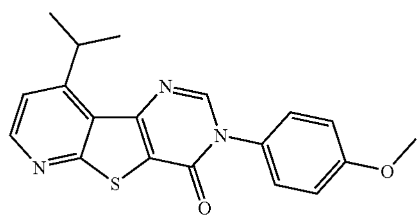 | C19H17N3O2S | 351.4 | 352.2 |
| 29I | 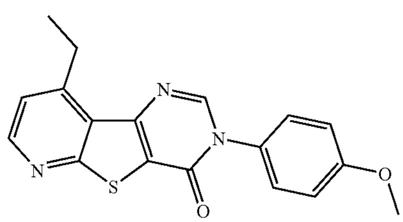 | C18H15N3O2S | 337.4 | 338.2 |
| 29J | 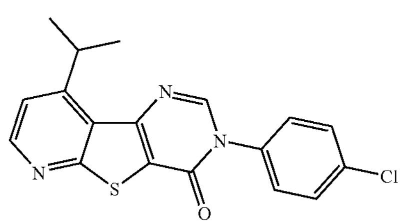 | C18H14ClN3OS | 355.8 | 356.2 |
| 29K | 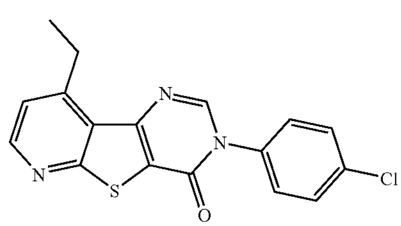 | C17H12ClN3OS | 341.8 | 342.2 |

The following compound was prepared using Method BB:

| Cpd | Structure | Formula | MW | m/z Found (M + 1)+ |
|---|---|---|---|---|
| 57E | 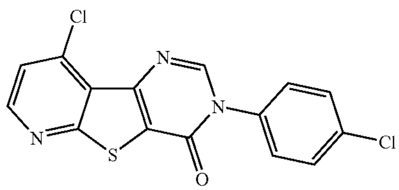 | C15H7Cl2N3OS | 348.2 | 348.2 |

The following compounds were prepared using Method BD:

| Cpd | Structure | Formula | MW | m/z Found (M + 1)+ |
|---|---|---|---|---|
| 167A | 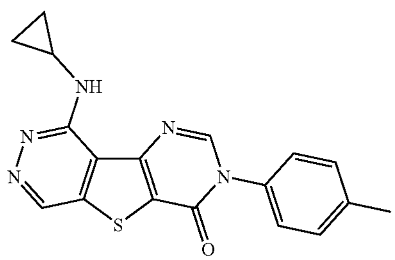 | C18H15N5OS | 349.4 | 350.2 |
| 167B | 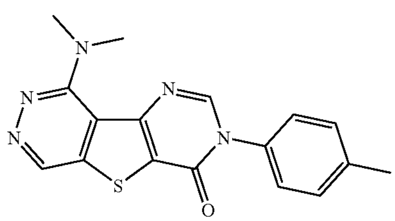 | C17H15N5OS | 337.4 | 338.2 |
| 167C | 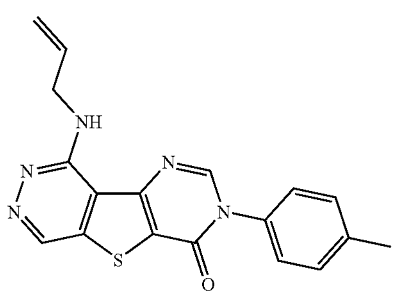 | C18H15N5OS | 349.4 | 350.2 |
| 167D | 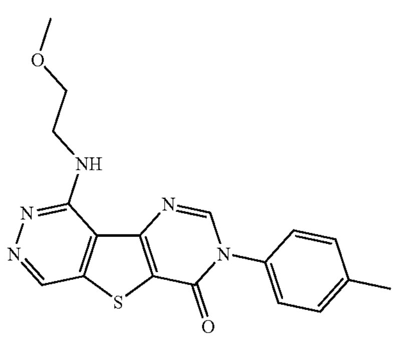 | C18H17N5O2S | 367.4 | 368.2 |

| Cpd | Structure | Formula | MW | m/z Found (M + 1)+ |
|---|---|---|---|---|
| 167E | 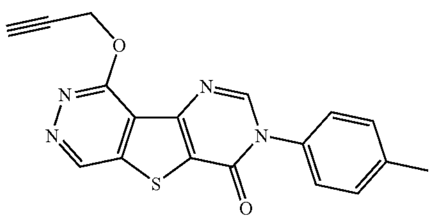 | C18H12N4O2S | 348.4 | 349.1 |
| 167F | 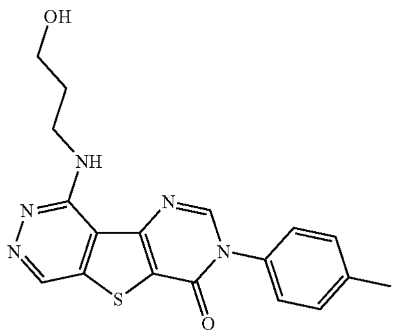 | C18H17N5O2S | 367.4 | 368.2 |
| 167G | 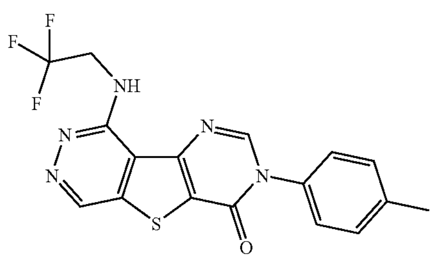 | C17H12F3N5OS | 391.4 | 392.2 |
| 167H | 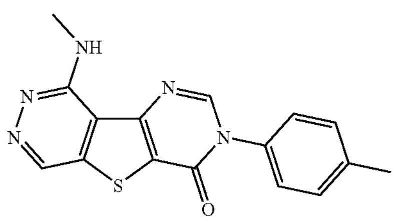 | C16H13N5OS | 323.4 | 324.2 |
| 167I | 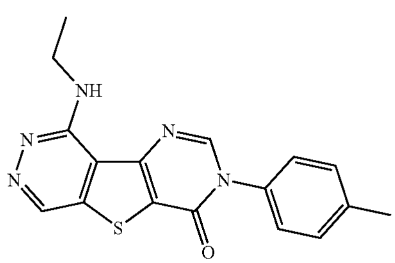 | C17H15N5OS | 337.4 | 338.1 |
| 167J | 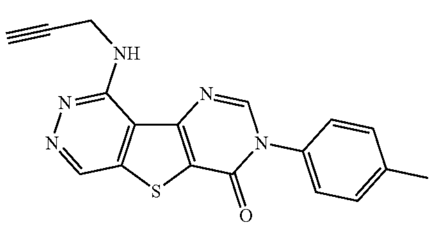 | C18H13N5OS | 347.4 | 348.1 |

The following compounds were prepared using Method BM:

| Cpd | Structure | Formula | MW | m/z Found (M + 1)+ |
|---|---|---|---|---|
| 161A | 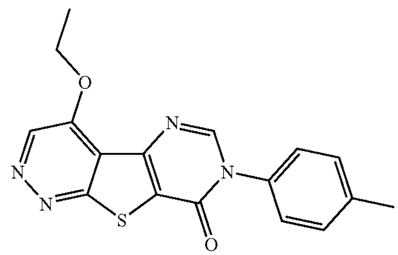 | C17H14N4O2S | 338.4 | 339.2 |
| 161B | 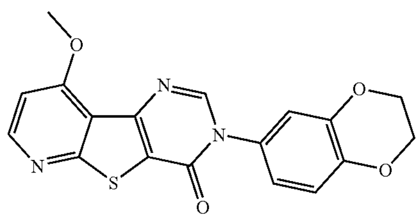 | C18H13N3O4S | 367.4 | 368.2 |
| 161C | 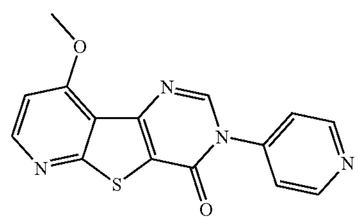 | C15H10N4O2S | 310.3 | 311.2 |
| 164 | 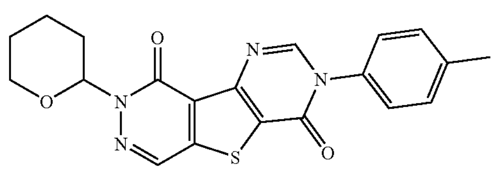 | C20H18N4O3S | 394.5 | 395.2 |
| 103G | 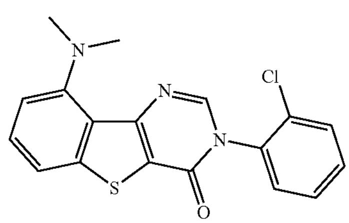 | C18H14ClN3OS | 355.8 | 356.2 |
| 103H | 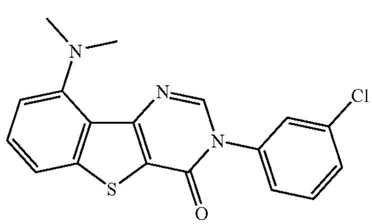 | C18H14ClN3OS | 355.8 | 356.2 |
| 103I | 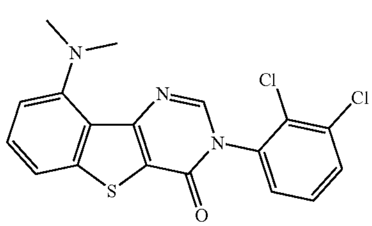 | C18H13Cl2N3OS | 390.3 | 392.2 |

-continued

| Cpd | Structure | Formula | MW | m/z Found (M + 1)+ |
|---|---|---|---|---|
| 103J | 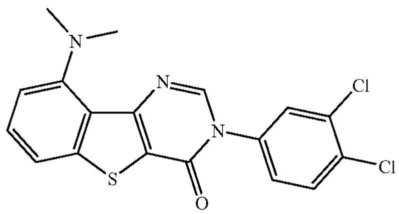 | C18H13Cl2N3OS | 390.3 | 392.2 |
| 103K | 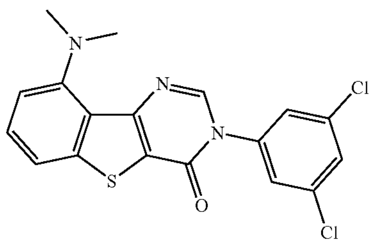 | C18H13Cl2N3OS | 390.3 | 392.2 |
| 103L | 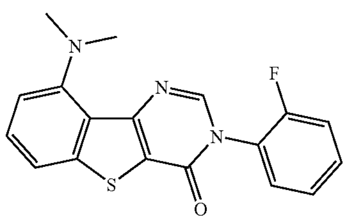 | C18H14FN3OS | 339.4 | 340.1 |
| 103M | 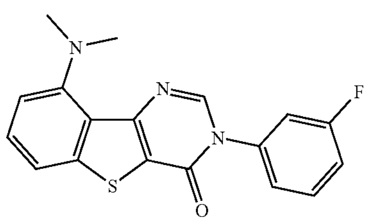 | C18H14FN3OS | 339.4 | 340.1 |
| 103N | 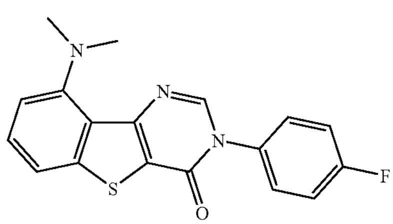 | C18H14FN3OS | 339.4 | 340.1 |
| 103O | 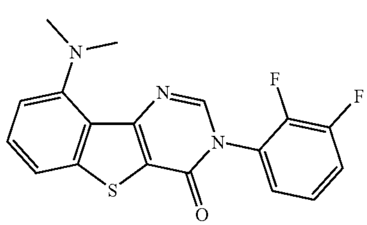 | C18H13F2N3OS | 357.4 | 358.1 |

-continued

| Cpd | Structure | Formula | MW | m/z Found (M + 1)+ |
|---|---|---|---|---|
| 103P | 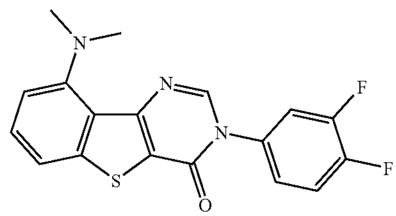 | C18H13F2N3OS | 357.4 | 358.1 |
| 103Q | 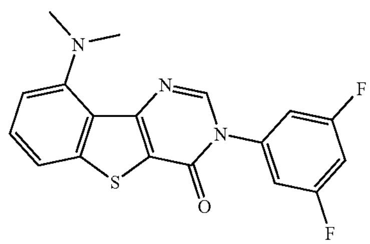 | C18H13F2N3OS | 357.4 | 358.2 |
| 103R | 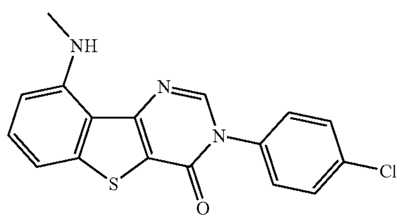 | C17H12ClN3OS | 341.8 | 342.2 |
| 103S | 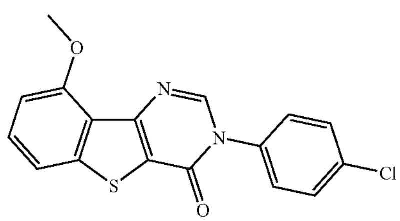 | C17H11ClN2O2S | 342.8 | 343.1 |
| 28EH | 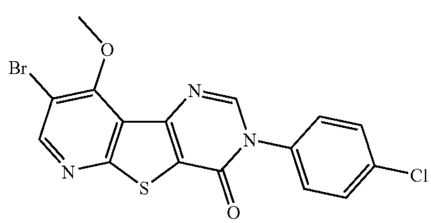 | C16H9BrClN3O2S | 422.7 | 424.2 |
| 28EI | 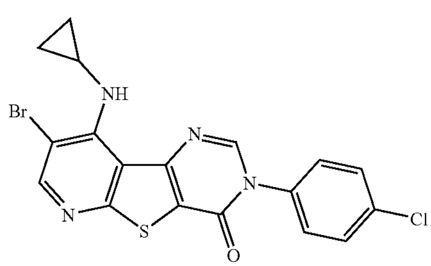 | C18H12BrClN4OS | 447.7 | 449.2 |

-continued

| Cpd | Structure | Formula | MW | m/z Found (M + 1)+ |
|---|---|---|---|---|
| 28EJ | 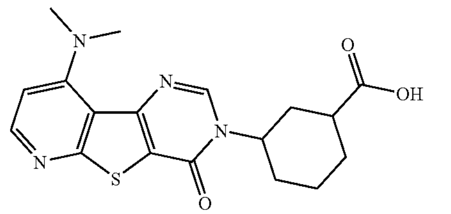 | C18H20N4O3S | 372.4 | 372.2 |
| 28EK | 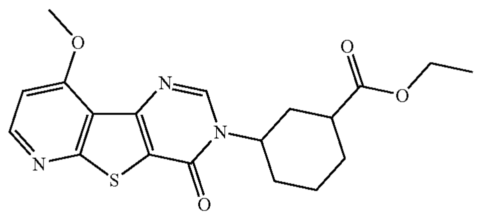 | C19H21N3O4S | 387.5 | 388.2 |
| 28EL | 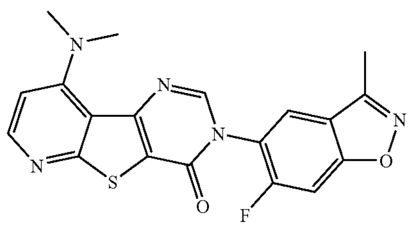 | C19H14FN5O2S | 395.4 | 396.2 |
| 28EM | 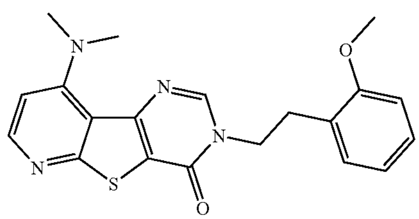 | C20H20N4O2S | 380.5 | 381.2 |
| 28EN | 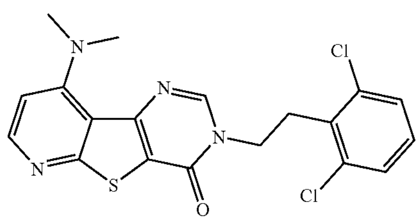 | C19H16Cl2N4OS | 419.3 | 419.2 |
| 95FM | 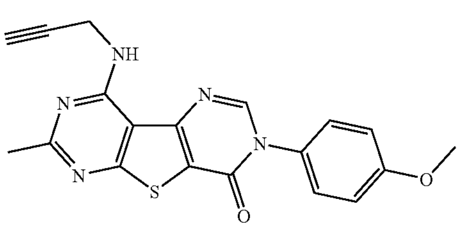 | C19H15N5O2S | 377.4 | 378.2 |
| 95FN | 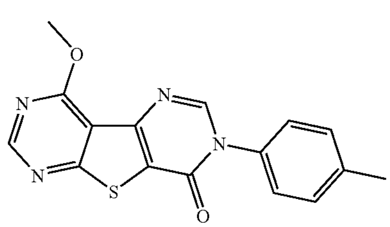 | C16H12N4O2S | 324.4 | 325.2 |

-continued

| Cpd | Structure | Formula | MW | m/z Found (M + 1)+ |
|---|---|---|---|---|
| 95FO | 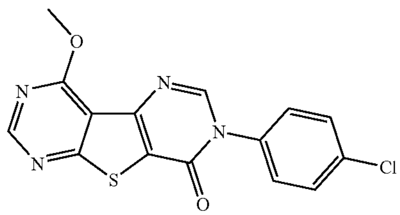 | C15H9ClN4O2S | 344.8 | 345.2 |

The following compound was prepared using Method BO:

| Cpd | Structure | Formula | MW | m/z Found (M + 1)+ |
|---|---|---|---|---|
| 28FQ | 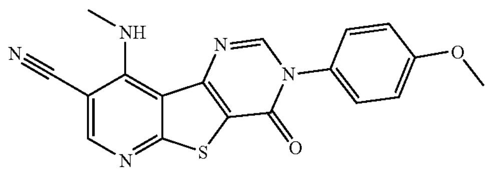 | C18H13N5O2S | 363.4 | 364.2 |

The following compounds were prepared using Method BZ:

| Cpd | Structure | Formula | MW | m/z Found (M + 1)+ |
|---|---|---|---|---|
| 131H | 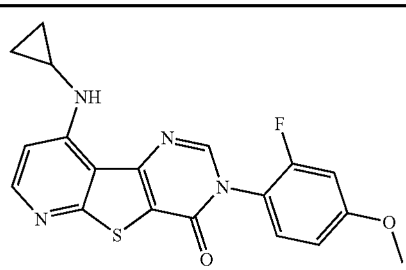 | C19H15FN4O2S | 382.4 | 383.2 |
| 131I | 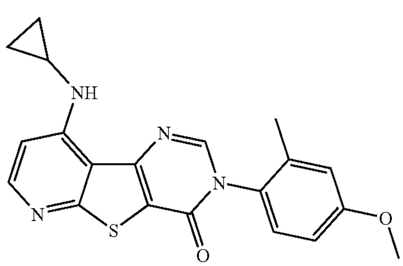 | C20H18N4O2S | 378.4 | 379.2 |
| 131J | 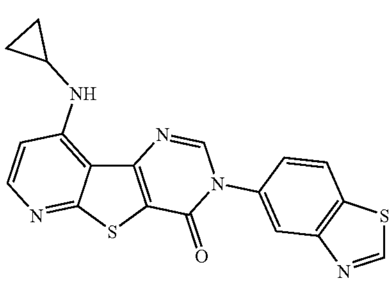 | C19H13N5OS2 | 391.5 | 392.2 |

-continued

| Cpd | Structure | Formula | MW | m/z Found (M + 1)+ |
|---|---|---|---|---|
| 131K | 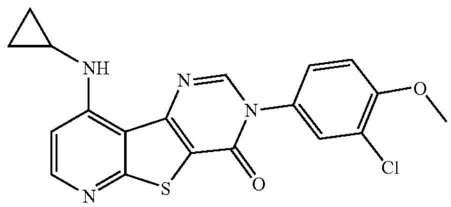 | C19H15ClN4O2S | 398.9 | 399.1 |
| 131L | 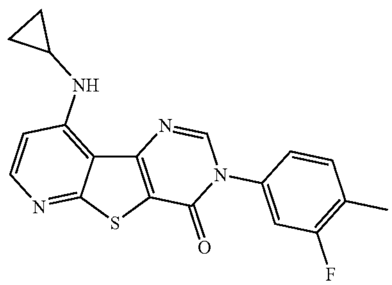 | C19H15FN4OS | 366.4 | 367.2 |
| 131M | 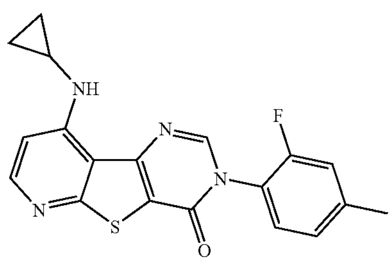 | C19H15FN4OS | 366.4 | 367.1 |
| 131N | 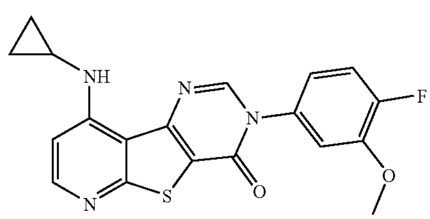 | C19H15FN4O2S | 382.4 | 383.2 |

The following compound was prepared using Method CC:

| Cpd | Structure | Formula | MW | m/z Found (M + 1)+ |
|---|---|---|---|---|
| 29E | 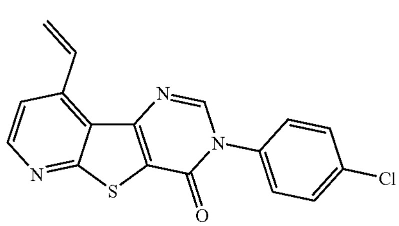 | C17H10ClN3OS | 339.8 | 340.1 |

The following compounds were prepared using Method CD:

| Cpd | Structure | Formula | MW | m/z Found (M + 1)+ |
|---|---|---|---|---|
| 137C | 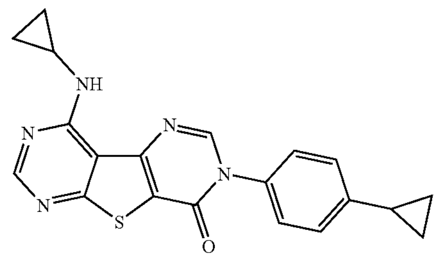 | C20H17N5OS | 375.4 | 376.1 |
| 137D | 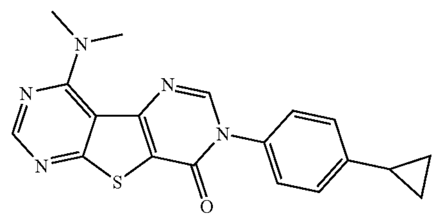 | C19H17N5OS | 363.4 | 364.1 |
| 137E | 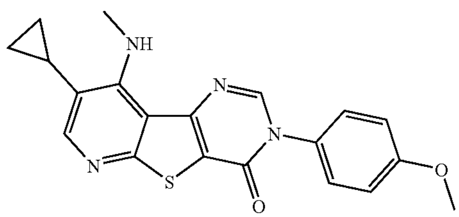 | C20H18N4O2S | 378.4 | 379.2 |
| 137F | 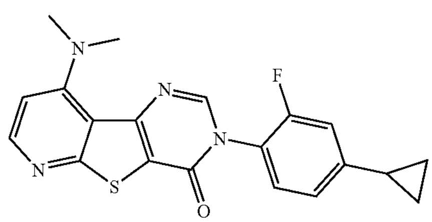 | C20H17FN4OS | 380.4 | 381.2 |
| 137G | 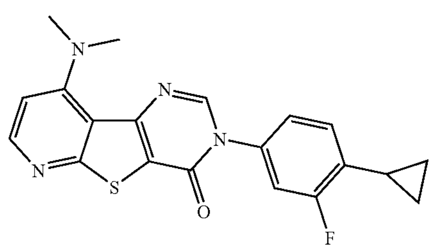 | C20H17FN4OS | 380.4 | 381.2 |
| 137H | 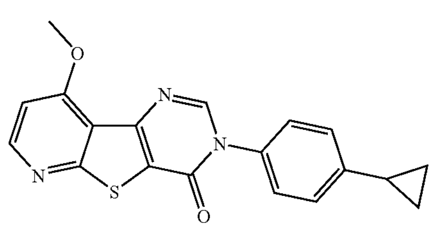 | C19H15N3O2S | 349.4 | 350.2 |

-continued

| Cpd | Structure | Formula | MW | m/z Found (M + 1)+ |
|---|---|---|---|---|
| 137I | 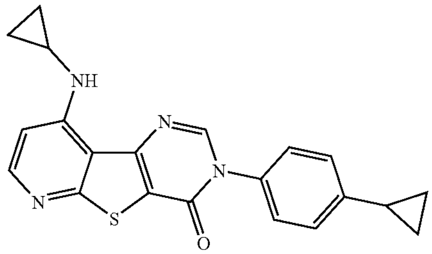 | C21H18N4OS | 374.5 | 375.2 |

IC$_{50}$ Determination

A CHO cell line stably expressing hmGluR1 receptor was established. One day prior to assay, cells were split in growth media at concentration of 50,000 cells/well in a volume of 100 µl and seeded into black clear-bottom 96-well plates. After two to six hours, when cells were well attached to the plate, growth medium was replaced with assay medium (100 µL) consisting of DMEM high glucose, supplemented with GPT (1 U/mL) and Sodium pyruvate, 1 mM. Following overnight incubation, medium was discarded and cells were loaded for 2 h with dye from the Calcium 3 Assay Reagent Kit (Molecular Devices, # R8033), prepared according to manufacturers' instructions. A 96-tip pipettor/fluorometric imaging plate reader (FLIPR 384; Molecular Devices) was used and intracellular calcium mobilization was measured by increases in fluorescence upon agonist Quisqualate stimulation following 6 sec-baseline measurement. Test compounds were added 10 minutes before Quisqualate. IC$_{50}$ determinations for tested compounds were generated against Quisqualate 1 µM corresponding to EC$_{80}$ value in a standard dose response curve.

IC$_{50}$s for representative compounds are shown in Tables 2 and 2a below. Compounds with IC$_{50}$ values greater than 1000 nM are designated as D class compounds. Compounds with IC$_{50}$ values between 150 nM and 1000 nM are designated as C class compounds. Compounds with IC$_{50}$ values between 50 nM and 150 nM are designated as B class compounds. Compounds with IC$_{50}$ values less than 50 nM are designated as A class compounds.

TABLE 2

| Cpd | mGluR 1 IC$_{50}$ (nM) | Structure |
|---|---|---|
| 7A | A | 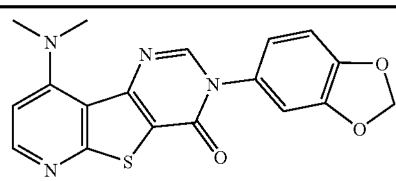 |
| 7B | A | 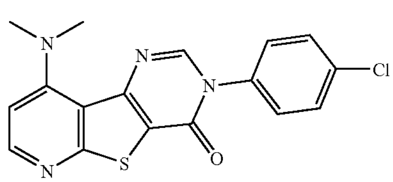 |

TABLE 2-continued

| Cpd | mGluR 1 IC$_{50}$ (nM) | Structure |
|---|---|---|
| 7C | B | 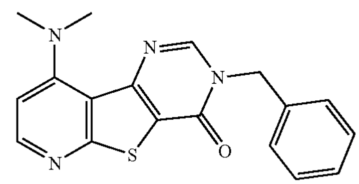 |
| 7D | A | 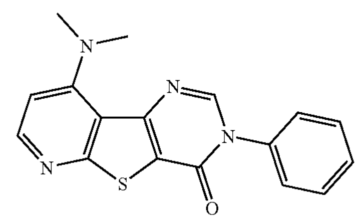 |
| 7E | D | 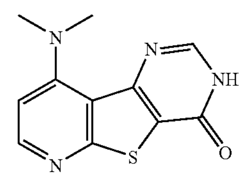 |
| 7F | B | 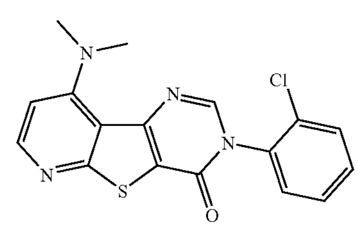 |
| 7G | A | 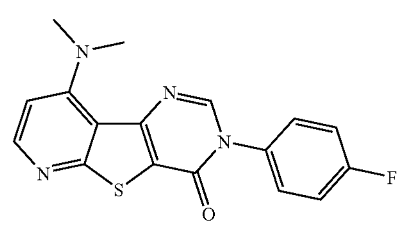 |

TABLE 2-continued

| Cpd | mGluR 1 IC$_{50}$ (nM) | Structure |
|---|---|---|
| 7H | A | (9-dimethylamino-pyrido-thieno-pyrimidinone with N-(4-bromophenyl)) |
| 7I | D | (9-dimethylamino-pyrido-thieno-pyrimidinone with N-(4-chlorobenzyl)) |
| 7J | D | (9-dimethylamino-pyrido-thieno-pyrimidinone with N-(1-ethoxycarbonylpiperidin-4-yl)) |
| 7K | A | (9-dimethylamino-pyrido-thieno-pyrimidinone with N-(4-cyanophenyl)) |
| 7L | A | (9-dimethylamino-pyrido-thieno-pyrimidinone with N-(3-chlorophenyl)) |
| 7M | D | (9-dimethylamino-pyrido-thieno-pyrimidinone with N-(4-iodophenyl)) |
| 7N | C | (9-dimethylamino-pyrido-thieno-pyrimidinone with N-(2-iodo-4-chlorophenyl)) |
| 7O | B | (9-dimethylamino-pyrido-thieno-pyrimidinone with N-(pyridin-3-yl)) |
| 7P | B | (9-dimethylamino-pyrido-thieno-pyrimidinone with N-butyl) |
| 7Q | A | (9-dimethylamino-pyrido-thieno-pyrimidinone with N-cyclohexyl) |
| 7R | C | (9-dimethylamino-pyrido-thieno-pyrimidinone with N-(3-chlorobenzyl)) |
| 7S | D | (9-dimethylamino-pyrido-thieno-pyrimidinone with N-(3,4-dichlorobenzyl)) |
| 7T | B | (9-dimethylamino-pyrido-thieno-pyrimidinone with N-(3-chloro-4-methoxyphenyl)) |

TABLE 2-continued
| Cpd | mGluR 1 IC$_{50}$ (nM) | Structure |
|---|---|---|
| 7U | B | 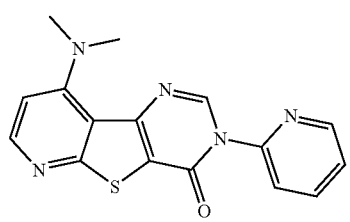 |
| 7V | D | 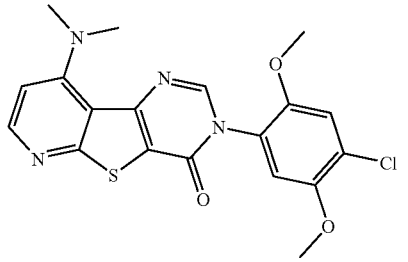 |
| 7W | A | 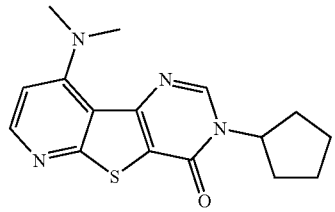 |
| 7X | A | 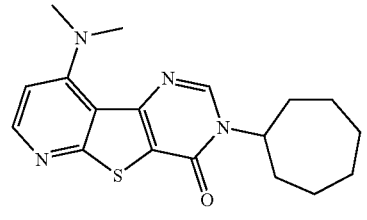 |
| 7Y | A | 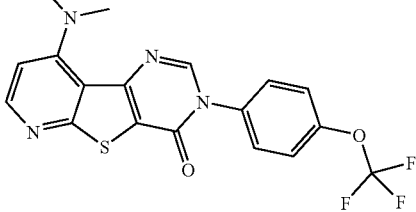 |
| 7Z | A | 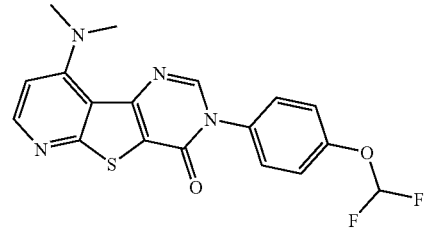 |
TABLE 2-continued
| Cpd | mGluR 1 IC$_{50}$ (nM) | Structure |
|---|---|---|
| 7AA | A | 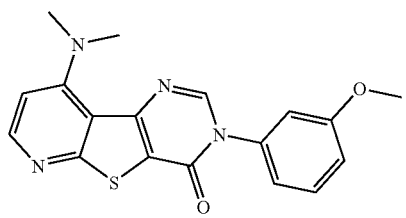 |
| 7AB | C | 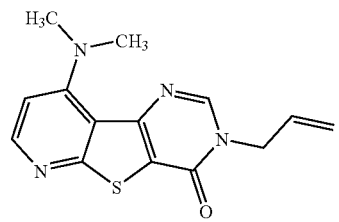 |
| 7AC | A | 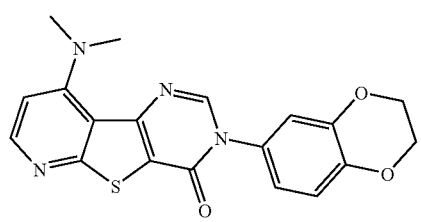 |
| 7AD | D | 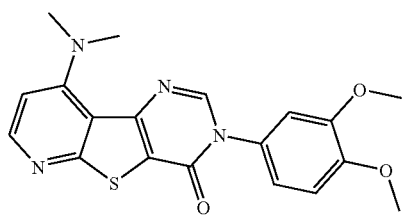 |
| 7AE | C | 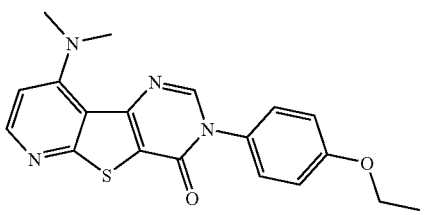 |
| 7AF | D | 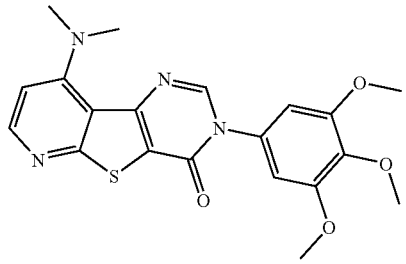 |

TABLE 2-continued
| Cpd | mGluR 1 IC$_{50}$ (nM) | Structure |
|---|---|---|
| 7AG | D | 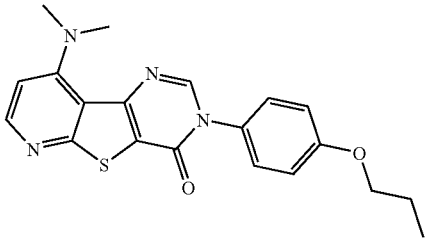 |
| 7AH | B | 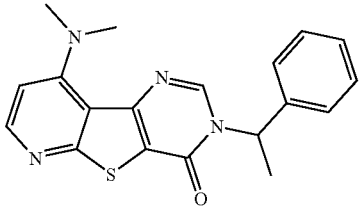 |
| 7AI | C | 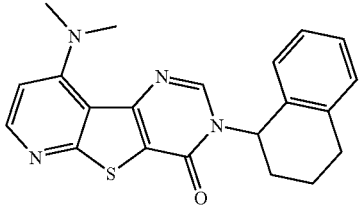 |
| 7AJ | A | 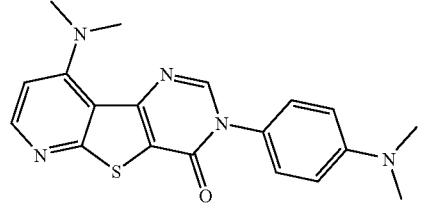 |
| 7AK | A | 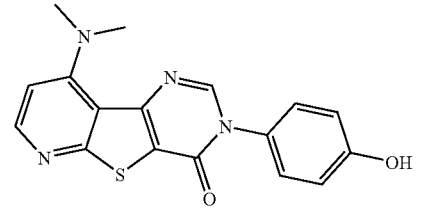 |
| 7AL | D | 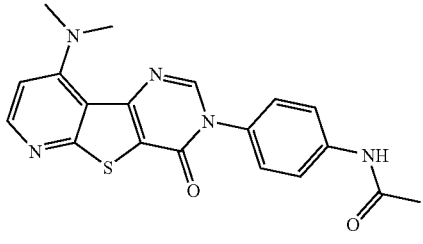 |
| 7AM | A | 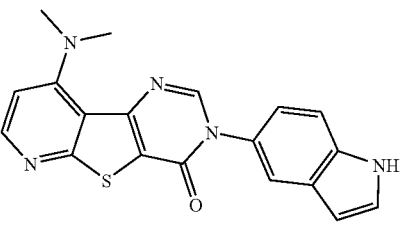 |
| 7AN | C | 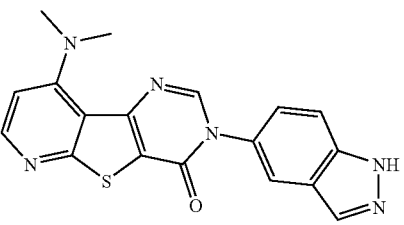 |
| 7AO | C | 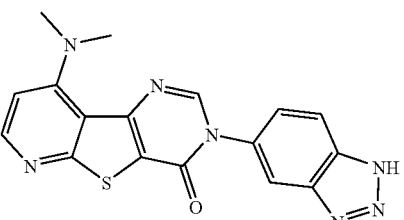 |
| 7AP | A | 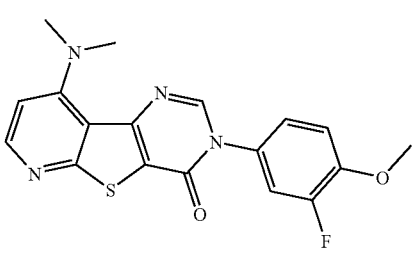 |
| 7AQ | D | 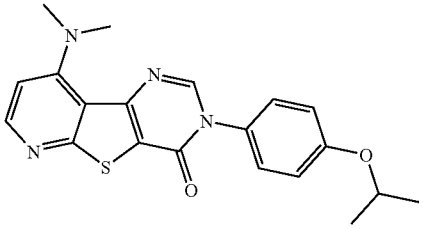 |
| 7AR | D | 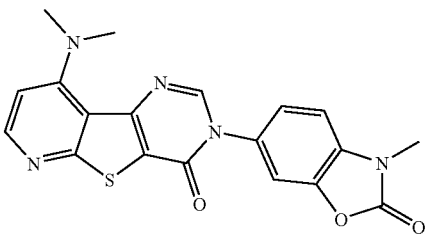 |

TABLE 2-continued

| Cpd | mGluR 1 IC$_{50}$ (nM) | Structure |
|---|---|---|
| 7AS | A | 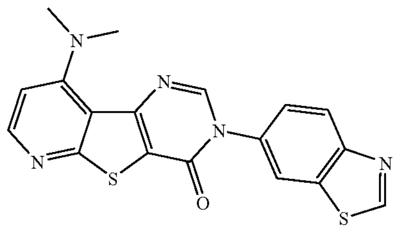 |
| 7AT | D | 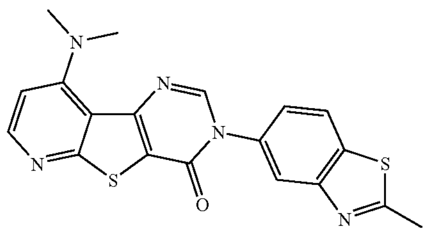 |
| 7AU | D | 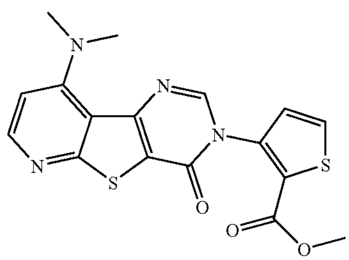 |
| 7AV | A | 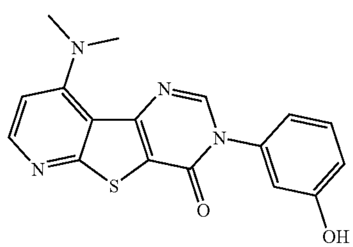 |
| 7AW | B | 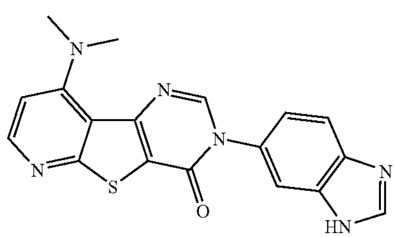 |
| 7AX | A | 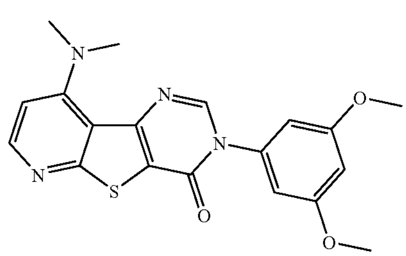 |
| 7AY | A | 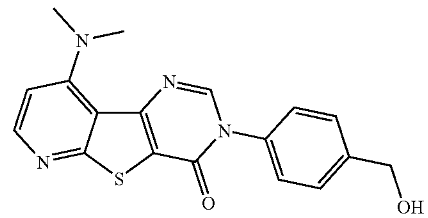 |
| 7AZ | D | 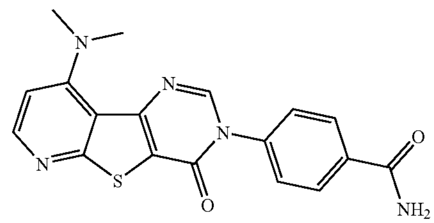 |
| 7BA | C | 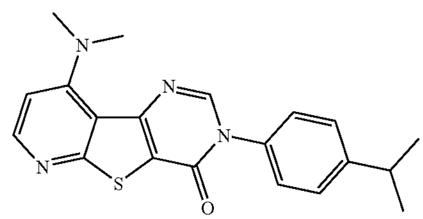 |
| 7BB | D | 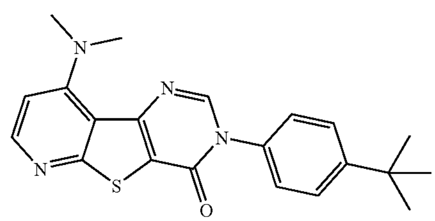 |
| 7BC | D | 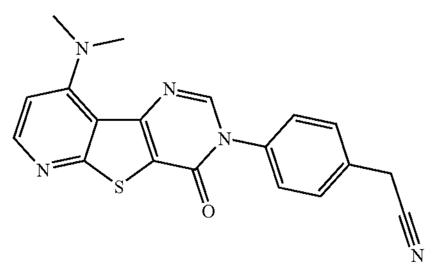 |
| 7BD | D | 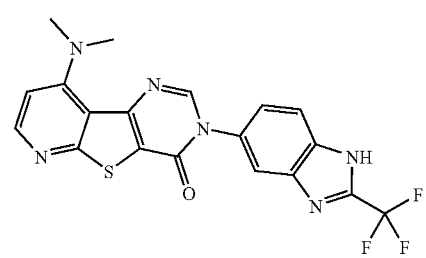 |

TABLE 2-continued

| Cpd | mGluR 1 IC$_{50}$ (nM) | Structure |
|---|---|---|
| 7BE | D | 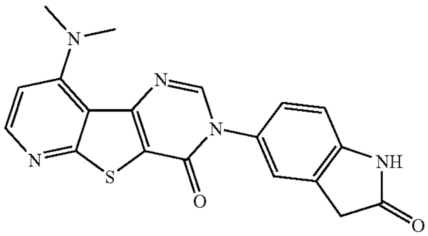 |
| 7BF | A | 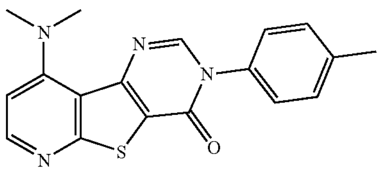 |
| 7BG | A | 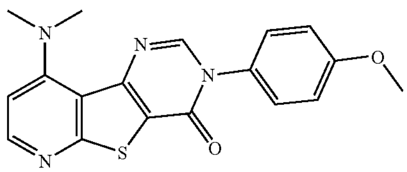 |
| 7BH | D | 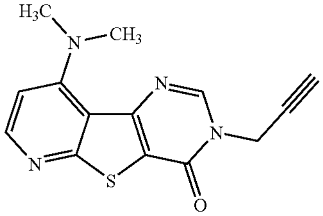 |
| 7BI | A | 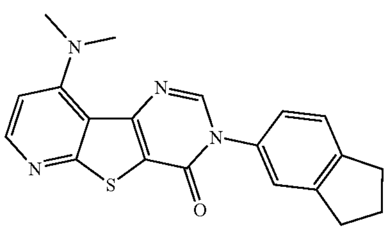 |
| 7BJ | A | 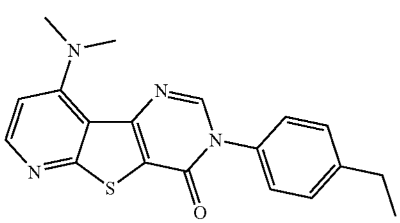 |
| 7BK | C | 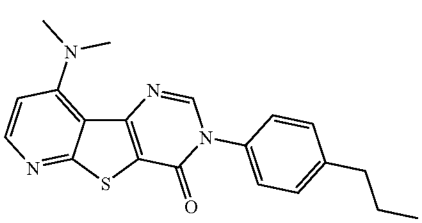 |
| 7BL | A | |
| 7BM | A | |
| 7BN | A | |
| 7BO | A | |
| 7BP | D | |
| 7BQ | C | |

TABLE 2-continued
| Cpd | mGluR 1 IC$_{50}$ (nM) | Structure |
|---|---|---|
| 7BR | C | 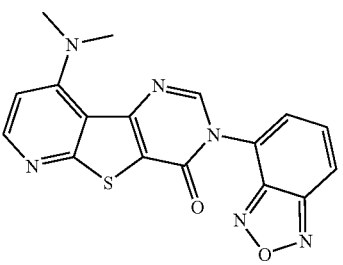 |
| 7BS | A | 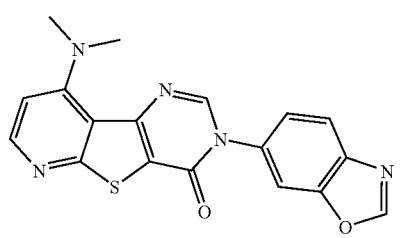 |
| 7BT | D | 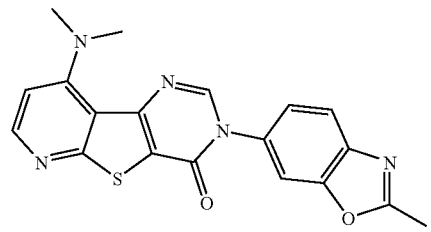 |
| 7BU | D | 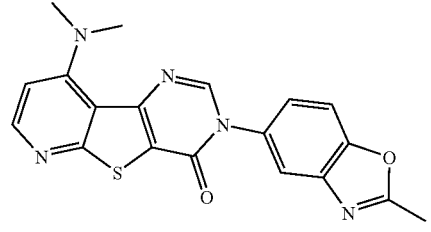 |
| 7BV | D | 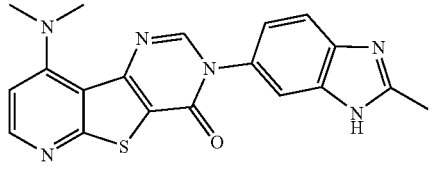 |
| 7BW | A | 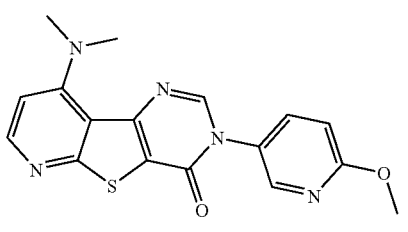 |
| 7BX | D | 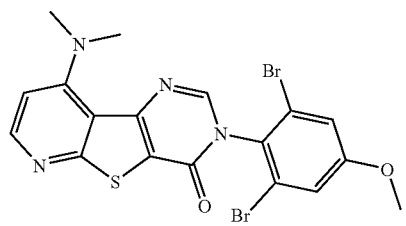 |
| 7BY | A | 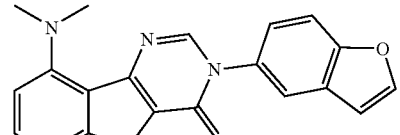 |
| 7BZ | A | 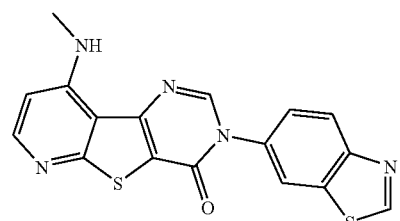 |
| 7CA | A | 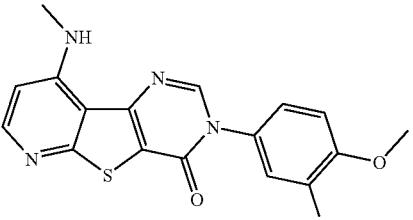 |
| 7CB | A | 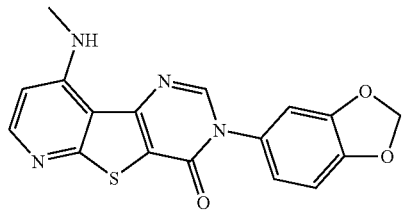 |
| 7CC | A | 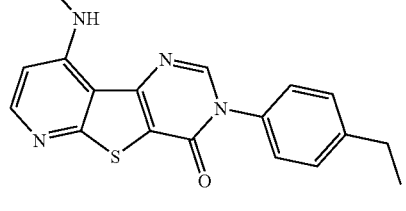 |
| 7CD | A | 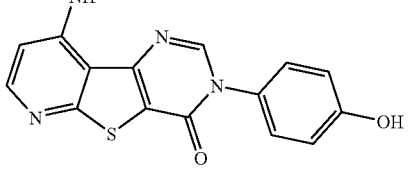 |

TABLE 2-continued
| Cpd | mGluR 1 IC$_{50}$ (nM) | Structure |
|---|---|---|
| 7CE | A | 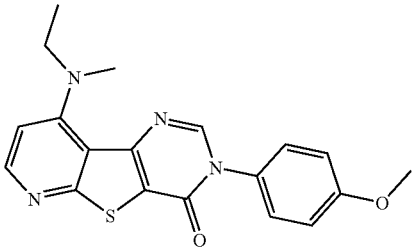 |
| 7CF | A | 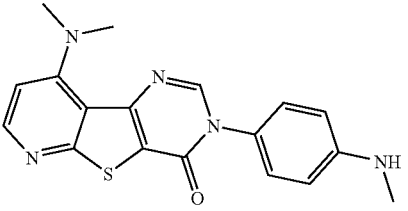 |
| 7CG | A | 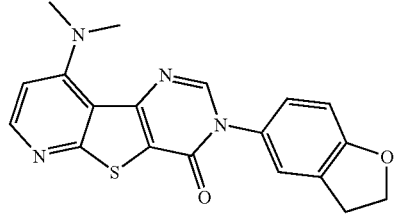 |
| 7CH | C | 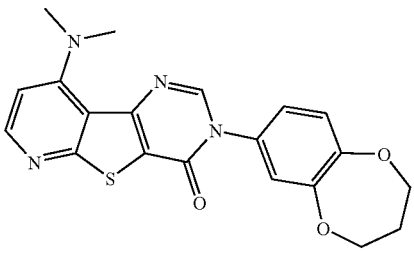 |
| 7CI | C | 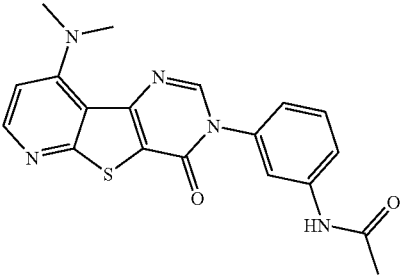 |
| 7CJ | B | 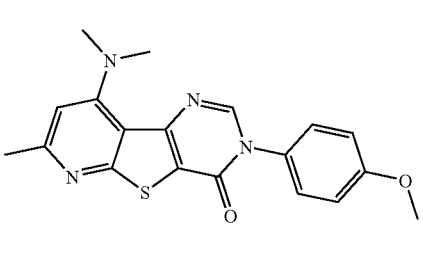 |
| 7CK | A | 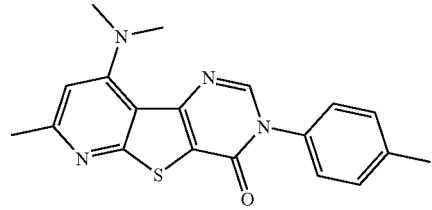 |
| 7CL | B | 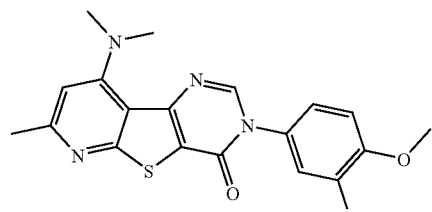 |
| 7CM | A | 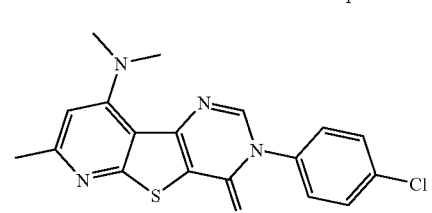 |
| 7CN | B | 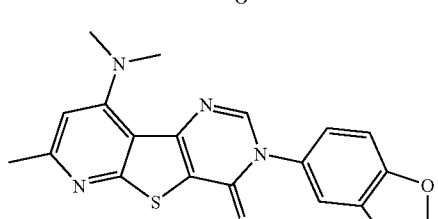 |
| 7CO | B | 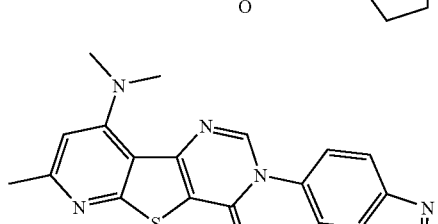 |
| 7CP | B | 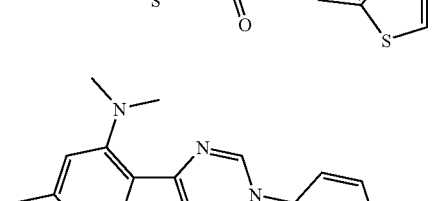 |
| 7CQ | A | 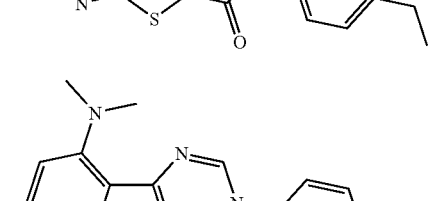 |

TABLE 2-continued

| Cpd | mGluR 1 IC$_{50}$ (nM) | Structure |
|---|---|---|
| 7CR | A | |
| 7CS | C | |
| 7CT | A | |
| 7CU | A | |
| 7CV | A | |
| 7CW | B | |
| 7CX | B | 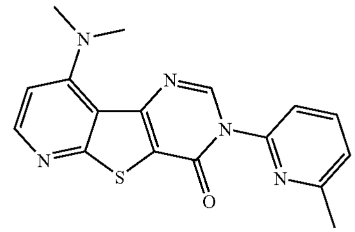 |
| 7CY | A | 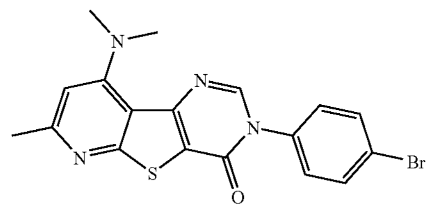 |
| 7CZ | A | 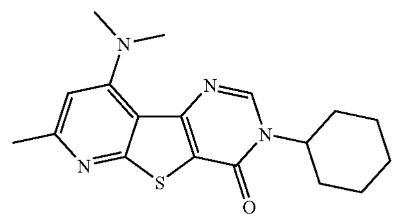 |
| 7DA | C | 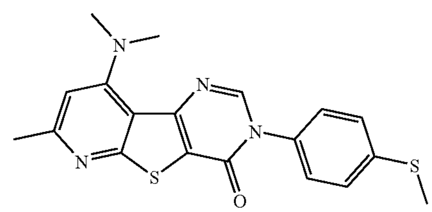 |
| 7DB | A | 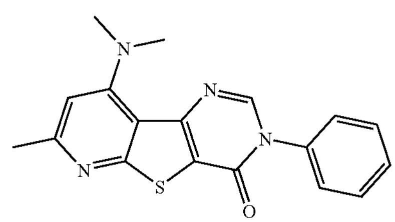 |
| 7DC | A | 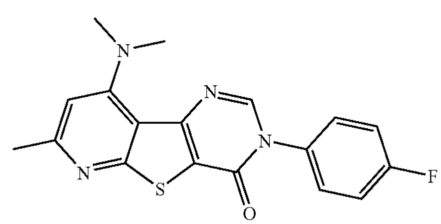 |
| 7DD | C | 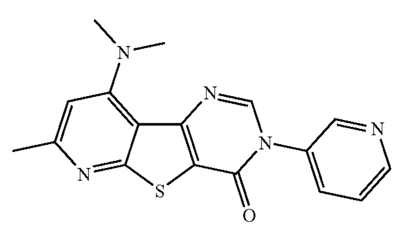 |

TABLE 2-continued
| Cpd | mGluR 1 IC$_{50}$ (nM) | Structure |
|---|---|---|
| 7DE | A | 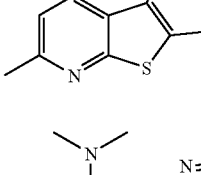 |
| 7DF | A | 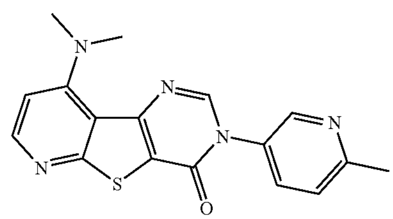 |
| 7DG | A | 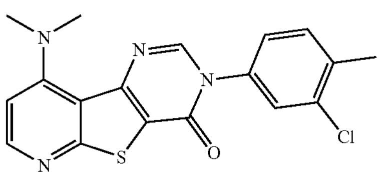 |
| 7DH | A | 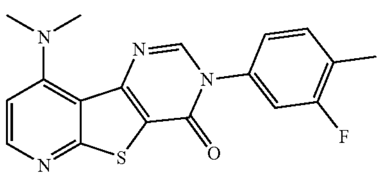 |
| 7DI | A | 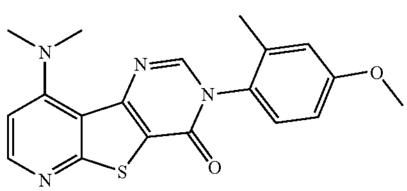 |
| 7DJ | A | 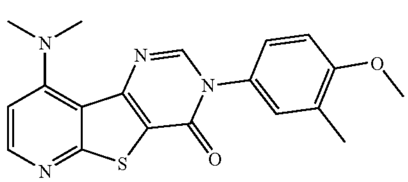 |
| 7DK | A | 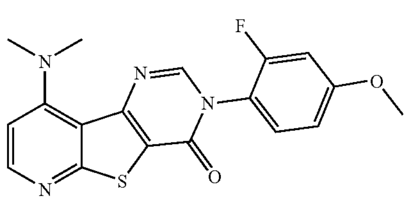 |
TABLE 2-continued
| Cpd | mGluR 1 IC$_{50}$ (nM) | Structure |
|---|---|---|
| 7DL | A | 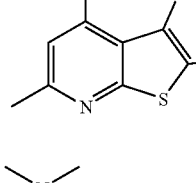 |
| 7DM | C | 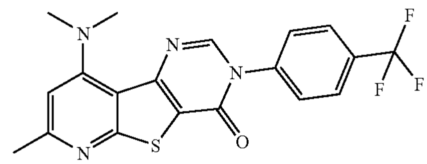 |
| 7DN | B | 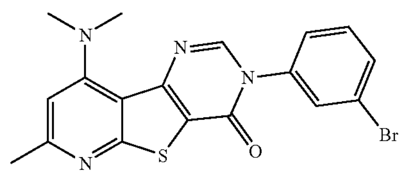 |
| 7DO | A | 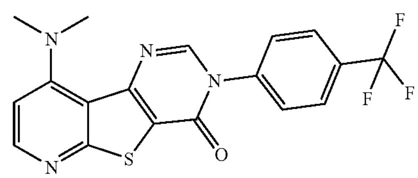 |
| 7DP | B | 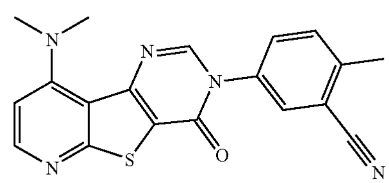 |
| 7DQ | A | 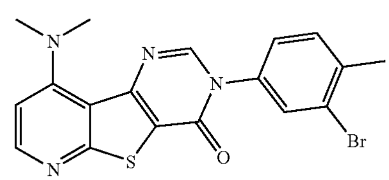 |
| 7DR | A | 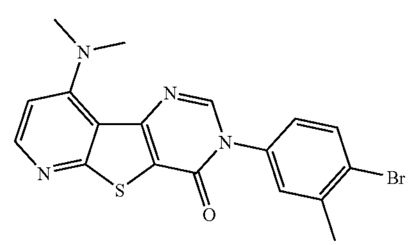 |

TABLE 2-continued
| Cpd | mGluR 1 IC$_{50}$ (nM) | Structure |
|---|---|---|
| 7DS | C | 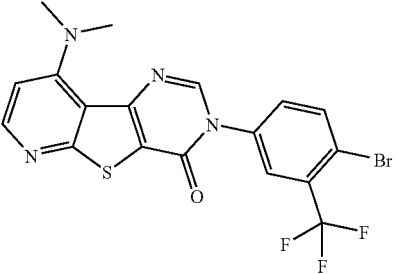 |
| 7DT | C | 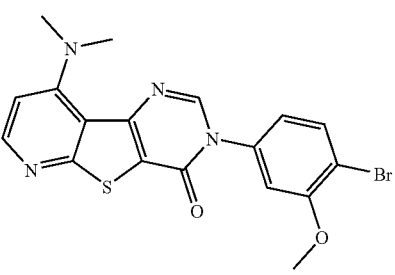 |
| 7DU | A | 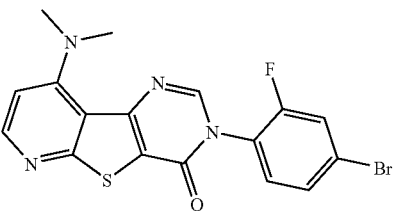 |
| 7DV | A | 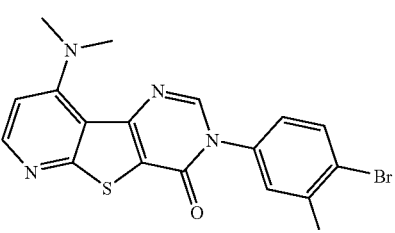 |
| 7DW | A | 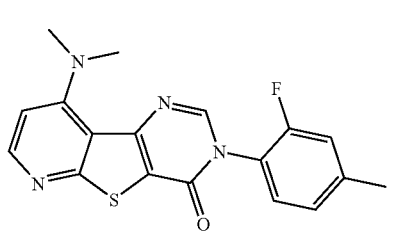 |
| 7DX | A | 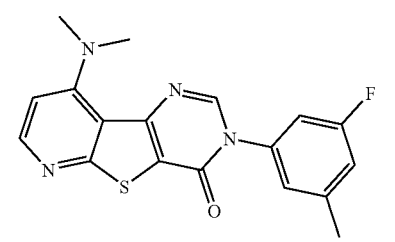 |
TABLE 2-continued
| Cpd | mGluR 1 IC$_{50}$ (nM) | Structure |
|---|---|---|
| 7DY | B | 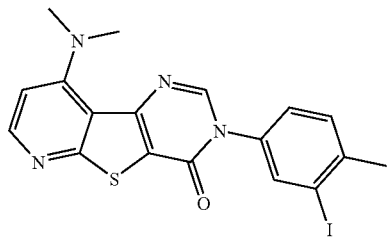 |
| 7DZ | A | 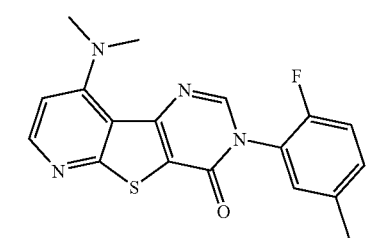 |
| 7EA | A | 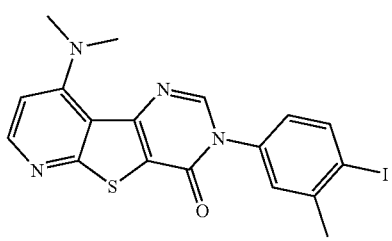 |
| 7EB | — | 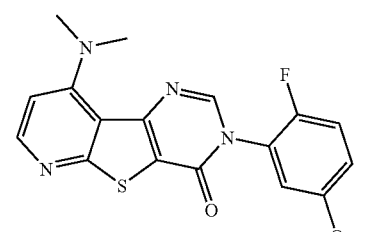 |
| 7EC | — | 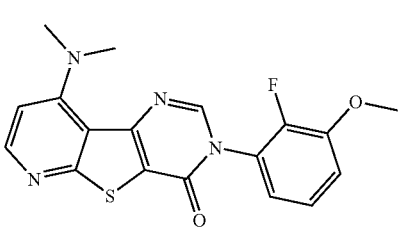 |
| 11 | D | 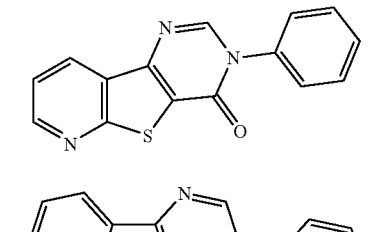 |
| 12A | C | 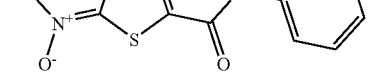 |

TABLE 2-continued

| Cpd | mGluR 1 IC$_{50}$ (nM) | Structure |
|---|---|---|
| 12B | B | 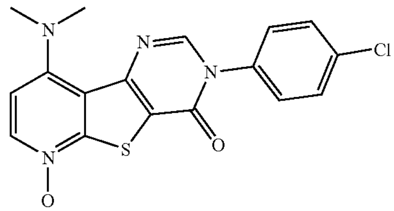 |
| 13 | C | 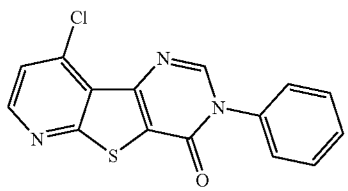 |
| 14 | D | 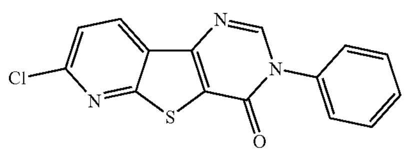 |
| 15A | D | 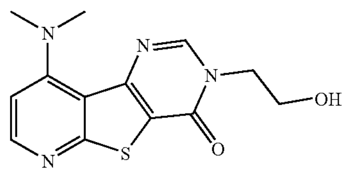 |
| 15B | C | 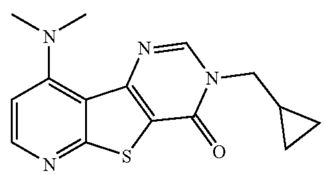 |
| 15C | A | 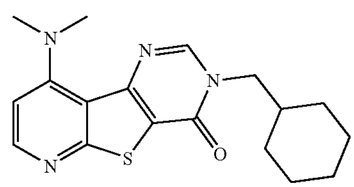 |
| 15D | D | 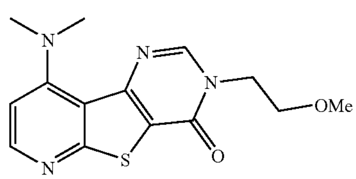 |
| 15E | B | 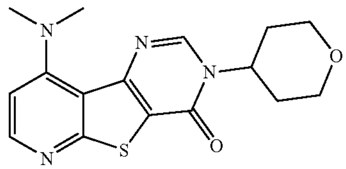 |

TABLE 2-continued

| Cpd | mGluR 1 IC$_{50}$ (nM) | Structure |
|---|---|---|
| 15F | C | |
| 15G | D | |
| 15H | C | |
| 15I | C | |
| 15J | B | |
| 15K | D | |
| 15L | D | |

TABLE 2-continued
| Cpd | mGluR 1 IC$_{50}$ (nM) | Structure |
|---|---|---|
| 15M | D | 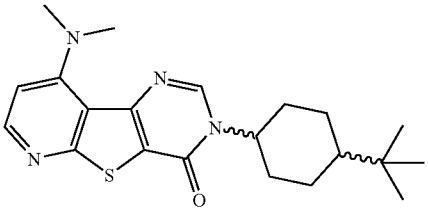 |
| 15N | D | 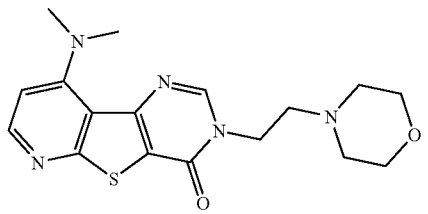 |
| 15O | D | 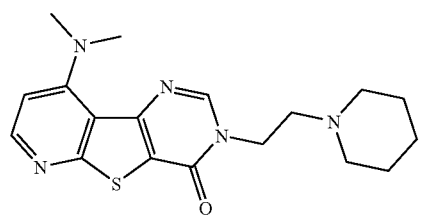 |
| 15P | C | 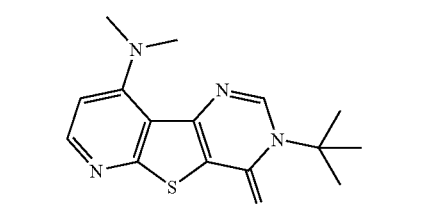 |
| 15Q | A | 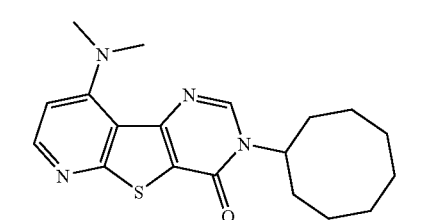 |
| 15T | C | 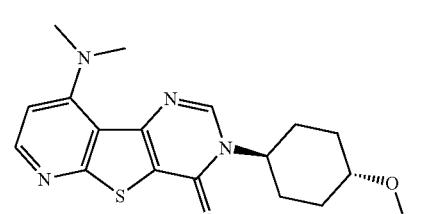 |
| 15U | C | 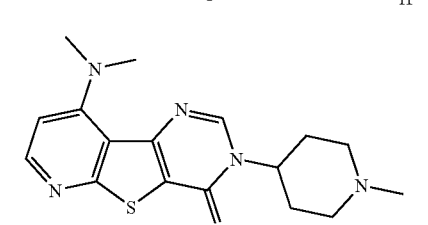 |
| 15V | C | 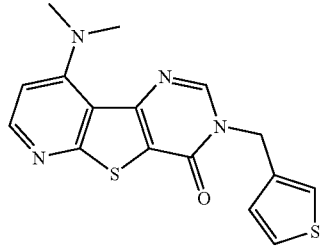 |
| 15W | D | 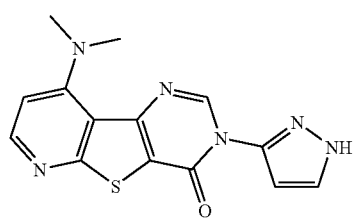 |
| 15X | D | 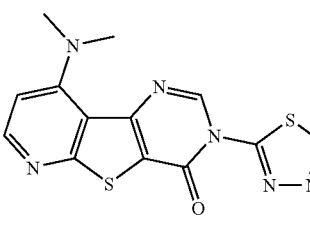 |
| 15Y | A | 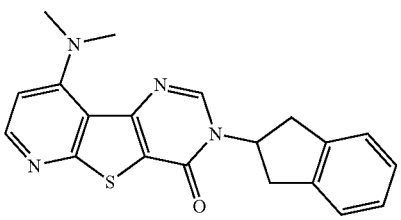 |
| 15Z | A | 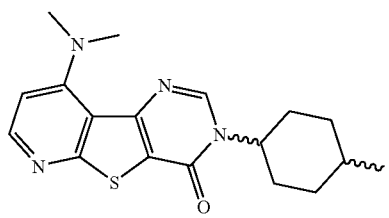 |
| 15AA | A | 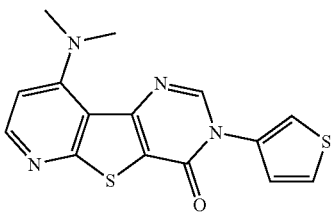 |

TABLE 2-continued

| Cpd | mGluR 1 IC$_{50}$ (nM) | Structure |
|---|---|---|
| 15AB | A | |
| 15AC | D | |
| 15AD | B | |
| 15AE | B | |
| 15AF | C | |
| 15AG | A | |
| 15AH | B | 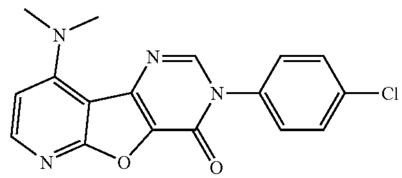 |
| 15AI | — | 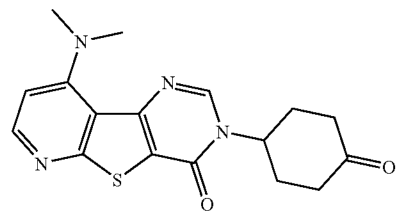 |
| 15AJ | — | 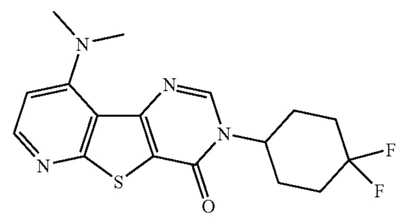 |
| 15AK | — | 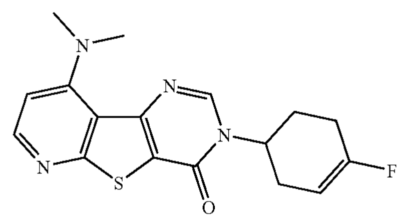 |
| 19 | C | 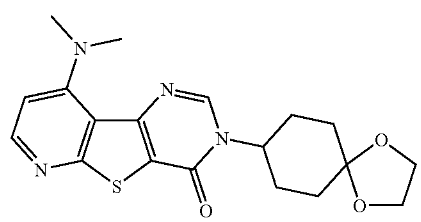 |
| 25A | C | 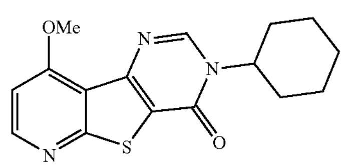 |
| 25B | C | 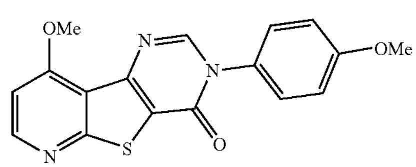 |

TABLE 2-continued

| Cpd | mGluR 1 IC$_{50}$ (nM) | Structure |
|---|---|---|
| 25C | B | 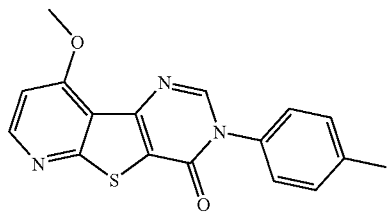 |
| 25D | C | 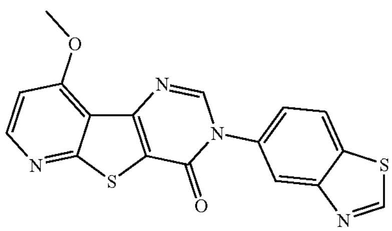 |
| 26A | D | 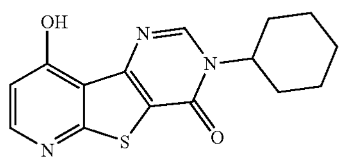 |
| 26C | D | 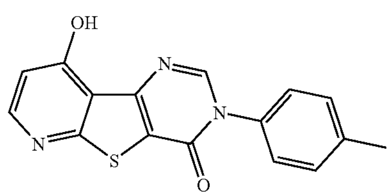 |
| 27A | D | 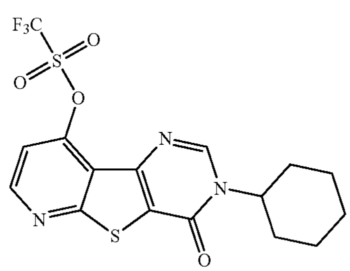 |
| 28A | D | 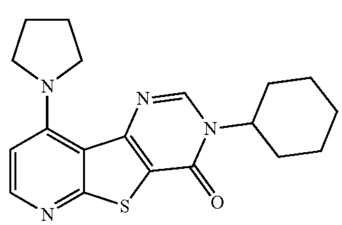 |
| 28B | D | 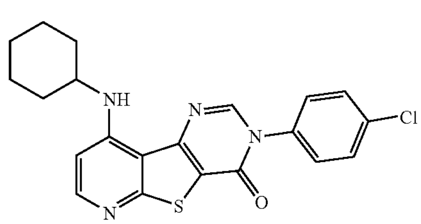 |
| 28C | D | |
| 28D | D | |
| 28E | D | |
| 28F | D | |
| 28G | C | |
| 28H | D | |
| 28I | A | |

TABLE 2-continued

| Cpd | mGluR 1 IC$_{50}$ (nM) | Structure |
|---|---|---|
| 28J | C | (structure) |
| 28K | D | (structure) |
| 28L | D | (structure) |
| 28M | D | (structure) |
| 28N | D | (structure) |
| 28O | D | (structure) |
| 28P | A | (structure) |
| 28Q | B | (structure) |
| 28R | C | (structure) |
| 28S | A | (structure) |
| 28T | D | (structure) |
| 28U | D | (structure) |
| 28V | C | (structure) |

TABLE 2-continued

| Cpd | mGluR 1 IC$_{50}$ (nM) | Structure |
|---|---|---|
| 28W | C | 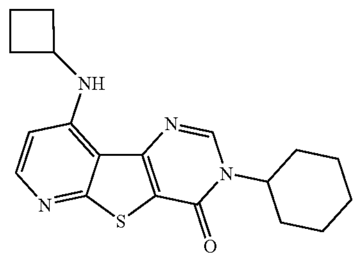 |
| 28X | A | 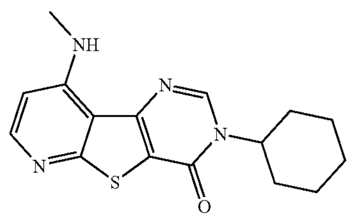 |
| 28Y | A | 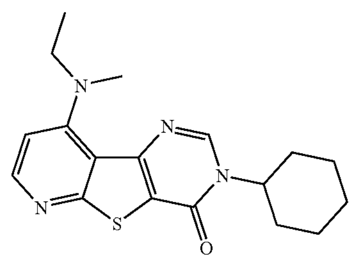 |
| 28Z | A | 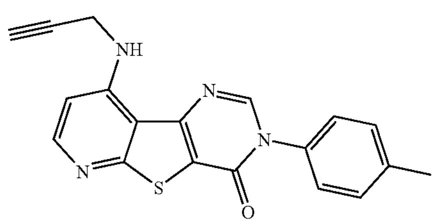 |
| 28AA | A | 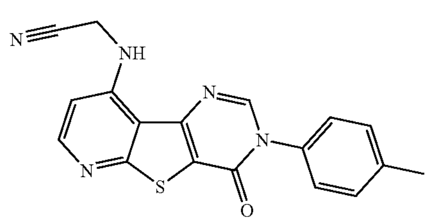 |
| 28AB | A | 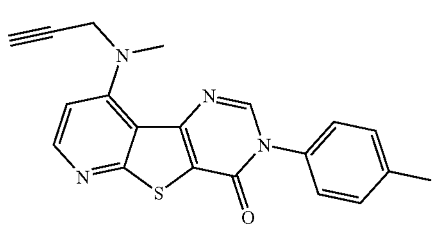 |
| 28AC | A | |
| 28AD | B | |
| 28AE | A | |
| 28AF | D | |
| 28AG | B | |

TABLE 2-continued

| Cpd | mGluR 1 IC$_{50}$ (nM) | Structure |
|---|---|---|
| 28AH | C | 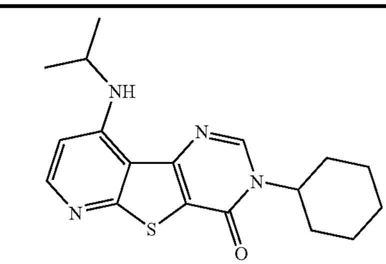 |
| 28AI | A | 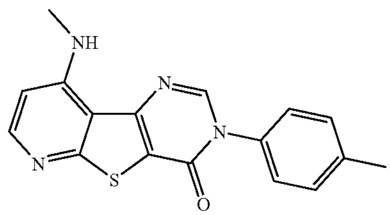 |
| 28AJ | C | 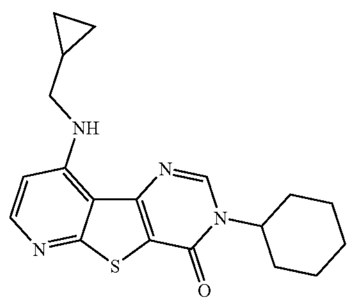 |
| 28AK | A | 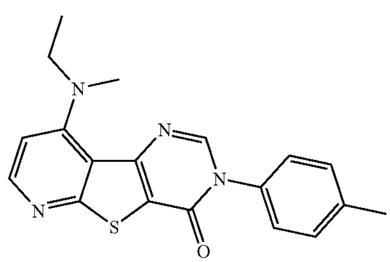 |
| 28AL | A | 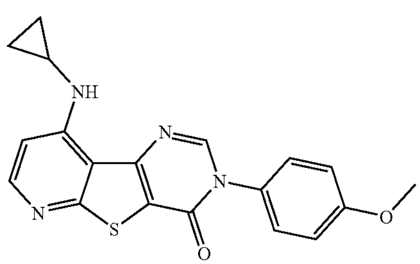 |
| 28AM | B | 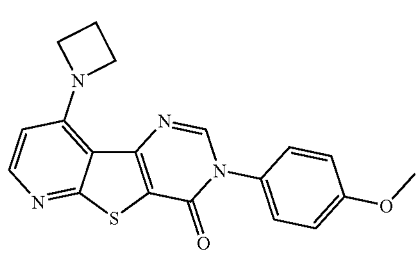 |
| 28AN | A | |
| 28AO | A | |
| 28AP | A | |
| 28AQ | B | |
| 28AR | A | |

TABLE 2-continued
| Cpd | mGluR 1 IC$_{50}$ (nM) | Structure |
|---|---|---|
| 28AS | A | 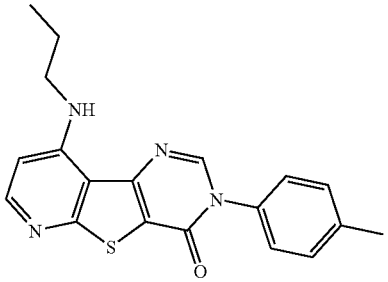 |
| 28AT | A | 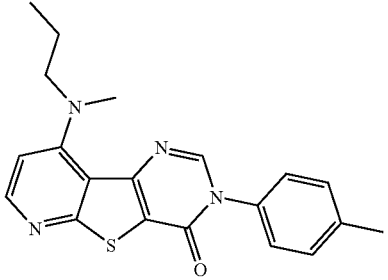 |
| 28AU | A | 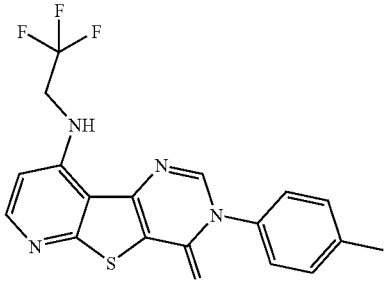 |
| 28AV | A | 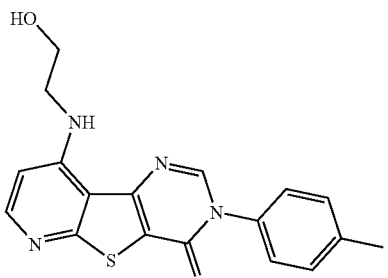 |
| 28AW | A | 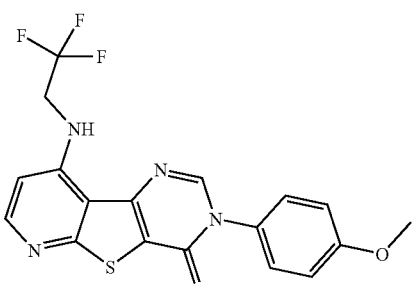 |
TABLE 2-continued
| Cpd | mGluR 1 IC$_{50}$ (nM) | Structure |
|---|---|---|
| 28AX | C | 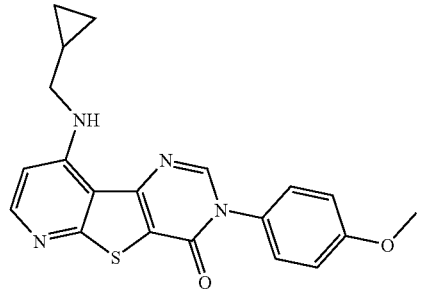 |
| 28AY | C | 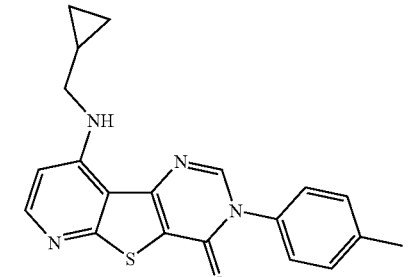 |
| 28AZ | A | 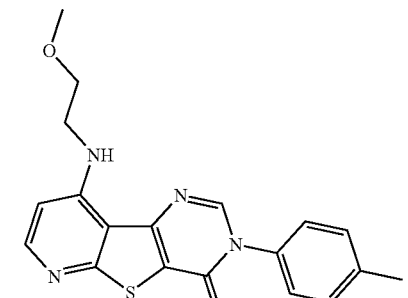 |
| 28BA | C | 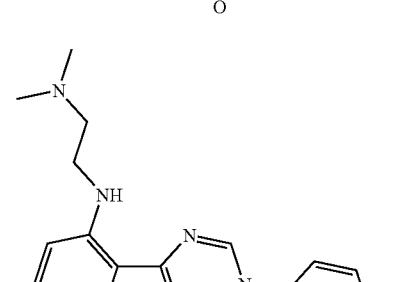 |
| 28BB | A | 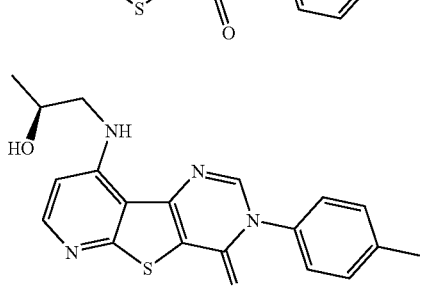 |

TABLE 2-continued

| Cpd | mGluR 1 IC$_{50}$ (nM) | Structure |
|---|---|---|
| 28BC | A | 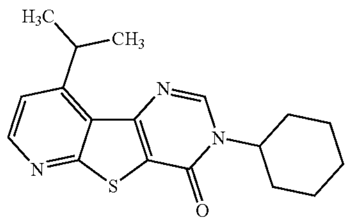 |
| 29A | C | 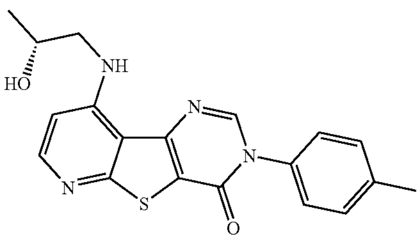 |
| 29B | D | 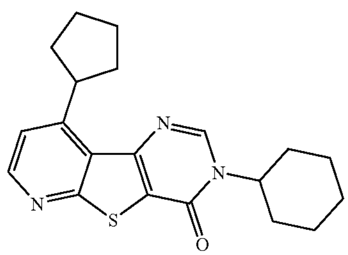 |
| 29C | B | 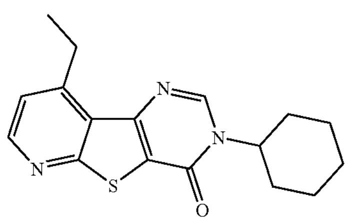 |
| 29D | B | 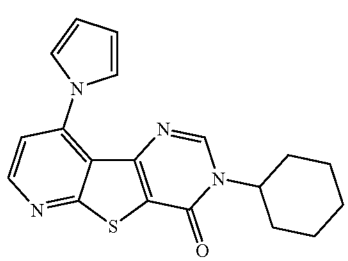 |
| 30A | D | 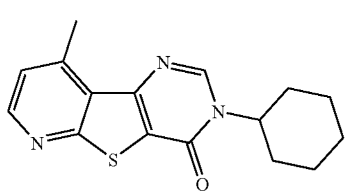 |
| 30B | D | 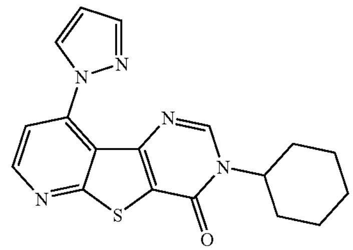 |
| 30C | D | 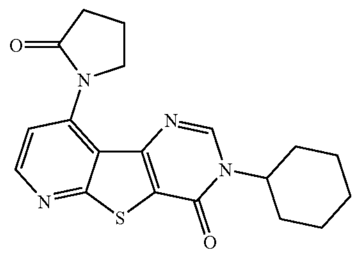 |
| 37A | C | 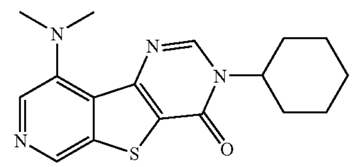 |
| 37B | C | 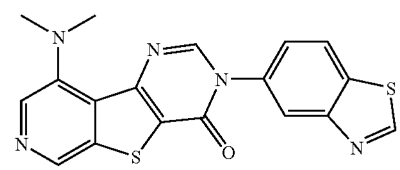 |
| 37C | B | 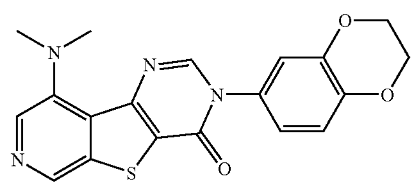 |
| 37D | C | 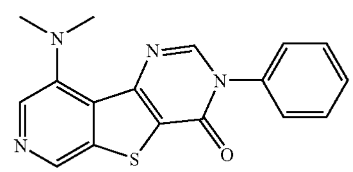 |
| 37E | A | 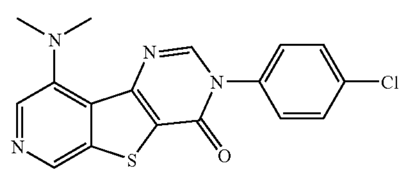 |
| 37F | B | 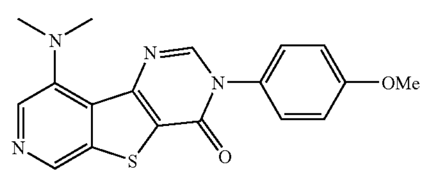 |

TABLE 2-continued

| Cpd | mGluR 1 IC$_{50}$ (nM) | Structure |
|---|---|---|
| 37G | C | 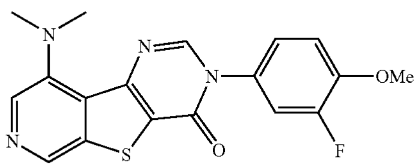 |
| 37H | D | 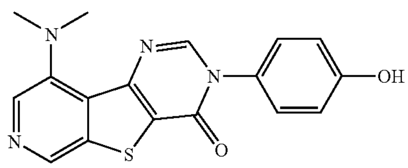 |
| 40 | D | 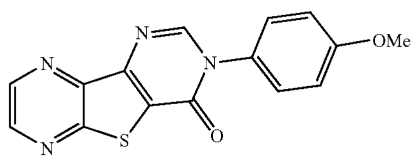 |
| 41 | B | 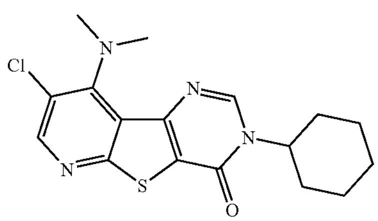 |
| 42 | B | 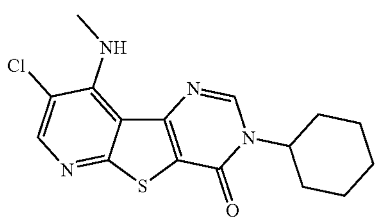 |
| 43 | C | 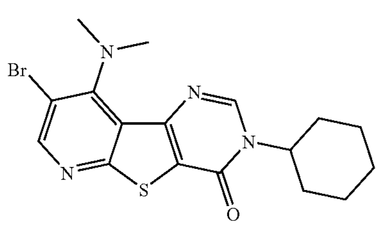 |
| 44 | A | 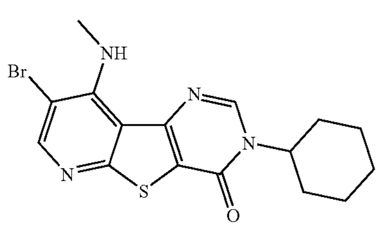 |

TABLE 2-continued

| Cpd | mGluR 1 IC$_{50}$ (nM) | Structure |
|---|---|---|
| 45 | A | 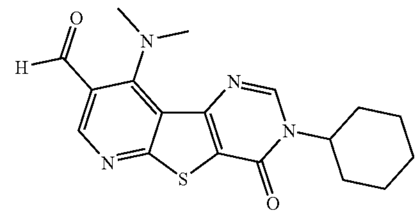 |
| 46 | A | 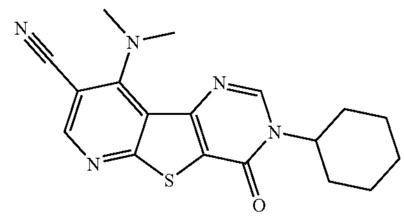 |
| 47A | C | 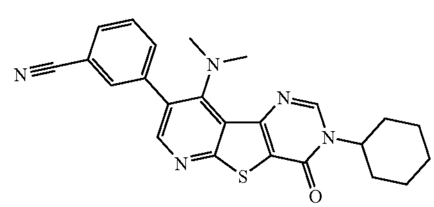 |
| 47B | D | 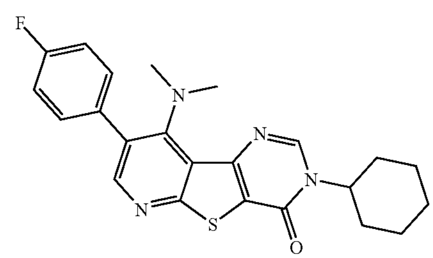 |
| 48 | C | 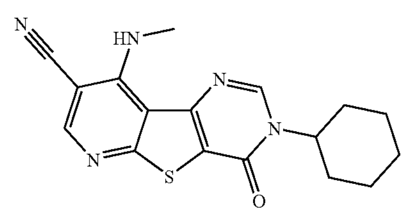 |
| 49 | D | 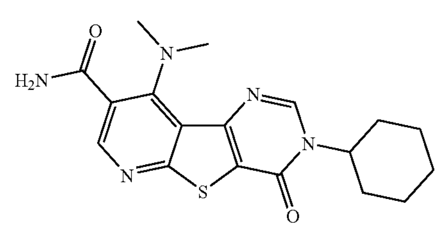 |

TABLE 2-continued
| Cpd | mGluR 1 IC$_{50}$ (nM) | Structure |
|---|---|---|
| 50 | C | 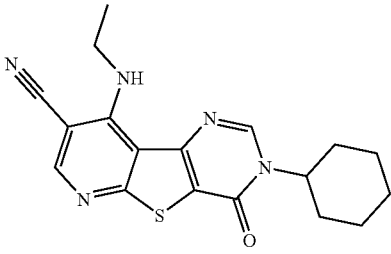 |
| 51 | A | 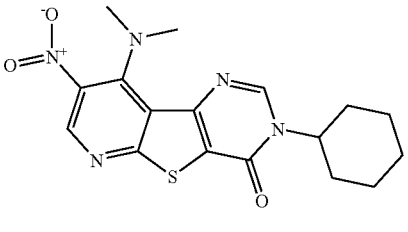 |
| 52 | C | 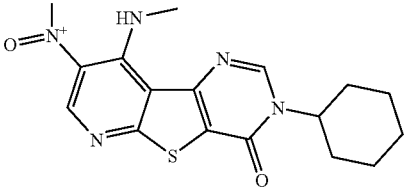 |
| 53 | D | 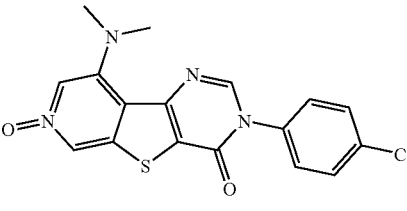 |
| 54 | C | 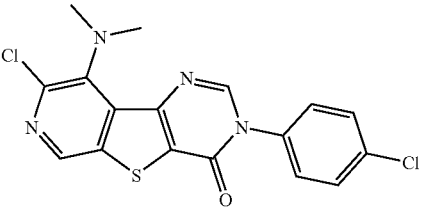 |
| 55 | B | 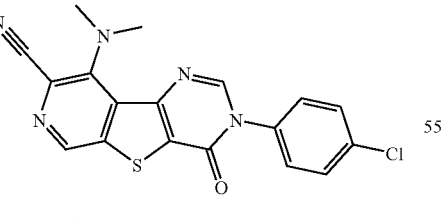 |
| 57 | — | 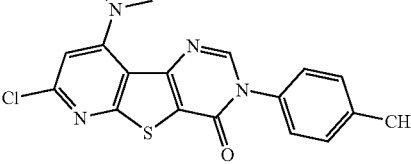 |
| 58 | A | 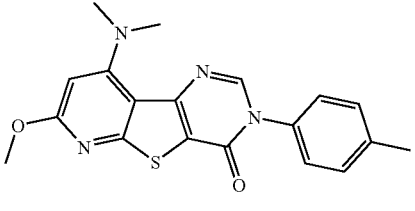 |
| 59A | D | 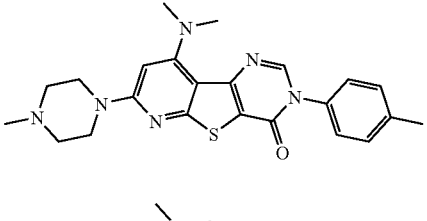 |
| 59B | D | 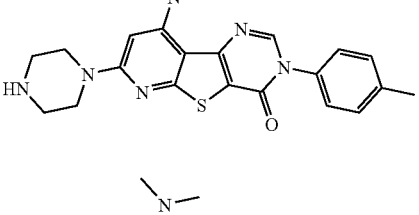 |
| 59C | D | 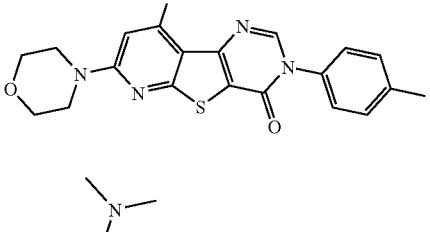 |
| 60A | A | 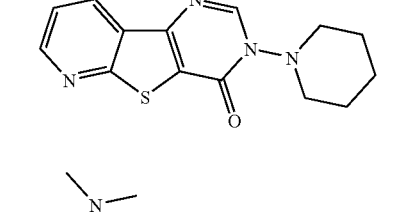 |
| 60B | A | 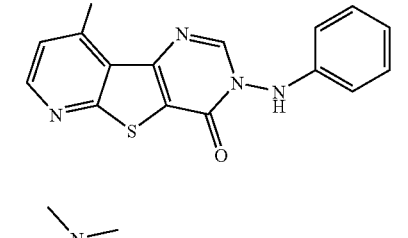 |
| 60C | A | 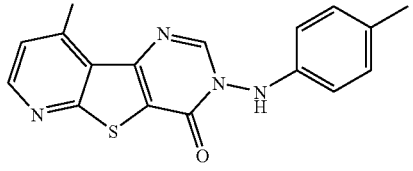 |

TABLE 2-continued
| Cpd | mGluR 1 IC$_{50}$ (nM) | Structure |
|---|---|---|
| 60D | A | 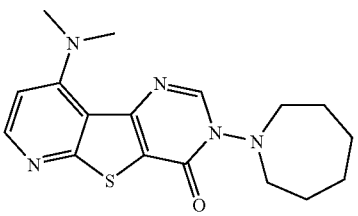 |
| 60E | A | 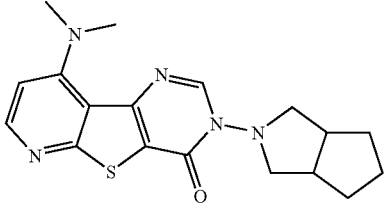 |
| 60F | B | 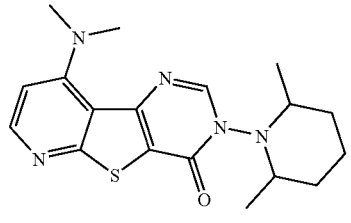 |
| 60G | A | 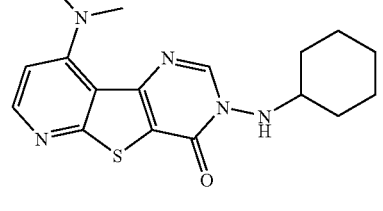 |
| 60H | D | 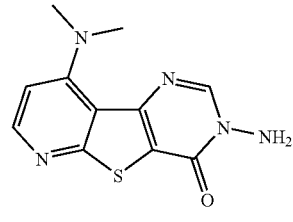 |
| 60I | B | 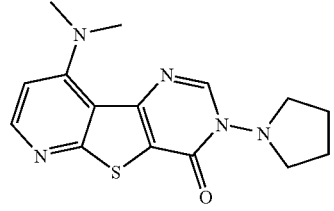 |
TABLE 2-continued
| Cpd | mGluR 1 IC$_{50}$ (nM) | Structure |
|---|---|---|
| 60J | D | 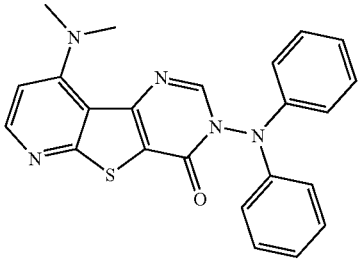 |
| 60L | C | 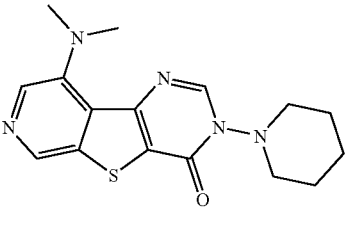 |
| 61A | D | 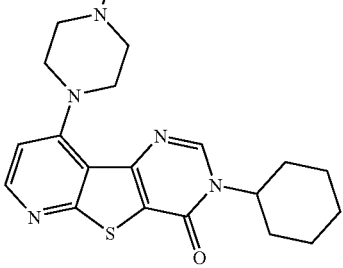 |
| 61B | D | 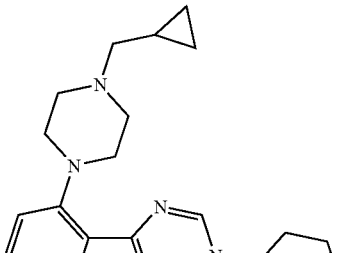 |
| 62 | D | 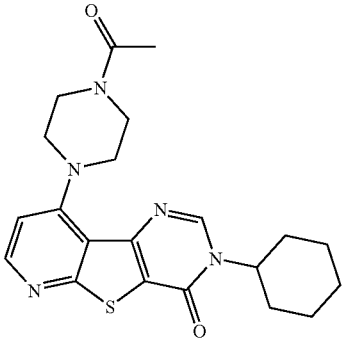 |

TABLE 2-continued

| Cpd | mGluR1 IC$_{50}$ (nM) | Structure |
|---|---|---|
| 63 | C | |
| 64 | D | |
| 65A | D | |
| 65B | D | |
| 65C | D | |
| 65D | D | 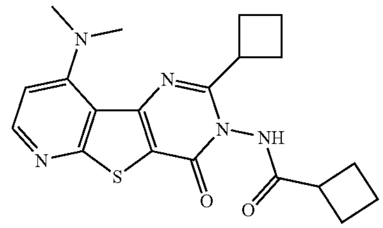 |
| 65E | D | 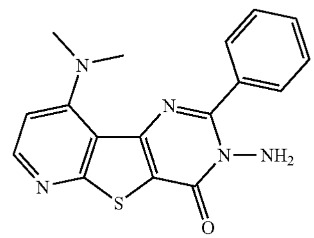 |
| 66A | A | 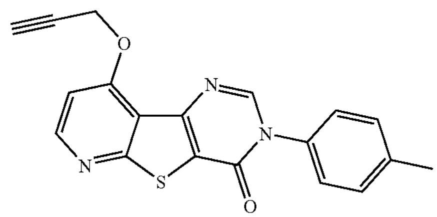 |
| 66B | D | 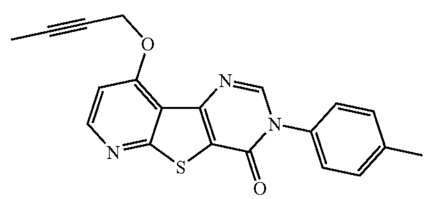 |
| 66C | D | 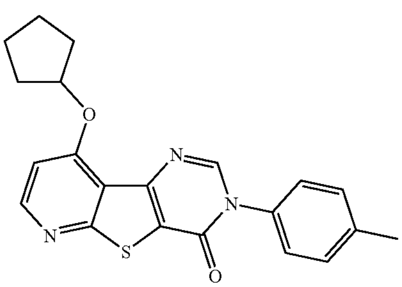 |
| 66D | A | 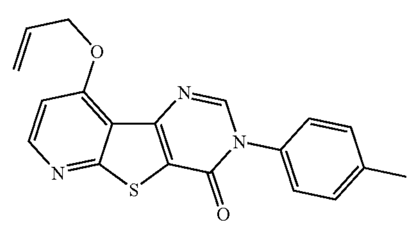 |

TABLE 2-continued
| Cpd | mGluR 1 IC$_{50}$ (nM) | Structure |
|---|---|---|
| 66E | D | 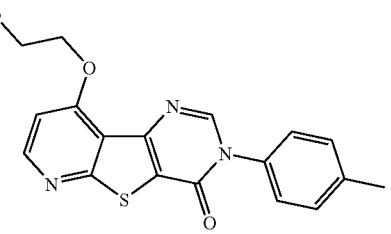 |
| 71A | A | 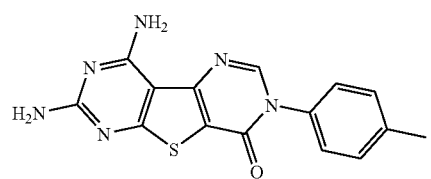 |
| 72A | A | 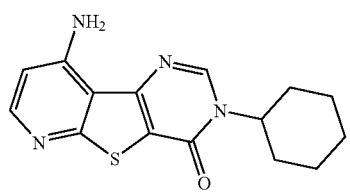 |
| 72B | A | 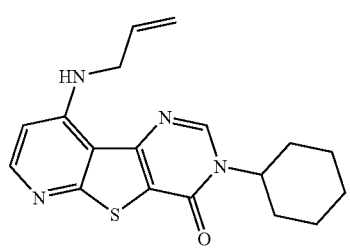 |
| 72C | A | 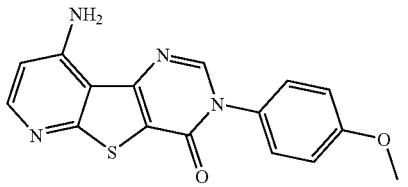 |
| 72D | D | 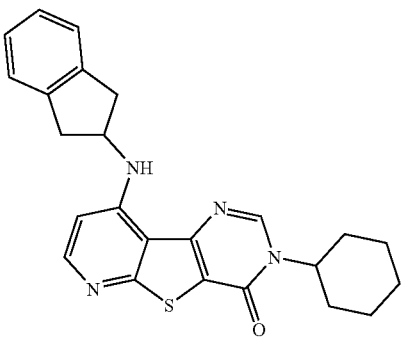 |
TABLE 2-continued
| Cpd | mGluR 1 IC$_{50}$ (nM) | Structure |
|---|---|---|
| 72E | D | 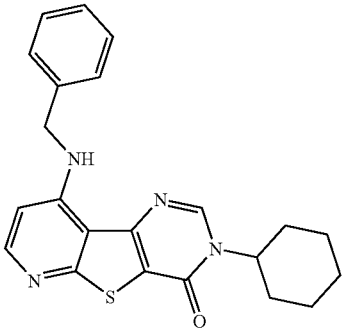 |
| 72F | D | 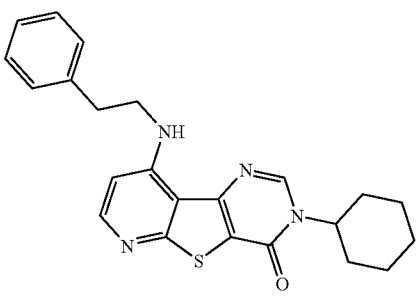 |
| 72G | A | 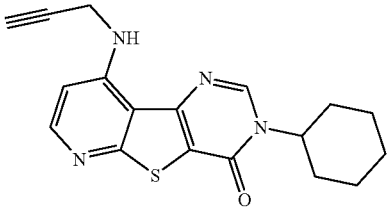 |
| 72H | A | 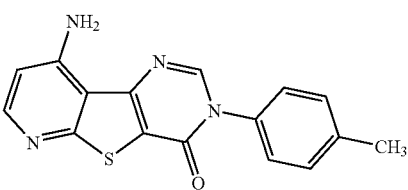 |
| 72I | A | 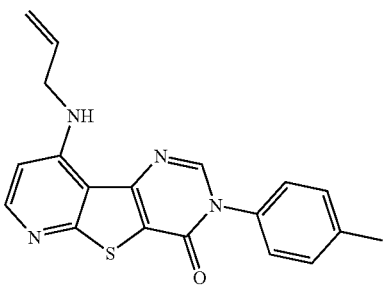 |

TABLE 2-continued
| Cpd | mGluR 1 IC$_{50}$ (nM) | Structure |
|---|---|---|
| 73A | D | 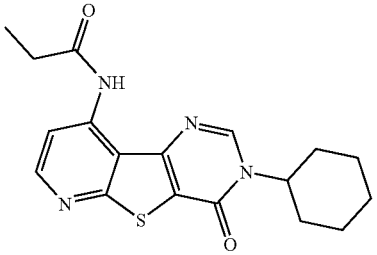 |
| 73B | D | 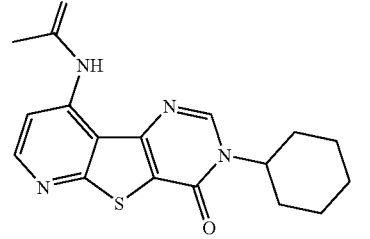 |
| 73C | D | 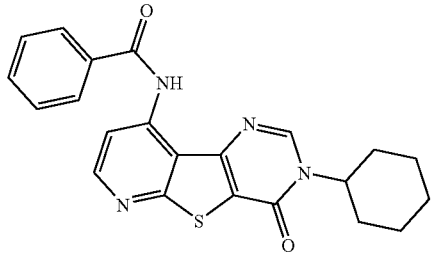 |
| 73D | D | 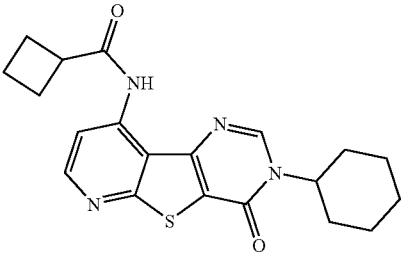 |
| 73E | D | 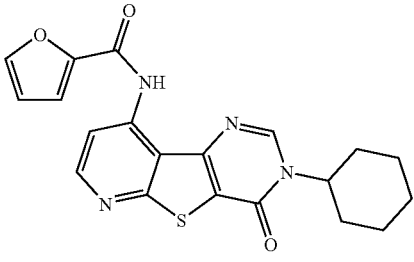 |
| 73F | D | 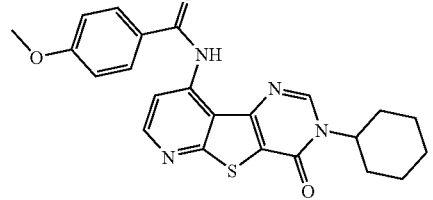 |
TABLE 2-continued
| Cpd | mGluR 1 IC$_{50}$ (nM) | Structure |
|---|---|---|
| 73G | D | 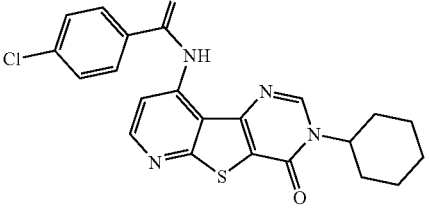 |
| 76 | D | 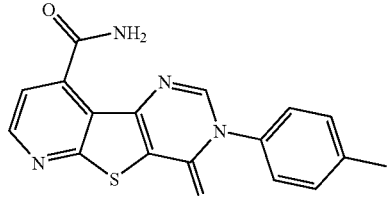 |
| 77 | D | 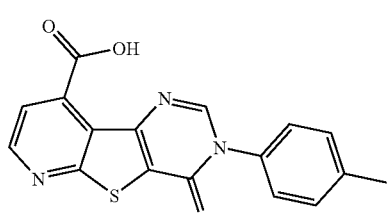 |
| 78 | D | 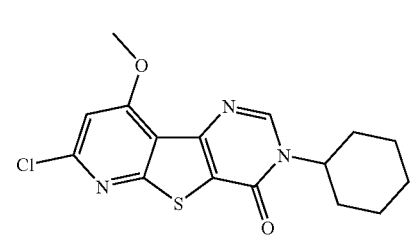 |
| 80 | D | 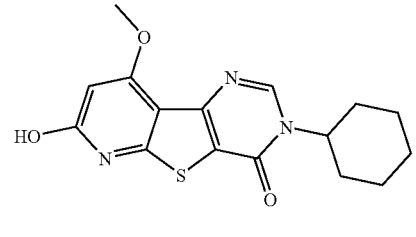 |
| 83 | B | 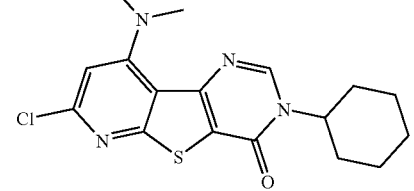 |

TABLE 2-continued
| Cpd | mGluR 1 IC$_{50}$ (nM) | Structure |
|---|---|---|
| 84 | B | 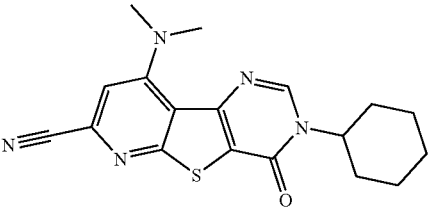 |
| 85 | D | 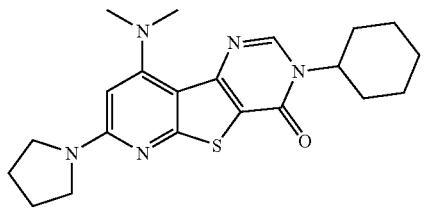 |
| 87A | C | 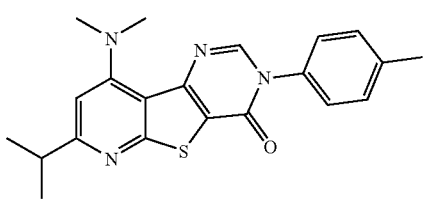 |
| 87B | B | 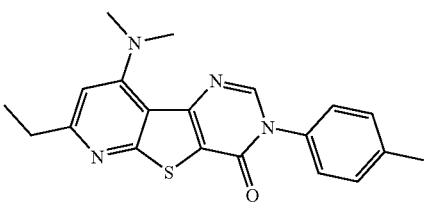 |
| 95B | A | 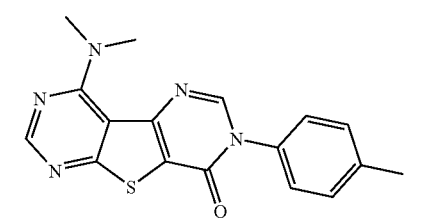 |
| 95C | A | 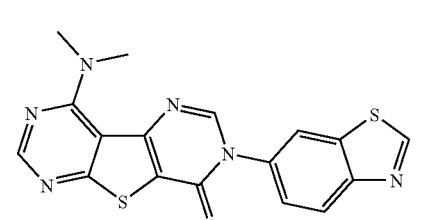 |
| 95D | A | 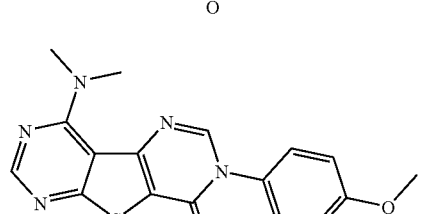 |
| 95E | A | 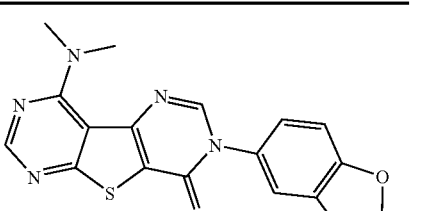 |
| 95F | A | 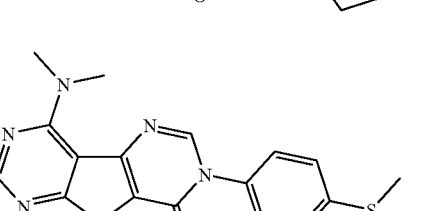 |
| 95G | A | 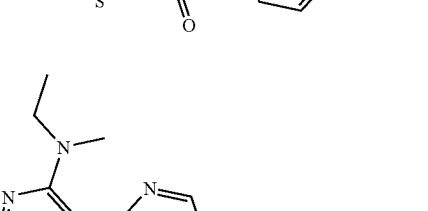 |
| 95H | A | 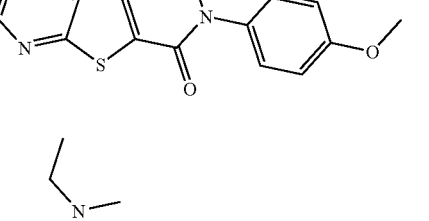 |
| 95I | A | 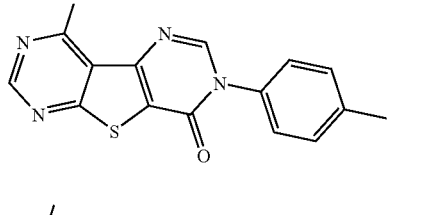 |
| 95J | C | 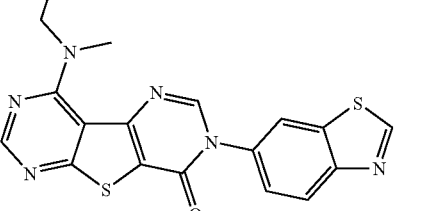 |

TABLE 2-continued

| Cpd | mGluR 1 IC$_{50}$ (nM) | Structure |
|---|---|---|
| 95K | A | 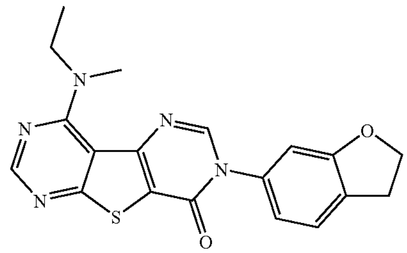 |
| 95L | A | 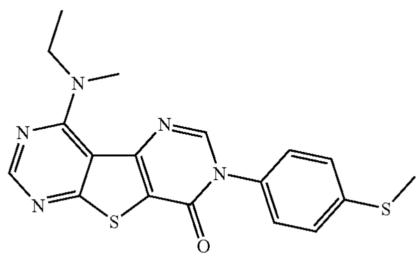 |
| 95M | B | 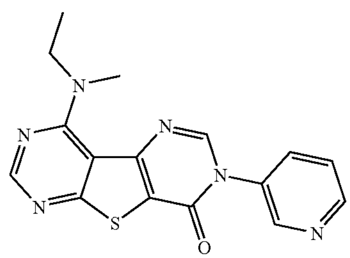 |
| 95N | A | 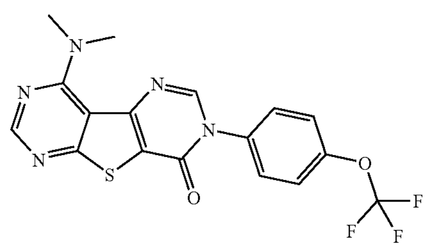 |
| 95O | A | 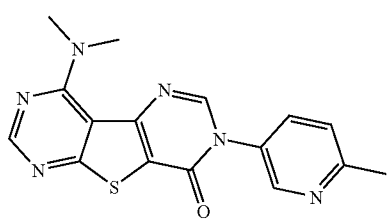 |
| 95P | A | 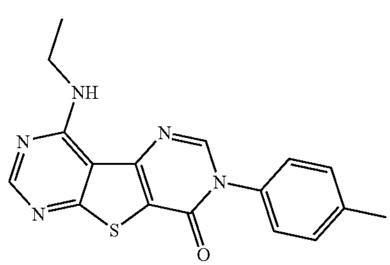 |
| 95Q | A | 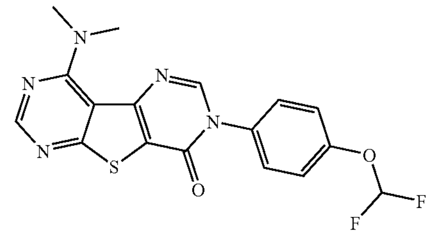 |
| 95R | A | 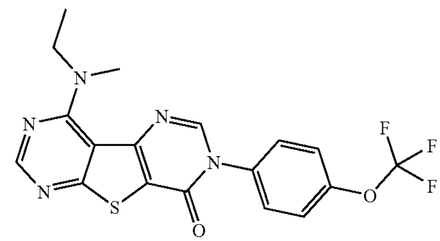 |
| 95S | A | 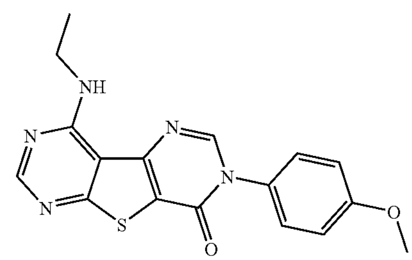 |
| 95T | A | 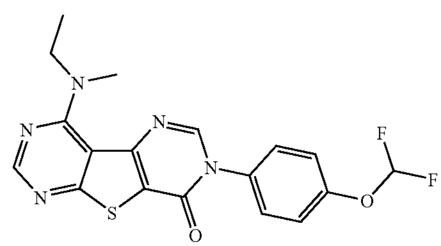 |
| 95U | A | 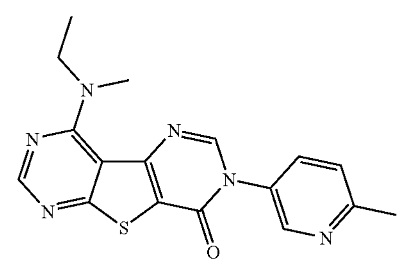 |
| 95V | C | 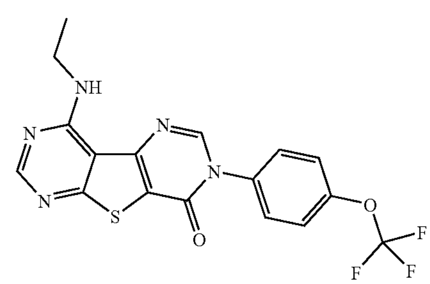 |

TABLE 2-continued
| Cpd | mGluR 1 IC$_{50}$ (nM) | Structure |
|---|---|---|
| 95W | A | 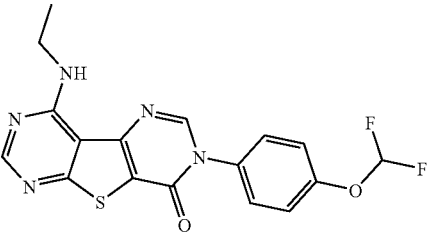 |
| 95X | A | 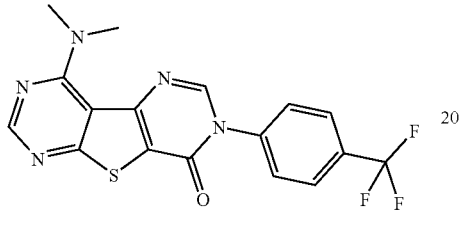 |
| 95Y | A | 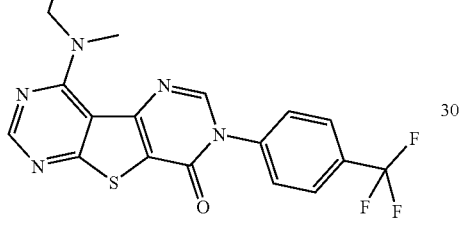 |
| 95Z | A | 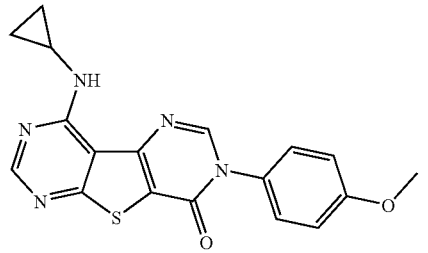 |
| 95AA | A | 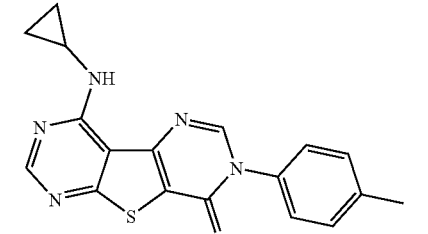 |
| 95AB | C | 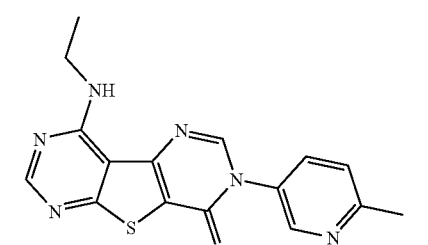 |
| 95AC | A | 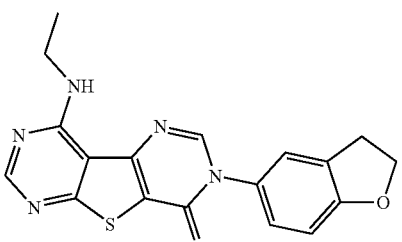 |
| 95AD | A | 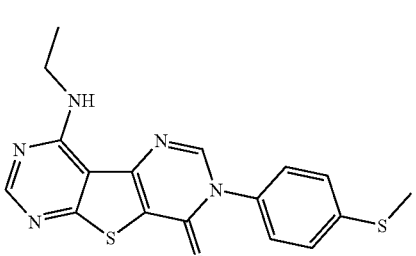 |
| 95AE | — | 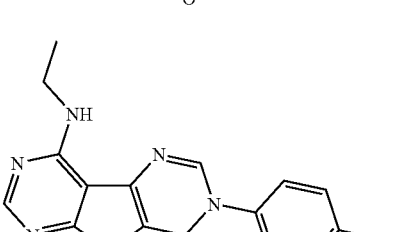 |
| 95AF | — | 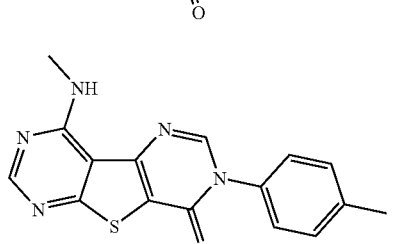 |
| 95AG | — | 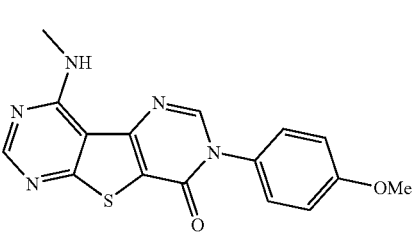 |
| 95AH | — | 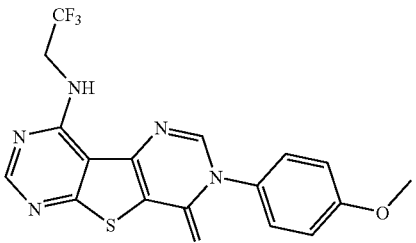 |

TABLE 2-continued

| Cpd | mGluR 1 IC$_{50}$ (nM) | Structure |
|---|---|---|
| 95AI | — | (structure) |
| 95AJ | — | (structure) |
| 95AK | — | (structure) |
| 95AL | — | (structure) |
| 95AM | — | (structure) |
| 95AN | — | (structure) |
| 103A | B | (structure) |
| 103B | C | (structure) |
| 103C | C | (structure) |
| 103D | B | (structure) |
| 103E | B | (structure) |
| 103F | C | (structure) |

TABLE 2-continued
| Cpd | mGluR 1 IC$_{50}$ (nM) | Structure |
|---|---|---|
| 104 | D | 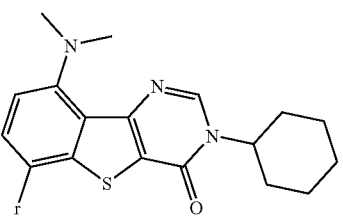 |
| 105 | D | 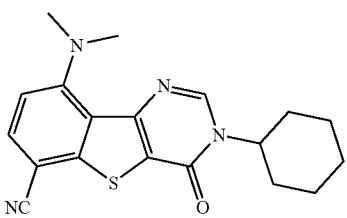 |
| 106 | — | 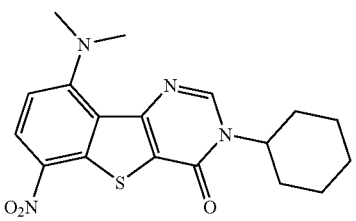 |
| 113A | A | 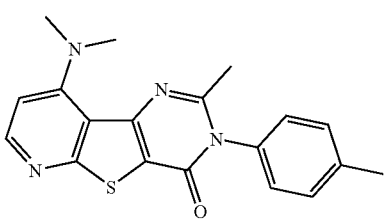 |
| 113B | A | 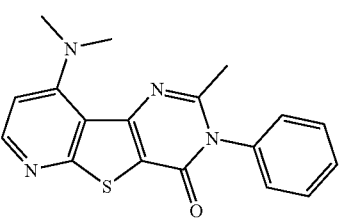 |
| 113C | C | 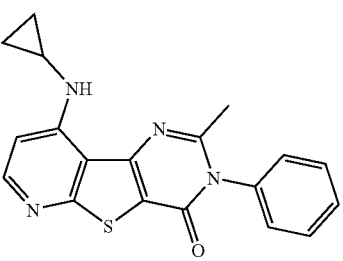 |
| 113D | A | 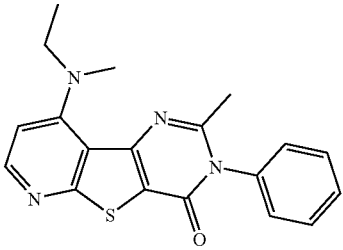 |
| 113E | A | 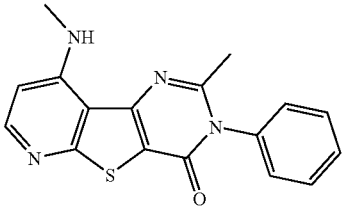 |
| 113F | A | 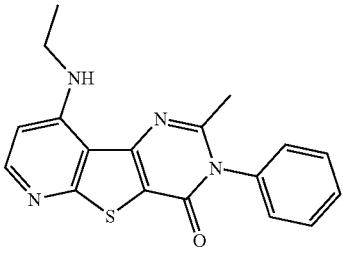 |
| 113G | A | 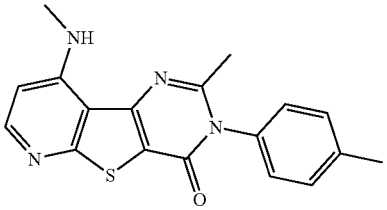 |
| 113H | A | 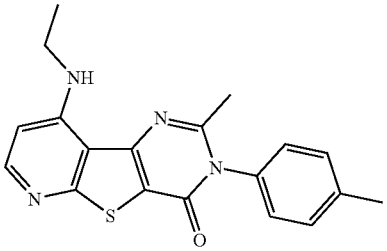 |
| 113I | A | 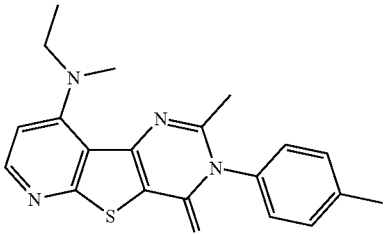 |

TABLE 2-continued
| Cpd | mGluR 1 IC$_{50}$ (nM) | Structure |
|---|---|---|
| 113J | C | 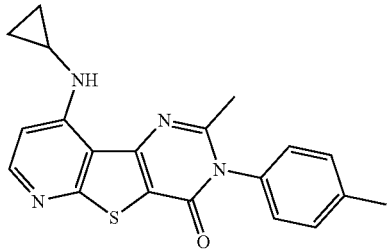 |
| 113K | A | 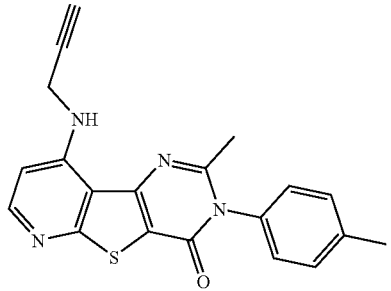 |
| 113L | C | 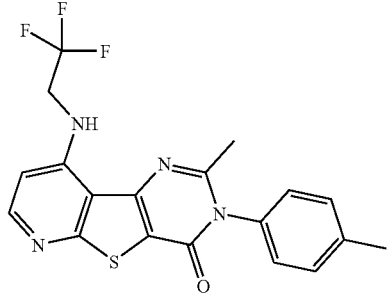 |
| 113M | B | 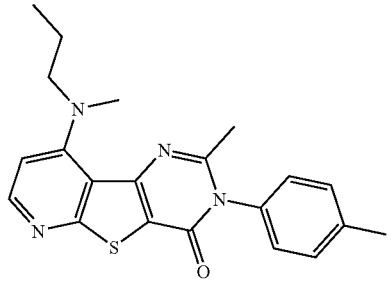 |
| 113N | B | 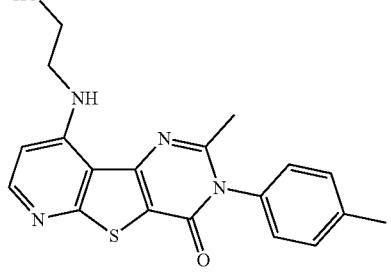 |
| 115 | D | 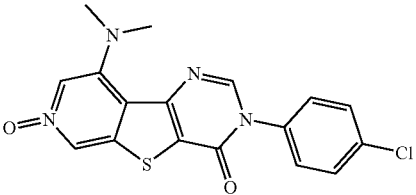 |
| 116 | C | 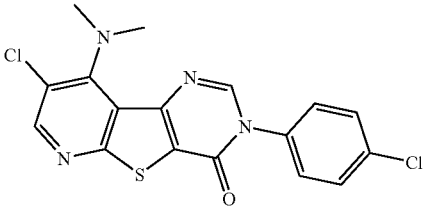 |
| 116A | B | 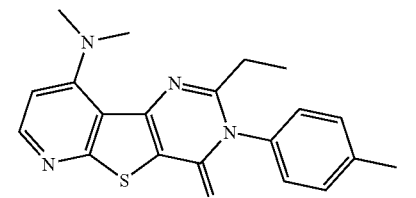 |
| 116B | C | 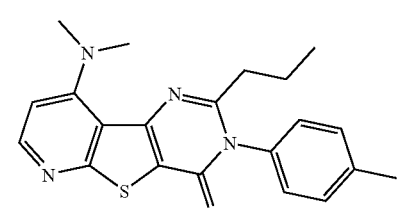 |
| 116C | C | 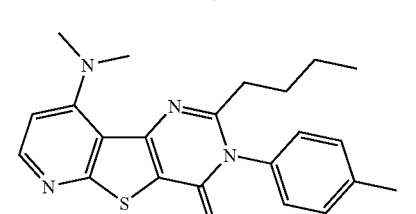 |
| 116D | A | 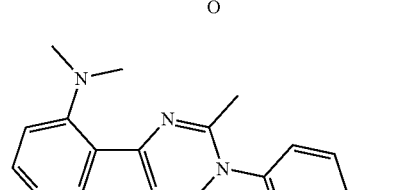 |
| 116E | B | 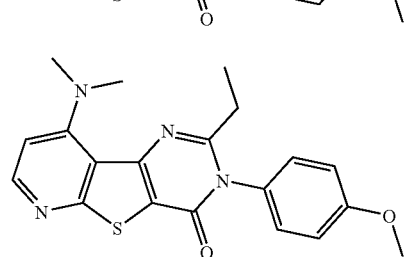 |

TABLE 2-continued
| Cpd | mGluR 1 IC$_{50}$ (nM) | Structure |
|---|---|---|
| 116F | C | 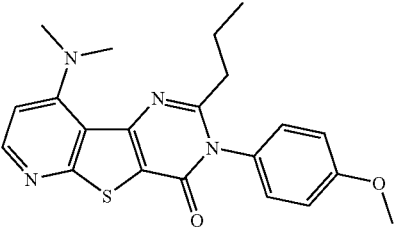 |
| 116G | C | 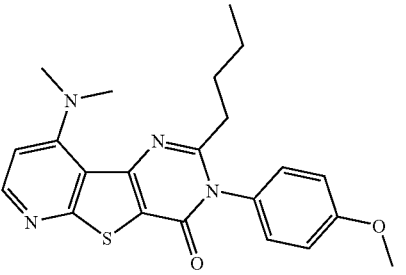 |
| 117 | B | 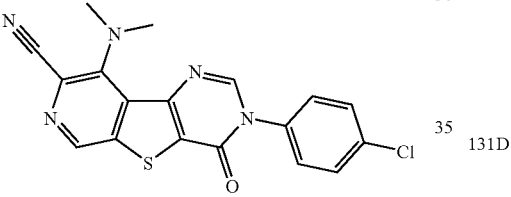 |
| 117A | C | 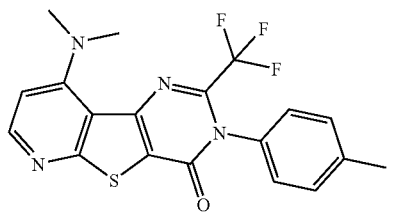 |
| 117B | C | 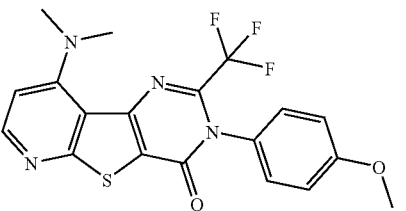 |
| 118 | — | 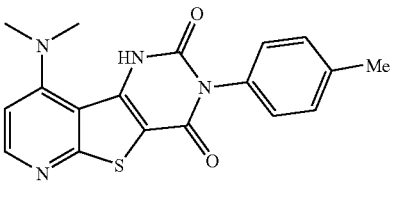 |
| 131A | A | 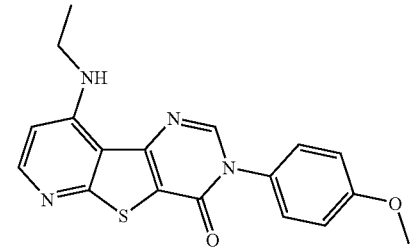 |
| 131B | A | 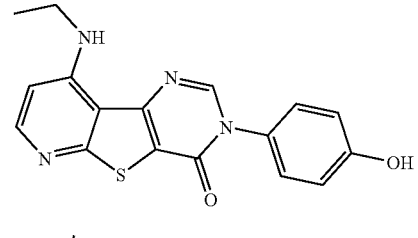 |
| 131C | A | 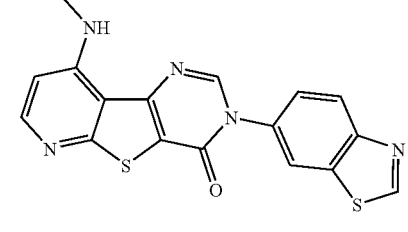 |
| 131D | A | 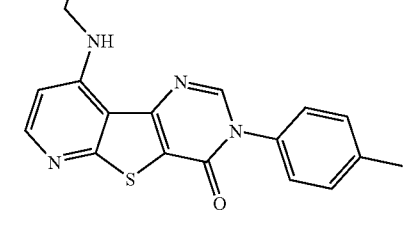 |
| 131E | A | 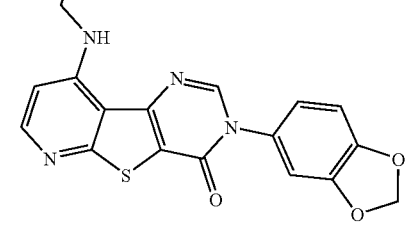 |
| 131F | B | 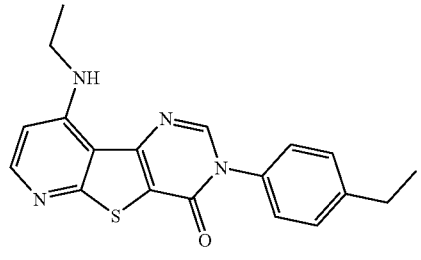 |

TABLE 2-continued

| Cpd | mGluR 1 IC$_{50}$ (nM) | Structure |
|---|---|---|
| 131G | A | (structure) |
| 134A | C | (structure) |
| 134B | C | (structure) |
| 134C | D | (structure) |
| 134D | D | (structure) |
| 134E | D | (structure) |
| 134F | C | (structure) |
| 134G | D | (structure) |
| 134H | D | (structure) |
| 134I | D | (structure) |
| 135A | D | (structure) |
| 136 | A | (structure) |

TABLE 2-continued
| Cpd | mGluR 1 IC$_{50}$ (nM) | Structure |
|---|---|---|
| 137A | A | 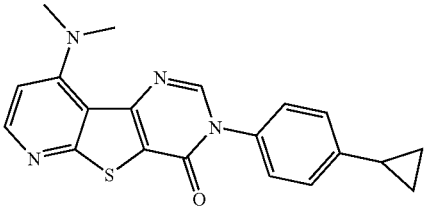 |
| 137B | A | 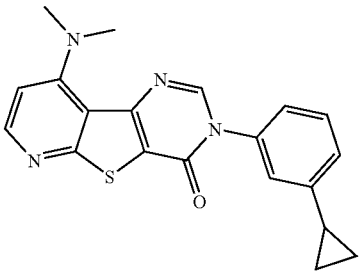 |
| 138 | A | 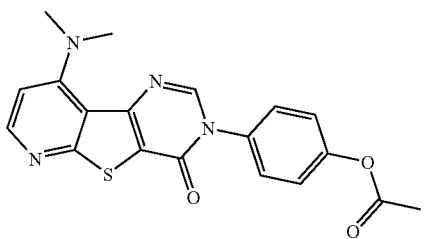 |
| 144A | B | 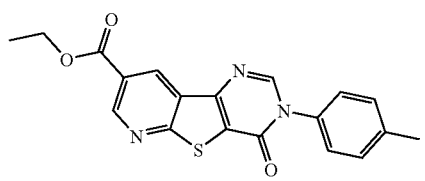 |
| 147A | C | 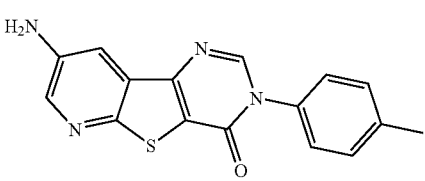 |
| 148 | A | 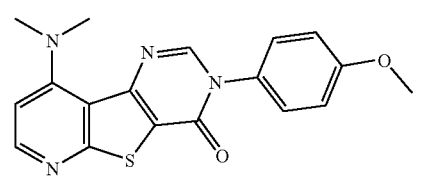 |
| 149 | D | 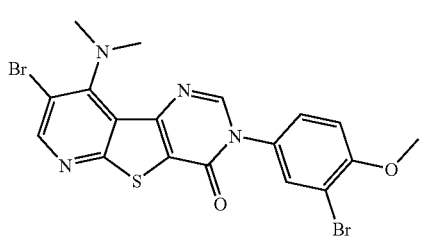 |
| 150 | C | 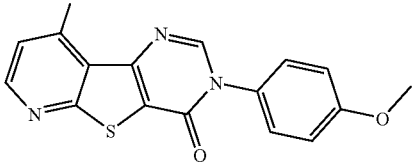 |
| 151 | A | 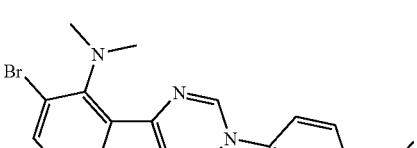 |
| 152 | A | 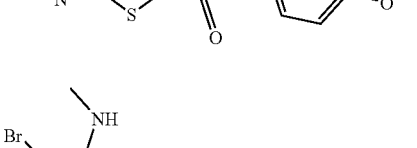 |
| P-1 | A | 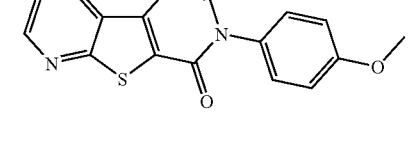 |
| P-2 | A | 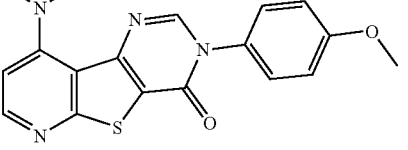 |
| P-3 | A | 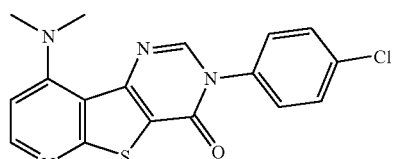 |
| P-4 | C | 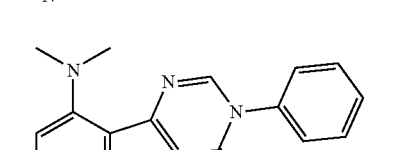 |

TABLE 2-continued
| Cpd | mGluR1 IC$_{50}$ (nM) | Structure |
|---|---|---|
| P-5 | C | 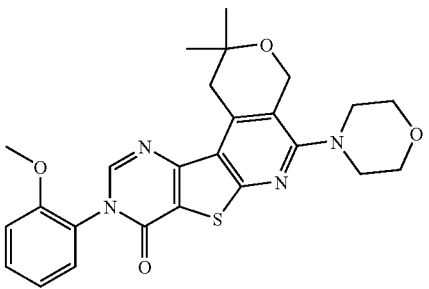 |
| P-6 | C | 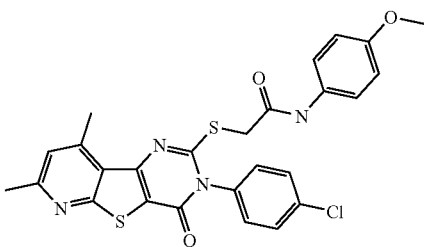 |
| P-7 | C | 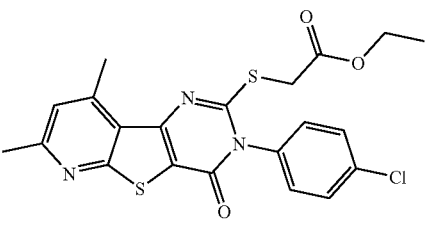 |
| P-8 | C | 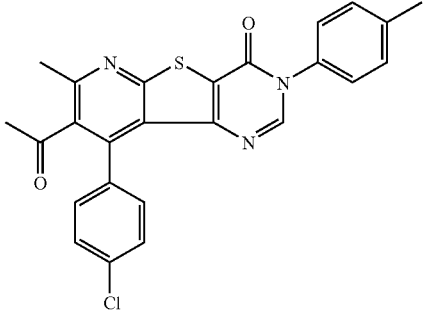 |
| P-9 | C | 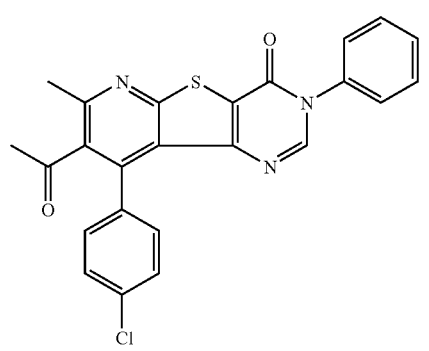 |
| P-10 | C | 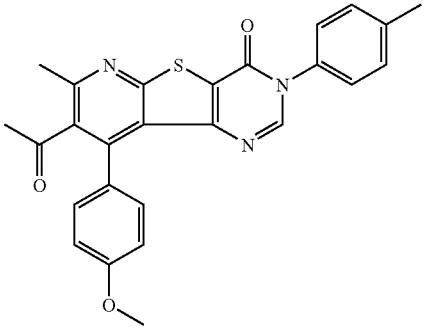 |
| P-11 | C | 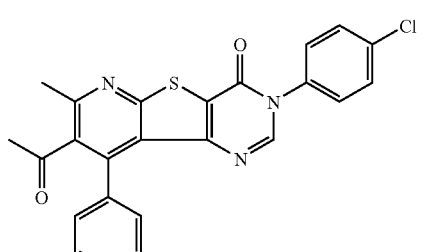 |
| P-12 | C | 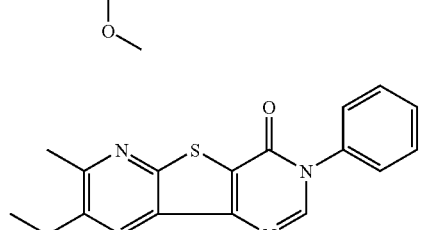 |
| P-13 | C | 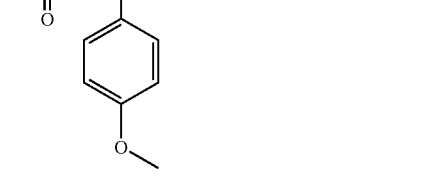 |
| P-14 | C | 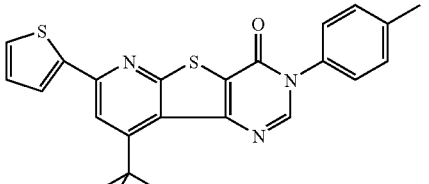 |

TABLE 2-continued

| Cpd | mGluR1 IC$_{50}$ (nM) | Structure |
|---|---|---|
| P-15 | C | (7,9-dimethyl-3-(4-methoxyphenyl)pyrido[3',2':4,5]thieno[3,2-d]pyrimidin-4(3H)-one) |

TABLE 2a

| Compound # | IC50 Class |
|---|---|
| 166 | D |
| 168 | D |
| 171 | D |
| 174 | C |
| 175 | A |
| 176 | D |
| 177 | D |
| 179 | C |
| 180 | C |
| 184 | B |
| 185 | B |
| 186 | D |
| 187 | A |
| 188 | A |
| 189 | B |
| 191 | D |
| 192 | A |
| 193 | A |
| 194 | C |
| 195 | C |
| 196 | A |
| 197 | A |
| 198 | A |
| 199 | A |
| 200 | A |
| 201 | A |
| 202 | A |
| 204 | B |
| 208 | C |
| 103G | D |
| 103H | D |
| 103I | D |
| 103J | D |
| 103K | D |
| 103L | D |
| 103M | C |
| 103N | C |
| 103O | D |
| 103P | C |
| 103Q | C |
| 103R | C |
| 103S | C |
| 131H | B |
| 131I | B |
| 131J | A |
| 131K | D |
| 131L | A |
| 131M | B |
| 131N | C |
| 137C | B |
| 137D | A |
| 137E | A |
| 137F | B |
| 137G | A |
| 137H | D |
| 137I | C |
| 144B | D |
| 144C | D |

TABLE 2a-continued

| Compound # | IC50 Class |
|---|---|
| 161A | D |
| 161B | D |
| 161C | D |
| 167A | C |
| 167B | B |
| 167C | C |
| 167D | D |
| 167E | D |
| 167F | D |
| 167G | D |
| 167H | C |
| 167I | C |
| 167J | B |
| 169A | D |
| 169B | D |
| 172A | A |
| 172B | A |
| 173A | A |
| 173B | A |
| 178A | B |
| 178B | A |
| 183A | C |
| 183B | C |
| 190A | D |
| 190B | B |
| 190C | C |
| 190D | C |
| 190E | C |
| 190F | C |
| 190G | D |
| 190H | D |
| 190I | C |
| 190J | D |
| 190K | C |
| 190L | D |
| 190M | D |
| 190N | D |
| 205A | D |
| 205B | D |
| 205C | C |
| 25E | D |
| 25F | C |
| 25G | C |
| 28BD | A |
| 28BE | A |
| 28BF | A |
| 28BG | A |
| 28BH | A |
| 28BI | A |
| 28BJ | B |
| 28BK | A |
| 28BL | D |
| 28BM | B |
| 28BN | A |
| 28BO | A |
| 28BP | C |
| 28BQ | A |
| 28BR | A |
| 28BS | A |
| 28BT | B |
| 28BU | A |
| 28BV | A |
| 28BW | A |
| 28BX | C |
| 28BY | A |
| 28BZ | A |
| 28CA | A |
| 28CB | B |
| 28CC | B |
| 28CD | A |
| 28CE | A |
| 28CF | A |
| 28CG | A |
| 28CH | A |
| 28CI | A |
| 28CJ | A |
| 28CK | A |

TABLE 2a-continued

| Compound # | IC50 Class |
|---|---|
| 28CL | A |
| 28CM | A |
| 28CN | A |
| 28CO | A |
| 28CP | A |
| 28CQ | A |
| 28CR | B |
| 28CS | B |
| 28CT | A |
| 28CU | D |
| 28CV | D |
| 28CW | D |
| 28CX | A |
| 28CY | A |
| 28CZ | A |
| 28DA | C |
| 28DB | A |
| 28DC | A |
| 28DD | C |
| 28DE | C |
| 28DF | D |
| 28DG | C |
| 28DH | C |
| 28DI | C |
| 28DJ | B |
| 28DK | C |
| 28DL | A |
| 28DM | D |
| 28DN | A |
| 28DO | A |
| 28DP | A |
| 28DQ | A |
| 28DR | A |
| 28DS | A |
| 28DT | A |
| 28DU | A |
| 28DV | A |
| 28DW | A |
| 28DX | A |
| 28DY | B |
| 28DZ | A |
| 28EA | A |
| 28EB | B |
| 28EC | A |
| 28ED | C |
| 28EE | C |
| 28EF | C |
| 28EG | C |
| 28EH | A |
| 28EI | C |
| 28EJ | D |
| 28EK | D |
| 28EL | D |
| 28EM | D |
| 28EN | C |
| 28EO | C |
| 28EP | C |
| 28EQ | C |
| 28ER |  |
| 28ES | D |
| 28ET | B |
| 28EU | C |
| 28EV | A |
| 28EW | A |
| 28EX | B |
| 28EY | A |
| 28EZ | C |
| 28FA | C |
| 28FB | A |
| 28FC | A |
| 28FD | A |
| 28FE | B |
| 28FF | C |
| 28FG | C |
| 28FH |  |
| 28FI |  |
| 28FK | A |
| 28FL | C |
| 28FM | C |
| 28FN | A |
| 28FO | C |
| 28FP | C |
| 28FQ | B |
| 28FR | A |
| 28FS | A |
| 28FT | C |
| 28FU | D |
| 28FV | D |
| 28FW | C |
| 28FX | C |
| 28FY | D |
| 28FZ | A |
| 28GA | A |
| 28GB | A |
| 28GC | B |
| 28GD | A |
| 28GE | A |
| 28GF | A |
| 28GG | C |
| 28GH | D |
| 28GI | D |
| 28GJ | B |
| 28GK | A |
| 28GL | A |
| 28GM | D |
| 28GN | A |
| 28GO | A |
| 28GP | A |
| 28GQ | A |
| 28GR | A |
| 28GS | A |
| 28GT | C |
| 28GU | A |
| 28GV | A |
| 28GW | C |
| 28GX | C |
| 28GY | A |
| 28GZ | D |
| 28HA | C |
| 28HB | A |
| 28HC | B |
| 28HD | C |
| 28HE | A |
| 28HF | A |
| 28HG | A |
| 28HH | B |
| 28HI | A |
| 28HJ | A |
| 28HK | A |
| 28HL | A |
| 28HM | A |
| 28HN | A |
| 28HO | A |
| 28HP | A |
| 28HQ | B |
| 28HR | C |
| 28HS | A |
| 28HT | D |
| 28HU | A |
| 28HV | A |
| 28HW | A |
| 28HX | C |
| 28HY | A |
| 28HZ | A |
| 28IA | A |
| 28IB | A |
| 28IC | A |
| 28ID | A |
| 28IE | A |
| 29E | A |
| 29F | A |
| 29G | A |
| 29H | A |
| 29I | A |

TABLE 2a-continued

| Compound # | IC50 Class |
|---|---|
| 29J | A |
| 29K | A |
| 57B | D |
| 57C | A |
| 57D | C |
| 57E | C |
| 59F | A |
| 59G | A |
| 59H | A |
| 59I | B |
| 66F | A |
| 66G | A |
| 66H | D |
| 66I | A |
| 66J | A |
| 66K | C |
| 66L | C |
| 66M | B |
| 71B | D |
| 71C | D |
| 71D | C |
| 71E | D |
| 71F | A |
| 73H | C |
| 73I | C |
| 73J | C |
| 95AO | A |
| 95AP | A |
| 95AQ | A |
| 95AR | A |
| 95AS | A |
| 95AT | A |
| 95AU | A |
| 95AV | A |
| 95AW | A |
| 95AX | B |
| 95AY | A |
| 95AZ | A |
| 95BA | A |
| 95BB | A |
| 95BC | A |
| 95BD | A |
| 95BE | B |
| 95BF | A |
| 95BG | A |
| 95BH | A |
| 95BI | A |
| 95BJ | A |
| 95BK | A |
| 95BL | A |
| 95BM | A |
| 95BN | B |
| 95BO | A |
| 95BP | A |
| 95DA | B |
| 95DB | A |
| 95DC | A |
| 95DD | C |
| 95DE | B |
| 95DF | C |
| 95DG | A |
| 95DH | C |
| 95DI | A |
| 95DJ | A |
| 95DK | A |
| 95DL | A |
| 95DM | A |
| 95DN | A |
| 95DO | A |
| 95DP | B |
| 95DQ | C |
| 95DR | B |
| 95DS | C |
| 95DT | A |
| 95DU | A |
| 95DV | A |
| 95DW | D |
| 95DX | D |
| 95DY | D |
| 95DZ | A |
| 95EA | D |
| 95EB | A |
| 95EC | D |
| 95ED | B |
| 95EE | A |
| 95EF | A |
| 95EG | A |
| 95EH | A |
| 95EI | A |
| 95EJ | B |
| 95EK | C |
| 95EL | A |
| 95EM | C |
| 95EN | B |
| 95EO | B |
| 95EP | C |
| 95EQ | A |
| 95ER | A |
| 95ES | A |
| 95ET | A |
| 95EU | C |
| 95EV | A |
| 95EW | B |
| 95EX | A |
| 95EY | A |
| 95EZ | A |
| 95FA | A |
| 95FB | B |
| 95FC | A |
| 95FD | A |
| 95FE | A |
| 95FF | A |
| 95FG | A |
| 95FH | A |
| 95FI | A |
| 95FJ | C |
| 95FK | B |
| 95FL | A |
| 95FM | B |
| 95FN | C |
| 95FO | C |
| 95FP | D |
| 95FQ | C |
| 95FR | A |
| 95FS | A |
| 95FT | A |
| 95FU | B |
| 95FV | C |
| 95FW | D |
| 95FX | C |
| 95FY | C |
| 95FZ | D |
| 95GA | D |
| 95GB | D |
| 95GC | D |
| 95GD | D |
| 95GE | D |
| 95GF | D |
| 95GG | D |
| 95GH | B |
| 95GI | C |
| 95GJ | B |
| 95GK | D |
| 95GL | C |
| 95GM | D |
| 95GN | D |
| 95GO | D |
| 95GP | A |
| 95GQ | C |

Representative preferred compounds have IC$_{50}$ values as shown in Table 3.
TABLE 3
| Cpd | mGluR1 IC$_{50}$ (nM) | Cpd | mGluR1 IC$_{50}$ (nM) |
|---|---|---|---|
| 7Q | 0.35 | 95A | 1.68 |
| 7X | 0.68 | 7DV | 1.71 |
| 95B | 1 | 7DR | 1.73 |
| 28AI | 1.27 | 28AA | 1.81 |
| 28Z | 1.47 | 7AC | 1.84 |
| 7BM | 1.48 | 7DH | 2.02 |
| 193 | 0.18 | 28GE | 0.28 |
| 95AT | 0.58 | 28GQ | 0.66 |
| 175 | 0.76 | 28GD | 0.77 |
| 28DL | 0.91 | 28DZ | 1.08 |
| 28HZ | 1.22 | 95BP | 1.31 |
| 95AU | 1.37 | 178B | 1.46 |
| 95AS | 1.48 | 95BO | 1.54 |
| 28BQ | 1.57 | 95AP | 1.6 |
| 28DP | 1.75 | 28DV | 1.87 |
| 95DV | 1.94 | 28DS | 1.95 |
| 28IC | 2.09 | 95BI | 28.25 |
What is claimed is:
1. A compound or a pharmaceutically acceptable salt, or ester thereof, wherein said compound is selected from the group consisting of:
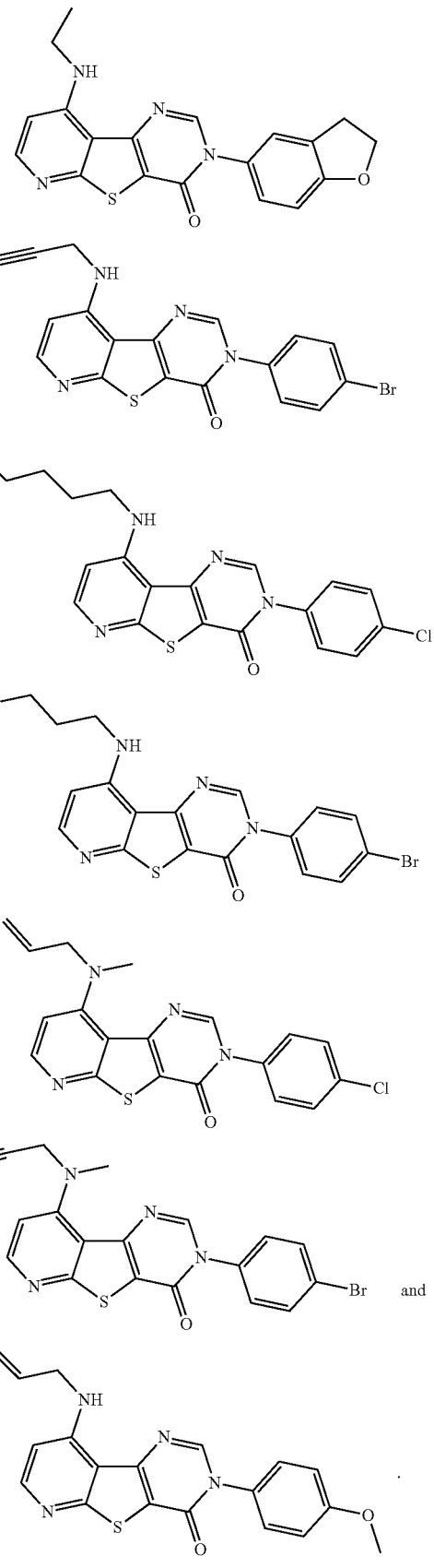

2. A pharmaceutical composition comprising at least one compound of claim 1, or a pharmaceutically acceptable salt, or ester thereof and at least one pharmaceutically acceptable carrier, adjuvant or vehicle.

3. The pharmaceutical composition of claim 2, further comprising one or more additional therapeutic agents.

4. The pharmaceutical composition of claim 3, wherein said additional therapeutic agents are selected from the group consisting of therapeutic agents suitable for pain management, anti-anxiety agents, anti-migraine agents, and therapeutic agents suitable for treating urinary incontinence.

5. A compound of the formula:

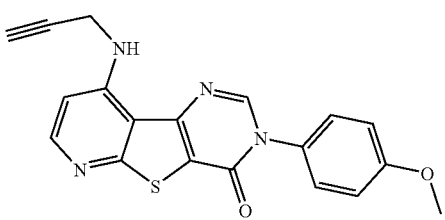

or a pharmaceutically acceptable salt, or ester thereof.

6. A compound of the formula:

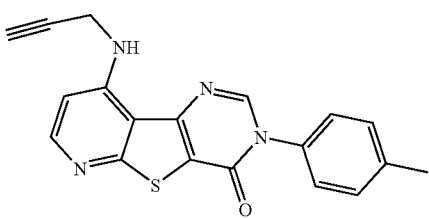

or a pharmaceutically acceptable salt, or ester thereof.

7. A compound of the formula:

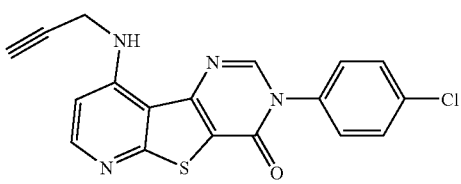

or a pharmaceutically acceptable salt, or ester thereof.

8. A compound of the formula:

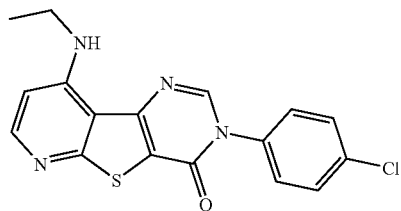

or a pharmaceutically acceptable salt, or ester thereof.

9. A compound of the formula:

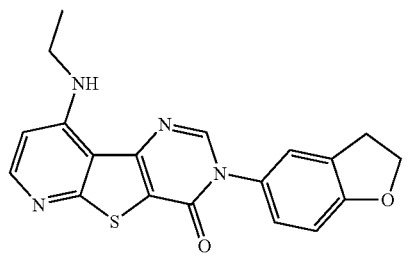

or a pharmaceutically acceptable salt, or ester thereof.

10. A compound of the formula:

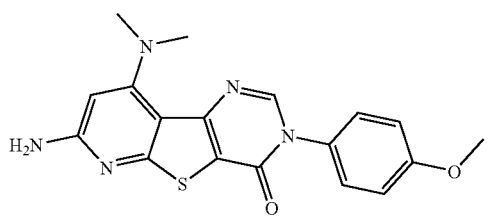

or a pharmaceutically acceptable salt, or ester thereof.

11. A pharmaceutical composition comprising a compound of any of claims 5, 6, 7, 8, 9, or 10.

* * * * *